US008476294B2

(12) United States Patent
Furet et al.

(10) Patent No.: US 8,476,294 B2
(45) Date of Patent: Jul. 2, 2013

(54) 1H-IMIDAZO[4,5-*C*]QUINOLINONE DERIVATIVES

(75) Inventors: Pascal Furet, Basel (CH); Frank Stephan Kalthoff, Vienna (AT); Robert Mah, Basel (CH); Christian Ragot, Basel (CH); Frédéric Stauffer, Basel (CH)

(73) Assignee: Novartis AG, Basel (CH)

( * ) Notice: Subject to any disclaimer, the term of this patent is extended or adjusted under 35 U.S.C. 154(b) by 370 days.

(21) Appl. No.: 12/792,471

(22) Filed: Jun. 2, 2010

(65) Prior Publication Data

US 2010/0317657 A1 Dec. 16, 2010

Related U.S. Application Data

(60) Provisional application No. 61/184,141, filed on Jun. 4, 2009.

(51) Int. Cl.
*C07D 471/04* (2006.01)
*A61K 31/437* (2006.01)

(52) U.S. Cl.
USPC ................................ 514/293; 546/82; 546/85

(58) Field of Classification Search
USPC ................................ 546/85, 86, 82; 514/293
See application file for complete search history.

(56) References Cited

U.S. PATENT DOCUMENTS

2009/0082387 A1 3/2009 Czarnik

FOREIGN PATENT DOCUMENTS

| | | | |
|---|---|---|---|
| WO | WO 03/097641 | A2 | 11/2003 |
| WO | WO 2005/054237 | A1 | 6/2005 |
| WO | WO 2005/054238 | A1 | 6/2005 |
| WO | WO 2006/031878 | A2 | 3/2006 |
| WO | WO 2006/122806 | A2 | 11/2006 |
| WO | WO 2007/056112 | A2 | 5/2007 |
| WO | WO 2008/064093 | A2 | 5/2008 |
| WO | WO 2008/103636 | A1 | 8/2008 |
| WO | WO 2009/013305 | A1 | 1/2009 |
| WO | WO 2009/118324 | A1 | 10/2009 |
| WO | WO 2009/155527 | A2 | 12/2009 |
| WO | WO 2010/038165 | A1 | 4/2010 |

OTHER PUBLICATIONS

Wolff, Manfred E. "Burger's Medicinal Chemistry, 5ed, Part I", John Wiley & Sons, 1995, pp. 975-977.*

Banker (Modern Pharmaceutics) Banker, G.S. et al, "Modern Pharmaceutics, 3ed.", Marcel Dekker, New York, 1996, pp. 451 and 596.*

Dorwald F. A. Side Reactions in Organic Synthesis, 2005, Wiley: VCH, Weinheim p. IX of Preface.*

Faber et al; "Differential induction of apoptosis in HER2 and GFR addicted cancers following PI3K inhibition"; Proc Nat Acad Sci USA 106(46):19503-19508 (2009).

Frédérick et al; "Phosphoinositide-3-kinase (PI3K) inhibitors: Identification of new scaffolds using virtual screening"; Bioorganic & Medicinal Chemistry Letters 19(20):5842-5847 (2009).

Konstantinidou et al; "Dual Phosphoinositide 3-Kinase/Mammalian Target of Rapamycin Blockade Is an Effective Radiosensitizing Strategy for the Treatment of Non-Small Cell Lung Cancer Harboring K-RAS Mutations"; Cancer Res 69(19):7644-7652 (2009).

Liu et al; "NVP-BEZ235, a novel dual phosphatidylinositol 3-kinase/mammalian target of rapamycin inhibitor, elicits multifaceted antitumor activities in human gliomas"; Mol Cancer Ther 8(8):2204-2210 (2009).

Sturgill et al; "Activating Mutations in TOR Are in Similar Structures as Oncogenic Mutations in PI3KC[alpha]"; ACS Chem Biol 4(12):999-1015 (2009).

* cited by examiner

*Primary Examiner* — Rita Desai
(74) *Attorney, Agent, or Firm* — Scott Loftus-Reid

(57) ABSTRACT

The invention relates to the use of 1H-imidazo[4,5-*c*]quinolinone derivatives and salts thereof in the treatment of protein and/or lipid kinase dependent diseases and for the manufacture of pharmaceutical preparations for the treatment of said diseases; 1H-imidazo[4,5-*c*]quinolinone derivatives for use in the treatment of protein and/or lipid kinase dependent diseases; a method of treatment against said diseases, comprising administering the 1H-imidazo[4,5-*c*]quinolinone derivatives to a warm-blooded animal, especially a human; pharmaceutical preparations comprising an 1H-imidazo[4,5-*c*]quinolinone derivative, especially for the treatment of a protein and/or lipid kinase dependent disease; novel 1H-imidazo[4,5-*c*]quinolinone derivatives; and a process for the preparation of the novel 1H-imidazo[4,5-*c*]quinolinone derivatives.

3 Claims, No Drawings

1H-IMIDAZO[4,5-*C*]QUINOLINONE DERIVATIVES

RELATED APPLICATIONS

This application claims priority to U.S. Application Ser. No. 61/184,141 filed 4 Jun. 2009, the contents of which are incorporated herein by reference in their entirety.

BACKGROUND OF THE INVENTION

The invention relates to imidazoquinolinones, salts and prodrugs thereof, processes for their preparation, their use in the treatment of protein or lipid kinase dependent diseases and in particular phosphatidylinositol-3-kinase (PI3K) dependent diseases, their use, either alone or in combination with at least one additional therapeutic agent and optionally in combination with a pharmaceutically acceptable carrier, for the manufacture of pharmaceutical preparations, use of the pharmaceutical preparations for the treatment of protein or lipid kinase dependant diseases and in particular PI3K dependent diseases, and a method of treatment of said diseases, comprising administering the imidazoquinolinones to a warm-blooded animal, especially a human. The invention also relates to pharmaceutical preparations comprising an imidazoquinolinone of the invention, either alone or in combination with at least one additional therapeutic agent, and optionally in combination with a pharmaceutically acceptable carrier.

SUMMARY OF THE INVENTION

The phosphatidylinositol-3-kinases superfamily comprises 4 different PI3K related lipid or protein kinases. Class I, II and III are lipid kinases that differ from their substrate specificities whereas class IV PI3K also called PI3-kinase-related protein kinase (PIKK) are protein kinases. Class I phosphatidylinositol-3-kinases comprise a family of lipid kinases that catalyze the transfer of phosphate to the D-3' position of inositol lipids to produce phosphoinositol-3-phosphate (PIP), phosphoinositol-3,4-diphosphate ($PIP_2$) and phosphoinositol-3,4,5-triphosphate ($PIP_3$) that, in turn, act as second messengers in signaling cascades by docking proteins containing pleckstrin-homology, FYVE, Phox and other phospholipid-binding domains into a variety of signaling complexes often at the plasma membrane ((Vanhaesebroeck et al., *Annu. Rev. Biochem* 70:535 (2001); Katso et al., *Annu. Rev. Cell Dev. Biol.* 17:615 (2001)). Of the two Class I PI3Ks, Class IA PI3Ks are heterodimers composed of a catalytic p110 subunit (α, β, δ isoforms) constitutively associated with a regulatory subunit that can be p85α, p55α, p50α, p85β or p55γ. The Class IB sub-class has one family member, a heterodimer composed of a catalytic p110γ subunit associated with one of two regulatory subunits, p101 or p84 (Fruman et al., *Annu Rev. Biochem.* 67:481 (1998); Suire et al., *Curr. Biol.* 15:566 (2005)). The modular domains of the p85/55/50 subunits include Src Homology (SH2) domains that bind phosphotyrosine residues in a specific sequence context on activated receptor and cytoplasmic tyrosine kinases, resulting in activation and localization of Class IA PI3Ks. Class IB PI3K is activated directly by G protein-coupled receptors that bind a diverse repertoire of peptide and non-peptide ligands (Stephens et al., *Cell* 89:105 (1997)); Katso et al., *Annu. Rev. Cell Dev. Biol.* 17:615-675 (2001)). Consequently, the resultant phospholipid products of class I PI3K link upstream receptors with downstream cellular activities including proliferation, survival, chemotaxis, cellular trafficking, motility, metabolism, inflammatory and allergic responses, transcription and translation (Cantley et al., *Cell* 64:281 (1991); Escobedo and Williams, *Nature* 335:85 (1988); Fantl et al., *Cell* 69:413 (1992)).

In many cases, PIP2 and PIP3 recruit Akt, the product of the human homologue of the viral oncogene v-Akt, to the plasma membrane where it acts as a nodal point for many intracellular signaling pathways important for growth and survival (Fantl et al., *Cell* 69:413-423(1992); Bader et al., *Nature Rev. Cancer* 5:921 (2005); Vivanco and Sawyer, *Nature Rev. Cancer* 2:489 (2002)). Aberrant regulation of PI3K, which often increases survival through Akt activation, is one of the most prevalent events in human cancer and has been shown to occur at multiple levels. The tumor suppressor gene PTEN, which dephosphorylates phosphoinositides at the 3' position of the inositol ring and in so doing antagonizes PI3K activity, is functionally deleted in a variety of tumors. In other tumors, the genes for the p110α, isoform, PIK3CA, and for Akt are amplified and increased protein expression of their gene products has been demonstrated in several human cancers. Furthermore, mutations and translocation of p85α that serve to up-regulate the p85-p110 complex have been described in human cancers. Also, somatic missense mutations in PIK3CA that activate downstream signaling pathways have been described at significant frequencies in a wide diversity of human cancers (Kang at al., *Proc. Natl. Acad. Sci. USA* 102:802 (2005); Samuels et al., *Science* 304:554 (2004); Samuels et al., *Cancer Cell* 7:561-573 (2005)). These observations show that deregulation of phosphoinositol-3 kinase and the upstream and downstream components of this signaling pathway is one of the most common deregulations associated with human cancers and proliferative diseases (Parsons et al., *Nature* 436:792 (2005); Hennessey at el., *Nature Rev. Drug Disc.* 4:988-1004 (2005)).

The mammalian target of rapamycin (mTOR) is a member of the class IV PI3K. mTOR assembles a signaling network that transduces nutrient signals and various other stimuli to regulate a wide range of cellular functions including cell growth, proliferation, survival, autophagy, various types of differentiation and metabolism. In mammalian cells, the mTOR protein is found complexed in two distinct entities called mTORC1 and mTORC2. The mTORC1 complex, that is to say mTOR associated with raptor, has been the matter of numerous studies. It is mTORC1 that integrates nutrient and growth factor input, and is in turn responsible for cell growth regulation, mainly through protein synthesis regulators such as 4EBP1 or RPS6. Activation of mTORC1 requires input from active PI3K and Akt kinases meaning that mTORC1 is a downstream effector of the PI3K pathway. mTOR when associated in the mTOR complex 2 (mTORC2) has been shown to be responsible for the activation of Akt by phosphorylation of S473 (Akt 1 numbering) (Sarbassov et al., Science 307: 7098 (2005)). mTORC2 is hence here considered as an upstream activator of Akt. Interestingly mTOR can therefore be considered as being important both upstream and downstream of Akt. Taken together, mTOR can be regarded as a downstream effector and an upstream activator of Aid depending on its association with the mTOCR1 and mTORC2 complex, respectively. mTOR catalytic inhibition might therefore represent a unique way of introducing a very strong block in the PI3K-Akt pathway, by addressing both upstream and downstream effectors. Syndromes with an established or potential molecular link to disregulation of mTOR kinase activity are, for instance, described in "K. Inoki et al.; Disregulation of the TSC-mTOR pathway in human disease, Nature Genetics, vol 37, 19-24"; "D. M. Sabatini; mTOR and cancer: insights into a complex relationship, Nature Reviews, vol. 6, 729-734"; and in "B. T. Hennessy et al.; Exploiting the PI3K/Akt pathway for cancer drug discovery, Nature Reviews, vol. 4, 988-1004", and are as follows:

- Organ or tissue transplant rejection, e.g. for the treatment of recipients of e.g. heart, lung, combined heart-lung, liver, kidney, pancreatic, skin or corneal transplants; graft-versus-host disease, such as following bone marrow transplantation;
- Restenosis
- Tuberous sclerosis
- Lymphangioleiomyomatosis
- Retinitis pigmentosis
- Autoimmune diseases including encephalomyelitis, insulin-dependent diabetes mellitus, lupus, dermatomyositis, arthritis and rheumatic diseases
- Steroid-resistant acute Lymphoblastic Leukaemia
- Fibrotic diseases including scleroderma, pulmonary fibrosis, renal fibrosis, cystic fibrosis
- Pulmonary hypertension
- Immunomodulation
- Multiple sclerosis
- VHL syndrome
- Carney complex
- Familial adenonamtous polyposis
- Juvenile polyposis syndrome
- Birt-Hogg-Duke syndrome
- Familial hypertrophic cardiomyopathy
- Wolf-Parkinson-White syndrome
- Neurodegenarative disorders such as Parkinson's, Huntingtin's, Alzheimer's and dementias caused by tau mutations, spinocerebellar ataxia type 3, motor neuron disease caused by SOD1 mutations, neuronal ceroid lipofucinoses/Batten disease (pediatric neurodegeneration)
- wet and dry macular degeneration
- muscle wasting (atrophy, cachexia) and myopathies such as Danon's disease.
- bacterial and viral infections including *M. tuberculosis*, group A *streptococcus*, HSV type I, HIV infection
- Neurofibromatosis including Neurofibromatosis type 1,
- Peutz-Jeghers syndrome or further any combinations thereof.

Compounds with an inhibitory activity on mTORC1 have shown benefit in immunomodulation and in treating proliferative diseases such as advance renal cell carcinoma or Tubero-Sclerosis (TSC) germ line mutation associated disorders.

The catalytic inhibition of mTOR Ser/Thr kinase activity or class I PI3 kinases activity and in particular dual class I PI3-kinase(s) and mTOR kinase inhibition is considered to be useful for the treatment of PI3K/Akt/mTOR pathway dependent diseases.

The efficacy of a dual PI3 kinase/mTOR inhibitor in malignant glioma has been recently described (Cancer Cell 9, 341-349).

In view of the above, inhibitors of class I and/or IV PI3Ks are considered to be of value in the treatment of proliferative disease and other disorders.

WO2003/097641, WO2005/054237, WO2005/054238 and WO2006/122806 describe imidazoquinolines for use in the treatment of protein kinase dependent diseases.

WO 2008/103636 describes imidazoquinolines as dual lipid kinase and mTor inhibitors.

It has now been found that the imidazoquinolinones derivatives of the formula (I) given below have advantageous pharmacological properties and inhibit, for example, lipid or protein kinases such as PI4K (phosphatidylinositol 4-kinase) and/or PI3 kinases (phosphatidylinositol 3-kinases), for example, inhibition of the PI3K superfamily which comprises PI3Kalpha, PI3Kbeta, PI3Kdelta, PI3Kgamma and mTOR, or one or more of the individual kinase members thereof. The class IV PI3K also called PI3-kinase-related protein kinase (PIKK) includes DNA-PK, ATM, ATR, hSMG-1 and mTOR. In particular, preferably imidazoquinolinones of the formula (I) given below show a high degree of selectivity in favour of one or more of the class I-IV P13K against other protein kinases, such as the receptor tyrosine kinases and/or the Ser/Thr kinases outside of the PIKK family in the biochemical and/or in the cellular assay. In addition, the imidazoquinolinones of the formula (I) preferably display a favourable solubility and/or membrane permeability at physiological pH. Hence, the compounds of formula (I) are suitable, for example, to be used in the treatment of diseases dependent on PI3 kinase, especially proliferative diseases such as tumor diseases, leukaemias, and myeloproliferative disorders such as polycythemia vera, essential thrombocythemia, and myelofibrosis with myeloid metaplasia, and proliferative skin diseases including basal cell carcinoma, squamous cell carcinoma and actinic keratosis and other benign hyperproliferative skin disorders caused by inflammation such as psoriasis or as a result of dysregulation of fibroblasts such as skin fibrosis, scleroderma or keloids.

DESCRIPTION OF THE INVENTION

In a first aspect, the present invention provides compounds of the formula (I)

(I)

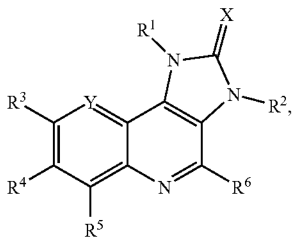

wherein

- X is O or S;
- Y is CH or N;
- $R^1$ is a substituted or unsubstituted 5-membered heteroaryl;
- $R^2$ is hydrogen, lower alkyl or lower alkenyl;
- $R^3$ is a substituted or unsubstituted aryl or heterocyclyl; and
- $R^4$, $R^5$ and $R^6$ are hydrogen;

or a pharmaceutically acceptable salt, solvate, hydrate or prodrug thereof.

The present invention is also directed to use of compounds of formula (I) in the treatment of protein and/or lipid kinase dependent diseases; use of compounds of formula (I) for the manufacture of pharmaceutical preparations for the treatment of protein and/or lipid kinase dependent diseases and in particular PI3K superfamily (especially class I PI3K and/or mTOR) dependent diseases; methods of treating protein and/or lipid kinase dependant diseases and in particular PI3K superfamily (especially class I PI3K and/or mTOR) dependent diseases comprising administering imidazoquinolinone compounds of the formula (I) to a warm-blooded animal, especially a human; pharmaceutical preparations comprising an imidazoquinolinone compound of the formula (I), especially for the treatment of a protein and/or lipid kinase dependant disease and in particular a PI3K superfamily (especially class I PI3K and/or mTOR) dependent disease; a process for the manufacture of the novel imidazoquinolinone compounds of the formula (I); the manufacture of a pharmaceutical preparation for the treatment of protein and/or lipid kinase dependant diseases and in particular PI3K superfamily (especially class I PI3K and/or mTOR) dependent diseases, and novel intermediates for their manufacture. Preferably, the PI3K superfamily dependent diseases are class I PI3K and/or mTOR dependent diseases.

The invention may be more fully appreciated by reference to the following description, including the following glossary of terms and the concluding examples. As used herein, the terms "including", "containing" and "comprising" are used herein in their open, non-limiting sense.

Any formula given herein is intended to represent compounds having structures depicted by the structural formula as well as certain variations or forms. In particular, compounds of any formula given herein may have asymmetric centers and therefore exist in different stereoisomeric forms such as different enantiomeric forms. If at least one asymmetrical carbon atom is present in a compound of the formula I, such a compound may exist in optically active form or in the form of a mixture of optical isomers, e.g. in the form of a racemic mixture. Thus an asymmetric carbon atom may be present in the (R)-, (S)- or (R,S)-configuration, preferably in the (R)- or (S)-configuration. All optical isomers and their mixtures, including the racemic mixtures, are part of the present invention. Thus, any given formula given herein is intended to represent a racemate, one or more enantiomeric forms, one or more diastereomeric forms, one or more atropisomeric forms, and mixtures thereof. Furthermore, certain structures may exist as geometric isomers (e.g. cis and trans isomers), as tautomers, or as atropisomers. For example, substituents at a double bond or a ring may be present in cis-(=Z-) or trans (=E-) form. The compounds of the invention may thus be present as mixtures of isomers or preferably as pure isomers, preferably as enantiomer-pure diastereomers or pure enantiomers.

Any formula given herein is intended to represent hydrates, solvates, and polymorphs of such compounds, and mixtures thereof.

Any formula given herein is also intended to represent unlabeled forms as well as isotopically labeled forms of the compounds. Isotopically labeled compounds have structures depicted by the formulas given herein except that one or more atoms are replaced by an atom having a selected atomic mass or mass number. Examples of isotopes that can be incorporated into compounds of the invention include isotopes of hydrogen, carbon, nitrogen, oxygen, phosphorous, fluorine, and chlorine, such as $^{2}H$, $^{3}H$, $^{11}C$, $^{13}C$, $^{14}C$, $^{15}N$, $^{31}P$, $^{32}P$, $^{18}F$, $^{35}S$, $^{36}Cl$, $^{125}I$ respectively. Various isotopically labeled compounds of the present invention, for example those into which radioactive isotopes such as $^{3}H$, $^{13}C$, and $^{14}C$ are incorporated. Such isotopically labelled compounds are useful in metabolic studies (preferably with $^{14}C$), reaction kinetic studies (with, for example $^{2}H$ or $^{3}H$), detection or imaging techniques, such as positron emission tomography (PET) or single-photon emission computed tomography (SPECT) including drug or substrate tissue distribution assays, or in radioactive treatment of patients. In particular, an $^{18}F$ or labeled compound may be particularly preferred for PET or SPECT studies. Further, substitution with heavier isotopes such as deuterium (i.e., $^{2}H$) may afford certain therapeutic advantages resulting from greater metabolic stability, for example increased in vivo half-life or reduced dosage requirements. Isotopically labeled compounds of this invention and prodrugs thereof can generally be prepared by carrying out the procedures disclosed in the schemes or in the examples and preparations described below by substituting a readily available isotopically labeled reagent for a non-isotopically labeled reagent.

When referring to any formula given herein, the selection of a particular moiety from a list of possible species for a specified variable is not intended to define the moiety for the variable appearing elsewhere. In other words, where a variable appears more than once, the choice of the species from a specified list is independent of the choice of the species for the same variable elsewhere in the formula (where one or more up to all more general expressions in embodiments characterized as preferred above or below can be replaced with a more specific definition, thus leading to a more preferred embodiment of the invention, respectively).

Where the plural form (e.g. compounds, salts, pharmaceutical preparations, diseases and the like) is used, this includes the singular (e.g. a single compound, a single salt, a single pharmaceutical preparation, a single disease, and the like). "A compound" does not exclude that (e.g. in a pharmaceutical formulation) more than one compound of the formula (I) (or a salt thereof) is present.

Salts are preferably the pharmaceutically acceptable salts of compounds of formula (I) if they are carrying salt-forming groups.

The salts of compounds of formula (I) are preferably pharmaceutically acceptable salts; acids/bases required to form the salts are generally known in the field.

Salt-forming groups in a compound of formula (I) are groups or radicals having basic or acidic properties. Compounds having at least one basic group or at least one basic radical, e.g., amino; a secondary amino group not forming a peptide bond or a pyridyl radical, may form acid addition salts, e.g., with inorganic acids, such as hydrochloric acid, sulfuric acid or a phosphoric acid; or with suitable organic carboxylic or sulfonic acids, e.g., aliphatic mono- or di-carboxylic acids, such as trifluoroacetic acid, acetic acid, propionic acid, glycolic acid, succinic acid, maleic acid, fumaric acid, hydroxymaleic acid, malic acid, tartaric acid, citric acid or oxalic acid; or amino acids, such as arginine or lysine; aromatic carboxylic acids, such as benzoic acid; 2-phenoxy-benzoic acid; 2-acetoxy-benzoic acid; salicylic acid; 4-aminosalicylic acid; aromatic-aliphatic carboxylic acids, such as mandelic acid or cinnamic acid; heteroaromatic carboxylic acids, such as nicotinic acid or isonicotinic acid; aliphatic sulfonic acids, such as methane-, ethane- or 2-hydroxy-ethanesulfonic acid; or aromatic sulfonic acids, e.g., benzene-, p-toluene- or naphthalene-2-sulfonic acid. When several basic groups are present mono- or poly-acid addition salts may be formed.

Compounds of formula (I) having acidic groups, a carboxy group or a phenolic hydroxy group, may form metal or ammonium salts, such as alkali metal or alkaline earth metal salts, e.g., sodium, potassium, magnesium or calcium salts; or ammonium salts with ammonia or suitable organic amines, such as tertiary monoamines, e.g., triethylamine or tri(2-hydroxyethyl)-amine, or heterocyclic bases, e.g., N-ethyl-piperidine or N,N'-dimethylpiperazine. Mixtures of salts are possible.

Compounds of formula (I) having both acidic and basic groups can form internal salts.

For the purposes of isolation or purification, as well as in the case of compounds that are used further as intermediates, it is also possible to use pharmaceutically-unacceptable salts, e.g., the picrates. Only pharmaceutically-acceptable, nontoxic salts may be used for therapeutic purposes, however, and those salts are therefore preferred.

Owing to the close relationship between the novel compounds in free form and in the form of their salts, including those salts that can be used as intermediates, e.g., in the purification of the novel compounds or for the identification thereof, any reference hereinbefore and hereinafter to the free compounds shall be understood as including the corresponding salts, where appropriate and expedient.

Compounds of the present invention may also form solvates and hydrates, and as such any reference to a compound of formula (I) is therefore to be understood as referring also to the corresponding solvate and/or hydrate of the compound of formula (I), as appropriate and expedient.

The present invention also relates to pro-drugs of a compound of formula (I) that convert in vivo to the compound of formula (I) as such. Any reference to a compound of formula (I) is therefore to be understood as referring also to the corresponding pro-drugs of the compound of formula (I), as appropriate and expedient.

The general terms used hereinbefore and hereinafter preferably have within the context of this disclosure the following meanings, unless otherwise indicated:

The prefix "lower" denotes a radical having 1 carbon atom up to and including a maximum of 7 carbon atoms, especially 1 carbon atom up to and including a maximum of 4 carbon atoms, the radicals in question being either linear or branched with single- or multiple-branching.

Halo or halogen is preferably fluoro, chloro, bromo or iodo, most preferably fluoro, chloro or bromo.

Alkyl preferably has 1 up 12 carbon atoms ($C_{1-12}$alkyl) and is linear or branched one or more times; in particular alkyl is lower alkyl, especially $C_1$-$C_4$alkyl. For example, alkyl includes methyl, ethyl, n-propyl, iso-propyl, n-butyl, isobutyl, sec-butyl, tert-butyl, n-pentyl, n-hexyl, n-heptyl, n-octyl, n-nonyl, n-decyl, n-undecyl, n-dodecyl, with particular preference given to methyl, ethyl, n-propyl, iso-propyl, n-butyl and iso-butyl. Lower alkyl, for example, is represented as $C_1$-$C_7$alkyl, e.g. methyl, ethyl, n-propyl, iso-propyl, n-butyl, isobutyl, sec-butyl, tert-butyl, n-pentyl, n-hexyl or n-heptyl, lower alkyl is especially represented as $C_1$-$C_4$alkyl, e.g. methyl, ethyl, n-propyl, iso-propyl, n-butyl, isobutyl, sec-butyl, tert-butyl, with preference given to methyl, ethyl or propyl.

Alkyl, in particular lower alkyl, is unsubstituted or substituted, preferably by one or more substituents independently selected from those mentioned below under "substituted". Exemplary substituents include, but are not limited to hydroxy, alkoxy, aryl, heterocyclyl, cycloalkyl, halogen, amino and nitro. An example of a substituted alkyl is haloalkyl, such as halomethyl, for example fluoromethyl, e.g. trifluoromethyl. Another example of a substituted alkyl is hydroxymethyl or hydroxyethyl. A further example of a substituted alkyl is alkoxyalkyl, such as methoxyethyl or methoxypropyl. The alkoxyalkyl may be further substituted, for example to give benzyloxyethyl or benzyloxypropyl.

Alkyl may also be cyclic as defined below under "cycloalkyl". Cycloalkyl may also be a substituent to alkyl. Cycloalkyl-lower alkyl is preferably lower alkyl that is substituted (preferably terminally) by unsubstituted or substituted cycloalkyl as defined below. An example of cycloalkyl as a substituent to alkyl is alkandiyl-cycloalkyl, such as alkandiyl-cycloloweralkyl, e.g. alkandiyl-cyclopropyl, e.g. $-CH_2$-cyclopropyl.

Aryl-lower alkyl is preferably lower alkyl that is substituted (preferably terminally or in 1-position) by unsubstituted or substituted aryl as defined below. Aryl-lower alkyl is especially phenyl-lower alkyl, such as benzyl (i.e. phenylmethyl) or phenylethyl, especially 1-phenylethyl.

Heterocyclyl-lower alkyl is preferably lower alkyl that is substituted (preferably terminally) by unsubstituted or substituted heterocyclyl as defined below.

Each alkyl part of other groups like "alkoxy", "alkoxyalkyl", "alkoxyalkoxy", "alkoxycarbonyl", "alkoxy-carbonylalkyl", "alkylsulfonyl", "alkylsulfonamide", "alkylsulfinyl", "alkylamino", "halogenalkyl" shall have the same meaning as described in the above-mentioned definition of "alkyl", including the prefix 'lower', including substitutions thereof.

For example, aryl-lower alkoxy is preferably lower alkoxy that is substituted (preferably terminally on the alkyl part) by unsubstituted or substituted aryl as defined below. Aryl-lower alkoxy is especially phenyl-lower alkoxy, such as phenyl methoxy (i.e. benzoxy) or phenyl ethoxy.

Alkoxyalkoxy is, for example, methoxyethoxy, or methoxypropoxy, and may include further substitutions e.g. by aryl such as phenyl, for example to give phenylmethoxyethoxy (alternatively stated benzoxy-ethoxy) or phenylmethoxypropoxy (alternatively stated benzoxy-propoxy).

Alkandiyl is a straight-chain or branched-chain divalent alkyl group. It preferably represents a straight-chain or branched-chain $C_{1-12}$ alkandiyl, particularly preferably represents a straight-chain or branched-chain $C_{1-6}$ alkandiyl; for example, methandiyl ($-CH_2-$), 1,2-ethanediyl ($-CH_2-CH_2-$), 1,1-ethanediyl (($-CH(CH_3)-$), 1,1-, 1,2-, 1,3-propanediyl and 1,1-, 1,2-, 1,3-, 1,4-butanediyl, with particular preference given to methandiyl, 1,1-ethanediyl, 1,2-ethanediyl, 1,3-propanediyl, 1,4-butanediyl.

Alkenyl is preferably a moiety with one or more double bonds and preferably has 2-12 carbon atoms; it is linear or branched one or more times (as far as possible in view of the number of carbon atoms). Preferred is $C_2$-$C_7$alkenyl, especially $C_3$-$C_4$alkenyl, such as allyl or crotyl. For example, $-CH=CH-$, $-CH=C(CH_3)-$, $-CH=CH-CH_2-$, $-C(CH_3)=CH-CH_2-$, $-CH=C(CH_3)-CH_2-$, $-CH=CH-C(CH_3)H-$, $-CH=CH-CH=CH-$, $-C(CH_3)=CH-CH=CH-$, $-CH=C(CH_3)-CH=CH-$. Alkenyl can be unsubstituted or substituted, especially by one or more, more especially up to three of the substituents mentioned below under "substituted". Substituents, such as amino or hydroxy (with free dissociable hydrogen) preferably are not bound to carbon atoms that participate at a double bond, and also other substituents that are not sufficiently stable are preferably excluded. Unsubstituted alkenyl, in particular, $C_2$-$C_7$alkenyl is preferred.

Alkynyl is preferably a moiety with one or more triple bonds and preferably has 2-12 carbon atoms; it is linear of branched one or more times (as far as possible in view of the number of carbon atoms). Preferred is $C_2$-$C_7$alkynyl, especially $C_3$-$C_4$alkynyl, such as ethynyl or propyn-2-yl. Alkynyl can be unsubstituted or substituted, especially by one or more, more especially up to three of the substituents mentioned below under "substituted". Substituents, such as amino or hydroxy (with free dissociable hydrogen) preferably are not bound to carbon atoms that participate at a triple bond, and also other substituents that are not sufficiently stable are preferably excluded. Unsubstituted alkynyl, in particular, $C_2$-$C_7$alkynyl is preferred.

Cycloalkyl is a saturated, monocyclic, fused polycyclic, or Spiro polycyclic, carbocycle having from 3 to 12 ring atoms per carbocycle. Cycloalkyl is preferably $C_3$-$C_{10}$cycloalkyl, and includes cyclo lower alkyl, especially cyclopropyl, cyclobutyl, cyclopentyl, cyclohexyl or cycloheptyl; cycloalkyl being unsubstituted or substituted by one or more substituents, especially 1-3 substituents independently selected from the group consisting of the substituents defined below under "substituted".

Cycloalkenyl is preferably $C_5$-$C_{10}$cycloalkenyl, especially cyclopentenyl, cyclohexenyl or cycloheptenyl; cycloalkenyl being unsubstituted or substituted by one or more substituents, especially 1-3 substituents, independently selected from the group consisting of the substituents defined below under "substituted".

Aryl refers to an unsaturated carbocyclic aromatic ring system, preferably, having a ring system of not more than 16 carbon atoms, especially not more than 10 carbon atoms, e.g. having 6 to 16, preferably 6 to 10 ring carbon atoms, is preferably mono- or bi-cyclic, and is unsubstituted or substituted preferably as defined below under "substituted". For example, aryl is selected from phenyl or naphthyl, preferably phenyl, and is preferably in each case unsubstituted or substituted with substituents described under "substituted", in particular from the group consisting of halo, especially fluoro, chloro, bromo or iodo, in particular fluoro; halo-lower alkyl, especially fluoroalkyl, in particular trifluoromethyl; hydroxyl; amino, mono or disubstituted amino, especially alkyl-substituted amino, hydroxyalkyl-substituted amino or alkoxyalkyl-substituted amino, e.g. dimethyl amino, 2-hydroxyethyl amino or 2-methoxyethylamino; cyclic amino, such as aziridinyl, azetidinyl or pyrrolidinyl; amino-lower alkyl, e.g., aminomethyl, 2-aminoethyl or 3-aminopropyl; alkylamino-lower alkyl, e.g. methylaminomethyl, ethylaminomethyl, methylaminoethyl or ethylaminoethyl; dialkylamino-loweralkyl, e.g. dimethylaminomethyl, dimethylaminoethyl, methylethylaminomethyl, methylethylaminoethyl, diethylaminomethyl or diethylaminoethyl; cycloalkylaminoalkyl, e.g. cyclopropylaminomethyl, cyclopropylaminoethyl, cyclobutylaminomethyl, cyclobutylaminoethyl, cyclopentylaminomethyl or cyclopentylaminoethyl; dicycloalkylaminoalkyl, e.g. dicyclopropylaminomethyl, dicyclopropylaminoethyl, cyclopropylcyclobutylaminomethyl or cyclopropylcyclobutylaminoethyl; alkylcycloalkylaminoalkyl, e.g. cyclopropylmethylaminomethyl, cyclopropylmethylaminoethyl, cyclopropylethylaminomethyl or cyclopropylethylaminoethyl; lower alkoxy, e.g., methoxy, ethoxy or propyloxy (e.g. iso-propyloxy); hydroxy-lower alkyl, e.g., hydroxymethyl or 2-hydroxyethyl; hydroxy lower alkoxy, e.g. hydroxyethoxy; alkoxy lower alkoxy, e.g. methoxyethoxy or ethoxyethoxy; lower alkyl, e.g., methyl, ethyl or iso-propyl; cyano; cyano-lower alkyl, e.g., 2-cyanoethyl, 2-cyanopropyl, 2-cyano-2-methylpropyl or 3-cyanopropyl; amidino; N-hydroxyamidino; amidino-lower alkyl, e.g., 2-amidino-ethyl; or N-hydroxyamidino-lower alkyl, e.g., 2-(N-hydroxyamidino)-ethyl; nitro; carboxylic acid; substituted sulfonyl, e.g. alkyl-substituted sulfonyl, such as methanesulfonyl; sulfonamide, e.g. N-methylsulfonamide (or lower alkylaminosulfonyl or N,N-di-loweralkyl aminosulfonyl, e.g. methylaminosufonyl or dimethylaminosulfonyl) or pyrrolidine-1-sulfonyl; lower alkyl sulfonyl amino, e.g. methylsulfonylamino; lower alkyl sulfonylalkandiylamino, e.g. methylsulfonylmethylamino; lower alkylsulfonyl-N-lower alkylamino, e.g. methylsulfonyl-N-methylamino; acylamino, e.g. acetylamino, acyl lower alkyl amino, e.g. acetyl methyl amino; [1,3]dioxolo; substituted [1,3]dioxolo, e.g. 2,2-difluoro-[1,3]dioxolo; alkoxy carbonyl, such as lower alkoxy carbonyl, e.g. methoxycarbonyl; carbamoyl; substituted carbamoyl, such as alkyl-substituted carbamoyl, e.g. methylcarbamoyl and dimethylcarbamoyl. The aryl group may also be substituted with a substituted or unsubstituted heterocycle, preferably a 4-7 membered ring, e.g. 1H-tetrazolyl (in particular 1H-tetrazol-5-yl), pyrazol, imidazole, triazole, azetidinyl, pyrrolidinyl, piperazinyl, methylpiperazinyl, ethylpiperazinyl, triazolonyl or methylimidazolyl. The aryl group may also be substituted with heterocyclyl lower alkyl, heteroaryl or heteroaryl lower alkyl as defined hereinbelow. Preferred unsubstituted or substituted aryl is selected from phenyl; hydroxyphenyl, e.g., 2-, 3- or 4-hydroxyphenyl; methoxyphenyl, e.g., 2-, 3- or 4-methoxyphenyl or 3,4-dimethoxyphenyl; ethoxyphenyl, e.g., 2-, 3- or 4-ethoxyphenyl or 3,4-diethon/phenyl; propoxyphenyl (e.g. iso-propoxyphenyl) such as 3-propoxyphenyl (e.g. 3-iso-propoxyphenyl); methoxy ethoxy-phenyl, e.g. 3-methoxy-4-ethoxy phenyl or 4-methoxy-3-ethoxy phenyl, or other lower-alkoxy phenyl, e.g. 3-methoxy-4-(2-methoxy ethoxy)-phenyl; halo-alkoxy-phenyl, e.g. fluoro-(iso-propoxy)-phenyl, e.g. 2-fluoro-3-(iso-propoxy)-phenyl; hydroxyalkoxy phenyl, e.g. 2-hydroxyethoxy-phenyl; hydroxy alkoxy phenyl, e.g. 3-methoxy-4-hydroxy phenyl; halo-hydroxy-phenyl, e.g. fluoro-hydroxy-phenyl such as 3-fluoro-5-hydroxy-phenyl; hydroxy-haloalkyl-phenyl, e.g. hydroxy-fluoroalkyl-phenyl such as 3-hydroxy-5-trifluoromethyl-phenyl; 2,2-difluoro-benzo[1,3]dioxolo, benzene sulfonamide, e.g. 3-N-methylbenzenesulfonamide, 3-N,N-dimethylbenzenesulfonamide, 3-(pyrrolidine-1-sulfonyl)-phenyl, N-phen-3-yl-methanesulfonamide or N-methyl-N-phen-3-yl-methanesulfonamide; alkyl-sulfonyl phenyl, e.g. 3-methanesulfonylphenyl; benzamide e.g. 3- or 4-benzamide, 3- or 4-N-methyl-benzamide or 2-, 3- or 4-N,N-dimethyl-benzamide; pyrazol-phenyl, e.g. 4-pyrazol-phenyl; imidazol-phenyl, e.g. (1H-imidazol-2-yl)phenyl.

Heterocyclyl refers to a heterocyclic radical that is unsaturated (=carrying the highest possible number of conjugated double bonds in the ring(s) e.g. heteroaryl, for example pyrazolyl, pyridyl, pyrimidinyl), saturated or partially saturated in the bonding ring and is preferably a monocyclic or in a broader aspect of the invention bicyclic ring; has 3-16 ring atoms, more preferably 4-10 ring atoms, such as 6, 9 or 10 ring atoms, wherein 1-4 ring atoms, especially one or two ring atoms are a heteroatom selected from the group consisting of nitrogen, oxygen and sulfur; the bonding ring preferably having 4-12 ring atoms, especially 4-7 ring atoms, for example 6 ring atoms, For bicyclic heterocyclyl, the ring which is bonded to the rest of the molecule of formula (I) may or may not contain a heteroatom. Also, for bicyclic heterocyclyl, both rings (i.e. both the bonding ring and non-bonding ring) may contain a heteroatom.

In an embodiment, heterocyclyl refers to a heterocyclic radical that is unsaturated (=carrying the highest possible number of conjugated double bonds in the ring(s) e.g. heteroaryl, for example pyrazolyl, pyridyl, pyrimidinyl), saturated or partially saturated in the bonding ring and is preferably a monocyclic or in a broader aspect of the invention bicyclic ring; has 3-16 ring atoms, more preferably 4-10 ring atoms, wherein at least in the ring bonding to the radical of the molecule of formula (I) one or more, preferably 1-4 ring atoms, especially one or two ring atoms are a heteroatom selected from the group consisting of nitrogen, oxygen and sulfur; the bonding ring preferably having 4-12 ring atoms, especially 4-7 ring atoms, for example 6-10 ring atoms, especially for heteroaryl, such as 6, 9 or 10 ring atoms.

In an embodiment, the heterocyclyl may be unsubstituted, or substituted by one or more, especially 1-4 substituents independently selected from the group consisting of the substituents defined below under "substituted"; especially being a heterocyclyl radical selected from the group consisting of oxiranyl, azirinyl, 1,2-oxathiolanyl, imidazolyl, thienyl, furyl, tetrahydrofuryl, tetrahydrothiophene, indolyl, 1-methyl-2,3-dihydro-1H-indolyl, 2,3-dihydro-1H-indolyl, 2-oxo-2,3-dihydro-1H-indolyl, azetidinyl, pyranyl, thiopyranyl, isobenzofuranyl, benzofuranyl, chromenyl, 2H-pyrrolyl, pyrrolyl, pyrrolinyl, pyrrolidinyl, imidazolyl, imidazolidinyl, benzimidazolyl, pyrazolyl, pyrazolidinyl, thiazolyl, isothiazolyl, dithiazolyl, oxazolyl, isoxazolyl, pyridyl, pyrazinyl, pyrimidinyl, piperidyl, piperazinyl, pyridazinyl, morpholinyl, thiomorpholinyl, indolizinyl, isoindolyl, 3H-indolyl, cumaryl, indazolyl, triazolyl, tetrazolyl, purinyl, 4H-quinolizinyl, isoquinolyl, quinolyl, tetrahydroquinolyl, tetrahydroisoquinolyl, decahydroquinolyl, octahydroisoquinolyl, benzofuranyl, dibenzofuranyl, benzothiophenyl, phthalazinyl, naphthyridinyl, 1H-pyrrolo[2,3-b]pyridinyl, quinoxalyl, quinazolinyl, quinazolinyl, cinnolinyl, pteridinyl, furazanyl, chromenyl, isochromanyl, chromanyl, 2-oxo-2,3-dihydro-1H-imidazo[4,5-b]pyridinyl (also termed 1H-imidazo[4,5-b] pyridin-2(3H)-one-6-yl), 1,3-Dimethyl-2-oxo-2,3-dihydro-1H-imidazo[4,5-b]pyridinyl (also termed 1,3-dimethyl-1H-imidazo[4,5-b]pyridin-2(3H)-oneyl), 1-ethyl-3-methyl-2-oxo-2,3-dihydro-1H-imidazo[4,5-b]pyridinyl (also termed 1-ethyl-3-methyl-1H-imidazo[4,5-b]pyridin-2(3H)-one-6-yl), 1-(2-methoxy-ethyl)-3-methyl-2-oxo-2,3-dihydro-1H-imidazo[4,5-b]pyridinyl (also termed 1-(2-methoxyethyl)-3-methyl-1H-imidazo[4,5-b]pyridin-2(3H)-one-6-yl), 3H-imidazo[4,5-b]pyridinyl, 3-methyl-3H-imidazo[4,5-b] pyridinyl, 2,3-Dimethyl-3H-imidazo[4,5-b]pyridinyl, 2-methoxy-3-methyl-3H-imidazo[4,5-b]pyridinyl, 2-Dimethylamino-3-methyl-3H-imidazo[4,5-b]pyridinyl, 3H-[1,2,3]triazolo[4,5-b]pyridinyl, 3-methyl-3H-[1,2,3]triazolo[4,5-b]pyridinyl, 1H-pyrrolo[3,2-b]pyridinyl, 1-methyl-1H-pyrrolo[3,2-b]pyridinyl, 1-methyl-1H-pyrrolo[2,3-b] pyridinyl, 2-oxo-1,4-dihydro-2H-pyrido[2,3-d][1,3] oxazinyl, 1-methyl-2-oxo-1,4-dihydro-2H-pyrido[2,3-d][1,3]oxazinyl, 3,4-dihydro-2H-pyrido[3,2-b][1,4]oxazinyl, 4-methyl-3,4-dihydro-2H-pyrido[3,2-b][1,4]oxazinyl, 2-oxo-2,3-dihydro-1H-pyrrolo[2,3-b]pyridinyl, 1,3,3-trimethyl-2-oxo-2,3-dihydro-1H-pyrrolo[2,3-b]pyridinyl, 2-oxo-1,4-dihydro-2H-pyrido[3,2-d][1,3]oxazinyl and 1-ethyl-2-oxo-1,4-dihydro-2H-pyrido[3,2-d][1,3]oxazinyl; each of these heterocycle radicals being unsubstituted or substituted by one to two radicals selected from the substituents described under "substituted", in particular from the group consisting of halo, especially fluoro, chloro, bromo or iodo, more especially fluoro or chloro, in particular fluoro; halo-lower alkyl, especially fluoroalkyl, in particular trifluoromethyl; hydroxyl; amino, mono or disubstituted amino, especially alkyl-substituted amino, hydroxyalkyl-substituted amino or alkoxyalkyl-substituted amino, e.g. dimethyl amino, 2-hydroxyethyl amino or 2-methoxyethyl amino; cyclic amino, such as aziridinyl, azetidinyl or pyrrolidinyl; substituted cyclic amino, e.g. hydroxy cyclic amino; amino-lower alkyl, e.g., aminomethyl, 2-aminoethyl or 3-aminopropyl; alkylamino-lower alkyl, e.g. methylaminomethyl, ethylaminomethyl, methylaminoethyl or ethylaminoethyl; dialkylamino-loweralkyl, e.g. dimethylaminomethyl, dimethylaminoethyl, methylethylaminomethyl, methylethylaminoethyl, diethylaminomethyl or diethylaminoethyl; cycloalkylaminoalkyl, e.g. cyclopropylaminomethyl, cyclopropylaminoethyl, cyclobutylaminomethyl, cyclobutylaminoethyl, cyclopentylaminomethyl or cyclopentylaminoethyl; dicycloalkylaminoalkyl, e.g. dicyclopropylaminomethyl, dicyclopropylaminoethyl, cyclopropylcyclobutylaminomethyl or cyclopropylcyclobutylaminoethyl; alkylcycloalkylaminoalkyl, e.g. cyclopropylmethylaminomethyl, cyclopropylmethylaminoethyl, cyclopropylethylaminomethyl or cyclopropylethylaminoethyl; lower alkoxy, e.g., methoxy, ethoxy or propyloxy; cycloalkoxy, e.g. cyclobutoxy; lower-alkoxyalkyl, e.g. methoxymethyl, methoxypropyl, ethoxypropyl; hydroxy-lower alkyl, e.g., hydroxymethyl or 2-hydroxyethyl; hydroxy lower cycloalkyl, e.g. hydroxy cyclopentyl; hydroxy lower alkoxy, e.g. hydroxyethoxy; alkoxy lower alkoxy, e.g. methoxyethoxy or ethoxyethoxy; lower alkyl, e.g., methyl, ethyl or iso-propyl; cyano; cyano-lower alkyl, e.g., 2-cyanoethyl, 2-cyanopropyl, 2-cyano-2-methylpropyl or 3-cyanopropyl; cyano lower cycloalkyl, e.g cyano cyclobutyl; amidino; N-hydroxyamidino; amidino-lower alkyl, e.g., 2-amidino-ethyl; or N-hydroxyamidino-lower alkyl, e.g., 2-(N-hydroxyamidino)-ethyl; nitro; carboxylic acid; substituted sulfonyl, e.g. alkyl-substituted sulfonyl, such as methanesulfonyl; sulfonamide, e.g. N-methylsulfonamide or pyrrolidine-1-sulfonyl; alkylsulfonylamino, e.g. methylsulfonylamino; alkylsulfonylalkylamino, e.g. methylsulfonylmethylamino; acylamino (also termed alkyl carbonyl amino), e.g. acetylamino; acyl alkyl amino, e.g. acetyl methyl amino; alkylcarbonylaminoalkyl, e.g. methylcarbonylaminomethyl; alkylaminocarbonylalkyl e.g. methylaminocarbonylmethyl; alkylcarbonyl-N-alkylamino, e.g. methylcarbonyl-N-methylamino; [1,3]dioxolo; substituted [1,3]dioxolo, e.g. 2,2-difluoro-[1,3]dioxolo; alkoxy carbonyl, such as lower alkoxy carbonyl, e.g. methoxycarbonyl; carbamoyl (also termed aminocarbonyl); substituted carbamoyl, such as alkyl-substituted carbamoyl, e.g. methylcarbamoyl, ethyl carbamoyl, iso-propyl carbamoyl or alkoxyalkyl-substituted carbamoyl (also termed alkoxyalkylaminocarbonyl), e.g. 2-methoxyethylcarbamoyl. The heterocycle group may also be substituted with another substituted or unsubstituted heterocycle, preferably a 4-7 membered ring, e.g. 1H-tetrazolyl (in particular 1H-tetrazol-5-yl), pyrazol, imidazole, triazole, azetidinyl, pyrrolidinyl, piperazinyl, methylpiperazinyl, ethylpiperazinyl, triazolonyl, methylimidazolyl or morpholino. The heterocycle group may also be substituted with heterocyclyl lower alkyl, heteroaryl or heteroaryl lower alkyl as defined herein.

In another embodiment, the heterocyclyl may be unsubstituted, or substituted by one or more, especially 1-4 substituents independently selected from the group consisting of the substituents defined below under "substituted"; especially being a heterocyclyl radical selected from the group consisting of oxiranyl, azirinyl, 1,2-oxathiolanyl, imidazolyl, thienyl, furyl, tetrahydrofuryl, tetrahydrothiophene, indolyl, 1-methyl-2,3-dihydro-1H-indolyl, 2-oxo-2,3-dihydro-1H-indolyl, azetidinyl, pyranyl, thiopyranyl, isobenzofuranyl, benzofuranyl, chromenyl, 2H-pyrrolyl, pyrrolyl, pyrrolinyl, pyrrolidinyl, imidazolyl, imidazolidinyl, benzimidazolyl, pyrazolyl, pyrazolidinyl, thiazolyl, isothiazolyl, dithiazolyl, oxazolyl, isoxazolyl, pyridyl, pyrazinyl, pyrimidinyl, piperidyl, piperazinyl, pyridazinyl, morpholinyl, thiomorpholinyl, indolizinyl, isoindolyl, 3H-indolyl, cumaryl, indazolyl, triazolyl, tetrazolyl, purinyl, 4H-quinolizinyl, isoquinolyl, quinolyl, tetrahydroquinolyl, tetrahydroisoquinolyl, decahydroquinolyl, octahydroisoquinolyl, benzofuranyl, dibenzofuranyl, benzothiophenyl, phthalazinyl, naphthyridinyl, 1H-pyrrolo[2,3-b]pyridinyl, quinoxalyl, quinazolinyl, quinazolinyl, cinnolinyl, pteridinyl, furazanyl, chromenyl, isochromanyl and chromanyl and; each of these heterocycle radicals being unsubstituted or substituted by one to two radicals selected from the substituents described under "substituted", in particular from the group consisting of halo, especially fluoro, chloro, bromo or iodo, more especially fluoro or chloro, in particular fluoro; halo-lower alkyl, especially fluoroalkyl, in particular trifluoromethyl; hydroxyl; amino, mono or disubstituted amino, especially alkyl-substituted amino, hydroxyalkyl-substituted amino or alkoxyalkyl-substituted amino, e.g. dimethyl amino, 2-hydroxyethyl amino or 2-methoxyethyl amino; cyclic amino, such as azidinyl, azetidinyl or pyrrolidinyl; amino-lower alkyl, e.g., aminomethyl, 2-aminoethyl or 3-aminopropyl; alkylamino-lower alkyl, e.g. methylaminomethyl, ethylaminomethyl, methylaminoethyl or ethylaminoethyl; dialkylamino-lower-alkyl, e.g. dimethylaminomethyl, dimethylaminoethyl, methylethylaminomethyl, methylethylaminoethyl, diethylaminomethyl or diethylaminoethyl; cycloalkylaminoalkyl, e.g. cyclopropylaminomethyl, cyclopropylaminoethyl, cyclobutylaminomethyl, cyclobutylaminoethyl, cyclopentylaminomethyl or cyclopentylaminoethyl; dicycloalkylaminoalkyl, e.g. dicyclopropylaminomethyl, dicyclopropylaminoethyl, cyclopropylcyclobutylaminomethyl or cyclopropylcyclobutylaminoethyl; alkylcycloalkylaminoalkyl, e.g. cyclopropylmethylaminomethyl, cyclopropylmethylaminoethyl, cyclopropylethylaminomethyl or cyclopropylethylaminoethyl; lower alkoxy, e.g., methoxy, ethoxy or propyloxy; hydroxy-lower alkyl, e.g., hydroxymethyl or 2-hydroxyethyl; hydroxy lower alkoxy, e.g. hydroxyethoxy; alkoxy lower alkoxy, e.g. methoxyethoxy or ethoxyethoxy; lower alkyl, e.g., methyl, ethyl or iso-propyl; cyano; cyano-lower alkyl, e.g., 2-cyanoethyl, 2-cyanopropyl, 2-cyano-2-methylpropyl or 3-cyanopropyl; amidino; N-hydroxyamidino; amidino-lower alkyl, e.g., 2-amidino-ethyl; or N-hydroxyamidino-lower alkyl, e.g., 2-(N-hydroxyamidino)-ethyl; nitro; carboxylic acid; substituted sulfonyl, e.g. alkyl-substituted sulfonyl, such as methanesulfonyl; sulfonamide, e.g. N-methylsulfonamide or pyrrolidine-1-sulfonyl; alkylsulfonylamino, e.g. methylsulfonylamino; alkylsulfonylalkylamino, e.g. methylsulfonylmethylamino; acylamino, e.g. acetylamino; acyl alkyl amino, e.g. acetyl methyl amino; [1,3]dioxolo; substituted [1,3]dioxolo, e.g. 2,2-difluoro-[1,3]dioxolo; alkoxy carbonyl, such as lower alkoxy carbonyl, e.g. methoxycarbonyl; carbamoyl; substituted carbamoyl, such as alkyl-substituted carbamoyl, e.g. methylcarbamoyl. The heterocycle group may also be substituted with another substituted or unsubstituted heterocycle, preferably a 4-7 membered ring, e.g. 1H-tetrazolyl (in particular 1H-tetrazol-5-yl), pyrazol, imidazole, triazole, azetidinyl, pyrrolidinyl, piperazinyl, methylpiperazinyl, ethylpiperazinyl, triazolonyl or methylimidazolyl. The heterocycle group may also be substituted with heterocyclyl lower alkyl, heteroaryl or heteroaryl lower alkyl as defined herein.

In an embodiment, very preferred heterocyclic groups, which may be substituted or unsubstituted, include indolyl, 1-methyl-2,3-dihydro-1H-indolyl, 2-oxo-2,3-dihydro-1H-indolyl, pyridyl, pyrimidinyl, 1H-pyrrolo[2,3-b]pyridinyl, 1-methyl-1H-pyrrolo[2,3-b]pyridinyl, pyrazolyl, pyrazinyl, quinolyl, quinoxalyl, 1,3-Dimethyl-2-oxo-2,3-dihydro-1H-imidazo[4,5-b]pyridinyl, 2-oxo-2,3-dihydro-1H-imidazo[4,5-b]pyridinyl, 1-ethyl-3-methyl-2-oxo-2,3-dihydro-1H-imidazo[4,5-b]pyridinyl, 1-(2-methoxy-ethyl)-3-methyl-2-oxo-2,3-dihydro-1H-imidazo[4,5-b]pyridinyl, 2-Dimethylamino-3-methyl-3H-imidazo[4,5-b]pyridinyl, 2-methoxy-3-methyl-3H-imidazo[4,5-b]pyridinyl, 3H-imidazo[4,5-b]pyridinyl, 3-methyl-3H-[1,2,3]triazolo[4,5-b]pyridinyl, 3H-[1,2,3]triazolo[4,5-b]pyridinyl, 2,3-Dimethyl-3H-imidazo[4,5-b]pyridinyl, 3-methyl-3H-imidazo[4,5-b]pyridinyl, 1H-pyrrolo[3,2-b]pyridinyl, 1-methyl-1H-pyrrolo[3,2-b]pyridinyl, 1-methyl-2-oxo-1,4-dihydro-2H-pyrido[2,3-d][1,3]oxazinyl, 2-oxo-1,4-dihydro-2H-pyrido[2,3-d][1,3]oxazinyl, 4-methyl-3,4-dihydro-2H-pyrido[3,2-b][1,4]oxazinyl, 3,4-dihydro-2H-pyrido[3,2-b][1,4]oxazinyl, 1,3,3-trimethyl-2-oxo-2,3-dihydro-1H-pyrrolo[2,3-b]pyridinyl, 2-oxo-2,3-dihydro-1H-pyrrolo[2,3-b]pyridinyl, 1-ethyl-2-oxo-1,4-dihydro-2H-pyrido[3,2-d][1,3]oxazinyl, and 2-oxo-1,4-dihydro-2H-pyrido[3,2-d][1,3]oxazinyl each of which may be unsubstituted or substituted.

In an further embodiment, very preferred heterocyclic groups, each of which may be substituted or unsubstituted, include 1-methyl-2,3-dihydro-1H-indolyl, 2-oxo-2,3-dihydro-1H-indolyl, pyridyl, pyrimidinyl, 1H-pyrrolo[2,3-b]pyridinyl, 1-methyl-1H-pyrrolo[2,3-b]pyridinyl, pyrazolyl, pyrazinyl, quinolyl, 1,3-Dimethyl-2-oxo-2,3-dihydro-1H-imidazo[4,5-b]pyridinyl, 2-oxo-2,3-dihydro-1H-imidazo[4,5-b]pyridinyl, 1-ethyl-3-methyl-2-oxo-2,3-dihydro-1H-imidazo[4,5-b]pyridinyl, 1-(2-methoxy-ethyl)-3-methyl-2-oxo-2,3-dihydro-1H-imidazo[4,5-b]pyridinyl, 2-Dimethylamino-3-methyl-3H-imidazo[4,5-b]pyridinyl, 2-methoxy-3-methyl-3H-imidazo[4,5-b]pyridinyl, 3H-imidazo[4,5-b]pyridinyl, 3-methyl-3H-[1,2,3]triazolo[4,5-b]pyridinyl, 3H-[1,2,3]triazolo[4,5-b]pyridinyl, 2,3-Dimethyl-3H-imidazo[4,5-b]pyridinyl, 3-methyl-3H-imidazo[4,5-b]pyridinyl, 1H-pyrrolo[3,2-b]pyridinyl, 1-methyl-1H-pyrrolo[3,2-b]pyridinyl, 1-methyl-2-oxo-1,4-dihydro-2H-pyrido[2,3-d][1,3]oxazinyl, 2-oxo-1,4-dihydro-2H-pyrido[2,3-d][1,3]oxazinyl, 4-methyl-3,4-dihydro-2H-pyrido[3,2-b][1,4]oxazinyl, 3,4-dihydro-2H-pyrido[3,2-b][1,4]oxazinyl, 1,3,3-trimethyl-2-oxo-2,3-dihydro-1H-pyrrolo[2,3-b]pyridinyl, 2-oxo-2,3-dihydro-1H-pyrrolo[2,3-b]pyridinyl, 1-ethyl-2-oxo-1,4-dihydro-2H-pyrido[3,2-d][1,3]oxazinyl, and 2-oxo-1,4-dihydro-2H-pyrido[3,2-d][1,3]oxazinyl.

In another embodiment, heterocyclic groups, which may be substituted or unsubstituted, include indolyl, 1-methyl-2,3-dihydro-1H-indolyl, 2-oxo-2,3-dihydro-1H-indolyl, pyridyl, pyrimidinyl, 1H-pyrrolo[2,3-b]pyridinyl, 1-methyl-1H-pyrrolo[2,3-b]pyridinyl, pyrazolyl, pyrazinyl, quinolyl, quinoxalyl, each of which may be unsubstituted or substituted.

In an embodiment, unsubstituted or substituted heterocyclyl is selected from pyridyl; alkylpyridyl, in particular lower-alkylpyridyl, e.g. methylpyridyl, e.g., 2-, 3- or 4-methylpyridyl, especially 2-methylpyridyl or 3-methylpyridyl; alkoxypyridyl, in particular lower-alkoxypyridyl, e.g. methyoxpyridyl, e.g., 2-, 3- or 4-methoxypyridyl, especially 2-methoxypyridyl or 3-methoxypyridyl or di-methoxypyridyl, e.g. 2,3-dimethoxypyridyl, or ethoxypyridyl, e.g., 2-, 3- or 4-ethoxypyridyl especially 2-ethoxypyridyl or 3-ethoxypyridyl or di-ethoxypyridyl e.g. 2,3-diethoxypyridyl, or propyloxypyridyl, e.g., 2- or 3-propyloxypyridyl or isopropyloxypyridyl, e.g., 2- or 3-isopropyloxypyridyl; cycloalkyloxypyridyl, e.g. 2- or 3-cyclobutyloxypyridyl; (haloalkoxy)pyridyl e.g. 3(1,3-difluoropropan-2-yloxy)-pyridyl or 3-(2-fluoroethan-1-yloxy)-pyridyl or 3-(difluoromethyloxy)-pyridyl; cycloalkylalkoxypyridyl, e.g. cyclopropylmethoxy-pyridyl, e.g. 2 or 3-cyclopropylmethoxy-pyridyl; alkoxyalkylpyridyl, e.g. methoxymethylpyridyl, e.g. 2 or 3-methoxymethylpyridyl or ethoxymethylpyridyl or 2-methoxy-prop-2-yl or 2-ethoxy-prop-2-yl; alkoxyalkoxypyridyl, in particular methoxyethoxypyridyl, e.g. 2 or 3-methoxyethoxypyridyl; (alkyl)(alkoxyalkoxy)pyridyl, e.g. (methyl)(methoxyethoxy)pyridyl; benzyloxyalkoxypyridyl, in particular benzyloxyethoxypyridyl or benzyloxypropoxypyridyl, e.g. 2-benzyloxyethoxypyridyl or 3-benzyloxypropoxypyridyl; hydroxyalkylpyridyl, e.g. 2 or 3(2-hydroxyethyl)-pyridyl or hydroxypentylpyridyl e.g. 3(3-hydroxypentyl)-pyridyl or hydroxypropylridyl, e.g. 3(2-hydroxyprop-2-yl)-pyridyl or hydroxy-1,1-dimethyl-ethylpyridyl; hydroxycycloalkylpyridyl, e.g. 3-(1-hydroxycyclopentyl)-pyridyl; hydroxyfluoroalkylpyridyl, e.g. hydroxyfluoropropylpyridyl; aminoalkylpyridyl, e.g. aminomethylpyridyl; alkyl-sulfonyl pyridyl, e.g. methanesulfonylpyridyl, especially 3-methanesulfonylpyridyl; hydroxyalkoxypyridyl, e.g. 2-(2-hydroxyethoxy)-pyridyl or 2-(3-hydroxypropoxy)-pyridyl; hydroxyalkylpyridyl, e.g.

hydroxymethylpyridyl, especially 2-(hydroxymethyl)-pyridyl; alkoxycarbonylpyridyl, e.g. methoxycarbonylpyridyl, especially 2-methoxycarbonyl-pyridyl; aminopyridyl, e.g. 2- or 3-aminopyridyl; alkylaminopyridyl, in particular lower alkylaminopyridyl, e.g. 2-, 3- or 4-methylaminopyridyl, especially 2- or 3-methylaminopyridyl, 2-, 3- or 4-ethylaminopyridyl, especially 2- or 3-ethylaminopyridyl, e.g. 2- or 3-(1- or 2-propyl)aminopyridyl; dialkylaminopyridyl, in particular di-loweralkylaminopyridyl, e.g. 2-, 3- or 4-dimethylaminopyridyl, especially 2-dimethylaminopyridyl or 2-, 3- or 4-diethylaminopyridyl, especially 2- or 3-diethylaminopyridyl or e.g. 2-, 3- or 4-ethylmethylaminopyridyl especially 2-ethylmethylaminopyridyl or 3-ethylmethylaminpyridyl or e.g. 2-, 3- or 4-isopropylmethylaminopyridyl, especially 2-isopropylmethylaminopyridyl or 3-isopropylmethylaminopyridyl; cycloalkylaminopyridyl, e.g. cyclobutylaminopyridyl; (N-alkyl-N-cycloalkylamino)pyridyl, e.g. (N-methyl-N-cyclobutyalmino)pyridyl; (alkyl)(amino)pyridyl, e.g. (loweralkyl)(amino)pyridyl, in particular (methyl)(amino) pyridyl such as 2-methyl-3-amino-pyridyl or (ethyl)(amino) pyridyl such as 2-ethyl-3-amino-pyridyl; (halo)(amino)pyridyl, e.g. (fluoro)(amino)pyridyl or (chloro)(amino)pyridyl; (halo)(alkylamino)pyridyl, e.g. (fluoro)(methylamino)pyridyl, (fluoro)(ethylamino)pyridyl; (halo)(dialkylamino)pyridyl, e.g. (fluoro)(dimethylamino)pyridyl; (halo)(hydroxyalkyl)pyridyl, e.g. (chloro)(hydroxymethyl)pyridyl; (alkoxy)(alkyl)pyridyl e.g. (methoxy)(methyl)pyridyl or (ethoxy)(methyl)pyridyl, or (propoxy)(methyl)pyridyl or (propoxy)(ethyl)pyridyl or (ethoxy)(ethyl)pyridyl; (alkoxy)(alkoxy)pyridyl e.g. (propoxy)(methoxy)pyridyl or (propoxy)(ethoxy)pyridyl or (methoxy)(methoxy)pyridyl or (ethoxy)(methoxy)pyridyl; (alkoxy)(alkoxyalkyl)pyridyl e.g. (isopropoxy)(methoxymethyl)pyridyl or (methoxy)(methoxymethyl)pyridyl or (methoxy)(ethoxymethyl)pyridyl or (ethoxy)(methoxymethyl)pyridyl; (alkoxy)(deuteroalkoxyalkyl)pyridyl e.g. (ethoxy)(trideuteromethoxymethyl)pyridyl; (alkoxy)(hydroxyalkyl)pyridyl e.g. (isopropoxy)(hydroxymethyl)pyridyl or (methoxy)(hydroxymethyl)pyridyl, such as 3-methoxy-2-hydroxymethyl-pyridyl or 2-methoxy-3-hydroxymethyl-pyridyl or (ethoxy)(hydroxymethyl)pyridyl, such as 3-ethoxy-2-hydroxymethyl-pyridyl; (haloalkoxy)(alkyl)pyridyl e.g. (halo-isopropoxy)(methyl) pyridyl, such as 3-(1,3-difluoropropan-2-yloxy)-2-(methyl)-pyridyl; (haloalkoxy)(hydroxyalkyl)pyridyl e.g. 3-(1,3-difluoropropan-2-yloxy)-2-(hydroxymethyl)-pyridyl; (alkoxyalkoxy)(hydroxyalkyl)pyridyl, e.g. (methoxyethoxy)(hydroxymethyl)pyridyl, such as 3-methoxyethoxy-2-hydroxymethyl-pyridyl (in particular 3-methoxyethoxy-2-hydroxymethyl-pyrid-5-yl); (alkyl)(alkylamino)pyridyl, e.g. (methyl)(ethylamino)pyridyl such as 2-methyl-3-ethylamino-pyridyl or (methyl)(methylamino)pyridyl such as 3-methyl-2-methylamino-pyridyl or (ethyl)(ethylamino)pyridyl such as 2-ethyl-3-ethylamino-pyridyl or (ethyl)(isopropylamino)pyridyl such as 2-ethyl-3-isopropylamino-pyridyl; (alkyl)(di-alkylamino)pyridyl, e.g. (methyl)(N-methyl-N-ethylamino)pyridyl such as 2-methyl-3-(N-methyl-N-ethylamino)-pyridyl or (methyl)(N,N-dimethylamino)pyridyl such as 2-methyl-3-(N,N-dimethylamino)-pyridyl; cycloaminopyridyl, e.g. azetidinylpyridyl, especially 2-azetidin-1-yl-pyridyl or pyrrolidinylpyridyl, especially 2-pyrrolidin-2-ylpyridyl; cyclic ether-substituted amino-pyridyl, e.g. tetrahydro-pyranylamino-pyridyl; hydroxy-cycloaminopyridyl, e.g. hydroxy-pyrrolidinylpyridyl; loweralkoxy-cycloaminopyridyl, e.g. methoxy-pyrrolidinylpyridyl; hydroxyalkylaminopyridyl, e.g. 2-(2-hydroxyethylamino)-pyridyl; (alkyl)(hydroxy)pyridyl, e.g. 2-(methyl)-3-(hydroxy)-pyridyl or 2-(ethyl)-3-(hydroxy)-pyridyl; (hydroxyalkyl)(alkylamino)pyridyl, e.g. (hydroxymethyl)(ethylamino)-pyridyl, e.g. or (hydroxymethyl)(methylamino)-pyridyl; (hydroxyalkyl)(amino)pyridyl, e.g. (hydroxymethyl)(amino)-pyridyl; (alkoxyalkyl)(alkylamino)pyridyl, e.g. (methoxymethyl)(ethylamino)-pyridyl, or (methoxymethyl)(methylamino)-pyridyl, or (ethoxmethyl)(ethylamino)-pyridyl; (alkoxyalkyl)(amino)pyridyl, e.g. (ethoxymethyl)(amino)-pyridyl, or (methoxymethyl)(amino)-pyridyl; amino-haloloweralkyl-pyridyl, e.g. amino-trifluoromethyl-pyridyl, especially 2-amino-3-trifluoromethyl-pyridyl; alkylamino-haloalkyl-pyridyl, e.g. methylamino-trifluoromethyl-pyridyl or e.g. ethylamino-trifluoromethyl-pyridyl; haloalkyl-deuteroloweralkylamino-pyridyl, e.g. trifluoromethyl-trideuteromethylamino-pyridyl; haloalkylpyridinyl, in particular haloloweralkylpyridyl, especially, 2-, 3- or 4-trifluoromethylpyridyl, most especially 2-trifluoromethylpyridyl; cyanoalkylpyridinyl, e.g. cyanopropylpyridyl; cyanocycloalkylpyridinyl, e.g. cyanocyclobutylpyridyl; halopyridyl, in particular fluoropyridyl, especially 2-fluoropyridyl; halo-alkoxy-pyridyl, e.g. fluoro-methoxy-pyridyl such as 3-fluoro-2-methoxy-pyridyl; carbamoylpyridyl, especially 2-(carbamoyl)pyridyl; alkyl-substituted carbamoyl, e.g. methylcarbamoyl, especially 2-(methylcarbamoyl)pyridyl; piperazinylpyridyl, e.g. 1-piperazinylpyridyl; N-alkylpiperazinylpyridyl, e.g. N-methylpiperazinylpyridyl; alkylsulfonamidopyridyl, e.g. methylsulfonamidopyridyl; dialkylsulfonamidopyridyl, e.g. dimethylsulfonamidopyridyl; (alkylsulfonamido)(alkyl)pyridyl e.g. (methylsutfonamido)(methyl)pyridyl; (alkylsulfonamido)(halo)pyridyl e.g. (methylsulfonamido)(chloro) pyridyl; (alkylsulfonamidoalkyl)pyridyl e.g. (methylsulfonamidomethyl)pyridyl; dialkylsulfonamido (alkyl)pyridyl, e.g. dimethylsulfonamido(methyl)pyridyl; 3H-tetrazol-5-yl pyridyl, e.g. 2-(3H-tetrazol-5-yl)pyridyl (in particular 2-(3H-tetrazol-5-yl)pyrid-5-yl); alkylcarbonylaminoalkylpyridyl, e.g. methylcarbonylaminomethylpyridyl; (halo)(alkylcarbonylamino)pyridyl, e.g. (chloro)(methylcarbonylamino)pyridyl; (alkoxy)(alkylcarbonylamino) pyridyl, e.g. (methoxy)(methylcarbonylamino)pyridyl or (ethoxy)(methylcarbonylamino)pyridyl; (alkoxy)(alkylcarbonyl-N-alkylamino)pyridyl, e.g. (methoxy)(methylcarbonyl-N-methylamino)pyridyl or (ethoxy)(methylcarbonyl-N-methylamino)pyridyl; (alkoxy)(nitro)pyridyl, e.g. (methoxy)(nitro)pyridyl; (alkoxy)(cyano)pyridyl, e.g. (methoxy)(cyano)pyridyl; (alkoxy)(amino)pyridyl, e.g. (methoxy)(amino)pyridyl; (alkoxy)(alkylamino)pyridyl, e.g. (methoxy)(ethylamino)pyridyl; (alkoxyalkyl)(alkylamino) pyridyl, e.g. (methoxymethyl)(methylamino)pyridyl, or (methoxymethyl)(ethylamino)pyridyl; (alkoxy)(alkylaminocarbonyl)pyridyl, e.g. (methoxy)(methylaminocarbonyl) pyridyl; alkylaminocarbonylalkylpyridyl, e.g. methylaminocarbonylmethylpyridyl; (amino)(alkylaminocarbonyl) pyridyl, e.g. (amino)(methylaminocarbonyl)pyridyl, or (amino)(ethylaminocarbonyl)pyridyl or (amino)(isopropylaminocarbonyl)pyridyl; (amino)(alkoxyalkylaminocarbonyl)pyridyl, e.g. (amino)(methoxyethylaminocarbonyl)pyridyl; (alkylamino)(alkylaminocarbonyl)pyridyl, e.g. (methylamino)(ethylaminocarbonyl)pyridyl; (alkoxy)(aminocarbonyl)pyridyl, e.g. (methoxy)(aminocarbonyl)pyridyl; (alkoxy)(hydroxycarbonyl)pyridyl, e.g. (methoxy)(hydroxycarbonyl)pyridyl; morpholinylpyridinyl, e.g. morpholin-4-ylpyridinyl; (1H-pyrazolyl)-pyridinyl, e.g. (1H-pyrazol-1yl)-pyridinyl; loweralkyl substituted (1H-imidazol-1-yl)-pyridinyl, e.g. methyl-substituted (1H-imidazol-1-yl)-pyridinyl; pyrimidinyl; loweralkylaminopyrimidinyl, e.g. 2- or 4-methylaminopyrimidinyl or 2- or 4-ethylaminopyrimidinyl; di-loweralkylaminopyrimidinyl, e.g. 2- or 4-methylethylaminopyrimidinyl, 2- or 4-dimethylaminopyrimidinyl, especially 2-dimethylaminopyrimidinyl; alkoxypyrimidinyl, in particular methoxypyrimidinyl or ethoxypyrimidinyl, e.g. 2-methoxypyrimidinyl or 2-ethoxypyrimidinyl; di-alkoxypyrimidinyl, e.g. 2,4-dimethoxypyrimidinyl; (alkylamino)(alkoxy)pyrimidinyl, e.g. (methylamino)(methoxy)pyrimidinyl or (ethylamino)(methoxy)pyrimidinyl; cycloaminopyrimidinyl, e.g. pyrrolidinylpyrimidinyl; aminopyrimidinyl, in particular 2-aminopyrimidinyl; alkylaminopyrimidinyl, e.g. 2-methylaminopyrimidinyl; dialkylaminopyrimidinyl, e.g. 2-dimethylaminopyrimidinyl; 1H-pyrrolo[2,3-b]pyridinyl; 1-methyl-1H-pyrrolo[2,3-b]pyridinyl; pyrazinyl; pyrazolyl; substituted pyrazolyl, e.g. hydroxyalkylpyrazolyl, especially 1-(2-hydroxy-ethyl)-1H-pyrazolyl or 1-[2-(tetrahydro-pyran-2-yloxy)-ethyl]-1H-pyrazolyl; quinolinyl; 2-oxo-2,3-dihydro-1H-indol-5-yl; 1-methyl-2,3-dihydro-1H-indol-5-yl; 1,3-Dimethyl-2-oxo-2,3-dihydro-1H-imidazo[4,5-b]pyridinyl, 1-ethyl-3-methyl-2-oxo-2,3-dihydro-1H-imidazo[4,5-b]pyridinyl, 1-(2-methoxy-ethyl)-3-methyl-2-oxo-2,3-dihydro-1H-imidazo[4,5-b]pyridinyl, 2-Dimethylamino-3-methyl-3H-imidazo[4,5-b]pyridinyl, 2-methoxy-3-methyl-3H-imidazo[4,5-b]pyridinyl, 3-methyl-3H-[1,2,3]triazolo[4,5-b]pyridinyl, 2,3-Dimethyl-3H-imidazo[4,5-b]pyridinyl, 3-methyl-3H-imidazo[4,5-b]pyridinyl, 1H-pyrrolo[3,2-b]pyridinyl, 1-methyl-1H-pyrrolo[3,2-b]pyridinyl, 1-methyl-2-oxo-1,4-dihydro-2H-pyrido[2,3-d][1,3]oxazinyl, 4-methyl-3,4-dihydro-2H-pyrido[3,2-b][1,4]oxazinyl, 1,3,3-trimethyl-2-oxo-2,3-dihydro-1H-pyrrolo[2,3-b]pyridinyl, and 1-ethyl-2-oxo-1,4-dihydro-2H-pyrido[3,2-d][1,3]oxazinyl.

In another embodiment, unsubstituted or substituted heterocyclyl is selected from pyridyl; alkylpyridyl, in particular lower-alkylpyridyl, e.g. methylpyridyl, e.g., 2-, 3- or 4-methylpyridyl, especially 2-methylpyridyl or 3-methylpyridyl; alkoxypyridyl, in particular lower-alkoxypyridyl, e.g. methoxypyridyl, e.g., 2-, 3- or 4-methoxypyridyl, especially 2-methoxypyridyl or 3-methoxypyridyl or di-methoxypyridyl, e.g. 2,3-dimethoxypyridyl, or ethoxypyridyl, e.g., 2-, 3- or 4-ethoxypyridyl especially 2-ethoxypyridyl or 3-ethoxypyridyl or di-ethoxypyridyl e.g. 2,3-diethoxypyridyl, or propyloxypyridyl, e.g., 2- or 3-propyloxypyridyl or isopropyloxypyridyl, e.g., 2- or 3-isopropyloxypyridyl; cycloalkyloxypyridyl, e.g. 2- or 3-cyclobutyloxypyridyl; cycloalkylalkoxypyridyl, e.g. cyclopropylmethoxy-pyridyl, e.g. 2 or 3-cyclopropylmethoxypyridyl; methoxymethylpyridyl, e.g. 2 or 3-methoxymethylpyridyl; alkoxyalkoxypyridyl, in particular methoxyethoxypyridyl, e.g. 2 or 3-methoxyethoxypyridyl; benzyloxyalkoxypyridyl, in particular benzyloxyethoxypyridyl or benzyloxypropoxypyridyl, e.g. 2-benzyloxyethoxypyridyl or 3-benzyloxypropoxypyridyl; hydroxyalkylpyridyl, e.g. 2 or 3-(2-hydroxyethyl)-pyridyl; alkylsulfonyl pyridyl, e.g. methanesulfonylpyridyl, especially 3-methanesulfonylpyridyl; hydroxyalkoxypyridyl, e.g. 2-(2-hydroxyethoxy)-pyridyl or 2-(3-hydroxypropoxy)-pyridyl; hydroxyalkylpyridyl, e.g. hydroxymethylpyridyl, especially 2-(hydroxymethyl)-pyridyl; alkoxycarbonylpyridyl, e.g. methoxycarbonylpyridyl, especially 2-methoxycarbonyl-pyridyl; aminopyridyl, e.g. 2- or 3-aminopyridyl; alkylaminopyridyl, in particular loweralkylaminopyridyl, e.g. 2-, 3- or 4-methylaminopyridyl, especially 2- or 3-methylaminopyridyl, 2-, 3- or 4-ethylaminopyridyl, especially 2- or 3-ethylaminopyridyl, e.g. 2- or 3-(1- or 2-propypaminopyridyl; dialkylaminopyridyl, in particular di-loweralkylaminopyridyl, e.g. 2-, 3- or 4-dimethylaminopyridyl, especially 2-dimethylaminopyridyl; cycloaminopyridyl, e.g. azetidinylpyridyl, especially 2-azetidin-1-yl-pyridyl or pyrrolidinylpyridyl, especially 2-pyrrolidin-2-ylpyridyl; hydroxyalkylaminopyridyl, e.g. 2-(2-hydroxyethylamino)-pyridyl; amino-haloloweralkyl-pyridyl, e.g. amino-trifluoromethylpyridyl, especially 2-amino-3-trifluoromethyl-pyridyl; haloalkylpyridinyl, in particular haloloweralkylpyridyl, especially, 2-, 3- or 4-trifluoromethylpyridyl, most especially 2-trifluoromethylpyridyl; halopyridyl, in particular fluoropyridyl, especially 2-fluoropyridyl; halo-alkoxy-pyridyl, e.g. fluoro-methoxy-pyridyl such as 3-fluoro-2-methoxy-pyridyl; carbamoylpyridyl, especially 2-(carbamoyl)pyridyl; alkyl-substituted carbamoyl, e.g. methylcarbamoyl, especially 2-(methylcarbamoyl)pyridyl; pyrimidinyl; loweralkylaminopyrimidinyl, e.g. 2- or 4-methylaminopyrimidinyl or 2- or 4-ethylaminopyrimidinyl; di-loweralkylaminopyrimidinyl, e.g. 2- or 4-methylethylaminopyrimidinyl, 2- or 4-dimethylaminopyrimidinyl, especially 2-dimethylaminopyrimidinyl; alkoxypyrimidinyl, in particular methoxypyrimidinyl or ethoxypyrimidinyl, e.g. 2-methoxypyrimidinyl or 2-ethoxypyrimidinyl; 1H-pyrrolo[2,3-b]pyridinyl; 1-methyl-1H-pyrrolo[2,3-b]pyridinyl; pyrazinyl; pyrazolyl; substituted pyrazolyl, e.g. hydroxyalkylpyrazolyl, especially 1-(2-hydroxy-ethyl)-1H-pyrazolyl or 1-[2-(tetrahydro-pyran-2-yloxy)-ethyl]-1H-pyrazolyl; quinolinyl; 2-oxo-2,3-dihydro-1H-indol-5-yl; 1-methyl-2,3-dihydro-1H-indol-5-yl.

The term 5-membered heteroaryl refers to aromatic 5-membered heterocyclyl. "5-membered" meaning that there are 5 ring atoms, one or more being a heteroatom, such as nitrogen, oxygen or sulfur, and, for example includes monocyclic rings, such as thienyl, furyl, pyrrolyl, pyrazolyl, thiazolyl, isothiazolyl, oxazolyl, isoxazolyl, oxadiazolyl, triazolyl, imidazolyl, tetrazolyl or thiadiazolyl, preferably pyrazolyl, each being unsubstituted or substituted with 1 to 3 substituents.

In an embodiment, the term 5-membered heteroaryl as defined above refers to pyrazolyl or isoxazolyl, each being unsubstituted or substituted with 1 to 3 substituents. Most preferably the 5-membered heteroaryl as defined above refers to pyrazolyl, which is unsubstituted or substituted with 1 to 3 substituents, "Substituted", wherever used for a moiety, means that one or more hydrogen atoms in the respective moiety, especially up to 5 hydrogen atoms, more especially up to three of the hydrogen atoms are replaced independently of each other by a corresponding number of substituents, which preferably are independently selected from the group consisting of lower alkyl, e.g., methyl, ethyl, isopropyl or propyl; halo, e.g., F, Cl, Br or I; halo-lower alkyl, e.g., fluoroalkyl, such as trifluoromethyl; hydroxy; carboxy; lower alkoxy, e.g., methoxy, ethoxy, propyloxy or isopropyloxy; aryl-lower alkyl, e.g. phenyl-lower alkyl; aryl-lower alkoxy, e.g. phenyl-lower alkoxy; lower alkanoyloxy; lower alkanoyl; hydroxy-lower alkyl, e.g., hydroxymethyl or 2-hydroxyethyl; alkoxy lower alkyl, e.g. 2-methoxyethyl; hydroxy lower alkoxy, e.g. hydroxyethoxy; amino; mono- or di-substituted amino; cyclic amino, e.g. aziridinyl, azetidinyl or pyrrrolidinyl; amino-lower alkyl, e.g., aminomethyl, 2-aminoethyl or 3-aminopropyl; alkylamino-lower alkandiyl; dialkylamino-lower alkandiyl; N-lower alkylamino; N,N-di-lower alkylamino; amino lower alkoxy; lower alkanoylamino; lower alkanoyl-lower alkylamino; benzoylamino; carbamoyl-lower alkoxy; N-lower alkylcarbamoyl-lower alkoxy or N,N-di-lower alkylcarbamoyl-lower alkoxy; amidino; N-hydroxy-amidino; hydroxylamine; alkoxyamino; nitro; guanidino; amidino-lower alkyl, e.g., 2-amidinoethyl; N-hydroxyamidino-lower alkyl, e.g., N-hydroxy-amidino-methyl or -2-ethyl; carboxy; lower alkoxycarbonyl; phenyl-lower alkoxycarbonyl, e.g., benzyloxycarbonyl; lower alkanoyl; sulfa; lower alkanesulfonyl, e.g., methanesulfonyl ($CH_3$—S(O)$_2$—); sulfonamide ($NH_2$—$S(O)_2$—); dioxolo; phosphono (—P(=O)$(OH)_2$); hydroxy-lower alkoxy phosphoryl or di-lower alkoxyphosphoryl; carbamoyl; mono- or di-lower alkylcarbamoyl; carbamoyl lower alkyl; sulfamoyl; sulfamide; mono- or di-lower alkylaminosutfonyl; lower alkanesulfonylamino; lower alkanesulfonyl-lower alkyl-amino; cyano; cyano-lower alkyl, e.g., cyanomethyl, 2-cyanoethyl or 3-cyanopropyl; aryl (e.g., phenyl), where aryl is unsubstituted or substituted with any of the substituents defined above, and especially is phenyl which is unsubstituted or substituted with up to 4 substituents, preferably up to 2 substituents, wherein the substituents are the same or different and are independently selected from halo, (e.g., Cl or F)cyano, cyano lower alkyl, (e.g., cyanomethyl, cyanoethyl and cyanopropyl)lower alkyl, lower alkoxy, amino-lower alkyl sulfanyl, thiol-lower alkyl, amino-lower alkyl, or amino-lower alkoxy, wherein the amino group in each case can be mono- or di-substituted, e.g., —$(C_1$-$C_7)_m$ $NR_8R_9$; or —O—$(C_1$-$C_7)_m NR_8R_9$, wherein m is 0 or 1; and $R_8$ and $R_9$ can be the same or different and are independently H; lower alkyl, e.g., methyl, ethyl or propyl; lower cycloalkyl, e.g., cyclopropyl, or $R_8$ and $R_9$, together with the N atom, form a 3- to 8-membered heterocyclic ring containing 1-4 nitrogen, oxygen or sulfur atoms, e.g., azetidinyl, pyrrolidinyl, piperidino, morpholinyl, imidazolinyl, piperazinyl or lower alkyl-piperazinyl.

"Substituted" also includes amino-carbonyl-lower alkyl, e.g., $R_8R_9N$—C(O)—$CH_2$—, wherein $R_8$ and $R_9$ are as defined above. "Substituted" also includes heterocyclyl, heterocyclyl-lower alkyl, heterocyclyl-lower alkoxy or heterocyclyl-lower alkanesulfanyl, wherein the heterocyclyl in each case is a substituted or unsubstituted 3- to 8-membered heterocyclic ring containing 1-4 nitrogen, oxygen or sulfur atoms, e.g., imidazolyl, imidazolinyl, pyrrolidinyl, morpholinyl, azetidinyl, pyridyl, pyrazolyl, piperidino, piperidyl, piperazinyl or lower alkyl-piperazinyl. "Substituted" also includes $C_3$-$C_{10}$cycloalkyl, e.g., cyclopropyl or cyclohexyl; hydroxy$C_3$-$C_8$cycloalkyl, e.g., hydroxy-cyclohexyl; heteroaryl with 4 or 6 ring atoms and 1-4 ring heteroatoms selected from O, N and S, especially furyl, 1,4 oxazinyl, or pyridyl. "Substituted" also includes —$NR_8R_9$, wherein $R_8$ and $R_9$ can be the same or different and are independently H; lower alkyl, e.g., methyl, ethyl or propyl; lower cycloalkyl, e.g., cyclopropyl; or the $R_8$ and $R_9$ can, with the N atom, form a 3- to 8-membered heterocyclic ring containing 1-4 nitrogen, oxygen or sulfur atoms, e.g., azetidinyl, pyrrolidinyl, piperidino, morpholinyl, imidazolinyl, piperazinyl or lower alkyl-piperazinyl.

In an embodiment, the present invention provides compounds of the formula (I)

(I)

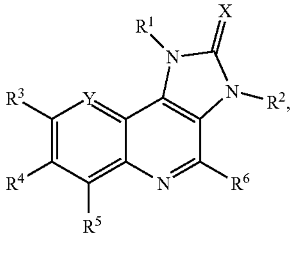

wherein

X is O or S;

Y is CH or N;

$R^1$ is a substituted or unsubstituted 5-membered heteroaryl;

$R^2$ is hydrogen or lower alkyl;

$R^3$ is a substituted or unsubstituted aryl or heterocyclyl; and $R^4$, $R^5$ and $R^6$ are hydrogen;

or a pharmaceutically acceptable salt, solvate, hydrate or prodrug thereof.

For the avoidance of doubt, substituents are only bound at positions where chemically possible, the person skilled in the art being able to decide (either experimentally or theoretically) without inappropriate effort, which substitutions are possible and which are not. For example, amino or hydroxy groups with free hydrogen may be unstable if bound to carbon atoms with unsaturated, e.g., olefinic, bonds.

The terms "treatment" or "therapy" refer to the prophylactic or preferably therapeutic including, but not limited to, palliative, curing, symptom-alleviating, symptom-reducing, kinase-regulating and/or kinase-inhibiting, treatment of said diseases, especially of the diseases mentioned below.

Where subsequently or above the term "use" is mentioned (as verb or noun) (relating to the use of a compound of the formula (I) or a pharmaceutically acceptable salt thereof), this includes any one or more of the following embodiments of the invention, respectively: the use in the treatment of a protein or lipid kinase dependant disease and in particular PI3K dependent disease, the use for the manufacture of pharmaceutical compositions for use in the treatment of a protein or lipid kinase dependant disease and in particular PI3K dependent disease, methods of use of one or more compounds of the formula (I) in the treatment of a protein or lipid kinase dependant disease and in particular PI3K dependent disease, the use of pharmaceutical preparations comprising one or more compounds of the formula (I) for the treatment of a protein or lipid kinase dependent disease, and one or more compounds of the formula (I) for use in the treatment of a protein or lipid kinase dependent disease, as appropriate and expedient and if not stated otherwise. In particular, diseases to be treated and are thus preferred for "use" of a compound of formula (I) are selected from protein or lipid kinase dependent ("dependent" meaning also "supported", not only "solely dependent") diseases mentioned herein, especially proliferative diseases mentioned herein, more especially any one or more of these or other diseases that depend on one or more of protein or lipid kinases such as PI4K (phosphatidylinositol 4-kinase) and/or PI3 kinases (phosphatidylinositol 3-kinase), for example, inhibition of the PI3K superfamily which comprises PI3Kalpha, PI3Kbeta, PI3Kdelta, PI3Kgamma and mTOR, or one or more of the individual kinase members thereof, including Vps34 (class III PI3K), PI3-kinase-related protein kinase family (PIKK, class IV PI3K) which includes DNA-PK, ATM, ATR, hSMG-1 and mTOR, or any combinations of two or more of these, or a mutant of any one or more of these, and a compound of the formula (I) can therefore be used in the treatment of a lipid or protein kinase dependent disease, especially a disease depending on one or more of the kinases mentioned above and below, where (especially in the case of aberrantly highly-expressed, constitutively activated and/or mutated kinases or defective dephosphorylation of their substrate(s)) said kinase-dependent disease is dependent on the activity of one or more of the said kinases or the pathways in which they are involved.

The compounds of formula (I) have valuable pharmacological properties and are useful in the treatment of lipid and/or protein kinase dependent diseases, e.g., as drugs to treat proliferative diseases.

In the following detailed description and embodiments, which are to be taken independently, collectively or in any combination or sub-combination, the invention relates to a compound of the formula (I), in e.g. free base form or in acid addition salt form, wherein the substituents are as defined herein.

DETAILED DESCRIPTION OF THE INVENTION

With respect to formula (I), the following detailed description is provided.

$R^1$

As indicated hereinabove, $R^1$ is a 5-membered heteroaryl having the appropriate corresponding meaning as for heteroaryl given above, with "5-membered" meaning that there are 5 ring atoms, one or more being a heteroatom, such as nitrogen, oxygen or sulfur. Such 5-membered heteroaryl groups include monocyclic rings, such as pyrazolyl, thienyl, furyl, pyrrolyl, thiazolyl, isothiazolyl, oxazolyl, isoxazolyl, oxadiazolyl, triazolyl, imidazolyl, tetrazolyl or thiadiazolyl, preferably pyrazolyl, each being unsubstituted or substituted, e.g. by the groups listed herein under "substituted".

In an embodiment, $R^1$ is pyrazolyl or isoxazolyl, each being unsubstituted or substituted, e.g. by the groups listed herein under "substituted".

In an embodiment, $R^1$ is unsubstituted or substituted pyrazolyl or unsubstituted or substituted isoxazolyl. Preferably the pyrazolyl is substituted, preferably by one, two or three substituents and the isoxazolyl is substituted, preferably by one or two substituents, wherein in each case, said substituents may for example be independently selected from halo, unsubstituted or substituted alkyl, unsubstituted or substituted alkenyl, unsubstituted or substituted alkynyl, unsubstituted or substituted lower alkoxy, unsubstituted or substituted lower alkylamino, unsubstituted or substituted alkoxy lower alkyl, unsubstituted or substituted cycloalkyl, unsubstituted or substituted cycloalkenyl, unsubstituted or substituted carbamoyl lower alkyl, lower mono- and di-alkyl carbamoyl lower alkyl, unsubstituted or substituted cycloaminocarbonyl lower alkyl, unsubstituted or substituted heterocyclylcarbonyl lower alkyl, unsubstituted or substituted hydroxyl lower alkyl, unsubstituted or substituted carboxy lower alkyl, haloloweralkyl, hydroxycarbonyl-loweralkyl, morpholinecarbonylalkyl, hydroxy or amino.

In an embodiment, $R^1$ is unsubstituted isoxazolyl.

In an embodiment, $R^1$ is isoxazolyl substituted by one or two substituents selected from halo, lower alkyl, unsubstituted or substituted lower alkenyl, unsubstituted or substituted alkynyl, unsubstituted or substituted cycloalkyl, unsubstituted or substituted cycloalkenyl, unsubstituted or substituted lower alkoxy, substituted or unsubstituted lower alkyl amino, hydroxy or amino. In an embodiment, $R^1$ is isoxazolyl substituted by one or two substituents selected from halo, unsubstituted or substituted lower alkyl, unsubstituted or substituted lower alkenyl, unsubstituted or substituted lower alkynyl, unsubstituted or substituted cycloalkyl, hydroxy or amino.

In an embodiment, $R^1$ is isoxazolyl substituted by one or two substituents selected from unsubstituted lower alkyl, unsubstituted lower alkenyl, unsubstituted alkynyl, unsubstituted cycloloweralkyl, hydroxy or amino.

In an embodiment, $R^1$ is isoxazolyl substituted by one or two, same or different, unsubstituted lower alkyl substituents (in particular $C_1$-$C_4$alkyl) such as methyl or ethyl, preferably methyl.

In an embodiment, when $R^1$ is unsubstituted or substituted isoxazolyl, said isoxazolyl is isoxazol-3-yl, isoxazol-4-yl or isoxazol-5-yl.

It is preferred that a substituent of said substituted isoxazolyl is bonded to the isoxazolyl ring at the alpha position to the ring atom which bonds the isoxazolyl ring to the rest of the molecule (that is, the alpha position is at a position on the isoxazolyl ring which is next to the isoxazolyl ring atom which is bonded to the imidazoquinolinone part of the molecule). The isoxazolyl ring atom which is bonded to the rest of the molecule (i.e. the imidazoquinolinone part) is a carbon atom. Thus, preferred isoxazolyl groups are alpha-substituted isoxazolyl. For the avoidance of doubt the ring atom at the alpha position may be a carbon, nitrogen or oxygen ring atom, with at least one atom in the alpha position being a carbon atom, but, for chemical valency reasons, only an alpha carbon atom may be substituted.

An embodiment of the invention includes compounds of formula (I) wherein $R^1$ is unsubstituted or substituted isoxazol-4-yl, thus $R^1$ in this embodiment is represented by a group of formula (AB):

(AB)

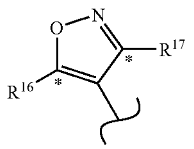

wherein, the curved line indicates the bonding position to the rest of the molecule and the alpha position is shown by the atoms labeled with a * symbol, and $R^{16}$ and $R^{17}$ are independently selected from hydrogen, halo, unsubstituted or substituted lower alkyl (especially $C_1$-$C_4$alkyl), unsubstituted or substituted lower alkenyl, unsubstituted or substituted lower alkynyl, unsubstituted or substituted lower alkoxy, unsubstituted or substituted lower alkylamino, unsubstituted or substituted cycloalkyl or unsubstituted or substituted cycloalkenyl.

In an embodiment, $R^{16}$ and $R^{17}$ are independently selected from hydrogen, halo or unsubstituted or substituted lower alkyl (especially $C_1$-$C_4$alkyl) such as methyl or ethyl.

In an embodiment, $R^{16}$ and $R^{17}$ are independently selected from hydrogen, methyl or ethyl.

In an embodiment, at least one of $R^{16}$ and $R^{17}$ is not hydrogen.

In an embodiment of the present invention, $R^1$ is of formula (AB) shown above; and $R^{16}$ is $C_1$-$C_4$alkyl (especially methyl or ethyl); and $R^{17}$ is $C_1$-$C_4$alkyl (especially methyl or ethyl);

In a specific embodiment of the present invention, $R^1$ is of formula (AB) shown above; and $R^{16}$ and $R^{17}$ are each methyl.

Preferably $R^1$ is unsubstituted or substituted pyrazolyl. Preferably the pyrazolyl is substituted, preferably by one, two or three substituents, wherein said substituents may for example be independently selected from halo, unsubstituted or substituted alkyl, unsubstituted or substituted alkenyl, unsubstituted or substituted alkynyl, unsubstituted or substituted lower alkoxy, unsubstituted or substituted lower alkylamino, unsubstituted or substituted alkoxy lower alkyl, unsubstituted or substituted cycloalkyl, unsubstituted or substituted cycloalkenyl, unsubstituted or substituted carbamoyl lower alkyl, lower mono- and di-alkyl carbamoyl lower alkyl, unsubstituted or substituted cycloaminocarbonyl lower alkyl, unsubstituted or substituted heterocyclylcarbonyl lower alkyl, unsubstituted or substituted hydroxyl lower alkyl, unsubstituted or substituted carboxy lower alkyl, halo-lower-alkyl, hydroxycarbonyl-loweralkyl, morpholinecarbonylalkyl, hydroxy or amino.

Preferred substituents are selected from the group consisting of halo, lower alkyl, lower alkenyl, lower alkynyl, cycloloweralkyl, hydroxy, amino, halo lower alkyl, 2-hydroxyethyl, methoxyethyl, hydroxycarbonylmethyl (HOC(O)$CH_2$—), dialkylaminocarbonylmethyl e.g. dimethylaminocarbonylmethyl ($Me_2NC(O)CH_2$—) or ethylmethylaminocarbonylmethyl (EtMeNC(O)$CH_2$—), (methoxyethyl)(methyl)aminocarbonylmethyl ((MeOEt)(Me)NC(O)$CH_2$—), azetidinylcarbonylmethyl e.g. 2-azetidin-1-yl-2-oxo-ethyl, morpholinecarbonylmethyl, (4-methylpiperazin-1yl)carbonylmethyl.

It is preferred that the substituent (if mono-substituted) or at least one of the substituents (if two or three substituents are present) is bonded to the pyrazole ring at the alpha position to the ring atom which bonds the pyrazole ring to the rest of the molecule (that is, the alpha position is at a position on the pyrazole ring which is next to the pyrazole ring atom which is bonded to the imidazoquinolinone part of the molecule). The pyrazole ring atom which is bonded to the rest of the molecule (i.e. the imidazoquinolinone part) is preferably a carbon atom. Thus, preferred pyrazolyl groups are alpha-substituted pyrazolyl. For the avoidance of doubt the ring atom at the alpha position may be a carbon or nitrogen ring atom. Thus an embodiment of the invention includes compounds of formula (I) wherein $R^1$ is a group selected from:

(A)

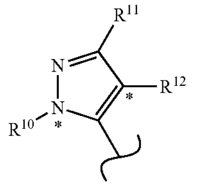

or (B)

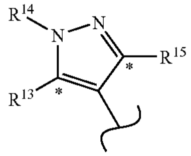

wherein, the curved line indicates the bonding position to the rest of the molecule and the alpha position is shown by the atoms labeled with a * symbol, and $R^{10}$ is independently selected from hydrogen, unsubstituted or substituted lower alkyl, unsubstituted or substituted lower alkenyl, unsubstituted or substituted alkynyl, unsubstituted or substituted cycloalkyl, unsubstituted or substituted cycloalkenyl, unsubstituted or substituted lower alkoxy, substituted or unsubstituted lower alkyl amino, hydroxy or amino.

Preferably, $R^{10}$ is independently selected from hydrogen, unsubstituted or substituted lower alkyl, unsubstituted or substituted lower alkenyl, unsubstituted or substituted lower alkynyl, unsubstituted or substituted cycloalkyl, hydroxy or amino.

More preferably, $R^{10}$ is independently selected from hydrogen, unsubstituted lower alkyl, unsubstituted lower alkenyl, unsubstituted alkynyl, unsubstituted cycloloweralkyl, hydroxy or amino.

More preferably, $R^{10}$ is independently selected from hydrogen or lower alkyl such as methyl or ethyl.

$R^{11}$ is independently selected from hydrogen, halo, unsubstituted or substituted alkyl, unsubstituted or substituted alkenyl, unsubstituted or substituted alkynyl, unsubstituted or substituted lower alkoxy, unsubstituted or substituted lower alkylamino, unsubstituted or substituted alkoxy lower alkyl, unsubstituted or substituted cycloalkyl or unsubstituted or substituted cycloalkenyl; unsubstituted or substituted carbamoyl lower alkyl; lower mono- and di-alkyl carbamoyl lower alkyl; unsubstituted or substituted cycloaminocarbonyl lower alkyl; unsubstituted or substituted heterocyclylcarbonyl lower alkyl.

More preferably $R^{11}$ is independently selected from hydrogen, unsubstituted or substituted lower alkyl such as methyl, ethyl, propyl, isopropyl; halo lower alkyl such as trifluoromethyl; hydroxyl lower alkyl such as hydroxyl ethyl; alkoxy lower alkyl such as methoxyethyl; carbamoyl lower alkyl such as carbamoylmethyl; lower mono- or di-alkyl carbamoyl lower alkyl such as methylcarbamoylmethyl, ethylcarbamoylmethyl, dimethylcarbamoylmethyl, ethylmethylcarbamoylmethyl or diethylcarbamoylmethyl; cycloaminocarbonyl lower alkyl such as azetidinylcarbonylmethyl; or carboxy lower alkyl such as carboxymethyl.

More preferably $R^{11}$ is independently selected from hydrogen, lower alkyl such as methyl, ethyl, propyl, isopropyl or halo lower alkyl such as trifluoromethyl.

More preferably, $R^{11}$ is independently selected from hydrogen, methyl, ethyl or trifluoromethyl.

$R^{14}$ is independently selected from hydrogen, unsubstituted or substituted alkyl, unsubstituted or substituted alkenyl, unsubstituted or substituted alkynyl, unsubstituted or substituted hydroxyl lower alkyl, unsubstituted or substituted lower alkoxy, unsubstituted or substituted lower alkylamino, unsubstituted or substituted alkoxy lower alkyl, unsubstituted or substituted cycloalkyl; unsubstituted or substituted cycloalkenyl; unsubstituted or substituted carbamoyl lower alkyl; lower mono- or di-alkyl carbamoyl lower alkyl; unsubstituted or substituted cycloaminocarbonyl lower alkyl; unsubstituted or substituted heterocyclylcarbonyl lower alkyl; unsubstituted or substituted carboxy lower alkyl.

More preferably $R^{14}$ is independently selected from hydrogen or unsubstituted or substituted lower alkyl such as unsubstituted or substituted hydroxyl lower alkyl; unsubstituted or substituted alkoxy lower alkyl; unsubstituted or substituted carbamoyl lower alkyl; lower mono- or di-alkyl carbamoyl lower alkyl; unsubstituted or substituted cycloaminocarbonyl lower alkyl; unsubstituted or substituted heterocyclylcarbonyl lower alkyl; unsubstituted or substituted carboxy lower alkyl.

More preferably $R^{14}$ is independently selected from hydrogen; unsubstituted lower alkyl such as methyl, ethyl, propyl or isopropyl; hydroxyl lower alkyl such as hydroxyl ethyl; alkoxy lower alkyl such as methoxyethyl; carbamoyl lower alkyl such as carbamoylmethyl; lower mono- or di-alkyl carbamoyl lower alkyl such as methylcarbamoylmethyl, ethylcarbamoylmethyl, dimethylcarbamoylmethyl, ethylmethylcarbamoylmethyl; diethylcarbamoylmethyl or (methoxyethyl)(methyl)carbamoylmethyl; cycloaminocarbonyl lower alkyl such as azetidinylcarbonylmethyl; unsubstituted or substituted heterocyclylcarbonyl lower alkyl such as morpholinecarbonyl lower alkyl or piperazinecarbonyl lower alkyl; or carboxy lower alkyl such as carboxymethyl;

More, preferably $R^{14}$ is independently selected from hydrogen; unsubstituted or substituted $C_1$-$C_4$alkyl, unsubstituted or substituted halo$C_1$-$C_4$alkyl, 2-hydroxyethyl, methoxyethyl, hydroxycarbonylmethyl (HOC(O)$CH_2$—), dialkylaminocarbonylmethyl e.g. dimethylaminocarbonylmethyl ($Me_2NC(O)CH_2$—) or ethylmethylaminocarbonylmethyl ($EtMeNC(O)CH_2$—), (methoxyethyl)(methyl)aminocarbonylmethylmethyl ((MeOEt)(Me)$NC(O)CH_2$—), azetidinylcarbonylmethyl e.g. 2-azetidin-1-yl-2-oxo-ethyl, morpholinecarbonylmethyl e.g. 4-morpholinecarbonylmethyl, (4-methylpiperazin-1yl)carbonylmethyl.

Most preferably $R^{14}$ is independently selected from hydrogen, methyl, ethyl, isopropyl, trifluoromethyl, 2-hydroxyethyl, methoxyethyl, hydroxycarbonylmethyl ($HOC(O)CH_2$—), dimethylaminocarbonylmethyl ($Me_2NC(O)CH_2$—), ethylmethylaminocarbonylmethyl ($EtMeNC(O)CH_2$—), (methoxyethyl)(methyl)aminocarbonylmethylmethyl ((MeOEt)(Me)$NC(O)CH_2$—), 2-azetidin-1-yl-2-oxo-ethyl, 4-morpholinecarbonylmethyl and (4-methylpiperazin-1yl)carbonylmethyl.

$R^{12}$, $R^{13}$ and $R^{15}$ are independently selected from hydrogen, halo, unsubstituted or substituted alkyl, unsubstituted or substituted alkenyl, unsubstituted or substituted alkynyl, unsubstituted or substituted lower alkoxy, unsubstituted or substituted lower alkylamino, unsubstituted or substituted cycloalkyl or unsubstituted or substituted cycloalkenyl.

More preferably $R^{12}$, $R^{13}$ and $R^{15}$ are independently selected from hydrogen, halo such as fluoro, chloro, bromo, or unsubstituted or substituted lower alkyl such as methyl or ethyl.

More preferably $R^{12}$, $R^{13}$ and $R^{15}$ are independently selected from hydrogen, chloro, methyl or ethyl.

Preferably, one of $R^{10}$ and $R^{12}$ is not hydrogen.

Preferably, at least one of $R^{13}$ and $R^{15}$ is not hydrogen.

In an embodiment of the present invention, $R_1$ is of formula (A) or (B) shown above; and $R^{10}$ is $C_1$-$C_4$alkyl (especially methyl or ethyl);

$R^{11}$ is hydrogen or $C_1$-$C_4$alkyl (especially methyl) or fluoro$C_1$-$C_4$alkyl (especially trifluoromethyl); and $R^{12}$ (is hydrogen or $C_1$-$C_4$alkyl (especially methyl);

$R^{13}$ is hydrogen or $C_1$-$C_4$alkyl (especially methyl);

$R^{14}$ is $C_1$-$C_4$alkyl (especially methyl, ethyl or isopropyl), 2-hydroxyethyl, methoxyethyl, hydroxycarbonylmethyl ($HOC(O)CH_2$—), dimethylaminocarbonylmethyl ($Me_2NC(O)CH_2$—), diethylaminocarbonylmethyl ($Et_2NC(O)CH_2$—), ethylmethylaminocarbonylmethyl ($EtMeNC(O)CH_2$—), (methoxyethyl)(methyl)aminocarbonylmethylmethyl ((MeOEt)(Me)$NC(O)CH_2$—), 4-morpholinecarbonylmethyl, (4-methylpiperazin-1yl)carbonylmethyl, 2-azetidin-1-yl-2-oxo-ethyl; and $R^{15}$ is methyl or chloro.

In another embodiment of the present invention, $R_1$ is of formula (A) shown above; and $R^{10}$ is $C_1$-$C_4$alkyl (especially methyl or ethyl);

$R^{11}$ is hydrogen or $C_1$-$C_4$alkyl (especially methyl) or fluoro$C_1$-$C_4$alkyl (especially trifluoromethyl); and $R^{12}$ is hydrogen or $C_1$-$C_4$alkyl (especially methyl).

In another embodiment of the present invention, $R_1$ is of formula (B) shown above; and $R^{13}$ is hydrogen or $C_1$-$C_4$alkyl (especially methyl);

$R^{14}$ is $C_1$-$C_4$alkyl (especially methyl, ethyl or isopropyl), 2-hydroxyethyl, methoxyethyl, hydroxycarbonylmethyl ($HOC(O)CH_2$—), dimethylaminocarbonylmethyl ($Me_2NC(O)CH_2$—), ethylmethylaminocarbonylmethyl ($EtMeNC(O)CH_2$—), (methoxyethyl)(methyl)aminocarbonylmethylmethyl ((MeOEt)(Me)$NC(O)CH_2$—), 2-azetidin-1-yl-2-oxo-ethyl, 4-morpholinecarbonylmethyl and (4-methylpiperazin-1yl)carbonylmethyl; and $R^{15}$ is methyl or chloro.

In an embodiment, $R^1$ is selected from 1,5-dimethyl-1H-pyrazol-4-yl, 2-ethyl-2H-pyrazol-3-yl, 2-methyl-2H-pyrazol-3-yl, 2,5-dimethyl-2H-pyrazol-3-yl, 1-isopropyl-3-methyl-1H-pyrazol-4-yl, 1-ethyl-3-methyl-1H-pyrazol-4-yl, 2,4-dimethyl-2H-pyrazol-3-yl, 1,3-dimethyl-1H-pyrazol-4-yl, 1,3,5-trimethyl-1H-pyrazol-4-yl, 2-methyl-5-trifluoromethyl-2H-pyrazol-3-yl, 1-hydroxycarbonyl methyl-3-methyl-pyrazol-4-yl, 1-dimethylaminocarbonylmethyl-3-methyl-pyrazol-4-yl, 1-dimethylaminocarbonylmethyl-3,5-dimethyl-pyrazol-4-yl, 1-diethylaminocarbonylmethyl-3-methyl-pyrazol-4-yl, 1-(2-hydroxyethyl)-3-methyl-pyrazol-4-yl, 1-(2-azetidin-1-yl-2-oxo-ethyl)-3-methyl-1H-pyrazol-4-yl, 1-(4-morpholin)-carbonylmethyl-3-methyl-pyrazol-4-yl, 3-methyl-1-[2-(4-methyl-piperazin-1-yl)-2-oxo-ethyl]-1H-pyrazol-4-yl, 1-methyl-3-chloro-pyrazol-4-yl, 1-(2-methoxyethyl)-3,5-dimethyl-pyrazol-4-yl, 1-N-ethyl-N-methylaminocarbonylmethyl-3-methyl-pyrazol-4-yl or 3,5-dimethyl-isoxazol-4-yl.

In another embodiment $R^1$ is selected from 1,5-dimethyl-1H-pyrazol-4-yl, 2-ethyl-2H-pyrazol-3-yl, 2-methyl-2H-pyrazol-3-yl, 2,5-dimethyl-2H-pyrazol-3-yl, 1-isopropyl-3-methyl-1H-pyrazol-4-yl, 1-ethyl-3-methyl-1H-pyrazol-4-yl, 2,4-dimethyl-2H-pyrazol-3-yl, 1,3-dimethyl-1H-pyrazol-4-yl, 1,3,5-trimethyl-1H-pyrazol-4-yl, 2-methyl-5-trifluoromethyl-2H-pyrazol-3-yl, 1-hydroxycarbonylmethyl-3-methyl-pyrazol-4-yl, 1-dimethylaminocarbonylmethyl-3-methyl-pyrazol-4-yl, 1-dimethylaminocarbonylmethyl-3,5-dimethyl-pyrazol-4-yl, 1-diethylaminocarbonylmethyl-3-methyl-pyrazol-4-yl, 1-(2-hydroxyethyl)-3-methyl-pyrazol-4-yl, 1-(2-azetidin-1-yl-2-oxo-ethyl)-3-methyl-1H-pyrazol-4-yl, 1-(4-morpholin)-carbonylmethyl-3-methyl-pyrazol-4-yl, 1-methyl-3-chloro-pyrazol-4-yl, 1-(2-methoxyethyl)-3,5-dimethyl-pyrazol-4-yl.

$R^2$

In an embodiment, $R^2$ is preferably selected from hydrogen, $C_1$-$C_4$alkyl or $C_1$-$C_4$alkenyl. In particular $R^2$ is selected from hydrogen, methyl, ethyl and propenyl (especially propen-3-yl).

In another embodiment, $R^2$ is preferably selected from hydrogen or $C_1$-$C_4$alkyl. Most preferably $R^2$ is selected from hydrogen, methyl and ethyl.

$R^3$ $R^3$ is unsubstituted or substituted aryl or unsubstituted or substituted heterocycyl as defined herein above, each of which, when substituted, is substituted by one or more, especially 1-3, substituents independently selected from the group consisting of the substituents defined under "substituted".

When $R^3$ is unsubstituted or substituted aryl, it is preferably $C_6$-$C_{10}$aryl which is unsubstituted, or substituted by one or more, especially 1-3, substituents independently selected from the group consisting of the substituents defined under "substituted".

When $R^3$ is an aryl group, (especially $C_6$-$C_{10}$aryl, more especially phenyl) it is unsubstituted, or substituted by one or more, especially 1-3, substituents independently selected from the group consisting of the substituents defined under "substituted".

When the $R^3$ group is an aryl group, (especially $C_6$-$C_{10}$aryl, more especially phenyl) when substituted, the substituents may be selected from the group consisting of halo, especially fluoro, chloro, bromo or iodo, in particular fluoro; halo-lower alkyl, especially fluoroalkyl, in particular trifluoromethyl; hydroxyl; amino; mono or disubstituted amino, especially alkyl-substituted amino or hydroxyalkyl-substituted amino, e.g. dimethyl amino or 2-hydroxyethyl amino; cyclic amino, such as aziridinyl or azetidinyl; amino-lower alkyl, e.g., aminomethyl, 2-aminoethyl or 3-aminopropyl; lower alkoxy, e.g., methoxy, ethoxy or propoxy (e.g. iso-propoxy); hydroxy-lower alkyl, e.g., hydroxymethyl or 2-hydroxyethyl; hydroxy lower alkoxy, e.g. hydroxyethoxy; lower alkyl, e.g., methyl, ethyl or iso-propyl; cyano; cyano-lower alkyl, e.g., 2-cyanoethyl or 3-cyanopropyl; amidino; N-hydroxyamidino; hydroxyamino; alkoxyamino; nitro; amidino-lower alkyl, e.g., 2-amidino-ethyl; or N-hydroxyamidino-lower alkyl, e.g., 2-(N-hydroxyamidino)-ethyl; substituted phenyl or (especially 1- or 2-)naphthyl; sulfonyl; substituted sulfonyl, e.g. alkyl-substituted sulfonyl, such as methanesulfonyl; sulfonamide, e.g. N-methylsulfonamide (or lower alkylaminosulfonyl or N,N-di-loweralkyl aminosulfonyl, e.g. methylaminosufonyl or dimethylaminosulfonyl) or pyrrolidine-1-sulfonyl; lower alkyl sulfonyl amino, e.g. methylsulfonylamino; lower alkyl sulfonylalkandiylamino, e.g. methylsulfonylmethylamino; lower alkylsulfonyl-N-lower alkylamino, e.g. methylsulfonyl-N-methylamino; [1,3]dioxolo; substituted [1,3]dioxolo, e.g. 2,2-difluoro-[1,3]dioxolo; alkoxy carbonyl, such as lower alkoxy carbonyl, e.g. methoxycarbonyl; carbamoyl; substituted carbamoyl, such as alkyl-substituted carbamoyl, e.g. methylcarbamoyl; heterocycle, e.g. pyrazol; heterocyclyl lower alkyl; heteroaryl or heteroaryl lower alkyl.

In an embodiment, when the $R^3$ group is an aryl group, (especially $C_6$-$C_{10}$aryl, more especially phenyl) when substituted, the substituents may be selected from the group consisting of halo, especially fluoro, chloro, bromo or iodo, in particular fluoro; halo-lower alkyl, especially fluoroalkyl, in particular trifluoromethyl; hydroxyl; amino; mono or disubstituted amino, especially alkyl-substituted amino or hydroxyalkyl-substituted amino, e.g. dimethyl amino or 2-hydroxyethyl amino; cyclic amino, such as aziridinyl or azetidinyl; amino-lower alkyl, e.g., aminomethyl, 2-aminoethyl or 3-aminopropyl; lower alkoxy, e.g., methoxy or ethoxy; hydroxy-lower alkyl, e.g., hydroxymethyl or 2-hydroxyethyl; hydroxy lower alkoxy, e.g. hydroxyethoxy; lower alkyl, e.g., methyl, ethyl or iso-propyl; cyano; cyano-lower alkyl, e.g., 2-cyanoethyl or 3-cyanopropyl; amidino; N-hydroxyamidino; hydroxyamino; alkoxyamino; nitro; amidino-lower alkyl, e.g., 2-amidino-ethyl; or N-hydroxyamidino-lower alkyl, e.g., 2-(N-hydroxyamidino)-ethyl; substituted phenyl or (especially 1- or 2-)naphthyl; sulfonyl; substituted sulfonyl, e.g. alkyl-substituted sulfonyl, such as methanesulfonyl; sulfonamide, e.g. N-methylsulfonamide or pyrrolidine-1-sulfonyl; [1,3]dioxolo; substituted [1,3]dioxolo, e.g. 2,2-difluoro-[1,3]dioxolo; alkoxy carbonyl, such as lower alkoxy carbonyl, e.g. methoxycarbonyl; carbamoyl; substituted carbamoyl, such as alkyl-substituted carbamoyl, e.g. methylcarbamoyl; heterocycle, e.g. pyrazol; heterocyclyl lower alkyl; heteroaryl or heteroaryl lower alkyl.

In an embodiment, unsubstituted or substituted aryl for $R^3$ is selected from phenyl; hydroxyphenyl, e.g., 2-, 3- or 4-hydroxyphenyl; methoxyphenyl, e.g., 2-, 3- or 4-methoxyphenyl or 3,4-dimethoxyphenyl; ethoxyphenyl, e.g., 2-, 3- or 4-ethoxyphenyl or 3,4-diethoxyphenyl; propoxyphenyl (e.g. iso-propoxyphenyl) such as 3-propoxyphenyl (e.g. 3-iso-propoxyphenyl); methoxy ethoxy-phenyl, e.g. 3-methoxy-4-ethoxy phenyl or 4-methoxy-3-ethoxy phenyl, other lower-alkoxy phenyl, e.g. 3-methoxy-4-(2-methoxy ethoxy)-phenyl, halo-alkoxy-phenyl, e.g. fluoro-(iso-propoxy)-phenyl, e.g. 2-fluoro-3-(iso-propoxy)-phenyl; hydroxy alkoxy phenyl, e.g. 3-methoxy-4-hydroxy phenyl; halo-hydroxy-phenyl, e.g. fluoro-hydroxy-phenyl such as 3-fluoro-5-hydroxy-phenyl; hydroxy-haloalkyl-phenyl, e.g. hydroxy-fluoroalkyl-phenyl such as 3-hydroxy-5-trifluoromethyl-phenyl; 2,2-difluoro-benzo[1,3]dioxolo; benzene sulfonamide, e.g. N-methylbenzenesulfonamide and N,N-dimethylbenzenesulfonamide; 3-(pyrrolidine-1-sulfonyl)-phenyl, N-(phen-3-yl)-methanesulfonamide or N-methyl-N-phen-3-yl-methanesulfonamide; alkyl-sulfonyl phenyl, e.g. 3-methanesulfonylphenyl; benzamide e.g. 2-, 3- or 4-benzamide, 2-, 3- or 4-N-methyl-benzamide or 2-, 3- or 4-N,N-dimethyl-benzamide; pyrazol-phenyl, e.g. 4-(pyrazol)-phenyl or alternatively (1H-pyrazol-1yl)-phenyl, in particular 4-(1H-pyrazol-1yl)-phenyl; imidazol-phenyl, especially (1H-imidazol-2-yl)phenyl, in particular 4-(1H-imidazol-2-yl)phenyl.

In an embodiment, unsubstituted or substituted aryl for $R^3$ is selected from phenyl; hydroxyphenyl, e.g., 2-, 3- or 4-hydroxyphenyl; methoxyphenyl, e.g., 2-, 3- or 4-methoxyphenyl or 3,4-dimethoxyphenyl; ethoxyphenyl, e.g., 2-, 3- or 4-ethoxyphenyl or 3,4-diethoxyphenyl; methoxy ethoxy-phenyl, e.g. 3-methoxy-4-ethoxy phenyl or 4-methoxy-3-ethoxy phenyl, other lower-alkoxy phenyl, e.g. 3-methoxy-4-(2-methoxy ethoxy)-phenyl, hydroxy alkoxy phenyl, e.g. 3-methoxy-4-hydroxy phenyl; halo-hydroxy-phenyl, e.g. fluoro-hydroxy-phenyl such as 3-fluoro-5-hydroxy-phenyl; hydroxy-haloalkyl-phenyl, e.g. hydroxy-fluoroalkyl-phenyl such as 3-hydroxy-5-trifluoromethyl-phenyl; 2,2-difluoro-benzo[1,3]dioxolo; benzene sulfonamide, e.g. N-methylbenzenesulfonamide; 3-(pyrrolidine-1-sulfonyl)-phenyl, N-(phen-3-yl)-methanesulfonamide or N-methyl-N-phen-3-yl-methanesulfonamide; alkyl-sulfonyl phenyl, e.g. 3-methanesulfonylphenyl; benzamide e.g. 2-, 3- or 4-benzamide, 2-, 3- or 4-N-methyl-benzamide or 2-, 3- or 4-N,N-dimethyl-benzamide; pyrazol-phenyl, e.g. 4-(pyrazol)-phenyl or alternatively (1H-pyrazol-1yl)-phenyl, in particular 4-(1H-pyrazol-1yl)-phenyl; imidazol-phenyl, especially (1H-imidazol-2-yl)phenyl, in particular 4-(1H-imidazol-2-yl)phenyl.

When the $R^3$ group is a heterocyclyl or preferably heteroaryl, said heterocyclyl or heteroaryl may be selected from the group consisting of indolyl, 2,3-dihydro-1H-indol-5-yl, 1-methyl-2,3-dihydro-1H-indol-5-yl, 2-oxo-2,3-dihydro-1H-indol-5-yl, pyridyl, pyrimidinyl (especially pyrimidin-5-yl), 1H-pyrrolo[2,3-b]pyridin-5-yl, 1-methyl-1H-pyrrolo[2,3-b]pyridin-5-yl, pyrazolyl, pyrazol-4-yl, pyrazinyl, quinolyl, quinol-3-yl, 1H-imidazo[4,5-b]pyridin-2(3H)-one-6-yl, 3H-imidazo[4,5-b]pyridin-6-yl, 3H-[1,2,3]triazolo[4,5-b]pyridin-6-yl each of these heterocycle radicals being unsubstituted or substituted by one or two radicals selected from the substituents described under "substituted", in particular from the group consisting of halo, especially fluoro, chloro, bromo or iodo, more especially fluoro or chloro; halo-lower alkyl, especially fluoroalkyl, in particular trifluoromethyl; hydroxyl; amino, mono or disubstituted amino, especially alkyl-substituted amino or hydroxyalkyl-substituted amino, e.g. dimethyl amino or 2-hydroxyethyl amino; cyclic amino, such as aziridinyl or azetidinyl; amino-lower alkyl, e.g., aminomethyl, 2-aminoethyl or 3-aminopropyl; lower alkoxy, e.g., methoxy or ethoxy; lower alkoxy lower alkyl, e.g. 2-methoxyethyl; hydroxy-lower alkyl, e.g., hydroxymethyl or 2-hydroxyethyl; hydroxy lower alkoxy, e.g. hydroxyethoxy; lower alkyl, e.g., methyl, ethyl or iso-propyl; cyano; cyano-lower alkyl, e.g., 2-cyanoethyl and 3-cyanopropyl; amidino; N-hydroxyamidino; amidino-lower alkyl, e.g., 2-amidino-ethyl; or N-hydroxyamidino-lower alkyl, e.g., 2-(N-hydroxyamidino)-ethyl; substituted phenyl or (especially 1- or 2-) naphthyl; sulfonyl; substituted sulfonyl, e.g. alkyl-substituted sulfonyl, such as methanesulfonyl; sulfonamide, e.g. N-methylsulfonamide or pyrrolidine-1-sulfonyl; [1,3]dioxolo; substituted [1,3]dioxolo, e.g. 2,2-difluoro-[1,3]dioxolo; alkoxy carbonyl, such as lower alkoxy carbonyl, e.g. methoxycarbonyl; carbamoyl; substituted carbamoyl, such as alkyl-substituted carbamoyl, e.g. methylcarbamoyl; aminocarbonylalkyl, such as aminocarbonyl loweralkyl, e.g. aminocarbonylmethyl; N-mono-substituted aminocarbonylalkyl, such as N-loweralkyl aminocarbonyl loweralkyl, e.g. methylaminocarbonylmethyl; N-di-substituted aminocarbonylalkyl, such as N-di-loweralkyl aminocarbonyl loweralkyl, e.g. dimethylaminocarbonylmethyl, or other N-di-substituted aminocarbonylalkyl, such as 4-morpholinecarbonylmethyl. The heterocycle group may also be substituted with another heterocycle, e.g. 3H-tetrazolyl (in particular 3H-tetrazol-5-yl), pyrazol, heterocyclyl lower alkyl, heteroaryl or heteroaryl lower alkyl as defined herein.

Very preferred heterocyclic groups, which may be substituted or unsubstituted, include indolyl, 1-methyl-2,3-dihydro-1H-indolyl, 2-oxo-2,3-dihydro-1H-indolyl, pyridyl, pyrimidinyl, 1H-pyrrolo[2,3-b]pyridinyl, 1-methyl-1H-pyrrolo[2,3-b]pyridinyl, pyrazolyl, pyrazinyl, quinolyl, 1,3-Dimethyl-2-oxo-2,3-dihydro-1H-imidazo[4,5-b]pyridinyl, 1-ethyl-3-methyl-2-oxo-2,3-dihydro-1H-imidazo[4,5-b]pyridinyl, 1-(2-methoxy-ethyl)-3-methyl-2-oxo-2,3-dihydro-1H-imidazo[4,5-b]pyridinyl, 2-Dimethylamino-3-methyl-3H-imidazo[4,5-b]pyridinyl, 2-methoxy-3-methyl-3H-imidazo[4,5-b]pyridinyl, 3-methyl-3H-[1,2,3]triazolo[4,5-b]pyridinyl, 2,3-Dimethyl-3H-imidazo[4,5-b]pyridinyl, 3-methyl-3H-imidazo[4,5-b]pyridinyl, 1H-pyrrolo[3,2-b]pyridinyl, 1-methyl-1H-pyrrolo[3,2-b]pyridinyl, 1-methyl-2-oxo-1,4-dihydro-2H-pyrido[2,3-d][1,3]oxazinyl, 4-methyl-3,4-dihydro-2H-pyrido[3,2-b][1,4]oxazinyl, 1,3,3-trimethyl-2-oxo-2,3-dihydro-1H-pyrrolo[2,3-b]pyridinyl and 1-ethyl-2-oxo-1,4-dihydro-2H-pyrido[3,2-d][1,3]oxazinyl each of these heterocycle radicals being unsubstituted or substituted by one to two radicals selected from the substituents described under "substituted", in particular from the group consisting of halo, especially fluoro, chloro, bromo or iodo, more especially fluoro or chloro, in particular fluoro; halo-lower alkyl, especially fluoroalkyl, in particular trifluoromethyl; hydroxyl; amino, mono or disubstituted amino, especially alkyl-substituted amino, hydroxyalkyl-substituted amino or alkoxyalkyl-substituted amino, e.g. dimethyl amino, 2-hydroxyethyl amino or 2-methoxyethyl amino; cyclic amino, such as aziridinyl, azetidinyl or pyrrolidinyl; substituted cyclic amino, e.g. hydroxy cyclic amino; amino-lower alkyl, e.g., aminomethyl, 2-aminoethyl or 3-aminopropyl; alkylamino-lower alkyl, e.g. methylaminomethyl, ethylaminomethyl, methylaminoethyl or ethylaminoethyl; dialkylamino-loweralkyl, e.g. dimethylaminomethyl, dimethylaminoethyl, methylethylaminomethyl, methylethylaminoethyl, diethylaminomethyl or diethylaminoethyl; cycloalkylaminoalkyl, e.g. cyclopropylaminomethyl, cyclopropylaminoethyl, cyclobutylaminomethyl, cyclobutylaminoethyl, cyclopentylaminomethyl or cyclopentylaminoethyl; dicycloalkylaminoalkyl, e.g. dicyclopropylaminomethyl, dicyclopropylaminoethyl, cyclopropylcyclobutylaminomethyl or cyclopropylcyclobutylaminoethyl; alkylcycloalkylaminoalkyl, e.g. cyclopropylmethylaminomethyl, cyclopropylmethylaminoethyl, cyclopropylethylaminomethyl or cyclopropylethylaminoethyl; lower alkoxy, e.g., methoxy, ethoxy or propyloxy; cycloalkoxy, e.g. cyclobutoxy; lower-alkoxyalkyl, e.g. methoxymethyl, methoxypropyl, ethoxypropyl; hydroxy-lower alkyl, e.g., hydroxymethyl or 2-hydroxyethyl; hydroxy lower cycloalkyl, e.g. hydroxy cyclopentyl; hydroxy lower alkoxy, e.g. hydroxyethoxy; alkoxy lower alkoxy, e.g. methoxyethoxy or ethoxyethoxy; lower alkyl, e.g., methyl, ethyl or iso-propyl; cyano; cyano-lower alkyl, e.g., 2-cyanoethyl, 2-cyanopropyl, 2-cyano-2-methylpropyl or 3-cyanopropyl; cyano lower cycloalkyl, e.g. cyano cyclobutyl; amidino; N-hydroxyamidino; amidino-lower alkyl, e.g., 2-amidino-ethyl; or N-hydroxyamidino-lower alkyl, e.g., 2-(N-hydroxyamidino)-ethyl; nitro; carboxylic acid; substituted sulfonyl, e.g. alkyl-substituted sulfonyl, such as methanesulfonyl; sulfonamide, e.g. N-methylsulfonamide or pyrrolidine-1-sulfonyl; alkylsulfonylamino, e.g. methylsulfonylamino; alkylsulfonylalkylamino, e.g. methylsulfonylmethylamino; acylamino (also termed alkyl carbonyl amino), e.g. acetylamino; acyl alkyl amino, e.g. acetyl methyl amino; alkylcarbonylaminoalkyl, e.g. methylcarbonylaminomethyl; alkylaminocarbonylalkyl e.g. methylaminocarbonylmethyl; alkylcarbonyl-N-alkylamino, e.g. methylcarbonyl-N-methylamino; [1,3]dioxolo; substituted [1,3]dioxolo, e.g. 2,2-difluoro-[1,3]dioxolo; alkoxy carbonyl, such as lower alkoxy carbonyl, e.g. methoxycarbonyl; carbamoyl (also termed aminocarbonyl); substituted carbamoyl, such as alkyl-substituted carbamoyl, e.g. methylcarbamoyl, ethyl carbamoyl, iso-propyl carbamoyl or alkoxyalkyl-substituted carbamoyl (also termed alkoxyalkylaminocarbonyl), e.g. 2-methoxyethylcarbamoyl. The heterocycle group may also be substituted with another substituted or unsubstituted heterocycle, preferably a 4-7 membered ring, e.g. 1H-tetrazolyl (in particular 1H-tetrazol-5-yl), pyrazol, imidazole, triazole, azetidinyl, pyrrolidinyl, piperazinyl, methylpiperazinyl, ethylpiperazinyl, triazolonyl, methylimidazolyl or morpholino. The heterocycle group may also be substituted with heterocyclyl lower alkyl, heteroaryl or heteroaryl lower alkyl as defined herein.

In an embodiment, $R^3$ is heterocycyl. In another embodiment, $R^3$ is heterocycyl which is heteroaryl. In an embodiment, said heterocycyl or heteroaryl is a monocyclic 6 membered ring wherein one or two ring heteroatoms are nitrogen atoms. In a preferred embodiment, $R^3$ is a monocyclic 6 membered heteroaryl wherein one or two ring heteroatoms are nitrogen atoms. In an embodiment, $R^3$ is pyridyl, pyrimidinyl or pyrazinyl, each independently being unsubstituted or substituted. In an embodiment, $R^3$ is pyridyl or pyrimidinyl, each independently being unsubstituted or substituted. In an embodiment, $R^3$ is unsubstituted or substituted pyridyl (especially pyrid-3-yl or pyridyl-5-yl). In another embodiment $R^3$ is unsubstituted or substituted pyrimidinyl (especially pyrimidin-5-yl).

In an embodiment, said pyrimidinyl (especially pyrimidin-5-yl) is unsubstituted or substituted, preferably substituted. When substituted, said pyrimidinyl is preferably substituted in the 2-, 4- or 2- and 4-positions on the pyrimidine ring. Typically, when mono-substituted, the pyrimidine ring is substituted in the 2-position, and when di-substituted, in the 2- and 4-positions.

When substituted, said pyrimidinyl is substituted by one or two substituents independently selected from:

di-loweralkylamino, di-alkoxy, alkylamino, alkoxy, cycloamino.

In an embodiment, heterocyclyl or heteroaryl for $R^3$ is pyridyl, especially pyrid-3-yl or pyrid-5-yl—both of these terms mean that the pyridine ring is bonded to the rest of the imidazoquinolinone part of the molecule of formula (I) at a pyridine carbon atom which is arrived at by counting 3 atoms or 5 atoms round the pyridine ring, starting at the nitrogen atom of the pyridine ring, which counts as 1. In an embodiment, said pyridyl (preferably pyrid-3-yl or pyrid-5-yl) is unsubstituted or substituted, preferably substituted. When substituted, said pyridinyl is preferably substituted in the 5-, 6-, or 5- and 6-position positions of the pyridine ring (with reference to pyridin-3-yl), When substituted, said pyridyl is substituted by one or two substituents independently selected from:

loweralkyl, lower-alkoxy, cycloalkoxy, haloalkyl, cycloalkylalkoxy, alkoxyalkyl, alkoxyalkoxy, benzyloxyalkoxy, hydroxyalkyl, hydroxycycloalkyl, hydroxyfluoroalkyl, aminoalkyl, alkyl-sulfonyl, hydroxyalkoxy, alkoxycarbonyl, amino, alkylamino, dialkylamino, cycloalkylamino, N-alkyl-N-cycloalkylamino, halo, deuteroalkoxy-alkyl, haloalkoxy, cycloamino, cyclic ether-substituted amino, hydroxy-cycloamino, loweralkoxy-cycloamino, hydroxyalkylamino, amino-haloloweralkyl, deuteroloweralkylamino, cyanoalkyl, cyanocycloalkyl, carbamoyl, piperazinyl, alkylsulfonamido, dialkylsulfonamido, alkylsulfonamidoalkyl, dialkylsulfonamido(alkyl), 3H-tetrazol-5-yl, alkylcarbonylaminoalkyl, alkylcarbonyl-N-alkylamino, nitro, alkylaminocarbonylalkyl, alkoxyalkylaminocarbonyl, morpholinyl, 1H-pyrazolyl, loweralkyl substituted (1H-imidazol-1-yl).

In an embodiment, specifically preferred unsubstituted or substituted heterocyclyl or heteroaryl for $R^3$ is selected from:

- pyridyl, e.g. pyrid-2-yl, pyrid-3-yl or pyrid-4-yl; especially pyrid-3-yl;
- alkylpyridyl, in particular loweralkylpyridyl, e.g. methylpyridyl, e.g., 2-, 3- or 4-methylpyridyl, especially 2-methylpyridyl or 3-methylpyridyl, in particular 2-methyl pyrid-5-yl or 3-methylpyrid-5-yl;
- alkoxypyridyl, in particular lower-alkoxypyridyl, e.g. methoxypyridyl, e.g., 2-, 3- or 4-methoxypyridyl, especially 2-methoxypyridyl or 3-methoxypyridyl (in particular 2-methoxypyridin-5-yl, 3-methoxypyridin-5-yl); ethoxypyridyl, e.g., 2-, 3- or 4-ethoxypyridyl especially 2-ethoxypyridyl or 3-ethoxypyridyl (in particular 3-ethoxypyrid-5-yl, 2-ethoxypyrid-5-yl, 2-ethoxypyrid-4-yl); propoxypyridyl, e.g. n-propoxypyridyl or iso-propoxypyridyl (in particular 6-(n-propoxy)pyrid-3-yl or 3-(iso-propoxy)pyridin-5-yl or 2-(iso-propoxy)pyridin-4-yl);
- cycloalkoxypyridyl, e.g. cyclobutoxy-pyridyl, especially 3-cyclobutoxy-pyridyl (in particular 3-cyclobutoxy-pyrid-5-yl);
- (haloalkoxy)pyridyl e.g. (halo-isopropoxy)pyridyl, such as 3-(1,3-difluoropropan-2-yloxy)-pyridyl (in particular 3-(1,3-difluoropropan-2-yloxy)-pyrid-5-yl) or 3-(2-fluoroethan-1-yloxy)-pyridyl (in particular 3-(2-fluoroethan-1-yloxy)-pyrid-5-yl) or 3-(difluoromethyloxy)-pyridyl (in particular 3-(difluoromethyloxy)-pyrid-5-yl);
- cycloalkylalkoxypyridyl, e.g. cyclopropylmethoxy-pyridyl, especially 2-cyclopropylmethoxy-pyridyl (in particular 2-cyclopropylmethoxy-pyrid-5-yl);
- alkoxyalkylpyridyl e.g. ethoxymethylpyridyl, 2-methoxymethylpyridyl (in particular 2-methyoxymethylpyrid-5-yl) or 3-methoxymethylpyridyl (in particular 3-methoxymethylpyrid-5-yl) or 3-(2-methoxy-prop-2-yl)pyridyl (in particular 3-(2-ethoxy-prop-2-yl)pyrid-5-yl;
- alkoxyalkoxypyridyl, in particular methoxyethoxypyridyl, e.g. 3-(2-methoxyethoxy)pyridyl or 2-(2-methoxyethoxy)pyridyl (in particular 3(2-methoxyethoxy)pyrid-5-yl or 2-(2-methoxyethoxy)pyrid-5-yl);
- (alkyl)(alkoxyalkoxy)pyridyl, in particular (loweralkyl)(loweralkoxyalkoxy)pyridyl, such as (methyl)(methoxyethoxy)pyridyl, e.g. (2-methyl)-(3-(2-methoxyethoxy))pyridyl (in particular (2-methyl)-(3-(2-methoxyethoxy)))pyrid-5-yl;
- benzyloxyalkoxypyridyl, in particular benzyloxyethoxypyridyl or benzyloxypropoxypyridyl, e.g. 2-benzyloxyethoxypyridyl or 3-benzyloxypropoxypyridyl (in particular 2-benzyloxyethoxypyrid-5-yl or 3-benzyloxypropoxypyrid-5-yl);
- hydroxyalkylpyridyl, e.g. hydroxymethylpyridyl, especially 2-(hydroxymethyl)-pyridyl (in particular 2-hydroxymethylpyrid-5-yl) or hydroxyethylpyridyl, especially 3-(1-hydroxyethyl)-pyridyl (in particular 3-(1-hydroxyethyl)pyrid-5-yl) or hydroxypentylpyridyl (alternatively termed 1-hydroxy-1-ethyl-propyl), such as 3-(3-hydroxypentyl)-pyridyl especially 3-(3-hydroxypent-3-yl)pyridyl (in particular 3-(3-hydroxypent-3-yl)pyrid-5-yl) or hydroxypropylpyridyl, especially 3-(2-hydroxyprop-2-yl)-pyridyl (in particular 3-(2-hydroxyprop-2yl)pyrid-5-yl) or hydroxy-1,1-dimethyl-ethylpyridyl, especially 3(2-hydroxy-1,1-dimethyl-ethyl)-pyridyl (in particular 3-(2-hydroxy-1,1-dimethyl-ethyl)pyrid-5-yl);
- hydroxycycloalkylpyridyl, e.g. hydroxylowercycloalkylpyridyl, especially 3-(1-hydroxycyclopentyl)-pyridyl (in particular 3-(1-hydroxycyclopentyl)-pyrid-5-yl);
- hydroxyfluoroalkylpyridyl, e.g. hydroxyfluoropropylpyridyl, especially 3(1,3-difluoro-2-hydroxyprop-2-yl)-pyridyl (in particular 3-(1,3-difluoro-2-hydroxyprop-2-yl)pyrid-5-yl)
- aminoalkylpyridyl, e.g. aminomethylpyridyl, especially 3-(aminomethyl)-pyridyl (in particular 3-aminomethylpyrid-5-yl);
- alkyl-sulfonyl pyridyl, e.g. methanesulfonylpyridyl, especially 3-methanesulfonylpyridyl (in particular 3-methanesulfonylpyrid-5-yl);
- hydroxyalkoxypyridyl, e.g. 2-(2-hydroxyethoxy)-pyridyl or 2-(3-hydroxypropoxy)-pyridyl (in particular 2-(2-hydroxyethoxy)-pyrid-5-yl or 2-(3-hydroxypropoxy)-pyrid-5-yl);
- alkoxycarbonylpyridyl, e.g. methoxycarbonylpyridyl, especially 2-methoxycarbonyl-pyridyl (in particular 2-methoxycarbonyl-pyrid-5-yl);
- aminopyridyl, e.g. 2- or 3-aminopyridyl (in particular 2-aminopyrid-5-yl or 3-aminopyrid-5-yl);
- alkylaminopyridyl, e.g. loweralkylaminopyridyl, in particular methylaminopyridyl such as 2-methylaminopyridyl, 3-methylaminopyridyl or ethylaminopyridyl such as 2-ethylaminopyridyl (especially 2-methylaminopyrid-5-yl, 3-methylaminopyrid-5-yl or 3-ethylaminopyrid-5-yl) or isopropylaminopyridyl such as 3-isopropylaminopyridyl (especially 3-isopropylaminopyrid-5-yl;
- dialkylaminopyridyl, in particular di-loweralkylaminopyridyl, e.g. 2-, 3- or 4-dimethylaminopyridyl, especially 2-dimethylaminopyridyl or 3-dimethylaminopyridyl (in particular 2-dimethylaminopyrid-5-yl or 3-dimethylaminopyrid-5-yl) or e.g. 2-, 3- or 4-diethylaminopyridyl, especially 2-diethylaminopyridyl or 3-diethylaminopyridyl (in particular 2-diethylaminopyrid-5-yl or 3-diethylaminopyrid-5-yl) or e.g. 2-, 3- or 4-ethylmethylaminopyridyl especially 2-ethylmethylaminopyridyl (in particular 2-ethylmethylaminopyrid-5-yl or 3-ethylmethylaminopyridyl (in particular 3-ethylmethylaminopyrid-5-yl) or e.g. 2-, 3- or 4-isopropylmethylaminopyridyl, especially 2-isopropylmethylaminopyridyl or 3-isopropylmethylaminopyridyl (in particular 2-isopropylmethylaminopyrid-5-yl or 3-isopropylmethylaminopyrid-5-yl;
- cycloalkylaminopyridyl, e.g. cycloloweralkylaminopyridyl, in particular cyclobutylaminopyridyl such as 3-cyclobutylaminopyridyl or (especially 3-methylaminopyrid-5-yl);
- (N-alkyl-N-cycloalkylamino)pyridyl, e.g. (N-loweralkyl-N-cycloloweralkylamino)pyridyl, in particular (N-methyl-N-cyclobutylamino)pyridyl such as 3-(N-methyl-N-cyclobutylamino)pyridyl or (especially 3-(N-methyl-N-cyclobutylamino)pyrid-5-yl);

(alkyl)(amino)pyridyl, e.g. (loweralkyl)(amino)pyridyl, in particular (methyl)(amino)pyridyl such as 2-methyl-3-amino-pyridyl (especially 2-methyl-3-amino-pyrid-5-yl) or (ethyl)(amino)pyridyl such as 2-ethyl-3-amino-pyridyl (especially 2-ethyl-3-amino-pyrid-5-yl);

(halo)(amino)pyridyl, e.g. (fluoro)(amino)pyridyl, in particular 3-fluoro-2-amino-pyridyl (especially 3-fluoro-2-amino-pyrid-5-yl), 2-fluoro-3-amino-pyridyl (especially 2-fluoro-3-amino-pyrid-5-yl), 3-chloro-2-amino-pyridyl (especially 3-chloro-2-amino-pyrid-5-yl) or 2-chloro-3-amino-pyridyl (especially 2-chloro-3-amino-pyrid-5-yl);

(halo)(alkylamino)pyridyl, e.g. (halo)(loweralkylamino) pyridyl, in particular (fluoro)(methylamino)pyridyl such as 3-fluoro-2-methylamino-pyridyl (especially 3-fluoro-2-methylamino-pyrid-5-yl), 2-fluoro-3-methylamino-pyridyl (especially 2-fluoro-3-methylamino-pyrid-5-yl), 2-fluoro-3-ethylamino-pyridyl (especially 2-fluoro-3-ethylamino-pyrid-5-yl), 3-chloro-2-methylamino-pyridyl (especially 3-chloro-2-methylamino-pyrid-5-yl), 3-chloro-2-ethylamino-pyridyl (especially 3-chloro-2-ethylamino-pyrid-5-yl) or 2-chloro-3-ethylamino-pyridyl (especially 2-chloro-3-ethylamino-pyrid-5-yl);

(halo)(dialkylamino)pyridyl, e.g. (halo)(di-loweralkylamino)pyridyl, in particular (fluoro)(dimethylamino) pyridyl such as 2-fluoro-3-dimethylamino-pyridyl (especially 2-fluoro-3-dimethylamino-pyrid-5-yl);

(halo)(hydroxyalkyl)pyridyl, e.g. (halo)(hydroxyloweralkyl)pyridyl, in particular (chloro)(hydroxymethyl)pyridyl such as 3-chloro-2-hydroxymethyl-pyridyl (especially 3-chloro-2-hydroxymethyl-pyrid-5-yl)

(alkoxy)(alkyl)pyridyl e.g. (methoxy)(methyl)pyridyl, such as 3-methoxy-2-methyl-pyridyl (in particular 3-methoxy-2-methyl-pyrid-5-yl), (ethoxy)(methyl)pyridyl, such as 3-ethoxy-2-methyl-pyridyl (in particular 3-ethoxy-2-methyl-pyrid-5-yl) or e.g. (propoxy)(methyl)pyridyl, such as 3-propoxy-2-methyl-pyridyl (in particular 3-propoxy-2-methyl-pyrid-5-yl) or e.g. (propoxy)(ethyl)pyridyl, such as 3-propoxy-2-ethyl-pyridyl (in particular 3-propoxy-2-ethyl-pyrid-5-yl) or e.g. (ethoxy)(ethyl)pyridyl, such as 3-ethoxy-2-ethyl-pyridyl (in particular 3-ethoxy-2-ethyl-pyrid-5-yl);

(alkoxy)(alkoxy)pyridyl e.g. (propoxy)(methoxy)pyridyl, such as 3-propoxy-2-methoxy-pyridyl (in particular 3-propoxy-2-methoxy-pyrid-5-yl); or e.g. (propoxy)(ethoxy)pyridyl, such as 3-propoxy-2-ethoxy-pyridyl (in particular 3-propoxy-2-ethoxy-pyrid-5-yl) or e.g. (methoxy)(methoxy)pyridyl, such as 3-methoxy-2-methoxy-pyridyl (in particular 3-methoxy-2-methoxy-pyrid-5-yl) or e.g. (ethoxy)(methoxy)pyridyl, such as 3-ethoxy-2-methoxy-pyridyl (in particular 3-ethoxy-2-methoxy-pyrid-5-yl);

(alkoxy)(alkoxyalkyl)pyridyl e.g. (isopropoxy)(methoxymethyl)pyridyl, such as 3-isopropoxy-2-methoxymethyl-pyridyl (in particular 3-isopropoxy-2-methoxymethyl-pyrid-5-yl) or (methoxy)(methoxymethyl) pyridyl, such as 3-methoxy-2-methoxymethyl-pyridyl or 2-methoxy-3-methoxymethyl-pyridyl (in particular 3-methoxy-2-methoxymethyl-pyrid-5-yl or 2-methoxy-3-methoxymethyl-pyrid-5-yl) or (methoxy)(ethoxymethyl)pyridyl, such as 3-methoxy-2-ethoxymethyl-pyridyl (in particular 3-methoxy-2-ethoxymethyl-pyrid-5-yl) or (ethoxy)(methoxymethyl)pyridyl, such as 3-ethoxy-2-methoxymethyl-pyridyl (in particular 3-ethoxy-2-methoxymethyl-pyrid-5-yl);

(alkoxy)(deuteroalkoxy-alkyl)pyridyl e.g. (ethoxy)(trideuteromethoxymethyl)pyridyl, such as 3-ethoxy-2-trideuteromethoxymethyl-pyridyl (in particular 3-ethoxy-2-trideuteromethoxymethyl-pyrid-5-yl);

(alkoxy)(hydroxyalkyl)pyridyl e.g. (isopropoxy)(hydroxymethyl)pyridyl, such as 3-isopropoxy-2-hydroxymethyl-pyridyl (in particular 3-isopropoxy-2-hydroxymethyl-pyrid-5-yl) or (methoxy)(hydroxymethyl) pyridyl, such as 3-methoxy-2-hydroxymethyl-pyridyl (in particular 3-methoxy-2-hydroxymethyl-pyrid-5-yl) or 2-methoxy-3-hydroxymethyl-pyridyl (in particular 2-methoxy-3-hydroxymethyl-pyrid-5-yl) or (ethoxy) (hydroxymethyl)pyridyl, such as 3-ethoxy-2-hydroxymethyl-pyridyl (in particular 3-ethoxy-2-hydroxymethyl-pyrid-5-yl);

(haloalkoxy)(alkyl)pyridyl e.g. (halo-isopropoxy)(methyl)pyridyl, such as 3-(1,3-difluoropropan-2-yloxy)-2-(methyl)-pyridyl (in particular 3-(1,3-difluoropropan-2-yloxy)-2-(methyl)-pyrid-5-yl);

(haloalkoxy)(hydroxyalkyl)pyridyl e.g. (halo-isopropoxy) (hydroxymethyl)pyridyl, such as 3-(1,3-difluoropropan-2-yloxy)-2-(hydroxymethyl)-pyridyl (in particular 3-(1,3-difluoropropan-2-yloxy)-2-(hydroxymethyl)-pyrid-5-yl);

(alkoxyalkoxy)(hydroxyalkyl)pyridyl, in particular (loweralkoxy loweralkoxy)(hydroxyloweralkyl)pyridyl, e.g. (methoxyethoxy)(hydroxymethyl)pyridyl, such as 3-methoxyethoxy-2-hydroxymethyl-pyridyl (in particular 3-methoxyethoxy-2-hydroxymethyl-pyrid-5-yl);

(alkyl)(alkylamino)pyridyl, e.g. (loweralkyl)(loweralkylamino)pyridyl, in particular (methyl)(ethylamino)pyridyl such as 2-methyl-3-ethylamino-pyridyl (especially 2-methyl-3-ethylamino-pyrid-5-yl) or (methyl)(methylamino)pyridyl such as 3-methyl-2-methylamino-pyridyl (especially 3-methyl-2-methylamino-pyrid-5-yl) or (ethyl)(ethylamino)pyridyl such as 2-ethyl-3-ethylamino-pyridyl (especially 2-methyl-3-ethylamino-pyrid-5-yl) or (ethyl)(isopropylamino)pyridyl such as 2-ethyl-3-isopropylamino-pyridyl (especially 2-ethyl-3-isopropylamino-pyrid-5-yl);

(alkyl)(di-alkylamino)pyridyl, e.g. (loweralkyl)(di-loweralkylamino)pyridyl, in particular (methyl)(N-methyl-N-ethylamino)pyridyl such as 2-methyl-3-(N-methyl-N-ethylamino)-pyridyl (especially 2-methyl-3-(N-methyl-N-ethylamino)-pyrid-5-yl) or (methyl)(N,N-dimethylamino)pyridyl such as 2-methyl-3-(N,N-dimethylamino)-pyridyl (especially 2-methyl-3-(N,N-dimethylamino)-pyrid-5-yl);

cycloaminopyridyl, e.g. azetidinylpyridyl, especially 2-azetidin-1-yl-pyridinyl (in particular 2-azetidin-1-yl-pyridin-5-yl) or 3-azetidin-1-yl-pyridinyl (in particular 3-azetidin-1-yl-pyridin-5-yl) or pyrrolidinylpyridyl, especially 2-pyrrolidinyl-1-yl-pyridinyl (in particular 2-pyrrolidinyl-1-yl-pyridin-5-yl);

cyclic ether-substituted amino-pyridyl, e.g. tetrahydropyranylamino-pyridyl, especially 2-(tetrahydro-pyran-4-ylamino)-pyridyl (in particular 2-(tetrahydro-pyran-4-ylamino)pyridyl-5-yl;

hydroxy-cycloaminopyridyl, such as hydroxy-pyrrolidinylpyridyl, e.g. 3-hydroxy-pyrrolidin-1-yl-pyridinyl (in particular 6-(3-hydroxy-pyrrolidin-1-yl)-pyridin-3-yl, more particularly, 6-((R)-3-hydroxy-pyrrolidin-1-yl)-pyridin-3-yl or 6-((S)3-hydroxy-pyrrolidin-1-yl)-pyridin-3-yl;

loweralkoxy-cycloaminopyridyl, such as methoxy-pyrrolidinylpyridyl, e.g. 3-methoxy-pyrrolidin-1-yl-pyridinyl (in particular 6-(3-methoxy-pyrrolidin-1-yl)-pyridin-3-yl, more particularly, 6-((R)-3-methoxy-pyrrolidin-1-yl)-pyridin-3-yl or 64(S)3-methoxy-pyrrolidin-1-yl)-pyridin-3-yl;

hydroxyalkylaminopyridyl, e.g. 2-(2-hydroxyethylamino)-pyridyl (in particular 2-(2-hydroxyethylamino)-pyrid-5-yl);

(alkyl)(hydroxy)pyridyl, in particular (loweralkyl)(hydroxy)pyridyl e.g. 2-(methyl)-3-(hydroxy)-pyridyl (in particular 2-(methyl)-3-(hydroxy)-pyrid-5-yl) or 2-(ethyl)-3-(hydroxy)-pyridyl (in particular 2-(ethyl)-3-(hydroxy)-pyrid-5-yl);

(hydroxyalkyl)(alkylamino)pyridyl, in particular (hydroxyloweralkyl)(loweralkylamino)pyridyl, such as (hydroxymethyl)(ethylamino)-pyridyl, e.g. 2-(hydroxymethyl)-3-(ethylamino)-pyridyl (in particular 2-(hydroxymethyl)-3-(ethylamino)-pyrid-5-yl) or such as (hydroxymethyl)(methylamino)-pyridyl, e.g. 2-(hydroxymethyl)-3-(methylamino)-pyridyl (in particular 2-(hydroxymethyl)-3-(methylamino)-pyrid-5-yl) 3-(hydroxymethyl)-2-(methylamino)-pyridyl (in particular 3-(hydroxymethyl)-2-(methylamino)-pyrid-5-yl);

(hydroxyalkyl)(amino)pyridyl, in particular (hydroxyloweralkyl)(amino)pyridyl, such as (hydroxymethyl)(amino)-pyridyl, e.g. 3-(hydroxymethyl)-2-(amino)-pyridyl (in particular 3-(hydroxymethyl)-2-(amino)-pyrid-5-yl);

(alkoxyalkyl)(alkylamino)pyridyl, in particular (loweralkoxyloweralkyl)(loweralkylamino)pyridyl, such as (methoxymethyl)(ethylamino)-pyridyl, e.g. 2-(methoxymethyl)-3-(ethylamino)-pyridyl (in particular 2-(methoxymethyl)-3-(ethylamino)-pyrid-5-yl) or such as (methoxymethyl)(methylamino)-pyridyl, e.g. 2-(methoxymethyl)-3-(methylamino)-pyridyl (in particular 2-(methoxymethyl)-3-(methylamino)-pyrid-5-yl or or such as (ethoxymethyl)(ethylamino)-pyridyl, e.g. 3-(ethoxymethyl)-2-(ethylamino)-pyridyl (in particular 3-(ethoxymethyl)-2-(methylamino)-pyrid-5-yl;

(alkoxyalkyl)(amino)pyridyl, in particular (alkoxyloweralkyl)(amino)pyridyl, such as (ethoxymethyl)(amino)-pyridyl, e.g. 3-(ethoxymethyl)-2-(amino)-pyridyl (in particular 3-(ethoxymethyl)-2-(amino)-pyrid-5-yl) or (methoxymethyl)(amino)-pyridyl, e.g. 3-(methoxymethyl)-2-(amino)-pyridyl (in particular 3-(methoxymethyl)-2-(amino)-pyrid-5-yl);

amino-haloloweralkyl-pyridyl, e.g. amino-trifluoromethyl-pyridyl, especially 2-amino-3-trifluoromethyl-pyridyl (in particular 2-amino-3-trifluoromethyl-pyrid-5-yl);

alkylamino-haloalkyl-pyridyl, such as loweralkylamino-haloloweralkyl-pyridyl, e.g. methylamino-trifluoromethyl-pyridyl, especially 2-methylamino-3-trifluoromethyl-pyridyl (in particular 2-methylamino-3-trifluoromethyl-pyrid-5-yl) or e.g. ethylamino-trifluoromethyl-pyridyl, especially 2-ethylamino-3-trifluoromethyl-pyridyl (in particular 2-ethylamino-3-trifluoromethyl-pyrid-5-yl);

haloalkyl-deuteroloweralkylamino-pyridyl, e.g. trifluoromethyl-trideuteromethylamino-pyridyl, especially 3-trifluoromethyl-2-trideuteromethylamino-pyridyl (in particular 3-trifluoromethyl-2-trideuteromethylamino-pyrid-5-yl);

haloalkylpyridinyl, in particular haloloweralkylpyridyl, especially, 2-, 3- or 4-trifluoromethylpyridyl, most especially 2-trifluoromethylpyridyl (in particular 2-trifluoromethylpyrid-5-yl);

cyanoalkylpyridinyl, in particular cyanoloweralkylpyridyl, especially, cyanopropylpyridyl, most especially 2-cyanoprop-2-ylpyridyl (in particular 3-(2-cyanoprop-2-yl)-pyrid-5-yl);

cyanocycloalkylpyridinyl, in particular cyanolowercycloalkylpyridyl, especially, cyanocyclobutylpyridyl, most especially 1-cyanocyclobutylpyridyl (in particular 3-(1-cyanocyclobutyl)-pyrid-5-yl);

halopyridyl, in particular fluoropyridyl, especially 2-fluoropyridyl (in particular 2-fluoropyrid-3-yl or 2-fluoropyrid-4-yl);

halo-alkoxy-pyridyl, e.g. fluoro-methoxy-pyridyl such as 3-fluoro-2-methoxy-pyridyl (in particular 3-fluoro-2-methoxy-pyrid-5-yl);

carbamoylpyridyl, especially 2-(carbamoyl)pyridyl (in particular 2-(carbamoyl)pyrid-5-yl); alkyl-substituted carbamoyl, e.g. methylcarbamoyl, especially 2-(methylcarbamoyl)pyridyl (in particular 2-(methylcarbamoyl)pyrid-5-yl);

piperazinylpyridyl, e.g. 1-piperazinylpyridyl, especially 2-(1-piperazinyl)pyridyl (in particular 2-(1-piperazinyl) pyrid-5-yl); N-alkylpiperazinylpyridyl, such as N-loweralkylpiperazinylpyridyl, e.g. N-methylpiperazinylpyridyl, especially 2-(4-methylpiperazin-1-yl)-pyridyl (in particular 2-(4-methylpiperazin-1-yl)-pyrid-5-yl);

alkylsulfonamidopyridyl, such as loweralkylsulfonamidopyridyl, especially methylsulfonamidopyridyl, e.g. 3-(methylsulfonamido) pyridyl (in particular 3-(methylsulfonamido)-pyridin-5-yl);

dialkylsulfonamidopyridyl, such as diloweralkylsulfonamidopyridyl, especially dimethylsulfonamidopyridyl, e.g. 3-(dimethylsulfonamido) pyridyl (in particular 3-(dimethylsulfonamido)-pyridin-5-yl);

(alkylsulfonamido)(alkyl)pyridyl such as (loweralkylsulfonamido)(loweralkyl)pyridyl, especially (methylsulfonamido)(methyl)pyridyl, e.g. 3-(methylsulfonamido) (methyl)pyridyl (in particular 3-(methylsulfonamido)-2-methyl pyridin-5-yl);

(alkylsulfonamido)(halo)pyridyl such as (loweralkylsulfonamido)(chloro)pyridyl, especially (methylsulfonamido)(chloro)pyridyl, e.g. 3-(methylsulfonamido) (chloro)pyridyl (in particular 3-(methylsulfonamido)-2-chloro-pyridin-5-yl);

(alkylsulfonamidoalkyl)pyridyl such as (loweralkylsulfonamido-loweralkyl)pyridyl, especially (methylsulfonamidomethyl)pyridyl, e.g. 3-(methylsulfonamidomethyl)pyridyl (in particular 3-(methylsulfonamidomethyl)-pyridin-5-yl);

dialkylsulfonamido(alkyl)pyridyl, such as diloweralkylsulfonamido(loweralkyl)pyridyl, especially dimethylsulfonamido(methyl)pyridyl, e.g. 3-(dimethylsulfonamido)(2-methyl)pyridyl (in particular 3-(dimethylsulfonamido)-(2-methyl)-pyridin-5-yl);

3H-tetrazol-5-yl pyridyl, e.g. 2-(3H-tetrazol-5-yl)pyridyl (in particular 2-(3H-tetrazol-5-yl)pyrid-5-yl);

alkylcarbonylaminoalkylpyridyl, such as loweralkylcarbonylaminoloweralkyl)pyridyl, e.g. methylcarbonylaminomethylpyridyl, especially 3-methylcarbonylaminomethylpyridyl (in particular 3-methylcarbonylaminomethylpyrid-5-yl);

(halo)(alkylcarbonylamino)pyridyl, such as (halo)(loweralkylcarbonylamino)pyridyl, e.g. (chloro)(methylcarbonylamino)pyridyl, especially 2-(chloro)-3-(methylcarbonylamino)pyridyl (in particular 2-(chloro)-3-(methylcarbonylamino)pyrid-5-yl);

(alkoxy)(alkylcarbonylamino)pyridyl, such as (loweralkoxy)(loweralkylcarbonylamino) pyridyl, e.g. (methoxy)(methylcarbonylamino)pyridyl or (ethoxy)(methylcarbonylamino)pyridyl, especially 2-(methoxy)-3-(methylcarbonylamino)pyridyl or 2-(ethoxy)-3-(methylcarbonylamino)pyridyl (in particular 2-(methoxy)-3-(methylcarbonylamino)pyrid-5-yl or 2-(ethoxy)-3-(methylcarbonylamino)pyrid-5-yl);

(alkoxy)(alkylcarbonyl-N-alkylamino)pyridyl, such as (loweralkoxy)(loweralkylcarbonyl-N-loweralkylamino)pyridyl, e.g. (methoxy)(methylcarbonyl-N-methylamino)pyridyl or (ethoxy)(methylcarbonyl-N-methylamino)pyridyl, especially 2-(methoxy)-3-(methylcarbonyl-N-methylamino)pyridyl or 2-(ethoxy)-3-(methylcarbonyl-N-methylamino)pyridyl (in particular 2-(methoxy)-3-(methylcarbonyl-N-methylamino)pyrid-5-yl or 2-(ethoxy)-3-(methylcarbonyl-N-methylamino)pyrid-5-yl);

(alkoxy)(nitro)pyridyl, such as (loweralkoxy)(nitro)pyridyl, e.g. (methoxy)(nitro)pyridyl, especially 2-(methoxy)-3-(nitro)-pyridyl (in particular 2-(methoxy)-3-(nitro)-pyrid-5-yl);

(alkoxy)(cyano)pyridyl, such as (loweralkoxy)(cyano)pyridyl, e.g. (methoxy)(cyano)pyridyl, especially 2-(methoxy)-3-(cyano)-pyridyl (in particular 2-(methoxy)-3-(cyano)-pyrid-5-yl);

(alkoxy)(amino)pyridyl, such as (loweralkoxy)(amino)pyridyl, e.g. (methoxy)(amino)pyridyl, especially 2-(methoxy)-3-(amino)-pyridyl (in particular 2-(methoxy)-3-(amino)-pyrid-5-yl);

(alkoxy)(alkylamino)pyridyl, such as (loweralkoxy)(alkylamino)pyridyl, e.g. (methoxy)(ethylamino)pyridyl, especially 2-(methoxy)-3-(ethylamino)pyridyl (in particular 2-(methoxy)-3-(ethylamino)pyrid-5-yl;

(alkoxyalkyl)(alkylamino)pyridyl, such as (loweralkoxy-loweralkyl)(alkylamino)pyridyl, e.g. (methoxymethyl)(methylamino)pyridyl, especially 3-(methoxymethyl)-2-(methylamino)pyridyl (in particular 3-(methoxymethyl)-2-(methylamino)pyrid-5-yl) or (methoxymethyl)(ethylamino)pyridyl, especially 3-(methoxymethyl)-2-(ethylamino)pyridyl (in particular 3-(methoxymethyl)-2-(ethylamino)pyrid-5-yl);

(alkoxy)(alkylaminocarbonyl)pyridyl, such as (loweralkoxy)(loweralkylaminocarbonyl)pyridyl, e.g. (methoxy)(methylaminocarbonyl)pyridyl, especially 2-(methoxy)-3-(methylaminocarbonyl)pyridyl (in particular 2-(methoxy)-3-(methylaminocarbonyl)pyrid-5-yl;

alkylaminocarbonylalkylpyridyl, such as loweralkylaminocarbonylloweralkylpyridyl, e.g. methylaminocarbonylmethylpyridyl, especially 3-methylaminocarbonylmethylpyridyl (in particular 3-methylaminocarbonylmethylpyrid-5-yl;

(amino)(alkylaminocarbonyl)pyridyl, such as (amino)(loweralkylaminocarbonyl)pyridyl, e.g. (amino)(methylaminocarbonyl)pyridyl, especially 2-(amino)-3-(methylaminocarbonyl)pyridyl (in particular 2-(amino)-3-(methylaminocarbonyl)pyrid-5-yl) or (amino)(ethylaminocarbonyl)pyridyl, especially 2-(amino)-3-(ethylaminocarbonyl)pyridyl (in particular 2-(amino)-3-(ethylaminocarbonyl)pyrid-5-yl) or (amino)(isopropylaminocarbonyl)pyridyl, especially 2-(amino)-3-(isopropylaminocarbonyl)pyridyl (in particular 2-(amino)-3-(isopropylaminocarbonyl)pyrid-5-yl);

(amino)(alkoxyalkylaminocarbonyl)pyridyl, such as amino)(loweralkoxyloweralkylaminocarbonyl)pyridyl, e.g. (amino)(methoxyethylaminocarbonyl)pyridyl, especially 2-(amino)-3-(2-methoxyethylaminocarbonyl)pyridyl (in particular 2-(amino)-3-(2-methoxyethylaminocarbonyl)pyrid-5-yl)

(alkylamino)(alkylaminocarbonyl)pyridyl, such as (loweralkylamino)(loweralkylaminocarbonyl)pyridyl, e.g. (methylamino)(ethylaminocarbonyl)pyridyl, especially 2-(methylamino)-3-(ethylaminocarbonyl)pyridyl (in particular 2-(methylamino)-3-(ethylaminocarbonyl)pyrid-5-yl);

(alkoxy)(aminocarbonyl)pyridyl, such as (loweralkoxy)(aminocarbonyl)pyridyl, e.g. (methoxy)(aminocarbonyl)pyridyl, especially 2-(methoxy)-3-(aminocarbonyl)pyridyl (in particular 2-(methoxy)-3-(aminocarbonyl)pyrid-5-yl);

(alkoxy)(hydroxycarbonyl)pyridyl, such as (loweralkoxy)(hydroxycarbonyl)pyridyl, e.g. (methoxy)(hydroxycarbonyl)pyridyl, especially 2-(methoxy)-3-(hydroxycarbonyl)pyridyl (in particular 2-(methoxy)-3-(hydroxycarbonyl)pyrid-5-yl;

morpholinylpyridinyl, such as morpholin-4-ylpyridinyl, e.g. 3-morpholin-4-ylpyridinyl, especially 3-morpholin-4-ylpyridin-5-yl;

(1H-pyrazolyl)-pyridinyl, such as (1H-pyrazol-1yl)-pyridinyl, especially 2-(1H-pyrazol-1yl)-pyridinyl, in particular (1H-pyrazol-1yl)-pyridin-5-yl;

loweralkyl substituted (1H-imidazol-1-yl)-pyridinyl, such as methyl-substituted (1H-imidazol-1-yl)-pyridinyl, e.g. (2-methyl-1H-imidazol-1-yl)-pyridinyl, especially (2-methyl-1H-imidazol-1-yl)-pyridin-5-yl;

pyrimidinyl, in particular pyrimidin-5-yl;

di-loweralkylaminopyrimidinyl, e.g. 2- or 4-dimethylaminopyrimidinyl, especially 2-dimethylaminopyrimidinyl (in particular 2-dimethylaminopyrimidin-5-yl);

alkoxypyrimidinyl, in particular methoxypyrimidinyl or ethoxypyrimidinyl, e.g. 2-methoxypyrimidinyl or 2-ethoxypyrimidinyl (in particular 2-methoxypyrimidin-5-yl or 2-ethoxypyrimidin-5-yl);

di-alkoxypyrimidinyl, in particular di-methoxypyrimidinyl, e.g. 2,4-dimethoxypyrimidinyl or (in particular 2,4-dimethoxypyrimidin-5-yl);

(alkylamino)(alkoxy)pyrimidinyl, in particular (loweralkylamino)(loweralkoxy)pyrimidinyl, e.g. (methylamino)(methoxy)pyrimidinyl or (ethylamino)(methoxy)pyrimidinyl e.g. 2-(methylamino)-4-(methoxy)pyrimidinyl or 2-(ethylamino)-4-(methoxy)pyrimidinyl (in particular 2-(methylamino)-4-(methoxy)pyrimidin-5-yl or 2-(ethylamino)-4-(methoxy)pyrimidin-5-yl);

cycloaminopyrimidinyl, e.g. pyrrolidinylpyrimidinyl, especially 2-(pyrrolidinyl)pyrimidinyl (in particular 2-(pyrrolidinyl)pyrimidin-5-yl);

aminopyrimidinyl, in particular 2-aminopyrimidinyl (especially 2-aminopyrimidin-5-yl;

alkylaminopyrimidinyl, in particular loweralkylaminopyrimidinyl, e.g. 2-methylaminopyrimidinyl (especially 2-methylaminopyrimidin-5-yl);

dialkylaminopyrimidinyl, in particular di-loweralkylaminopyrimidinyl, e.g. 2-dimethylaminopyrimidinyl (especially 2-dimethylaminopyrimidin-5-yl);

1H-pyrrolo[2,3-b]pyridinyl (in particular 1H-pyrrolo[2,3-b]pyridin-5-yl);

1-methyl-1H-pyrrolo[2,3-b]pyridinyl (in particular 1-methyl-1H-pyrrolo[2,3-b]pyridin-5-yl);

pyrazinyl;

pyrazolyl, e.g. pyrazol-4yl;

substituted pyrazolyl, e.g. hydroxyalkylpyrazolyl, especially 1-(2-hydroxy-ethyl)-1H-pyrazolyl (in particular 1-(2-hydroxy-ethyl)-1H-pyrazol-4-yl) or 1-[2-(tetrahydro-pyran-2-yloxy)-ethyl]-1H-pyrazolyl (in particular 1-[2-(tetrahydro-pyran-2-yloxy)-ethyl]-1H-pyrazol-4-yl);

quinolinyl (in particular quinolin-3-yl);

2-oxo-2,3-dihydro-1H-indol-5-yl;

1-methyl-2,3-dihydro-1H-indol-5-yl;

1H-imidazo[4,5-b]pyridin-2(3H)-one-6-yl (in particular 1,3-dimethyl-1H-imidazo[4,5-b]pyridin-2(3H)-one-6-yl, 1-ethyl-3-methyl-1H-imidazo[4,5-b]pyridin-2(3H)-one-6-yl or 1-(2-methoxyethyl)-3-methyl-1H-imidazo[4,5-b]pyridin-2(3H)-one-6-yl;

3H-imidazo[4,5-b]pyridin-6-yl, e.g. (3-methyl)-3H-imidazo[4,5-b]pyridin-6-yl, (2-methyl)-(3-methyl)-3H-imidazo[4,5-b]pyridin-6-yl, (2-methoxy)-(3-methyl)-3H-imidazo[4,5-b]pyridin-6-yl, (2-dimethylamino)-(3-methyl)-3H-imidazo[4,5-b]pyridin-6-yl;

3H-[1,2,3]triazolo[4,5-b]pyridin-6-yl, e.g. (3-methyl)-3H-[1,2,3]triazolo[4,5-b]pyridin-6-yl;

1H-pyrrolo[3,2-b]pyridinyl, e.g. 1H-pyrrolo[3,2-b]pyridin-6-yl;

1-methyl-1H-pyrrolo[3,2-b]pyridinyl, e.g. 1-methyl-1H-pyrrolo[3,2-b]pyridin-6-yl;

2-oxo-1,4-dihydro-2H-pyrido[2,3-d][1,3]oxazinyl, e.g. 2-oxo-1,4-dihydro-2H-pyrido[2,3-d][1,3]oxazin-6-yl, in particular 1-methyl-2-oxo-1,4-dihydro-2H-pyrido[2,3-d][1,3]oxazinyl, especially 1-methyl-2-oxo-1,4-dihydro-2H-pyrido[2,3-d][1,3]oxazin-6-yl;

3,4-dihydro-2H-pyrido[3,2-b][1,4]oxazinyl, e.g. 3,4-dihydro-2H-pyrido[3,2-b][1,4]oxazin-7-yl, in particular 4-methyl-3,4-dihydro-2H-pyrido[3,2-b][1,4]oxazinyl, especially 4-methyl-3,4-dihydro-2H-pyrido[3,2-b][1,4]oxazin-7-yl;

1,3,3-trimethyl-2-oxo-2,3-dihydro-1H-pyrrolo[2,3-b]pyridinyl, in particular 1,3,3-trimethyl-2-oxo-2,3-dihydro-1H-pyrrolo[2,3-b]pyridin-5-yl;

2-oxo-1,4-dihydro-2H-pyrido[3,2-d][1,3]oxazinyl, e.g. 2-oxo-1,4-dihydro-2H-pyrido[3,2-d][1,3]oxazin-7-yl, in particular 1-ethyl-2-oxo-1,4-dihydro-2H-pyrido[3,2-d][1,3]oxazinyl, especially 1-ethyl-2-oxo-1,4-dihydro-2H-pyrido[3,2-d][1,3]oxazin-7-yl.

In another embodiment, specifically preferred unsubstituted or substituted heterocyclyl or heteroaryl for $R^3$ is selected from:

pyridyl, e.g. pyrid-2-yl, pyrid-3-yl or pyrid-4-yl;

alkylpyridyl, in particular loweralkylpyridyl, e.g. methylpyridyl, e.g., 2-, 3- or 4-methylpyridyl, especially 2-methylpyridyl or 3-methylpyridyl, in particular 2-methylpyrid-5-yl or 3-methylpyrid-5-yl;

alkoxypyridyl, in particular lower-alkoxypyridyl, e.g. methoxypyridyl, e.g., 2-, 3- or 4-methoxypyridyl, especially 2-methoxypyridyl or 3-methoxypyridyl (in particular 2-methoxypyridin-5-yl, 3-methoxypyridin-5-yl); ethoxypyridyl, e.g., 2-, 3- or 4-ethoxypyridyl especially 2-ethoxypyridyl or 3-ethoxypyridyl (in particular 3-ethoxypyrid-5-yl, 2-ethoxypyrid-5-yl, 2-ethoxypyrid-4-yl); propoxypyridyl, e.g. n-propoxypyridyl or iso-propoxypyridyl (in particular 6-(n-propoxy)pyrid-3-yl or 3-(iso-propoxy)pyridin-5-yl);

cycloalkylalkoxypyridyl, e.g. cyclopropylmethoxy-pyridyl, especially 2-cyclopropylmethoxy-pyridyl (in particular 2-cyclopropylmethoxy-pyrid-5-yl);

alkoxyalkylpyridyl e.g. ethoxymethylpyridyl, 2-methoxymethylpyridyl (in particular 2-methoxymethylpyrid-5-yl);

alkoxyalkoxypyridyl, in particular methoxyethoxypyridyl, e.g. 3-(2-methoxyethoxy)pyridyl or 2-(2-methoxyethoxy)pyridyl (in particular 3-(2-methoxyethoxy)pyrid-5-yl or 2-(2-methoxyethoxy)pyrid-5-yl);

benzyloxyalkoxypyridyl, in particular benzyloxyethoxypyridyl or benzyloxypropoxypyridyl, e.g. 2-benzyloxyethoxypyridyl or 3-benzyloxypropoxypyridyl (in particular 2-benzyloxyethoxypyrid-5-yl or 3-benzyloxypropoxypyrid-5-yl);

hydroxyalkylpyridyl, e.g. hydroxymethylpyridyl, especially 2-(hydroxymethyl)-pyridyl (in particular 2-hydroxymethylpyrid-5-yl);

alkyl-sulfonyl pyridyl, e.g. methanesulfonylpyridyl, especially 3-methanesulfonylpyridyl (in particular 3-methanesulfonylpyrid-5-yl);

hydroxyalkoxypyridyl, e.g. 2-(2-hydroxyethoxy)-pyridyl or 2-(3-hydroxypropoxy)-pyridyl (in particular 2-(2-hydroxyethoxy)-pyrid-5-yl or 2-(3-hydroxypropoxy)-pyrid-5-yl);

alkoxycarbonylpyridyl, e.g. methoxycarbonylpyridyl, especially 2-methoxycarbonyl-pyridyl (in particular 2-methoxycarbonyl-pyrid-5-yl);

aminopyridyl, e.g. 2- or 3-aminopyridyl (in particular 2-aminopyrid-5-yl or 3-aminopyrid-5-yl);

alkylaminopyridyl, e.g. loweralkylaminopyridyl, in particular methylaminopyridyl such as 2-methylaminopyridyl or ethylaminopyridyl such as 2-ethylaminopyridyl (especially 2-methylaminopyrid-5-yl or 3-ethylaminopyrid-5-yl);

dialkylaminopyridyl, in particular di-loweralkylaminopyridyl, e.g. 2-, 3- or 4-dimethylaminopyridyl, especially 2-dimethylaminopyridyl (in particular 2-dimethylaminopyrid-5-yl) or e.g. 2-, 3- or 4-diethylaminopyridyl, especially 2-diethylaminopyridyl (in particular 3-diethylaminopyrid-5-yl) or e.g. 2-, 3- or 4-ethylmethylaminopyridyl especially 2-ethylmethylaminopyridyl (in particular 2-ethylmethylaminopyrid-5-yl);

(alkyl)(amino)pyridyl, e.g. (loweralkyl)(amino)pyridyl, in particular (methyl)(amino)pyridyl such as 2-methyl-3-amino-pyridyl (especially 2-methyl-3-amino-pyrid-5-yl);

(alkoxy)(amino)pyridyl, e.g. (loweralkoxy)(amino)pyridyl, in particular (methoxy)(amino)pyridyl such as 2-methoxy-3-amino-pyridyl (especially 2-methoxy-3-amino-pyrid-5-yl);

(alkoxy)(alkyl)pyridyl e.g. (ethoxy)(methyl)pyridyl, such as 3-ethoxy-2-methyl-pyridyl (in particular 3-ethoxy-2-methyl-pyrid-5-yl) or e.g. (propoxy)(methyl)pyridyl, such as 3-propoxy-2-methyl-pyridyl (in particular 3-propoxy-2-methyl-pyrid-5-yl);

(alkoxy)(alkoxy)pyridyl e.g. (propoxy)(methoxy)pyridyl, such as 3-propoxy-2-methoxy-pyridyl (in particular 3-propoxy-2-methoxy-pyrid-5-yl); or e.g. (propoxy)(ethoxy)pyridyl, such as 3-propoxy-2-ethoxy-pyridyl (in particular 3-propoxy-2-ethoxy-pyrid-5-yl);

(alkyl)(alkylamino)pyridyl, e.g. (loweralkyl)(loweralkylamino)pyridyl, in particular (methyl)(ethylamino)pyridyl such as 2-methyl-3-ethylamino-pyridyl (especially 2-methyl-3-ethylamino-pyrid-5-yl);

(alkyl)(di-alkylamino)pyridyl, e.g. (loweralkyl)(di-loweralkylamino)pyridyl, in particular (methyl)(N-methyl-N-ethylamino)pyridyl such as 2-methyl-3-(N-methyl-N-ethylamino)-pyridyl (especially 2-methyl-3-(N-methyl-N-ethylamino)-pyrid-5-yl)

cycloaminopyridyl, e.g. azetidinylpyridyl, especially 2-azetidin-1-yl-pyridinyl (in particular 2-azetidin-1-yl-pyridin-5-yl);

hydroxyalkylaminopyridyl, e.g. 2-(2-hydroxyethylamino)-pyridyl (in particular 2-(2-hydroxyethylamino)-pyrid-5-yl); amino-haloloweralkyl-pyridyl, e.g. amino-trifluoromethyl-pyridyl, especially 2-amino-3-trifluoromethyl-pyridyl (in particular 2-amino-3-trifluoromethyl-pyrid-5-yl);

haloalkylpyridinyl, in particular haloloweralkylpyridyl, especially, 2-, 3- or 4-trifluoromethylpyridyl, most especially 2-trifluoromethylpyridyl (in particular 2-trifluoromethylpyrid-5-yl);

halopyridyl, in particular fluoropyridyl, especially 2-fluoropyridyl (in particular 2-fluoropyrid-3-yl or 2-fluoropyrid-4-yl);

halo-alkoxy-pyridyl, e.g. fluoro-methoxy-pyridyl such as 3-fluoro-2-methoxy-pyridyl (in particular 3-fluoro-2-methoxy-pyrid-5-yl);

carbamoylpyridyl, especially 2-(carbamoyl)pyridyl (in particular 2-(carbamoyl) pyrid-5-yl); alkyl-substituted carbamoyl, e.g. methylcarbamoyl, especially 2-(methylcarbamoyl)pyridyl (in particular 2-(methylcarbamoyl)pyrid-5-yl);

piperazinylpyridyl, e.g. 1-piperazinylpyridyl, especially 2-(1-piperazinyl)pyridyl (in particular 2-(1-piperazinyl) pyrid-5-yl); N-alkylpiperazinylpyridyl, such as N-loweralkylpiperazinylpyridyl, e.g. N-methylpiperazinylpyridyl, especially 2-(4-methylpiperazin-1-yl)-pyridyl (in particular 2-(4-methylpiperazin-1-yl)-pyrid-5-yl);

alkylsulfonamidopyridyl, such as loweralkylsulfonamidopyridyl, especially methylsulfonamidopyridyl, e.g. 3-(methylsulfonamido) pyridyl (in particular 3-(methylsulfonamido)-pyridin-5-yl);

dialkylsulfonamidopyridyl, such as diloweralkylsulfonamidopyridyl, especially dimethylsulfonamidopyridyl, e.g. 3-(dimethylsulfonamido) pyridyl (in particular 3-(dimethylsulfonamido)-pyridin-5-yl);

(alkylsulfonamido)(alkyl)pyridyl such as (loweralkylsulfonamido)(loweralkyl)pyridyl, especially (methylsulfonamido)(methyl)pyridyl, e.g. 3-(methylsulfonamido) (methyl)pyridyl (in particular 3-(methylsulfonamido)-2-methyl pyridin-5-yl);

dialkylsulfonamido(alkyl)pyridyl, such as diloweralkylsulfonamido(loweralkyl)pyridyl, especially dimethylsulfonamido(methyl)pyridyl, e.g. 3-(dimethylsulfonamido)(2-methyl)pyridyl (in particular 3-(dimethylsulfonamido)-(2-methyl)-pyridin-5-yl);

3H-tetrazol-5-yl pyridyl, e.g. 2-(3H-tetrazol-5-yl)pyridyl (in particular 2-(3H-tetrazol-5-yl)pyrid-5-yl);

(alkoxy)(alkylcarbonylamino)pyridyl, such as (loweralkoxy)(loweralkylcarbonylamino) pyridyl, e.g. (methoxy)(methylcarbonylamino)pyridyl or (ethoxy)(methylcarbonylamino)pyridyl, especially 2-(methoxy)-3-(methylcarbonylamino)pyridyl or 2-(ethoxy)-3-(methylcarbonylamino)pyridyl (in particular 2-(methoxy)-3-(methylcarbonylamino)pyrid-5-yl or 2-(ethoxy)-3-(methylcarbonylamino)pyrid-5-yl);

(alkoxy)(alkylcarbonyl-N-alkylamino)pyridyl, such as (loweralkoxy)(loweralkylcarbonyl-N-loweralkylamino)pyridyl, e.g. (methoxy)(methylcarbonyl-N-methylamino)pyridyl or (ethoxy)(methylcarbonyl-N-methylamino)pyridyl, especially 2-(methoxy)-3-(methylcarbonyl-N-methylamino)pyridyl or 2-(ethoxy)-3-(methylcarbonyl-N-methylamino)pyridyl (in particular 2-(methoxy)-3-(methylcarbonyl-N-methylamino)pyrid-5-yl or 2-(ethoxy)-3-(methylcarbonyl-N-methylamino)pyrid-5-yl);

(alkoxy)(nitro)pyridyl, such as (loweralkoxy)(nitro)pyridyl, e.g. (methoxy)(nitro)pyridyl, especially 2-(methoxy)-3-(nitro)-pyridyl (in particular 2-(methoxy)-3-(nitro)-pyrid-5-yl);

(alkoxy)(cyano)pyridyl, such as (loweralkoxy)(cyano)pyridyl, e.g. (methoxy)(cyano)pyridyl, especially 2-(methoxy)-3-(cyano)-pyridyl (in particular 2-(methoxy)-3-(cyano)-pyrid-5-yl);

(alkoxy)(amino)pyridyl, such as (loweralkoxy)(amino)pyridyl, e.g. (methoxy)(amino)pyridyl, especially 2-(methoxy)-3-(amino)-pyridyl (in particular 2-(methoxy)-3-(amino)-pyrid-5-yl);

(alkoxy)(alkylamino)pyridyl, such as (loweralkoxy)(alkylamino)pyridyl, e.g. (methoxy)(ethylamino)pyridyl, especially 2-(methoxy)-3-(ethylamino)pyridyl (in particular 2-(methoxy)-3-(ethylamino)pyrid-5-yl;

(alkoxy)(alkylaminocarbonyl)pyridyl, such as (loweralkoxy)(loweralkylaminocarbonyl)pyridyl, e.g. (methoxy)(methylaminocarbonyl)pyridyl, especially 2-(methoxy)-3-(methylaminocarbonyl)pyridyl (in particular 2-(methoxy)-3-(methylaminocarbonyl)pyrid-5-yl;

(alkoxy)(hydroxycarbonyl)pyridyl, such as (loweralkoxy) (hydroxycarbonyl)pyridyl, e.g. (methoxy)(hydroxycarbonyl)pyridyl, especially 2-(methoxy)-3-(hydroxycarbonyl)pyridyl (in particular 2-(methoxy)-3-(hydroxycarbonyl)pyrid-5-yl;

pyrimidinyl, in particular pyrimidin-5-yl;

di-loweralkylaminopyrimidinyl, e.g. 2- or 4-dimethylaminopyrimidinyl, especially 2-dimethylaminopyrimidinyl (in particular 2-dimethylaminopyrimidin-5-yl);

alkoxypyrimidinyl, in particular methoxypyrimidinyl or ethoxypyrimidinyl, e.g. 2-methoxypyrimidinyl or 2-ethoxypyrimidinyl (in particular 2-methoxypyrimidin-5-yl or 2-ethoxypyrimidin-5-yl);

1H-pyrrolo[2,3-b]pyridinyl (in particular 1H-pyrrolo[2,3-b]pyridin-5-yl);

1-methyl-1H-pyrrolo[2,3-b]pyridinyl (in particular 1-methyl-1H-pyrrolo[2,3-b]pyridin-5-yl);

pyrazinyl;

pyrazolyl, e.g. pyrazol-4yl;

substituted pyrazolyl, e.g. hydroxyalkylpyrazolyl, especially 1-(2-hydroxy-ethyl)-1H-pyrazolyl (in particular 1-(2-hydroxy-ethyl)-1H-pyrazol-4-yl) or 1-[2-(tetrahydro-pyran-2-yloxy)-ethyl]-1H-pyrazolyl (in particular 1-[2-(tetrahydro-pyran-2-yloxy)-ethyl]-1H-pyrazol-4-yl);

quinolinyl (in particular quinolin-3-yl);

2-oxo-2,3-dihydro-1H-indol-5-yl;

1-methyl-2,3-dihydro-1H-indol-5-yl;

1H-imidazo[4,5-b]pyridin-2(3H)-one-6-yl (in particular 1,3-dimethyl-1H-imidazo[4,5-b]pyridin-2(3H)-one-6-yl, 1-ethyl-3-methyl-1H-imidazo[4,5-b]pyridin-2(3H)-one-6-yl or 1-(2-methoxyethyl)-3-methyl-1H-imidazo [4,5-b]pyridin-2(3H)-one-6-yl;

3H-imidazo[4,5-b]pyridin-6-yl, e.g. (3-methyl)-3H-imidazo[4,5-b]pyridin-6-yl, (2-methyl)-(3-methyl)-3H-imidazo[4,5-b]pyridin-6-yl, (2-methoxy)-(3-methyl)-3H-imidazo[4,5-b]pyridin-6-yl, (2-dimethylamino)-(3-methyl)-3H-imidazo[4,5-b]pyridin-6-yl;

3H-[1,2,3]triazolo[4,5-b]pyridin-6-yl, e.g. (3-methyl)-3H-[1,2,3]triazolo[4,5-b]pyridin-6-yl.

In an embodiment, $R^3$ is selected from:

pyridyl, 2-methylpyridyl, 3-methylpyridyl, 2-methoxypyridinyl, 3-methoxypyridinyl, 3-ethoxypyridyl, 2-ethoxypyridyl, 2-ethoxypyridyl, 6-(n-propoxy)pyridyl or 3-(iso-propoxy)pyridinyl or 2-(iso-propoxy)pyridinyl, 3-cyclobutoxy-pyridyl, 3-(1,3-difluoropropan-2-yloxy)-pyridyl, 3-(2-fluoroethan-1-yloxy)-pyridyl, 3-(difluoromethyloxy)-pyridyl, 2-cyclopropylmethoxy-pyridyl, 2-methoxymethylpyridyl, 3-methoxymethylpyridyl, 3-(2-methoxy-prop-2-yl) pyridyl, 3-(2-ethoxy-prop-2-yl)pyridyl, 3-(2-methoxyethoxy) pyridyl, 2-(2-methoxyethoxy)pyridyl, (2-methyl)-(3-(2-methoxyethoxy))pyridyl, 2-benzyloxyethoxypyridyl, 3-benzyloxypropoxypyridyl, 2-hydroxymethylpyridyl, 3-(1-hydroxyethyl)pyridyl, 3-(3-hydroxypent-3-yl)pyridyl, 3-(2-hydroxyprop-2-yl)pyridyl, 3-(2-hydroxy-1,1-dimethyl-ethyl) pyridyl, 3-(1-hydroxycyclopentyl)-pyridyl, 3-(1,3-difluoro-2-hydroxyprop-2-yl)pyridyl, 3-aminomethylpyridyl, 3-methanesulfonylpyridyl, 2-(2-hydroxyethoxy)-pyridyl, 2-(3-hydroxypropoxy)-pyridyl, 2-methoxycarbonyl-pyridyl, 2-aminopyridyl or 3-aminopyridyl, 2-methylaminopyridyl, 3-methylaminopyridyl, 3-ethylaminopyridyl, 3-isopropylaminopyridyl, 2-dimethylaminopyridyl or 3-dimethylaminopyridyl, 2-diethylaminopyridyl, 3-diethylaminopyridyl, 2-ethylmethylaminopyridyl, 3-ethylmethylaminopyridyl, 2-isopropylmethylaminopyridyl, 3-isopropylmethylaminopyridyl, 3-methylaminopyridyl, 3-(N-methyl-N-cyclobutylamino)pyridyl, 2-methyl-3-amino-pyridyl, 2-ethyl-3-amino-pyridyl, 3-fluoro-2-amino-pyridyl, 2-fluoro-3-amino-pyridyl, 3-chloro-2-amino-pyridyl, 2-chloro-3-amino-pyridyl, 3-fluoro-2-methylamino-pyridyl, 2-fluoro-3-methylamino-pyridyl, 2-fluoro-3-ethylamino-pyridyl, 3-chloro-2-methylamino-pyridyl, 3-chloro-2-ethylamino-pyridyl, 2-chloro-3-ethylamino-pyridyl, 2-fluoro-3-dimethylamino-pyridyl, 3-chloro-2-hydroxymethyl-pyridyl, 3-ethoxy-2-methyl-pyridyl, 3-propoxy-2-methyl-pyridyl, 3-propoxy-2-ethyl-pyridyl, 3-ethoxy-2-ethyl-pyridyl, 3-propoxy-2-methoxy-pyridyl, 3-propoxy-2-ethoxy-pyridyl, 3-methoxy-2-methoxy-pyridyl, 3-ethoxy-2-methoxy-pyridyl, 3-isopropoxy-2-methoxymethyl-pyridyl, 3-methoxy-2-methoxymethyl-pyridyl, 2-methoxy-3-methoxymethyl-pyridyl, 3-methoxy-2-ethoxymethyl-pyridyl, 3-ethoxy-2-methoxymethyl-pyridyl, 3-ethoxy-2-trideuteromethoxymethyl-pyridyl, 3-isopropoxy-2-hydroxymethyl-pyridyl, 3-methoxy-2-hydroxymethyl-pyridyl, 2-methoxy-3-hydroxymethyl-pyridyl, 3-ethoxy-2-hydroxymethyl-pyridyl, 3-(1,3-difluoro-propan-2-yloxy)-2-(methyl)-pyridyl, 3-(1,3-difluoro-propan-2-yloxy)-2-(hydroxymethyl)-pyridyl, 3-methoxyethoxy-2-hydroxymethyl-pyridyl, 2-methyl-3-ethylamino-pyridyl, 3-methyl-2-methylamino-pyridyl, 2-methyl-3-ethylamino-pyridyl, 2-ethyl-3-isopropylamino-pyridyl, 2-methyl-3-(N-methyl-N-ethylamino)-pyridyl, 2-methyl-3-(N,N-dimethylamino)-pyridyl, 3-azetidin-1-yl-pyridinyl, 2-pyrrolidinyl-1-yl-pyridinyl, 2-(tetrahydro-pyran-4-ylamino)pyridylyl, 6-(3-hydroxy-pyrrolidin-1-yl)-pyridinyl, 6-((R)-3-hydroxy-pyrrolidin-1-yl)-pyridinyl, 6-((S)3-hydroxy-pyrrolidin-1-yl)-pyridinyl, 2-(2-hydroxyethylamino)-pyridyl, 2-(methyl)-3-(hydroxy)-pyridyl, 2-(ethyl)-3-(hydroxy)-pyridyl, 2-(hydroxymethyl)-3-(ethylamino)-pyridyl, 2-(hydroxymethyl)-3-(methylamino)-pyridyl, 3-(hydroxymethyl)-2-(methylamino)-pyridyl, 3-(hydroxymethyl)-2-(amino)-pyridyl, 2-(methoxymethyl)-3-(ethylamino)-pyridyl, 2-(methoxymethyl)-3-(methylamino)-pyridyl, 3-(ethoxymethyl)-2-(methylamino)-pyridyl, 3-(ethoxymethyl)-2-(amino)-pyridyl, 3-(methoxymethyl)-2-(amino)-pyridyl, 2-amino-3-trifluoromethyl-pyridyl, 2-methylamino-3-trifluoromethyl-pyridyl, 2-ethylamino-3-trifluoromethyl-pyridyl, 3-trifluoromethyl-2-trideuteromethylamino-pyridyl, 2-trifluoromethylpyridyl, 3-(2-cyanoprop-2-yl)-pyridyl, 3-(1-cyanocyclobutyl)-pyridyl, 2-fluoropyridyl, 3-fluoro-2-methoxy-pyridyl, 2-(carbamoyl)pyridyl, 2-(methylcarbamoyl)pyridyl, 2-(1-piperazinyl)pyridyl, 2-(4-methylpiperazin-1-yl)-pyridyl, 3-(methylsulfonamido)-pyridinyl, 3-(dimethylsulfonamido)-pyridinyl, 3-(methylsulfonamido)-2-methyl pyridinyl, 3-(methylsulfonamido)-2-chloro-pyridinyl, 3-(methylsulfonamidomethyl)-pyridinyl, 3-(dimethylsulfonamido)-(2-methyl)-pyridinyl, 2-(3H-tetrazol-5-yl)pyridyl, 3-methylcarbonylaminomethylpyridyl, 2-(chloro)-3-(methylcarbonylamino)pyridyl, 2-(methoxy)-3-(methylcarbonylamino)pyridyl, 2-(ethoxy)-3-(methylcarbonylamino)pyridyl, 2-(methoxy)-3-(methylcarbonyl-N-methylamino)pyridyl, 2-(ethoxy)-3-(methylcarbonyl-N-methylamino)pyridyl, 2-(methoxy)-3-(nitro)-pyridyl, 2-(methoxy)-3-(cyano)-pyridyl, 2-(methoxy)-3-(amino)-pyridyl, 2-(methoxy)-3-(ethylamino) pyridyl, 3-(methoxymethyl)-2-(methylamino)pyridyl, 3-(methoxymethyl)-2-(ethylamino)pyridyl, 2-(methoxy)-3-(methylaminocarbonyl)pyridyl, 3-methylaminocarbonylmethylpyridyl, 2-(amino)-3-(methylaminocarbonyl)pyridyl, 2-(amino)-3-(ethylaminocarbonyl) pyridyl, 2-(amino)-3-(isopropylaminocarbonyl)pyridyl, 2-(amino)-3-(2-methoxyethylaminocarbonyl)pyridyl, 2-(methylamino)-3-(ethylaminocarbonyl)pyridyl, 2-(methoxy)-3-(aminocarbonyl)pyridyl, 2-(methoxy)-3-(hydroxycarbonyl)pyridyl, 3-morpholin-4-ylpyridinyl, (1H-pyrazol-1yl)-pyridinyl, (2-methyl-1H-imidazol-1-yl)-pyridinyl, pyrimidinyl, 2-dimethylaminopyrimidinyl, 2-methoxypyrimidinyl, 2-ethoxypyrimidinyl, 2,4-dimethoxypyrimidinyl, 2-(methylamino)-4-(methoxy)pyrimidinyl, 2-(ethylamino)-4-(methoxy)pyrimidinyl, 2-(pyrrolidinyl)pyrimidinyl, 2-aminopyrimidinyl, 2-methylaminopyrimidinyl, 2-dimethylaminopyrimidinyl, 1H-pyrrolo[2,3-b]pyridinyl, 1-methyl-1H-pyrrolo[2,3-b]pyridinyl, pyrazinyl, pyrazolyl, 1-(2-hydroxy-ethyl)-1H-pyrazolyl, 1-[2-(tetrahydro-pyran-2-yloxy)-ethyl]-1H-pyrazolyl, quinolinyl, 2-oxo-2,3-dihydro-1H-indolyl, 1-methyl-2,3-dihydro-1H-indolyl, 1,3-dimethyl-1H-imidazo[4,5-b]pyridin-2(31-1)-oneyl, 1-ethyl-3-methyl-1H-imidazo[4,5-b]pyridin-2(3H)-oneyl, 1-(2-methoxyethyl)-3-methyl-1H-imidazo[4,5-b]pyridin-2(3H)-oneyl, (3-methyl)-3H-imidazo[4,5-b]pyridinyl, (2-methyl)-(3-methyl)-3H-imidazo[4,5-b]pyridinyl, (2-methoxy)-(3-methyl)-3H-imidazo[4,5-b]pyridinyl, (2-dimethylamino)-(3-methyl)-3H-imidazo[4,5-b]pyridinyl, (3-methyl)-3H-[1,2,3]triazolo[4,5-b]pyridinyl, 1H-pyrrolo[3,2-b]pyridinyl, 1-methyl-1H-pyrrolo[3,2-b]pyridinyl, 1,3,3-trimethyl-2-oxo-2,3-dihydro-1H-pyrrolo[2,3-b]pyridinyl, 4-methyl-3,4-dihydro-2H-pyrido[3,2-b][1,4]oxazinyl, 1-methyl-2-oxo-1,4-dihydro-2H-pyrido[2,3-d][1,3]oxazinyl, 1-ethyl-2-oxo-1,4-dihydro-2H-pyrido[3,2-d][1,3]oxazinyl.

In another embodiment, $R^3$ is selected from:

pyrid-3-yl, 2-methylpyrid-5-yl, 3-methylpyrid-5-yl, 2-methoxypyridin-5-yl, 3-methoxypyridin-5-yl, 3-ethoxypyrid-5-yl, 2-ethoxypyrid-5-yl, 2-ethoxypyrid-4-yl, 6-(n-propoxy)pyrid-3-yl or 3-(iso-propoxy)pyridin-5-yl or 2-(iso-propoxy)pyridin-4-yl, 3-cyclobutoxy-pyrid-5-yl, 3-(1,3-difluoropropan-2-yloxy)-pyrid-5-yl, 3-(2-fluoroethan-1-yloxy)-pyrid-5-yl, 3-(difluoromethyloxy)-pyrid-5-yl, 2-cyclopropylmethoxy-pyrid-5-yl, 2-methoxymethylpyrid-5-yl, 3-methoxymethylpyrid-5-yl, 3-(2-methoxy-prop-2-yl)pyrid-5-yl, 3-(2-ethoxy-prop-2-yl)pyrid-5-yl, 3-(2-methoxyethoxy) pyrid-5-yl, 2-(2-methoxyethoxy)pyrid-5-yl, (2-methyl)-(3-(2-methoxyethoxy))pyrid-5-yl, 2-benzyloxyethoxypyrid-5-yl, 3-benzyloxypropoxypyrid-5-yl, 2-hydroxymethylpyrid-5-yl, 3-(1-hydroxyethyl)pyrid-5-yl, 3-(3-hydroxypent-3-yl)pyrid-5-yl, 3-(2-hydroxyprop-2-yl)pyrid-5-yl, 3-(2-hydroxy-1,1-dimethylethyl)pyrid-5-yl, 3-(1-hydroxycyclopentyl)-pyrid-5-yl, 3-(1,3-difluoro-2-hydroxyprop-2-yl)pyrid-5-yl, 3-aminomethylpyrid-5-yl, 3-methanesulfonylpyrid-5-yl, 2-(2-hydroxyethoxy)-pyrid-5-yl, 2-(3-hydroxypropoxy)-pyrid-5-yl, 2-methoxycarbonyl-pyrid-5-yl, 2-aminopyrid-5-yl or 3-aminopyrid-5-yl, 2-methylaminopyrid-5-yl, 3-methylaminopyrid-5-yl, 3-ethylaminopyrid-5-yl, 3-isopropylaminopyrid-5-yl, 2-dimethylaminopyrid-5-yl or 3-dimethylaminopyrid-5-yl, 2-diethylaminopyrid-5-yl, 3-diethylaminopyrid-5-yl, 2-ethylmethylaminopyrid-5-yl, 3-ethylmethylaminopyrid-5-yl, 2-isopropylmethylaminopyrid-5-yl, 3-isopropylmethylaminopyrid-5-yl, 3-methylaminopyrid-5-yl, 3-(N-methyl-N-cyclobutylamino)pyrid-5-yl, 2-methyl-3-amino-pyrid-5-yl, 2-ethyl-3-amino-pyrid-5-yl, 3-fluoro-2-amino-pyrid-5-yl, 2-fluoro-3-amino-pyrid-5-yl, 3-chloro-2-amino-pyrid-5-yl, 2-chloro-3-amino-pyrid-5-yl, 3-fluoro-2-methylamino-pyrid-5-yl, 2-fluoro-3-methylamino-pyrid-5-yl, 2-fluoro-3-ethylamino-pyrid-5-yl, 3-chloro-2-methylamino-pyrid-5-yl, 3-chloro-2-ethylamino-pyrid-5-yl, 2-chloro-3-ethylamino-pyrid-5-yl, 2-fluoro-3-dimethylamino-pyrid-5-yl, 3-chloro-2-hydroxymethyl-pyrid-5-yl, 3-ethoxy-2-methyl-pyrid-5-yl, 3-propoxy-2-methyl-pyrid-5-yl, 3-propoxy-2-ethyl-pyrid-5-yl, 3-ethoxy-2-ethyl-pyrid-5-yl, 3-propoxy-2-methoxy-pyrid-5-yl, 3-propoxy-2-ethoxy-pyrid-5-yl, 3-methoxy-2-methoxy-pyrid-5-yl, 3-ethoxy-2-methoxy-pyrid-5-yl, 3-isopropoxy-2-methoxymethyl-pyrid-5-yl, 3-methoxy-2-methoxymethyl-pyrid-5-yl, 2-methoxy-3-methoxymethyl-pyrid-5-yl, 3-methoxy-2-ethoxymethyl-pyrid-5-yl, 3-ethoxy-2-methoxymethyl-pyrid-5-yl, 3-ethoxy-2-trideuteromethoxymethyl-pyrid-5-yl, 3-isopropoxy-2-hydroxymethyl-pyrid-5-yl, 3-methoxy-2-hydroxymethyl-pyrid-5-yl, 2-methoxy-3-hydroxymethyl-pyrid-5-yl, 3-ethoxy-2-hydroxymethyl-pyrid-5-yl, 3-(1,3-difluoropropan-2-yloxy)-2-(methyl)-pyrid-5-yl, 3-(1,3-difluoropropan-2-yloxy)-2-(hydroxymethyl)-pyrid-5-yl, 3-methoxyethoxy-2-hydroxymethyl-pyrid-5-yl, 2-methyl-3-ethylamino-pyrid-5-yl, 3-methyl-2-methylamino-pyrid-5-yl, 2-methyl-3-ethylamino-pyrid-5-yl, 2-ethyl-3-isopropylamino-pyrid-5-yl, 2-methyl-3-(N-methyl-N-ethylamino)-pyrid-5-yl, 2-methyl-3-(N,N-dimethylamino)-pyrid-5-yl, 3-azetidin-1-yl-pyridin-5-yl, 2-pyrrolidinyl-1-yl-pyridin-5-yl, 2-(tetrahydro-pyran-4-ylamino)pyridyl-5-yl, 6-(3-hydroxy-pyrrolidin-1-yl)-pyridin-3-yl, 6-((R)-3-hydroxy-pyrrolidin-1-yl)-pyridin-3-yl, 6-((S)3-hydroxy-pyrrolidin-1-yl)-pyridin-3-yl, 2-(2-hydroxyethylamino)-pyrid-5-yl, 2-(methyl)-3-(hydroxy)-pyrid-5-yl, 2-(ethyl)-3-(hydroxy)-pyrid-5-yl, 2-(hydroxymethyl)-3-(ethylamino)-pyrid-5-yl, 2-(hydroxymethyl)-3-(methylamino)-pyrid-5-yl, 3-(hydroxymethyl)-2-(methylamino)-pyrid-5-yl, 3-(hydroxymethyl)-2-(amino)-pyrid-5-yl, 2-(methoxymethyl)-3-(ethylamino)-pyrid-5-yl, 2-(methoxymethyl)-3-(methylamino)-pyrid-5-yl, 3-(ethoxymethyl)-2-(methylamino)-pyrid-5-yl, 3-(ethoxymethyl)-2-(amino)-pyrid-5-yl, 3-(methoxymethyl)-2-(amino)-pyrid-5-yl, 2-amino-3-trifluoromethyl-pyrid-5-yl, 2-methylamino-3-trifluoromethyl-pyrid-5-yl, 2-ethylamino-3-trifluoromethyl-pyrid-5-yl, 3-trifluoromethyl-2-trideuteromethylamino-pyrid-5-yl, 2-trifluoromethyl pyrid-5-yl, 3-(2-cyanoprop-2-yl)-pyrid-5-yl, 3-(1-cyanocyclobutyl)-pyrid-5-yl, 2-fluoropyrid-3-yl, 2-fluoropyrid-4-yl, 3-fluoro-2-methoxy-pyrid-5-yl, 2-(carbamoyl) pyrid-5-yl, 2-(methylcarbamoyl)pyrid-5-yl, 2-(1-piperazinyl)pyrid-5-yl, 2-(4-methylpiperazin-1-yl)-pyrid-5-yl, 3-(methylsulfonamido)-pyridin-5-yl, 3-(dimethylsulfonamido)-pyridin-5-yl, 3-(methylsulfonamido)-2-methyl pyridin-5-yl, 3-(methylsulfonamido)-2-chloro-pyridin-5-yl, 3-(methylsulfonamidomethyl)-pyridin-5-yl, 3-(dimethylsulfonamido)-(2-methyl)-pyridin-5-yl, 2-(3H-tetrazol-5-yl) pyrid-5-yl, 3-methylcarbonylaminomethylpyrid-5-yl, 2-(chloro)-3-(methylcarbonylamino)pyrid-5-yl, 2-(methoxy)-3-(methylcarbonylamino)pyrid-5-yl, 2-(ethoxy)-3-(methylcarbonylamino)pyrid-5-yl, 2-(methoxy)-3-(methylcarbonyl-N-methylamino)pyrid-5-yl, 2-(ethoxy)-3-(methylcarbonyl-N-methylamino)pyrid-5-yl, 2-(methoxy)-3-(nitro)-pyrid-5-yl, 2-(methoxy)-3-(cyano)-pyrid-5-yl, 2-(methoxy)-3-(amino)-pyrid-5-yl, 2-(methoxy)-3-(ethylamino)pyrid-5-yl, 3-(methoxymethyl)-2-(methylamino)pyrid-5-yl, 3-(methoxymethyl)-2-(ethylamino)pyrid-5-yl, 2-(methoxy)-3-(methylaminocarbonyl)pyrid-5-yl, 3-methylaminocarbonylmethylpyrid-5-yl, 2-(amino)-3-(methylaminocarbonyl)pyrid-5-yl, 2-(amino)-3-(ethylaminocarbonyl)pyrid-5-yl, 2-(amino)-3-(isopropylaminocarbonyl)pyrid-5-yl, 2-(amino)-3-(2-methoxyethylaminocarbonyl)pyrid-5-yl, 2-(methylamino)-3-(ethylaminocarbonyl)pyrid-5-yl, 2-(methoxy)-3-(aminocarbonyl) pyrid-5-yl, 2-(methoxy)-3-(hydroxycarbonyl)pyrid-5-yl, 3-morpholin-4-ylpyridin-5-yl, (1H-pyrazol-1yl)-pyridin-5-yl, (2-methyl-1H-imidazol-1-yl)-pyridin-5-yl, pyrimidin-5-yl, 2-dimethylaminopyrimidin-5-yl, 2-methoxypyrimidin-5-yl, 2-ethoxypyrimidin-5-yl, 2,4-dimethoxypyrimidin-5-yl, 2-(methylamino)-4-(methoxy)pyrimidin-5-yl, 2-(ethylamino)-4-(methoxy)pyrimidin-5-yl, 2-(pyrrolidinyl)pyrimidin-5-yl, 2-aminopyrimidin-5-yl, 2-methylaminopyrimidin-5-yl, 2-dimethylaminopyrimidin-5-yl, 1H-pyrrolo[2,3-b]pyridin-5-yl, 1-methyl-1H-pyrrolo[2,3-b]pyridin-5-yl, pyrazinyl, pyrazol-4yl, 1-(2-hydroxy-ethyl)-1H-pyrazol-4-yl, 1-[2-(tetrahydro-pyran-2-yloxy)-ethyl]-1H-pyrazol-4-yl, quinolin-3-yl, 2-oxo-2,3-dihydro-1H-indol-5-yl, 1-methyl-2,3-dihydro-1H-indol-5-yl, 1,3-dimethyl-1H-imidazo[4,5-b]pyridin-2(3H)-one-6-yl, 1-ethyl-3-methyl-1H-imidazo[4,5-b]pyridin-2(3H)-one-6-yl, 1-(2-methoxyethyl)-3-methyl-1H-imidazo[4,5-b]pyridin-2(3H)-one-6-yl, (3-methyl)-3H-imidazo[4,5-b]pyridin-6-yl, (2-methyl)-(3-methyl)-3H-imidazo[4,5-b]pyridin-6-yl, (2-methoxy)-(3-methyl)-3H-imidazo[4,5-b]pyridin-6-yl, (2-dimethylamino)-(3-methyl)-3H-imidazo[4,5-b]pyridin-6-yl, (3-methyl)-3H-[1,2,3]triazolo[4,5-b]pyridin-6-yl, 1H-pyrrolo[3,2-b]pyridin-6-yl, 1-methyl-1H-pyrrolo[3,2-b]pyridin-6-yl, 1,3,3-trimethyl-2-oxo-2,3-dihydro-1H-pyrrolo[2,3-b]pyridin-5-yl, 4-methyl-3,4-dihydro-2H-pyrido[3,2-b][1,4]oxazin-7-yl, 1-methyl-2-oxo-1,4-dihydro-2H-pyrido[2,3-d][1,3]oxazin-6-yl, 1-ethyl-2-oxo-1,4-dihydro-2H-pyrido[3,2-d][1,3]oxazin-7-yl.

With the groups of preferred compounds of formula (I) mentioned herein, definitions of substituents from the general definitions mentioned hereinbefore may reasonably be used, e.g., to replace more general definitions with more specific definitions or especially with definitions characterized as being preferred.

A preferred group of compounds of the present invention of formula (I) are those wherein X is O.

Another preferred group of compounds of the present invention of formula (I) are those wherein Y is CH.

Another preferred group of compounds of the present invention of formula (I) are those wherein X is O or S and Y is CH.

Another preferred group of compounds of the present invention of formula (I) are those wherein X is O and Y is CH.

An alternative group of compounds of the present invention of formula (I) are those wherein Y is N.

An alternative group of compounds of the present invention of formula (I) are those wherein X is O or S and Y is N.

An preferred group of compounds of the present invention of formula (I) are those wherein X is O and Y is N.

An embodiment of the present invention includes compounds of formula (I) or pharmaceutically acceptable salts, solvates or hydrates thereof, wherein:

X is O or S;

Y is CH or N;

$R^1$ is unsubstituted pyrazolyl or pyrazolyl substituted with one, two or three substituents, at least one of which is in the alpha-position, said substituents being independently selected from lower alkyl; halo; halo lower alkyl, hydroxy lower alkyl, alkoxy lower alkyl, carbamoyl lower alkyl, hydroxycarbonyl lower alkyl, dialkylaminocarbonyl lower alkyl, cycloaminocarbonyl lower alkyl, morpholinecarbonylalkyl, piperazinecarbonyl lower alkyl or alkyl-substituted piperazinecarbonyl lower alkyl; or $R^1$ is unsubstituted isoxazolyl or isoxazolyl substituted with one or two lower alkyl substituents;

$R^2$ is hydrogen, lower alkyl or lower alkenyl;

$R^3$ is unsubstituted phenyl, or phenyl substituted with one or two groups independently selected from the group consisting of halo; halo-lower alkyl; hydroxyl; amino; mono or disubstituted amino; cyclic amino; amino-lower alkyl; lower alkoxy; hydroxy-lower alkyl; hydroxy lower alkoxy; lower alkyl; cyano; cyano-lower alkyl; amidino; N-hydroxyamidino; amidino-lower alkyl; or N-hydroxyamidino-lower alkyl; sulfonyl; alkyl-substituted sulfonyl; sulfonamide; pyrrolidinesulfonyl; lower alkyl sulfonyl amino; lower alkyl sulfonylalkandiylamino; lower alkylsulfonyl-N-lower alkylamino; [1,3]dioxolo; halo-substituted [1,3]dioxolo; alkoxy carbonyl; carbamoyl; substituted carbamoyl; heterocycle; heterocyclyl lower alkyl; heteroaryl or heteroaryl lower alkyl; or $R^3$ is indolyl, 1-methyl-2,3-dihydro-1H-indolyl, 2-oxo-2,3-dihydro-1H-indolyl, pyridyl, pyrimidinyl, 1H-pyrrolo[2,3-b]pyridinyl, 1-methyl-1H-pyrrolo[2,3-b]pyridinyl, pyrazolyl, pyrazinyl, quinolyl, 1,3-Dimethyl-2-oxo-2,3-dihydro-1H-imidazo[4,5-b]pyridinyl, 1-ethyl-3-methyl-2-oxo-2,3-dihydro-1H-imidazo[4,5-b]pyridinyl, 1-(2-methoxy-ethyl)-3-methyl-2-oxo-2,3-dihydro-1H-imidazo[4,5-b]pyridinyl, 2-Dimethylamino-3-methyl-3H-imidazo[4,5-b]pyridinyl, 2-methoxy-3-methyl-3H-imidazo[4,5-b]pyridinyl, 3-methyl-3H-[1,2,3]triazolo[4,5-b]pyridinyl, 2,3-Dimethyl-3H-imidazo[4,5-b]pyridinyl, 3-methyl-3H-imidazo[4,5-b]pyridinyl, 1H-pyrrolo[3,2-b]pyridinyl, 1-methyl-1H-pyrrolo[3,2-b]pyridinyl, 1-methyl-2-oxo-1,4-dihydro-2H-pyrido[2,3-d][1,3]oxazinyl, 4-methyl-3,4-dihydro-2H-pyrido[3,2-b][1,4]oxazinyl, 1,3,3-trimethyl-2-oxo-2,3-dihydro-1H-pyrrolo[2,3-b]pyridinyl and 1-ethyl-2-oxo-1,4-dihydro-2H-pyrido[3,2-d][1,3]oxazinyl each of these heterocycle radicals being unsubstituted or substituted by one to two radicals selected from the group consisting of halo; halo-lower alkyl; hydroxyl; amino; mono or disubstituted amino; cyclic amino; substituted cyclic amino; amino-lower alkyl; alkylamino-lower alkyl; dialkylamino-loweralkyl; cycloalkylaminoalkyl; dicycloalkylaminoalkyl; alkylcycloalkylaminoalkyl; lower alkoxy; cycloalkoxy; lower-alkoxyalkyl; hydroxy-lower alkyl; hydroxy lower cycloalkyl; hydroxy lower alkoxy; alkoxy lower alkoxy; lower alkyl; cyano; cyano-lower alkyl; cyano lower cycloalkyl; amidino; N-hydroxyamidino; amidino-lower alkyl; N-hydroxyamidino-lower alkyl; nitro; carboxylic acid; substituted sulfonyl; sulfonamide; alkylsulfonylamino; alkylsulfonylalkylamino; acylamino; acyl alkyl amino; alkylcarbonylaminoalkyl; alkylaminocarbonylalkyl; alkylcarbonyl-N-alkylamino; [1,3]dioxolo; substituted [1,3]dioxolo; alkoxy carbonyl; carbamoyl; substituted carbamoyl; 1H-tetrazolyl; pyrazol; imidazole; triazole; azetidinyl; pyrrolidinyl; piperazinyl; methylpiperazinyl; ethylpiperazinyl; triazolonyl; methylimidazolyl or morpholino.

A further embodiment of the present invention includes compounds of formula (I) or pharmaceutically acceptable salts, solvates or hydrates thereof, wherein:

X is O or S;

Y is CH or N;

$R^1$ is unsubstituted pyrazolyl or pyrazolyl substituted with one, two or three substituents, at least one of which is in the alpha-position, said substituents being independently selected from lower alkyl; halo; halo lower alkyl, hydroxy lower alkyl, alkoxy lower alkyl, carbamoyl lower alkyl, hydroxycarbonyl lower alkyl, dialkylaminocarbonyl lower alkyl, cycloaminocarbonyl lower alkyl, morpholinecarbonylalkyl, piperazinecarbonyl lower alkyl or alkyl-substituted piperazinecarbonyl lower alkyl; or $R^1$ is unsubstituted isoxazolyl or isoxazolyl substituted with one or two unsubstituted lower alkyl substituents;

$R^2$ is hydrogen, lower alkyl or lower alkenyl;

$R^3$ is selected from phenyl; hydroxyphenyl; methoxyphenyl; 3,4-dimethoxyphenyl; ethoxyphenyl; 3,4-diethoxyphenyl; iso-propoxyphenyl; methoxy ethoxy-phenyl; 3-methoxy-4-(2-methoxy ethoxy)-phenyl; fluoro-(iso-propoxy)-phenyl; 3-methoxy-4-hydroxy phenyl; fluoro-hydroxy-phenyl; hydroxy-fluoroalkyl-phenyl; 2,2-difluoro-benzo[1,3]dioxolo; benzene sulfonamide; N,N-dimethylbenzenesulfonamide; 3-(pyrrolidine-1-sulfonyl)-phenyl; N-(phen-3-yl)-methanesulfonamide; N-methyl-N-phen-3-yl-methanesulfonamide; 3-methanesulfonylphenyl; 3- or 4-benzamide; 3- or 4-N-methyl-benzamide; 3- or 4-N,N-dimethyl-benzamide; pyrazol-phenyl; imidazol-phenyl; pyridyl; alkylpyridyl; alkoxypyridyl; cycloalkoxypyridyl; (haloalkoxy)pyridyl; cycloalkylalkoxypyridyl; alkoxyalkylpyridyl; alkoxyalkoxypyridyl; (alkyl)(alkoxyalkoxy)pyridyl; benzyloxyalkoxypyridyl; hydroxyalkylpyridyl; hydroxycycloalkylpyridyl; hydroxyfluoroalkylpyridyl; aminoalkylpyridyl; alkyl-sulfonyl pyridyl; hydroxyalkoxypyridyl; alkoxycarbonylpyridyl; aminopyridyl; alkylaminopyridyl; dialkylaminopyridyl; cycloalkylaminopyridyl; (N-alkyl-N-cycloalkylamino)pyridyl; (alkyl)(amino)pyridyl; (halo)(amino)pyridyl; (halo)(alkylamino)pyridyl; (halo)(dialkylamino)pyridyl; (halo)(hydroxyalkyl)pyridyl; (alkoxy)(alkyl)pyridyl; (alkoxy)(alkoxy)pyridyl; (alkoxy)(alkoxyalkyl)pyridyl; (alkoxy)(deuteroalkoxy-alkyl)pyridyl; (alkoxy)(hydroxyalkyl)pyridyl; (haloalkoxy)(alkyl)pyridyl; (haloalkoxy)(hydroxyalkyl)pyridyl; (alkoxyalkoxy)(hydroxyalkyl)pyridyl; (alkyl)(alkylamino)pyridyl; (alkyl)(di-alkylamino)pyridyl; cycloaminopyridyl; cyclic ether-substituted amino-pyridyl; hydroxy-cycloaminopyridyl; loweralkoxy-cycloaminopyridyl; hydroxyalkylaminopyridyl; (alkyl)(hydrone)pyridyl; (hydroxyalkyl)(alkylamino)pyridyl; (hydroxyalkyl)(amino)pyridyl; (alkoxyalkyl)(alkylamino)pyridyl; (alkoxyalkyl)(amino)pyridyl; amino-haloloweralkyl-pyridyl; alkylamino-haloalkyl-pyridyl; haloalkyl-deuteroloweralkylamino-pyridyl; haloalkylpyridinyl; cyanoalkylpyridinyl; cyanocycloalkylpyridinyl; halopyridyl; halo-alkoxy-pyridyl; carbamoylpyridyl; alkyl-substituted carbamoylpyridyl; piperazinylpyridyl; N-alkylpiperazinylpyridyl; alkylsulfonamidopyridyl; dialkylsulfonamidopyridyl; (alkylsulfonamido)(alkyl)pyridyl; (alkylsulfonamido)(halo)pyridyl; (alkylsulfonamidoalkyl)pyridyl; dialkylsulfonamido(alkyl)pyridyl; 3H-tetrazol-5-yl pyridyl; alkylcarbonylaminoalkylpyridyl; (halo)(alkylcarbonylamino)pyridyl; (alkoxy)(alkylcarbonylamino)pyridyl; (alkoxy)(alkylcarbonyl-N-alkylamino)pyridyl; (alkoxy)(nitro)pyridyl; (alkoxy)(cyano)pyridyl; (alkoxy)(amino)pyridyl; (alkoxy)(alkylamino)pyridyl; (alkoxyalkyl)(alkylamino)pyridyl; (alkoxy)(alkylaminocarbonyl)pyridyl; (alkoxyalkyl)(alkylamino)pyridyl; (amino)(alkylaminocarbonyl)pyridyl; (amino)(alkoxyalkylaminocarbonyl)pyridyl; (alkylamino)(alkylaminocarbonyl)pyridyl; (alkoxy)(aminocarbonyl)pyridyl; (alkoxy)(hydroxycarbonyl)pyridyl; morpholinylpyridinyl; (1H-pyrazolyl)-pyridinyl; loweralkyl substituted (1H-imidazol-1-yl)-pyridinyl; pyrimidinyl; di-lower-alkylaminopyrimidinyl; alkoxypyrimidinyl; di-alkoxypyrimidinyl; (alkylamino)(alkoxy)pyrimidinyl; cycloaminopyrimidinyl; aminopyrimidinyl; alkylaminopyrimidinyl; dialkylaminopyrimidinyl; 1H-pyrrolo[2,3-b]pyridinyl; 1-methyl-1H-pyrrolo[2,3-b]pyridinyl; pyrazinyl; pyrazolyl; hydroxyalkylpyrazolyl; 1-[2-(tetrahydro-pyran-2-yloxy)-ethyl]-1H-pyrazolyl; quinolinyl; 2-oxo-2,3-dihydro-1H-indol-5-yl; 1-methyl-2,3-dihydro-1H-indol-5-yl; 1H-imidazo[4,5-b]pyridin-2(3H)-one-6-yl; 3H-imidazo[4,5-b]pyridin-6-yl; (3-methyl)-3H-imidazo[4,5-b]pyridin-6-yl; (2-methyl)-(3-methyl)-3H-imidazo[4,5-b]pyridin-6-yl; (2-methoxy)-(3-methyl)-3H-imidazo[4,5-b]pyridin-6-yl; (2-dimethylamino)-(3-methyl)-3H-imidazo[4,5-b]pyridin-6-yl; 3H-[1,2,3]triazolo[4,5-b]pyridin-6-yl; (3-methyl)-3H-[1,2,3]triazolo[4,5-b]pyridin-6-yl; H-pyrrolo[3,2-b]pyridin-6-yl; 1-methyl-1H-pyrrolo[3,2-b]pyridin-6-yl; 2-oxo-1,4-dihydro-2H-pyrido[2,3-d][1,3]oxazin-6-yl; 1-methyl-2-oxo-1,4-dihydro-2H-pyrido[2,3-d][1,3]oxazin-6-yl; 3,4-dihydro-2H-pyrido[3,2-b][1,4]oxazin-7-yl; 4-methyl-3,4-dihydro-2H-pyrido[3,2-b][1,4]oxazin-7-yl; 1,3,3-trimethyl-2-oxo-2,3-dihydro-1H-pyrrolo[2,3-b]pyridin-5-yl; 2-oxo-1,4-dihydro-2H-pyrido[3,2-d][1,3]oxazin-7-yl; 1-ethyl-2-oxo-1,4-dihydro-2H-pyrido[3,2-d][1,3]oxazin-7-yl.

An embodiment of the present invention includes compounds of formula (I) or pharmaceutically acceptable salts, solvates or hydrates thereof, wherein:

X is O or S;

Y is CH or N;

$R^1$ is unsubstituted pyrazolyl or pyrazolyl substituted with one, two or three substituents, at least one of which is in the alpha-position, said substituents being independently selected from lower alkyl; halo; halo lower alkyl, hydroxy lower alkyl, alkoxy lower alkyl, carbamoyl lower alkyl, hydroxycarbonyl lower alkyl, dialkylaminocarbonyl lower alkyl, cycloaminocarbonyl lower alkyl, morpholinecarbonylalkyl or piperazinecarbonyl lower alkyl;

$R^2$ is hydrogen or lower alkyl;

$R^3$ is unsubstituted phenyl, or phenyl substituted with one or two groups independently selected from the group consisting of halo; halo-lower alkyl; hydroxyl; amino; mono or disubstituted amino; cyclic amino; amino-lower alkyl; lower alkoxy; hydroxy-lower alkyl; hydroxy lower alkoxy; lower alkyl; cyano; cyano-lower alkyl; amidino; N-hydroxyamidino; amidino-lower alkyl; or N-hydroxyamidino-lower alkyl; sulfonyl; alkyl-substituted sulfonyl; sulfonamide; pyrrolidine-sulfonyl; [1,3]dioxolo; halo-substituted [1,3]dioxolo; alkoxy carbonyl; carbamoyl; substituted carbamoyl; heterocycle; heterocyclyl lower alkyl; heteroaryl or heteroaryl lower alkyl; or $R^3$ is indolyl, 2,3-dihydro-1H-indol-5-yl, 1-methyl-2,3-dihydro-1H-indol-5-yl, 2-oxo-2,3-dihydro-1H-indol-5-yl, pyridyl, pyrimidinyl, 1H-pyrrolo[2,3-b]pyridin-5-yl, 1-methyl-1H-pyrrolo[2,3-b]pyridin-5-yl, pyrazolyl, pyrazol-4-yl, pyrazinyl, quinolyl, quinol-3-yl, 1H-imidazo[4,5-b]pyridin-2(3H)-one-6-yl, 3H-imidazo[4,5-b]pyridin-6-yl, 3H-[1,2,3]triazolo[4,5-b]pyridin-6-yl each independently being unsubstituted or substituted by one or two radicals independently selected from the group consisting of halo; halo-lower alkyl; hydroxyl; amino; mono or disubstituted amino; cyclic amino; amino-lower alkyl; lower alkoxy; lower alkoxy lower alkyl; hydroxy-lower alkyl; hydroxy lower alkoxy; lower alkyl; cyano; cyano-lower alkyl; amidino; N-hydroxyamidino; amidino-lower alkyl; or N-hydroxyamidino-lower alkyl; sulfonyl; alkyl-substituted sulfonyl; sulfonamide; pyrrolidine-1-sulfonyl; [1,3]dioxolo; halo substituted [1,3]dioxolo; alkoxy carbonyl; carbamoyl; aminocarbonylalkyl; N-mono-substituted aminocarbonylalkyl; N-di-substituted aminocarbonylalkyl; 3H-tetrazolyl, pyrazol, heterocyclyl lower alkyl, heteroaryl or heteroaryl lower alkyl.

A further embodiment of the present invention includes compounds of formula (I) or pharmaceutically acceptable salts, solvates or hydrates thereof, wherein:

X is O or S;

Y is CH or N;

$R^1$ is unsubstituted pyrazolyl or pyrazolyl substituted with one, two or three substituents, at least one of which is in the alpha-position, said substituents being independently selected from lower alkyl; halo; halo lower alkyl, hydroxy lower alkyl, alkoxy lower alkyl, carbamoyl lower alkyl, hydroxycarbonyl lower alkyl, dialkylaminocarbonyl lower alkyl, cycloaminocarbonyl lower alkyl, morpholinecarbonylalkyl or piperazinecarbonyl lower alkyl;

$R^2$ is hydrogen or lower alkyl;

$R^3$ is selected from phenyl; hydroxyphenyl; methoxyphenyl; 3,4-dimethoxyphenyl; ethoxyphenyl; 3,4-diethoxyphenyl; methoxy ethoxy-phenyl; 3-methoxy-4-(2-methoxy ethoxy)-phenyl; 3-methoxy-4-hydroxy phenyl; fluoro-hydroxy-phenyl; hydroxy-fluoroalkyl-phenyl; 2,2-difluoro-benzo[1,3]dioxolo; benzene sulfonamide; 3-(pyrrolidine-1-sulfonyl)-phenyl; N-(phen-3-yl)-methanesulfonamide; N-methyl-N-phen-3-yl-methanesulfonamide; 3-methanesulfonylphenyl; 3- or 4-benzamide; 3- or 4-N-methyl-benzamide; 3- or 4-N,N-dimethyl-benzamide; pyrazol-phenyl; imidazol-phenyl; pyridyl; alkylpyridyl; alkoxypyridyl; cycloalkylalkoxypyridyl; alkoxyalkylpyridyl; alkoxyalkoxypyridyl, benzyloxyalkoxypyridyl, hydroxyalkylpyridyl; alkyl-sulfonyl pyridyl; hydroxyalkoxypyridyl; alkoxycarbonylpyridyl; aminopyridyl; alkylaminopyridyl; dialkylaminopyridyl; (alkyl)(amino)pyridyl; (alkoxy)(alkyl)pyridyl; (alkoxy)(alkoxy)pyridyl; (alkyl)(alkylamino)pyridyl; (alkyl)(dialkylamino)pyridyl; cycloaminopyridyl; hydroxyalkylaminopyridyl; amino-haloloweralkyl-pyridyl; haloalkylpyridinyl; halopyridyl; halo-alkoxy-pyridyl; carbamoylpyridyl; alkyl-substituted carbamoylpyridyl; piperazinylpyridyl; N-alkylpiperazinylpyridyl; alkylsulfonamidopyridyl; dialkylsulfonamidopyridyl; (alkylsulfonamido)(alkyl)pyridyl; dialkylsulfonamido(alkyl)pyridyl; 3H-tetrazol-5-yl pyridyl; (alkoxy)(alkylcarbonylamino)pyridyl; (alkoxy)(alkylcarbonyl-N-alkylamino)pyridyl; (alkoxy)(nitro)pyridyl; (alkoxy)(cyano)pyridyl; (alkoxy)(amino)pyridyl; (alkoxy)(alkylamino)pyridyl; (alkoxy)(alkylaminocarbonyl)pyridyl; (alkoxy)(hydroxycarbonyl)pyridyl; pyrimidinyl; di-loweralkylaminopyrimidinyl; alkoxypyrimidinyl; 1H-pyrrolo[2,3-b]pyridinyl; 1-methyl-1H-pyrrolo[2,3-b]pyridinyl; pyrazinyl; pyrazolyl; hydroxyalkylpyrazolyl; 1-[2-(tetrahydro-pyran-2-yloxy)-ethyl]-1H-pyrazolyl; quinolinyl; 2-oxo-2,3-dihydro-1H-indol-5-yl; 1-methyl-2,3-dihydro-1H-indol-5-yl; 1H-imidazo[4,5-b]pyridin-2(3H)-one-6-yl; 3H-imidazo[4,5-b]pyridin-6-yl; (3-methyl)-3H-imidazo[4,5-b]pyridin-6-yl; (2-methyl)-(3-methyl)-3H-imidazo[4,5-b]pyridin-6-yl; (2-methoxy)-(3-methyl)-3H-imidazo[4,5-b]pyridin-6-yl; (2-dimethylamino)-(3-methyl)-3H-imidazo[4,5-b]pyridin-6-yl; 3H-[1,2,3]triazolo[4,5-b]pyridin-6-yl; (3-methyl)-3H-[1,2,3]triazolo[4,5-b]pyridin-6-yl.

Most preferred is a compound of the formula (I), or a pharmaceutically acceptable salt, solvate or hydrate thereof, as exemplified hereinbelow under “Examples”.

The present invention is further directed to a method of treating a protein kinase dependent disease comprising administering a compound of formula (I), where the disease to be treated is a proliferative disease, preferably a benign or especially malignant tumor, more preferably carcinoma of the brain, kidney, liver, adrenal gland, bladder, breast, stomach, gastric tumors, ovaries, colon, rectum, prostate, pancreas, lung, vagina or thyroid, sarcoma, glioblastomas, multiple myeloma or gastrointestinal cancer, especially colon carcinoma or colorectal adenoma or a tumor of the neck and head, an epidermal hyperproliferation, psoriasis, prostate hyperplasia, a neoplasia, a neoplasia of epithelial character, lymphomas, a mammary carcinoma or a leukemia, and including proliferative diseases such as tumor diseases, leukaemias and myeloproliferative disorders such as polycythemia vera, essential thrombocythemia, and myelofibrosis with myeloid metaplasia, basal cell carcinoma, squamous cell carcinoma and actinic keratosis and other benign hyperproliferative skin disorders caused by inflammation such as psoriasis or as a result of dysregulation of fibroblasts such as skin fibrosis, scleroderma or keloids.

Other diseases include Cowden syndrome, Lhermitte-Dudos disease and Bannayan-Zonana syndrome or diseases in which the PI3K/PKB pathway is aberrantly activated.

Most preferred is the use in accordance with the present invention of a compound of the formula (I), or a pharmaceutically acceptable salt, solvate or hydrate thereof, as exemplified hereinbelow under “Examples”.

The compounds of formula (I) that inhibit the protein or lipid kinase activities mentioned, especially mTOR Ser/Thr kinase activity and/or class I PI3 kinases activity, may therefore be useful in the treatment of protein or lipid kinase dependant diseases, especially diseases depending on class I and/or class IV PI3 kinases, for example, PI3Kalpha, PI3Kbeta, PI3Kdelta, PI3Kgamma and/or mTOR, or one or more of the individual kinase members thereof, including other PI3-kinases such as DNA-PK, ATM, ATR, hSMG-1 and Vps34 or any combination of two or more of the mentioned kinases.

Protein or lipid kinase dependent diseases are especially proliferative diseases, a benign or especially malignant tumor, a carcinoma of the brain, kidney, liver, adrenal gland, bladder, breast, stomach (especially gastric tumors), ovaries, colon, rectum, prostate, pancreas, lung, vagina, thyroid, sarcoma, glioblastomas, multiple myeloma or gastrointestinal cancer, especially colon carcinoma or colorectal adenoma, or a tumor of the neck and head, other diseases such as Cowden syndrome, Lhermitte-Duclos disease and Bannayan-Zonana syndrome, or diseases in which the PI3K/PKB pathway is aberrantly activated, an epidermal hyperproliferation, especially psoriasis, prostate hyperplasia, a neoplasia, especially of epithelial character, preferably mammary carcinoma or squamous cell carcinoma, or a leukemia. The compounds desirably are able to bring about the regression of tumors and to prevent the formation of tumor metastases and the growth of (also micro) metastases. In addition, they may be used in epidermal hyperproliferation, e.g., psoriasis; in prostate hyperplasia; in the treatment of neoplasias, especially of epithelial character, e.g., mammary carcinoma; in leukemias; and in basal cell carcinoma, squamous cell carcinoma and actinic keratosis. It may also be possible to use the compounds of formula (I) in the treatment of diseases of the immune system insofar as several or, especially, individual lipid kinases and/or (further) serine/threonine protein kinases are involved.

The compounds of the formula (I) can be prepared according to the following methods:

A compound of formula (I) is converted into a compound of formula (I) by known in the art chemical reactions such as protecting group deprotection, e.g. tert-butyloxycarbonyl (boc) group deprotection with TFA, neat or in presence of a solvent such as a polyhalogeneated alkane, e.g. dichloromethane, at a temperature between 0° C. to 40° C.; functional group substitution e.g. alkylation of a hydroxyl group to form an alkoxy group by treatment with a strong based such as metal hydride, e.g. sodium hydride, in an aprotic solvent, e.g. THF or dimethylformamide, followed by addition of an akylhalide, e.g. methyliodide, at a temperature between −20° C. and 40° C.; or functional group modification e.g. conversion of a carbonyl to a thiocarbonyl by treatment with Lawesson's reagent in a cyclyether solvent, e.g. dioxane at a temperature between 60° C. and 120° C. or at reflux.

A compound of formula (I) wherein Y=CH is prepared by reacting a compound of the formula (II)

(II)

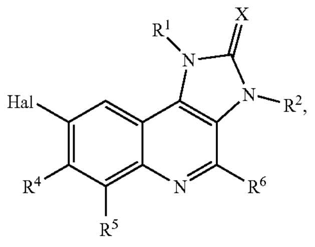

wherein

Hal refers to halogen preferably bromine; and

X, $R^1$, $R^2$, $R^4$, $R^5$ and $R^6$ are as defined herein above;

A: with a boronic acid of the formula III $R_3$—B$(OH)_2$ (III)

or a boronate ester such as of formula IIIa (IIIa)

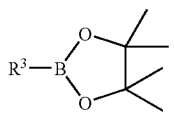

wherein $R^3$ is as defined for a compound of the formula (I), in the presence of a base and a catalyst in a suitable solvent; to provide a compound of formula (I)

or,

B: with a bis(diborane), such as bis(pinacolato)-diborane, in the presence of a base and a catalyst in a suitable solvent, to provide an intermediate of formula IIA:

(IIa)

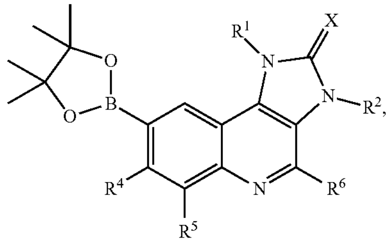

followed by reaction of the compound according to formula (IIa) with a compound according to formula (IIIb):

$R^3$-Hal (IIIb)

wherein Hal refers to halogen preferably bromine, in the presence of a base and a catalyst in a suitable solvent; to provide a compound of formula (I);

where the above starting compounds II, IIa, III, IIIa and IIIb may also be present with functional groups in protected form if necessary and/or in the form of salts, provided a salt-forming group is present and the reaction in salt form is possible;

any protecting groups in a protected derivative of a compound of the formula I are optionally removed; and if desired, transforming an obtainable compound of formula (I) into a different compound of formula (I), or a N-oxide thereof, transforming a salt of an obtainable compound of formula (I) into the free compound or a different salt, or an obtainable free compound of formula (I) into a salt; and/or separating an obtainable mixture of isomers of compounds of formula (I) into the individual isomers.

In the following, more detailed description of the preferred process conditions, X, $R^1$, $R^2$, $R^3$, $R^4$, $R^5$ and $R^6$ have the meanings given herein for compounds of the formula (I), if not indicated otherwise.

Conversion of $R^2$ from H to a substituent different from H as defined above for $R^2$ can be achieved by treating compound of formula (I) or (II) in presence of a strong base in a suitable solvent and subsequent adjunction of a halogenated reagent Hal-$R^2$ wherein Hal refers to halogen preferably iodine or bromine, e.g. methyliodide.

A compound of formula (II) is prepared by reacting a compound of formula (IV)

(IV)

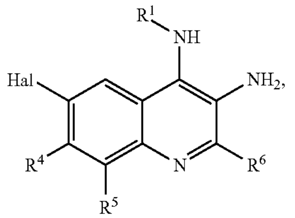

with phosgene or trichloromethyl chloroformate in a suitable solvent in presence of a base wherein $R^1$, $R^4$, $R^5$ and $R^6$ are as mentioned for a compound of the formula (I).

A compound of the formula (IV) is prepared by reduction of a compound of the formula (V)

(V)

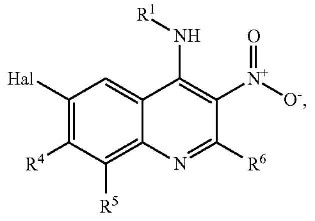

wherein the substituents and symbols are defined as for compounds of the formula (I) in the presence of an appropriate catalyst, e.g., a skeleton based catalyst, such as Raney-Ni with hydrogen in an appropriate solvent, e.g., an alcohol and or a cycloalkylether, such as methanol and/or tetrahydrofurane; at preferred temperatures e.g. between 0° C. and 50° C., e.g., at RT.

A compound of formula (V) is preferably prepared by reacting a compound of the formula (VI)

(VI)

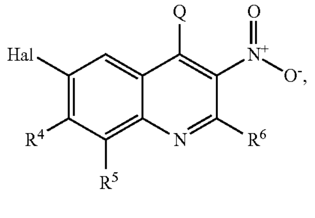

wherein

Q is halo, especially chloro; and the other moieties and symbols have the meanings indicated for compounds of the formula (I) with a compound of the formula (VII)

$R_1$—$NH_2$ (VII), wherein $R_1$ is as defined for a compound of the formula (I), in the presence of a base such as a tertiaryamine, e.g. 1,2,2,6,6-pentamethylpiperidine, in an appropriate solvent; preferably a polar aprotic solvent such as dimethylacetamide, at preferred temperatures between 20° C. and 120° C. temperature of the reaction mixture, e.g., between 20° C. and 70° C.

A compound of the formula (VI) can be prepared by reacting a compound of the formula (VIII)

(VIII)

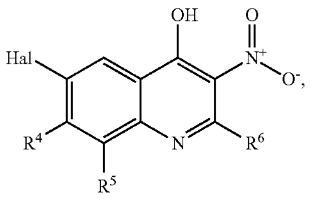

wherein the moieties and symbols have the meanings indicated for a compound of the formula (I), with an inorganic acid halogenide, especially $POCl_3$ (preferably without solvent) at elevated temperatures, e.g., between 100° C. and 150° C. or under reflux.

A compound of the formula (VIII) is known in the art, can be synthesized according to methods known in the art and/or is commercially-available. For example, it can be synthesized by reacting a compound of the formula (IX)

(IX)

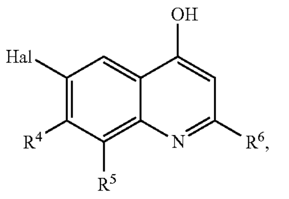

wherein the moieties and symbols have the meanings indicated for a compound of the formula (I) (x is preferably zero), with nitric acid (aqueous) at a preferred temperature between 50° C. and 100° C., e.g., at 85° C.

A compound of the formula (VIII), can alternatively be synthesized by reacting a compound of the formula (X)

(X)

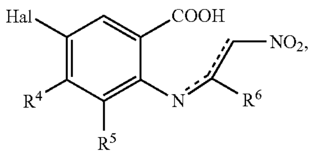

wherein the moieties and symbols have the meanings indicated for a compound of the formula (I), with an anhydride of a carbonic acid, especially acetic anhydride, preferably in the presence of an alkali metal salt of a carboxylic acid, e.g., potassium acetate, at a preferred temperature between 50° C. and 150° C., e.g., at ca. 100-140° C.

A compound of the formula (X) can be obtained, e.g., by converting a compound of the formula (XI)

(XI)

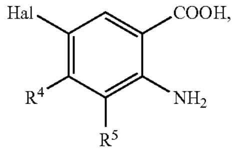

to the corresponding compound of the formula (X) by reacting nitromethane in the presence of an alkali metal hydroxide, especially sodium hydroxide, at preferred temperatures between approximately 0° C. and 60° C., e.g., between 0° C. and RT; then pouring the product under cooling to approximately 0° C. into concentrated HCl and adding the compound of the formula (XI) and further concentrated HCl, subsequently allowing for further reaction at preferred temperatures between 0° C. and RT to result in the corresponding compound of formula (X).

A compound of formula (I) wherein Y=N is prepared in two steps by saponification of the ester group by treatment with a base such as an alkali metal hydroxide, e.g. lithium hydroxide in a solvent such as wet cycloaklylether, e.g. dioxane/water, at a temperature between 20° C. and 100° C., preferably between 30° C. and 60° C., a compound of the formula (XII)

(XII)

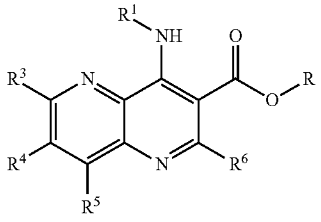

wherein $R^1$, $R^3$, $R^4$, $R^5$ and $R^6$ are as defined herein above and R is unsubstituted or substituted lower alkyl, e.g. ethyl;

The freed intermediate obtained after neutralization of the reaction mixture with an acid, such as a mineral acid, e.g. hydrochloric acid, and evaporation to dryness is converted by a Cursius rearrangement to compound of formula (I) via in situ formation of the acylazide intermediate by treatment with diphenylphosporylazide in an aprotic solvent, such as polar aprotic and/or polar protic, e.g. toluene/N-methylpyrolidinone, in presence of a base, such as a tertiaryamine, e.g. triethylamine, at temperature between 60° C. and 120° C., e.g. between 80° C. and 110° C.; the isocyanato intermediate spontaneously cyclized to form compound of formula (I) in the reaction conditions.

A compound of formula (XII) is preferably prepared by reacting a compound of the formula (XIII)

(XIII)

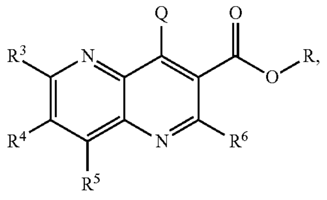

wherein

Q is halo, especially chloro; and the other moieties have the meanings indicated for compounds of the formula (I), and R is unsubstituted or substituted lower alkyl, e.g. ethyl, with a compound of the formula (VII)

$R_1$—$NH_2$ (VII), wherein $R_1$ is as defined for a compound of the formula (I), in the presence of a base such as a tertiaryamine, e.g. 1,2,2,6,6-pentamethylpiperidine, in an appropriate solvent; preferably a polar aprotic solvent such as dimethylacetamide, at preferred temperatures between 20° C. and 120° C. temperature of the reaction mixture, e.g., between 20° C. and 70° C.

A compound of formula (XIII) is preferably prepared by reacting a compound of the formula (XIV)

(XIV)

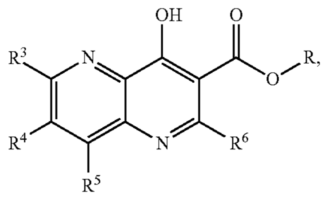

wherein the moieties have the meanings indicated for a compound of the formula (I) and R is unsubstituted or substituted lower alkyl, e.g. ethyl, with an inorganic acid halogenide, especially $POCl_3$ (preferably without solvent) at elevated temperatures, e.g., between 100° C. and 150° C. or under reflux.

A compound of formula (XIV) is preferably prepared by reacting a compound of the formula (XV)

(XV)

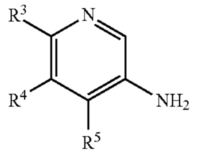

wherein the moieties have the meanings indicated for a compound of the formula (I) with a compound of formula (XVI)

(XVI)

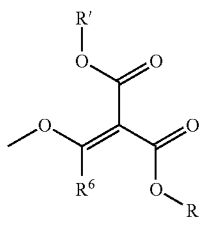

R and R' being selected independently from unsubstituted or substituted alkyl, e.g. being both ethyl; in a solvent and pressure condition, e.g. xylene in a seal tube, allowing reaction at a temperature between 150° C. and 300° C., e.g. between 220° C. and 250° C.

A compound of formula (XV) is known in the art and can be prepared by reduction of a compound of the formula (XVII)

(XVII)

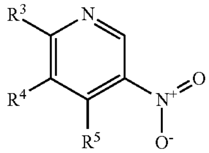

wherein the moieties have the meanings indicated for a compound of the formula (I) with a compound of formula (XVI) in the presence of an appropriate catalyst, e.g., a skeleton based catalyst, such as Raney-Ni with hydrogen in an appropriate solvent, e.g., an alcohol and or a cycloalkylether, such as methanol and/or tetrahydrofurane; at preferred temperatures e.g. between 0° C. and 50° C., e.g., at RT.

A compound of formula (XVII) is known in the art and can be prepared by reacting a compound of formula (XVIII)

(XVIII)

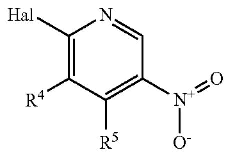

with a boronic acid of the formula III $R_3$—$B(OH)_2$ (III)

or a boronate ester such as of formula IIIa (IIIa)

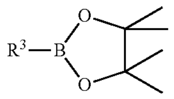

wherein $R_3$ is as defined for a compound of the formula (I), in the presence of a base and a catalyst in a suitable solvent.

Other starting materials are either known in the art, can be prepared according to methods that are known in the art, e.g., in analogy to the methods described hereinabove or in the examples, and/or are commercially-available.

The present invention relates also to novel starting materials and/or intermediates and to processes for their preparation. The starting materials used and the reaction conditions selected are preferably those that result in the compounds described as being preferred.

Other starting materials are either known in the art, can be prepared according to methods that are known in the art, e.g., in analogy to the methods described hereinabove or in the examples, and/or are commercially-available.

The present invention relates also to novel starting materials and/or intermediates and to processes for their preparation. The starting materials used and the reaction conditions selected are preferably those that result in the compounds described as being preferred.

Salts of compounds of formula (I) having at least one salt-forming group may be prepared in a manner known per se. For example, salts of compounds of formula (I) having acid groups may be formed, e.g., by treating the compounds with metal compounds, such as alkali metal salts of suitable organic carboxylic acids, e.g., the sodium salt of 2-ethylhexanoic acid; with organic alkali metal or alkaline earth metal compounds, such as the corresponding hydroxides, carbonates or hydrogen carbonates, such as sodium or potassium hydroxide, carbonate or hydrogen carbonate; with corresponding calcium compounds or with ammonia or a suitable organic amine, stoichiometric amounts or only a small excess of the salt-forming agent preferably being used. Acid addition salts of compounds of formula (I) are obtained in customary manner, e.g., by treating the compounds with an acid or a suitable anion exchange reagent. Internal salts of compounds of formula (I) containing acid and basic salt-forming groups, e.g., a free carboxy group and a free amino group, may be formed, e.g., by the neutralization of salts, such as acid addition salts, to the isoelectric point, e.g., with weak bases, or by treatment with ion exchangers.

Salts can be converted in customary manner into the free compounds; metal and ammonium salts can be converted, e.g., by treatment with suitable acids; and acid addition salts, e.g., by treatment with a suitable basic agent.

Mixtures of isomers obtainable according to the invention can be separated in a manner known per se into the individual isomers; diastereoisomers can be separated, e.g., by partitioning between polyphasic solvent mixtures, recrystallization and/or chromatographic separation, e.g., over silica gel or by, e.g., medium pressure liquid chromatography over a reversed phase column; and racemates can be separated, e.g., by the formation of salts with optically pure salt-forming reagents and separation of the mixture of diastereoisomers so obtainable, e.g., by means of fractional crystallization, or by chromatography over optically active column materials.

Intermediates and final products can be worked up and/or purified according to standard methods, e.g., using chromatographic methods, distribution methods, re-crystallization and the like.

Additional Process Steps

In the additional process steps, carried out as desired, functional groups of the starting compounds which should not take part in the reaction may be present in unprotected form or may be protected, e.g., by one or more protecting groups. The protecting groups are then wholly or partly removed according to one of the known methods.

Protecting groups, and the manner in which they are introduced and removed are described, e.g., *Protective Groups in Organic Chemistry*, Plenum Press, London, N.Y. (1973); *Methoden der organischen Chemie, Houben-Weyl*, 4*th* Edition, Vol. 15/1, Georg-Thieme-Verlag, Stuttgart (1974); and Theodora W. Greene, *Protective Groups in Organic Synthesis*, John Wiley & Sons, NY (1981). A characteristic of protecting groups is that they can be removed readily, i.e., without the occurrence of undesired secondary reactions, e.g., by solvolysis, reduction, photolysis or alternatively under physiological conditions.

The end products of formula (I) may however also contain substituents that can also be used as protecting groups in starting materials for the preparation of other end products of formula (I). Thus, within the scope of this text, only a readily removable group that is not a constituent of the particular desired end product of formula (I) is designated a “protecting group”, unless the context indicates otherwise.

General Process Conditions

The following applies in general to all processes mentioned hereinbefore and hereinafter, while reaction conditions specifically mentioned above or below are preferred:

All the above-mentioned process steps can be carried out under reaction conditions that are known per se, preferably those mentioned specifically, in the absence or, customarily, in the presence of solvents or diluents, preferably solvents or diluents that are inert towards the reagents used and dissolve them, in the absence or presence of catalysts, condensation or neutralizing agents, e.g., ion exchangers, such as cation exchangers, e.g., in the $H^+$ form; depending on the nature of the reaction and/or of the reactants at reduced, normal or elevated temperature, e.g., in a temperature range of from about −100° C. to about 190° C.; preferably from approximately −80° C. to approximately 150° C., e.g., at from −80° C. to −60° C. at RT, at from −20° C. to 40° C. or at reflux temperature; under atmospheric pressure or in a closed vessel, where appropriate under pressure and/or in an inert atmosphere, e.g., under an argon or nitrogen atmosphere.

At all stages of the reactions, mixtures of isomers that are formed can be separated into the individual isomers, e.g., diastereoisomers or enantiomers; or into any desired mixtures of isomers, e.g., racemates or mixtures of diastereoisomers, e.g., analogously to the methods described under “additional process steps”.

The solvents from which those solvents that are suitable for any particular reaction may be selected include those mentioned specifically or, e.g., water; esters, such as lower alkyl-lower alkanoates, e.g., ethyl acetate; ethers, such as aliphatic ethers, e.g., diethyl ether; or cyclic ethers, e.g., tetrahydrofuran or dioxane; liquid aromatic hydrocarbons, such as benzene or toluene; alcohols, such as methanol, ethanol or 1- or 2-propanol; nitriles, such as acetonitrile; halogenated hydrocarbons, such as methylene chloride or chloroform; acid amides, such as dimethylformamide or dimethyl acetamide; bases, such as heterocyclic nitrogen bases, e.g., pyridine or N-methylpyrrolidin-2-one; carboxylic acid anhydrides, such as lower alkanoic acid anhydrides, e.g., acetic anhydride; cyclic, linear or branched hydrocarbons, such as cyclohexane, hexane or isopentane; or mixtures of those solvents, e.g., aqueous solutions, unless otherwise indicated in the description of the processes. Such solvent mixtures may also be used in working up, e.g., by chromatography or partitioning.

The compounds, including their salts, may also be obtained in the form of hydrates, or their crystals may, e.g., include the solvent used for crystallization. Different crystalline forms may be present.

The invention relates also to those forms of the process in which a compound obtainable as intermediate at any stage of the process is used as starting material and the remaining process steps are carried out, or in which a starting material is formed under the reaction conditions or is used in the form of a derivative, e.g., in protected form or in the form of a salt, or a compound obtainable by the process according to the invention is produced under the process conditions and processed further in situ. In the process of the present invention those starting materials are preferably used which result in new compounds of formula (I) described at the beginning as being especially valuable. Special preference is given to reaction conditions that are analogous to those mentioned in the examples.

Pharmaceutical Compositions

The invention relates also to pharmaceutical compositions comprising a compound of formula (I), to their use in the therapeutic (in a broader aspect of the invention also prophylactic) treatment or a method of treatment of a lipid or protein kinase dependent disease, especially the preferred diseases mentioned above, to the compounds for said use and to the preparation of pharmaceutical preparations, especially for said uses.

The present invention also relates to pro-drugs of a compound of formula (I) that convert in vivo to the compound of formula (I) as such. Any reference to a compound of formula (I) is therefore to be understood as referring also to the corresponding pro-drugs of the compound of formula (I), as appropriate and expedient. The pharmacologically acceptable compounds of the present invention may be used, e.g., for the preparation of pharmaceutical compositions that comprise an effective amount of a compound of the formula (I), or a pharmaceutically acceptable salt thereof, as active ingredient together or in admixture with a significant amount of one or more inorganic or organic, solid or liquid, pharmaceutically acceptable carriers.

The invention relates also to a pharmaceutical composition that is suitable for administration to a warm-blooded animal, especially a human (or to cells or cell lines derived from a warm-blooded animal, especially a human, e.g., lymphocytes), for the treatment or, in a broader aspect of the invention, prevention of (=prophylaxis against) a disease that responds to inhibition of protein kinase activity, comprising an amount of a compound of formula (I) or a pharmaceutically acceptable salt thereof, which is effective for said inhibition, especially the in, together with at least one pharmaceutically acceptable carrier.

The pharmaceutical compositions according to the invention are those for enteral, such as nasal; rectal or oral; parenteral, such as intramuscular or intravenous; or topical, such as dermal administration to warm-blooded animals (especially a human), that comprise an effective dose of the pharmacologically active ingredient, alone or together with a significant amount of a pharmaceutically acceptable carrier. The dose of the active ingredient depends on the species of warm-blooded animal, the body weight, the age and the individual condition, individual pharmacokinetic data, the disease to be treated and the mode of administration.

The invention relates also to a method of treatment for a disease that responds to inhibition of a lipid or protein kinase, which comprises administering an (against the mentioned disease) prophylactically or especially therapeutically effective amount of a compound of formula (I) according to the invention, especially to a warm-blooded animal, e.g., a human, that, on account of one of the mentioned diseases, requires such treatment.

The dose of a compound of the formula (I) or a pharmaceutically acceptable salt thereof to be administered to warm-blooded animals, e.g., humans of approximately 70 kg body weight, is preferably from approximately 3 mg to approximately 10 g, more preferably from approximately 10 mg to approximately 1.5 g, most preferably from about 100 mg to about 1000 mg/person/day, divided preferably into 1-3 single doses which may, e.g., be of the same size. Usually, children receive half of the adult dose.

The pharmaceutical compositions comprise from approximately 1% to approximately 95%, preferably from approximately 20% to approximately 90%, active ingredient. Pharmaceutical compositions according to the invention may be, e.g., in unit dose form, such as in the form of ampoules, vials, suppositories, dragées, tablets or capsules.

The pharmaceutical compositions of the present invention are prepared in a manner known per se, e.g., by means of conventional dissolving, lyophilizing, mixing, granulating or confectioning processes.

Solutions of the active ingredient, and also suspensions, and especially isotonic aqueous solutions or suspensions, are preferably used, it being possible, e.g., in the case of lyophilized compositions that comprise the active ingredient alone or together with a carrier, e.g., mannitol, for such solutions or suspensions to be produced prior to use. The pharmaceutical compositions may be sterilized and/or may comprise excipients, e.g., preservatives, stabilizers, wetting and/or emulsifying agents, solubilizers, salts for regulating the osmotic pressure and/or buffers; and are prepared in a manner known per se, e.g., by means of conventional dissolving or lyophilizing processes. The said solutions or suspensions may comprise viscosity-increasing substances, such as sodium carboxymethylcellulose, carboxymethylcellulose, dextran, polyvinylpyrrolidone or gelatin.

Suspensions in oil comprise as the oil component the vegetable, synthetic or semi-synthetic oils customary for injection purposes. There may be mentioned as such especially liquid fatty acid esters that contain as the acid component a long-chained fatty acid having from 8-22 carbon atoms, especially from 12-22 carbon atoms, e.g., lauric acid, tridecylic acid, myristic acid, pentadecylic acid, palmitic acid, margaric acid, stearic acid, arachidic acid, behenic acid or corresponding unsaturated acids, e.g., oleic acid, elaidic acid, erucic acid, brasidic acid or linoleic acid, if desired with the addition of antioxidants, e.g., vitamin E, β-carotene or 3,5-di-tert-butyl-4-hydroxytoluene. The alcohol component of those fatty acid esters has a maximum of 6 carbon atoms and is a mono- or poly-hydroxy, e.g., a mono-, di- or tri-hydroxy; alcohol, e.g., methanol, ethanol, propanol, butanol or pentanol; or the isomers thereof, but especially glycol and glycerol. The following examples of fatty acid esters are therefore to be mentioned: ethyl oleate, isopropyl myristate, isopropyl palmitate, "Labrafil M 2375" (polyoxyethylene glycerol trioleate, Gattefossé, Paris), "Miglyol 812" (triglyceride of saturated fatty acids with a chain length of $C_8$-$C_{12}$, Hüls A G, Germany), but especially vegetable oils, such as cottonseed oil, almond oil, olive oil, castor oil, sesame oil, soybean oil and more especially groundnut oil.

The injection compositions are prepared in customary manner under sterile conditions; the same applies also to introducing the compositions into ampoules or vials and sealing the containers.

Pharmaceutical compositions for oral administration can be obtained by combining the active ingredient with solid carriers, if desired granulating a resulting mixture, and processing the mixture, if desired or necessary, after the addition of appropriate excipients, into tablets, dragée cores or capsules. It is also possible for them to be incorporated into plastics carriers that allow the active ingredients to diffuse or be released in measured amounts.

Suitable carriers are especially fillers, such as sugars, e.g., lactose, saccharose, mannitol or sorbitol; cellulose preparations and/or calcium phosphates, e.g., tricalcium phosphate or calcium hydrogen phosphate; and binders, such as starch pastes using, e.g., corn, wheat, rice or potato starch, gelatin, tragacanth, methylcellulose, hydroxypropylmethylcellulose, sodium carboxymethylcellulose and/or polyvinylpyrrolidone; and/or, if desired, disintegrators, such as the above-mentioned starches; and/or carboxymethyl starch, crosslinked polyvinylpyrrolidone, agar, alginic acid or a salt thereof, such as sodium alginate. Excipients are especially flow conditioners and lubricants, e.g., silicic acid, talc, stearic acid or salts thereof, such as magnesium or calcium stearate; and/or polyethylene glycol. Dragée cores are provided with suitable, optionally enteric, coatings, there being used, inter alia, concentrated sugar solutions which may comprise gum arabic, talc, polyvinylpyrrolidone, polyethylene glycol and/or titanium dioxide; or coating solutions in suitable organic solvents, or, for the preparation of enteric coatings, solutions of suitable cellulose preparations, such as ethylcellulose phthalate or hydroxypropylmethylcellulose phthalate. Capsules are dry-filled capsules made of gelatin and soft sealed capsules made of gelatin and a plasticizer, such as glycerol or sorbitol. The dry-filled capsules may comprise the active ingredient in the form of granules, e.g., with fillers, such as lactose; binders, such as starches; and/or glidants, such as talc or magnesium stearate; and if desired with stabilizers. In soft capsules the active ingredient is preferably dissolved or suspended in suitable oily excipients, such as fatty oils, paraffin oil or liquid polyethylene glycols, it being possible also for stabilizers and/or antibacterial agents to be added. Dyes or pigments may be added to the tablets or dragée coatings or the capsule casings, e.g., for identification purposes or to indicate different doses of active ingredient.

Pharmaceutical compositions for topical administration can be obtained by combining the active ingredient with a liquid carrier (e.g. an aqueous liquid carrier) to dissolve or disperse the active, together with further optional formulating ingredients such as solvents/solubilisers, gelling agents, oils, stabilisers, buffers and preservatives to provide for example a solution, lotion, cream, gel or ointment. The pharmaceutical compositions for topical administration may be provided, for example, for dermal application. The pharmaceutical compositions for topical administration may comprise from approximately 0.1% to approximately 2% of active ingredient, the active ingredient being especially a compound of formula (I), in particular, a compound described in the individual examples herein.

Compounds of the invention display particularly high solubilities in organic solvents. The compounds of the invention are thus particularly useful for topical administration, e.g. to a mammal such as a human, e.g. to the skin of said mammal. The compounds are thus useful for formulation into compositions suitable for topical administration. Compounds displaying high solubility thus provide an advantage for topical administration over compounds having a lower solubility.

The solubility of certain compounds was determined in the organic solvents PEG400, propyleneglycol and ethanol. The results are provided in the following table, showing high solubilities of the specified compounds, demonstrating that those compounds are particularly suitable for formulation into compositions for topical administration.

| Excipient | Example 4.1 Solubility [mg/mL] | Example 58.1 Solubility [mg/mL] | Example 84.1 Solubility [mg/mL] | Example 191.1 Solubility [mg/mL] |
|---|---|---|---|---|
| PEG400 | >20 | >26 | >19 | >23 |
| Propyleneglycol | >20 | >24 | >20 | >19 |
| Ethanol abs. | 4.11 | >22 | >21 | >24 |

Combinations

A compound of the formula (I) may also be used to advantage in combination with each other or in combination with other therapeutic agents, especially other antiproliferative agents. Such antiproliferative agents include, but are not limited to, aromatase inhibitors; antiestrogens; topoisomerase I inhibitors; topoisomerase II inhibitors; microtubule active agents; alkylating agents; histone deacetylase inhibitors; compounds, which induce cell differentiation processes; cyclooxygenase inhibitors; MMP inhibitors; mTOR inhibitors; antineoplastic antimetabolites; platin compounds; compounds targeting/decreasing a protein or lipid kinase activity and further anti-angiogenic compounds; compounds which target, decrease or inhibit the activity of a protein or lipid phosphatase; gonadorelin agonists; anti-androgens; methionine aminopeptidase inhibitors; bisphosphonates; biological response modifiers; antiproliferative antibodies; heparanase inhibitors; inhibitors of Ras oncogenic isoforms; telomerase inhibitors; proteasome inhibitors; agents used in the treatment of hematologic malignancies; compounds which target, decrease or inhibit the activity of Flt-3; Hsp90 inhibitors; temozolomide (TEMODAL®); and leucovorin.

The term “aromatase inhibitor”, as used herein, relates to a compound which inhibits the estrogen production, i.e., the conversion of the substrates androstenedione and testosterone to estrone and estradiol, respectively. The term includes, but is not limited to, steroids, especially atamestane, exemestane and formestane; and, in particular, non-steroids, especially aminoglutethimide, roglethimide, pyridoglutethimide, trilostane, testolactone, ketokonazole, vorozole, fadrozole, anastrozole and letrozole. Exemestane can be administered, e.g., in the form as it is marketed, e.g., under the trademark AROMASIN. Formestane can be administered, e.g., in the form as it is marketed, e.g., under the trademark LENTARON. Fadrozole can be administered, e.g., in the form as it is marketed, e.g., under the trademark AFEMA. Anastrozole can be administered, e.g., in the form as it is marketed, e.g., under the trademark ARIMIDEX. Letrozole can be administered, e.g., in the form as it is marketed, e.g., under the trademark FEMARA or FEMAR. Aminoglutethimide can be administered, e.g., in the form as it is marketed, e.g., under the trademark ORIMETEN. A combination of the invention comprising a chemotherapeutic agent which is an aromatase inhibitor is particularly useful for the treatment of hormone receptor positive tumors, e.g., breast tumors.

The term “anti-estrogen”, as used herein, relates to a compound which antagonizes the effect of estrogens at the estrogen receptor level. The term includes, but is not limited to, tamoxifen, fulvestrant, raloxifene and raloxifene hydrochloride. Tamoxifen can be administered, e.g., in the form as it is marketed, e.g., under the trademark NOLVADEX. Raloxifene hydrochloride can be administered, e.g., in the form as it is marketed, e.g., under the trademark EVISTA. Fulvestrant can be formulated as disclosed in U.S. Pat. No. 4,659,516 or it can be administered, e.g., in the form as it is marketed, e.g., under the trademark FASLODEX. A combination of the invention comprising a chemotherapeutic agent which is an antiestrogen is particularly useful for the treatment of estrogen receptor positive tumors, e.g., breast tumors.

The term “anti-androgen”, as used herein, relates to any substance which is capable of inhibiting the biological effects of androgenic hormones and includes, but is not limited to, bicalutamide (CASODEX), which can be formulated, e.g., as disclosed in U.S. Pat. No. 4,636,505.

The term “gonadorelin agonist”, as used herein, includes, but is not limited to, abarelix, goserelin and goserelin acetate. Goserelin is disclosed in U.S. Pat. No. 4,100,274 and can be administered, e.g., in the form as it is marketed, e.g., under the trademark ZOLADEX. Abarelix can be formulated, e.g., as disclosed in U.S. Pat. No. 5,843,901.

The term “topoisomerase I inhibitor”, as used herein, includes, but is not limited to, topotecan, gimatecan, irinotecan, camptothecian and its analogues, 9-nitrocamptothecin and the macromolecular camptothecin conjugate PNU-166148 (compound A1 in WO 99/17804). Irinotecan can be administered, e.g., in the form as it is marketed, e.g., under the trademark CAMPTOSAR. Topotecan can be administered, e.g., in the form as it is marketed, e.g., under the trademark HYCAMTIN.

The term “topoisomerase II inhibitor”, as used herein, includes, but is not limited to, the anthracyclines, such as doxorubicin, including liposomal formulation, e.g., CAE- LYX; daunorubicin; epirubicin; idarubicin; nemorubicin; the anthraquinones mitoxantrone and losoxantrone; and the podophillotoxines etoposide and teniposide. Etoposide can be administered, e.g., in the form as it is marketed, e.g., under the trademark ETOPOPHOS. Teniposide can be administered, e.g., in the form as it is marketed, e.g., under the trademark VM 26-BRISTOL. Doxorubicin can be administered, e.g., in the form as it is marketed, e.g., under the trademark ADRIBLASTIN or ADRIAMYCIN. Epirubicin can be administered, e.g., in the form as it is marketed, e.g., under the trademark FARMORUBICIN. Idarubicin can be administered, e.g., in the form as it is marketed, e.g., under the trademark ZAVEDOS. Mitoxantrone can be administered, e.g., in the form as it is marketed, e.g., under the trademark NOVANTRON.

The term "microtubule active agent" relates to microtubule stabilizing, microtubule destabilizing agents and microtublin polymerization inhibitors including, but not limited to, taxanes, e.g., paclitaxel and docetaxel; vinca alkaloids, e.g., vinblastine, especially vinblastine sulfate; vincristine, especially vincristine sulfate and vinorelbine; discodermolides; cochicine; and epothilones and derivatives thereof, e.g., epothilone B or D or derivatives thereof. Paclitaxel may be administered, e.g., in the form as it is marketed, e.g., TAXOL. Docetaxel can be administered, e.g., in the form as it is marketed, e.g., under the trademark TAXOTERE. Vinblastine sulfate can be administered, e.g., in the form as it is marketed, e.g., under the trademark VINBLASTIN R.P. Vincristine sulfate can be administered, e.g., in the form as it is marketed, e.g., under the trademark FARMISTIN. Discodermolide can be obtained, e.g., as disclosed in U.S. Pat. No. 5,010,099. Also included are epothilone derivatives which are disclosed in WO 98/10121, U.S. Pat. No. 6,194,181, WO 98/25929, WO 98/08849, WO 99/43653, WO 98/22461 and WO 00/31247. Especially preferred are epothilone A and/or B.

The term "alkylating agent", as used herein, includes, but is not limited to, cyclophosphamide, ifosfamide, melphalan or nitrosourea (BCNU or Gliadel). Cyclophosphamide can be administered, e.g., in the form as it is marketed, e.g., under the trademark CYCLOSTIN. Ifosfamide can be administered, e.g., in the form as it is marketed, e.g., under the trademark HOLOXAN.

The term "histone deacetylase inhibitors" or "HDAC inhibitors" relates to compounds which inhibit the histone deacetylase and which possess antiproliferative activity. This includes compounds disclosed in WO 02/22577, especially N-hydroxy-3-[4-[[(2-hydroxyethyl)[2-(1H-indol-3-yl) ethyl]-amino]methyl]phenyl]-2E-2-propenamide, N-hydroxy-3-[4-[[[2-(2-methyl-1H-indol-3-yl)-ethyl]-amino] methyl]phenyl]-2E-2-propenamide and pharmaceutically acceptable salts thereof. It further especially includes suberoylanilide hydroxamic acid (SAHA).

The term "antineoplastic antimetabolite" includes, but is not limited to, 5-fluorouracil or 5-FU; capecitabine; gemcitabine; DNA demethylating agents, such as 5-azacytidine and decitabine; methotrexate and edatrexate; and folic acid antagonists, such as pemetrexed. Capecitabine can be administered, e.g., in the form as it is marketed, e.g., under the trademark XELODA. Gemcitabine can be administered, e.g., in the form as it is marketed, e.g., under the trademark GEMZAR. Also included is the monoclonal antibody trastuzumab which can be administered, e.g., in the form as it is marketed, e.g., under the trademark HERCEPTIN.

The term "platin compound", as used herein, includes, but is not limited to, carboplatin, cis-platin, cisplatinum and oxaliplatin. Carboplatin can be administered, e.g., in the form as it is marketed, e.g., under the trademark CARBOPLAT. Oxaliplatin can be administered, e.g., in the form as it is marketed, e.g., under the trademark ELOXATIN.

The term "compounds targeting/decreasing a protein or lipid kinase activity; or a protein or lipid phosphatase activity; or further anti-angiogenic compounds", as used herein, includes, but is not limited to, protein tyrosine kinase and/or serine and/or threonine kinase inhibitors or lipid kinase inhibitors, e.g., a) compounds targeting, decreasing or inhibiting the activity of the platelet-derived growth factor-receptors (PDGFR), such as compounds which target, decrease or inhibit the activity of PDGFR, especially compounds which inhibit the PDGF receptor, e.g., a N-phenyl-2-pyrimidine-amine derivative, e.g., imatinib, SU101, SU6668 and GFB-111;
b) compounds targeting, decreasing or inhibiting the activity of the fibroblast growth factor-receptors (FGFR);
c) compounds targeting, decreasing or inhibiting the activity of the insulin-like growth factor receptor I (IGF-IR), such as compounds which target, decrease or inhibit the activity of IGF-IR, especially compounds which inhibit the IGF-IR receptor, such as those compounds disclosed in WO 02/092599;
d) compounds targeting, decreasing or inhibiting the activity of the Trk receptor tyrosine kinase family;
e) compounds targeting, decreasing or inhibiting the activity of the Axl receptor tyrosine kinase family;
f) compounds targeting, decreasing or inhibiting the activity of the c-Met receptor;
g) compounds targeting, decreasing or inhibiting the activity of the Kit/SCFR receptor tyrosine kinase;
h) compounds targeting, decreasing or inhibiting the activity of the C-kit receptor tyrosine kinases—(part of the PDGFR family), such as compounds which target, decrease or inhibit the activity of the c-Kit receptor tyrosine kinase family, especially compounds which inhibit the c-Kit receptor, e.g., imatinib;
i) compounds targeting, decreasing or inhibiting the activity of members of the c-Abl family and their gene-fusion products, e.g., BCR-Abl kinase, such as compounds which target decrease or inhibit the activity of c-Abl family members and their gene fusion products, e.g., a N-phenyl-2-pyrimidine-amine derivative, e.g., imatinib, PD180970, AG957, NSC 680410 or PD173955 from ParkeDavis;
j) compounds targeting, decreasing or inhibiting the activity of members of the protein kinase C (PKC) and Raf family of serine/threonine kinases, members of the MEK, SRC, JAK, FAK, PDK and Ras/MAPK family members, or PI(3) kinase family, or of the PI(3)-kinase-related kinase family, and/or members of the cyclin-dependent kinase family (CDK) and are especially those staurosporine derivatives disclosed in U.S. Pat. No. 5,093,330, e.g., midostaurin; examples of further compounds include, e.g., UCN-01; safingol; BAY 43-9006; Bryostatin 1; Perifosine; Ilmofosine; RO 318220 and RO 320432; GO 6976; Isis 3521; LY333531/LY379196; isochinoline compounds, such as those disclosed in WO 00/09495; FTIs; PD184352; or QAN697 (a P13K inhibitor);
k) compounds targeting, decreasing or inhibiting the activity of protein-tyrosine kinase inhibitors, such as compounds which target, decrease or inhibit the activity of protein-tyrosine kinase inhibitors include imatinib mesylate (GLEEVEC) or tyrphostin. A tyrphostin is preferably a low molecular weight (Mr<1500) compound, or a pharmaceutically acceptable salt thereof, especially a compound selected from the benzylidenemalonitrile class or the S-arylbenzenemalonirile or bisubstrate quinoline class of compounds, more especially any compound selected from the group consisting of Tyrphostin A23/RG-50810, AG 99, Tyrphostin AG 213, Tyrphostin AG 1748, Tyrphostin AG 490, Tyrphostin B44, Tyrphostin B44 (+) enantiomer, Tyrphostin AG 555, AG 494, Tyrphostin AG 556, AG957 and adaphostin (4-{[(2,5-dihydroxyphenyl)methyl]amino}-benzoic acid adamantyl ester, NSC 680410, adaphostin; and l) compounds targeting, decreasing or inhibiting the activity of the epidermal growth factor family of receptor tyrosine kinases (EGFR, ErbB2, ErbB3, ErbB4 as homo- or hetero-dimers), such as compounds which target, decrease or inhibit the activity of the epidermal growth factor receptor family are especially compounds, proteins or antibodies which inhibit members of the EGF receptor tyrosine kinase family, e.g., EGF receptor, ErbB2, ErbB3 and ErbB4 or bind to EGF or EGF related ligands, and are in particular those compounds, proteins or monoclonal antibodies generically and specifically disclosed in WO 97/02266, e.g., the compound of Example 39, or in EP 0 564 409; WO 99/03854; EP 0520722; EP 0 566 226; EP 0 787 722; EP 0 837 063; U.S. Pat. No. 5,747,498; WO 98/10767; WO 97130034; WO 97/49688; WO 97/38983 and, especially, WO 96/30347, e.g., compound known as CP 358774; WO 96/33980, e.g., compound ZD 1839; and WO 95/03283, e.g., compound ZM105180, e.g., trastuzumab (HERCEPTIN), cetuximab, Iressa, Tarceva, OSI-774, CI-1033, EKB-569, GW-2016, E1.1, E2.4, E2.5, E6.2, E6.4, E2.11, E6.3 or E7.6.3; and 7H-pyrrolo-[2,3-d] pyrimidine derivatives which are disclosed in WO 03/013541.

Further anti-angiogenic compounds include compounds having another mechanism for their activity, e.g., unrelated to protein or lipid kinase inhibition, e.g., thalidomide (THALOMID) and TNP-470.

Compounds which target, decrease or inhibit the activity of a protein or lipid phosphatase are, e.g., inhibitors of phosphatase 1, phosphatase 2A, PTEN or CDC25, e.g., okadaic acid or a derivative thereof.

Compounds which induce cell differentiation processes are e.g. retinoic acid, α- γ- or δ-tocopherol or α- γ- or δ-tocotrienol.

The term cyclooxygenase inhibitor, as used herein, includes, but is not limited to, e.g., Cox-2 inhibitors, 5-alkyl substituted 2-arylaminophenylacetic acid and derivatives, such as celecoxib (CELEBREX), rofecoxib (VIOXX), etoricoxib, valdecoxib or a 5-alkyl-2-arylaminophenylacetic acid, e.g., 5-methyl-2-(2'-chloro-6'-fluoroanilino)phenyl acetic acid or lumiracoxib.

The term "bisphosphonates", as used herein, includes, but is not limited to, etridonic, clodronic, tiludronic, pamidronic, alendronic, ibandronic, risedronic and zoledronic acid. "Etridonic acid" can be administered, e.g., in the form as it is marketed, e.g., under the trademark DIDRONEL. "Clodronic acid" can be administered, e.g., in the form as it is marketed, e.g., under the trademark BONEFOS. "Tiludronic acid" can be administered, e.g., in the form as it is marketed, e.g., under the trademark SKELID. "Pamidronic acid" can be administered, e.g., in the form as it is marketed, e.g., under the trademark AREDIA™. "Alendronic acid" can be administered, e.g., in the form as it is marketed, e.g., under the trademark FOSAMAX. "Ibandronic acid" can be administered, e.g., in the form as it is marketed, e.g., under the trademark BONDRANAT. "Risedronic acid" can be administered, e.g., in the form as it is marketed, e.g., under the trademark ACTONEL. "Zoledronic acid" can be administered, e.g., in the form as it is marketed, e.g., under the trademark ZOMETA.

The term "mTOR inhibitors" relates to compounds which inhibit the mammalian target of rapamycin (mTOR) and which possess antiproliferative activity, such as sirolimus (Rapamune®), everolimus (Certican™), CCI-779 and ABT578.

The term "heparanase inhibitor", as used herein, refers to compounds which target, decrease or inhibit heparin sulphate degradation. The term includes, but is not limited to, PI-88.

The term "biological response modifier", as used herein, refers to a lymphokine or interferons, e.g., interferon γ.

The term "inhibitor of Ras oncogenic isoforms", e.g., H-Ras, K-Ras or N-Ras, as used herein, refers to compounds which target, decrease or inhibit the oncogenic activity of Ras, e.g., a "farnesyl transferase inhibitor", e.g., L-744832, DK8G557 or R115777 (Zarnestra).

The term "telomerase inhibitor", as used herein, refers to compounds which target, decrease or inhibit the activity of telomerase. Compounds which target, decrease or inhibit the activity of telomerase are especially compounds which inhibit the telomerase receptor, e.g., telomestatin.

The term "methionine aminopeptidase inhibitor", as used herein, refers to compounds which target, decrease or inhibit the activity of methionine aminopeptidase. Compounds which target, decrease or inhibit the activity of methionine aminopeptidase are, e.g., bengamide or a derivative thereof.

The term "proteasome inhibitor", as used herein, refers to compounds which target, decrease or inhibit the activity of the proteasome. Compounds which target, decrease or inhibit the activity of the proteasome include, e.g., PS-341 and MLN 341.

The term "matrix metalloproteinase inhibitor" or "MMP inhibitor", as used herein, includes, but is not limited to, collagen peptidomimetic and nonpeptidomimetic inhibitors, tetracycline derivatives, e.g., hydroxamate peptidomimetic inhibitor batimastat and its orally bioavailable analogue marimastat (BB-2516), prinomastat (AG3340), metastat (NSC 683551) BMS-279251, BAY 12-9566, TAA211, MMI270B or AAJ996.

The term "agents used in the treatment of hematologic malignancies", as used herein, includes, but is not limited to, FMS-like tyrosine kinase inhibitors, e.g., compounds targeting, decreasing or inhibiting the activity of FMS-like tyrosine kinase receptors (Flt-3R); interferon, 1-b-D-arabinofuransylcytosine (ara-c) and bisulfan; and ALK inhibitors, e.g., compounds which target, decrease or inhibit anaplastic lymphoma kinase.

Compounds which target, decrease or inhibit the activity of FMS-like tyrosine kinase receptors (Flt-3R) are especially compounds, proteins or antibodies which inhibit members of the Flt-3R receptor kinase family, e.g., PKC412, midostaurin, a staurosporine derivative, SU11248 and MLN518.

The term "HSP90 inhibitors", as used herein, includes, but is not limited to, compounds targeting, decreasing or inhibiting the intrinsic ATPase activity of HSP90; degrading, targeting, decreasing or inhibiting the HSP90 client proteins via the ubiquitin proteasome pathway. Compounds targeting, decreasing or inhibiting the intrinsic ATPase activity of HSP90 are especially compounds, proteins or antibodies which inhibit the ATPase activity of HSP90, e.g., 17-allylamino,17-demethoxygeldanamycin (17AAG), a geldanamycin derivative, other geldanamycin related compounds, radicicol and HDAC inhibitors.

The term "antiproliferative antibodies", as used herein, includes, but is not limited to, trastuzumab (Herceptin™), Trastuzumab-DM1, erlotinib (Tarceva™), bevacizumab (Avastin™), rituximab (Rituxan®), PRO64553 (anti-CD40) and 2C4 antibody. By antibodies is meant, e.g., intact monoclonal antibodies, polyclonal antibodies, multispecific antibodies formed from at least two intact antibodies, and antibodies fragments so long as they exhibit the desired biological activity.

For the treatment of acute myeloid leukemia (AML), compounds of formula (I) can be used in combination with standard leukemia therapies, especially in combination with therapies used for the treatment of AML. In particular, compounds of formula (I) can be administered in combination with, e.g., farnesyl transferase inhibitors and/or other drugs useful for the treatment of AML, such as Daunorubicin, Adriamycin, Ara-C, VP-16, Teniposide, Mitoxantrone, Idarubicin, Carboplatinum and PKC412.

The structure of the active agents identified by code nos., generic or trade names may be taken from the actual edition of the standard compendium "The Merck Index" or from databases, e.g., Patents International, e.g., IMS World Publications.

The above-mentioned compounds, which can be used in combination with a compound of the formula (I), can be prepared and administered as described in the art, such as in the documents cited above.

A compound of the formula (I) may also be used to advantage in combination with known therapeutic processes, e.g., the administration of hormones or especially radiation.

A compound of formula (I) may in particular be used as a radiosensitizer, especially for the treatment of tumors which exhibit poor sensitivity to radiotherapy.

By "combination", there is meant either a fixed combination in one dosage unit form, or a kit of parts for the combined administration where a compound of the formula (I) and a combination partner may be administered independently at the same time or separately within time intervals that especially allow that the combination partners show a cooperative, e.g., synergistic, effect or any combination thereof. The terms "co-administration" or "combined administration" or the like as utilized herein are meant to encompass administration of the selected combination partner to a single subject in need thereof (e.g. a patient), and are intended to include treatment regimens in which the agents are not necessarily administered by the same route of administration or at the same time. The term "pharmaceutical combination" as used herein means a product that results from the mixing or combining of more than one active ingredient and includes both fixed and non-fixed combinations of the active ingredients. The term "fixed combination" means that the active ingredients, e.g. a compound of formula I and a combination partner, are both administered to a patient simultaneously in the form of a single entity or dosage. The term "non-fixed combination" means that the active ingredients, e.g. a compound of formula (I) and a combination partner, are both administered to a patient as separate entities either simultaneously, concurrently or sequentially with no specific time limits, wherein such administration provides therapeutically effective levels of the two compounds in the body of the patient. The latter also applies to cocktail therapy, e.g. the administration of three or more active ingredients.

The following examples are merely illustrative and not meant to limit the scope of the present claims in any manner.

EXAMPLES

The following examples serve to illustrate the invention without limiting the scope thereof:

Temperatures are measured in degrees Celsius. Unless otherwise indicated, the reactions take place at rt. The following HPLC/MS and MS methods are used in the preparation of the Intermediates and Examples:

HPLC Method:

Method A

HPLC linear gradient between A=$H_2O$/TFA 1000:1 and B=acetonitrile/TFA 1000:1 Grad 1: 2-100% Bin 4.5 min and 1 min at 100% B; column: Chromolith Performance 100 mm×4.5 mm (Merck, Darmstadt, Germany); flow rate 2 ml/min. Detection at 215 nM.

LC-MS Method:

Method B

System: Agilent 1100 Series with Waters Micromass ZQ

Column: XBridge C18, 3×30 mm, 2.5 micron

Flow Rate: 1.4-2.4 mL/min

Eluent A: $H_2O$, containing 5% acetonitrile and 0.8% HCOOH

Eluent B: acetonitrile, containing 0.6% HCOOH

Gradient: 0-2.4 min: 10% to 95% of B

In the following examples, the abbreviations given below are used:

| | |
|---|---|
| DCM | dichloromethane |
| DIPEA | N,N-diisopropylethylamine |
| DMA | dimethylacetamide |
| DME | 1,2-dimethoxyethane |
| DMF | N,N-dimethylformamide |
| DMSO | dimethyl sulfoxide |
| EtOAc | ethyl acetate |
| h | hour(s) |
| HPLC | high performance liquid chromatography |
| HV | high vacuum |
| Intermed. | intermediate |
| iPrMgCl | isopropylmagnesium chloride |
| iPrOH | isopropanol |
| LC-MS | liquid chromatography coupled with mass spectrometry |
| MeOH | methanol |
| ml | milliliter(s) |
| min | minute(s) |
| MS-ES | electrospray mass spectrometry |
| NMP | N-methyl-2-pyrrolidone |
| $PdCl_2$(dppf) | [1,1'-bis(diphenylphosphino)ferrocene]dichloropalladium (II) |
| $PdCl_2(PPh_3)_2$ | bis(triphenylphosphine)palladium (II) dichloride |
| $Pd_2(dba)_3$ | tris(dibenzylideneacetone)dipalladium (0) |
| Prep.HPLC | preparative high performance liquid chromatography |
| qt | quintuplet |
| RM | reaction mixture |
| rt | room temperature |
| TEA | triethylamine |
| TFA | trifluoroacetic acid |
| THF | tedrahydrofurane |
| $t_R$ | retention time |
| TPTU | O-(1,2-dihydro-2-oxo-1-pyridyl)-N,N,N'-N'-tetramethyluronium tetrafluoroborate |

Intermediate A: 8-Bromo-1-(1,3-dimethyl-1H-pyrazol-4-yl)-3-methyl-1,3-dihydro-imidazo[4,5-c]quinolin-2-one

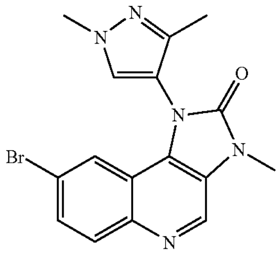 [SMILES: Cc1nn(C)cc1-n1c(=O)n(C)c2cnc3ccc(Br)cc3c21]

NaOH (0.568 g, 14.19 mmol) and tetrabutylammonium bromide (0.229 g, 0.710 mmol) were added to a mixture of 8-bromo-1-(1,3-dimethyl-1H-pyrazol-4-yl)-1,3-dihydro-imidazo[4,5-c]quinolin-2-one (Stage A.1, 3.10 g, 7.100 mmol) in DCM (108 ml) and $H_2O$ (54 ml) and stirred at rt for 5 min. Then iodomethane (1.52 ml, 24.1 mmol) was added and the mixture was stirred for 14 h at rt. Iodomethane (0.4 ml, 6.35 mmol) was added and the RM was stirred at rt for 23.5 h. Then the RM was extracted with DCM (2×), washed with saturated aqueous $NaHCO_3$ and brine, dried over $Na_2SO_4$, filtered and evaporated to dryness. The residue was dissolved in DCM and purified by flash chromatography (DCM/MeOH 0%-4.5%) to give the title compound as a brownish solid (HPLC: $t_R$ 2.37 min (Method A); M+H=374 MS-ES; $^1$H-NMR ($d_6$-DMSO, 400 MHz) 9.00 (s, 1H), 8.08 (s, 1H), 7.91-7.99 (m, 1H), 7.64-7.71 (m, 1H), 7.41-7.47 (m, 1H), 3.90 (s, 3H), 3.55 (s, 3H), 1.94 (s, 3H))

Stage A.1: 8-Bromo-1-(1,3-dimethyl-1H-pyrazol-4-yl)-1,3-dihydro-imidazo[4,5-c]quinolin-2-one

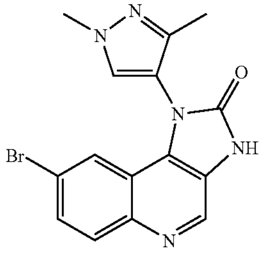

To a solution of 6-bromo-N*4*-(1,3-dimethyl-1H-pyrazol-4-yl)-quinoline-3,4-diamine (Stage A.2, 3.15 g, 8.15 mmol) and TEA (1.36 ml, 9.79 mmol) in DCM (65 ml) was added under argon, after cooling with an ice-bath, a solution of trichloromethyl chloroformate (1.08 ml, 8.97 mmol in DCM (65 ml). The mixture was stirred for 25 min at 0° C. Then the RM was quenched with sat. aqueous $NaHCO_3$ (300 ml) and 10 M aqueous NaOH (4 ml) and well stirred. The phases were separated and extracted with EtOAc (3×). The combined organic layers were washed with brine (2×), dried over $Na_2SO_4$, filtered and evaporated to dryness to give the title compound as a brownish solid (HPLC $t_R$ 2.29 min (Method A); M+H=360; M−H=358 MS-ES)

Stage A.2 6-Bromo-N*4*-(1,3-dimethyl-1H-pyrazol-4-yl)-quinoline-3,4-diamine

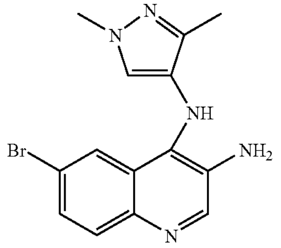 [SMILES: Cc1nn(C)cc1Nc1c(N)cnc2ccc(Br)cc12]

(6-Bromo-3-nitro-quinolin-4-yl)-(1,3-dimethyl-1H-pyrazol-4-yl)-amine (Stage A.3, 3.67 g 9.73 mmol) was shacked in MeOH/THF 1:1 (120 ml) under 1.1 bar $H_2$ in presence of Raney nickel (1.50 g) as catalyst for 5 h at rt. The RM was filtered over celite, the catalyst was washed with MeOH/DCM and the solution was evaporated to dryness to give the title compound as a red solid (HPLC $t_R$ 2.44 min (Method A); M+H=334; M−H=332 MS-ES)

Stage A.3 (6-Bromo-3-nitro-quinolin-4-yl)-(1,3-dimethyl-1H-pyrazol-4-yl)-amine

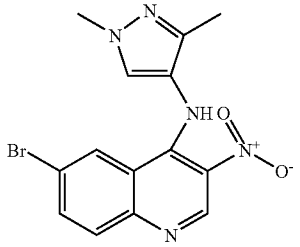 [SMILES: Cc1nn(C)cc1Nc1c([N+](=O)[O-])cnc2ccc(Br)cc12]

To a mixture of 6-bromo-4-chloro-3-nitro-quinoline (Stage A.4, 3.0 g, 20.43 mmol) and 4-amino-1,3-dimethylpyrazole.HCl (ChemCollect, Remscheid, Germany, 1.85 g, 12.53 mmol) in DMA (45 ml) was added 1,2,2,6,6-pentamethylpiperidine (6.67 ml, 36.5 mmol). The RM was stirred at 50° C. for 4.5 h. Then the RM was cooled down to rt and quenched with $H_2O$. The suspension was filtered, the solid cake was washed with $H_2O$ and dried under vacuum, before being dissolved in EtOAc. The solution was washed with brine (2×), dried over $Na_2SO_4$, filtered and evaporated to dryness to give the title compound as an orange solid (HPLC $t_R$ 2.55 min (Method A); M+H=362; M−H=360 MS-ES)

Stage A.4 6-Bromo-4-chloro-3-nitro-quinoline

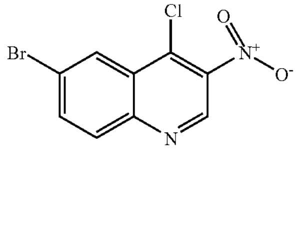 [SMILES: O=[N+]([O-])c1cnc2ccc(Br)cc2c1Cl]

6-Bromo-3-nitro-quinolin-4-ol (Fluorochem Ltd., Derbyshire, UK, 10 g, 37.2 mmol) was added to $POCl_3$ (70 ml). The RM was stirred at 120° C. for 17 h. Then the RM was cooled with an ice-bath, before being slowly dropped onto ice-water. The precipitate was filtered and washed with cold water. The residue was dissolved in DCM, washed with brine, dried over $Na_2SO_4$, filtered and evaporated to give the title compound as a beige solid (HPLC $t_R$ 3.64 min (Method A))

The following intermediates were synthesized in a similar manner as described for intermediate A using as replacement for the 4-amino-1,3-dimethylpyrazole.HCl a different aminopyrrazole starting material:

5-Amino-1-ethylpyrazole (Aldrich, Buchs, Switzerland; B)

5-Amino-1,3-dimethylpyrazole (Aldrich, Buchs, Switzerland; C)

5-Amino-1-methyl-3-(trifluoromethyl)pyrazole (Art-Chem, Akos, Steinen, Germany; D)

5-Amino-1-methylpyrazole (Combi-Blocks, San Diego, USA; E)

4-Amino-1-ethyl-3-methylpyrazole.HCl (Art-Chem, Akos, Steinen, Germany; F)

4-Amino-1-isopropyl-3-methylpyrazole.HCl (Art-Chem, Akos, Steinen, Germany; G)

4-Amino-1,3,5-trimethylpyrazole (ABCR, Karlsruhe, Germany; H)

5-Amino-1,4-dimethylpyrazole (ChemBridge, San Diego, USA; I)

4-Amino-1,5-dimethylpyrazole.2HCl (Art-Chem, Akos, Steinen, Germany; J)

| Intermed. | structure | Name of the intermediate | MS-ES (M + H) | HPLC $t_R$ (min) |
|---|---|---|---|---|
| B | 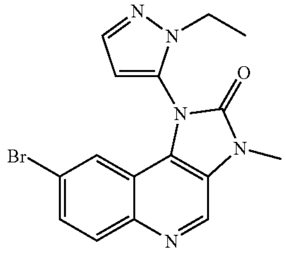 [SMILES: CCn1nccc1-n1c(=O)n(C)c2cnc3ccc(Br)cc3c21] | 8-Bromo-1-(2-ethyl-2H-pyrazol-3-yl)-3-methyl-1,3-dihydro-imidazo[4,5-c]quinolin-2-one | 372, 374 | 2.66 |
| C | 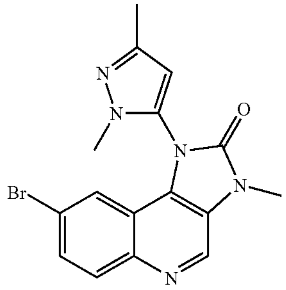 [SMILES: Cc1cc(-n2c(=O)n(C)c3cnc4ccc(Br)cc4c32)n(C)n1] | 8-Bromo-1-(2,5-dimethyl-2H-pyrazol-3-yl)-3-methyl-1,3-dihydro-imidazo [4,5-c]quinolin-2-one | 372, 374 | 2.65 |
| D | 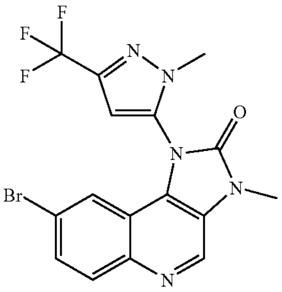 [SMILES: Cn1nc(C(F)(F)F)cc1-n1c(=O)n(C)c2cnc3ccc(Br)cc3c21] | 8-Bromo-3-methyl-1-(2-methyl-5-trifluoromethyl-2H-pyrazol-3-yl)-1,3-dihydro-imidazo[4,5-c]quinolin-2-one | 426, 428 | 3.22 |
| E | 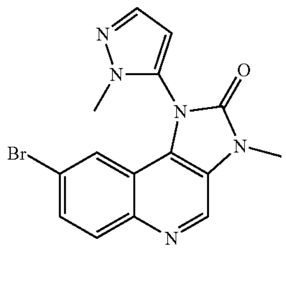 [SMILES: Cn1nccc1-n1c(=O)n(C)c2cnc3ccc(Br)cc3c21] | 8-Bromo-3-methyl-1-(2-methyl-2H-pyrazol-3-yl)-1,3-dihydro-imidazo[4,5-c]quinolin-2-one | 358, 360 | 2.54 |

-continued

| Intermed. | structure | Name of the intermediate | MS-ES (M + H) | HPLC $t_R$ (min) |
|---|---|---|---|---|
| F | 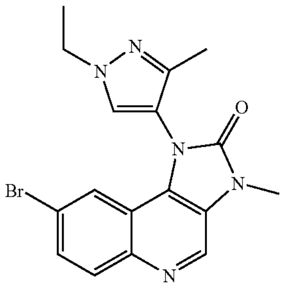 [SMILES: CCn1cc(-n2c(=O)n(C)c3cnc4ccc(Br)cc4c32)c(C)n1] | 8-Bromo-1-(1-ethyl-3-methyl-1H-pyrazol-4-yl)-3-methyl-1,3-dihydro-imidazo[4,5-c]quinolin-2-one | 386, 388 | 2.54 |
| G | 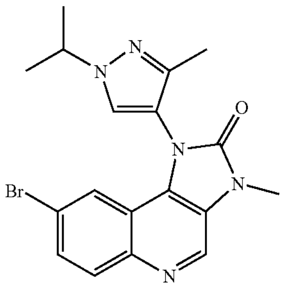 [SMILES: Cc1nn(C(C)C)cc1-n1c(=O)n(C)c2cnc3ccc(Br)cc3c21] | 8-Bromo-1-(1-isopropyl-3-methyl-1H-pyrazol-4-yl)-3-methyl-1,3-dihydro-imidazo[4,5-c]quinolin-2-one | 400, 402 | 2.70 |
| H | 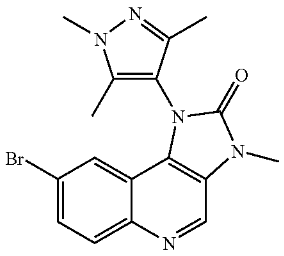 [SMILES: Cc1nn(C)c(C)c1-n1c(=O)n(C)c2cnc3ccc(Br)cc3c21] | 8-Bromo-3-methyl-1-(1,3,5-trimethyl-1H-pyrazol-4-yl)-1,3-dihydro-imidazo[4,5-c]quinolin-2-one | 386, 388 | 2.44 |
| I | 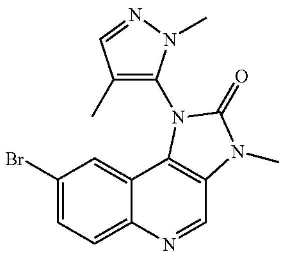 [SMILES: Cc1cnn(C)c1-n1c(=O)n(C)c2cnc3ccc(Br)cc3c21] | 8-Bromo-1-(2,4-dimethyl-2H-pyrazol-3-yl)-3-methyl-1,3-dihydro-imidazo [4,5-c]quinolin-2-one | 372, 374 | 2.65 |
| J | 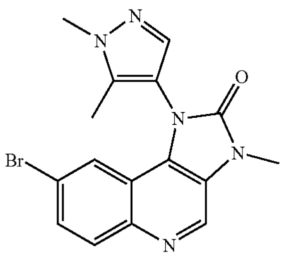 [SMILES: Cc1c(-n2c(=O)n(C)c3cnc4ccc(Br)cc4c32)cnn1C] | 8-Bromo-1-(1,5-dimethyl-1H-pyrazol-4-yl)-3-methyl-1,3-dihydro-imidazo [4,5-c]quinolin-2-one | 372, 374 | 2.39 |

-continued

| Intermed. | structure | Name of the intermediate | MS-ES (M + H) | HPLC $t_R$ (min) |
|---|---|---|---|---|
| K | 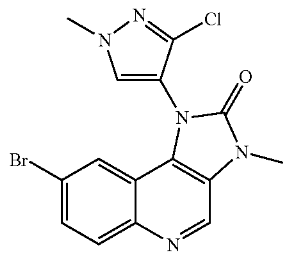 [SMILES: Cn1cc(-n2c(=O)n(C)c3cnc4ccc(Br)cc4c32)c(Cl)n1] | 8-Bromo-1-(3-chloro-1-methyl-1H-pyrazol-4-yl)-3-methyl-1,3-dihydro-imidazo[4,5-c]quinolin-2-one | 392, 394 BrCl pattern | 2.55 |
| L | 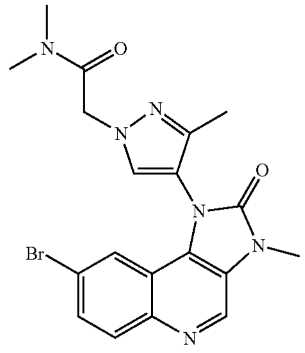 | 2-[4-(8-Bromo-3-methyl-2-oxo-2,3-dihydro-imidazo[4,5-c]quinolin-1-yl)-3-methyl-pyrazol-1-yl]-N,N-dimethyl-acetamide | 443, 445 | 2.39 |
| M | 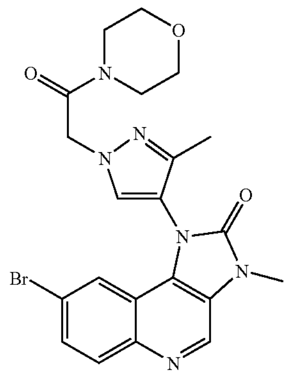 [SMILES: Cc1nn(CC(=O)N2CCOCC2)cc1-n1c(=O)n(C)c2cnc3ccc(Br)cc3c21] | 8-Bromo-3-methyl-1-[3-methyl-1-(2-morpholin-4-yl-2-oxo-ethyl)-1H-pyrazol-4-yl]-1,3-dihydro-imidazo[4,5-c]quinolin-2-one | 475, 477 | 2.52 |
| N | 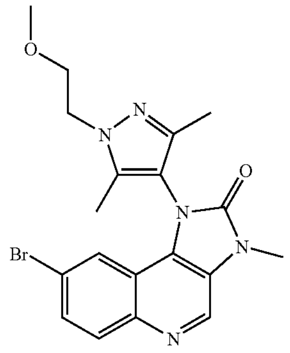 [SMILES: COCCn1nc(C)c(-n2c(=O)n(C)c3cnc4ccc(Br)cc4c32)c1C] | 8-Bromo-1-[1-(2-methoxy-ethyl)-3,5-dimethyl-1H-pyrazol-4-yl]-3-methyl-1,3-dihydro-imidazo[4,5-c]quinolin-2-one | 430, 432 | 2.51 |

-continued

| Intermed. | structure | Name of the intermediate | MS-ES (M + H) | HPLC $t_R$ (min) |
|---|---|---|---|---|
| O | 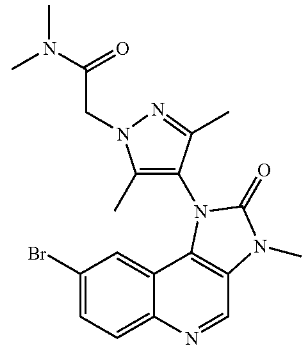 | 2-[4-(8-Bromo-3-methyl-2-oxo-2,3-dihydro-imidazo[4,5-c]quinolin-1-yl)-3,5-dimethyl-pyrazol-1-yl]-N,N-dimethyl-acetamide | 457, 459 | 2.36 |
| P | 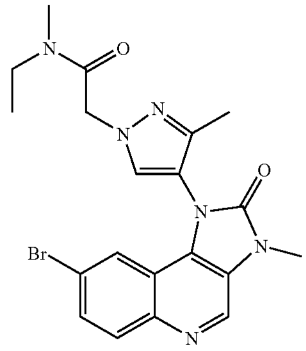 [SMILES: CCN(C)C(=O)Cn1cc(-n2c(=O)n(C)c3cnc4ccc(Br)cc4c32)c(C)n1] | 2-[4-(8-Bromo-3-methyl-2-oxo-2,3-dihydro-imidazo[4,5-c]quinolin-1-yl)-3-methyl-pyrazol-1-yl]-N-ethyl-N-methyl-acetamide | 457, 459 | 2.46 |

Stage K.1 3-Chloro-1-methyl-1H-pyrazol-4-ylamine

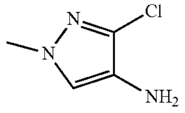

3-Chloro-1-methyl-4-nitro-1H-pyrazole (Stage K.2, 1.0 g 6.19 mmol) was shacked in MeOH/THF 1:1 (62 ml) under 1.1 bar $H_2$ in presence of Raney nickel (0.35 g) as catalyst for 24 h at rt. The RM was filtered over Celite, the catalyst was washed several times with MeOH/THF and the filtrate was evaporated to dryness to give the title compound as a blue oil (HPLC $t_R$ 0.89 min (Method A); M+H=132 MS-ES)

Stage K.2 3-Chloro-1-methyl-4-nitro-1H-pyrazole

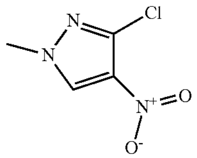

To a solution of 3-chloro-1-methylpyrazole (Maybridge, Basel, Switzerland, 953 mg, 8.18 mmol) in concentrated sulfuric acid (1.4 ml), cooled with an ice-bath, was added over 30 min fuming nitric acid (1.19 mL, 28.6 mmol). The reaction mixture was stirred at rt for 2 h before being poured on ice/water and extracted with EtOAc (2×). The organic layers were washed with saturated aqueous $NaHCO_3$ (2×) and brine, dried over $Na_2SO_4$, filtered, evaporated and dried over vacuum to give the title compound as a white solid (HPLC $t_R$ 2.24 min (Method A); M+H=162 MS-ES)

Stage L.1 2-(4-Amino-3-methyl-pyrazol-1-yl)-N,N-dimethyl-acetamide

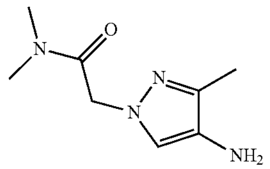

The title compound was synthesized in a similar manner as described for stage K.1 using N,N-dimethyl-2-(3-methyl-4-nitro-pyrazol-1-yl)-acetamide (stage L.2) to give the title compound as an oil (HPLC $t_R$ 1.03 min (Method A); M+H=183 MS-ES).

Stage L.2 N,N-Dimethyl-2-(3-methyl-4-nitro-pyrazol-1-yl)-acetamide

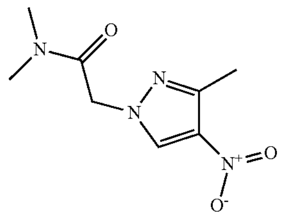

To a solution of 3-methyl-4-nitropyrazole (Apollo, Cheshire, UK, 500 mg, 3.93 mmol) in DMF (10 ml) was added 55% NaH in oil (198 mg, 4.54 mmol) and the reaction mixture was stirred for 30 min at rt. Then to the reaction mixture was added a solution of 2-bromo-N,N-dimethylacetamide (stage L.3, 720 mg, 4.34 mmol) in DMF (3 ml). The reaction mixture was stirred for 1 h at it then quenched with saturated aqueous $NaHCO_3$ and extracted with EtOAc (2×). The combined organic layers were washed with water (2×), brine, dried over $Na_2SO_4$, filtered and evaporated. The crude product was purified by Prep. HPLC ($H_2O$ (0.1% TFA)/$CH_3CN$ 97:2 to 75:25; reverse phase silica gel). The fractions containing product were collected together, basified with $NaHCO_3$ and concentrated before being extracted with EtOAc (3×). The combined organic layers were washed with brine, dried over $Na_2SO_4$, filtered and evaporated to give the title compound as a white solid (HPLC $t_R$ 2.06 min (Method A); M+H=213 MS-ES).

Stage L.3 2-Bromo-N,N-dimethyl-acetamide

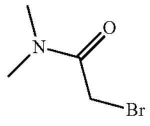

To a solution of bromoacetylbromide (Aldrich, Buchs, Switzerland, 4.56 g, 22.6 mmol) in dichloromethane (90 ml) were added sequentially a 2 M solution of dimethylamine in THF (Aldrich, Buchs, Switzerland, 14 ml, 28 mmol) and triethylamine (3.8 ml, 27.3 mmol). The reaction mixture was stirred for 1 h at it then diluted with dichloromethane and washed with 2 M aqueous HCl, sat. aqueous $NaHCO_3$ and brine, dried over $Na_2SO_4$, filtered and evaporated to give the title compound as a brownish oil (HPLC $t_R$ 1.64 min (Method A); M+H=166, 168 MS-ES).

Stage M.1 2-(4-Amino-3-methyl-pyrazol-1-yl)-1-morpholin-4-yl-ethanone

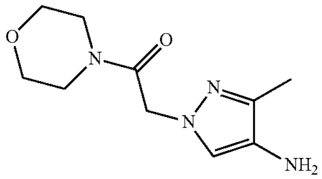 [SMILES: Cc1nn(CC(=O)N2CCOCC2)cc1N]

The title compound was synthesized in a similar manner as described for Stage L.1-2 using 2-bromo-1-morpholin-4-yl-ethanone (ChemBridge, San Diego, USA) to give the title compound as a pink solid (HPLC $t_R$ 1.05 min (Method A); M+H=225 MS-ES).

Stage N.1 1-(2-Methoxy-ethyl)-3,5-dimethyl-1H-pyrazol-4-ylamine

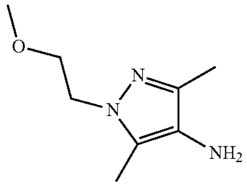

The title compound was synthesized in a similar manner as described for Stage K.1 using 1-(2-methoxy-ethyl)-3,5-dimethyl-4-nitro-1H-pyrazole (Stage N.2) to give the title compound as an oil (HPLC $t_R$ 1.15 min (Method A); M+H=170 MS-ES).

Stage N.2 1-(2-Methoxy-ethyl)-3,5-dimethyl-4-nitro-1H-pyrazole

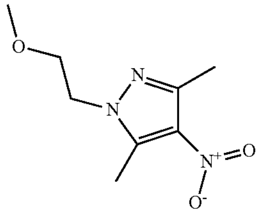

To a solution of 3,5-dimethyl-4-nitropyrazole (Fluorochem, Derbyshire, UK, 989 mg, 7.01 mmol) in DMF (40 ml) was added in two portions 55% NaH in oil (420 mg, 9.63 mmol). The reaction mixture was stirred for 30 min at rt then 2-bromoethyl methyl ether (Aldrich, Buchs, Switzerland, 1.17 g, 8.42 mmol) was added and the reaction mixture stirred for 2 h at rt. The reaction mixture was quenched with water and extracted with EtOAc. The organic layer was washed with water (2×) and brine (2×), dried over $Na_2SO_4$, filtered and evaporated. The crude product was purified by Prep. HPLC ($H_2O$ (0.1% TFA)/$CH_3CN$ 95:5 to 50:50; reverse phase silica gel). The fractions containing product were collected together, basified with $NaHCO_3$ and concentrated before being extracted with EtOAc (3×). The combined organic layers were washed with brine, dried over $Na_2SO_4$, filtered and evaporated to give the title compound as a white solid (HPLC $t_R$ 2.57 min (Method A); M+H=200 MS-ES)

Stage O.1 2-(4-Amino-3,5-dimethyl-pyrazol-1-yl)-N,N-dimethyl-acetamide

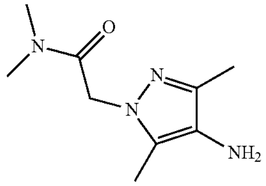

The title compound was synthesized in a similar manner as described for stage L.1-3 using 3,5-dimethyl-4-nitropyrazole (Fluorochem, Derbyshire, UK) to give the title compound as an oil (HPLC $t_R$ 1.13 min (Method A); M+H=197 MS-ES).

Stage P.1 2-(4-Amino-3-methyl-pyrazol-1-yl)-N-ethyl-N-methyl-acetamide

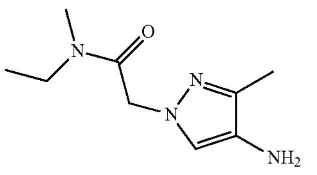

The title compound was synthesized in a similar manner as described for Stage K1 using 2-bromo-1-morpholin-4-yl-ethanone (ChemBridge, San Diego, USA) to give the title compound as a pink solid (HPLC $t_R$ 1.05 min (Method A); M+H=225 MS-ES).

Stage P.2 N-Ethyl-N-methyl-2-(3-methyl-4-nitro-pyrazol-1-yl)-acetamide

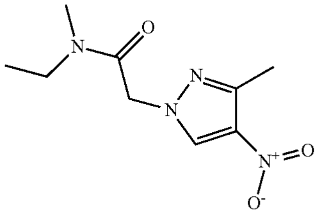 [SMILES: CCN(C)C(=O)Cn1cc([N+](=O)[O-])c(C)n1]

A mixture of 3-Methyl-4-nitro-pyrazol-1-yl-acetic acid methylester (ChemCollect, Remscheid, Germany, 1.0 g, 5.02 mmol) in dioxane (40 ml) and 1 M aqueous LiOH (10 ml, 10 mmol) was stirred for 1 h at 50° C. Were added 2 M aqueous HCl (5 ml, 10 mmol) and the solution was evaporated to dryness. The dried residue, TPTU (2.98 g, 10.04 mmol) and DIPEA (2.63 ml, 15.06 mmol) in DMA (30 ml) was stirred under argon at it for 5 min. Then N-ethylmethylamine (Aldrich, Buchs, Switzerland, 1.78 ml, 20.08 mmol) was added and the RM was stirred at it for 20 h. The RM was diluted with EtOAc and washed with saturated aqueous $NaHCO_3$ (2×) and with brine. The aqueous layers were extracted with dichloromethane (3×) and the combined organic layers were dried over $Na_2SO_4$, filtered and evaporated. The residue was taken in DMA and purified by Prep. HPLC ($H_2O$ (0.1% TFA)/$CH_3CN$ 97:3 to 75:25). The fractions containing products were collected together and concentrated. The solution was basified with $NaHCO_3$ and extracted with dichloromethane (2×). The organic layers were washed with brine, dried over $Na_2SO_4$, filtered and evaporated to dryness to give the title compound as a light yellow oil. (HPLC: $t_R$ 2.25 min (Method A); M+H=227, M−H=225 MS-ES)

Intermediate Q: 8-Bromo-1-(3,5-dimethyl-isoxazol-4-yl)-3-methyl-1,3-dihydro-imidazo[4,5-c]quinolin-2-one

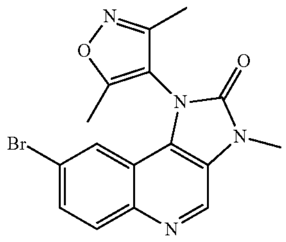 [SMILES: Cc1noc(C)c1-n1c(=O)n(C)c2cnc3ccc(Br)cc3c21]

The intermediate Q was synthesized in a similar manner as described for intermediate A and stage A1 to A3 using as replacement for the (6-bromo-3-nitro-quinolin-4-yl)-(1,3-dimethyl-1H-pyrazol-4-yl)-amine the (6-bromo-3-nitro-quinolin-4-yl)-(3,5-dimethyl-isoxazol-4-yl)-amine (stage Q1). (HPLC: $t_R$ 2.58 min (Method A); M+H=373, 375 MS-ES)

Stage Q1: (6-Bromo-3-nitro-quinolin-4-yl)-(3,5-dimethyl-isoxazol-4-yl)-amine

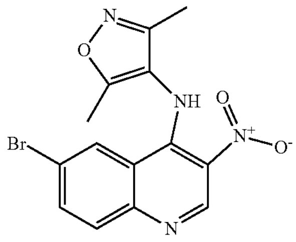 [SMILES: Cc1noc(C)c1Nc1c([N+](=O)[O-])cnc2ccc(Br)cc12]

A mixture of 6-bromo-4-chloro-3-nitro-quinoline (Stage A.4, 1.1 g, 3.83 mmol) and 3,5-dimethyl-4-aminoisoxazol (Aldrich, Buchs, Switzerland, 472 mg, 4.21 mmol) in acetic acid (10 ml) was stirred at it for 4 h. Then the RM was quenched with $H_2O$ (40 ml). The suspension was filtered, the solid cake was washed with $H_2O$ (2×) and dried under vacuum, before being dissolved in EtOAc. The solution was washed with saturated aqueous $NaHCO_3$, dried over $Na_2SO_4$, filtered and evaporated to dryness to give the title compound as an orange solid (HPLC $t_R$ 2.96 min (Method A); M+H=363, 365; M−H=361, 363 MS-ES).

Example 1.1

8-(3,4-Dimethoxy-phenyl)-1-(1,5-dimethyl-1H-pyrazol-4-yl)-3-methyl-1,3-dihydro-imidazo[4,5-c]quinolin-2-one

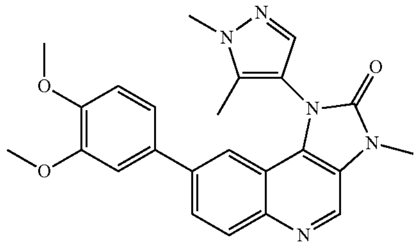

A mixture of 8-bromo-1-(1,5-dimethyl-1H-pyrazol-4-yl)-3-methyl-1,3-dihydro-imidazo[4,5-c]quinolin-2-one (Intermediate J, 50 mg, 0.132 mmol), 3,4-dimethoxyphenylboronic acid (Aldrich, Buchs, Switzerland, 29 mg, 0.156 mmol) and $PdCl_2(PPh_3)_2$ (6 mg, 0.0085 mmol) in DMF (1.2 ml) and 1 M aqueous $K_2CO_3$ (0.329 ml) was stirred under argon at 105° C. for 1.5 h. Then the RM was cooled to rt, diluted with MeOH/DMA+3 drops TFA and purified directly by Prep. HPLC ($H_2O$ (0.1% TFA)/$CH_3CN$ 95:5 to 55:45). The fractions containing product were collected together and basified with $NaHCO_3$ (0.3 g), before being concentrated. The resulting suspension was filtered and the cake was washed with water, before being dried under high vacuum to give the title compound as an off-white solid. (HPLC: $t_R$ 2.66 min (Method A); M+H=430 MS-ES; $^1$H-NMR ($d_6$-DMSO, 400 MHz) 8.92 (s, 1H), 8.08-8.01 (m, 1H), 7.95-7.88 (m, 1H), 7.76 (s, 1H), 7.60-7.55 (m, 1H), 7.13-7.08 (m, 1H), 7.05-7.00 (m, 1H), 6.99-6.94 (m, 1H), 3.88-382 (m, 6H), 3.78 (s, 3H), 3.56 (s, 3H), 2.11 (s, 3H))

The following examples were synthesized in a similar manner as described for Example 1.1 using as replacement for intermediate J a different intermediate.

| Example | Intermed. | structure | Name of the example | MS-ES (M + H) | HPLC $t_R$ (min) |
|---|---|---|---|---|---|
| 1.2 | B | 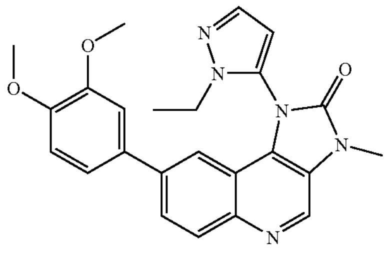 [SMILES: CCn1nccc1-n1c(=O)n(C)c2cnc3ccc(-c4ccc(OC)c(OC)c4)cc3c21] | 8-(3,4-Dimethoxy-phenyl)-1-(2-ethyl-2H-pyrazol-3-yl)-3-methyl-1,3-dihydro-imidazo[4,5-c]quinolin-2-one | 430 | 2.76 |
| 1.3 | E | 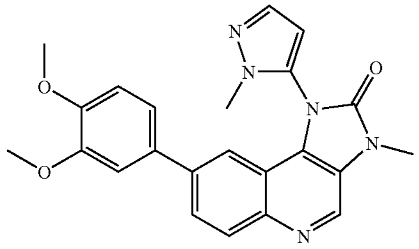 | 8-(3,4-Dimethoxy-phenyl)-3-methyl-1-(2-methyl-2H-pyrazol-3-yl)-1,3-dihydro-imidazo[4,5-c]quinolin-2-one | 416 | 2.68 |
| 1.4 | C | 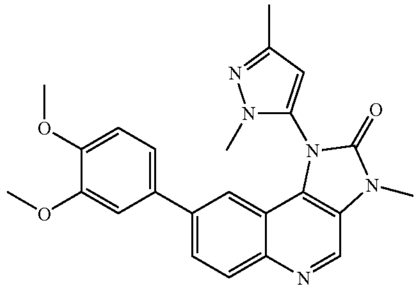 | 8-(3,4-Dimethoxy-phenyl)-1-(2,5-di-methyl-2H-pyrazol-3-yl)-3-methyl-1,3-dihydro-imidazo[4,5-c]quinolin-2-one | 430 | 2.79 |
| 1.5 | G | 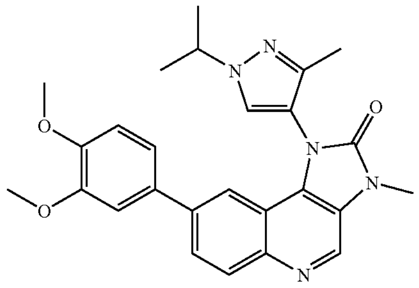 | 8-(3,4-Dimethoxy-phenyl)-1-(1-iso-propyl-3-methyl-1H-pyrazol-4-yl)-3-methyl-1,3-dihydro-imidazo[4,5-c]quinolin-2-one | 458 | 2.82 |

-continued

| Example | Intermed. | structure | Name of the example | MS-ES (M + H) | HPLC $t_R$ (min) |
|---|---|---|---|---|---|
| 1.6 | F | 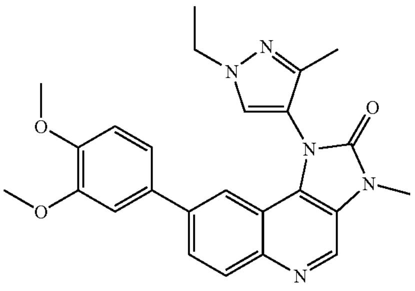 | 8-(3,4-Dimethoxy-phenyl)-1-(1-ethyl-3-methyl-1H-pyrazol-4-yl)-3-methyl-1,3-dihydro-imidazo[4,5-c]quinolin-2-one | 444 | 2.72 |
| 1.7 | I | 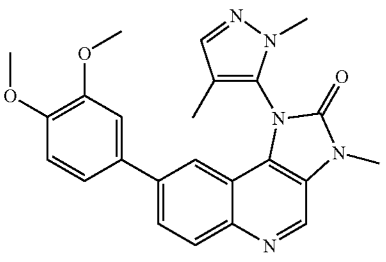 [SMILES: COc1ccc(-c2ccc3ncc4c(c3c2)n(-c2c(C)cnn2C)c(=O)n4C)cc1OC] | 8-(3,4-Dimethoxy-phenyl)-1-(2,4-di-methyl-2H-pyrazol-3-yl)-3-methyl-1,3-dihydro-imidazo[4,5-c]quinolin-2-one | 430 | 2.77 |
| 1.8 | A | 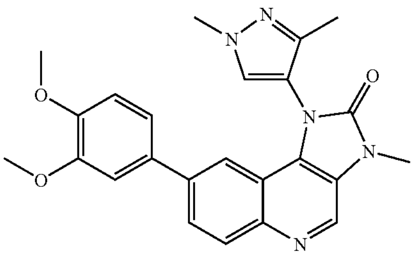 | 8-(3,4-Dimethoxy-phenyl)-1-(1,3-di-methyl-1H-pyrazol-4-yl)-3-methyl-1,3-dihydro-imidazo[4,5-c]quinolin-2-one | 430 | 2.65 |
| 1.9 | H | 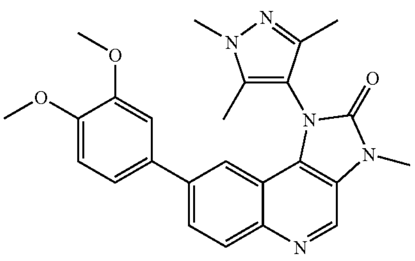 | 8-(3,4-Dimethoxy-phenyl)-3-methyl-1-(1,3,5-trimethyl-1H-pyrazol-4-yl)-1,3-dihydro-imidazo[4,5-c]quinolin-2-one | 444 | 2.69 |
| 1.10 | K | 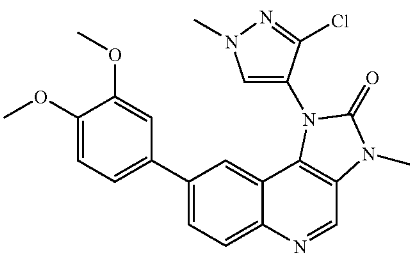 | 1-(3-Chloro-1-methyl-1H-pyrazol-4-yl)-8-(3,4-dimethoxy-phenyl)-3-methyl-1,3-dihydro-imidazo[4,5-c]quinolin-2-one | 450 | 2.73 |

Example 2.1

1-(2,4-Dimethyl-2H-pyrazol-3-yl)-8-(6-methoxy-pyridin-3-yl)-3-methyl-1,3-dihydro-imidazo[4,5-c]quinolin-2-one

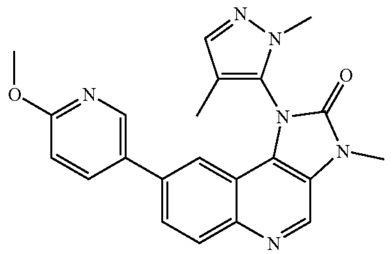 [SMILES: COc1ccc(-c2ccc3ncc4c(c3c2)n(-c2c(C)cnn2C)c(=O)n4C)cn1]

The title compound was synthesized in a similar manner as described for Example 1.1 using 8-bromo-1-(2,4-dimethyl-2H-pyrazol-3-yl)-3-methyl-1,3-dihydro-imidazo[4,5-c]quinolin-2-one (Intermediate I, 40 mg, 0.106 mmol) and 2-methoxy-5-pyridineboronic acid (Aldrich, Buchs, Switzerland, 20 mg, 0.131 mmol) to give the title compound as a white solid. (HPLC: $t_R$ 2.69 min (Method A); M+H=401 MS-ES; $^1$H-NMR ($d_6$-DMSO, 400 MHz) 9.03 (s, 1H), 8.27-8.21 (m, 1H), 8.16-8.09 (m, 1H), 7.96-7.89 (m, 1H), 7.84-7.77 (m, 1H), 7.65 (s, 1H), 7.00-6.88 (m, 2H), 3.88 (s, 3H), 3.61 (s, 6H), 1.82 (s, 3H))

The following examples were synthesized in a similar manner as described for Example 1.1 using 2-methoxy-5-pyridineboronic acid and the specified intermediate.

| Example | Intermed. | structure | Name of the example | MS-ES (M + H) | HPLC $t_R$ (min) |
|---|---|---|---|---|---|
| 2.2 | E | 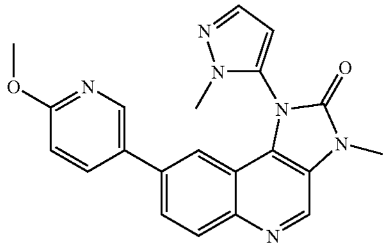 [SMILES: COc1ccc(-c2ccc3ncc4c(c3c2)n(-c2ccnn2C)c(=O)n4C)cn1] | 8-(6-Methoxy-pyridin-3-yl)-3-methyl-1-(2-methyl-2H-pyrazol-3-yl)-1,3-dihydro-imidazo[4,5-c]quinolin-2-one | 387 | 2.60 |
| 2.3 | C | 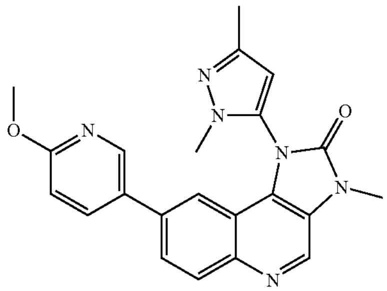 [SMILES: COc1ccc(-c2ccc3ncc4c(c3c2)n(-c2cc(C)nn2C)c(=O)n4C)cn1] | 1-(2,5-Dimethyl-2H-pyrazol-3-yl)-8-(6-methoxy-pyridin-3-yl)-3-methyl-1,3-dihydro-imidazo[4,5-c]quinolin-2-one | 401 | 2.72 |
| 2.4 | H | 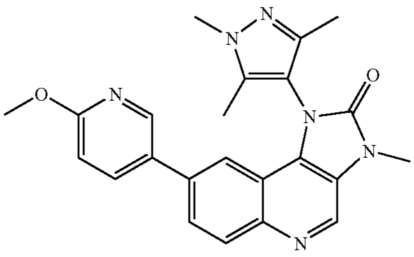 | 8-(6-Methoxy-pyridin-3-yl)-3-methyl-1-(1,3,5-trimethyl-1H-pyrazol-4-yl)-1,3-dihydro-imidazo[4,5-c]quinolin-2-one | 415 | 2.61 |
| 2.5 | A | 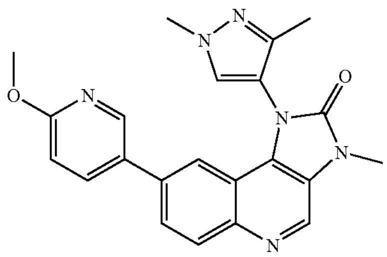 [SMILES: COc1ccc(-c2ccc3ncc4c(c3c2)n(-c2cn(C)nc2C)c(=O)n4C)cn1] | 1-(1,3-Dimethyl-1H-pyrazol-4-yl)-8-(6-methoxy-pyridin-3-yl)-3-methyl-1,3-dihydro-imidazo[4,5-c]quinolin-2-one | 401 | 2.55 |

-continued

| Example | Intermed. | structure | Name of the example | MS-ES (M + H) | HPLC $t_R$ (min) |
|---|---|---|---|---|---|
| 2.6 | B | 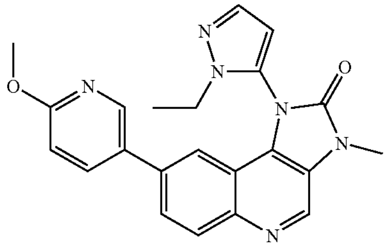 [SMILES: CCn1nccc1-n1c(=O)n(C)c2cnc3ccc(-c4ccc(OC)nc4)cc3c21] | 1-(2-Ethyl-2H-pyrazol-3-yl)-8-(6-methoxy-pyridin-3-yl)-3-methyl-1,3-dihydro-imidazo[4,5-c]quinolin-2-one | 401 | 2.69 |
| 2.7 | F | 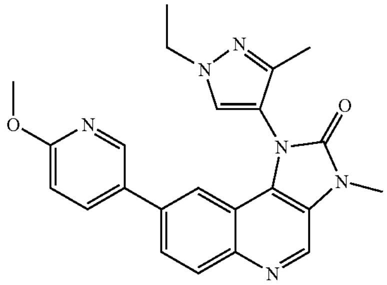 [SMILES: CCn1cc(-n2c(=O)n(C)c3cnc4ccc(-c5ccc(OC)nc5)cc4c32)c(C)n1] | 1-(1-Ethyl-3-methyl-1H-pyrazol-4-yl)-8-(6-methoxy-pyridin-3-yl)-3-methyl-1,3-dihydro-imidazo[4,5-c]quinolin-2-one | 415 | 2.66 |
| 2.8 | G | 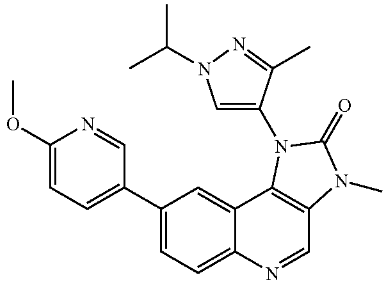 [SMILES: COc1ccc(-c2ccc3ncc4c(c3c2)n(-c2cn(C(C)C)nc2C)c(=O)n4C)cn1] | 1-(1-Isopropyl-3-methyl-1H-pyrazol-4-yl)-8-(6-methoxy-pyridin-3-yl)-3-methyl-1,3-dihydro-imidazo[4,5-c] quinolin-2-one | 429 | 2.78 |
| 2.9 | J | 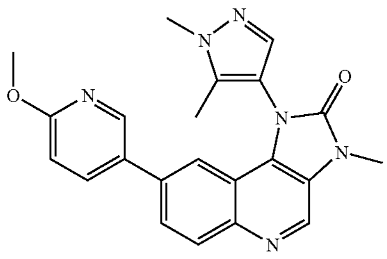 [SMILES: COc1ccc(-c2ccc3ncc4c(c3c2)n(-c2cnn(C)c2C)c(=O)n4C)cn1] | 1-(1,5-Dimethyl-1H-pyrazol-4-yl)-8-(6-methoxy-pyridin-3-yl)-3-methyl-1,3-dihydro-imidazo[4,5-c]quinolin-2-one | 401 | 2.56 |

Example 3.1

1-(1,3-Dimethyl-1H-pyrazol-4-yl)-8-(6-ethoxy-pyridin-3-yl)-3-methyl-1,3-dihydro-imidazo[4,5-c]quinolin-2-one

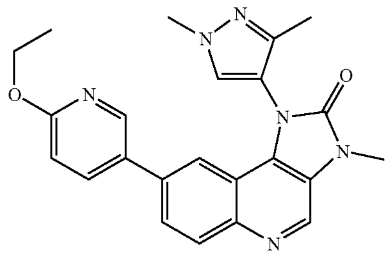 [SMILES: CCOc1ccc(-c2ccc3ncc4c(c3c2)n(-c2cn(C)nc2C)c(=O)n4C)cn1]

The title compound was synthesized in a similar manner as described for Example 1.1 using 8-bromo-1-(1,3-dimethyl-1H-pyrazol-4-yl)-3-methyl-1,3-dihydro-imidazo[4,5-c]quinolin-2-one (Intermediate A, 60 mg, 0.161 mmol) and 6-ethoxypyridine-3-boronic acid (ABCR, Karlsruhe, Germany, 36 mg, 0.211 mmol) to give the title compound as a white solid. (HPLC: $t_R$ 2.69 min (Method A); M+H=415 MS-ES; $^1$H-NMR ($d_6$-DMSO, 400 MHz) 8.96 (s, 1H), 8.32-8.24 (m, 1H), 8.15-8.05 (m, 2H), 7.92-7.85 (m, 1H), 7.79-7.72 (m, 1H), 7.47 (s, 1H), 6.94-6.87 (m, 1H), 4.32 (q, 2H), 3.90 (s, 3H), 3.57 (s, 3H), 1.95 (s, 3H), 1.32 (t, 3H))

The following examples were synthesized in a similar manner as described for Example 1.1 using 6-ethoxypyridine-3-boronic acid and the specified intermediate.

| Example | Intermed. | structure | Name of the example | MS-ES (M + H) | HPLC $t_R$ (min) |
|---|---|---|---|---|---|
| 3.2 | D | 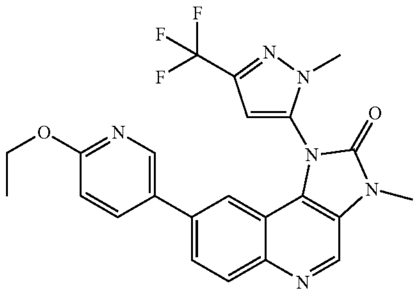 [SMILES: CCOc1ccc(-c2ccc3ncc4c(c3c2)n(-c2cc(C(F)(F)F)nn2C)c(=O)n4C)cn1] | 8-(6-Ethoxy-pyridin-3-yl)-3-methyl-1-(2-methyl-5-trifluoromethyl-2H-pyrazol-3-yl)-1,3-dihydro-imidazo[4,5-c]quinolin-2-one | 469 | 3.31 |
| 3.3 | H | 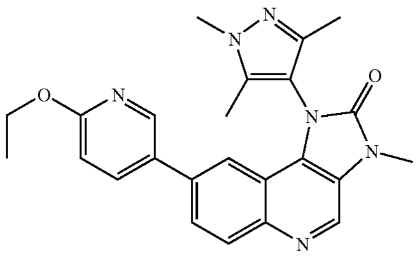 [SMILES: CCOc1ccc(-c2ccc3ncc4c(c3c2)n(-c2c(C)nn(C)c2C)c(=O)n4C)cn1] | 8-(6-Ethoxy-pyridin-3-yl)-3-methyl-1-(1,3,5-trimethyl-1H-pyrazol-4-yl)-1,3-dihydro-imidazo[4,5-c]quinolin-2-one | 429 | 2.73 |
| 3.4 | B | 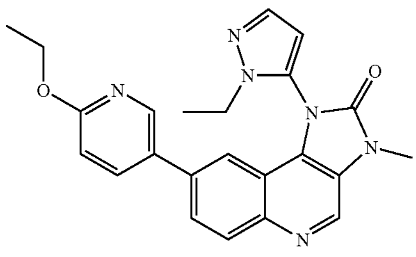 [SMILES: CCOc1ccc(-c2ccc3ncc4c(c3c2)n(-c2ccnn2CC)c(=O)n4C)cn1] | 8-(6-Ethoxy-pyridin-3-yl)-1-(2-ethyl-2H-pyrazol-3-yl)-3-methyl-1,3-dihydro-imidazo[4,5-c]quinolin-2-one | 415 | 2.58 |

-continued

| Example | Intermed. | structure | Name of the example | MS-ES (M + H) | HPLC $t_R$ (min) |
|---|---|---|---|---|---|
| 3.5 | F | 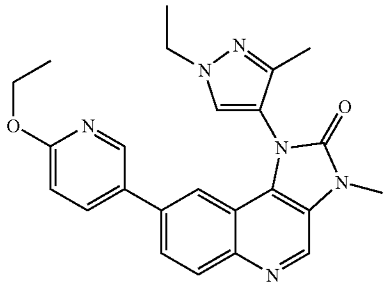 [SMILES: CCOc1ccc(-c2ccc3ncc4c(c3c2)n(-c2cn(CC)nc2C)c(=O)n4C)cn1] | 8-(6-Ethoxy-pyridin-3-yl)-1-(1-ethyl-3-methyl-1H-pyrazol-4-yl)-3-methyl-1,3-dihydro-imidazo[4,5-c]quinolin-2-one | 429 | 2.80 |
| 3.6 | J | 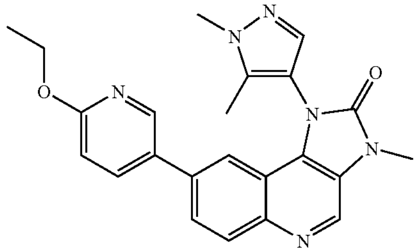 [SMILES: CCOc1ccc(-c2ccc3ncc4c(c3c2)n(-c2cnn(C)c2C)c(=O)n4C)cn1] | 1-(1,5-Dimethyl-1H-pyrazol-4-yl)-8-(6-ethoxy-pyridin-3-yl)-3-methyl-1,3-dihydro-imidazo[4,5-c]quinolin-2-one | 415 | 2.68 |
| 3.7 | G | 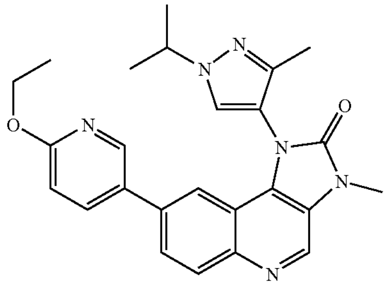 [SMILES: CCOc1ccc(-c2ccc3ncc4c(c3c2)n(-c2cn(C(C)C)nc2C)c(=O)n4C)cn1] | 8-(6-Ethoxy-pyridin-3-yl)-1-(1-isopropyl-3-methyl-1H-pyrazol-4-yl)-3-methyl-1,3-dihydro-imidazo[4,5-c] quinolin-2-one | 443 | 2.94 |
| 3.8 | K | 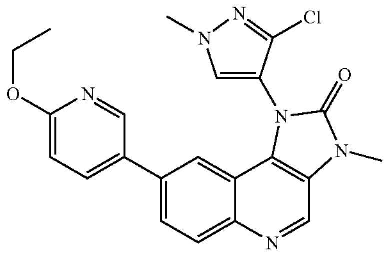 [SMILES: CCOc1ccc(-c2ccc3ncc4c(c3c2)n(-c2cn(C)nc2Cl)c(=O)n4C)cn1] | 1-(3-Chloro-1-methyl-1H-pyrazol-4-yl)-8-(6-ethoxy-pyridin-3-yl)-3-methyl-1,3-dihydro-imidazo[4,5-c]quinolin-2-one | 435 | 2.81 |
| 3.9 | L | 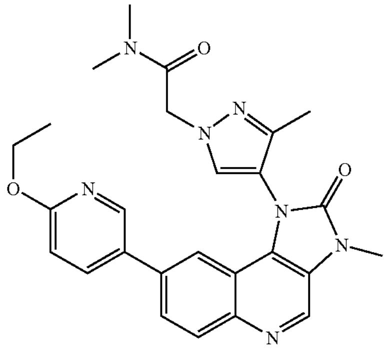 [SMILES: CCOc1ccc(-c2ccc3ncc4c(c3c2)n(-c2cn(CC(=O)N(C)C)nc2C)c(=O)n4C)cn1] | 2-{4-[8-(6-Ethoxy-pyridin-3-yl)-3-methyl-2-oxo-2,3-dihydro-imidazo[4,5-c]quinolin-1-yl]-3-methyl-pyrazol-1-yl}-N,N-dimethyl-acetamide | 486 | 2.68 |

-continued

| Example | Intermed. | structure | Name of the example | MS-ES (M + H) | HPLC $t_R$ (min) |
|---|---|---|---|---|---|
| 3.10 | M | 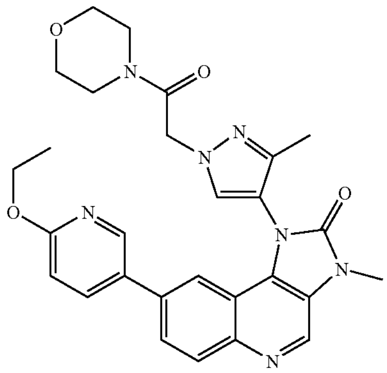 [SMILES: CCOc1ccc(-c2ccc3ncc4c(c3c2)n(-c2cn(CC(=O)N3CCOCC3)nc2C)c(=O)n4C)cn1] | 8-(6-Ethoxy-pyridin-3-yl)-3-methyl-1-[3-methyl-1-(2-morpholin-4-yl-2-oxo-ethyl)-1H-pyrazol-4-yl]-1,3-dihydro-imidazo[4,5-c]quinolin-2-one | 528 | 2.66 |
| 3.11 | N | 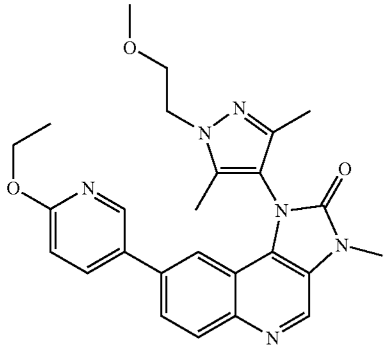 [SMILES: CCOc1ccc(-c2ccc3ncc4c(c3c2)n(-c2c(C)nn(CCOC)c2C)c(=O)n4C)cn1] | 8-(6-Ethoxy-pyridin-3-yl)-1-[1-(2-methoxy-ethyl)-3,5-dimethyl-1H-pyrazol-4-yl]-3-methyl-1,3-dihydro-imidazo[4,5-c]quinolin-2-one | 473 | 2.76 |
| 3.12 | O | 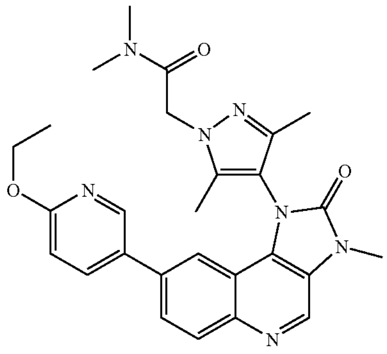 [SMILES: CCOc1ccc(-c2ccc3ncc4c(c3c2)n(-c2c(C)nn(CC(=O)N(C)C)c2C)c(=O)n4C)cn1] | 2-{4-[8-(6-Ethoxy-pyridin-3-yl)-3-methyl-2-oxo-2,3-dihydro-imidazo[4,5-c]quinolin-1-yl]-3,5-dimethyl-pyrazol-1-yl}-N,N-dimethyl-acetamide | 500 | 2.62 |

Example 4.1

8-(6-Dimethylamino-pyridin-3-yl)-1-(1-isopropyl-3-methyl-1H-pyrazol-4-yl)-3-methyl-1,3-dihydro-imidazo[4,5-c]quinolin-2-one

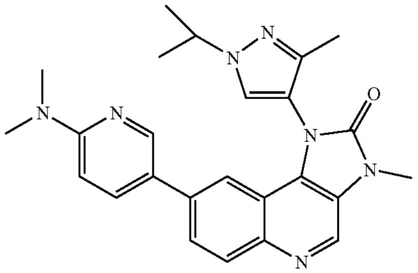

The title compound was synthesized in a similar manner as described for Example 1.1 using 8-bromo-1-(1-isopropyl-3-methyl-1H-pyrazol-4-yl)-3-methyl-1,3-dihydro-imidazo[4,5-c]quinolin-2-one (Intermediate G, 50 mg, 0.125 mmol) and 2-(dimethylamino)pyridine-5-boronic acid hydrate (Fluorochem Ltd., Derbyshire, United Kingdom, 31 mg, 0.163 mmol) to give the title compound as a yellow solid. (HPLC: $t_R$ 2.31 min (Method A); M+H=442 MS-ES; $^1$H-NMR ($d_6$-DMSO, 400 MHz) 8.90 (s, 1H), 8.27-8.18 (m, 2H), 8.07-7.99 (m, 1H), 7.90-7.82 (m, 1H), 7.62-7.55 (m, 1H), 7.41 (s, 1H), 6.70-6.61 (m, 1H), 4.62-4.49 (m, 1H), 3.56 (s, 3H), 3.04 (s, 6H), 1.96 (s, 3H), 1.49 (s, 6H))

The following examples were synthesized in a similar manner as described for Example 1.1 using 2-(dimethylamino)pyridine-5-boronic acid hydrate and the specified intermediate.

| Example | Intermed. | structure | Name of the example | MS-ES (M + H) | HPLC $t_R$ (min) |
|---|---|---|---|---|---|
| 4.2 | F | 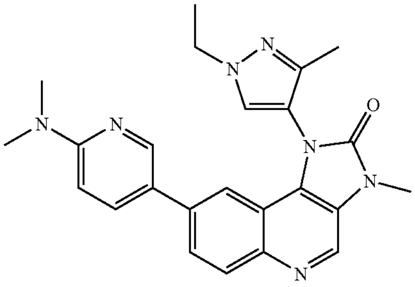 | 8-(6-Dimethylamino-pyridin-3-yl)-1-(1-ethyl-3-methyl-1H-pyrazol-4-yl)-3-methyl-1,3-dihydro-imidazo[4,5-c] quinolin-2-one | 428 | 2.25 |
| 4.3 | H | 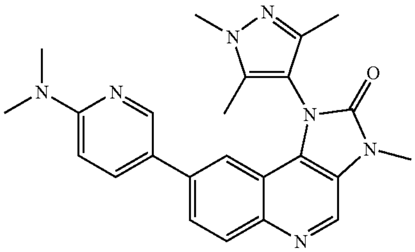 | 8-(6-Dimethylamino-pyridin-3-yl)-3-methyl-1-(1,3,5-trimethyl-1H-pyrazol-4-yl)-1,3-dihydro-imidazo[4,5-c] quinolin-2-one | 428 | 2.25 |
| 4.4 | J | 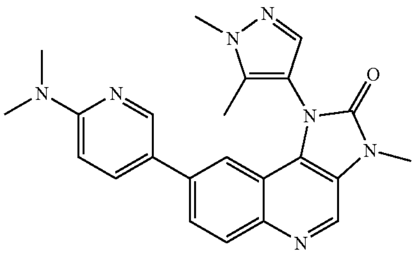 | 8-(6-Dimethylamino-pyridin-3-yl)-1-(1,5-dimethyl-1H-pyrazol-4-yl)-3-methyl-1,3-dihydro-imidazo[4,5-c]quinolin-2-one | 414 | 2.21 |

-continued

| Example | Intermed. | structure | Name of the example | MS-ES (M + H) | HPLC $t_R$ (min) |
|---|---|---|---|---|---|
| 4.5 | A | 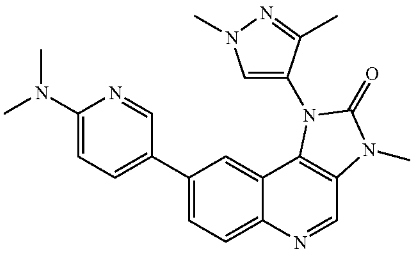 | 8-(6-Dimethylamino-pyridin-3-yl)-1-(1,3-dimethyl-1H-pyrazol-4-yl)-3-methyl-1,3-dihydro-imidazo[4,5-c]quinolin-2-one | 414 | 2.19 |
| 4.6 | C | 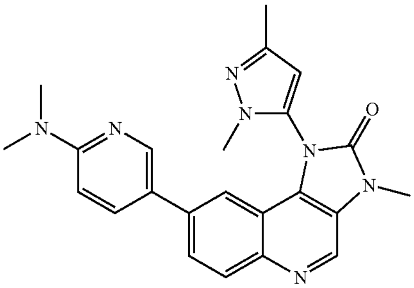 | 8-(6-Dimethylamino-pyridin-3-yl)-1-(2,5-dimethyl-2H-pyrazol-3-yl)-3-methyl-1,3-dihydro-imidazo[4,5-c]quinolin-2-one | 414 | 2.31 |
| 4.7 | E | 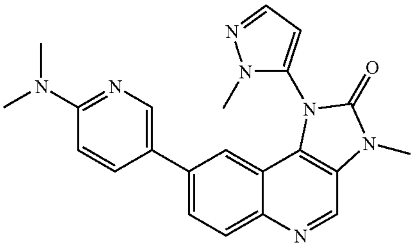 | 8-(6-Dimethylamino-pyridin-3-yl)-3-methyl-1-(2-methyl-2H-pyrazol-3-yl)-1,3-dihydro-imidazo[4,5-c]quinolin-2-one | 400 | 2.23 |
| 4.8 | B | 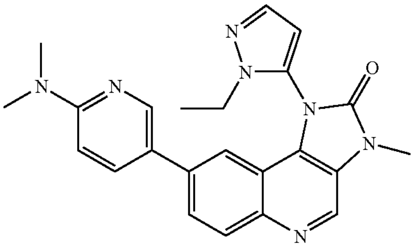 | 8-(6-Dimethylamino-pyridin-3-yl)-1-(2-ethyl-2H-pyrazol-3-yl)-3-methyl-1,3-dihydro-imidazo[4,5-c]quinolin-2-one | 414 | 2.28 |
| 4.9 | K | 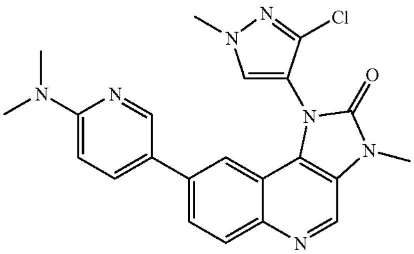 | 1-(3-Chloro-1-methyl-1H-pyrazol-4-yl)-8-(6-dimethylamino-pyridin-3-yl)-3-methyl-1,3-dihydro-imidazo[4,5-c]quinolin-2-one | 434 | 2.24 |

Example 5.1

8-(6-Azetidin-1-yl-pyridin-3-yl)-1-(1,3-dimethyl-1H-pyrazol-4-yl)-3-methyl-1,3-dihydro-imidazo[4,5-c]quinolin-2-one

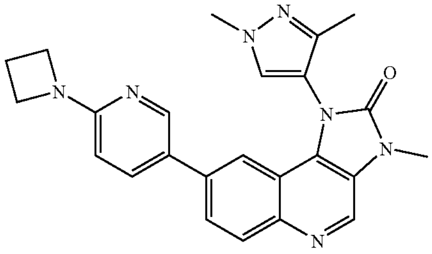 [SMILES: Cc1nn(C)cc1-n1c(=O)n(C)c2cnc3ccc(-c4ccc(N5CCC5)nc4)cc3c21]

The title compound was synthesized in a similar manner as described for Example 1.1 using 8-bromo-1-(1,3-dimethyl-1H-pyrazol-4-yl)-3-methyl-1,3-dihydro-imidazo[4,5-c] quinolin-2-one (Intermediate A, 40 mg, 0.107 mmol) and 2-azetidin-1-yl-5-(4,4,5,5-tetramethyl-[1,3,2]dioxaborolan-2-yl)-pyridine (Stage 5.1.1, 39 mg, 0.150 mmol) to give the title compound as a white solid. (HPLC: $t_R$ 2.24 min (Method A); M+H=426 MS-ES; $^1$H-NMR ($d_6$-DMSO, 400 MHz) 8.91 (s, 1H), 8.25-8.18 (m, 1H), 8.14-8.09 (m, 1H), 8.06-8.02 (m, 1H), 7.89-7.81 (m, 1H), 7.62-7.53 (m, 1H), 7.42 (s, 1H), 6.48-6.42 (m, 1H), 4.01-3.93 (m, 4H), 3.91 (s, 3H), 3.56 (s, 3H), 2.36-2.28 (m, 2H), 1.96 (s, 3H))

Stage 5.1.1 2-Azetidin-1-yl-5-(4,4,5,5-tetramethyl-[1,3,2]dioxaborolan-2-yl)-pyridine

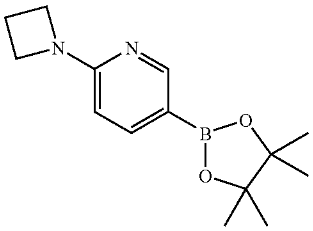 [SMILES: CC1(C)OB(c2ccc(N3CCC3)nc2)OC1(C)C]

A mixture of 2-azetidin-1-yl-5-bromo-pyridine (Stage 5.1.2, 55 mg, 0.259 mmol), bis(pinacolato)-diborane (74 mg, 0.285 mmol), potassium acetate (76 mg, 0.778 mmol) and $PdCl_2$(dppf) (9 mg, 0.012 mmol) in dioxane (1.2 ml) was stirred in a closed vial flushed with argon at 90° C. for 2 h. Then the RM was diluted with EtOAc and washed with brine (2×). The organic layer was dried over $Na_2SO_4$, filtered and evaporated to dryness to give the title compound as a crude brownish sticky solid. (HPLC: $t_R$ 1.79 min (Method A); M+H=261 MS-ES).

Stage 5.1.2 2-Azetidin-1-yl-5-bromo-pyridine

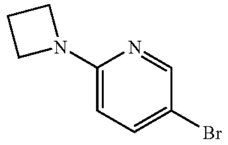 [SMILES: Brc1ccc(N2CCC2)nc1]

A mixture of 5-bromo-2-chloropyridine (Sigma-Aldrich, Buchs, Switzerland, 196 mg, 1.018 mmol), azetidine (Sigma-Aldrich, Buchs, Switzerland, 0.213 ml, 3.06 mmol) and pyridine (0.124 ml, 1.528 mmol) in DMA (2.5 ml) was heated under microwave irradiation at 150° C. for 10 min and 170° C. for 10 min. The reaction was not completed. Again azetidine (0.106 ml) was added and the RM was heated under microwave irradiation at 170° C. for 1 h. Then the RM was quenched with saturated aqueous $NaHCO_3$ (50 ml) and extracted with EtOAc (2×). The combined organic layers were washed with brine (2×), dried over $Na_2SO_4$, filtered and evaporated to dryness to give the title compound as an off-white solid. (HPLC: $t_R$ 1.97 min (Method A); M+H=213, 215 (Br-pattern) MS-ES. $^1$H-NMR ($d_6$-DMSO, 400 MHz) 8.12 (s, 1H), 7.70-7.60 (m, 1H), 6.37-6.29 (m, 1H), 3.96-3.86 (m, 4H), 2.34-2.24 (m, 2H))

The following example was synthesized in a similar manner as described for Example 1.1 using 2-azetidin-1-yl-5-(4,4,5,5-tetramethyl-[1,3,2]dioxaborolan-2-yl)-pyridine (Stage 5.1.1) and the specified intermediate.

| Example | Intermed. | structure | Name of the example | MS-ES (M + H) | HPLC $t_R$ (min) |
|---|---|---|---|---|---|
| 5.2 | G | 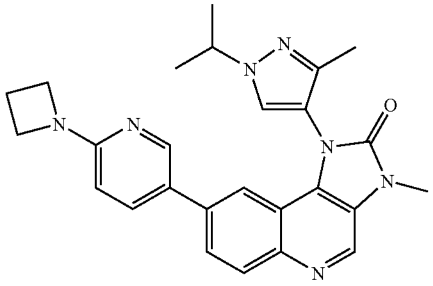 [SMILES: Cc1nn(C(C)C)cc1-n1c(=O)n(C)c2cnc3ccc(-c4ccc(N5CCC5)nc4)cc3c21] | 8-(6-Azetidin-1-yl-pyridin-3-yl)-1-(1-isopropyl-3-methyl-1H-pyrazol-4-yl)-3-methyl-1,3-dihydro-imidazo[4,5-c]quinolin-2-one | 454 | 2.35 |

Example 6.1

8-(2-Dimethylamino-pyrimidin-5-yl)-1-(1-isopropyl-3-methyl-1H-pyrazol-4-yl)-3-methyl-1,3-dihydro-imidazo[4,5-c]quinolin-2-one

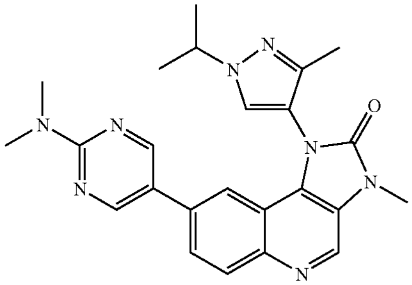

The title compound was synthesized in a similar manner as described for Example 1.1 using 8-bromo-1-(1-isopropyl-3-methyl-1H-pyrazol-4-yl)-3-methyl-1,3-dihydro-imidazo[4,5-c]quinolin-2-one (Intermediate G, 50 mg, 0.125 mmol) and 2-dimethylamino-pyrimidine-5-boronic acid pinacol ester (Frontier Scientific, Logan, USA, 38 mg, 0.153 mmol) to give the title compound as a white solid. (HPLC: $t_R$ 2.68 min (Method A); M+H=443 MS-ES; $^1$H-NMR ($d_6$-DMSO, 400 MHz) 8.93 (s, 1H), 8.46 (s, 2H), 8.20 (s, 1H), 8.09-8.02 (m, 1H), 7.91-7.84 (m, 1H), 7.38 (s, 1H), 4.60-4.51 (m, 1H), 3.56 (s, 3H), 3.13 (s, 6H), 1.97 (s, 3H), 1.49-1.44 (m, 6H))

The following examples were synthesized in a similar manner as described for Example 1.1 using 2-dimethylamino-pyrimidine-5-boronic acid pinacol ester and the specified intermediate.

| Example | Intermed. | structure | Name of the example | MS-ES (M + H) | HPLC $t_R$ (min) |
|---|---|---|---|---|---|
| 6.2 | A | 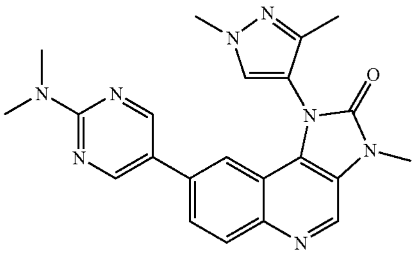 | 8-(2-Dimethylamino-pyrimidin-5-yl)-1-(1,3-dimethyl-1H-pyrazol-4-yl)-3-methyl-1,3-dihydro-imidazo[4,5-c]quinolin-2-one | 415 | 2.46 |
| 6.3 | K | 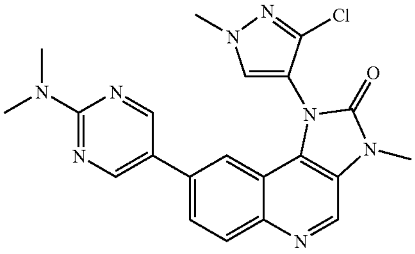 | 1-(3-Chloro-1-methyl-1H-pyrazol-4-yl)-8-(2-dimethylamino-pyrimidin-5-yl)-3-methyl-1,3-dihydro-imidazo[4,5-c]quinolin-2-one | 435 | 2.56 |
| 6.4 | F | 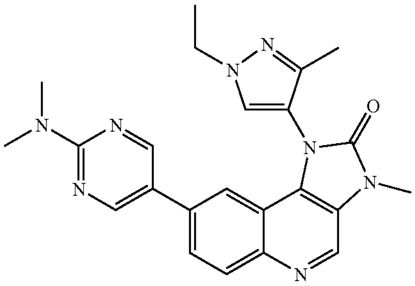 | 8-(2-Dimethylamino-pyrimidin-5-yl)-1-(1-ethyl-3-methyl-1H-pyrazol-4-yl)-3-methyl-1,3-dihydro-imidazo[4,5-c]quinolin-2-one | 429 | 2.48 |

Example 7.1

1-(2,5-Dimethyl-2H-pyrazol-3-yl)-3-methyl-8-(6-methyl-pyridin-3-yl)-1,3-dihydro-imidazo[4,5-c]quinolin-2-one

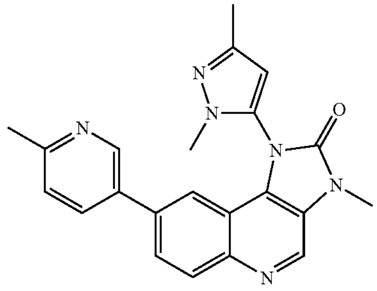

The title compound was synthesized in a similar manner as described for Example 1.1 using 8-bromo-1-(2,5-dimethyl-2H-pyrazol-3-yl)-3-methyl-1,3-dihydro-imidazo[4,5-c]quinolin-2-one (Intermediate C, 50 mg, 0.135 mmol) and 2-methylpyridine-5-boronic acid (Frontier Scientific, Logan, USA, 28 mg, 0.181 mmol) to give the title compound as a red solid. (HPLC: $t_R$ 2.20 min (Method A); M+H=385 MS-ES; $^1$H-NMR ($d_6$-DMSO, 400 MHz) 9.02 (s, 1H), 8.62-8.52 (m, 1H), 8.17-8.08 (m, 1H), 8.00-7.91 (m, 1H), 7.81-7.73 (m, 1H), 7.39-7.32 (m, 1H), 7.13 (s, 1H), 6.52 (s, 1H), 3.62 (s, 3H), 3.51 (s, 3H), 2.55-2.45 (3H), 2.29 (s, 3H))

The following example was synthesized in a similar manner as described for Example 1.1 using 2-methylpyridine-5-boronic acid and the specified intermediate.

| Example | Intermed. | structure | Name of the example | MS-ES (M + H) | HPLC $t_R$ (min) |
|---|---|---|---|---|---|
| 7.2 | A | 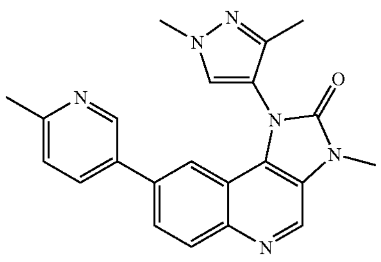 | 1-(1,3-Dimethyl-1H-pyrazol-4-yl)-3-methyl-8-(6-methyl-pyridin-3-yl)-1,3-dihydro-imidazo[4,5-c]quinolin-2-one | 385 | 2.05 |

Example 8.1

3-Methyl-1-(2-methyl-2H-pyrazol-3-yl)-8-(6-trifluoromethyl-pyridin-3-yl)-1,3-dihydro-imidazo[4,5-c]quinolin-2-one

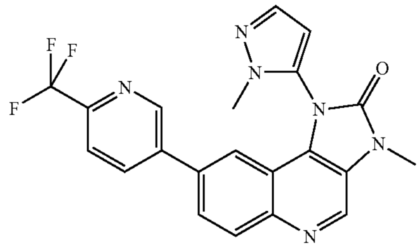 [SMILES: Cn1nccc1-n1c(=O)n(C)c2cnc3ccc(-c4ccc(C(F)(F)F)nc4)cc3c21]

The title compound was synthesized in a similar manner as described for Example 1.1 using 8-bromo-3-methyl-1-(2-methyl-2H-pyrazol-3-yl)-1,3-dihydro-imidazo[4,5-c]quinolin-2-one (Intermediate E, 58 mg, 0.163 mmol) and 2-trifluoromethylpyridine-5-boronic acid (Frontier Scientific, Logan, USA, 40.5 mg, 0.212 mmol) to give the title compound as a red solid. (HPLC: $t_R$ 2.87 min (Method A); M+H=425 MS-ES; $^1$H-NMR ($d_6$-DMSO, 400 MHz) 9.08 (s, 1H), 8.82 (d, 1H), 8.27-8.16 (m, 2H), 8.10-7.98 (m, 2H), 7.82 (d, 1H), 7.18-7.16 (m, 1H), 6.72 (s, 1H), 3.72 (s, 3H), 3.63 (s, 3H))

The following example was synthesized in a similar manner as described for Example 1.1 using 2-trifluoromethylpyridine-5-boronic acid and the specified intermediate.

| Example | Intermed. | structure | Name of the example | MS-ES (M + H) | HPLC $t_R$ (min) |
|---|---|---|---|---|---|
| 8.2 | C | 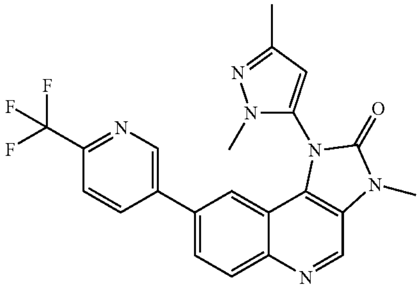 [SMILES: Cc1cc(-n2c(=O)n(C)c3cnc4ccc(-c5ccc(C(F)(F)F)nc5)cc4c32)n(C)n1] | 1-(2,5-Dimethyl-2H-pyrazol-3-yl)-3-methyl-8-(6-trifluoromethyl-pyridin-3-yl)-1,3-dihydro-imidazo[4,5-c] quinolin-2-one | 439 | 2.94 |

Example 9

1-(2,5-Dimethyl-2H-pyrazol-3-yl)-8-(2-fluoro-pyridin-3-yl)-3-methyl-1,3-dihydro-imidazo[4,5-c] quinolin-2-one

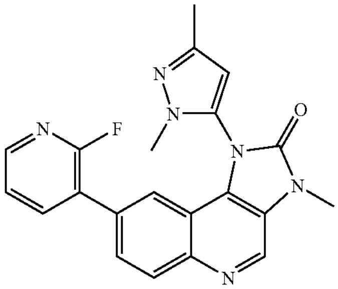 [SMILES: Cc1cc(-n2c(=O)n(C)c3cnc4ccc(-c5cccnc5F)cc4c32)n(C)n1]

The title compound was synthesized in a similar manner as described for Example 1.1 using 8-bromo-1-(2,5-dimethyl-2H-pyrazol-3-yl)-3-methyl-1,3-dihydro-imidazo[4,5-c] quinolin-2-one (Intermediate C, 50 mg, 0.135 mmol) and 2-fluoropyridine-3-boronic acid (Aldrich, Buchs, Switzerland, 25 mg, 0.179 mmol) to give the title compound as a red solid. (HPLC: $t_R$ 2.57 min (Method A); M+H=389 MS-ES; $^1$H-NMR ($d_6$-DMSO, 400 MHz) 9.07 (s, 1H), 8.27-8.22 (m, 1H), 8.18-8.13 (m, 1H), 8.06-7.99 (m, 1H), 7.89-7.83 (m, 1H), 7.51-7.45 (m, 1H), 7.24-7.20 (m, 1H), 6.45 (s, 1H), 3.60 (s, 3H), 3.55 (s, 3H), 2.24 (s, 3H))

Example 10.1

3-Methyl-8-pyridin-3-yl-1-(1,3,5-trimethyl-1H-pyrazol-4-yl)-1,3-dihydro-imidazo[4,5-c]quinolin-2-one

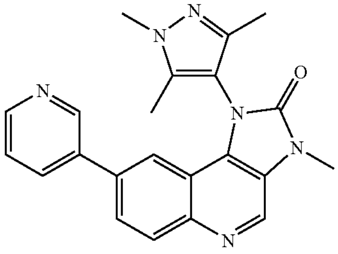 [SMILES: Cc1nn(C)c(C)c1-n1c(=O)n(C)c2cnc3ccc(-c4cccnc4)cc3c21]

The title compound was synthesized in a similar manner as described for Example 1.1 using 8-bromo-3-methyl-1-(1,3,5-trimethyl-1H-pyrazol-4-yl)-1,3-dihydro-imidazo[4,5-c] quinolin-2-one (Intermediate H, 39 mg, 0.100 mmol) and 3-pyridineboronic acid (Aldrich, Buchs, Switzerland, 15 mg, 0.122 mmol) to give the title compound as an off-white foam. (HPLC: $t_R$ 2.08 min (Method A); M+H=385 MS-ES; $^1$H-NMR ($d_6$-DMSO, 400 MHz) 9.00 (s, 1H), 8.70-8.64 (m, 1H), 8.60-8.55 (m, 1H), 8.16-8.10 (m, 1H), 7.99-7.92 (m, 1H), 7.90-7.84 (m, 1H), 7.54-7.47 (m, 2H), 3.82 (s, 3H), 3.60 (s, 3H), 2.09 (s, 3H), 1.92 (s, 3H))

The following example was synthesized in a similar manner as described for Example 1.1 using 3-pyridineboronic acid and the specified intermediate.

| Example | Intermed. | structure | Name of the example | MS-ES (M + H) | HPLC $t_R$ (min) |
|---|---|---|---|---|---|
| 10.2 | A | 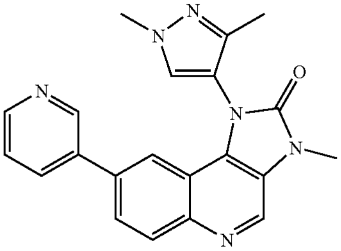 [SMILES: Cc1nn(C)cc1-n1c(=O)n(C)c2cnc3ccc(-c4cccnc4)cc3c21] | 1-(1,3-Dimethyl-1H-pyrazol-4-yl)-3-methyl-8-pyridin-3-yl-1,3-dihydro-imidazo[4,5-c]quinolin-2-one | 371 | 2.01 |

Example 11

8-(2-Fluoro-pyridin-4-yl)-3-methyl-1-(2-methyl-2H-pyrazol-3-yl)-1,3-dihydro-imidazo[4,5-c]quinolin-2-one

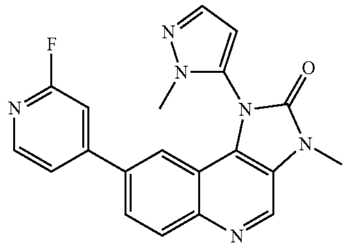 [SMILES: Cn1nccc1-n1c(=O)n(C)c2cnc3ccc(-c4ccnc(F)c4)cc3c21]

The title compound was synthesized in a similar manner as described for Example 1.1 using 8-bromo-3-methyl-1-(2-methyl-2H-pyrazol-3-yl)-1,3-dihydro-imidazo[4,5-c]quinolin-2-one (Intermediate E, 65 mg, 0.181 mmol) and 2-fluoropyridine-4-boronic acid (Frontier Scientific, Logan, USA, 33 mg, 0.236 mmol) to give the title compound as a pink solid. (HPLC: $t_R$ 2.55 min (Method A); M+H=375 MS-ES; $^1$H-NMR ($d_6$-DMSO, 400 MHz) 9.08 (s, 1H), 8.35-8.26 (m, 1H), 8.22-8.13 (m, 1H), 8.10-8.01 (m, 1H), 7.84-7.76 (m, 1H), 7.43-7.35 (m, 1H), 7.29-7.23 (m, 1H), 7.23-7.16 (m, 1H), 6.73 (s, 1H), 3.68 (s, 3H), 3.60 (s, 3H))

Example 12

1-(1,3-Dimethyl-1H-pyrazol-4-yl)-8-(5-methoxy-pyridin-3-yl)-3-methyl-1,3-dihydro-imidazo[4,5-c]quinolin-2-one

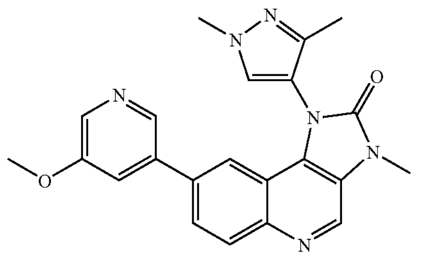

The title compound was synthesized in a similar manner as described for Example 1.1 using 8-bromo-1-(1,3-dimethyl-1H-pyrazol-4-yl)-3-methyl-1,3-dihydro-imidazo[4,5-c]quinolin-2-one (Intermediate A, 40 mg, 0.105 mmol) and 3-methoxypyridine-5-boronic acid pinacol ester (Aldrich, Buchs, Switzerland, 30 mg, 0.125 mmol) to give the title compound as an off-white solid. (HPLC: $t_R$ 2.17 min (Method A); M+H=401 MS-ES; $^1$H-NMR ($d_6$-DMSO, 400 MHz) 8.98 (s, 1H), 8.39-8.26 (m, 2H), 8.21-8.07 (m, 2H), 8.04-7.96 (m, 1H), 7.66-7.56 (m, 1H), 7.45-7.36 (m, 1H), 3.91 (s, 6H), 3.60 (s, 3H), 1.97 (s, 3H))

Example 13

1-(1,3-Dimethyl-1H-pyrazol-4-yl)-8-(5-fluoro-6-methoxy-pyridin-3-yl)-3-methyl-1,3-dihydro-imidazo[4,5-c]quinolin-2-one

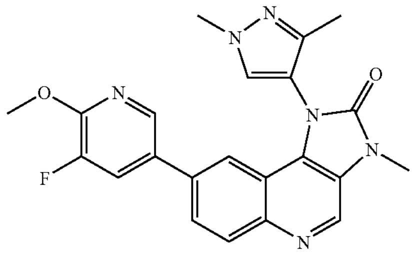

The title compound was synthesized in a similar manner as described for Example 1.1 using 8-bromo-1-(1,3-dimethyl-1H-pyrazol-4-yl)-3-methyl-1,3-dihydro-imidazo[4,5-c]quinolin-2-one (Intermediate A, 40 mg, 0.105 mmol) and 3-fluoro-2-methoxypyridine-5-boronic acid (Apollo Scientific, Cheshire, United Kingdom, 21 mg, 0.123 mmol) to give the title compound as a pink solid. (HPLC: $t_R$ 2.70 min (Method A); M+H=419 MS-ES; $^1$H-NMR ($d_6$-DMSO, 400 MHz) 8.97 (s, 1H), 8.18-8.05 (m, 3H), 7.96-7.89 (m, 1H), 7.81-7.74 (m, 1H), 7.49 (s, 1H), 3.99 (s, 3H), 3.92 (s, 3H), 3.59 (s, 3H), 1.98 (s, 3H))

Example 14

5-[1-(1,3-Dimethyl-1H-pyrazol-4-yl)-3-methyl-2-oxo-2,3-dihydro-1H-imidazo[4,5-c]quinolin-8-yl]-pyridine-2-carboxylic acid amide

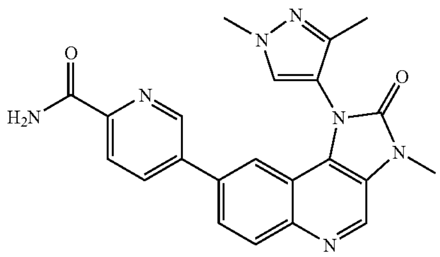 [SMILES: Cc1nn(C)cc1-n1c(=O)n(C)c2cnc3ccc(-c4ccc(C(N)=O)nc4)cc3c21]

The title compound was synthesized in a similar manner as described for Example 1.1 using 8-bromo-1-(1,3-dimethyl-1H-pyrazol-4-yl)-3-methyl-1,3-dihydro-imidazo[4,5-c]quinolin-2-one (Intermediate A, 40 mg, 0.105 mmol) and 5-(4,4,5,5-tetramethyl-[1,3,2]dioxaborolan-2-yl)-pyridine-2-carboxylic acid amide (Stage 14.1.1, 106 mg, 0.427 mmol) to give the title compound as a lightly yellow solid. (HPLC: $t_R$ 2.28 min (Method A); M+H=414 MS-ES; $^1$H-NMR ($d_6$-DMSO, 400 MHz) 9.01 (s, 1H), 8.73-8.67 (m, 1H), 8.22-8.04 (m, 5H), 8.03-7.98 (m, 1H), 7.71-7.61 (m, 2H), 3.92 (s, 3H), 3.59 (s, 3H), 1.97 (s, 3H))

Stage 14.1.1 5-(4,4,5,5-Tetramethyl-[1,3,2]dioxaborolan-2-yl)-pyridine-2-carboxylic acid amide

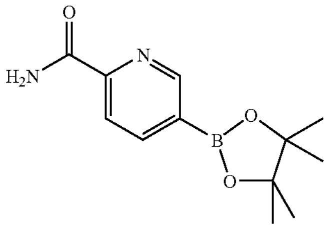 [SMILES: CC1(C)OB(c2ccc(C(N)=O)nc2)OC1(C)C]

The title compound was synthesized in a similar manner as described for Stage 5.1.1 using 5-bromo-pyridine-2-carboxylic acid amide (Combi-Blocks, San Diego, USA, 360 mg, 1.791 mmol) to give the title compound as a brownish sticky solid. (HPLC: $t_R$ 2.27 min (Method A); M+H=249 MS-ES.

Example 15.1

5-[1-(1,3-Dimethyl-1H-pyrazol-4-yl)-3-methyl-2-oxo-2,3-dihydro-1H-imidazo[4,5-c]quinolin-8-yl]-pyridine-2-carboxylic acid methylamide

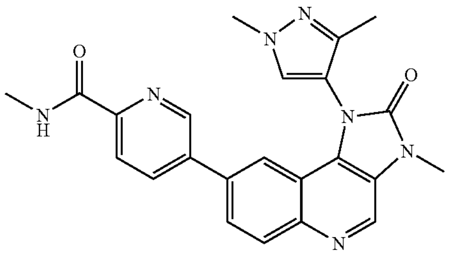

The title compound was synthesized in a similar manner as described for Example 1.1 using 8-bromo-1-(1,3-dimethyl-1H-pyrazol-4-yl)-3-methyl-1,3-dihydro-imidazo[4,5-c]quinolin-2-one (Intermediate A, 40 mg, 0.105 mmol) and 5-(4,4,5,5-tetramethyl-[1,3,2]dioxaborolan-2-yl)-pyridine-2-carboxylic acid methylamide (Stage 15.1.1, 42 mg, 0.160 mmol) to give the title compound as a lightly yellow solid. (HPLC: $t_R$ 2.39 min (Method A); M+H=428 MS-ES; $^1$H-NMR ($d_6$-DMSO, 400 MHz) 9.01 (s, 1H), 8.87-8.80 (m, 1H), 8.71-8.67 (m, 1H), 8.18-8.07 (m, 4H), 8.04-7.98 (m, 1H), 7.65 (s, 1H), 3.92 (s, 3H), 3.58 (s, 3H), 2.83 (s, 3H), 1.97 (s, 3H))

Stage 15.1.1 5-(4,4,5,5-Tetramethyl-[1,3,2]dioxaborolan-2-yl)-pyridine-2-carboxylic acid methylamide

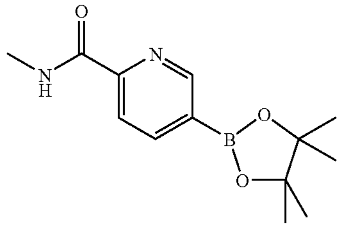

The title compound was synthesized in a similar manner as described for Stage 5.1.1 using 5-bromo-pyridine-2-carboxylic acid methylamide (Combi-Blocks, San Diego, USA, 240 mg, 1.116 mmol) to give the title compound as a brownish sticky solid. (HPLC: $t_R$ 2.46 min (Method A); M+H=263 MS-ES.

The following examples were synthesized in a similar manner as described for Example 1.1 using 5-(4,4,5,5-tetramethyl-[1,3,2]dioxaborolan-2-yl)-pyridine-2-carboxylic acid methylamide and the specified intermediate.

| Example | Intermed. | structure | Name of the example | MS-ES (M + H) | HPLC $t_R$ (min) |
|---|---|---|---|---|---|
| 15.2 | H | 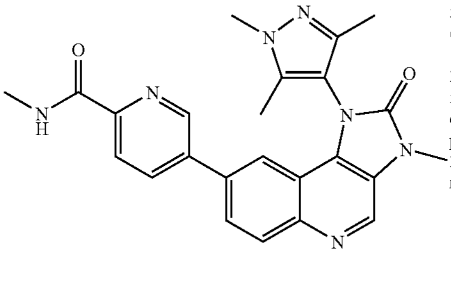 | 5-[3-Methyl-2-oxo-1-(1,3,5-trimethyl-1H-pyrazol-4-yl)-2,3-dihydro-1H-imidazo[4,5-c]quinolin-8-yl]-pyridine-2-carboxylic acid methylamide | 442 | 2.45 |

-continued

| Example | Intermed. | structure | Name of the example | MS-ES (M + H) | HPLC $t_R$ (min) |
|---|---|---|---|---|---|
| 15.3 | G | 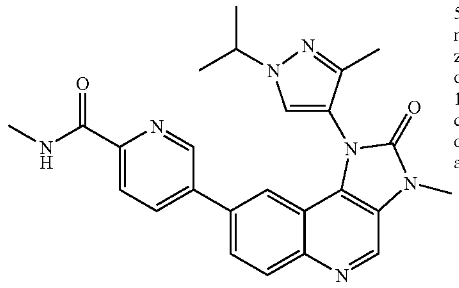 | 5-[1-(1-Isopropyl-3-methyl-1H-pyrazol-4-yl)-3-methyl-2-oxo-2,3-dihydro-1H-imidazo[4,5-c]quinolin-8-yl]-pyridine-2-carboxylic acid methylamide | 456 | 2.56 |

Example 16.1

1-(1-Ethyl-3-methyl-1H-pyrazol-4-yl)-8-(6-hydroxymethyl-pyridin-3-yl)-3-methyl-1,3-dihydro-imidazo[4,5-c]quinolin-2-one

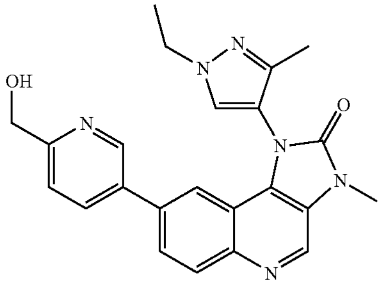 [SMILES: CCn1cc(-n2c(=O)n(C)c3cnc4ccc(-c5ccc(CO)nc5)cc4c32)c(C)n1]

The title compound was synthesized in a similar manner as described for Example 1.1 using 8-bromo-1-(1-ethyl-3-methyl-1H-pyrazol-4-yl)-3-methyl-1,3-dihydro-imidazo[4,5-c]quinolin-2-one (Intermediate F, 80 mg, 0.207 mmol) and 6-(hydroxymethyl)pyridine-3-boronic acid (Combi-Blocks, San Diego, USA, 39 mg, 0.254 mmol) to give the title compound as a white solid. (HPLC: $t_R$ 2.04 min (Method A); M+H=415 MS-ES; $^1$H-NMR ($d_6$-DMSO, 400 MHz) 8.98 (s, 1H), 8.61-8.56 (m, 1H), 8.21-8.17 (m, 1H), 8.15-8.09 (m, 1H), 7.97-7.93 (m, 1H), 7.90-7.85 (m, 1H), 7.57-7.49 (m, 2H), 5.47 (t, 1H), 4.61-4.55 (m, 2H), 4.23-4.14 (m, 2H), 3.57 (s, 3H), 1.95 (s, 3H), 1.43 (t, 3H))

The following examples were synthesized in a similar manner as described for Example 1.1 using 6-(hydroxymethyl)pyridine-3-boronic acid and the specified intermediate.

| Example | Intermed. | structure | Name of the example | MS-ES (M + H) | HPLC $t_R$ (min) |
|---|---|---|---|---|---|
| 16.2 | A | 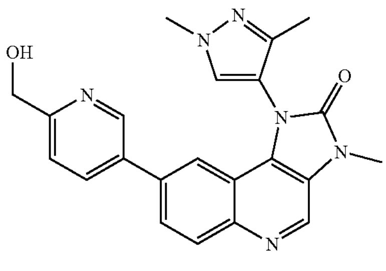 [SMILES: Cc1nn(C)cc1-n1c(=O)n(C)c2cnc3ccc(-c4ccc(CO)nc4)cc3c21] | 1-(1,3-Dimethyl-1H-pyrazol-4-yl)-8-(6-hydroxymethyl-pyridin-3-yl)-3-methyl-1,3-dihydro-imidazo[4,5-c]quinolin-2-one | 401 | 1.99 |
| 16.3 | G | 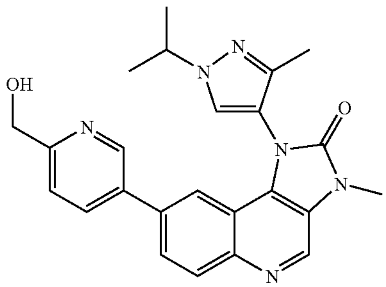 [SMILES: Cc1nn(C(C)C)cc1-n1c(=O)n(C)c2cnc3ccc(-c4ccc(CO)nc4)cc3c21] | 8-(6-Hydroxymethyl-pyridin-3-yl)-1-(1-isopropyl-3-methyl-1H-pyrazol-4-yl)-3-methyl-1,3-dihydro-imidazo[4,5-c]quinolin-2-one | 429 | 2.11 |

-continued

| Example | Intermed. | structure | Name of the example | MS-ES (M + H) | HPLC $t_R$ (min) |
|---|---|---|---|---|---|
| 16.4 | H | 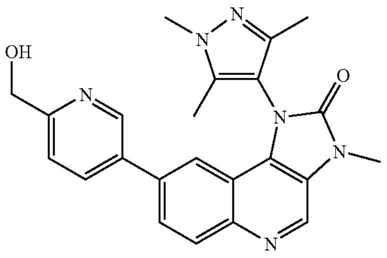 | 8-(6-Hydroxymethyl-pyridin-3-yl)-3-methyl-1-(1,3,5-trimethyl-1H-pyrazol-4-yl)-1,3-dihydro-imidazo[4,5-c] quinolin-2-one | 415 | 2.04 |
| 16.5 | K | 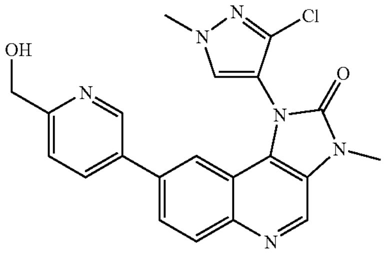 [SMILES: Cn1cc(-n2c(=O)n(C)c3cnc4ccc(-c5ccc(CO)nc5)cc4c32)c(Cl)n1] | 1-(3-Chloro-1-methyl-1H-pyrazol-4-yl)-8-(6-hydroxymethyl-pyridin-3-yl)-3-methyl-1,3-dihydro-imidazo[4,5-c]quinolin-2-one | 421 | 2.06 |

Example 17.1

1-(1-Ethyl-3-methyl-1H-pyrazol-4-yl)-8-(2-methoxy-pyrimidin-5-yl)-3-methyl-1,3-dihydro-imidazo [4,5-c]quinolin-2-one

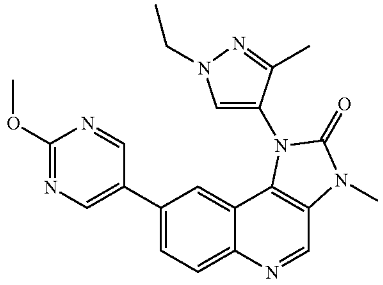 [SMILES: CCn1cc(-n2c(=O)n(C)c3cnc4ccc(-c5cnc(OC)nc5)cc4c32)c(C)n1]

The title compound was synthesized in a similar manner as described for Example 1.1 using 8-bromo-1-(1-ethyl-3-methyl-1H-pyrazol-4-yl)-3-methyl-1,3-dihydro-imidazo[4,5-c] quinolin-2-one (Intermediate F, 49 mg, 0.126 mmol) and 2-methoxy-5-pyrimidineboronic acid (ABCR, Karlsruhe, Germany, 25 mg, 0.162 mmol) to give the title compound as a white solid. (HPLC: $t_R$ 2.47 min (Method A); M+H=416 MS-ES; $^1$H-NMR ($d_6$-DMSO, 400 MHz) 8.98 (s, 1H), 8.76-8.68 (m, 2H), 8.23-8.16 (m, 1H), 8.16-8.09 (m, 1H), 7.99-7.93 (m, 1H), 7.52-7.45 (m, 1H), 4.19 (q, 2H), 3.96 (s, 3H), 3.59 (s, 3H), 1.97 (s, 3H), 1.42 (t, 3H))

The following examples were synthesized in a similar manner as described for Example 1.1 using 2-methoxy-5-pyrimidineboronic acid and the specified intermediate.

| Example | Intermed. | structure | Name of the example | MS-ES (M + H) | HPLC $t_R$ (min) |
|---|---|---|---|---|---|
| 17.2 | A | 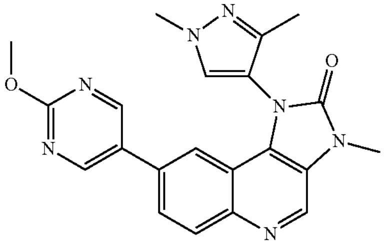 [SMILES: COc1ncc(-c2ccc3ncc4c(c3c2)n(-c2cn(C)nc2C)c(=O)n4C)cn1] | 1-(1,3-Dimethyl-1H-pyrazol-4-yl)-8-(2-methoxy-pyrimidin-5-yl)-3-methyl-1,3-dihydro-imidazo[4,5-c]quinolin-2-one | 402 | 2.38 |

-continued

| Example | Intermed. | structure | Name of the example | MS-ES (M + H) | HPLC $t_R$ (min) |
|---|---|---|---|---|---|
| 17.3 | K | 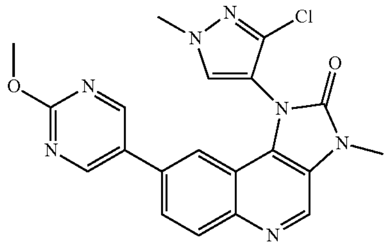 [SMILES: COc1ncc(-c2ccc3ncc4c(c3c2)n(-c2cn(C)nc2Cl)c(=O)n4C)cn1] | 1-(3-Chloro-1-methyl-1H-pyrazol-4-yl)-8-(2-methoxy-pyrimidin-5-yl)-3-methyl-1,3-dihydro-imidazo[4,5-c]quinolin-2-one | 422 | 2.49 |

Example 18

1-(1,3-Dimethyl-1H-pyrazol-4-yl)-8-[6-(2-methoxy-ethoxy)-pyridin-3-yl]-3-methyl-1,3-dihydro-imidazo[4,5-c]quinolin-2-one

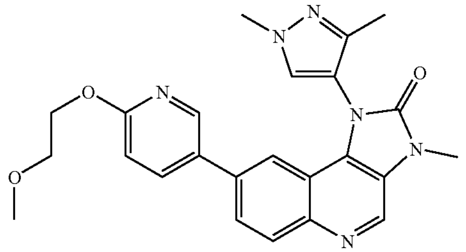 [SMILES: COCCOc1ccc(-c2ccc3ncc4c(c3c2)n(-c2cn(C)nc2C)c(=O)n4C)cn1]

The title compound was synthesized in a similar manner as described for Example 1.1 using 8-bromo-1-(1,3-dimethyl-1H-pyrazol-4-yl)-3-methyl-1,3-dihydro-imidazo[4,5-c]quinolin-2-one (Intermediate A, 40 mg, 0.105 mmol) and 2-(2-methoxy-ethoxy)-5-(4,4,5,5-tetramethyl-[1,3,2]dioxaborolan-2-yl)-pyridine (Stage 18.1.1, 38 mg, 0.137 mmol) to give the title compound as an off-white foam. (HPLC: $t_R$ 2.58 min (Method A); M+H=445 MS-ES; $^1$H-NMR ($d_6$-DMSO, 400 MHz) 8.96 (s, 1H), 8.32-8.25 (m, 1H), 8.16-8.04 (m, 2H), 7.93-7.86 (m, 1H), 7.81-7.74 (m, 1H), 7.51-7.45 (m, 1H), 6.99-6.92 (m, 1H), 4.45-4.38 (m, 2H), 3.92 (s, 3H), 3.70-3.64 (m, 2H), 3.57 (s, 3H), 3.31 (s, 3H), 1.96 (s, 3H))

Stage 18.1.1 2-(2-Methoxy-ethoxy)-5-(4,4,5,5-tetramethyl-[1,3,2]dioxaborolan-2-yl)-pyridine

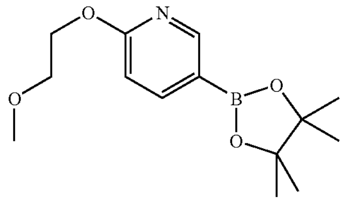 [SMILES: COCCOc1ccc(B2OC(C)(C)C(C)(C)O2)cn1]

The title compound was synthesized in a similar manner as described for Stage 5.1.1 using 5-bromo-2-(2-methoxy-ethoxy)-pyridine (Stage 18.1.2, 251 mg, 1.082 mmol) to give the title compound as a brownish oil. (HPLC: $t_R$ 1.88 min (Method A); M+H=280 MS-ES)

Stage 18.1.2 5-Bromo-2-(2-methoxy-ethoxy)-pyridine

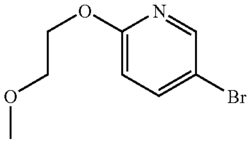

A mixture of NaH 55% (133 mg, 3.06 mmol) in DME (3 ml) was cooled to 0° C., then 2-methoxyethanol (Aldrich, Buchs, Switzerland, 0.362 ml, 4.58 mmol) was added. The solution was stirred at rt for 15 min. After that 5-bromo-2-chloropyridine (Aldrich, Buchs, Switzerland, 294 mg, 1.528 mmol) was added and the RM was heated by microwaves at 150° C. for 10 min. Then the RM was quenched with saturated aqueous $NaHCO_3$ (50 ml) and extracted with EtOAc (2×). The combined organic layers were washed with brine (2×), dried over $Na_2SO_4$, filtered and evaporated. The residue was absorbed on silica gel and purified by MPLC (hexane/EtOAc 0 to 30%). The fractions containing product were evaporated together to give the title compound as a colorless oil. (LC-MS: $t_R$ 1.20 min (Method B); M+H=232, 234 (Br-pattern) MS-ES. $^1$H-NMR ($d_6$-DMSO, 400 MHz) 8.28.8.21 (m, 1H), 7.91-7.84 (m, 1H), 6.86-6.79 (m, 1H), 4.31 (t, 2H), 3.62 (t, 2H), 3.26 (s, 3H))

Example 19

8-[6-(2-Benzyloxy-ethoxy)-pyridin-3-yl]-1-(1,3-dimethyl-1H-pyrazol-4-yl)-3-methyl-1,3-dihydro-imidazo[4,5-c]quinolin-2-one

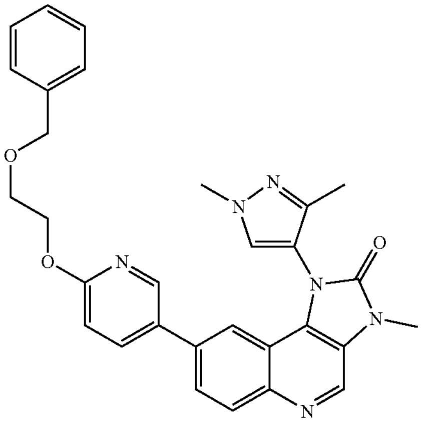 [SMILES: Cc1nn(C)cc1-n1c(=O)n(C)c2cnc3ccc(-c4ccc(OCCOCc5ccccc5)nc4)cc3c21]

The title compound was synthesized in a similar manner as described for Example 1.1 using 8-bromo-1-(1,3-dimethyl-1H-pyrazol-4-yl)-3-methyl-1,3-dihydro-imidazo[4,5-c]quinolin-2-one (Intermediate A, 50 mg, 0.132 mmol) and 2-(2-benzyloxy-ethoxy)-5-(4,4,5,5-tetramethyl-[1,3,2]dioxaborolan-2-yl)-pyridine (Stage 19.1.1, 65 mg, 0.184 mmol) to give the title compound as a white solid. (HPLC: $t_R$ 3.12 min (Method A); M+H=521 MS-ES; $^1$H-NMR ($d_6$-DMSO, 400 MHz) 8.95 (s, 1H), 8.33-8.24 (m, 1H), 8.16-8.05 (m, 2H), 7.93-7.86 (m, 1H), 7.81-7.75 (m, 1H), 7.51-7.45 (m, 1H), 7.40-7.22 (m, 5H), 7.01-6.93 (m, 1H), 4.55 (s, 2H), 4.47 (t, 2H), 3.92 (s, 3H), 3.78 (t, 2H), 3.57 (s, 3H), 1.97 (s, 3H))

Stage 19.1.1 2-(2-Benzyloxy-ethoxy)-5-(4,4,5,5-tetramethyl-[1,3,2]dioxaborolan-2-yl)-pyridine

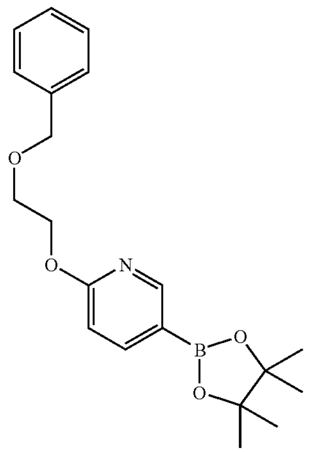 [SMILES: CC1(C)OB(c2ccc(OCCOCc3ccccc3)nc2)OC1(C)C]

The title compound was synthesized in a similar manner as described for Stages 18.1.1 and 18.1.2 using 2-benzyloxy-ethanol (Aldrich, Buchs, Switzerland) to give the title compound as a brownish oil. (HPLC: $t_R$ 2.59 min (Method A); M+H=356 MS-ES)

Example 20

8-[6-(3-Benzyloxy-propoxy)-pyridin-3-yl]-1-(1,3-dimethyl-1H-pyrazol-4-yl)-3-methyl-1,3-dihydro-imidazo[4,5-c]quinolin-2-one

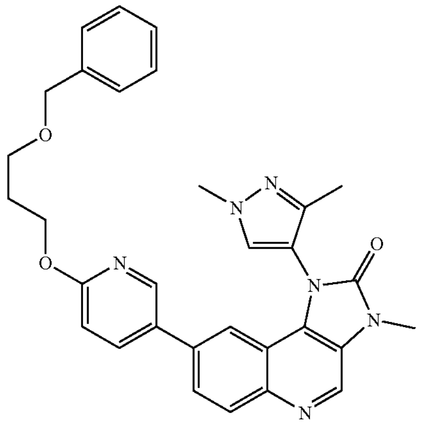 [SMILES: Cc1nn(C)cc1-n1c(=O)n(C)c2cnc3ccc(-c4ccc(OCCCOCc5ccccc5)nc4)cc3c21]

The title compound was synthesized in a similar manner as described for Example 1.1 using 8-bromo-1-(1,3-dimethyl-1H-pyrazol-4-yl)-3-methyl-1,3-dihydro-imidazo[4,5-c]quinolin-2-one (Intermediate A, 50 mg, 0.132 mmol) and 2-(3-benzyloxy-propoxy)-5-(4,4,5,5-tetramethyl-[1,3,2]dioxaborolan-2-yl)-pyridine (Stage 20.1.1, 68 mg, 0.184 mmol) to give the title compound as an off-white solid. (HPLC: $t_R$ 3.22 min (Method A); M+H=535 MS-ES; $^1$H-NMR ($d_6$-DMSO, 400 MHz) 8.95 (s, 1H), 8.31-8.26 (m, 1H), 8.15-8.05 (m, 2H), 7.93-7.86 (m, 1H), 7.79-7.73 (m, 1H), 7.50-7.45 (m, 1H), 7.35-7.22 (m, 5H), 6.93-6.87 (m, 1H), 4.55 (s, 2H), 4.36 (t, 2H), 3.91 (s, 3H), 3.60-3.55 (m, 5H), 2.05-1.97 (m, 2H), 1.95 (s, 3H))

Stage 20.1.1 2-(3-Benzyloxy-propoxy)-5-(4,4,5,5-tetramethyl-[1,3,2]dioxaborolan-2-yl)-pyridine

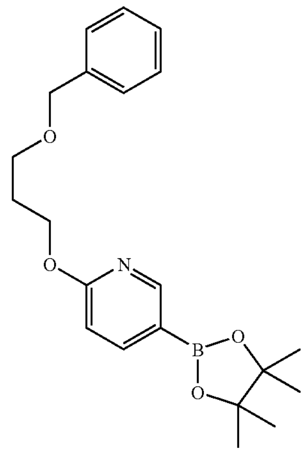 [SMILES: CC1(C)OB(c2ccc(OCCCOCc3ccccc3)nc2)OC1(C)C]

The title compound was synthesized in a similar manner as described for Stages 18.1.1 and 18.1.2 using 3-benzyloxypropanol (Aldrich, Buchs, Switzerland) to give the title compound as a brownish oil. (HPLC: $t_R$ 2.66 min (Method A); M+H=370 MS-ES)

Example 21.1

8-[6-(2-Hydroxy-ethylamino)-pyridin-3-yl]-3-methyl-1-(2-methyl-2H-pyrazol-3-yl)-1,3-dihydro-imidazo[4,5-c]quinolin-2-one

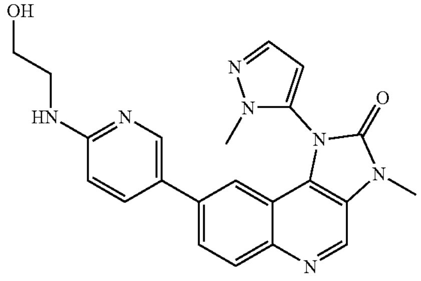 [SMILES: Cn1nccc1-n1c(=O)n(C)c2cnc3ccc(-c4ccc(NCCO)nc4)cc3c21]

The title compound was synthesized in a similar manner as described for Example 1.1 using 8-bromo-3-methyl-1-(2-methyl-2H-pyrazol-3-yl)-1,3-dihydro-imidazo[4,5-c]quinolin-2-one (Intermediate E, 65 mg, 0.181 mmol) and 2-[5-(4,4,5,5-tetramethyl-[1,3,2]dioxaborolan-2-yl)-pyridin-2-ylamino]-ethanol (stage 21.1.1, 82 mg, 0.218 mmol) to give the title compound as an off-white foam. (HPLC: $t_R$ 2.08 min (Method A); M+H=416 MS-ES; $^1$H-NMR ($d_6$-DMSO, 400 MHz) 8.96 (s, 1H), 8.12-8.02 (m, 2H), 7.80-7.75 (m, 2H), 7.51-7.44 (m, 1H), 6.95-6.89 (m, 1H), 6.85-6.73 (br, 1H), 6.69 (s, 1H), 6.60-6.53 (m, 1H), 3.66 (s, 3H), 3.58 (s, 3H), 3.54-3.49 (m, 2H), 3.37-3.31 (m, 2H))

Stage 21.1.1 2-[5-(4,4,5,5-Tetramethyl-[1,3,2]dioxaborolan-2-yl)-pyridin-2-ylamino]-ethanol

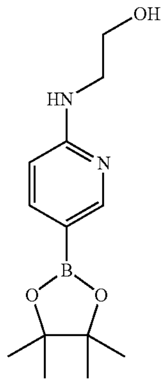 [SMILES: CC1(C)OB(c2ccc(NCCO)nc2)OC1(C)C]

The title compound was synthesized in a similar manner as described for Stages 5.1.1 using 2-(5-Bromo-pyridin-2-ylamino)-ethanol (stage 21.1.2) to give the title compound as a white solid trifluoroacetate salt. (M+H=379 MS-ES)

Stage 21.1.2 2-(5-Bromo-pyridin-2-ylamino)-ethanol

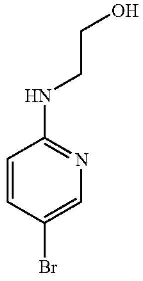 [SMILES: OCCNc1ccc(Br)cn1]

A mixture of 5-bromo-2-chloropyridine (Aldrich, Buchs, Switzerland, 1 g, 5.2 mmol) and 2-hydroxyethylamine (1.59 g, 26 mmol) in 3 ml DMA was heated by microwaves at 170° C. for 1 h. Then the RM was quenched with saturated aqueous $NaHCO_3$ (50 ml) and extracted with EtOAc. The organic layers were washed with saturated aqueous $NaHCO_3$ (4×), dried over $Na_2SO_4$, filtered and evaporated. The residue was purified by flash chromatography (DCM/MeOH 0 to 5%). The fractions containing product were evaporated together to give the title compound as an off-white solid. (HPLC: $t_R$ 1.66 min (Method A); M+H=217, 219 (Br-pattern) MS-ES)

The following example was synthesized in a similar manner as described for Example 1.1 using 2-[5-(4,4,5,5-tetramethyl-[1,3,2]dioxaborolan-2-yl)-pyridin-2-ylamino]-ethanol and the specified intermediate.

| Example | Intermed. | structure | Name of the example | MS-ES (M + H) | HPLC $t_R$ (min) |
|---|---|---|---|---|---|
| 21.2 | A | 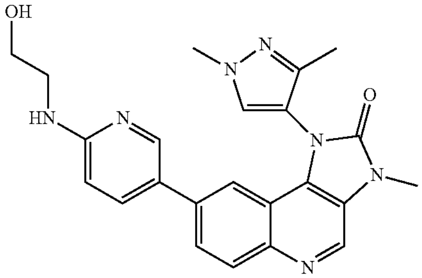 [SMILES: Cc1nn(C)cc1-n1c(=O)n(C)c2cnc3ccc(-c4ccc(NCCO)nc4)cc3c21] | 1-(1,3-Dimethyl-1H-pyrazol-4-yl)-8-[6-(2-hydroxy-ethylamino)-pyridin-3-yl]-3-methyl-1,3-dihydro-imidazo[4,5-c]quinolin-2-one | 430 | 2.04 |

Example 22

1-(1,3-Dimethyl-1H-pyrazol-4-yl)-8-(5-methanesulfonyl-pyridin-3-yl)-3-methyl-1,3-dihydro-imidazo[4,5-c]quinolin-2-one

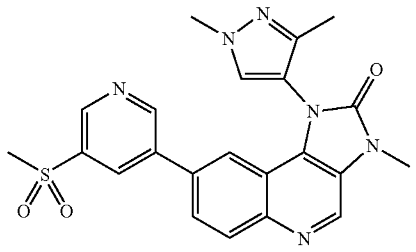

The title compound was synthesized in a similar manner as described for Example 1.1 using 8-bromo-1-(1,3-dimethyl-1H-pyrazol-4-yl)-3-methyl-1,3-dihydro-imidazo[4,5-c]quinolin-2-one (Intermediate A, 40 mg, 0.105 mmol) and 5-(methylsulfonyl)pyridine-3-boronic acid (Combi-Blocks, San Diego, USA, 25 mg, 0.125 mmol) to give the title compound as a white solid. (HPLC: $t_R$ 2.30 min (Method A); M+H=449 MS-ES; $^1$H-NMR ($d_6$-DMSO, 400 MHz) 9.09-9.01 (m, 3H), 8.32-8.27 (m, 1H), 8.21-8.14 (m, 2H), 8.11-8.06 (m, 1H), 7.67-7.62 (m, 1H), 3.92 (s, 3H), 3.59 (s, 3H), 3.40 (s, 3H), 1.94 (s, 3H))

Example 23.1

8-(6-Amino-pyridin-3-yl)-1-(1,3-dimethyl-1H-pyrazol-4-yl)-3-methyl-1,3-dihydro-imidazo[4,5-c]quinolin-2-one

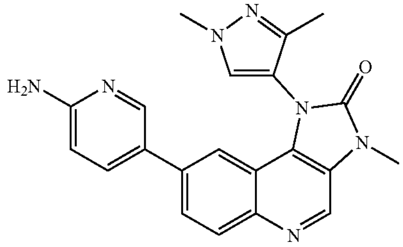 [SMILES: Cc1nn(C)cc1-n1c(=O)n(C)c2cnc3ccc(-c4ccc(N)nc4)cc3c21]

The title compound was synthesized in a similar manner as described for Example 1.1 using 8-bromo-1-(1,3-dimethyl-1H-pyrazol-4-yl)-3-methyl-1,3-dihydro-imidazo[4,5-c]quinolin-2-one (Intermediate A, 40 mg, 0.105 mmol) and 2-aminopyridine-5-boronic acid pinacol ester (Aldrich, Buchs, Switzerland, 26 mg, 0.125 mmol) to give the title compound as a white solid. (HPLC: $t_R$ 2.02 min (Method A); M+H=386 MS-ES; $^1$H-NMR ($d_6$-DMSO, 400 MHz) 8.90 (s, 1H), 8.16-8.10 (m, 1H), 8.07-7.98 (m, 2H), 7.86-7.78 (m, 1H), 7.54-7.46 (m, 1H), 7.42-7.36 (m, 1H), 6.54-6.46 (m, 1H), 6.20 (s, br, 2H), 3.91 (s, 3H), 3.56 (s, 3H), 1.95 (s, 3H))

The following example was synthesized in a similar manner as described for Example 1.1 using 2-aminopyridine-5-boronic acid pinacol ester and the specified intermediate.

| Example | Intermed. | structure | Name of the example | MS-ES (M + H) | HPLC $t_R$ (min) |
|---|---|---|---|---|---|
| 23.2 | G | 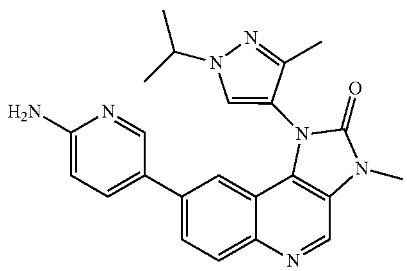 [SMILES: Cc1nn(C(C)C)cc1-n1c(=O)n(C)c2cnc3ccc(-c4ccc(N)nc4)cc3c21] | 8-(6-Amino-pyridin-3-yl)-1-(1-isopropyl-3-methyl-1H-pyrazol-4-yl)-3-methyl-1,3-dihydro-imidazo[4,5-c]quinolin-2-one | 414 | 2.10 |

Example 24

1-(1,3-Dimethyl-1H-pyrazol-4-yl)-3-methyl-8-(5-methyl-pyridin-3-yl)-1,3-dihydro-imidazo[4,5-c]quinolin-2-one

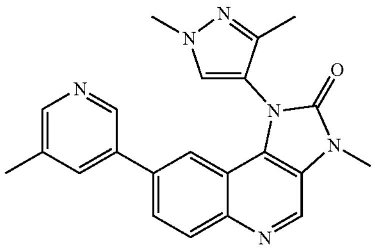

The title compound was synthesized in a similar manner as described for Example 1.1 using 8-bromo-1-(1,3-dimethyl-1H-pyrazol-4-yl)-3-methyl-1,3-dihydro-imidazo[4,5-c]quinolin-2-one (Intermediate A, 40 mg, 0.105 mmol) and 5-methylpyridine-3-boronic acid (Combi-Blocks, San Diego, USA, 17 mg, 0.123 mmol) to give the title compound as an off-white solid. (HPLC: $t_R$ 2.07 min (Method A); M+H=385 MS-ES; $^1$H-NMR ($d_6$-DMSO, 400 MHz) 8.98 (s, 1H), 8.54-8.48 (m, 1H), 8.45-8.39 (m, 1H), 8.19-8.08 (m, 2H), 7.99-7.92 (m, 1H), 7.71-7.66 (m, 1H), 7.58-7.53 (m, 1H), 3.92 (s, 3H), 3.59 (s, 3H), 2.37 (s, 3H), 1.95 (s, 3H))

Example 25.1

8-(6-Amino-5-trifluoromethyl-pyridin-3-yl)-1-(1,3-dimethyl-1H-pyrazol-4-yl)-3-methyl-1,3-dihydro-imidazo[4,5-c]quinolin-2-one

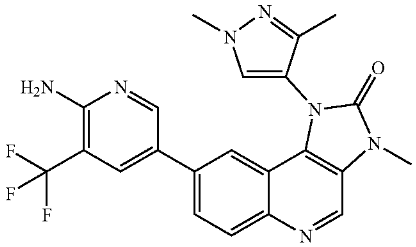 [SMILES: Cc1nn(C)cc1-n1c(=O)n(C)c2cnc3ccc(-c4cnc(N)c(C(F)(F)F)c4)cc3c21]

The title compound was synthesized in a similar manner as described for Example 1.1 using 8-bromo-1-(1,3-dimethyl-1H-pyrazol-4-yl)-3-methyl-1,3-dihydro-imidazo[4,5-c]quinolin-2-one (Intermediate A, 40 mg, 0.105 mmol) and 2-amino-3-(trifluoromethyl)pyridine-5-boronic acid pinacol ester (stage 25.1.1, 37 mg, 0.128 mmol) to give the title compound as a pinkish solid. (HPLC: $t_R$ 2.40 min (Method A); M+H=454 MS-ES; $^1$H-NMR ($d_6$-DMSO, 400 MHz) 8.93 (s, 1H), 8.43-8.36 (m, 1H), 8.16-8.11 (m, 1H), 8.09-8.02 (m, 1H), 7.97-7.90 (m, 1H), 7.76-7.70 (m, 1H), 7.45-7.39 (m, 1H), 6.76 (s, br, 2H), 3.88 (s, 3H), 3.56 (s, 3H), 1.95 (s, 3H))

Stage 25.1.1 5-(4,4,5,5-Tetramethyl-[1,3,2]dioxaborolan-2-yl)-3-trifluoromethyl-pyridin-2-ylamine

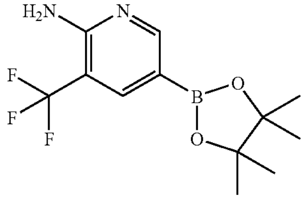 [SMILES: CC1(C)OB(c2cnc(N)c(C(F)(F)F)c2)OC1(C)C]

The title compound was synthesized in a similar manner as described for stage 5.1.1 using 5-bromo-3-trifluoromethyl-pyridin-2-ylamine (Stage 25.1.2, 8.04 g, 31.7 mmol) to give the title compound as an off-white solid. (HPLC: $t_R$ 1.62 min (Method A); M+H=289 MS-ES)

Stage 25.1.2
5-Bromo-3-trifluoromethyl-pyridin-2-ylamine

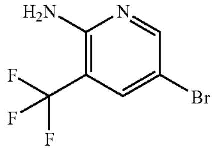 [SMILES: Nc1ncc(Br)cc1C(F)(F)F]

To a solution of 3-trifluoromethyl-pyridin-2-ylamine (Fluorochem Ltd., Derbyshire, United Kingdom, 5.37 g, 32.8 mmol) in 100 ml of dry $CH_3CN$ under argon were added N-bromosuccinimide (6.45 g, 36.2 mmol) in 4 equal portions over a period of 1 h at 0-5° C. The cooling bath was removed and stirring was continued for 3 h. The solvent was evaporated under vacuum, then the residue was dissolved in EtOAc and washed with water and brine. The organic layer was dried over $Na_2SO_4$ and evaporated to give the title compound as a orange oil. (M+H=239; 241).

The following example was synthesized in a similar manner as described for Example 1.1 using 5-(4,4,5,5-tetramethyl-[1,3,2]dioxaborolan-2-yl)-3-trifluoromethyl-pyridin-2-ylamine and the specified intermediate.

| Example | Intermed. | structure | Name of the example | MS-ES (M + H) | HPLC $t_R$ (min) |
|---|---|---|---|---|---|
| 25.2 | O | 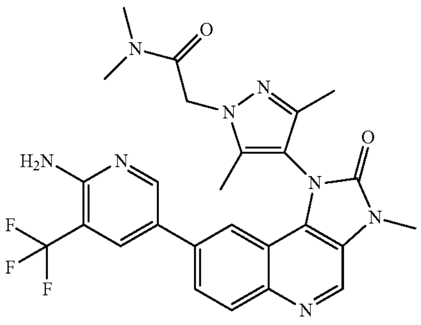 [SMILES: Cc1nn(CC(=O)N(C)C)c(C)c1-n1c(=O)n(C)c2cnc3ccc(-c4cnc(N)c(C(F)(F)F)c4)cc3c21] | 2-{4-[8-(6-Amino-5-trifluoromethyl-pyridin-3-yl)-3-methyl-2-oxo-2,3-dihydro-imidazo[4,5-c]quinolin-1-yl]-3,5-dimethyl-pyrazol-1-yl}-N,N-dimethyl-acetamide | 539 | 2.34 |
| 25.3 | H | 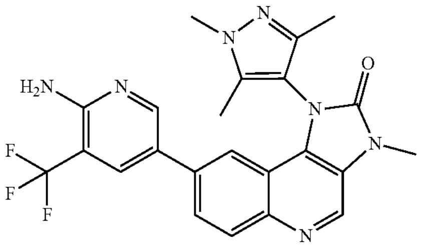 [SMILES: Cc1nn(C)c(C)c1-n1c(=O)n(C)c2cnc3ccc(-c4cnc(N)c(C(F)(F)F)c4)cc3c21] | 8-(6-Amino-5-trifluoromethyl-pyridin-3-yl)-3-methyl-1-(1,3,5-trimethyl-1H-pyrazol-4-yl)-1,3-dihydro-imidazo[4,5-c]quinolin-2-one | 468 | 2.39 |
| 25.4 | G | 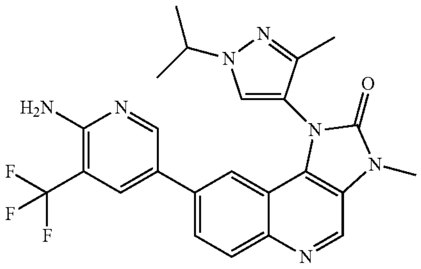 [SMILES: Cc1nn(C(C)C)cc1-n1c(=O)n(C)c2cnc3ccc(-c4cnc(N)c(C(F)(F)F)c4)cc3c21] | 8-(6-Amino-5-trifluoromethyl-pyridin-3-yl)-1-(1-isopropyl-3-methyl-1H-pyrazol-4-yl)-3-methyl-1,3-dihydro-imidazo[4,5-c]quinolin-2-one | 482 | 2.55 |
| 25.5 | Q | 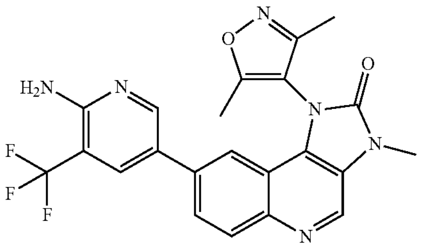 | 8-(6-Amino-5-trifluoromethyl-pyridin-3-yl)-1-(3,5-dimethyl-isoxazol-4-yl)-3-methyl-1,3-dihydro-imidazo[4,5-c]quinolin-2-one | 455 | 2.52 |
| 25.6 | C | 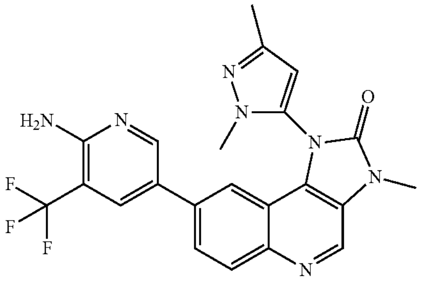 [SMILES: Cc1cc(-n2c(=O)n(C)c3cnc4ccc(-c5cnc(N)c(C(F)(F)F)c5)cc4c32)n(C)n1] | 8-(6-Amino-5-trifluoromethyl-pyridin-3-yl)-1-(2,5-dimethyl-2H-pyrazol-3-yl)-3-methyl-1,3-dihydro-imidazo[4,5-c]quinolin-2-one | 454 | 2.54 |

Example 26

1-(1,3-Dimethyl-1H-pyrazol-4-yl)-3-methyl-8-pyrimidin-5-yl-1,3-dihydro-imidazo[4,5-c]quinolin-2-one

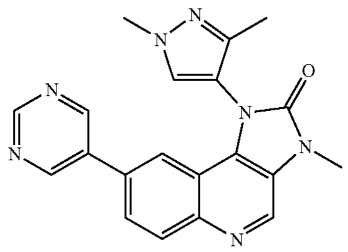 [SMILES: Cc1nn(C)cc1-n1c(=O)n(C)c2cnc3ccc(-c4cncnc4)cc3c21]

The title compound was synthesized in a similar manner as described for Example 1.1 using 8-bromo-1-(1,3-dimethyl-1H-pyrazol-4-yl)-3-methyl-1,3-dihydro-imidazo[4,5-c]quinolin-2-one (Intermediate A, 40 mg, 0.105 mmol) and pyrimidine-5-boronic acid (Frontier Scientific, Logan, USA, 16 mg, 0.129 mmol) to give the title compound as a white solid. (HPLC: $t_R$ 2.24 min (Method A); M+H=372 MS-ES; $^1$H-NMR ($d_6$-DMSO, 400 MHz) 9.20 (s, 1H), 9.02 (s, 1H), 8.93 (s, 2H), 8.20-8.12 (m, 2H), 8.06-7.99 (m, 1H), 7.62-7.56 (m, 1H), 3.90 (s, 3H), 3.58 (s, 3H), 1.97 (s, 3H))

Example 27.1

8-(3,4-Diethoxy-phenyl)-1-(1-ethyl-3-methyl-1H-pyrazol-4-yl)-3-methyl-1,3-dihydro-imidazo[4,5-c]quinolin-2-one

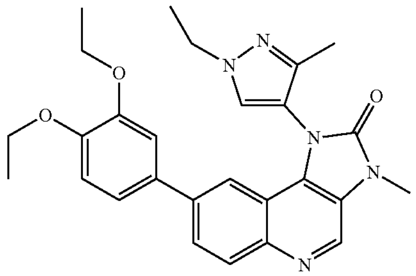 [SMILES: CCOc1ccc(-c2ccc3ncc4c(c3c2)n(-c2cn(CC)nc2C)c(=O)n4C)cc1OCC]

The title compound was synthesized in a similar manner as described for Example 1.1 using 8-bromo-1-(1-ethyl-3-methyl-1H-pyrazol-4-yl)-3-methyl-1,3-dihydro-imidazo[4,5-c]quinolin-2-one (Intermediate F, 49 mg, 0.126 mmol) and 2-(3,4-diethoxy-phenyl)-4,4,5,5-tetramethyl-[1,3,2]dioxaborolane (stage 27.1.1, 47 mg, 0.161 mmol) to give the title compound as an off-white solid. (HPLC: $t_R$ 3.02 min (Method A); M+H=472 MS-ES; $^1$H-NMR ($d_6$-DMSO, 400 MHz) 8.97 (s, 1H), 8.18 (s, 1H), 8.08-8.02 (m, 1H), 7.95-7.84 (m, 1H), 7.52-7.48 (m, 1H), 7.06-6.97 (m, 3H), 4.22-3.98 (m, 6H), 3.58 (s, 3H), 1.97 (s, 3H) 1.45-1.25 (m, 9H))

Stage 27.1.1 2-(3,4-Diethoxy-phenyl)-4,4,5,5-tetramethyl-[1,3,2]dioxaborolane

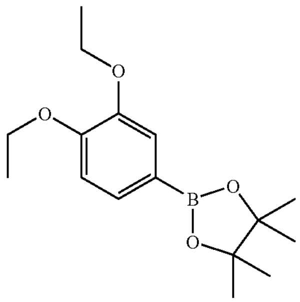 [SMILES: CCOc1ccc(B2OC(C)(C)C(C)(C)O2)cc1OCC]

The title compound was synthesized in a similar manner as described for Stage 5.1.1 using 4-Bromo-1,2-diethoxy-benzene (Stage 27.1.2, 500 mg, 2.04 mmol) to give the title compound as a colourless oil. (HPLC: $t_R$ 3.94 min (Method A); M+H=293 MS-ES).

Stage 27.1.2 4-Bromo-1,2-diethoxy-benzene

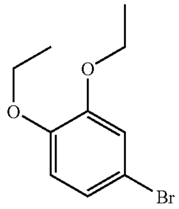

A mixture of 4-bromocatechol (Aldrich, Buchs, Switzerland, 500 mg, 2.65 mmol), potassium carbonate (1.1 g, 7.94 mmol) and iodoethane (1.03 g, 6.61 mmol) in 10 ml DMF was stirred protected from the light for 17 h at rt. The reaction mixture was quenched with 50 ml saturated aqueous $NaHCO_3$ and extracted with EtOAc (2×). The organic layers were washed with saturated aqueous $NaHCO_3$ (4×) and brine, dried over $Na_2SO_4$, filtered and evaporated. The residue was purified by flash chromatography (petrol ether/diethyl ether 0% to 10%) to give the title compound as a colorless oil. (HPLC: $t_R$ 3.79 min (Method A)).

The following example was synthesized in a similar manner as described for Example 1.1 using 2-(3,4-diethoxy-phenyl)-4,4,5,5-tetramethyl-[1,3,2]dioxaborolane and the specified intermediate.

| Example | Intermed. | structure | Name of the example | MS-ES (M + H) | HPLC $t_R$ (min) |
|---|---|---|---|---|---|
| 27.2 | H | 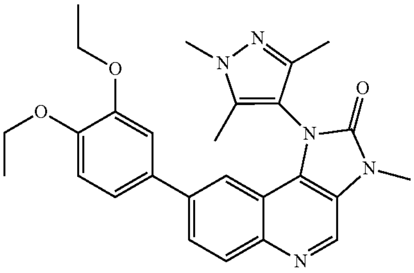 [SMILES: CCOc1ccc(-c2ccc3ncc4c(c3c2)n(-c2c(C)nn(C)c2C)c(=O)n4C)cc1OCC] | 8-(3,4-Diethoxy-phenyl)-3-methyl-1-(1,3,5-trimethyl-1H-pyrazol-4-yl)-1,3-dihydro-imidazo[4,5-c]quinolin-2-one | 472 | 2.97 |

Example 28.1

8-(3-Ethoxy-4-methoxy-phenyl)-1-(1-ethyl-3-methyl-1H-pyrazol-4-yl)-3-methyl-1,3-dihydro-imidazo[4,5-c]quinolin-2-one

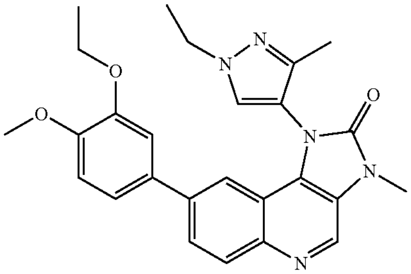

The title compound was synthesized in a similar manner as described for Example 1.1 using 8-bromo-1-(1-ethyl-3-methyl-1H-pyrazol-4-yl)-3-methyl-1,3-dihydro-imidazo[4,5-c]quinolin-2-one (Intermediate F, 39 mg, 0.100 mmol) and 3-ethoxy-4-methoxyphenylboronic acid (Combi-Blocks, San Diego, USA, 25.5 mg, 0.130 mmol) to give the title compound as an off-white foam. (HPLC: $t_R$ 2.86 min (Method A); M+H=458 MS-ES; $^1$H-NMR ($d_6$-DMSO, 400 MHz) 8.92 (s, 1H), 8.16 (s, 1H), 8.08-8.01 (m, 1H), 7.93-7.87 (m, 1H), 7.52-7.46 (m, 1H), 7.06-6.96 (m, 3H), 4.20-4.03 (m, 4H), 3.77 (s, 3H), 3.57 (s, 3H), 1.97 (s, 3H), 1.45-1.33 (m, 6H))

The following examples were synthesized in a similar manner as described for Example 1.1 using 3-ethoxy-4-methoxyphenylboronic acid and the specified intermediate.

| Example | Intermed. | structure | Name of the example | MS-ES (M + H) | HPLC $t_R$ (min) |
|---|---|---|---|---|---|
| 28.2 | H | 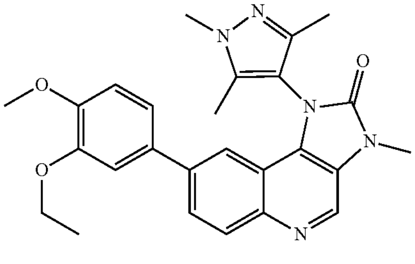 | 8-(3-Ethoxy-4-methoxy-phenyl)-3-methyl-1-(1,3,5-trimethyl-1H-pyrazol-4-yl)-1,3-dihydro-imidazo[4,5-c]quinolin-2-one | 458 | 2.81 |
| 28.3 | A | 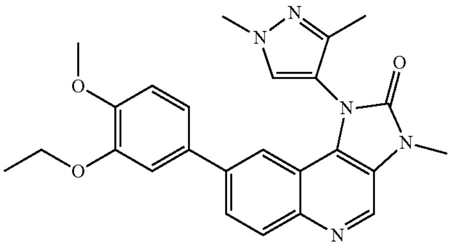 [SMILES: CCOc1cc(-c2ccc3ncc4c(c3c2)n(-c2cn(C)nc2C)c(=O)n4C)ccc1OC] | 1-(1,3-Dimethyl-1H-pyrazol-4-yl)-8-(3-ethoxy-4-methoxy-phenyl)-3-methyl-1,3-dihydro-imidazo[4,5-c]quinolin-2-one | 444 | 2.76 |

Example 29.1

8-(4-Ethoxy-3-methoxy-phenyl)-1-(1-ethyl-3-methyl-1H-pyrazol-4-yl)-3-methyl-1,3-dihydro-imidazo[4,5-c]quinolin-2-one

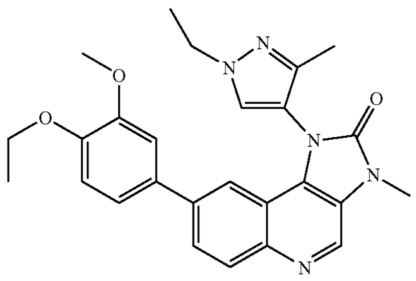 [SMILES: CCOc1ccc(-c2ccc3ncc4c(c3c2)n(-c2cn(CC)nc2C)c(=O)n4C)cc1OC]

The title compound was synthesized in a similar manner as described for Example 1.1 using 8-bromo-1-(1-ethyl-3-methyl-1H-pyrazol-4-yl)-3-methyl-1,3-dihydro-imidazo[4,5-c]quinolin-2-one (Intermediate F, 39 mg, 0.100 mmol) and 2-(4-ethoxy-3-methoxy-phenyl)-4,4,5,5-tetramethyl-[1,3,2]dioxaborolane (Stage 29.1.1, 34 mg, 0.123 mmol) to give the title compound as a white solid. (HPLC: $t_R$ 2.88 min (Method A); M+H=458 MS-ES; $^1$H-NMR ($d_6$-DMSO, 400 MHz) 8.92 (s, 1H), 8.16 (s, 1H), 8.07-8.02 (m, 1H), 7.94-7.88 (m, 1H), 7.51-7.47 (m, 1H), 7.06-6.96 (m, 3H), 4.20-4.12 (m, 2H), 4.06-3.98 (m, 2H), 3.85 (s, 3H), 3.57 (s, 3H), 1.97 (s, 3H), 1.42-1.29 (m, 6H))

Stage 29.1.1 2-(4-Ethoxy-3-methoxy-phenyl)-4,4,5,5-tetramethyl-[1,3,2]dioxaborolane

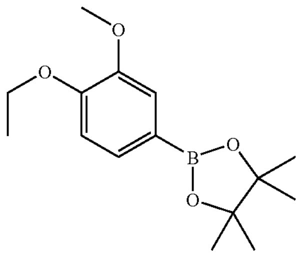 [SMILES: CCOc1ccc(B2OC(C)(C)C(C)(C)O2)cc1OC]

To a mixture of 4-hydroxy-3-methoxyphenylboronic acid pinacol ester (Aldrich, Buchs, Switzerland, 200 mg, 0.800 mmol), triphenylphosphine (315 mg, 1.200 mmol) and ethanol (0.056 ml, 0.960 mmol) in THF (4 ml) under Argon was added dropwise diisopropyl azodicarboxylate (0.253 ml, 1.20 mmol). The RM was stirred at it for 17.5 h. Then the RM was diluted with EtOAc and the organic layer was washed with brine (2×), before being dried over $Na_2SO_4$, filtered and evaporated. The residue was absorbed on silica gel and purified by MPLC (hexane/EtOAc 0 to 30%). The fractions containing product were together evaporated to give the title compound as a white solid. (HPLC: $t_R$ 3.58 min (Method A); M+H=279 MS-ES)

The following examples were synthesized in a similar manner as described for Example 1.1 using 2-(4-ethoxy-3-methoxy-phenyl)-4,4,5,5-tetramethyl-[1,3,2]dioxaborolane and the specified intermediate.

| Example | Intermed. | structure | Name of the example | MS-ES (M + H) | HPLC $t_R$ (min) |
|---|---|---|---|---|---|
| 29.2 | H | 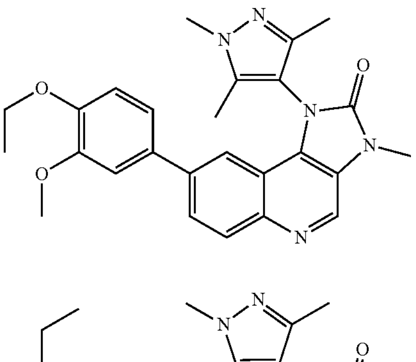 | 8-(4-Ethoxy-3-methoxy-phenyl)-3-methyl-1-(1,3,5-trimethyl-1H-pyrazol-4-yl)-1,3-dihydro-imidazo[4,5-c]quinolin-2-one | 458 | 2.85 |
| 29.3 | A | 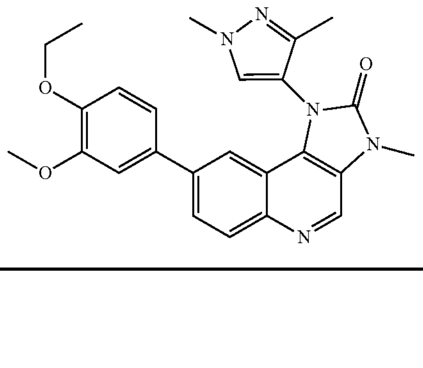 | 1-(1,3-Dimethyl-1H-pyrazol-4-yl)-8-(4-ethoxy-3-methoxy-phenyl)-3-methyl-1,3-dihydro-imidazo[4,5-c]quinolin-2-one | 444 | 2.80 |

Example 30.1

1-(1,3-Dimethyl-1H-pyrazol-4-yl)-8-[3-methoxy-4-(2-methoxy-ethoxy)-phenyl]-3-methyl-1,3-dihydro-imidazo[4,5-c]quinolin-2-one

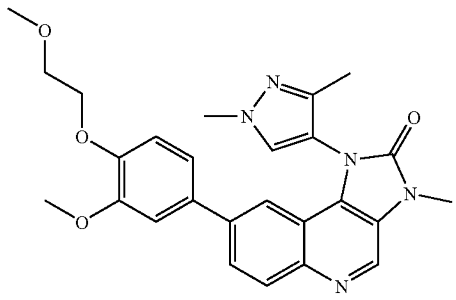

The title compound was synthesized in a similar manner as described for Example 1.1 using 8-bromo-1-(1,3-dimethyl-1H-pyrazol-4-yl)-3-methyl-1,3-dihydro-imidazo[4,5-c]quinolin-2-one (Intermediate A, 39 mg, 0.105 mmol) and 2-[3-methoxy-4-(2-methoxy-ethoxy)-phenyl]-4,4,5,5-tetramethyl-[1,3,2]dioxaborolane (Stage 30.1.1, 39 mg, 0.126 mmol) to give the title compound as a white solid. (HPLC: $t_R$ 2.71 min (Method A); M+H=474 MS-ES; $^1$H-NMR ($d_6$-DMSO, 400 MHz) 8.93 (s, 1H), 8.15-8.02 (m, 2H), 7.97-7.89 (m, 1H), 7.59-7.51 (m, 1H), 7.11-7.02 (m, 2H), 7.00-6.94 (m, 1H), 4.16-4.07 (m, 2H), 3.94-3.84 (m, 6H), 3.70-3.64 (m, 2H), 3.58 (s, 3H), 3.31 (s, 3H), 1.97 (s, 3H))

Stage 30.1.1 2-[3-Methoxy-4-(2-methoxy-ethoxy)-phenyl]-4,4,5,5-tetramethyl-[1,3,2]dioxaborolane

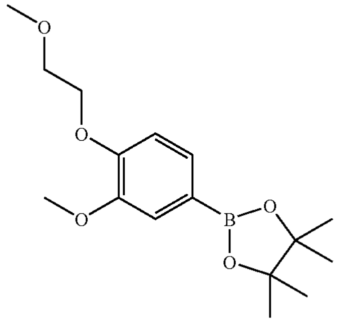

The title compound was synthesized in a similar manner as described for stage 29.1.1 using 2-methoxyethanol (Aldrich, Buchs, Switzerland) to give the title compound as a colorless oil. (HPLC: $t_R$ 3.42 min (Method A); M+H=309 MS-ES)

The following example was synthesized in a similar manner as described for Example 1.1 using 2-[3-methoxy-4-(2-methoxy-ethoxy)-phenyl]-4,4,5,5-tetramethyl-[1,3,2]dioxaborolane and the specified intermediate.

| Example | Intermed. | structure | Name of the example | MS-ES (M + H) | HPLC $t_R$ (min) |
|---|---|---|---|---|---|
| 30.2 | F | 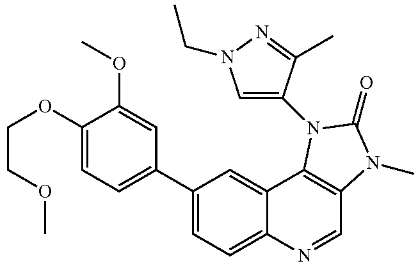 [SMILES: CCn1cc(-n2c(=O)n(C)c3cnc4ccc(-c5ccc(OCCOC)c(OC)c5)cc4c32)c(C)n1] | 1-(1-Ethyl-3-methyl-1H-pyrazol-4-yl)-8-[3-methoxy-4-(2-methoxy-ethoxy)-phenyl]-3-methyl-1,3-dihydro-imidazo[4,5-c]quinolin-2-one | 488 | 2.78 |

Example 31

8-(4-Hydroxy-3-methoxy-phenyl)-3-methyl-1-(1,3,5-trimethyl-1H-pyrazol-4-yl)-1,3-dihydro-imidazo[4,5-c]quinolin-2-one

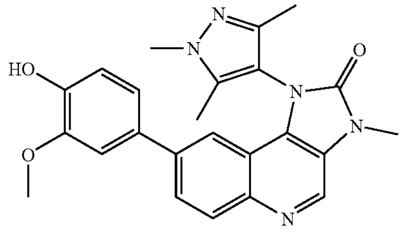 [SMILES: COc1cc(-c2ccc3ncc4c(c3c2)n(-c2c(C)nn(C)c2C)c(=O)n4C)ccc1O]

The title compound was synthesized in a similar manner as described for Example 1.1 using 8-bromo-3-methyl-1-(1,3,5-trimethyl-1H-pyrazol-4-yl)-1,3-dihydro-imidazo[4,5-c]quinolin-2-one (Intermediate H, 39 mg, 0.100 mmol) and 4-hydroxy-3-methoxyphenylboronic acid pinacol ester (Aldrich, Buchs, Switzerland, 30 mg, 0.120 mmol) to give the title compound as a lightly yellow foam. (HPLC: $t_R$ 2.50 min (Method A); M+H=430 MS-ES; $^1$H-NMR ($d_6$-DMSO, 400 MHz) 9.23 (s, 1H), 8.93 (s, 1H), 8.06-7.99 (m, 1H), 7.92-7.85 (m, 1H), 7.51-7.46 (m, 1H), 7.03-6.96 (m, 1H), 6.94-6.89 (m, 1H), 6.87-6.81 (m, 1H), 3.85 (s, 3H), 3.79 (s, 3H), 3.58 (s, 3H), 2.08 (s, 3H), 1.94 (s, 3H))

Example 32.1

1-(1,3-Dimethyl-1H-pyrazol-4-yl)-8-(3-hydroxy-phenyl)-3-methyl-1,3-dihydro-imidazo[4,5-c]quinolin-2-one

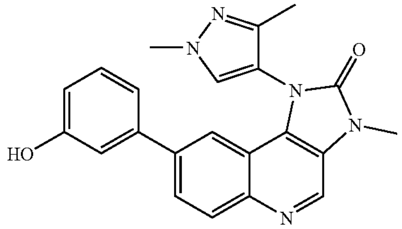 [SMILES: Cc1nn(C)cc1-n1c(=O)n(C)c2cnc3ccc(-c4cccc(O)c4)cc3c21]

The title compound was synthesized in a similar manner as described for Example 1.1 using 8-bromo-1-(1,3-dimethyl-1H-pyrazol-4-yl)-3-methyl-1,3-dihydro-imidazo[4,5-c]quinolin-2-one (Intermediate A, 39 mg, 0.105 mmol) and 3-hydroxyphenylboronic acid (Aldrich, Buchs, Switzerland, 17 mg, 0.123 mmol) to give the title compound as a white solid. (HPLC: $t_R$ 2.46 min (Method A); M+H=386 MS-ES; $^1$H-NMR ($d_6$-DMSO, 400 MHz) 9.58 (s, 1H), 8.95 (s, 1H), 8.20-8.11 (m, 1H), 8.10-8.01 (m, 1H), 7.88-7.77 (m, 1H), 7.57-7.47 (m, 1H), 7.31-7.20 (m, 1H), 6.93-6.83 (m, 2H), 6.82-6.73 (m, 1H), 3.95 (s, 3H), 3.58 (s, 3H), 1.95 (s, 3H))

The following example was synthesized in a similar manner as described for Example 1.1 using 3-hydroxyphenylboronic acid and the specified intermediate.

| Example | Intermed. | structure | Name of the example | MS-ES (M + H) | HPLC $t_R$ (min) |
|---|---|---|---|---|---|
| 32.2 | H | 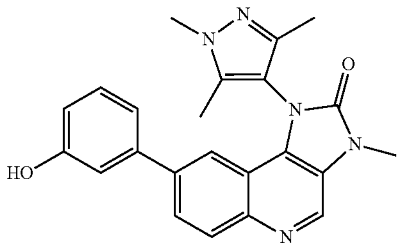 [SMILES: Cc1nn(C)c(C)c1-n1c(=O)n(C)c2cnc3ccc(-c4cccc(O)c4)cc3c21] | 8-(3-Hydroxy-phenyl)-3-methyl-1-(1,3,5-trimethyl-1H-pyrazol-4-yl)-1,3-dihydro-imidazo[4,5-c]quinolin-2-one | 400 | 2.52 |

Example 33

1-(1,3-Dimethyl-1H-pyrazol-4-yl)-8-(3-fluoro-5-hydroxy-phenyl)-3-methyl-1,3-dihydro-imidazo[4,5-c]quinolin-2-one

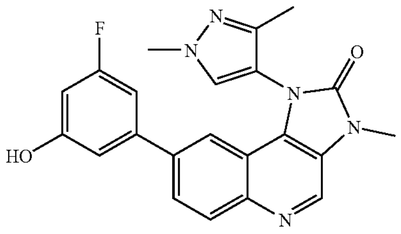 [SMILES: Cc1nn(C)cc1-n1c(=O)n(C)c2cnc3ccc(-c4cc(O)cc(F)c4)cc3c21]

The title compound was synthesized in a similar manner as described for Example 1.1 using 8-bromo-1-(1,3-dimethyl-1H-pyrazol-4-yl)-3-methyl-1,3-dihydro-imidazo[4,5-c]quinolin-2-one (Intermediate A, 40 mg, 0.107 mmol) and 3-fluoro-5-hydroxyphenylboronic acid (Combi-Blocks, San Diego, USA, 21 mg, 0.132 mmol) to give the title compound as a white solid. (HPLC: $t_R$ 2.58 min (Method A); M+H=404 MS-ES; $^1$H-NMR ($d_6$-DMSO, 400 MHz) 10.09 (s, 1H), 8.96 (s, 1H), 8.17 (s, 1H), 8.10-8.03 (m, 1H), 7.87-7.80 (m, 1H), 7.52-7.46 (m, 1H), 6.75-6.64 (m, 2H), 6.63-6.52 (m, 1H), 3.92 (s, 3H), 3.57 (s, 3H), 1.94 (s, 3H))

Example 34

1-(1,3-Dimethyl-1H-pyrazol-4-yl)-8-(3-hydroxy-5-trifluoromethyl-phenyl)-3-methyl-1,3-dihydro-imidazo[4,5-c]quinolin-2-one

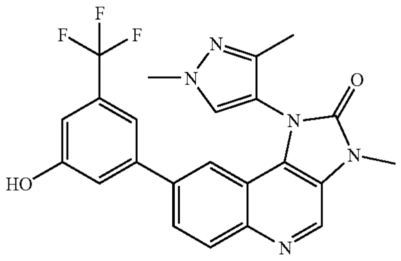 [SMILES: Cc1nn(C)cc1-n1c(=O)n(C)c2cnc3ccc(-c4cc(O)cc(C(F)(F)F)c4)cc3c21]

The title compound was synthesized in a similar manner as described for Example 1.1 using 8-bromo-1-(1,3-dimethyl-1H-pyrazol-4-yl)-3-methyl-1,3-dihydro-imidazo[4,5-c]quinolin-2-one (Intermediate A, 40 mg, 0.107 mmol) and 3-hydroxy-5-(trifluoromethyl)phenylboronic acid (Combi-Blocks, San Diego, USA, 27 mg, 0.132 mmol) to give the title compound as a white solid. (HPLC: $t_R$ 2.83 min (Method A); M+H=454 MS-ES; $^1$H-NMR ($d_6$-DMSO, 400 MHz) 10.38 (s, br, 1H), 8.98 (s, 1H), 8.18 (s, 1H), 8.12-8.07 (m, 1H), 7.93-7.87 (m, 1H), 7.58-7.53 (m, 1H), 7.21-7.16 (m, 1H), 7.13-7.09 (m, 1H), 7.07-7.03 (m, 1H), 3.89 (s, 3H), 3.58 (s, 3H), 1.93 (s, 3H))

Example 35

8-(2,2-Difluoro-benzo[1,3]dioxol-4-yl)-1-(1,3-dimethyl-1H-pyrazol-4-yl)-3-methyl-1,3-dihydro-imidazo[4,5-c]quinolin-2-one

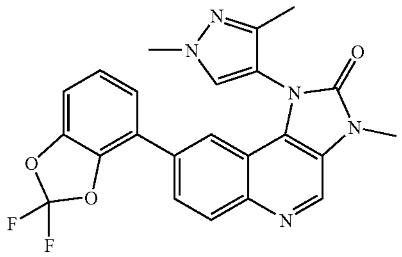 [SMILES: Cc1nn(C)cc1-n1c(=O)n(C)c2cnc3ccc(-c4cccc5c4OC(F)(F)O5)cc3c21]

The title compound was synthesized in a similar manner as described for Example 1.1 using 8-bromo-1-(1,3-dimethyl-1H-pyrazol-4-yl)-3-methyl-1,3-dihydro-imidazo[4,5-c]quinolin-2-one (Intermediate A, 40 mg, 0.107 mmol) and 2,2-difluorobenzo[1,3]dioxole-4-boronic acid (Apollo, Cheshire, United Kingdom, 26 mg, 0.130 mmol) to give the title compound as a white solid. (HPLC: $t_R$ 2.95 min (Method A); M+H=450 MS-ES; $^1$H-NMR ($d_6$-DMSO, 400 MHz) 9.01 (s, 1H), 8.18-8.13 (m, 1H), 8.08 (s, 1H), 7.97-7.91 (m, 1H), 7.88-7.84 (m, 1H), 7.441-7.38 (m, 2H), 7.36-7.29 (m, 1H), 3.85 (s, 3H), 3.58 (s, 3H), 1.94 (s, 3H))

Example 36

1-(1,3-Dimethyl-1H-pyrazol-4-yl)-3-methyl-8-(1H-pyrrolo[2,3-b]pyridin-5-yl)-1,3-dihydro-imidazo[4,5-c]quinolin-2-one

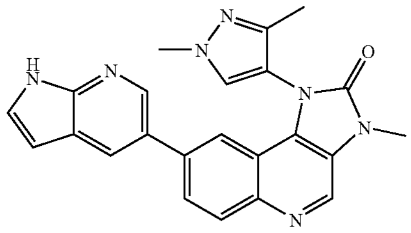 [SMILES: Cc1nn(C)cc1-n1c(=O)n(C)c2cnc3ccc(-c4cnc5[nH]ccc5c4)cc3c21]

The title compound was synthesized in a similar manner as described for Example 1.1 using 8-bromo-1-(1,3-dimethyl-1H-pyrazol-4-yl)-3-methyl-1,3-dihydro-imidazo[4,5-c]quinolin-2-one (Intermediate A, 39 mg, 0.105 mmol) and 7-azaindole-5-boronic acid pinacol ester (ABCR, Karlsruhe, Germany, 31 mg, 0.127 mmol) to give the title compound as a white solid. (HPLC: $t_R$ 2.35 min (Method A); M+H=410 MS-ES; $^1$H-NMR ($d_6$-DMSO, 400 MHz) 11.75 (s, br, 1H), 8.95 (s, 1H), 8.38-8.28 (m, 1H), 8.22-8.15 (m, 1H), 8.13-8.03

(m, 2H), 8.01-7.95 (m, 1H), 7.59-7.51 (m, 2H), 6.55-6.47 (m, 1H), 3.93 (s, 3H), 3.58 (s, 3H), 1.97 (s, 3H))

Example 37.1

1-(1,3-Dimethyl-1H-pyrazol-4-yl)-3-methyl-8-phenyl-1,3-dihydro-imidazo[4,5-c]quinolin-2-one

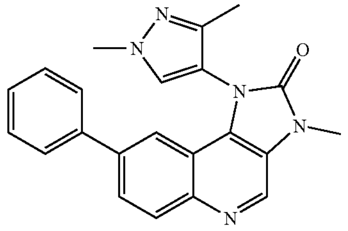 [SMILES: Cc1nn(C)cc1-n1c(=O)n(C)c2cnc3ccc(-c4ccccc4)cc3c21]

The title compound was synthesized in a similar manner as described for Example 1.1 using 8-bromo-1-(1,3-dimethyl-1H-pyrazol-4-yl)-3-methyl-1,3-dihydro-imidazo[4,5-c]quinolin-2-one (Intermediate A, 40 mg, 0.107 mmol) and phenylboronic acid (Aldrich, Buchs, Switzerland, 16.5 mg, 0.135 mmol) to give the title compound as a white solid. (HPLC: $t_R$ 2.70 min (Method A); M+H=370 MS-ES; $^1$H-NMR ($d_6$-DMSO, 400 MHz) 8.95 (s, 1H), 8.16 (s, 1H), 8.11-8.06 (m, 1H), 7.93-7.88 (m, 1H), 7.56-7.53 (m, 1H), 7.50-7.44 (m, 4H), 7.42-7.34 (m, 1H), 3.92 (s, 3H), 3.57 (s, 3H), 1.95 (s, 3H))

The following examples were synthesized in a similar manner as described for Example 1.1 using phenylboronic acid and the specified intermediate.

| Example | Intermed. | structure | Name of the example | MS-ES (M + H) | HPLC $t_R$ (min) |
|---|---|---|---|---|---|
| 37.2 | H | 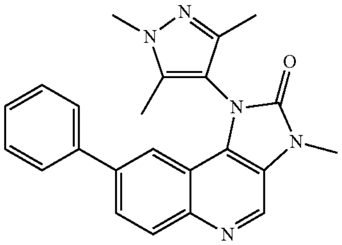 [SMILES: Cc1nn(C)c(C)c1-n1c(=O)n(C)c2cnc3ccc(-c4ccccc4)cc3c21] | 3-Methyl-8-phenyl-1-(1,3,5-trimethyl-1H-pyrazol-4-yl)-1,3-dihydro-imidazo[4,5-c]quinolin-2-one | 384 | 2.73 |
| 37.3 | L | 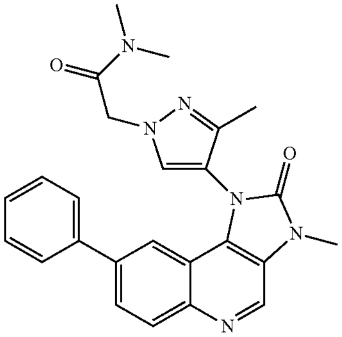 [SMILES: Cc1nn(CC(=O)N(C)C)cc1-n1c(=O)n(C)c2cnc3ccc(-c4ccccc4)cc3c21] | N,N-Dimethyl-2-[3-methyl-4-(3-methyl-2-oxo-8-phenyl-2,3-dihydro-imidazo[4,5-c]quinolin-1-yl)-pyrazol-1-yl]-acetamide | 441 | 2.65 |
| 37.4 | O | 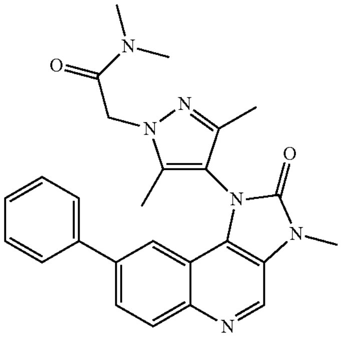 [SMILES: Cc1nn(CC(=O)N(C)C)c(C)c1-n1c(=O)n(C)c2cnc3ccc(-c4ccccc4)cc3c21] | 2-[3,5-Dimethyl-4-(3-methyl-2-oxo-8-phenyl-2,3-dihydro-imidazo[4,5-c]quinolin-1-yl)-pyrazol-1-yl]-N,N-dimethyl-acetamide | 455 | 2.68 |

Example 38

1-(1,3-Dimethyl-1H-pyrazol-4-yl)-3-methyl-8-quinolin-3-yl-1,3-dihydro-imidazo[4,5-c]quinolin-2-one

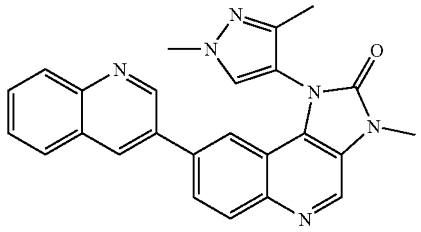 [SMILES: Cc1nn(C)cc1-n1c(=O)n(C)c2cnc3ccc(-c4cnc5ccccc5c4)cc3c21]

The title compound was synthesized in a similar manner as described for Example 1.1 using 8-bromo-1-(1,3-dimethyl-1H-pyrazol-4-yl)-3-methyl-1,3-dihydro-imidazo[4,5-c]quinolin-2-one (Intermediate A, 39 mg, 0.105 mmol) and 3-quinolineboronic acid (Aldrich, Buchs, Switzerland, 22 mg, 0.127 mmol) to give the title compound as an off-white solid. (HPLC: $t_R$ 2.40 min (Method A); M+H=421 MS-ES; $^1$H-NMR ($d_6$-DMSO, 400 MHz) 9.03-8.96 (m, 2H), 8.52 (s, 1H), 8.21-7.99 (m, 5H), 7.83-7.76 (m, 1H), 7.75-7.71 (m, 1H), 7.71-7.65 (m, 1H), 3.95 (s, 3H), 3.59 (s, 3H), 1.98 (s, 3H))

Example 39

3-[1-(1,3-Dimethyl-1H-pyrazol-4-yl)-3-methyl-2-oxo-2,3-dihydro-1H-imidazo[4,5-c]quinolin-8-yl]-N-methyl-benzenesulfonamide

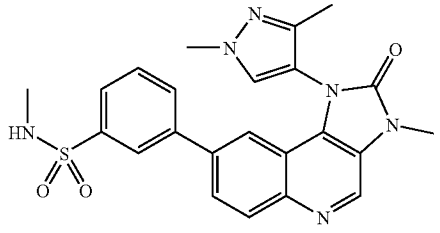

The title compound was synthesized in a similar manner as described for Example 1.1 using 8-bromo-1-(1,3-dimethyl-1H-pyrazol-4-yl)-3-methyl-1,3-dihydro-imidazo[4,5-c]quinolin-2-one (Intermediate A, 40 mg, 0.107 mmol) and methyl-3-boronobenzenesulfonamide (Combi-Blocks, San Diego, USA, 28 mg, 0.128 mmol) to give the title compound as a white solid. (HPLC: $t_R$ 2.47 min (Method A); M+H=463 MS-ES; $^1$H-NMR ($d_6$-DMSO, 400 MHz) 9.00 (s, 1H), 8.18-8.11 (m, 2H), 7.97-7.91 (m, 1H), 7.83-7.70 (m, 4H), 7.66-7.60 (m, 1H), 7.53-7.47 (m, 1H), 3.93 (s, 3H), 3.58 (s, 3H), 2.44 (s, 3H), 1.95 (s, 3H))

Example 40

1-(1,3-Dimethyl-1H-pyrazol-4-yl)-8-(3-methane-sulfonyl-phenyl)-3-methyl-1,3-dihydro-imidazo[4,5-c]quinolin-2-one

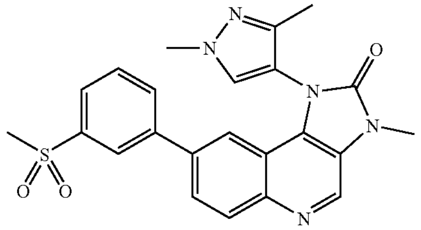

The title compound was synthesized in a similar manner as described for Example 1.1 using 8-bromo-1-(1,3-dimethyl-1H-pyrazol-4-yl)-3-methyl-1,3-dihydro-imidazo[4,5-c]quinolin-2-one (Intermediate A, 40 mg, 0.107 mmol) and (3-methylsulfonylphenyl)boronic acid (Combi-Blocks, San Diego, USA, 26 mg, 0.127 mmol) to give the title compound as a white solid. (HPLC: $t_R$ 2.45 min (Method A); M+H=448 MS-ES; $^1$H-NMR ($d_6$-DMSO, 400 MHz) 9.00 (s, 1H), 8.19-8.11 (m, 2H), 8.02-7.97 (m, 1H), 7.95-7.86 (m, 3H), 7.80-7.74 (m, 1H), 7.64-7.60 (m, 1H), 3.93 (s, 3H), 3.59 (s, 3H), 3.33-3.30 (3H), 1.94 (s, 3H))

Example 41

4-[1-(1,3-Dimethyl-1H-pyrazol-4-yl)-3-methyl-2-oxo-2,3-dihydro-1H-imidazo[4,5-c]quinolin-8-yl]-benzamide

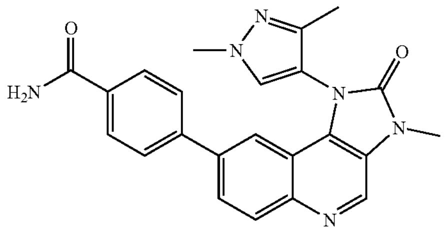 [SMILES: Cc1nn(C)cc1-n1c(=O)n(C)c2cnc3ccc(-c4ccc(C(N)=O)cc4)cc3c21]

The title compound was synthesized in a similar manner as described for Example 1.1 using 8-bromo-1-(1,3-dimethyl-1H-pyrazol-4-yl)-3-methyl-1,3-dihydro-imidazo[4,5-c]quinolin-2-one (Intermediate A, 40 mg, 0.107 mmol) and (3-methylsulfonylphenyl)boronic acid (Aldrich, Buchs, Switzerland, 21 mg, 0.130 mmol) to give the title compound as a white solid. (HPLC: $t_R$ 2.31 min (Method A); M+H=413 MS-ES; $^1$H-NMR ($d_6$-DMSO, 400 MHz) 8.98 (s, 1H), 8.19-8.15 (m, 1H), 8.14-8.08 (m, 1H), 8.07-8.01 (m, 1H), 7.99-7.93 (m, 3H), 7.61-7.52 (m, 3H), 7.47-7.39 (m, 1H), 3.94 (s, 3H), 3.58 (s, 3H), 1.95 (s, 3H))

Example 42

8-(6-Cyclopropylmethoxy-pyridin-3-yl)-1-(1,3-dimethyl-1H-pyrazol-4-yl)-3-methyl-1,3-dihydro-imidazo[4,5-c]quinolin-2-one

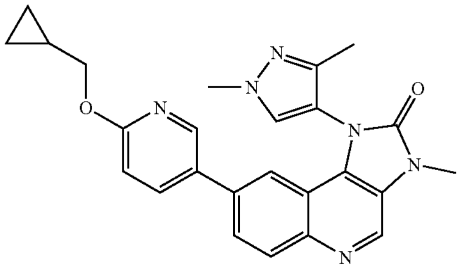 [SMILES: Cc1nn(C)cc1-n1c(=O)n(C)c2cnc3ccc(-c4ccc(OCC5CC5)nc4)cc3c21]

The title compound was synthesized in a similar manner as described for Example 1.1 using 8-bromo-1-(1,3-dimethyl-1H-pyrazol-4-yl)-3-methyl-1,3-dihydro-imidazo[4,5-c]quinolin-2-one (Intermediate A, 40 mg, 0.107 mmol) and 6-(cyclopropylmethoxy)pyridine-3-boronic acid pinacol ester (ABCR, Karlsruhe, Germany, 36 mg, 0.131 mmol) to give the title compound as a white solid. (HPLC: $t_R$ 2.88 min (Method A); M+H=441 MS-ES; $^1$H-NMR ($d_6$-DMSO, 400 MHz) 8.95 (s, 1H), 8.29-8.23 (m, 1H), 8.16-8.04 (m, 2H), 7.92-7.85 (m, 1H), 7.80-7.72 (m, 1H), 7.49-7.43 (m, 1H), 6.98-6.90 (m, 1H), 4.15-4.09 (m, 2H), 3.90 (s, 3H), 3.57 (s, 3H), 1.94 (s, 3H), 1.31-1.17 (m, 1H), 0.62-0.48 (m, 2H), 0.40-0.30 (m, 2H))

Example 43.1

4-[1-(1,3-Dimethyl-1H-pyrazol-4-yl)-3-methyl-2-oxo-2,3-dihydro-1H-imidazo[4,5-c]quinolin-8-yl]-N-methyl-benzamide

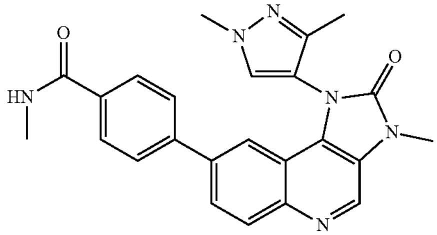 [SMILES: CNC(=O)c1ccc(-c2ccc3ncc4c(c3c2)n(-c2cn(C)nc2C)c(=O)n4C)cc1]

The title compound was synthesized in a similar manner as described for Example 1.1 using 8-bromo-1-(1,3-dimethyl-1H-pyrazol-4-yl)-3-methyl-1,3-dihydro-imidazo[4,5-c]quinolin-2-one (Intermediate A, 48 mg, 0.129 mmol) and 4-(N-methylaminocarbonyl)phenylboronic acid (ABCR, Karlsruhe, Germany, 27 mg, 0.153 mmol) to give the title compound as a white solid. (HPLC: $t_R$ 2.40 min (Method A); M+H=427 MS-ES; $^1$H-NMR ($d_6$-DMSO, 400 MHz) 8.97 (s, 1H), 8.54-8.48 (m, 1H), 8.19-8.15 (m, 1H), 8.13-8.07 (m, 1H), 7.98-7.89 (m, 3H), 7.61-7.53 (m, 3H), 3.94 (s, 3H), 3.57 (s, 3H), 2.79 (d, 3H), 1.95 (s, 3H))

The following example was synthesized in a similar manner as described for Example 1.1 using 4-(N-methylaminocarbonyl)phenylboronic acid and the specified intermediate.

| Example | Intermed. | structure | Name of the example | MS-ES (M + H) | HPLC $t_R$ (min) |
|---|---|---|---|---|---|
| 43.2 | K | 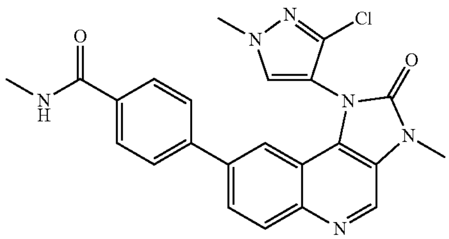 | 4-[1-(3-Chloro-1-methyl-1H-pyrazol-4-yl)-3-methyl-2-oxo-2,3-dihydro-1H-imidazo[4,5-c]quinolin-8-yl]-N-methyl-benzamide | 447 | 2.47 |

Example 44

1-(1,3-Dimethyl-1H-pyrazol-4-yl)-3-methyl-8-[3-(pyrrolidine-1-sulfonyl)-phenyl]-1,3-dihydro-imidazo[4,5-c]quinolin-2-one

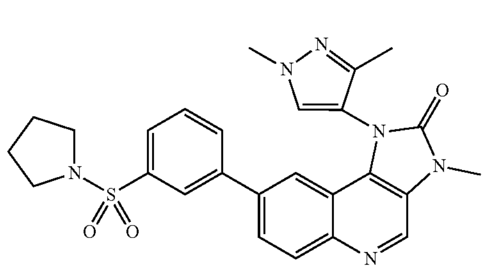 [SMILES: Cc1nn(C)cc1-n1c(=O)n(C)c2cnc3ccc(-c4cccc(S(=O)(=O)N5CCCC5)c4)cc3c21]

The title compound was synthesized in a similar manner as described for Example 1.1 using 8-bromo-1-(1,3-dimethyl-1H-pyrazol-4-yl)-3-methyl-1,3-dihydro-imidazo[4,5-c]quinolin-2-one (Intermediate A, 40 mg, 0.106 mmol) and 3-(pyrrolidinylsulfonyl)phenylboronic acid (Combi-Blocks, San Diego, USA, 33 mg, 0.129 mmol) to give the title compound as a white solid. (HPLC: $t_R$ 2.78 min (Method A); M+H=503 MS-ES; $^1$H-NMR ($d_6$-DMSO, 400 MHz) 9.00 (s, 1H), 8.16-8.11 (m, 2H), 8.02-7.96 (m, 1H), 7.94-7.89 (m, 1H), 7.83-7.78 (m, 1H), 7.77-7.71 (m, 2H), 7.69-7.65 (m, 1H), 3.92 (s, 3H), 3.58 (s, 3H), 3.21-3.14 (m, 4H), 1.95 (s, 3H), 1.70-1.63 (m, 4H))

Example 45.1

8-(5-Amino-pyridin-3-yl)-1-(1,3-dimethyl-1H-pyrazol-4-yl)-3-methyl-1,3-dihydro-imidazo[4,5-c]quinolin-2-one

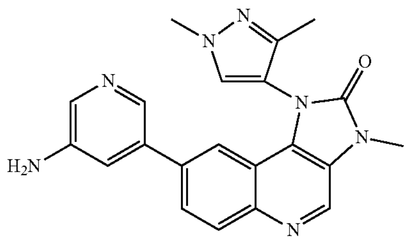 [SMILES: Cc1nn(C)cc1-n1c(=O)n(C)c2cnc3ccc(-c4cncc(N)c4)cc3c21]

The title compound was synthesized in a similar manner as described for Example 1.1 using 8-bromo-1-(1,3-dimethyl-1H-pyrazol-4-yl)-3-methyl-1,3-dihydro-imidazo[4,5-c]quinolin-2-one (Intermediate A, 40 mg, 0.106 mmol) and 3-aminopyridine-5-boronic acid pinacol ester (Apollo Scientific, Cheshire, United Kingdom, 29 mg, 0.132 mmol) to give the title compound as a white solid. (HPLC: $t_R$ 1.99 min (Method A); M+H=386 MS-ES; $^1$H-NMR ($d_6$-DMSO, 400 MHz) 8.97 (s, 1H), 8.16-8.05 (m, 2H), 7.94-7.89 (m, 1H), 7.81-7.74 (m, 2H), 7.54-7.48 (m, 1H), 7.04-6.98 (m, 1H), 5.45 (s, br, 2H), 3.91 (s, 3H), 3.57 (s, 3H), 1.95 (s, 3H))

The following examples were synthesized in a similar manner as described for Example 1.1 using 3-aminopyridine-5-boronic acid pinacol ester and the specified intermediate.

| Example | Intermed. | structure | Name of the example | MS-ES (M + H) | HPLC $t_R$ (min) |
|---|---|---|---|---|---|
| 45.2 | F | 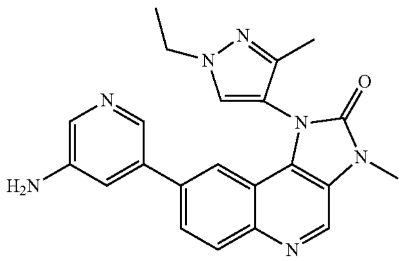 [SMILES: CCn1cc(-n2c(=O)n(C)c3cnc4ccc(-c5cncc(N)c5)cc4c32)c(C)n1] | 8-(5-Amino-pyridin-3-yl)-1-(1-ethyl-3-methyl-1H-pyrazol-4-yl)-3-methyl-1,3-dihydro-imidazo[4,5-c]quinolin-2-one | 400 | 1.98 |

-continued

| Example | Intermed. | structure | Name of the example | MS-ES (M + H) | HPLC $t_R$ (min) |
|---|---|---|---|---|---|
| 45.3 | A | 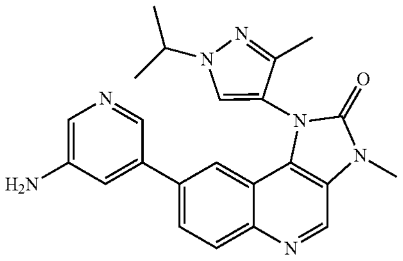 [SMILES: Cc1nn(C(C)C)cc1-n1c(=O)n(C)c2cnc3ccc(-c4cncc(N)c4)cc3c21] | 8-(5-Amino-pyridin-3-yl)-1-(1-isopropyl-3-methyl-1H-pyrazol-4-yl)-3-methyl-1,3-dihydro-imidazo[4,5-c]quinolin-2-one | 414 | 2.05 |

Example 46

3-[1-(1,3-Dimethyl-1H-pyrazol-4-yl)-3-methyl-2-oxo-2,3-dihydro-1H-imidazo[4,5-c]quinolin-8-yl]-benzamide

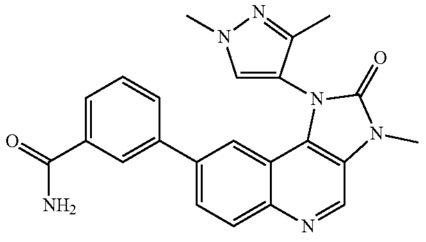 [SMILES: Cc1nn(C)cc1-n1c(=O)n(C)c2cnc3ccc(-c4cccc(C(N)=O)c4)cc3c21]

The title compound was synthesized in a similar manner as described for Example 1.1 using 8-bromo-1-(1,3-dimethyl-1H-pyrazol-4-yl)-3-methyl-1,3-dihydro-imidazo[4,5-c]quinolin-2-one (Intermediate A, 40 mg, 0.106 mmol) and benzamide-3-boronic acid (ABCR, Karlsruhe, Germany, 21 mg, 0.129 mmol) to give the title compound as a white solid. (HPLC: $t_R$ 2.34 min (Method A); M+H=413 MS-ES; $^1$H-NMR ($d_6$-DMSO, 400 MHz) 8.98 (s, 1H), 8.19-8.16 (m, 1H), 8.14-8.10 (m, 1H), 8.09-8.04 (m, 1H), 8.02-7.95 (m, 2H), 7.89-7.83 (m, 1H), 7.65-7.59 (m, 2H), 7.58-7.47 (m, 2H), 3.94 (s, 3H), 3.58 (s, 3H), 1.93 (s, 3H))

Example 47

N-{3-[1-(1,3-Dimethyl-1H-pyrazol-4-yl)-3-methyl-2-oxo-2,3-dihydro-1H-imidazo[4,5-c]quinolin-8-yl]-phenyl}-methanesulfonamide

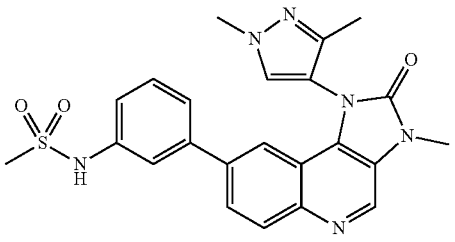

The title compound was synthesized in a similar manner as described for Example 1.1 using 8-bromo-1-(1,3-dimethyl-1H-pyrazol-4-yl)-3-methyl-1,3-dihydro-imidazo[4,5-c]quinolin-2-one (Intermediate A, 40 mg, 0.106 mmol) and 3-(Methanesulfonylamino)phenylboronic acid (ABCR, Karlsruhe, Germany, 28 mg, 0.126 mmol) to give the title compound as a white solid. (HPLC: $t_R$ 2.46 min (Method A); M+H=463 MS-ES; $^1$H-NMR ($d_6$-DMSO, 400 MHz) 9.88 (s, 1H), 8.97 (s, 1H), 8.12-8.10 (m, 2H), 7.82-7.79 (m, 1H), 7.56-7.54 (m, 1H), 7.45-7.41 (m, 1H), 7.36-7.34 (m, 1H), 7.21-7.16 (m, 2H), 3.90 (s, 3H), 3.58 (s, 3H), 3.03 (s, 3H), 1.96 (s, 3H))

Example 48

4-[1-(1,3-Dimethyl-1H-pyrazol-4-yl)-3-methyl-2-oxo-2,3-dihydro-1H-imidazo[4,5-c]quinolin-8-yl]-N,N-dimethyl-benzamide

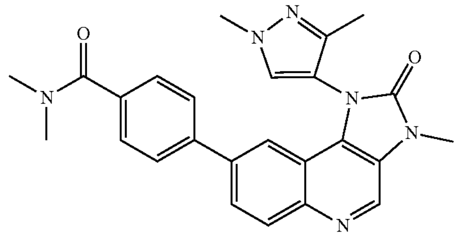

The title compound was synthesized in a similar manner as described for Example 1.1 using 8-bromo-1-(1,3-dimethyl-1H-pyrazol-4-yl)-3-methyl-1,3-dihydro-imidazo[4,5-c]quinolin-2-one (Intermediate A, 40 mg, 0.106 mmol) and 4-(N,N-dimethylaminocarbonyl)phenylboronic acid (Combi-Blocks, San Diego, USA, 25 mg, 0.126 mmol) to give the title compound as a white solid. (HPLC: $t_R$ 2.51 min (Method A); M+H=441 MS-ES; $^1$H-NMR ($d_6$-DMSO, 400 MHz) 8.97 (s, 1H), 8.17 (s, 1H), 8.12-8.10 (m, 1H), 7.96-7.93 (m, 1H), 7.59-7.58 (m, 1H), 7.55-7.50 (m, 4H), 3.93 (s, 3H), 3.58 (s, 3H), 2.99 (s, 3H), 2.94 (s, 3H), 1.95 (s, 3H))

Example 49

1-(1,3-Dimethyl-1H-pyrazol-4-yl)-3-methyl-8-(2-oxo-2,3-dihydro-1H-indol-5-yl)-1,3-dihydro-imidazo[4,5-c]quinolin-2-one

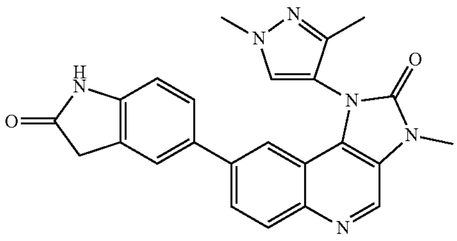 [SMILES: Cc1nn(C)cc1-n1c(=O)n(C)c2cnc3ccc(-c4ccc5c(c4)CC(=O)N5)cc3c21]

The title compound was synthesized in a similar manner as described for Example 1.1 using 8-bromo-1-(1,3-dimethyl-1H-pyrazol-4-yl)-3-methyl-1,3-dihydro-imidazo[4,5-c]quinolin-2-one (Intermediate A, 40 mg, 0.106 mmol) and 5-(4,4,5,5-tetramethyl-[1,3,2]dioxaborolan-2-yl)-1,3-dihydro-indol-2-one (Combi-Blocks, San Diego, USA, 35 mg, 0.128 mmol) to give the title compound as an off-white solid. (HPLC: $t_R$ 2.40 min (Method A); M+H=425 MS-ES; $^1$H-NMR ($d_6$-DMSO, 400 MHz) 10.52 (s, 1H), 8.92 (s, 1H), 8.17 (s, 1H), 8.05-8.03 (m, 1H), 7.86-7.83 (m, 1H), 7.46 (s, 1H), 7.33-7.29 (m, 2H), 6.90-6.88 (m, 1H), 3.94 (s, 3H), 3.57 (s, 3H), 3.54 (s, 2H), 1.93 (s, 3H))

Example 50

1-(1,3-Dimethyl-1H-pyrazol-4-yl)-3-methyl-8-(1-methyl-2,3-dihydro-1H-indol-5-yl)-1,3-dihydro-imidazo[4,5-c]quinolin-2-one

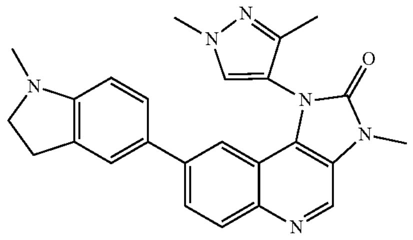 [SMILES: Cc1nn(C)cc1-n1c(=O)n(C)c2cnc3ccc(-c4ccc5c(c4)CCN5C)cc3c21]

The title compound was synthesized in a similar manner as described for Example 1.1 using 8-bromo-1-(1,3-dimethyl-1H-pyrazol-4-yl)-3-methyl-1,3-dihydro-imidazo[4,5-c]quinolin-2-one (Intermediate A, 40 mg, 0.106 mmol) and 1-methylindoline-5-boronic acid pinacol ester (Maybridge, Basel, Switzerland, 34 mg, 0.127 mmol) to give the title compound as a yellow solid. (HPLC: $t_R$ 2.52 min (Method A); M+H=425 MS-ES; $^1$H-NMR ($d_6$-DMSO, 400 MHz) 8.87 (s, 1H), 8.16 (s, 1H), 8.00-7.97 (m, 1H), 7.83-7.81 (m, 1H), 7.41-7.40 (m, 1H), 7.20-7.17 (m, 1H), 7.14-7.13 (m, 1H), 6.57-6.55 (m, 1H), 3.94 (s, 3H), 3.56 (s, 3H), 3.33-3.29 (m, 2H), 2.92 (t, 2H), 2.73 (s, 3H), 1.94 (s, 3H))

Example 51.1

1-(1,3-Dimethyl-1H-pyrazol-4-yl)-3-methyl-8-(4-pyrazol-1-yl-phenyl)-1,3-dihydro-imidazo[4,5-c]quinolin-2-one

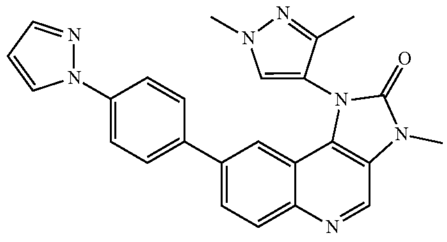 [SMILES: Cc1nn(C)cc1-n1c(=O)n(C)c2cnc3ccc(-c4ccc(-n5cccn5)cc4)cc3c21]

The title compound was synthesized in a similar manner as described for Example 1.1 using 8-bromo-1-(1,3-dimethyl-1H-pyrazol-4-yl)-3-methyl-1,3-dihydro-imidazo[4,5-c]quinolin-2-one (Intermediate A, 40 mg, 0.106 mmol) and 4-(1H-pyrazol-1-yl)phenylboronic acid (Combi-Blocks, San Diego, USA, 24 mg, 0.126 mmol) to give the title compound as a white solid. (HPLC: $t_R$ 2.79 min (Method A); M+H=436 MS-ES; $^1$H-NMR ($d_6$-DMSO, 400 MHz) 8.96 (s, 1H), 8.60-8.56 (m, 1H), 8.19-8.15 (m, 1H), 8.13-8.07 (m, 1H), 7.99-7.93 (m, 3H), 7.80-7.75 (m, 1H), 7.63-7.56 (m, 3H), 6.59-6.53 (m, 1H), 3.95 (s, 31-1), 3.57 (s, 3H), 1.97 (s, 3H))

The following examples were synthesized in a similar manner as described for Example 1.1 using 4-(1H-pyrazol-1-yl)phenylboronic acid and the specified intermediate.

| Example | Intermed. | structure | Name of the example | MS-ES (M + H) | HPLC $t_R$ (min) |
|---|---|---|---|---|---|
| 51.2 | L | 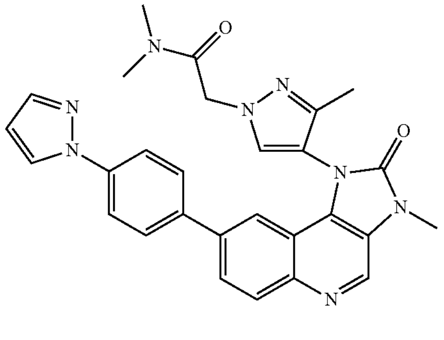 [SMILES: Cc1nn(CC(=O)N(C)C)cc1-n1c(=O)n(C)c2cnc3ccc(-c4ccc(-n5cccn5)cc4)cc3c21] | N,N-Dimethyl-2-{3-methyl-4-[3-methyl-2-oxo-8-(4-pyrazol-1-yl-pheny-2,3-dihydro-imidazo[4,5-c]quinolin-1-yl]-pyrazol-1-yl}-acetamide | 507 | 2.72 |
| 51.3 | F | 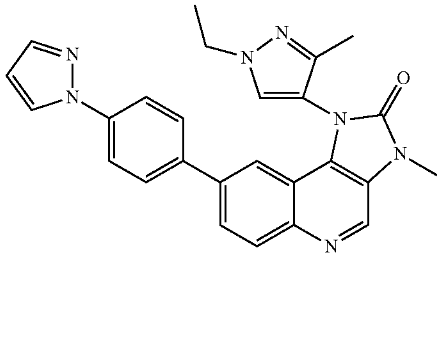 [SMILES: CCn1cc(-n2c(=O)n(C)c3cnc4ccc(-c5ccc(-n6cccn6)cc5)cc4c32)c(C)n1] | 1-(1-Ethyl-3-methyl-1H-pyrazol-4-yl)-3-methyl-8-(4-pyrazol-1-yl-pheny-1,3-dihydro-imidazo[4,5-c]quinolin-2-one | 451 | 2.76 |

-continued

| Example | Intermed. | structure | Name of the example | MS-ES (M + H) | HPLC $t_R$ (min) |
|---|---|---|---|---|---|
| 51.4 | O | 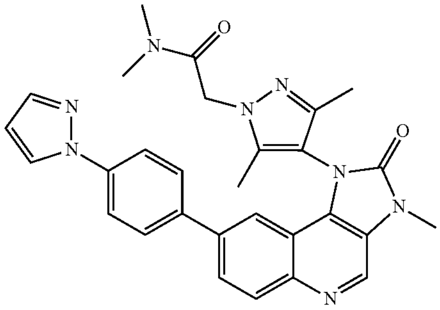 [SMILES: Cc1nn(CC(=O)N(C)C)c(C)c1-n1c(=O)n(C)c2cnc3ccc(-c4ccc(-n5cccn5)cc4)cc3c21] | 2-{3,5-Dimethyl-4-[3-methyl-2-oxo-8-(4-pyrazol-1-yl-phenyl)-2,3-dihydro-imidazo[4,5-c]quinolin-1-yl]-pyrazol-1-yl}-N,N-dimethyl-acetamide | 521 | 2.76 |
| 51.5 | N | 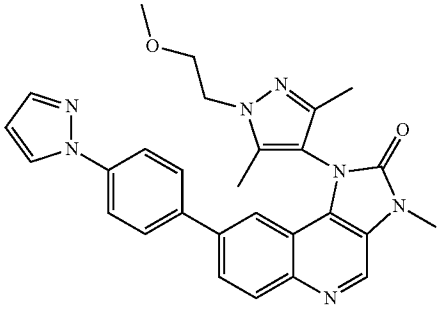 [SMILES: COCCn1nc(C)c(-n2c(=O)n(C)c3cnc4ccc(-c5ccc(-n6cccn6)cc5)cc4c32)c1C] | 2-{3,5-Dimethyl-4-[3-methyl-2-oxo-8-(4-pyrazol-1-yl-phenyl)-2,3-dihydro-imidazo[4,5-c]quinolin-1-yl]-pyrazol-1-yl}-N,N-dimethyl-acetamide | 494 | 2.83 |
| 51.6 | P | 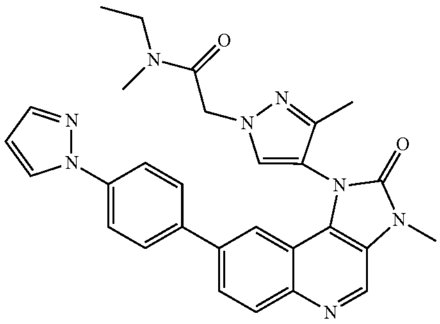 [SMILES: CCN(C)C(=O)Cn1cc(-n2c(=O)n(C)c3cnc4ccc(-c5ccc(-n6cccn6)cc5)cc4c32)c(C)n1] | N-Ethyl-N-methyl-2-{3-methyl-4-[3-methyl-2-oxo-8-(4-pyrazol-1-yl-phenyl)-2,3-dihydro-imidazo[4,5-c]quinolin-1-yl]-pyrazol-1-yl}-acetamide | 521 | 2.83 |

Example 52

1-(1,3-Dimethyl-1H-pyrazol-4-yl)-8-(2-ethoxy-pyrimidin-5-yl)-3-methyl-1,3-dihydro-imidazo[4,5-c]quinolin-2-one

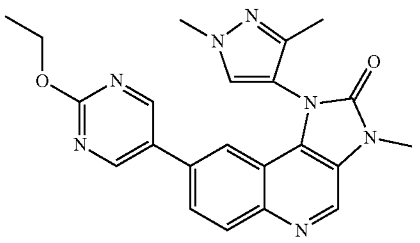 [SMILES: CCOc1ncc(-c2ccc3ncc4c(c3c2)n(-c2cn(C)nc2C)c(=O)n4C)cn1]

The title compound was synthesized in a similar manner as described for Example 1.1 using 8-bromo-1-(1,3-dimethyl-1H-pyrazol-4-yl)-3-methyl-1,3-dihydro-imidazo[4,5-c]quinolin-2-one (Intermediate A, 40 mg, 0.106 mmol) and 2-ethoxypyrimidine-5-boronic acid (Synthonix, Wake Forest, USA, 22 mg, 0.130 mmol) to give the title compound as a white solid. (HPLC: $t_R$ 2.51 min (Method A); M+H=416 MS-ES; $^1$H-NMR ($d_6$-DMSO, 400 MHz) 8.98 (s, 1H), 8.73-8.67 (m, 2H), 8.16-8.09 (m, 2H), 7.98-7.91 (m, 1H), 7.51-7.46 (m, 1H), 4.39 (q, 2H), 3.89 (s, 3H), 3.57 (s, 3H), 1.96 (s, 3H), 1.35 (t, 3H))

Example 53.1

3-[1-(1,3-Dimethyl-1H-pyrazol-4-yl)-3-methyl-2-oxo-2,3-dihydro-1H-imidazo[4,5-c]quinolin-8-yl]-N,N-dimethyl-benzenesulfonamide

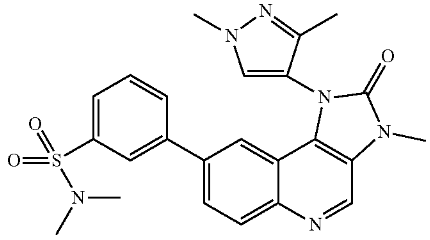 [SMILES: Cc1nn(C)cc1-n1c(=O)n(C)c2cnc3ccc(-c4cccc(S(=O)(=O)N(C)C)c4)cc3c21]

The title compound was synthesized in a similar manner as described for Example 1.1 using 8-bromo-1-(1,3-dimethyl-1H-pyrazol-4-yl)-3-methyl-1,3-dihydro-imidazo[4,5-c]quinolin-2-one (Intermediate A, 40 mg, 0.106 mmol) and 3-(N,N-dimethylsulfonamide)phenylboronic acid (Combi-Blocks, San Diego, USA, 20 mg, 0.128 mmol) to give the title compound as a white solid. (HPLC: $t_R$ 2.66 min (Method A); M+H=477 MS-ES; $^1$H-NMR ($d_6$-DMSO, 400 MHz) 8.97 (s, 1H), 8.17-8.09 (m, 2H), 8.01-7.90 (m, 2H), 7.80-7.72 (m, 2H), 7.71-7.64 (m, 2H), 3.91 (s, 3H), 3.58 (s, 3H), 2.66 (s, 6H), 1.96 (s, 3H))

The following example was synthesized in a similar manner as described for Example 1.1 using 3-(N,N-dimethylsulfonamide)phenylboronic acid and the specified intermediate.

| Example | Intermed. | structure | Name of the example | MS-ES (M + H) | HPLC $t_R$ (min) |
|---|---|---|---|---|---|
| 53.2 | H | 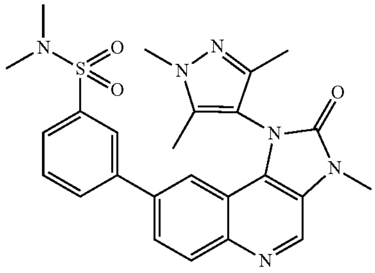 | N,N-Dimethyl-3-[3-methyl-2-oxo-1-(1,3,5-trimethyl-1H-pyrazol-4-yl)-2,3-dihydro-1H-imidazo[4,5-c]quinolin-8-yl]-benzenesulfonamide | 491 | 2.70 |

Example 54.1

1-(1,3-Dimethyl-1H-pyrazol-4-yl)-8-(5-methoxymethyl-pyridin-3-yl)-3-methyl-1,3-dihydro-imidazo[4,5-c]quinolin-2-one

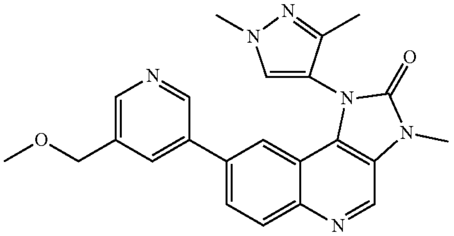

The title compound was synthesized in a similar manner as described for Example 1.1 using 8-bromo-1-(1,3-dimethyl-1H-pyrazol-4-yl)-3-methyl-1,3-dihydro-imidazo[4,5-c]quinolin-2-one (Intermediate A, 40 mg, 0.107 mmol) and 5-(methoxymethyl)pyridine-3-boronic acid pinacol ester (PepTeck, Burlington, USA, 32 mg, 0.128 mmol) to give the title compound as a white solid. (HPLC: $t_R$ 2.08 min (Method A); M+H=415 MS-ES; $^1$H-NMR ($d_6$-DMSO, 400 MHz) 9.01 (s, 1H), 8.70-8.67 (m, 1H), 8.56-8.54 (m, 1H), 8.19-8.13 (m, 2H), 8.02-7.98 (m, 1H), 7.82-7.80 (m, 1H), 7.62-7.59 (m, 1H), 4.53 (s, 2H), 3.94 (s, 3H), 3.60 (s, 3H), 3.37 (s, 3H), 1.97 (s, 3H))

The following example was synthesized in a similar manner as described for Example 1.1 using 5-(methoxymethyl)pyridine-3-boronic acid pinacol ester and the specified intermediate.

| Example | Intermed. | structure | Name of the example | MS-ES (M + H) | HPLC $t_R$ (min) |
|---|---|---|---|---|---|
| 54.2 | K | 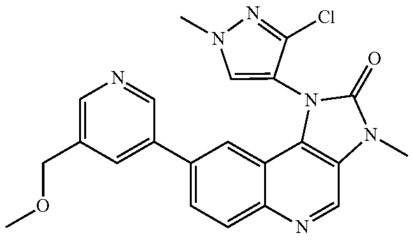 | 1-(3-Chloro-1-methyl-1H-pyrazol-4-yl)-8-(5-methoxymethyl-pyridin-3-yl)-3-methyl-1,3-dihydro-imidazo [4,5-c]quinolin-2-one | 435 | 2.25 |

Example 55

1-(1,3-Dimethyl-1H-pyrazol-4-yl)-3-methyl-8-(6-propoxy-pyridin-3-yl)-1,3-dihydro-imidazo[4,5-c] quinolin-2-one

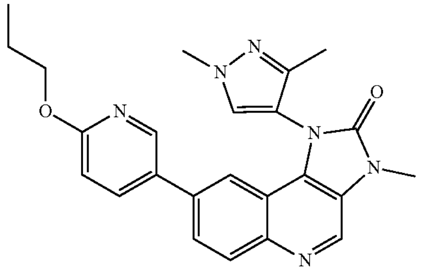 [SMILES: CCCOc1ccc(-c2ccc3ncc4c(c3c2)n(-c2cn(C)nc2C)c(=O)n4C)cn1]

The title compound was synthesized in a similar manner as described for Example 1.1 using 8-bromo-1-(1,3-dimethyl-1H-pyrazol-4-yl)-3-methyl-1,3-dihydro-imidazo[4,5-c] quinolin-2-one (Intermediate A) and 2-propoxy-5-(4,4,5,5-tetramethyl-[1,3,2]dioxaborolan-2-yl)-pyridine (stage 55.1.1) to give the title compound as a white solid. (HPLC: $t_R$ 2.87 min (Method A); M+H=429 MS-ES; $^1$H-NMR ($d_6$-DMSO, 400 MHz) 8.95 (s, 1H), 8.28 (s, 1H), 8.15-8.11 (m, 1H), 8.11-8.05 (m, 1H), 7.92-7.86 (m, 1H), 7.79-7.73 (m, 1H), 7.50-7.45 (m, 1H), 6.95-6.89 (m, 1H), 4.24 (t, 2H), 3.91 (s, 3H), 3.57 (s, 3H), 1.95 (s, 3H), 1.78-1.68 (m, 2H), 0.98 (t, 3H))

Stage 55.1.1 2-Propoxy-5-(4,4,5,5-tetramethyl-[1,3,2]dioxaborolan-2-yl)-pyridine

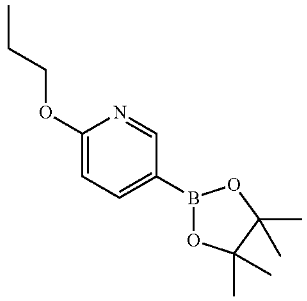 [SMILES: CCCOc1ccc(B2OC(C)(C)C(C)(C)O2)cn1]

The title compound was synthesized in a similar manner as described for Stage 5.1.1 using 5-bromo-2-propoxypyridine (Combi-Blocks, San Diego, USA) to give the title compound as a brown oil. (HPLC: $t_R$ 2.00 min (Method A); M+H=264 MS-ES).

Example 56.1

1-(1,3-Dimethyl-1H-pyrazol-4-yl)-8-(5-ethoxy-pyridin-3-yl)-3-methyl-1,3-dihydro-imidazo[4,5-c] quinolin-2-one

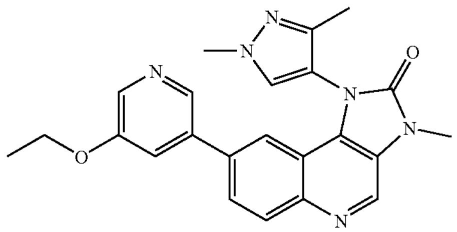 [SMILES: CCOc1cncc(-c2ccc3ncc4c(c3c2)n(-c2cn(C)nc2C)c(=O)n4C)c1]

The title compound was synthesized in a similar manner as described for Example 1.1 using 8-bromo-1-(1,3-dimethyl-1H-pyrazol-4-yl)-3-methyl-1,3-dihydro-imidazo[4,5-c] quinolin-2-one (Intermediate A) and 3-ethoxy-5-(4,4,5,5-tetramethyl-[1,3,2]dioxaborolan-2-yl)-pyridine (stage 56.1.1) to give the title compound as a white solid. (HPLC: $t_R$ 2.28 min (Method A); M+H=415 MS-ES; $^1$H-NMR ($d_6$-DMSO, 400 MHz) 8.98 (s, 1H), 8.34-8.24 (m, 2H), 8.16-8.08 (m, 2H), 8.02-7.96 (m, 1H), 7.61-7.57 (m, 1H), 7.40-7.34 (m, 1H), 4.17 (q, 2H), 3.89 (s, 3H), 3.57 (s, 3H), 1.96 (s, 3H), 1.40 (t, 3H))

Stage 56.1.1 3-Ethoxy-5-(4,4,5,5-tetramethyl-[1,3,2] dioxaborolan-2-yl)-pyridine

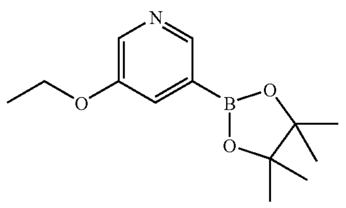 [SMILES: CCOc1cncc(B2OC(C)(C)C(C)(C)O2)c1]

The title compound was synthesized in a similar manner as described for Stage 5.1.1 using 3-bromo-5-ethoxypyridine (SynChem, Des Plaines, USA) to give the title compound as a brown oil. (HPLC: $t_R$ 2.45 min (Method A); M+H=250 MS-ES).

The following examples were synthesized in a similar manner as described for Example 1.1 using 3-ethoxy-5-(4,4,5,5-tetramethyl-[1,3,2]dioxaborolan-2-yl)-pyridine and the specified intermediate.

| Example | Intermed. | structure | Name of the example | MS-ES (M + H) | HPLC $t_R$ (min) |
|---|---|---|---|---|---|
| 56.2 | L | 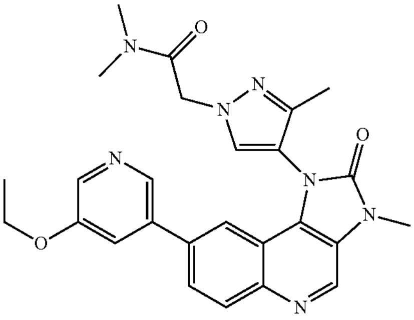 [SMILES: CCOc1cncc(-c2ccc3ncc4c(c3c2)n(-c2cn(CC(=O)N(C)C)nc2C)c(=O)n4C)c1] | 2-{4-[8-(5-Ethoxy-pyridin-3-yl)-3-methyl-2-oxo-2,3-dihydro-imidazo[4,5-c]quinolin-1-yl]-3-methyl-pyrazol-1-yl}-N,N-dimethyl-acetamide | 486 | 2.30 |
| 56.3 | H | 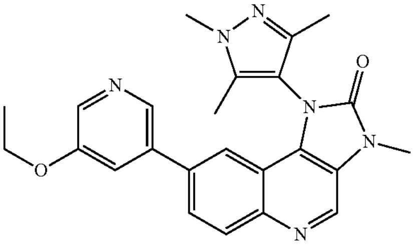 [SMILES: CCOc1cncc(-c2ccc3ncc4c(c3c2)n(-c2c(C)nn(C)c2C)c(=O)n4C)c1] | 8-(5-Ethoxy-pyridin-3-yl)-3-methyl-1-(1,3,5-trimethyl-1H-pyrazol-4-yl)-1,3-dihydro-imidazo[4,5-c]quinolin-2-one | 429 | .25 |
| 56.4 | K | 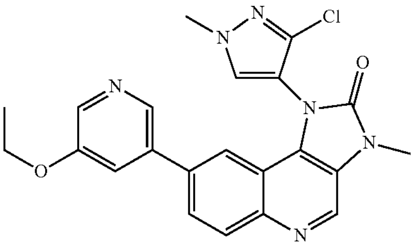 [SMILES: CCOc1cncc(-c2ccc3ncc4c(c3c2)n(-c2cn(C)nc2Cl)c(=O)n4C)c1] | 1-(3-Chloro-1-methyl-1H-pyrazol-4-yl)-8-(5-ethoxy-pyridin-3-yl)-3-methyl-1,3-dihydro-imidazo[4,5-c]quinolin-2-one | 435 | 2.0 |
| 56.5 | I | 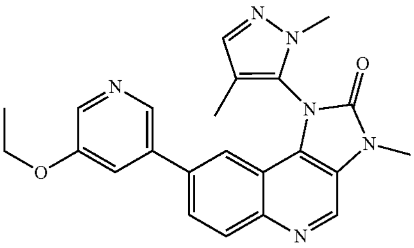 [SMILES: CCOc1cncc(-c2ccc3ncc4c(c3c2)n(-c2c(C)cnn2C)c(=O)n4C)c1] | 1-(2,4-Dimethyl-2H-pyrazol-3-yl)-8-(5-ethoxy-pyridin-3-yl)-3-methyl-1,3-dihydro-imidazo[4,5-c]quinolin-2-one | 415 | 2.36 |

Example 57

1-(1,3-Dimethyl-1H-pyrazol-4-yl)-8-(3-ethoxy-phenyl)-3-methyl-1,3-dihydro-imidazo[4,5-c]quinolin-2-one

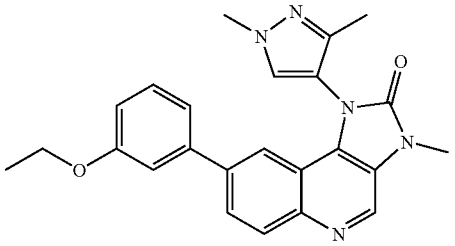 [SMILES: CCOc1cccc(-c2ccc3ncc4c(c3c2)n(-c2cn(C)nc2C)c(=O)n4C)c1]

The title compound was synthesized in a similar manner as described for Example 1.1 using 8-bromo-1-(1,3-dimethyl-1H-pyrazol-4-yl)-3-methyl-1,3-dihydro-imidazo[4,5-c]quinolin-2-one (Intermediate A, 40 mg, 0.107 mmol) and 3-ethoxyphenylboronic acid (Aldrich, Buchs, Switzerland, 21.4 mg, 0.129 mmol) to give the title compound as a white solid. (HPLC: $t_R$ 2.84 min (Method A); M+H=414 MS-ES; $^1$H-NMR ($d_6$-DMSO, 400 MHz) 8.96 (s, 1H), 8.16 (s, 1H), 8.09-8.06 (m, 1H), 7.94-7.91 (m, 1H), 7.57-7.59 (m, 1H), 7.39-7.35 (m, 1H), 7.12-6.92 (m, 3H), 4.09 (q, 2H), 3.92 (s, 3H), 3.58 (s, 3H), 1.96 (s, 3H), 1.37 (t, 3H))

Example 58.1

1-(1,3-Dimethyl-1H-pyrazol-4-yl)-8-(5-isopropoxy-pyridin-3-yl)-3-methyl-1,3-dihydro-imidazo[4,5-c]quinolin-2-one

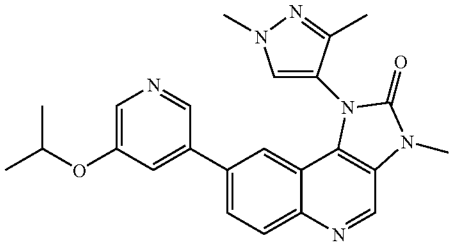 [SMILES: Cc1nn(C)cc1-n1c(=O)n(C)c2cnc3ccc(-c4cncc(OC(C)C)c4)cc3c21]

The title compound was synthesized in a similar manner as described for Example 1.1 using 8-bromo-1-(1,3-dimethyl-1H-pyrazol-4-yl)-3-methyl-1,3-dihydro-imidazo[4,5-c]quinolin-2-one (Intermediate A) and 3-isopropoxy-5-(4,4,5,5-tetramethyl-[1,3,2]dioxaborolan-2-yl)-pyridine (Stage 58.1.1) to give the title compound as a white solid. (HPLC: $t_R$ 2.30 min (Method A); M+H=429 MS-ES; $^1$H-NMR ($d_6$-DMSO, 400 MHz) 8.99 (s, 1H), 8.33-8.28 (m, 1H), 8.28-8.23 (m, 1H), 8.16-8.08 (m, 2H), 8.02-7.96 (m, 1H), 7.61-7.55 (m, 1H), 7.38-7.33 (m, 1H), 4.84-4.73 (m, 1H), 3.89 (s, 3H), 3.58 (s, 3H), 1.96 (s, 3H), 1.33 (d, 6H))

Stage 58.1.1 3-Isopropoxy-5-(4,4,5,5-tetramethyl-[1,3,2]dioxaborolan-2-yl)-pyridine

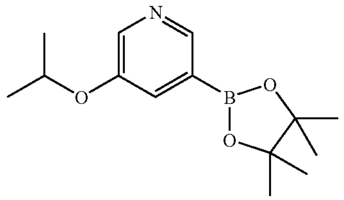 [SMILES: CC(C)Oc1cncc(B2OC(C)(C)C(C)(C)O2)c1]

The title compound was synthesized in a similar manner as described for Stage 5.1.1 using 3-bromo-5-isopropoxypyridine (Stage 58.1.2) to give the title compound as a brown sticky solid. (HPLC: $t_R$ 2.12 min (Method A); M+H=264 MS-ES).

Stage 58.1.2 3-Bromo-5-isopropoxypyridine

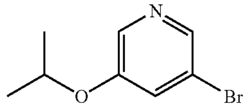

The title compound was synthesized in a similar manner as described for Stage 29.1.1 using 3-bromo-5-hydroxypyridine (Aldrich, Buchs, Switzerland) and isopropanol (Merck, Dietikon, Switzerland) to give the title compound as a colorless oil. (HPLC: $t_R$ 2.92 min (Method A); M+H=216, 218 MS-ES).

The following examples were synthesized in a similar manner as described for Example 1.1 using 3-isopropoxy-5-(4,4,5,5-tetramethyl-[1,3,2]dioxaborolan-2-yl)-pyridine (Stage 58.1.1) and the specified intermediate.

| Example | Intermed. | structure | Name of the example | MS-ES (M + H) | HPLC $t_R$ (min) |
|---|---|---|---|---|---|
| 58.2 | K | 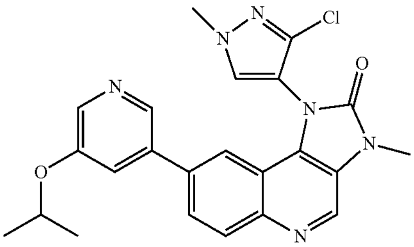 [SMILES: CC(C)Oc1cncc(-c2ccc3ncc4c(c3c2)n(-c2cn(C)nc2Cl)c(=O)n4C)c1] | 1-(3-Chloro-1-methyl-1H-pyrazol-4-yl)-8-(5-isopropoxy-pyridin-3-yl)-3-methyl-1,3-dihydro-imidazo[4,5-c]quinolin-2-one | 449 | 2.51 |
| 58.3 | I | 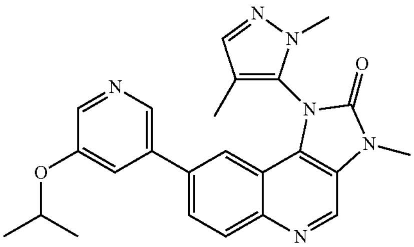 [SMILES: Cc1cnn(C)c1-n1c(=O)n(C)c2cnc3ccc(-c4cncc(OC(C)C)c4)cc3c21] | 1-(2,4-Dimethyl-2H-pyrazol-3-yl)-8-(5-isopropoxy-pyridin-3-yl)-3-methyl-1,3-dihydro-imidazo[4,5-c]quinolin-2-one | 429 | 2.47 |
| 58.4 | F | 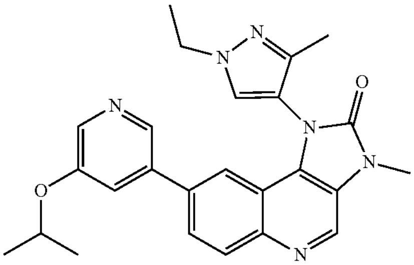 [SMILES: CCn1cc(-n2c(=O)n(C)c3cnc4ccc(-c5cncc(OC(C)C)c5)cc4c32)c(C)n1] | 1-(1-Ethyl-3-methyl-1H-pyrazol-4-yl)-8-(5-isopropoxy-pyridin-3-yl)-3-methyl-1,3-dihydro-imidazo[4,5-c]quinolin-2-one | 443 | 2.38 |
| 58.5 | P | 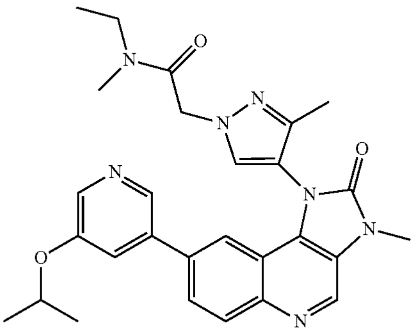 [SMILES: CCN(C)C(=O)Cn1cc(-n2c(=O)n(C)c3cnc4ccc(-c5cncc(OC(C)C)c5)cc4c32)c(C)n1] | N-Ethyl-2-{4-[8-(5-isopropoxy-pyridin-3-yl)-3-methyl-2-oxo-2,3-dihydro-imidazo[4,5-c]quinolin-1-yl]-3-methyl-pyrazol-1-yl}-N-methyl-acetamide | 514 | 2.41 |

Example 59.1

1-(1,3-Dimethyl-1H-pyrazol-4-yl)-8-[5-(2-methoxy-ethoxy)-pyridin-3-yl]-3-methyl-1,3-dihydro-imidazo[4,5-c]quinolin-2-one

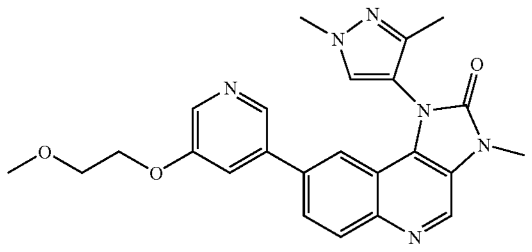

The title compound was synthesized in a similar manner as described for Example 1.1 using 8-bromo-1-(1,3-dimethyl-1H-pyrazol-4-yl)-3-methyl-1,3-dihydro-imidazo[4,5-c]quinolin-2-one (Intermediate A) and 3-(2-methoxy-ethoxy)-5-(4,4,5,5-tetramethyl-[1,3,2]dioxaborolan-2-yl)-pyridine (Stage 59.1.1) to give the title compound as a white solid. (HPLC: $t_R$ 2.17 min (Method A); M+H=445 MS-ES; $^1$H-NMR ($d_6$-DMSO, 400 MHz) 8.99 (s, 1H), 8.35-8.27 (m, 2H), 8.18-8.08 (m, 2H), 8.04-7.97 (m, 1H), 7.61-7.56 (m, 1H), 7.44-7.38 (m, 1H), 4.25 (t, 2H), 3.89 (s, 3H), 3.71 (t, 2H), 3.57 (s, 3H), 3.31 (s, 3H), 1.96 (s, 3H))

Stage 59.1.1 3-(2-Methoxy-ethoxy)-5-(4,4,5,5-tetramethyl-[1,3,2]dioxaborolan-2-yl)-pyridine

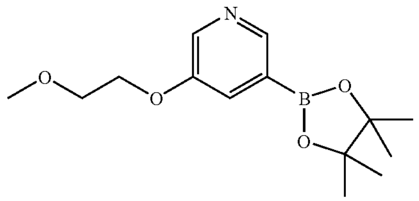

The title compound was synthesized in a similar manner as described for Stage 5.1.1 using 3-bromo-5-(2-methoxy-ethoxy)-pyridine (Stage 59.1.2) to give the title compound as a brown oil. (HPLC: $t_R$ 2.10 min (Method A)).

Stage 59.1.2

3-Bromo-5-(2-methoxy-ethoxy)-pyridine

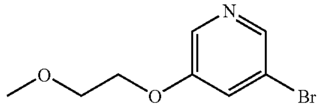

A mixture of 3-bromo-5-hydroxypyridine (Aldrich, Buchs, Switzerland, 611 mg, 3.51 mmol), potassium carbonate (971 mg, 7.02 mmol) and 2-bromoethyl methyl ether (537 mg, 3.86 mmol) in 30 ml DMF was stirred for 14 h at rt and for 2 h at 80° C. The reaction mixture was quenched with water and extracted with EtOAc (2×). The organic layers were washed with brine (3×), dried over $Na_2SO_4$, filtered and evaporated. The residue was purified by flash chromatography (dichloromethane/MeOH 0% to 3%) to give the title compound as an oil. (HPLC: $t_R$ 2.38 min (Method A); M+H=232, 234 MS-ES).

The following example was synthesized in a similar manner as described for Example 1.1 using 3-(2-methoxy-ethoxy)-5-(4,4,5,5-tetramethyl-[1,3,2]dioxaborolan-2-yl)-pyridine (Stage 59.1.1) and the specified intermediate.

| Example | Intermed. | structure | Name of the example | MS-ES (M + H) | HPLC $t_R$ (min) |
|---|---|---|---|---|---|
| 59.2 | H | 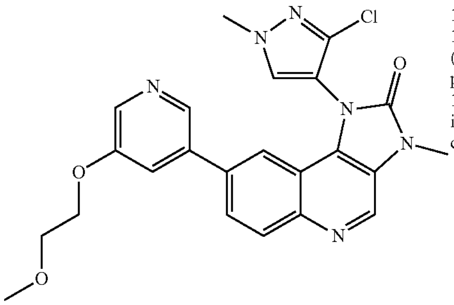 | 1-(3-Chloro-1-methyl-1H-pyrazol-4-yl)-8-[5-(2-methoxy-ethoxy)-pyridin-3-yl]-3-methyl-1,3-dihydro-imidazo[4,5-c]quinolin-2-one | 465 | 2.33 |

Example 60.1

8-(5-Cyclobutoxy-pyridin-3-yl)-1-(1,3-dimethyl-1H-pyrazol-4-yl)-3-methyl-1,3-dihydro-imidazo[4,5-c]quinolin-2-one

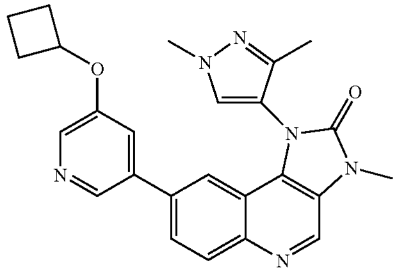 [SMILES: Cc1nn(C)cc1-n1c(=O)n(C)c2cnc3ccc(-c4cncc(OC5CCC5)c4)cc3c21]

The title compound was synthesized in a similar manner as described for Example 1.1 using 8-bromo-1-(1,3-dimethyl- 1H-pyrazol-4-yl)-3-methyl-1,3-dihydro-imidazo[4,5-c]quinolin-2-one (Intermediate A) and 3-cyclobutoxy-5-(4,4,5,5-tetramethyl-[1,3,2]dioxaborolan-2-yl)-pyridine (Stage 60.1.1) to give the title compound as a white solid. (HPLC: $t_R$ 2.43 min (Method A); M+H=441 MS-ES; $^1$H-NMR ($d_6$-DMSO, 400 MHz) 9.00 (s, 1H), 8.32-8.30 (m, 1H), 8.24-8.20 (m, 1H), 8.15 (s, 1H), 8.14-8.10 (m, 1H), 8.00-7.95 (m, 1H), 7.58-7.56 (m, 1H), 7.26-7.24 (m, 1H), 4.84 (qt, 1H), 3.91 (s, 3H), 3.58 (s, 3H), 2.53-2.45 (m, 2H), 2.15-2.00 (m, 2H), 1.96 (s, 3H), 1.88-1.66 (m, 2H))

Stage 60.1.1 3-Cyclobutoxy-5-(4,4,5,5-tetramethyl-[1,3,2]dioxaborolan-2-yl)-pyridine

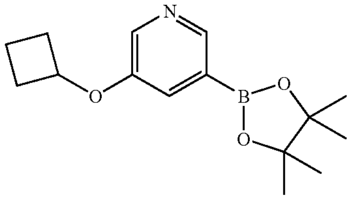 [SMILES: CC1(C)OB(c2cncc(OC3CCC3)c2)OC1(C)C]

The title compound was synthesized in a similar manner as described for Stage 58.1.1-2 using cyclobutanol (Aldrich, Buchs, Switzerland) to give the title compound as a brown oil. (HPLC: $t_R$ 2.25 min (Method A); M+H=276 MS-ES).

The following example was synthesized in a similar manner as described for Example 1.1 using 3-cyclobutoxy-5-(4,4,5,5-tetramethyl-[1,3,2]dioxaborolan-2-yl)-pyridine (Stage 60.1.1) and the specified intermediate.

Example 61

8-(5-Cyclopropylmethoxy-pyridin-3-yl)-1-(1,3-dimethyl-1H-pyrazol-4-yl)-3-methyl-1,3-dihydro-imidazo[4,5-c]quinolin-2-one

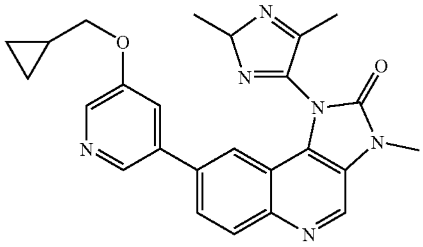

The title compound was synthesized in a similar manner as described for Example 1.1 using 8-bromo-1-(1,3-dimethyl-1H-pyrazol-4-yl)-3-methyl-1,3-dihydro-imidazo[4,5-c]quinolin-2-one (Intermediate A) and 3-cyclobutoxy-5-(4,4,5,5-tetramethyl-[1,3,2]dioxaborolan-2-yl)-pyridine (Stage 60.1.1) to give the title compound as a white solid. (HPLC: $t_R$ 2.39 min (Method A); M+H=441 MS-ES; $^1$H-NMR ($d_6$-DMSO, 400 MHz) 8.99-8.98 (m, 1H), 8.32-8.27 (m, 2H), 8.15 (s, 1H), 8.13-8.09 (m, 1H), 8.02-7.97 (m, 1H), 7.59-7.57

| Example | Intermed. | structure | Name of the example | MS-ES (M + H) | HPLC $t_R$ (min) |
|---|---|---|---|---|---|
| 60.2 | O | 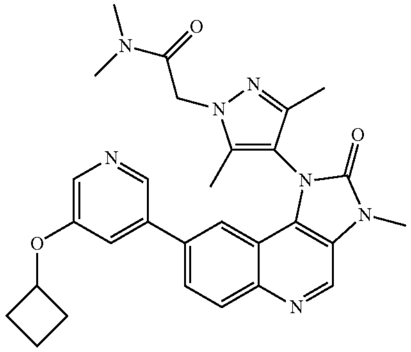 [SMILES: Cc1nn(CC(=O)N(C)C)c(C)c1-n1c(=O)n(C)c2cnc3ccc(-c4cncc(OC5CCC5)c4)cc3c21] | 2-{4-[8-(5-Cyclobutoxy-pyridin-3-yl)-3-methyl-2-oxo-2,3-dihydro-imidazo[4,5-c]quinolin-1-yl]-3,5-dimethyl-pyrazol-1-yl}-N,N-dimethyl-acetamide | 526 | 2.46 |

(m, 1H), 7.37-7.35 (m, 1H), 4.02-3.92 (m, 2H), 3.90 (s, 3H), 3.58 (s, 3H), 1.96 (s, 3H), 1.32-1.23 (m, 1H), 0.65-0.59 (m, 2H), 0.41-0.36 (m, 2H))

Stage 61.1.1 3-Cyclopropylmethoxy-5-(4,4,5,5-tetramethyl-[1,3,2]dioxaborolan-2-yl)-pyridine

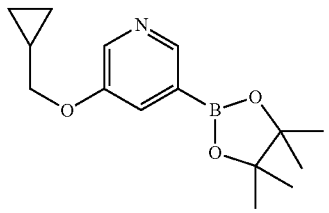 [SMILES: CC1(C)OB(c2cncc(OCC3CC3)c2)OC1(C)C]

The title compound was synthesized in a similar manner as described for Stage 58.1.1-2 using cyclopropylmethanol (Aldrich, Buchs, Switzerland) to give the title compound as a brown oil. (HPLC: $t_R$ 2.25 min (Method A); M+H=276 MS-ES).

Example 62

N-{5-[1-(1,3-Dimethyl-1H-pyrazol-4-yl)-3-methyl-2-oxo-2,3-dihydro-1H-imidazo[4,5-c]quinolin-8-yl]-2-methoxy-pyridin-3-yl}-N-methyl-acetamide

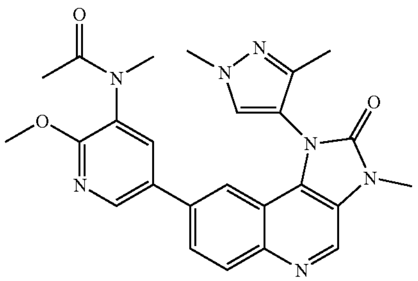

The title compound was synthesized in a similar manner as described for Example 1.1 using 8-bromo-1-(1,3-dimethyl-1H-pyrazol-4-yl)-3-methyl-1,3-dihydro-imidazo[4,5-c]quinolin-2-one (Intermediate A) and N-[2-methoxy-5-(4,4,5,5-tetramethyl-[1,3,2]dioxaborolan-2-yl)-pyridin-3-yl]-N-methyl-acetamide (Stage 62.1.1) to give the title compound as a white solid. (HPLC: $t_R$ 2.52 min (Method A); M+H=472 MS-ES; $^1$H-NMR ($d_6$-DMSO, 400 MHz) 8.97 (s, 1H), 8.40-8.31 (m, 1H), 8.18-8.06 (m, 2H), 8.03-7.90 (m, 1H), 7.86-7.71 (m, 1H), 7.55-7.43 (m, 1H), 3.97 (s, 3H), 3.88 (s, 3H), 3.57 (s, 3H), 3.07 (s, 3H), 1.94 (s, 3H), 1.74 (s, 3H))

Stage 62.1.1 N-[2-Methoxy-5-(4,4,5,5-tetramethyl-[1,3,2]dioxaborolan-2-yl)-pyridin-3-yl]-N-methyl-acetamide

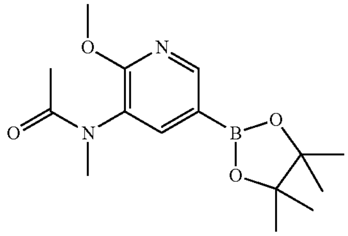 [SMILES: COc1ncc(B2OC(C)(C)C(C)(C)O2)cc1N(C)C(C)=O]

The title compound was synthesized in a similar manner as described for Stage 5.1.1 using N-(5-bromo-2-methoxy-pyridin-3-yl)-N-methyl-acetamide (Stage 62.1.2) to give the title compound as a brown solid. (HPLC: $t_R$ 1.99 min (Method A); M+H=307 MS-ES).

Stage 62.1.2 N-(5-Bromo-2-methoxy-pyridin-3-yl)-N-methyl-acetamide

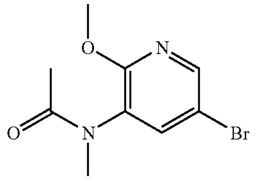

To N-(5-bromo-2-methoxy-pyridin-3-yl)-acetamide (Stage 62.1.3, 100 mg, 0.408 mmol) DMF (1 ml) was added NaH 55% in oil (19.6 mg, 0.45 mmol). The reaction mixture was stirred for 10 min at rt then was added MeI (0.031 ml, 0.49 mmol). The reaction mixture was stirred for 1 h at rt then quenched with brine and extracted with EtOAc (2×). The organic layers are washed with brine (3×), dried over $Na_2SO_4$, filtered and evaporated. The crude product was purified by Prep.HPLC. The fractions containing the product were collected together and basified with $NaHCO_3$, before being concentrated and extracted with EtOAc (3×). The organic layers were dried over $Na_2SO_4$, filtered and evaporated to dryness to give the title compound as an off-white solid (HPLC: $t_R$ 2.75 min (Method A); M+H=259, 261 MS-ES).

Stage 62.1.3 N-(5-Bromo-2-methoxy-pyridin-3-yl)-acetamide

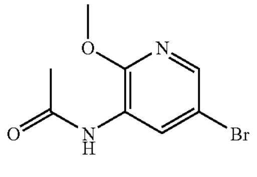

A suspension of 5-bromo-2-methoxy-3-nitro-pyridine (Stage 63.1.4, 450 mg, 1.93 mmol) and tin dichloride (1.465 mg, 7.72 mmol) in EtOAc (30 ml) was refluxed for 3 h. The reaction mixture was evaporated to dryness and then quenched with cold 3 M aqueous NaOH (50 ml) and $CH_2Cl_2$ (50 ml) and stirred for 3 h at rt. The organic layer was separated and the aqueous layer was extracted with $CH_2Cl_2$. The combined organic layers were washed with 30 ml sat. aqueous $NaHCO_3$, dried over $Na_2SO_4$, filtered and evaporated. The crude product was dry loaded on silica gel and purified by MPLC ($CH_2Cl_2$/MeOH 0% to 4%) to give after evaporation the title compound as an off-white solid (HPLC: $t_R$ 2.72 min (Method A); M+H=245, 247 MS-ES).

Stage 62.1.4 5-Bromo-2-methoxy-3-nitro-pyridine

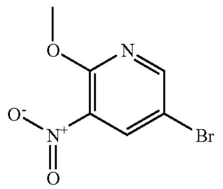

In a vial are introduced 1 ml of MeOH and 50.8 mg (2.21 mmol) of Na. After dissolution of the metal, the solution was added to a suspension of 5-bromo-2-chloro-3-nitropyridine (Matrix, Columbia, USA, 500 mg, 2.11 mmol) in MeOH (2 ml). The reaction mixture is stirred for 1 h at 0° C. and for 15 h at rt, then concentrated and quenched with water. The precipitate was filtered, washed with water (2×) and dried under vacuum to give the title compound as a pale yellow solid (HPLC: $t_R$ 3.06 min (Method A).

Example 63

N-{5-[1-(1,3-Dimethyl-1H-pyrazol-4-yl)-3-methyl-2-oxo-2,3-dihydro-1H-imidazo[4,5-c]quinolin-8-yl]-2-ethoxy-pyridin-3-yl}-N-methyl-acetamide

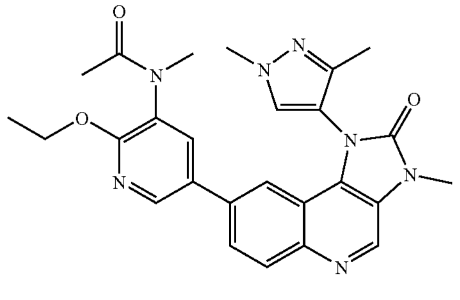 [SMILES: CCOc1ncc(-c2ccc3ncc4c(c3c2)n(-c2cn(C)nc2C)c(=O)n4C)cc1N(C)C(C)=O]

The title compound was synthesized in a similar manner as described for Example 1.1 using 8-bromo-1-(1,3-dimethyl-1H-pyrazol-4-yl)-3-methyl-1,3-dihydro-imidazo[4,5-c]quinolin-2-one (Intermediate A) and N-[2-ethoxy-5-(4,4,5,5-tetramethyl-[1,3,2]dioxaborolan-2-yl)-pyridin-3-yl]-N-methyl-acetamide (Stage 63.1.1) to give the title compound as a white solid. (HPLC: $t_R$ 2.64 min (Method A); M+H=486 MS-ES; $^1$H-NMR ($d_6$-DMSO, 400 MHz) 8.97 (s, 1H), 8.40-8.28 (m, 1H), 8.18-8.06 (m, 2H), 8.04-7.91 (m, 1H), 7.85-7.69 (m, 1H), 7.54-7.41 (m, 1H), 4.52-4.33 (m, 2H), 3.88 (s, 3H), 3.58 (s, 3H), 3.08 (s, 3H), 1.93 (s, 3H), 1.75 (s, 3H), 1.32 (t, 3H))

Stage 63.1.1 N-[2-Ethoxy-5-(4,4,5,5-tetramethyl-[1,3,2]dioxaborolan-2-yl)-pyridin-3-yl]-N-methyl-acetamide

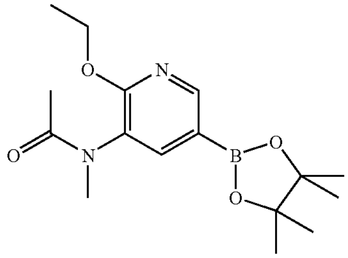 [SMILES: CCOc1ncc(B2OC(C)(C)C(C)(C)O2)cc1N(C)C(C)=O]

The title compound was synthesized in a similar manner as described for Stage 62.1.1-4 using ethanol as solvent and a sodium ethanolate solution to give the title compound as an off-white solid. (HPLC: $t_R$ 2.21min (Method A); M+H=3217 MS-ES).

Example 64

N-{5-[1-(1,3-Dimethyl-1H-pyrazol-4-yl)-3-methyl-2-oxo-2,3-dihydro-1H-imidazo[4,5-c]quinolin-8-yl]-2-methoxy-pyridin-3-yl}-acetamide

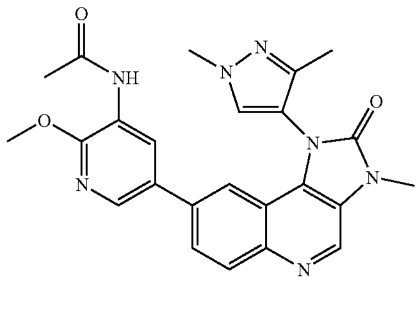

The title compound was synthesized in a similar manner as described for Example 1.1 using 8-bromo-1-(1,3-dimethyl-1H-pyrazol-4-yl)-3-methyl-1,3-dihydro-imidazo[4,5-c]quinolin-2-one (Intermediate A) and N-[2-methoxy-5-(4,4,5,5-tetramethyl-[1,3,2]dioxaborolan-2-yl)-pyridin-3-yl]-acetamide (Stage 64.1.1) to give the title compound as a white solid. (HPLC: $t_R$ 2.51 min (Method A); M+H=458 MS-ES; $^1$H-NMR ($d_6$-DMSO, 400 MHz) 9.52 (s, br, 1H), 8.96 (s, 1H), 8.50-8.41 (m, 1H), 8.15-8.09 (m, 2H), 8.06-8.02 (m, 1H), 7.88-7.83 (m, 1H), 7.55-7.49 (m, 1H), 3.97 (s, 3H), 3.91 (s, 3H), 3.57 (s, 3H), 2.14 (s, 3H), 1.93 (s, 3H))

Stage 64.1.1

N-[2-Methoxy-5-(4,4,5,5-tetramethyl-[1,3,2]dioxaborolan-2-yl)-pyridin-3-yl]-acetamide

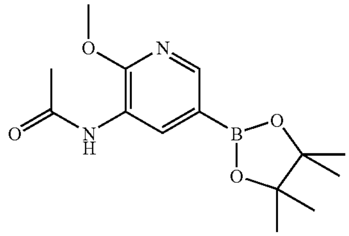 [SMILES: COc1ncc(B2OC(C)(C)C(C)(C)O2)cc1NC(C)=O]

The title compound was synthesized in a similar manner as described for Stage 5.1.1 using N-(5-bromo-2-methoxy-pyridin-3-yl)-acetamide (Stage 62.1.3) to give the title compound as a beige solid. (HPLC: $t_R$ 1.84 min (Method A); M+H=293 MS-ES).

Example 65

N-{5-[1-(1,3-Dimethyl-1H-pyrazol-4-yl)-3-methyl-2-oxo-2,3-dihydro-1H-imidazo[4,5-c]quinolin-8-yl]-2-ethoxy-pyridin-3-yl}-acetamide

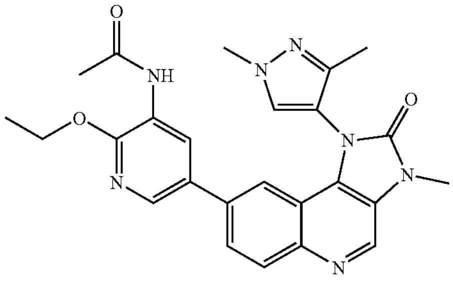 [SMILES: CCOc1ncc(-c2ccc3ncc4c(c3c2)n(-c2cn(C)nc2C)c(=O)n4C)cc1NC(C)=O]

The title compound was synthesized in a similar manner as described for Example 1.1 using 8-bromo-1-(1,3-dimethyl-1H-pyrazol-4-yl)-3-methyl-1,3-dihydro-imidazo[4,5-c]quinolin-2-one (Intermediate A) and N-[2-ethoxy-5-(4,4,5,5-tetramethyl-[1,3,2]dioxaborolan-2-yl)-pyridin-3-yl]-acetamide (synthesized in a similar manner as Stage 64.1.1, (HPLC: $t_R$ 1.84 min (Method A); M+H=293 MS-ES)) to give the title compound as a white solid. (HPLC: $t_R$ 2.64 min (Method A); M+H=472 MS-ES; $^1$H-NMR ($d_6$-DMSO, 400 MHz) 9.37 (s, 1H), 8.96 (s, 1H), 8.45-8.43 (m, 1H), 8.12-8.08 (m, 2H), 8.01-8.00 (m, 1H), 7.85-7.82 (m, 1H), 7.52-7.50 (m, 1H), 4.44 (q, 2H), 3.91 (s, 3H), 3.57 (s, 3H), 2.15 (s, 31-1), 1.92 (s, 3H), 1.37 (t, 3H))

Example 66

1-(1,3-Dimethyl-1H-pyrazol-4-yl)-8-(6-methoxy-5-nitro-pyridin-3-yl)-3-methyl-1,3-dihydro-imidazo[4,5-c]quinolin-2-one

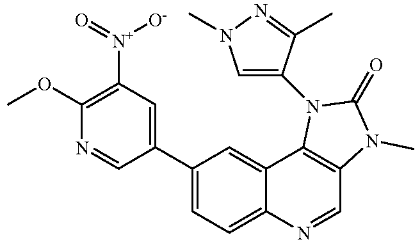

The title compound was synthesized in a similar manner as described for Example 1.1 using 8-bromo-1-(1,3-dimethyl-1H-pyrazol-4-yl)-3-methyl-1,3-dihydro-imidazo[4,5-c]quinolin-2-one (Intermediate A) and 2-methoxy-3-nitro-5-(4,4,5,5-tetramethyl-[1,3,2]dioxaborolan-2-yl)-pyridine (Stage 66.1.1) to give the title compound as a white solid. (HPLC: $t_R$ 2.62 min (Method A); M+H=446 MS-ES; $^1$H-NMR ($d_6$-DMSO, 400 MHz) 9.00 (s, 1H), 8.72-8.66 (m, 1H), 8.46-8.39 (m, 1H), 8.18-8.10 (m, 2H), 8.05-7.96 (m, 1H), 7.58-7.53 (m, 1H), 4.07 (s, 3H), 3.91 (s, 3H), 3.59 (s, 3H), 1.94 (s, 3H))

Stage 66.1.1 2-Methoxy-3-nitro-5-(4,4,5,5-tetramethyl-[1,3,2]dioxaborolan-2-yl)-pyridine

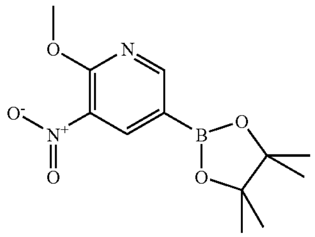 [SMILES: COc1ncc(B2OC(C)(C)C(C)(C)O2)cc1[N+](=O)[O-]]

The title compound was synthesized in a similar manner as described for Stage 5.1.1 using 5-bromo-2-methoxy-3-nitro-pyridine (Stage 62.1.4) to give the title compound as a brown solid. (HPLC: $t_R$ 2.22 min (Method A); M+H=281 MS-ES).

Example 67

8-(1,3-Dimethyl-2-oxo-2,3-dihydro-1H-imidazo[4,5-b]pyridin-6-yl)-1-(1,3-dimethyl-1H-pyrazol-4-yl)-3-methyl-1,3-dihydro-imidazo[4,5-c]quinolin-2-one

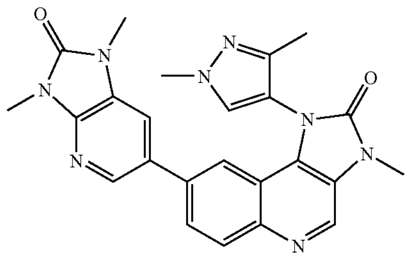

The title compound was synthesized in a similar manner as described for Example 1.1 using 8-bromo-1-(1,3-dimethyl-1H-pyrazol-4-yl)-3-methyl-1,3-dihydro-imidazo[4,5-c]quinolin-2-one (Intermediate A) and 1,3-dimethyl-6-(4,4,5,5-tetramethyl-[1,3,2]dioxaborolan-2-yl)-1,3-dihydro-imidazo[4,5-b]pyridin-2-one (Stage 67.1.1) to give the title compound as a white solid. (HPLC: $t_R$ 2.39 min (Method A); M+H=455 MS-ES; $^1$H-NMR ($d_6$-DMSO, 400 MHz) 8.97 (s, 1H), 8.16-8.07 (m, 3H), 7.99-7.94 (m, 111, 7.58-7.53 (m, 2H), 3.91 (s, 3H), 3.57 (s, 3H), 3.41 (s, 3H), 3.35 (s, 3H), 1.97 (s, 3H))

Stage 67.1.1 1,3-Dimethyl-6-(4,4,5,5-tetramethyl-[1,3,2]dioxaborolan-2-yl)-1,3-dihydro-imidazo[4,5-b]pyridin-2-one

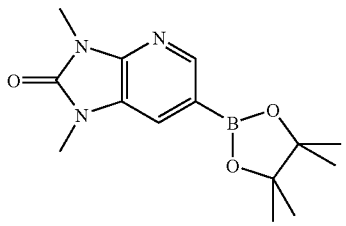 [SMILES: Cn1c(=O)n(C)c2ncc(B3OC(C)(C)C(C)(C)O3)cc21]

The title compound was synthesized in a similar manner as described for Stage 5.1.1 using 5-bromo-2-methoxy-3-nitro-pyridine (Stage 67.1.2) to give the title compound as an off-white solid. (HPLC: $t_R$ 1.93 min (Method A); M+H=290 MS-ES).

Stage 67.1.2 6-Bromo-1,3-dimethyl-1,3-dihydro-imidazo[4,5-b]pyridin-2-one

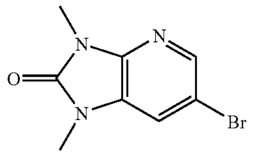

The title compound was synthesized in a similar manner as described for Intermediate A using 5-bromo-2-methoxy-3-nitro-pyridine (Stage 67.1.3) to give the title compound as a violet solid. (HPLC: $t_R$ 2.63 min (Method A); M+H=242, 244 MS-ES).

Stage 67.1.3 6-Bromo-3-methyl-1,3-dihydro-imidazo[4,5-b]pyridin-2-one

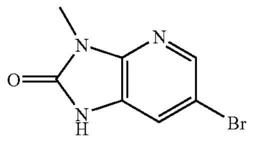

The title compound was synthesized in a similar manner as described for Stage A.1 using 5-bromo-N*2*-methyl-pyridine-2,3-diamine (Stage 67.1.4) to give the title compound as a gray solid. (HPLC: $t_R$ 2.37 min (Method A); M+H=228, 230 MS-ES).

Stage 67.1.4
5-Bromo-N*2*-methyl-pyridine-2,3-diamine

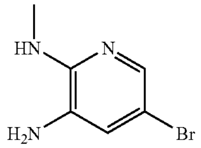

A suspension of (5-bromo-3-nitro-pyridin-2-yl)-methyl-amine (Stage 67.1.5, 4.58 g, 19.75 mmol) and tin dichloride dihydrate (Acros, Basel, Switzerland, 13.38 g, 59.3 mmol) in 200 ml of THF was heated at 70° C. for 220 min. The solvent was removed by evaporation and the residue taken in $CH_2Cl_2$ (100 ml) and 5 M aqueous NaOH (50 ml) and stirred until all the solid was dissolved. The organic layer was separated and the aqueous layer was extracted with $CH_2Cl_2$. The combined organic layers were washed with brine, dried over $Na_2SO_4$, filtered and evaporated to give the title compound as a brown solid. (HPLC: $t_R$ 1.69 min (Method A); M+H=202, 204 MS-ES).

Stage 67.1.5
(5-Bromo-3-nitro-pyridin-2-yl)-methyl-amine

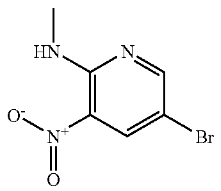

To a solution of 5-bromo-2-chloro-3-nitropyridine (Matrix, Columbia, USA, 9.8 g, 41.3 mmol) in 250 ml THF was added 8 M methylamine in EtOH (Aldrich, Buchs, Switzerland, 12.9 ml, 103 mmol). The reaction mixture was stirred 1 h at rt then was quenched with 300 ml water. The precipite was filtered and the filtrate concentrated before being filtered again. The yellow solids were combined and dried to give the title compound as a yellow solid (HPLC: $t_R$ 3.13 min (Method A)).

Example 68

1-(1,3-Dimethyl-1H-pyrazol-4-yl)-8-(1-ethyl-3-methyl-2-oxo-2,3-dihydro-1H-imidazo[4,5-b]pyridin-6-yl)-3-methyl-1,3-dihydro-imidazo[4,5-c]quinolin-2-one

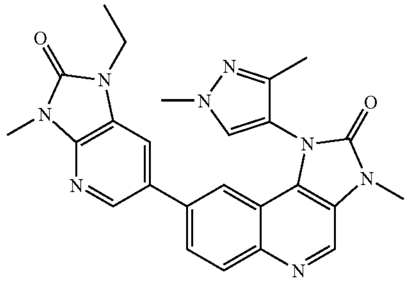

The title compound was synthesized in a similar manner as described for Example 1.1 using 8-bromo-1-(1,3-dimethyl-1H-pyrazol-4-yl)-3-methyl-1,3-dihydro-imidazo[4,5-c]quinolin-2-one (Intermediate A) and 1-ethyl-3-methyl-6-(4,4,5,5-tetramethyl-[1,3,2]dioxaborolan-2-yl)-1,3-dihydro-imidazo[4,5-b]pyridin-2-one (Stage 68.1.1) to give the title compound as a white solid. (HPLC: $t_R$ 2.47 min (Method A); M+H=469 MS-ES; $^1$H-NMR ($d_6$-DMSO, 400 MHz) 8.97 (s, 1H), 8.14-8.08 (m, 3H), 8.01-7.94 (m, 1H), 7.62-7.58 (m, 1H), 7.58-7.54 (m, 1H), 3.94 (q, 2H), 3.89 (s, 3H), 3.57 (s, 3H), 3.37 (s, 3H), 1.97 (s, 3H), 1.28 (t, 3H))

Stage 68.1.1 1-Ethyl-3-methyl-6-(4,4,5,5-tetramethyl-[1,3,2]dioxaborolan-2-yl)-1,3-dihydro-imidazo[4,5-b]pyridin-2-one

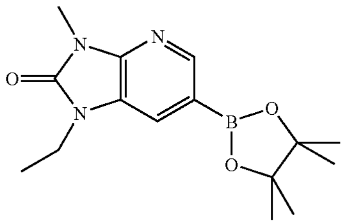 [SMILES: CCn1c(=O)n(C)c2ncc(B3OC(C)(C)C(C)(C)O3)cc21]

The title compound was synthesized in a similar manner as described for Stage 67.1.1-2 using ethyliodide (Aldrich, Buchs, Switzerland) to give the title compound as a white solid. (HPLC: $t_R$ 1.98 min (Method A); M+H=304 MS-ES).

Example 69

1-(1,3-Dimethyl-1H-pyrazol-4-yl)-8-[1-(2-methoxy-ethyl)-3-methyl-2-oxo-2,3-dihydro-1H-imidazo[4,5-b]pyridin-6-yl]-3-methyl-1,3-dihydro-imidazo[4,5-c]quinolin-2-one

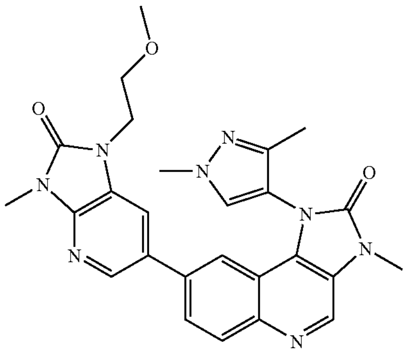

The title compound was synthesized in a similar manner as described for Example 1.1 using 8-bromo-1-(1,3-dimethyl-1H-pyrazol-4-yl)-3-methyl-1,3-dihydro-imidazo[4,5-c]quinolin-2-one (Intermediate A) and 1-(2-methoxy-ethyl)-3-methyl-6-(4,4,5,5-tetramethyl-[1,3,2]dioxaborolan-2-yl)-1,3-dihydro-imidazo[4,5-b]pyridin-2-one (Stage 69.1.1) to give the title compound as a white solid. (HPLC: $t_R$ 2.46 min (Method A); M+H=499 MS-ES; 1H-NMR ($d_6$-DMSO, 400 MHz) 8.97 (s, 1H), 8.15-8.05 (m, 3H), 7.97-7.91 (m, 1H), 7.64-7.60 (m, 1H), 7.57-7.53 (m, 1H), 4.11-4.03 (m, 2H), 3.90 (s, 31-1), 3.67-3.62 (m, 2H), 3.57 (s, 3H), 3.36 (s, 3H), 3.23 (s, 3H), 1.98 (s, 3H))

Stage 69.1.1 1-(2-Methoxy-ethyl)-3-methyl-6-(4,4,5,5-tetramethyl-[1,3,2]dioxaborolan-2-yl)-1,3-dihydro-imidazo[4,5-b]pyridin-2-one

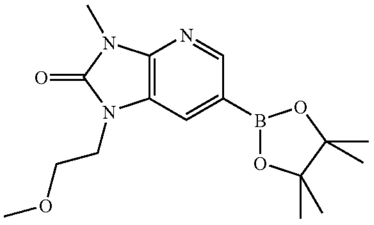

The title compound was synthesized in a similar manner as described for Stage 67.1.1-2 using 2-bromoethyl methyl ether (Aldrich, Buchs, Switzerland) to give the title compound as a brown solid. (HPLC: $t_R$ 2.03 min (Method A); M+H=334 MS-ES).

Example 70

8-(2-Dimethylamino-3-methyl-3H-imidazo[4,5-b]pyridin-6-yl)-1-(1,3-dimethyl-1H-pyrazol-4-yl)-3-methyl-1,3-dihydro-imidazo[4,5-c]quinolin-2-one

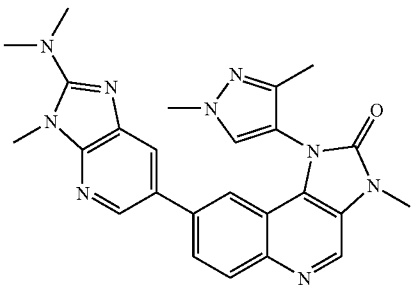

The title compound was synthesized in a similar manner as described for Example 1.1 using 8-bromo-1-(1,3-dimethyl-1H-pyrazol-4-yl)-3-methyl-1,3-dihydro-imidazo[4,5-c]quinolin-2-one (Intermediate A) and dimethyl-[3-methyl-6-(4,4,5,5-tetramethyl-[1,3,2]dioxaborolan-2-yl)-3H-imidazo[4,5-b]pyridin-2-yl]-amine (Stage 70.1.1) to give the title compound as a white solid. (HPLC: $t_R$ 2.21 min (Method A); M+H=468 MS-ES; $^1$H-NMR ($d_6$-DMSO, 400 MHz) 8.95 (s, 1H), 8.17-8.06 (m, 3H), 7.96-7.90 (m, 1H), 7.72-7.67 (m, 1H), 7.56-7.52 (m, 1H), 3.91 (s, 3H), 3.71 (s, 3H), 3.57 (s, 3H), 3.06 (s, 6H), 1.97 (s, 3H))

Stage 70.1.1 Dimethyl-[3-methyl-6-(4,4,5,5-tetramethyl-[1,3,2]dioxaborolan-2-yl)-3H-imidazo[4,5-b]pyridin-2-yl]-amine

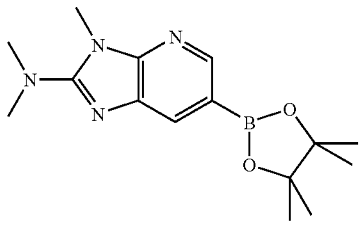

The title compound was synthesized in a similar manner as described for Stage 5.1.1 using (6-bromo-3-methyl-3H-imidazo[4,5-b]pyridin-2-yl)-dimethyl-amine (Stage 70.1.2) to give the title compound as a brown oil. (HPLC: $t_R$ 1.76 min (Method A); M+H=303 MS-ES).

Stage 70.1.2 (6-Bromo-3-methyl-3H-imidazo[4,5-b]pyridin-2-yl)-dimethyl-amine

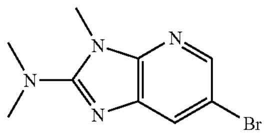

A solution of 5-bromo-N*2*-methyl-pyridine-2,3-diamine (Stage 67.1.4, 2.09 g, 10.34 mmol) and dichloromethylene-dimethyliminium chloride (Aldrich, Buchs, Switzerland, 5.04 g, 31.0 mmol) in NMP (60 ml) was stirred for 17 h at rt. The reaction mixture was quenched with saturated aqueous $NaHCO_3$ and EtOAc. The aqueous layer was extracted with EtOAc and the combined organic layers washed with saturated aqueous $NaHCO_3$ and with brine, then dried over $Na_2SO_4$, filtered and evaporated. The crude product was dry loaded on silica gel and purified by MPLC (DCM/MeOH 0%-5%) to give the title compound as a red solid. (HPLC: $t_R$ 2.13 min (Method A); M+H=255, 257 MS-ES).

Example 71

1-(1,3-Dimethyl-1H-pyrazol-4-yl)-8-(2-methoxy-3-methyl-3H-imidazo[4,5-b]pyridin-6-yl)-3-methyl-1,3-dihydro-imidazo[4,5-c]quinolin-2-one

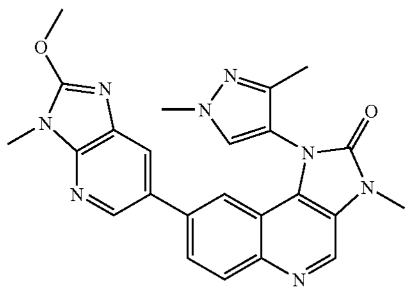

The title compound was synthesized in a similar manner as described for Example 1.1 using 8-bromo-1-(1,3-dimethyl-1H-pyrazol-4-yl)-3-methyl-1,3-dihydro-imidazo[4,5-c]quinolin-2-one (Intermediate A) and 2-methoxy-3-methyl-6-(4,4,5,5-tetramethyl-[1,3,2]dioxaborolan-2-yl)-3H-imidazo[4,5-b]pyridine (Stage 71.1.1) to give the title compound as a white solid. (HPLC: $t_R$ 2.62 min (Method A); M+H=455 MS-ES; $^1$H-NMR ($d_6$-DMSO, 400 MHz) 8.97 (s, 1H), 8.24-8.20 (m, 1H), 8.17-8.13 (m, 1H), 8.13-8.08 (m, 1H), 7.97-7.92 (m, 1H), 7.87-7.83 (m, 1H), 7.55-7.53 (m, 1H), 4.16 (s, 3H), 3.91 (s, 3H), 3.57 (s, 6H), 1.97 (s, 3H))

Stage 71.1.1 2-Methoxy-3-methyl-6-(4,4,5,5-tetramethyl-[1,3,2]dioxaborolan-2-yl)-3H-imidazo[4,5-b]pyridine

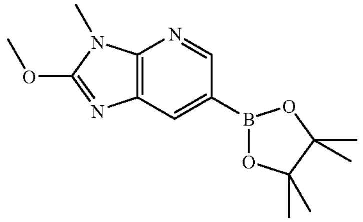

The title compound was synthesized in a similar manner as described for Stage 5.1.1 using 6-bromo-2-methoxy-3-methyl-3H-imidazo[4,5-b]pyridine (Stage 71.1.2) to give the title compound as a yellow solid. (HPLC: $t_R$ 1.94 min (Method A); M+H=290 MS-ES).

Stage 71.1.2 6-Bromo-2-methoxy-3-methyl-3H-imidazo[4,5-b]pyridine

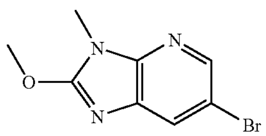

A solution of 5-bromo-N*2*-methyl-pyridine-2,3-diamine (Stage 67.1.4, 960 mg, 4.75 mmol) and tetramethylorthocarbonate (Aldrich, Buchs, Switzerland, 2 ml, 14.7 mmol) and acetic acid (0.273 ml, 4.75 mmol) was stirred for 90 min at 100° C. The reaction mixture was diluted with EtOAc and washed with saturated aqueous $NaHCO_3$ and brine. The aqueous layer was extracted with EtOAc and the combined organic layers washed with saturated aqueous $NaHCO_3$ and with brine, then dried over $Na_2SO_4$, filtered and evaporated. The crude product was dry loaded on silica gel and purified by MPLC (DCM/MeOH 0%-4%) to give the title compound as a green solid. (HPLC: $t_R$ 2.83 min (Method A); M+H=242, 244 MS-ES).

Example 72

1-(1,3-Dimethyl-1H-pyrazol-4-yl)-3-methyl-8-(3-methyl-3H-[1,2,3]triazolo[4,5-b]pyridin-6-yl)-1,3-dihydro-imidazo[4,5-c]quinolin-2-one

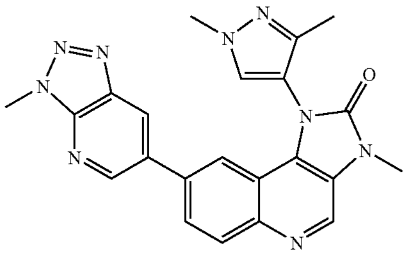

The title compound was synthesized in a similar manner as described for Example 1.1 using 8-bromo-1-(1,3-dimethyl-1H-pyrazol-4-yl)-3-methyl-1,3-dihydro-imidazo[4,5-c]quinolin-2-one (Intermediate A) and 2-methoxy-3-methyl-6-(4,4,5,5-tetramethyl[1,3,2]dioxaborolan-2-yl)-3H-imidazo[4,5-b]pyridine (Stage 72.1.1) to give the title compound as a white solid. (HPLC: $t_R$ 2.43 min (Method A); M+H=426 MS-ES; $^1$H-NMR ($d_6$-DMSO, 400 MHz) 9.01 (s, 1H), 8.86-8.81 (m, 1H), 8.65-8.61 (m, 1H), 8.21-8.13 (m, 2H), 8.10-8.04 (m, 1H), 7.63-7.59 (m, 1H), 4.33 (s, 3H), 3.92 (s, 3H), 3.58 (s, 3H), 1.96 (s, 3H))

Stage 72.1.1 3-Methyl-6-(4,4,5,5-tetramethyl-[1,3,2]dioxaborolan-2-yl)-3H-[1,2,3]triazolo[4,5-b]pyridine

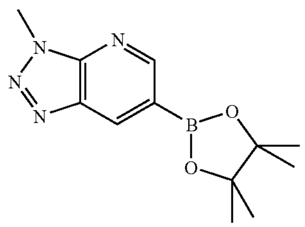 [SMILES: Cn1nnc2cc(B3OC(C)(C)C(C)(C)O3)cnc21]

The title compound was synthesized in a similar manner as described for Stage 5.1.1 using 6-bromo-3-methyl-3H-[1,2,3]triazolo[4,5-b]pyridine (Stage 72.1.2) to give the title compound as a yellow solid. (HPLC: $t_R$ 1.85 min (Method A); M+H=261 MS-ES).

Stage 72.1.2 6-Bromo-3-methyl-3H-[1,2,3]triazolo[4,5-b]pyridine

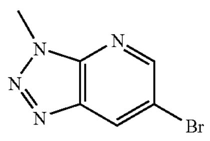

To a solution of 5-bromo-N*2*-methyl-pyridine-2,3-diamine (Stage 67.1.4, 1.2 g, 5.94 mmol) in 2 M aqueous HCl (70 ml) cooled with an ice-bath was added a solution of sodium nitrite (Fluka, Buchs, Switzerland, 492 mg, 7.13 mmol) in water (10 ml). The reaction mixture was stirred at 0° C. for 1 h and at rt for 75 min then basified with 2 M aqueous NaOH (75 ml) and extracted with EtOAc. The organic layer was washed with brine, dried over $Na_2SO_4$, filtered and evaporated. The crude product was dry loaded on silica gel and purified by MPLC (heptane/EtOAc 0%-30%) to give the title compound as a blue solid. (HPLC: $t_R$ 2.46 min (Method A); M+H=213, 215 MS-ES).

Example 73

8-(2,3-Dimethyl-3H-imidazo[4,5-b]pyridin-6-yl)-1-(1,3-dimethyl-1H-pyrazol-4-yl)-3-methyl-1,3-dihydro-imidazo[4,5-c]quinolin-2-one

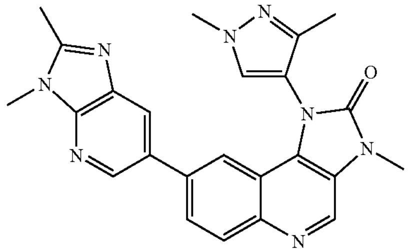

The title compound was synthesized in a similar manner as described for Example 1.1 using 8-bromo-1-(1,3-dimethyl-1H-pyrazol-4-yl)-3-methyl-1,3-dihydro-imidazo[4,5-c]quinolin-2-one (Intermediate A) and 3-methyl-6-(4,4,5,5-tetramethyl-[1,3,2]dioxaborolan-2-yl)-3H-imidazo[4,5-b]pyridine (stage 73.1.1) to give the title compound as an off-white solid. (HPLC: $t_R$ 2.20 min (Method A); M+H=439 MS-ES; $^1$H-NMR ($d_6$-DMSO, 400 MHz) 8.98 (s, 1H), 8.41-8.38 (m, 1H), 8.18-8.15 (m, 1H), 8.13-8.09 (m, 1H), 8.02-7.96 (m, 2H), 7.58-7.54 (m, 1H), 3.92 (s, 3H), 3.77 (s, 3H), 3.58 (s, 3H), 2.59 (s, 3H), 1.97 (s, 3H))

Stage 73.1.1 2,3-Dimethyl-6-(4,4,5,5-tetramethyl-[1,3,2]dioxaborolan-2-yl)-3H-imidazo[4,5-b]pyridine

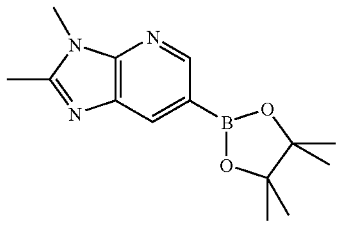

The title compound was synthesized in a similar manner as described for stage 5.1.1 using 6-bromo-2,3-dimethyl-3H-imidazo[4,5-b]pyridine (stage 73.1.2) to give the title compound as a green solid. (HPLC: $t_R$ 1.51 min (Method A); M+H=274 MS-ES).

Stage 73.1.2
6-Bromo-2,3-dimethyl-3H-imidazo[4,5-b]pyridine

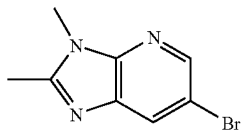

A solution of 5-bromo-N*2*-methyl-pyridine-2,3-diamine (Stage 67.1.4, 960 mg, 4.75 mmol) in triethylorthoacetate (Aldrich, Buchs, Switzerland, 25 ml) was stirred for 38.5 h at 140° C. The reaction mixture was evaporated to dryness. The residue was dissolved in EtOAc and washed with saturated aqueous $NaHCO_3$. The aqueous layer was extracted with EtOAc and the combined organic layers washed with brine, dried over $Na_2SO_4$, filtered and evaporated. The crude product was dry loaded on silica gel and purified by MPLC (DCM/MeOH 0%-4%) to give the title compound as a brown solid. (HPLC: $t_R$ 1.95 min (Method A); M+H=226, 228 MS-ES).

Example 74

1-(1,3-Dimethyl-1H-pyrazol-4-yl)-3-methyl-8-(3-methyl-3H-imidazo[4,5-b]pyridin-6-yl)-1,3-dihydro-imidazo[4,5-c]quinolin-2-one

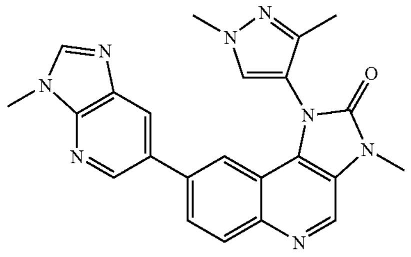

The title compound was synthesized in a similar manner as described for Example 1.1 using 8-bromo-1-(1,3-dimethyl-1H-pyrazol-4-yl)-3-methyl-1,3-dihydro-imidazo[4,5-c]quinolin-2-one (Intermediate A) and 3-methyl-6-(4,4,5,5-tetramethyl-[1,3,2]dioxaborolan-2-yl)-3H-imidazo[4,5-b]pyridine (Stage 74.1.1) to give the title compound as a white solid. (HPLC: $t_R$ 2.26 min (Method A); M+H=425 MS-ES; $^1$H-NMR ($d_6$-DMSO, 400 MHz) 8.97 (s, 1H), 8.52-8.46 (m, 2H), 8.20-8.08 (m, 3H), 8.05-7.98 (m, 1H), 7.60-7.55 (m, 1H), 3.93 (s, 3H), 3.86 (s, 3H), 3.58 (s, 3H), 1.97 (s, 3H))

Stage 74.1.1 3-Methyl-6-(4,4,5,5-tetramethyl-[1,3,2]dioxaborolan-2-yl)-3H-imidazo[4,5-b]pyridine

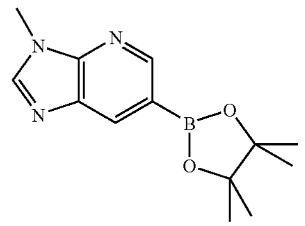 [SMILES: Cn1cnc2cc(B3OC(C)(C)C(C)(C)O3)cnc21]

The title compound was synthesized in a similar manner as described for Stage 73.1.1-2 using triethylorthoformate (Aldrich, Buchs, Switzerland) to give the title compound as a brown solid. (HPLC: $t_R$ 1.39 min (Method A); M+H=260 MS-ES).

Example 75

N-{5-[1-(1,3-Dimethyl-1H-pyrazol-4-yl)-3-methyl-2-oxo-2,3-dihydro-1H-imidazo[4,5-c]quinolin-8-yl]-2-methyl-pyridin-3-yl}-N-methyl-methanesulfonamide

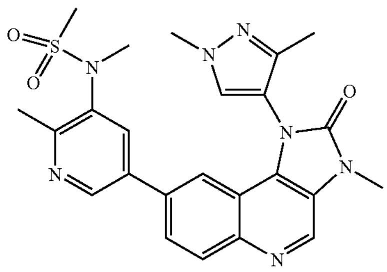 [SMILES: Cc1ncc(-c2ccc3ncc4c(c3c2)n(-c2cn(C)nc2C)c(=O)n4C)cc1N(C)S(C)(=O)=O]

The title compound was synthesized in a similar manner as described for Example 1.1 using 8-bromo-1-(1,3-dimethyl-1H-pyrazol-4-yl)-3-methyl-1,3-dihydro-imidazo[4,5-c]quinolin-2-one (Intermediate A) and N-methyl-N-[2-methyl-5-(4,4,5,5-tetramethyl-[1,3,2]dioxaborolan-2-yl)-pyridin-3-yl]-methanesulfonamide (Stage 75.1.1) to give the title compound as a white solid. (HPLC: $t_R$ 2.19 min (Method A); M+H=492 MS-ES; $^1$H-NMR ($d_6$-DMSO, 400 MHz) 8.99 (s, 1H), 8.55-8.51 (m, 1H), 8.16-8.10 (m, 2H), 8.03-7.97 (m, 1H), 7.95-7.91 (m, 1H), 7.60-7.56 (m, 1H), 3.89 (s, 3H), 3.58 (s, 3H), 3.23 (s, 3H), 3.16 (s, 3H), 2.53 (s, 3H), 1.96 (s, 3H))

Stage 75.1.1 N-Methyl-N-[2-methyl-5-(4,4,5,5-tetramethyl-[1,3,2]dioxaborolan-2-yl)-pyridin-3-yl]-methanesulfonamide

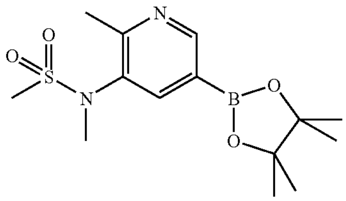

The title compound was synthesized in a similar manner as described for Stage 5.1.1 using 6-bromo-2,3-dimethyl-3H-imidazo[4,5-b]pyridine (Stage 75.1.2) to give the title compound as a brown oil. (HPLC: $t_R$ 2.15 min (Method A); M+H=327 MS-ES).

Stage 75.1.2 N-(5-Bromo-2-methyl-pyridin-3-yl)-N-methyl-methanesulfonamide

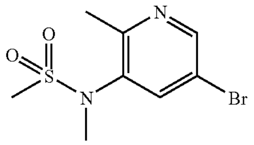

The title compound was synthesized in a similar manner as described for Stage 62.1.2 using N-(5-bromo-2-methyl-pyridin-3-yl)-methanesulfonamide (Stage 75.1.2) to give the title compound as a brownish solid. (HPLC: $t_R$ 2.28 min (Method A); M+H=279, 281 MS-ES).

Stage 75.1.3 N-(5-Bromo-2-methyl-pyridin-3-yl)-methanesulfonamide

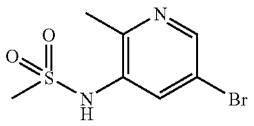

To a solution of 5-bromo-2-methyl-pyridin-3-ylamine (Stage 75.1.4, 573 mg, 3.06 mmol) in pyridine (6 ml) was added dropwise methanesulfonyl chloride (Aldrich, Buchs, Switzerland, 0.286 ml, 3.68 mmol). The reaction mixture was stirred for 18 h at rt then are added methanesulfonyl chloride (0.03 ml, 0.39 mmol). The reaction mixture was stirred 4 h at rt before being evaporated to dryness. The residue was dissolved in EtOAc and washed with saturated aqueous $NaHCO_3$ and brine, dried over $Na_2SO_4$, filtered and evaporated. The crude product was dry loaded on silica gel and purified by MPLC (DCM/MeOH 0%-5%) to give the title compound as a pinkish solid. (HPLC: $t_R$ 2.05 min (Method A); M+H=265, 267 MS-ES).

Stage 75.1.4 5-Bromo-2-methyl-pyridin-3-ylamine

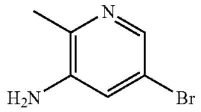

To a solution of 5-bromo-2-methyl-3-nitro-pyridine (stage 75.1.5, 765 mg, 3.53 mmol) in acetic acid (7 ml) and water (1.75 ml) was added in three portions iron powder (591 mg, 10.6 mmol). The reaction mixture was stirred for 2.5 h at rt then quenched with 20 ml of 10 M aqueous NaOH, 20 g ice and 20 ml EtOAc before being filtered over Celite. The solid was washed with EtOAc and the filtrate was extracted with EtOAc. The combined organic layers were washed with brine, dried over $Na_2SO_4$, filtered and evaporated to give the title compound as a gray solid. (HPLC: $t_R$ 1.52 min (Method A); M+H=187, 189 MS-ES).

Stage 75.1.5 5-Bromo-2-methyl-3-nitro-pyridine

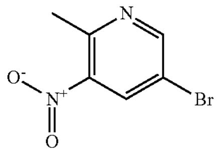

To a suspension of NaH 55% in oil (300 mg, 6.87 mmol) in 6 ml DMF was added dropwise diethyl malonate (Aldrich, Buchs, Switzerland, 1.0 g, 6.24 mmol). The reaction mixture was stirred for 20 min at rt before adding 5-bromo-2-chloro-3-nitropyridine (Matrix, Columbia, USA, 1.19 g, 5.0 mmol). The reaction mixture was stirred for 30 min at rt and for 1 h at 40° C. The reaction mixture was quenched with 10% aqueous $NH_4Cl$ and extracted with EtOAc (2×). The combined organic layers were washed with brine (4×), dried over $Na_2SO_4$, filtered and evaporated. The residue was stirred in concentrated HCl (20 ml) for 13 h at 100° C. After cooling, the reaction mixture was basified with 10 M aqueous NaOH and extracted with EtOAc (2×). The organic layers were washed with brine, dried over $Na_2SO_4$, filtered and evaporated. The residue was dry loaded on silica gel and purified by MPLC (heptane/EtOAc 0% to 15%) to give the title compound as a yellow solid. (HPLC: $t_R$ 2.84 (Method A).

Example 76

N-{5-[1-(1,3-Dimethyl-1H-pyrazol-4-yl)-3-methyl-2-oxo-2,3-dihydro-1H-imidazo[4,5-c]quinolin-8-yl]-2-methyl-pyridin-3-yl}-methanesulfonamide

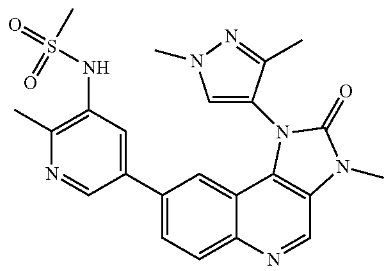

The title compound was synthesized in a similar manner as described for Example 1.1 using 8-bromo-1-(1,3-dimethyl-1H-pyrazol-4-yl)-3-methyl-1,3-dihydro-imidazo[4,5-c] quinolin-2-one (Intermediate A) and N-[2-methyl-5-(4,4,5,5-tetramethyl-[1,3,2]dioxaborolan-2-yl)-pyridin-3-yl]-methanesulfonamide (Stage 76.1.1) to give the title compound as a white solid. (HPLC: $t_R$ 2.06 min (Method A); M+H=478 MS-ES; $^1$H-NMR ($d_6$-DMSO, 400 MHz) 9.51-9.47 (m, 1H), 8.98 (s, 1H), 8.46-8.42 (m, 1H), 8.15-8.09 (m, 2H), 7.94-7.88 (m, 1H), 7.72-7.68 (m, 1H), 7.60-7.56 (m, 1H), 3.90 (s, 3H), 3.57 (s, 3H), 3.09 (s, 3H), 3.54 (s, 3H), 1.95 (s, 3H))

Stage 76.1.1 N-[2-Methyl-5-(4,4,5,5-tetramethyl-[1,3,2]dioxaborolan-2-yl)-pyridin-3-yl]-methanesulfonamide

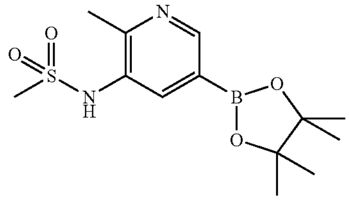

The title compound was synthesized in a similar manner as described for Stage 5.1.1 using N-(5-bromo-2-methyl-pyridin-3-yl)-methanesulfonamide (Stage 75.1.2) to give the title compound as a brown oil. (HPLC: $t_R$ 1.96 min (Method A); M+H=313 MS-ES).

Example 77

1-(1,3-Dimethyl-1H-pyrazol-4-yl)-8-[4-(1H-imidazol-2-yl)-phenyl]-3-methyl-1,3-dihydro-imidazo[4,5-c]quinolin-2-one

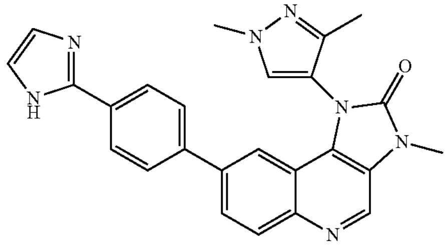 [SMILES: Cc1nn(C)cc1-n1c(=O)n(C)c2cnc3ccc(-c4ccc(-c5ncc[nH]5)cc4)cc3c21]

The title compound was synthesized in a similar manner as described for Example 1.1 using 8-bromo-1-(1,3-dimethyl-1H-pyrazol-4-yl)-3-methyl-1,3-dihydro-imidazo[4,5-c] quinolin-2-one (Intermediate A) and N-[2-methyl-5-(4,4,5,5-tetramethyl-[1,3,2]dioxaborolan-2-yl)-pyridin-3-yl]-methanesulfonamide (Stage 77.1.1) to give the title compound as a white solid. (HPLC: $t_R$ 2.15 min (Method A); M+H=436 MS-ES; $^1$H-NMR ($d_6$-DMSO, 400 MHz) 12.58 (s, br, 1H), 8.96 (s, 1H), 8.20-8.15 (m, 1H), 8.14-8.07 (m, 1H), 8.05-7.94 (m, 3H), 7.63-7.53 (m, 3H), 7.31-7.07 (m, br, 2H), 3.95 (s, 3H), 3.57 (s, 3H), 1.97 (s, 3H))

Stage 77.1.1

2-[4-(4,4,5,5-Tetramethyl-[1,3,2]dioxaborolan-2-yl)-phenyl]-1H-imidazole

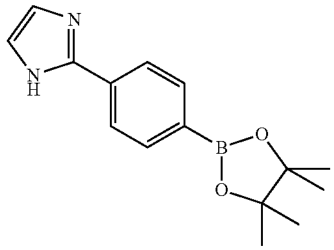 [SMILES: CC1(C)OB(c2ccc(-c3ncc[nH]3)cc2)OC1(C)C]

The title compound was synthesized in a similar manner as described for Stage 5.1.1 using 2-(4-bromo-phenyl)-1H-imidazole (Chem-Impex, Cogliate, Italy) to give the title compound as a brown oil. (HPLC: $t_R$ 1.67 min (Method A); M+H=271 MS-ES).

Example 78

1-(1,3-Dimethyl-1H-pyrazol-4-yl)-3-methyl-8-[6-(2-methyl-imidazol-1-yl)-pyridin-3-yl]-1,3-dihydro-imidazo[4,5-c]quinolin-2-one

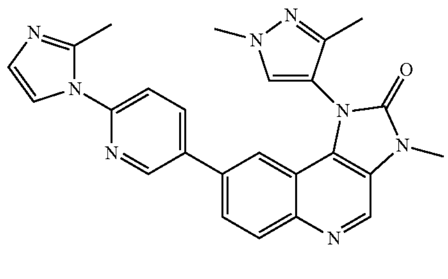 [SMILES: Cc1nn(C)cc1-n1c(=O)n(C)c2cnc3ccc(-c4ccc(-n5ccnc5C)nc4)cc3c21]

The title compound was synthesized in a similar manner as described for Example 1.1 using 8-bromo-1-(1,3-dimethyl-1H-pyrazol-4-yl)-3-methyl-1,3-dihydro-imidazo[4,5-c]quinolin-2-one (Intermediate A) and 2-(2-methyl-imidazol-1-yl)-5-(4,4,5,5-tetramethyl-[1,3,2]dioxaborolan-2-yl)-pyridine (Stage 78.1.1) to give the title compound as a white solid. (HPLC: $t_R$ 2.10 min (Method A); M+H=451 MS-ES; $^1$H-NMR ($d_6$-DMSO, 400 MHz) 9.01 (s, 1H), 8.68-8.66 (m, 1H), 8.18-8.13 (m, 2H), 8.09-8.00 (m, 2H), 7.78-7.74 (m, 1H), 7.63-7.59 (m, 2H), 6.94-6.93 (m, 1H), 3.93 (s, 3H), 3.59 (s, 3H), 2.54 (s, 3H), 1.96 (s, 3H))

Stage 78.1.1. 2-(2-Methyl-imidazol-1-yl)-5-(4,4,5,5-tetramethyl-[1,3,2]dioxaborolan-2-yl)-pyridine

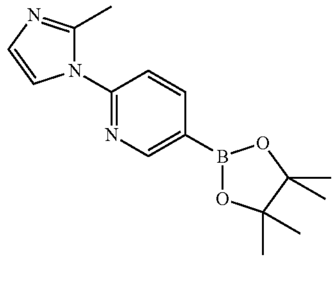 [SMILES: Cc1nccn1-c1ccc(B2OC(C)(C)C(C)(C)O2)cn1]

The title compound was synthesized in a similar manner as described for Stage 5.1.1 using 5-bromo-2-(2-methyl-imidazol-1-yl)-pyridine (Stage 78.1.2) to give the title compound as a brown solid. (HPLC: $t_R$ 1.57 min (Method A); M+H=286 MS-ES).

Stage 78.1.2. 5-Bromo-2-(2-methyl-imidazol-1-yl)-pyridine

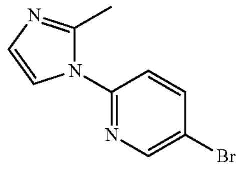

A mixture of 5-bromo-2-chloro-pyridine (Aldrich, Buchs, Switzerland, 392 mg, 2.04 mmol), 2-methyl-1H-imidazole (Aldrich, Buchs, Switzerland, 251 mg, 3.06 mmol) and cesium carbonate (1.33 g, 4.08 mmol) in DMA (10 ml) was heated by microwave irradiation for 20 min at 100° C. and 2.5 h at 150° C. The reaction mixture was quenched with diluted brine (200 ml) and cooled. The precipitate was filtered, washed with water and dried to give the title compound as off-white solid. (HPLC: $t_R$ 2.03 min (Method A); M+H=238, 240 MS-ES).

Example 79

1-(1,3-Dimethyl-1H-pyrazol-4-yl)-3-methyl-8-(6-pyrazol-1-yl-pyridin-3-yl)-1,3-dihydro-imidazo[4,5-c]quinolin-2-one

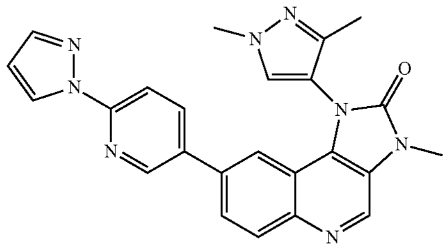 [SMILES: Cc1nn(C)cc1-n1c(=O)n(C)c2cnc3ccc(-c4ccc(-n5cccn5)nc4)cc3c21]

The title compound was synthesized in a similar manner as described for Example 1.1 using 8-bromo-1-(1,3-dimethyl-1H-pyrazol-4-yl)-3-methyl-1,3-dihydro-imidazo[4,5-c]quinolin-2-one (Intermediate A) and 2-pyrazol-1-yl-5-(4,4,5,5-tetramethyl-[1,3,2]dioxaborolan-2-yl)-pyridine (Stage 79.1.1) to give the title compound as a white solid. (HPLC: $t_R$ 2.64 min (Method A); M+H=437 MS-ES; $^1$H-NMR ($d_6$-DMSO, 400 MHz) 9.00 (s, 1H), 8.68-8.66 (m, 1H), 8.59-8.57 (m, 1H), 8.16-8.12 (m, 2H), 8.10-7.98 (m, 3H), 7.87-7.85 (m, 1H), 7.60-7.58 (m, 1H), 6.62-6.59 (m, 1H), 3.93 (s, 3H), 3.58 (s, 3H), 1.97 (s, 3H))

Stage 79.1.1. 2-Pyrazol-1-yl-5-(4,4,5,5-tetramethyl-[1,3,2]dioxaborolan-2-yl)-pyridine

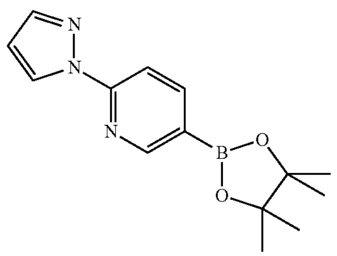 [SMILES: CC1(C)OB(c2ccc(-n3cccn3)nc2)OC1(C)C]

The title compound was synthesized in a similar manner as described for Stage 5.1.1 using 5-bromo-2-pyrazol-1-yl-pyridine (Combi-Blocks, San Diego, USA) to give the title compound as a brown solid. (HPLC: $t_R$ 2.19 min (Method A); M+H=272 MS-ES).

Example 80.1

1-(1,3-Dimethyl-1H-pyrazol-4-yl)-3-methyl-8-(2-methylamino-pyrimidin-5-yl)-1,3-dihydro-imidazo[4,5-c]quinolin-2-one

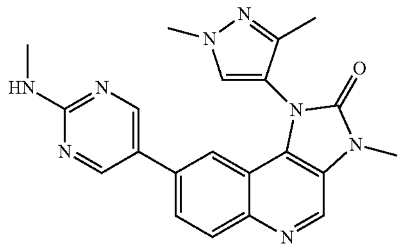 [SMILES: CNc1ncc(-c2ccc3ncc4c(c3c2)n(-c2cn(C)nc2C)c(=O)n4C)cn1]

The title compound was synthesized in a similar manner as described for Example 1.1 using 8-bromo-1-(1,3-dimethyl-1H-pyrazol-4-yl)-3-methyl-1,3-dihydro-imidazo[4,5-c]quinolin-2-one (Intermediate A) and methyl-[5-(4,4,5,5-tetramethyl-[1,3,2]dioxaborolan-2-yl)-pyrimidin-2-yl]-amine (Stage 80.1.1) to give the title compound as a white solid. (HPLC: $t_R$ 2.18 min (Method A); M+H=401 MS-ES; $^1$H-NMR ($d_6$-DMSO, 400 MHz) 8.93 (s, 1H), 8.49-8.34 (s, br, 2H), 8.13-8.11 (m, 1H), 8.07-8.04 (m, 1H), 7.89-7.85 (m, 1H), 7.42-7.37 (m, 2H), 3.90 (s, 3H), 3.57 (s, 3H), 2.84 (d, 3H), 1.96 (s, 3H))

Stage 80.1.1. Methyl-[5-(4,4,5,5-tetramethyl-[1,3,2]dioxaborolan-2-yl)-pyrimidin-2-yl]amine

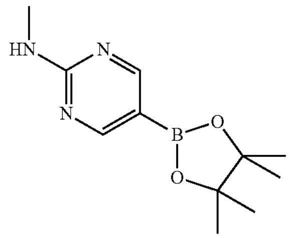 [SMILES: CNc1ncc(B2OC(C)(C)C(C)(C)O2)cn1]

The title compound was synthesized in a similar manner as described for Stage 5.1.1 using (5-bromo-pyrimidin-2-yl)-methyl-amine (Combi-Blocks, San Diego, USA) to give the title compound as a beige solid. (HPLC: $t_R$ 1.20 min (Method A); M+H=236 MS-ES).

The following example was synthesized in a similar manner as described for Example 1.1 using methyl-[5-(4,4,5,5-tetramethyl-[1,3,2]dioxaborolan-2-yl)-pyrimidin-2-yl]-amine (Stage 80.1.1) and the specified intermediate.

| Example | Intermed. | structure | Name of the example | MS-ES (M + H) | HPLC $t_R$ (min) |
|---|---|---|---|---|---|
| 80.2 | H | 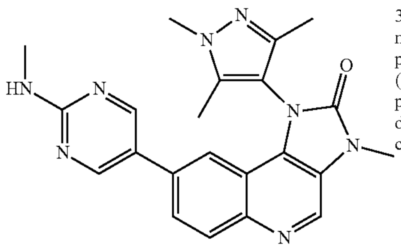 | 3-Methyl-8-(2-methylamino-pyrimidin-5-yl)-1-(1,3,5-trimethyl-1H-pyrazol-4-yl)-1,3-dihydro-imidazo[4,5-c]quinolin-2-one | 415 | 2.27 |

Example 81.1

8-(2-Amino-pyrimidin-5-yl)-1-(1,3-dimethyl-1H-pyrazol-4-yl)-3-methyl-1,3-dihydro-imidazo[4,5-c]quinolin-2-one

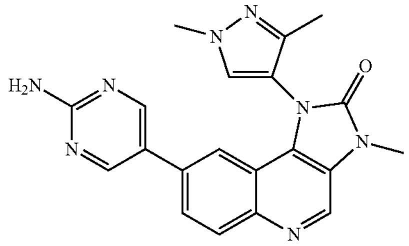 [SMILES: Cc1nn(C)cc1-n1c(=O)n(C)c2cnc3ccc(-c4cnc(N)nc4)cc3c21]

The title compound was synthesized in a similar manner as described for Example 1.1 using 8-bromo-1-(1,3-dimethyl-1H-pyrazol-4-yl)-3-methyl-1,3-dihydro-imidazo[4,5-c]quinolin-2-one (Intermediate A) and 5-(4,4,5,5-tetramethyl-[1,3,2]dioxaborolan-2-yl)-pyrimidin-2-ylamine (Combi-Blocks, San Diego, USA) to give the title compound as a white solid. (HPLC: $t_R$ 2.04 min (Method A); M+H=387 MS-ES; $^1$H-NMR ($d_6$-DMSO, 400 MHz) 8.93 (s, 1H), 8.37 (s, 2H), 8.14-8.12 (m, 1H), 8.07-8.03 (m, 1H), 7.90-7.86 (m, 1H), 7.41-7.38 (m, 1H), 6.93 (s, br, 2H), 3.91 (s, 3H), 3.57 (s, 3H), 1.95 (s, 3H))

The following example was synthesized in a similar manner as described for Example 1.1 using 5-(4,4,5,5-tetramethyl-[1,3,2]dioxaborolan-2-yl)-pyrimidin-2-ylamine and the specified intermediate.

| Example | Intermed. | structure | Name of the example | MS-ES (M + H) | HPLC $t_R$ (min) |
|---|---|---|---|---|---|
| 81.2 | H | 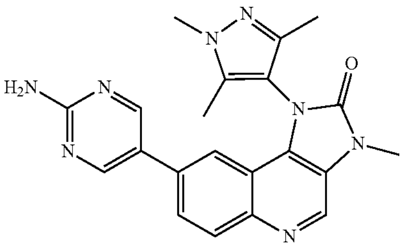 [SMILES: Cc1nn(C)c(C)c1-n1c(=O)n(C)c2cnc3ccc(-c4cnc(N)nc4)cc3c21] | 8-(2-Amino-pyrimidin-5-yl)-3-methyl-1-(1,3,5-trimethyl-1H-pyrazol-4-yl)-1,3-dihydro-imidazo[4,5-c]quinolin-2-one | 401 | 2.13 |

Example 82

1-(1,3-Dimethyl-1H-pyrazol-4-yl)-8-(3-isopropoxy-phenyl)-3-methyl-1,3-dihydro-imidazo[4,5-c]quinolin-2-one

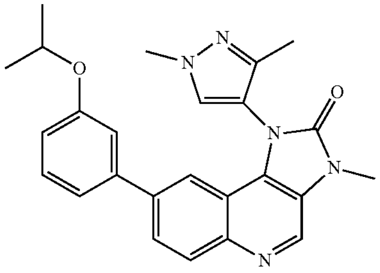 [SMILES: Cc1nn(C)cc1-n1c(=O)n(C)c2cnc3ccc(-c4cccc(OC(C)C)c4)cc3c21]

The title compound was synthesized in a similar manner as described for Example 1.1 using 8-bromo-1-(1,3-dimethyl-1H-pyrazol-4-yl)-3-methyl-1,3-dihydro-imidazo[4,5-c]quinolin-2-one (Intermediate A) and 3-isopropoxyphenylboronic acid (Aldrich, Buchs, Switzerland) to give the title compound as a white solid. (HPLC: $t_R$ 2.95 min (Method A); M+H=428 MS-ES; $^1$H-NMR ($d_6$-DMSO, 400 MHz) 8.96 (s, 1H), 8.19-8.16 (m, 1H), 8.09-8.05 (m, 1H), 7.94-7.89 (m, 1H), 7.57-7.54 (m, 1H), 7.39-7.33 (m, 1H), 7.10-7.06 (m, 1H), 6.94-9-6.90 (m, 2H), 4.68 (hp, 1H), 3.92 (s, 3H), 3.57 (s, 3H), 1.95 (s, 3H), 1.30 (t, 6H))

Example 83

1-(1,3-Dimethyl-1H-pyrazol-4-yl)-8-(2-fluoro-3-isopropoxy-phenyl)-3-methyl-1,3-dihydro-imidazo[4,5-c]quinolin-2-one

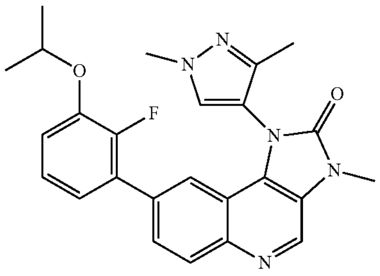 [SMILES: Cc1nn(C)cc1-n1c(=O)n(C)c2cnc3ccc(-c4cccc(OC(C)C)c4F)cc3c21]

The title compound was synthesized in a similar manner as described for Example 1.1 using 8-bromo-1-(1,3-dimethyl-1H-pyrazol-4-yl)-3-methyl-1,3-dihydro-imidazo[4,5-c]quinolin-2-one (Intermediate A) and 2-fluoro-3-isopropoxyphenylboronic acid (Combi-Blocks, San Diego, USA) to give the title compound as a white solid. (HPLC: $t_R$ 2.91 min (Method A); M+H=446 MS-ES; $^1$H-NMR ($d_6$-DMSO, 400 MHz) 8.99 (s, 1H), 8.11-8.07 (m, 2H), 7.77-7.73 (m, 1H), 7.56-7.54 (m, 1H), 7.22-7.15 (m, 2H), 6.99-6.92 (m, 1H), 4.64 (hp, 1H), 3.87 (s, 3H), 3.58 (s, 3H), 1.94 (s, 3H), 1.33-1.28 (m, 6H))

Example 84.1

1-(1,3-Dimethyl-1H-pyrazol-4-yl)-8-(5-isopropoxy-6-methyl-pyridin-3-yl)-3-methyl-1,3-dihydro-imidazo[4,5-c]quinolin-2-one

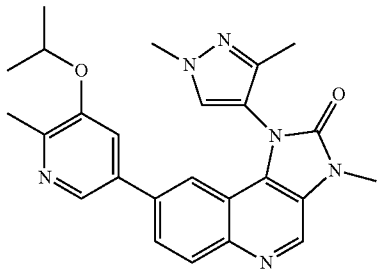 [SMILES: Cc1ncc(-c2ccc3ncc4c(c3c2)n(-c2cn(C)nc2C)c(=O)n4C)cc1OC(C)C]

The title compound was synthesized in a similar manner as described for Example 1.1 using 8-bromo-1-(1,3-dimethyl-1H-pyrazol-4-yl)-3-methyl-1,3-dihydro-imidazo[4,5-c]quinolin-2-one (Intermediate A) and 3-isopropoxy-2-methyl-5-(4,4,5,5-tetramethyl-[1,3,2]dioxaborolan-2-yl)-pyridine (Stage 84.1.1) to give the title compound as a white solid. (HPLC: $t_R$ 2.31 min (Method A); M+H=443 MS-ES; $^1$H-NMR ($d_6$-DMSO, 400 MHz) 8.98 (s, 1H), 8.17-8.16 (m, 1H), 8.13-8.09 (m, 2H), 8.00-7.96 (m, 1H), 7.59-7.57 (m, 1H), 7.31-7.29 (m, 1H), 4.74 (hp, 1H), 3.89 (s, 3H), 3.58 (s, 3H), 2.36 (s, 3H), 1.97 (s, 3H), 1.35 (t, 6H))

Stage 84.1.1. 3-Isopropoxy-2-methyl-5-(4,4,5,5-tetramethyl-[1,3,2]dioxaborolan-2-yl)-pyridine

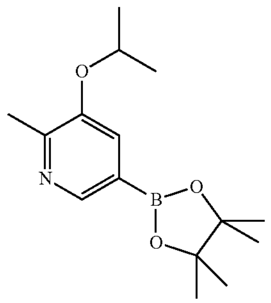

The title compound was synthesized in a similar manner as described for Stage 5.1.1 using 5-bromo-3-isopropoxy-2-methyl-pyridine (Stage 84.1.2) to give the title compound as a brown oil. (HPLC: $t_R$ 2.21 min (Method A); M+H=278 MS-ES).

Stage 84.1.2. 5-Bromo-3-isopropoxy-2-methyl-pyridine

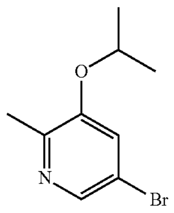

To a solution of 5-bromo-2-methyl-pyridin-3-ylamine (Stage 75.1.4, 400 mg, 2.13 mmol) in isopropanol (33 ml) were added 4 M HCl in dioxane (0.535 ml, 2.13 mmol) and isoamyl nitrite (1.25 g, 10.7 mmol). The reaction mixture was heated at 80° C. for 2.5 h, before being evaporated to dryness. The residue was dissolved in EtOAc and washed with saturated aqueous $NaHCO_3$. The aqueous layer was extracted with EtOAc and the combined organic layers were dried over $Na_2SO_4$, filtered and evaporated. The residue was dry loaded on silica gel and purified by MPLC (heptane/EtOAc 0% to 30%) to give the title compound as an orange oil (HPLC: $t_R$ 2.47 min (Method A); M+H=230, 232 MS-ES).

The following example was synthesized in a similar manner as described for Example 1.1 using 3-isopropoxy-2-methyl-5-(4,4,5,5-tetramethyl-[1,3,2]dioxaborolan-2-yl)-pyridine (Stage 84.1.1) and the specified intermediate.

| Example | Intermed. | structure | Name of the example | MS-ES (M + H) | HPLC $t_R$ (min) |
|---|---|---|---|---|---|
| 84.2 | F | 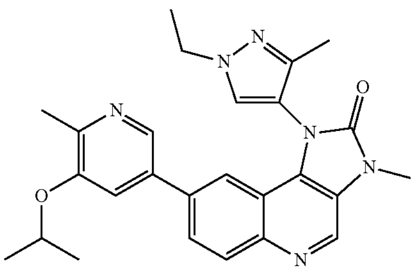 [SMILES: CCn1cc(-n2c(=O)n(C)c3cnc4ccc(-c5cnc(C)c(OC(C)C)c5)cc4c32)c(C)n1] | 1-(1-Ethyl-3-methyl-1H-pyrazol-4-yl)-8-(5-isopropoxy-6-methyl-pyridin-3-yl)-3-methyl-1,3-dihydro-imidazo[4,5-c]quinolin-2-one | 457 | 2.38 |

Example 85.1

1-(1,3-Dimethyl-1H-pyrazol-4-yl)-8-(5-ethoxy-6-methyl-pyridin-3-yl)-3-methyl-1,3-dihydro-imidazo[4,5-c]quinolin-2-one

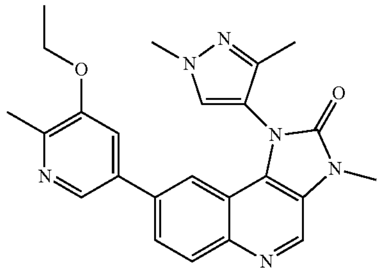

The title compound was synthesized in a similar manner as described for Example 1.1 using 8-bromo-1-(1,3-dimethyl-1H-pyrazol-4-yl)-3-methyl-1,3-dihydro-imidazo[4,5-c]quinolin-2-one (Intermediate A) and 3-ethoxy-2-methyl-5-(4,4,5,5-tetramethyl-[1,3,2]dioxaborolan-2-yl)-pyridine (Stage 85.1.1) to give the title compound as a white solid. (HPLC: $t_R$ 2.22 min (Method A); M+H=429 MS-ES; $^1$H-NMR ($d_6$-DMSO, 400 MHz) 8.98 (s, 1H), 8.19-8.17 (m, 1H), 8.13-8.09 (m, 2H), 8.02-7.98 (m, 1H), 7.61-7.59 (m, 1H), 7.30-7.28 (m, 1H), 4.20-4.12 (m, 2H), 3.89 (s, 3H), 3.58 (s, 3H), 2.39 (s, 3H), 1.97 (s, 3H), 1.43 (t, 3H))

Stage 85.1.1. 3-Ethoxy-2-methyl-5-(4,4,5,5-tetramethyl-[1,3,2]dioxaborolan-2-yl)-pyridine

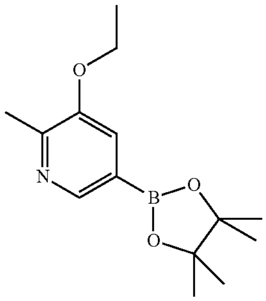

The title compound was synthesized in a similar manner are described for Stage 84.1.1-2 using ethanol instead of isopropanol. (HPLC: $t_R$ 2.03 min (Method A); M+H=264 MS-ES)

The following examples were synthesized in a similar manner as described for Example 1.1 using 3-ethoxy-2-methyl-5-(4,4,5,5-tetramethyl-[1,3,2]dioxaborolan-2-yl)-pyridine (Stage 85.1.1) and the specified intermediate.

| Example | Intermed. | structure | Name of the example | MS-ES (M + H) | HPLC $t_R$ (min) |
|---|---|---|---|---|---|
| 85.2 | N | 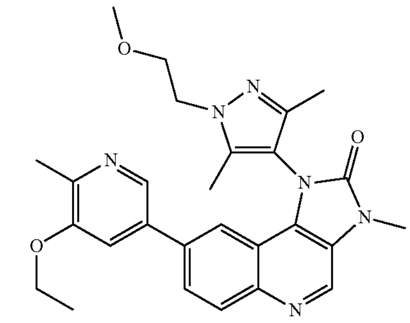 | 8-(5-Ethoxy-6-methyl-pyridin-3-yl)-1-[1-(2-methoxy-ethyl)-3,5-dimethyl-1H-pyrazol-4-yl]-3-methyl-1,3-dihydro-imidazo[4,5-c]quinolin-2-one | 487 | 2.33 |
| 85.3 | O | 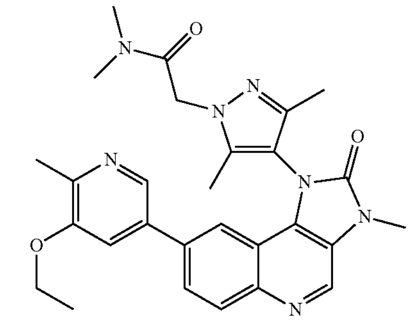 | 2-{4-[8-(5-Ethoxy-6-methyl-pyridin-3-yl)-3-methyl-2-oxo-2,3-dihydro-imidazo[4,5-c]quinolin-1-yl]-3,5-dimethyl-pyrazol-1-yl}-N,N-dimethyl-acetamide | 514 | 2.30 |

Example 86.1

1-(3-Chloro-1-methyl-1H-pyrazol-4-yl)-8-[5-(2-methoxy-ethoxy)-6-methyl-pyridin-3-yl]-3-methyl-1,3-dihydro-imidazo[4,5-c]quinolin-2-one

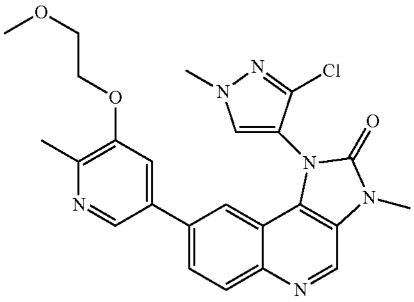

The title compound was synthesized in a similar manner as described for Example 1.1 using 8-bromo-1-(1,3-dimethyl-1H-pyrazol-4-yl)-3-methyl-1,3-dihydro-imidazo[4,5-c]quinolin-2-one (Intermediate A) and 3-(2-methoxy-ethoxy)-2-methyl-5-(4,4,5,5-tetramethyl-[1,3,2]dioxaborolan-2-yl)- pyridine (Stage 86.1.1) to give the title compound as a white solid. (HPLC: $t_R$ 2.33 min (Method A); M+H=479 MS-ES; $^1$H-NMR ($d_6$-DMSO, 400 MHz) 9.01 (s, 1H), 8.38 (s, 1H), 8.22-8.20 (m, 1H), 8.15-8.12 (m, 1H), 8.03-8.00 (m, 1H), 7.58-7.57 (m, 1H), 7.39-7.37 (m, 1H), 4.30-4.19 (m, 2H), 3.97 (s, 3H), 3.76 (t, 2H), 3.60 (s, 3H), 3.36 (s, 3H), 2.40 (s, 3H))

Stage 86.1.1. 3-(2-Methoxy-ethoxy)-2-methyl-5-(4,4,5,5-tetramethyl-[1,3,2]dioxaborolan-2-yl)-pyridine

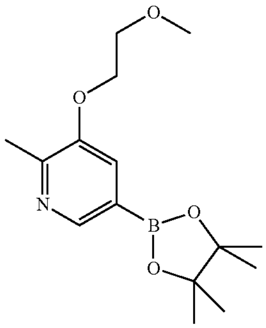

The title compound was synthesized in a similar manner are described for Stage 84.1.1-2 using 2-methoxyethanol instead of isopropanol. (HPLC: tR 2.05 min (Method A); M+H=294 MS-ES)

The following example was synthesized in a similar manner as described for Example 1.1 using 3-(2-methoxy-ethoxy)-2-methyl-5-(4,4,5,5-tetramethyl-[1,3,2]dioxaborolan-2-yl)-pyridine (Stage 86.1.1) and the specified intermediate.

Example 87.1

1-(1,3-Dimethyl-1H-pyrazol-4-yl)-8-(5-ethylamino-6-methyl-pyridin-3-yl)-3-methyl-1,3-dihydro-imidazo[4,5-c]quinolin-2-one

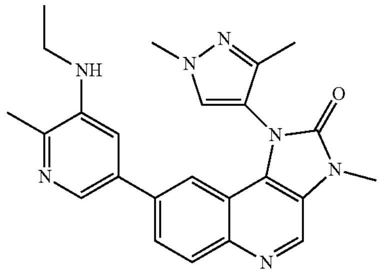

The title compound was synthesized in a similar manner as described for Example 1.1 using 8-bromo-1-(1,3-dimethyl-1H-pyrazol-4-yl)-3-methyl-1,3-dihydro-imidazo[4,5-c]quinolin-2-one (Intermediate A) and ethyl-[2-methyl-5-(4,4,5,5-tetramethyl-[1,3,2]dioxaborolan-2-yl)-pyridin-3-yl]-amine (Stage 87.1.1) to give the title compound as a white solid. (HPLC: $t_R$ 2.18 min (Method A); M+H=428 MS-ES; $^1$H-NMR ($d_6$-DMSO, 400 MHz) 8.96 (s, 1H), 8.11-8.07 (m, 2H), 7.95-7.91 (m, 1H), 7.88-7.86 (m, 1H), 7.61-7.59 (m, 1H), 6.78-6.76 (m, 1H), 5.23 (t, 1H), 3.88 (s, 3H), 3.58 (s, 3H), 3.21-3.14 (m, 2H), 2.33 (s, 3H), 1.97 (s, 3H), 1.25 (t, 3H))

Stage 87.1.1. Ethyl-[2-methyl-5-(4,4,5,5-tetramethyl-[1,3,2]dioxaborolan-2-yl)-pyridin-3-yl]-amine

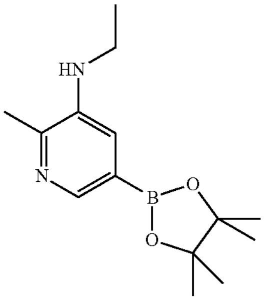

| Example | Intermed. | structure | Name of the example | MS-ES (M + H) | HPLC tR (min) |
|---|---|---|---|---|---|
| 86.2 | A | 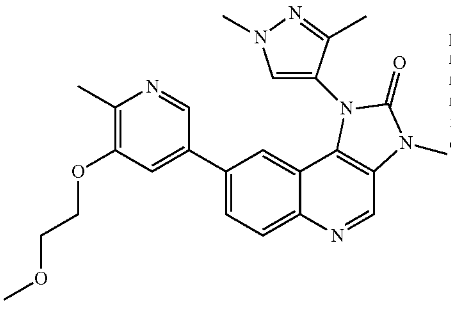 | 1-(1,3-Dimethyl-1H-pyrazol-4-yl)-8-[5-(2-methoxy-ethoxy)-6-methyl-pyridin-3-yl]-3-methyl-1,3-dihydro-imidazo[4,5-c]quinolin-2-one | 459 | 2.15 |

The title compound was synthesized in a similar manner as described for Stage 5.1.1 using (5-bromo-2-methyl-pyridin-3-yl)-ethyl-amine (Stage 87.1.2) to give the title compound as a brown oil. (HPLC: $t_R$ 1.85 min (Method A); M+H=263 MS-ES).

Stage 87.1.2. (5-Bromo-2-methyl-pyridin-3-yl)-ethyl-amine

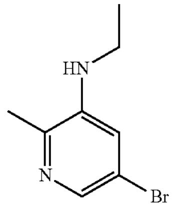

A solution of 5-bromo-2-methyl-pyridin-3-ylamine (Stage 75.1.4, 300 mg, 1.604 mmol), acetaldehyde (Fluka, Buchs, Switzerland, 71 mg, 1.6 mmol) in dichloromethane (30 ml) was stirred for 1.5 h at rt in presence of acetic acid (0.3 ml, 5.24 mmol). Was added sodium triacetoxyborohydride (850 mg, 4.01 mmol) and the reaction mixture was stirred 4 h at rt, then was added acetaldehyde (45 mg, 1.02 mmol) twice at 1.5 h interval and the reaction was stirred at rt for 15 h before being quenched with aqueous saturated $NaHCO_3$ and extracted with dichloromethane (2×). The combined organic layers were dried over $Na_2SO_4$, filtered and evaporated to dryness. (HPLC: $t_R$ 2.08 min (Method A); M+H=215, 217 MS-ES).

The following examples were synthesized in a similar manner as described for Example 1.1 using ethyl-[2-methyl-5-(4,4,5,5-tetramethyl-[1,3,2]dioxaborolan-2-yl)-pyridin-3-yl]-amine (Stage 87.1.1) and the specified intermediate.

| Example | Intermed. | structure | Name of the example | MS-ES (M + H) | HPLC $t_R$ (min) |
|---|---|---|---|---|---|
| 87.2 | K | 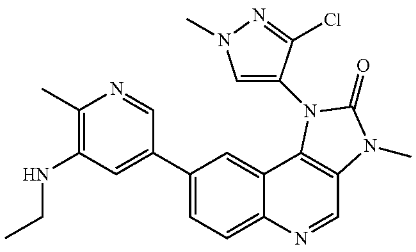 [SMILES: CCNc1cc(-c2ccc3ncc4c(c3c2)n(-c2cn(C)nc2Cl)c(=O)n4C)cnc1C] | 1-(3-Chloro-1-methyl-1H-pyrazol-4-yl)-8-(5-ethylamino-6-methyl-pyridin-3-yl)-3-methyl-1,3-dihydro-imidazo[4,5-c]quinolin-2-one | 448 | 2.35 |
| 87.3 | F | 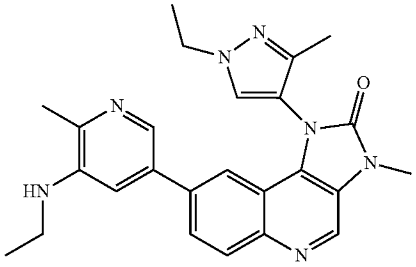 [SMILES: CCNc1cc(-c2ccc3ncc4c(c3c2)n(-c2cn(CC)nc2C)c(=O)n4C)cnc1C] | 8-(5-Ethylamino-6-methyl-pyridin-3-yl)-1-(1-ethyl-3-methyl-1H-pyrazol-4-yl)-3-methyl-1,3-dihydro-imidazo[4,5-c]quinolin-2-one | 442 | 2.22 |
| 87.4 | N | 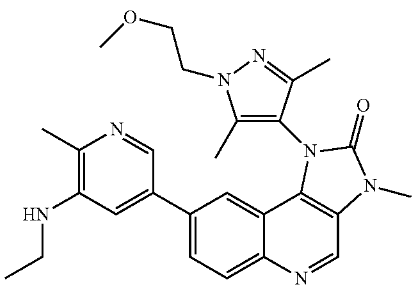 [SMILES: CCNc1cc(-c2ccc3ncc4c(c3c2)n(-c2c(C)nn(CCOC)c2C)c(=O)n4C)cnc1C] | 8-(5-Ethylamino-6-methyl-pyridin-3-yl)-1-[1-(2-methoxy-ethyl)-3,5-dimethyl-1H-pyrazol-4-yl]-3-methyl-1,3-dihydro-imidazo[4,5-c]quinolin-2-one | 486 | 2.26 |

-continued

| Example | Intermed. | structure | Name of the example | MS-ES (M + H) | HPLC $t_R$ (min) |
|---|---|---|---|---|---|
| 87.5 | O | 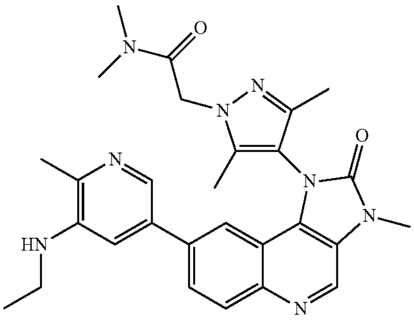 [SMILES: CCNc1cc(-c2ccc3ncc4c(c3c2)n(-c2c(C)nn(CC(=O)N(C)C)c2C)c(=O)n4C)cnc1C] | 2-{4-[8-(5-Ethylamino-6-methyl-pyridin-3-yl)-3-methyl-2-oxo-2,3-dihydro-imidazo[4,5-c]quinolin-1-yl]-3,5-dimethyl-pyrazol-1-yl}-N,N-dimethyl-acetamide | 513 | 2.25 |

Example 88.1

8-(5-Amino-6-methyl-pyridin-3-yl)-1-(3-chloro-1-methyl-1H-pyrazol-4-yl)-3-methyl-1,3-dihydro-imidazo[4,5-c]quinolin-2-one

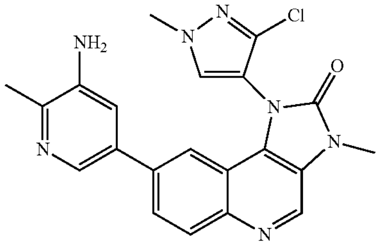

The title compound was synthesized in a similar manner as described for Example 1.1 using 8-bromo-1-(3-chloro-1-methyl-1H-pyrazol-4-yl)-3-methyl-1,3-dihydro-imidazo[4,5-c]quinolin-2-one Intermediate K) and 2-methyl-5-(4,4,5,5-tetramethyl-[1,3,2]dioxaborolan-2-yl)-pyridin-3-ylamine (Stage 88.1.1) to give the title compound as a white solid. (HPLC: $t_R$ 2.14 min (Method A); M+H=420 MS-ES; $^1$H-NMR ($d_6$-DMSO, 400 MHz) 8.99 (s, 1H), 8.38 (s, 1H), 8.13-8.10 (m, 1H), 7.80-7.77 (m, 1H), 7.75-7.73 (m, 1H), 7.48-7.47 (m, 1H), 7.08-7.06 (m, 1H), 5.21-5.16 (m, br, 2H), 3.99 (s, 3H), 3.59 (s, 3H), 2.30 (s, 3H))

Stage 88.1.1. 2-Methyl-5-(4,4,5,5-tetramethyl-[1,3,2]dioxaborolan-2-yl)-pyridin-3-ylamine lp;2p

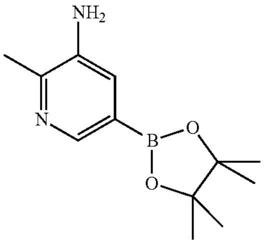

The title compound was synthesized in a similar manner as described for stage 5.1.1 using 5-bromo-2-methyl-pyridin-3-ylamine (Stage 75.1.4) to give the title compound as a brown oil. (HPLC: $t_R$ 1.30 min (Method A); M+H=235 MS-ES).

The following example was synthesized in a similar manner as described for Example 1.1 using 3-(2-methoxy-ethoxy)-2-methyl-5-(4,4,5,5-tetramethyl-[1,3,2]dioxaborolan-2-yl)-pyridine (stage 86.1.1) and the specified intermediate.

| Example | Intermed. | structure | Name of the example | MS-ES (M + H) | HPLC $t_R$ (min) |
|---|---|---|---|---|---|
| 88.2 | A | 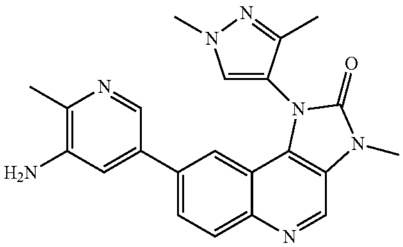 | 8-(5-Amino-6-methyl-pyridin-3-yl)-1-(1,3-dimethyl-1H-pyrazol-4-yl)-3-methyl-1,3-dihydro-imidazo[4,5-c]quinolin-2-one | 400 | 2.01 |

Example 89

8-(5-Amino-6-methoxy-pyridin-3-yl)-1-(3-chloro-1-methyl-1H-pyrazol-4-yl)-3-methyl-1,3-dihydro-imidazo[4,5-c]quinolin-2-one

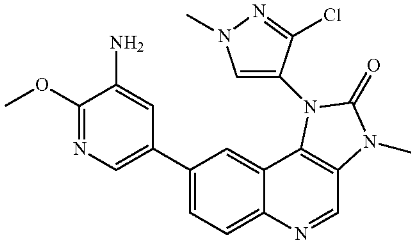

The title compound was synthesized in a similar manner as described for Example 1.1 using 8-bromo-1-(3-chloro-1-methyl-1H-pyrazol-4-yl)-3-methyl-1,3-dihydro-imidazo[4,5-c]quinolin-2-one (Intermediate K) and 2-methoxy-5-(4,4,5,5-tetramethyl-[1,3,2]dioxaborolan-2-yl)-pyridin-3-ylamine (Stage 89.1.1) to give the title compound as an off-white solid. (HPLC: $t_R$ 2.45 min (Method A); M+H=436 MS-ES; $^1$H-NMR ($d_6$-DMSO, 400 MHz) 8.97 (s, 1H), 8.38 (s, 1H), 8.11-8.07 (m, 1H), 7.80-7.75 (m, 1H), 7.48-7.42 (m, 2H), 7.03-7.00 (m, 1H), 5.15-5.07 (s, br, 2H), 4.00 (s, 3H), 3.90 (s, 3H), 3.59 (s, 3H))

Stage 89.1.1. 2-Methoxy-5-(4,4,5,5-tetramethyl-[1,3,2]dioxaborolan-2-yl)-pyridin-3-ylamine

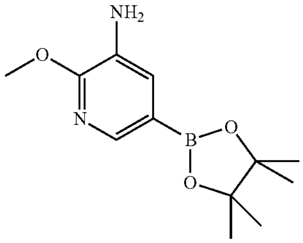

The title compound was synthesized in a similar manner as described for Stage 5.1.1 using 5-bromo-2-methoxy-pyridin-3-ylamine (Stage 89.1.2) to give the title compound as a brown oil. (HPLC: $t_R$ 1.10 min (Method A); M+H=251 MS-ES).

Stage 89.1.2. 5-Bromo-2-methoxy-pyridin-3-ylamine

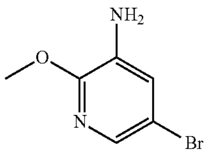

The title compound was synthesized in a similar manner as described for Stage 67.1.4 using 5-Bromo-2-methoxy-3-nitro-pyridine (Stage 62.1.4) to give the title compound as an off-white solid. (HPLC: $t_R$ 2.51 min (Method A); M+H=203, 205 MS-ES).

Example 90.1

1-(3-Chloro-1-methyl-1H-pyrazol-4-yl)-8-(5-ethylamino-6-methoxy-pyridin-3-yl)-3-methyl-1,3-dihydro-imidazo[4,5-c]quinolin-2-one

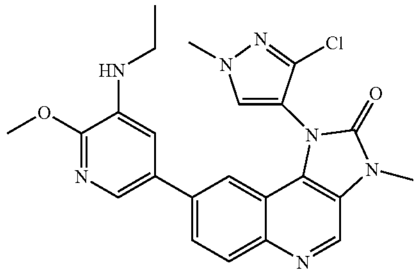

The title compound was synthesized in a similar manner as described for Example 1.1 using 8-bromo-1-(3-chloro-1-methyl-1H-pyrazol-4-yl)-3-methyl-1,3-dihydro-imidazo[4,5-c]quinolin-2-one (Intermediate K) and ethyl-[2-methoxy-5-(4,4,5,5-tetramethyl-[1,3,2]dioxaborolan-2-yl)-pyridin-3-yl]-amine (stage 90.1.1, 0.138 mmol) to give the title compound as a white solid. (HPLC: $t_R$ 2.45 min (Method A); M+H=415 MS-ES; $^1$H-NMR ($d_6$-DMSO, 400 MHz) 8.99 (s, 1H), 8.24-8.16 (m, 2H), 8.14-8.07 (m, 1H), 8.02-7.94 (m, 1H), 7.66-7.59 (m, 1H), 7.09-7.02 (m, 1H), 6.87-6.80 (m, 1H), 4.32 (q, 2H), 3.94 (s, 3H), 3.57 (s, 3H), 1.96 (s, 3H), 1.34 (t, 3H))

Stage 90.1.1. Ethyl-[2-methoxy-5-(4,4,5,5-tetramethyl-[1,3,2]dioxaborolan-2-yl)-pyridin-3-yl]-amine

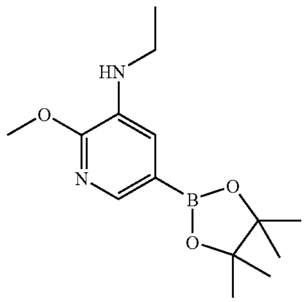

The title compound was synthesized in a similar manner as described for Stage 87.1.1-2 using 5-bromo-2-methoxy-pyridin-3-ylamine (Stage 89.1.2) to give the title compound as a brown oil. (HPLC: $t_R$ 1.75 min (Method A); M+H=279 MS-ES)

The following example was synthesized in a similar manner as described for Example 1.1 using ethyl-[2-methoxy-5-(4,4,5,5-tetramethyl-[1,3,2]dioxaborolan-2-yl)-pyridin-3-yl]-amine (Stage 90.1.1) and the specified intermediate.

| Example | Intermed. | structure | Name of the example | MS-ES (M + H) | HPLC $t_R$ (min) |
|---|---|---|---|---|---|
| 90.2 | N | 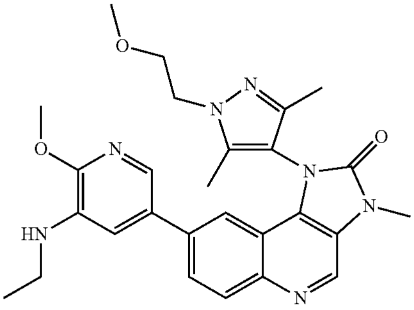 [SMILES: CCNc1cc(-c2ccc3ncc4c(c3c2)n(-c2c(C)nn(CCOC)c2C)c(=O)n4C)cnc1OC] | 8-(5-Ethylamino-6-methoxy-pyridin-3-yl)-1-[1-(2-methoxy-ethyl)-3,5-dimethyl-1H-pyrazol-4-yl]-3-methyl-1,3-dihydro-imidazo[4,5-c] quinolin-2-one | 502 | 2.74 |

Example 91

1-(1,3-Dimethyl-1H-pyrazol-4-yl)-8-(2-ethoxy-pyridin-4-yl)-3-methyl-1,3-dihydro-imidazo[4,5-c] quinolin-2-one

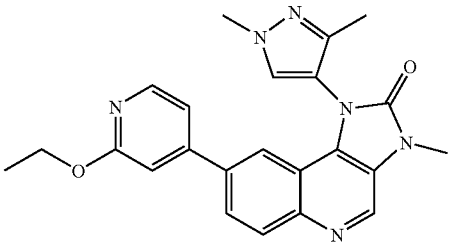 [SMILES: CCOc1cc(-c2ccc3ncc4c(c3c2)n(-c2cn(C)nc2C)c(=O)n4C)ccn1]

The title compound was synthesized in a similar manner as described for Example 1.1 using 8-bromo-1-(1,3-dimethyl-1H-pyrazol-4-yl)-3-methyl-1,3-dihydro-imidazo[4,5-c] quinolin-2-one (Intermediate A, 40 mg, 0.107 mmol) and 2-ethoxy-4-pyridinylboronic acid (Combi-Blocks, San Diego, USA, 22.4 mg, 0.134 mmol) to give the title compound as a white solid. (HPLC: $t_R$ 2.45 min (Method A); M+H=415 MS-ES; $^1$H-NMR ($d_6$-DMSO, 400 MHz) 8.99 (s, 1H), 8.24-8.16 (m, 2H), 8.14-8.07 (m, 1H), 8.02-7.94 (m, 1H), 7.66-7.59 (m, 1H), 7.09-7.02 (m, 1H), 6.87-6.80 (m, 1H), 4.32 (q, 2H), 3.94 (s, 3H), 3.57 (s, 3H), 1.96 (s, 3H), 1.34 (t, 3H))

Example 92

1-(1,3-Dimethyl-1H-pyrazol-4-yl)-8-(2-isopropoxy-pyridin-4-yl)-3-methyl-1,3-dihydro-imidazo[4,5-c] quinolin-2-one

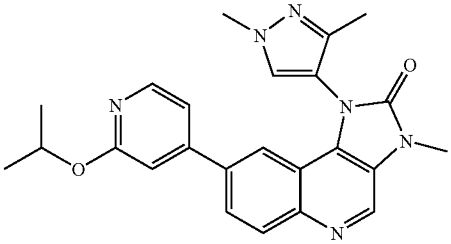 [SMILES: Cc1nn(C)cc1-n1c(=O)n(C)c2cnc3ccc(-c4ccnc(OC(C)C)c4)cc3c21]

The title compound was synthesized in a similar manner as described for Example 1.1 using 8-bromo-1-(1,3-dimethyl-1H-pyrazol-4-yl)-3-methyl-1,3-dihydro-imidazo[4,5-c] quinolin-2-one (Intermediate A) and 2-Isopropoxy-4-(4,4,5,5-tetramethyl-[1,3,2]dioxaborolan-2-yl)-pyridine (Stage 92.1.1) to give the title compound as a white solid. (HPLC: $t_R$ 2.56 min (Method A); M+H=429 MS-ES; $^1$H-NMR ($d_6$-DMSO, 400 MHz) 9.00 (s, 1H), 8.23-8.19 (m, 2H), 8.14-8.09 (m, 1H), 8.00-7.96 (m, 1H), 7.64-7.62 (m, 1H), 7.05-7.02 (m, 1H), 6.80-6.78 (m, 1H), 5.28 (hp, 2H), 3.96 (s, 3H), 3.59 (s, 3H), 1.94 (s, 311, 1.34-1.29 (m, 6H))

Stage 92.1.1. 2-Isopropoxy-4-(4,4,5,5-tetramethyl-[1,3,2]dioxaborolan-2-yl)-pyridine

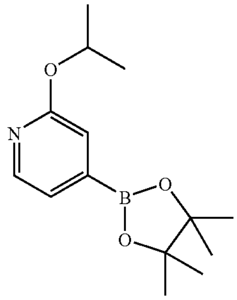 [SMILES: CC(C)Oc1cc(B2OC(C)(C)C(C)(C)O2)ccn1]

The title compound was synthesized in a similar manner as described for Stage 5.1.1 using 4-bromo-2-isopropoxy-pyridine (Stage 92.1.2) to give the title compound as a brown oil. (HPLC: $t_R$ 2.36 min (Method A); M+H=264 MS-ES)

Stage 92.1.2. 4-Bromo-2-isopropoxy-pyridine

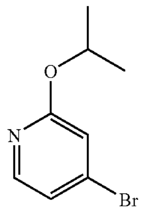

To isopropanol (12 ml) under Ar was added 55% sodium hydride in oil (343 mg, 7.86 mmol) in two portions. After 30 min stirring at rt was added 4-bromo-2-chloropyridine (Aldrich, Buchs, Switzerland, 1.01 g, 5.24 mmol) and the reaction mixture was heated with microwave irradiation to 150° C. for 30 min. The reaction mixture was concentrated, quenched with saturated aqueous $NaHCO_3$ and extracted with EtOAc. The organic layer was washed with brine, dried over $Na_2SO_4$, filtered and evaporated. The crude product was purified by MPLC (heptane/EtOAc 0% to 20%) to give the title compound as an oil. (HPLC: $t_R$ 3.58 min (Method A); M+H=216, 218 MS-ES)

Example 93

1-(1,3-Dimethyl-1H-pyrazol-4-yl)-8-(5-isopropoxy-6-methoxy-pyridin-3-yl)-3-methyl-1,3-dihydro-imidazo[4,5-c]quinolin-2-one

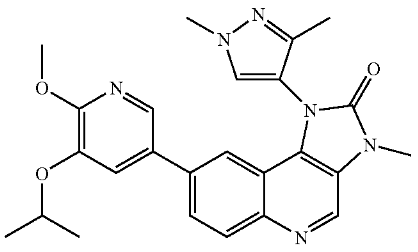 [SMILES: COc1ncc(-c2ccc3ncc4c(c3c2)n(-c2cn(C)nc2C)c(=O)n4C)cc1OC(C)C]

The title compound was synthesized in a similar manner as described for Example 1.1 using 8-bromo-1-(1,3-dimethyl-1H-pyrazol-4-yl)-3-methyl-1,3-dihydro-imidazo[4,5-c]quinolin-2-one (Intermediate A) and 3-isopropoxy-2-methoxy-5-(4,4,5,5-tetramethyl-[1,3,2]dioxaborolan-2-yl)-pyridine (Stage 93.1.1) to give the title compound as a white solid. (HPLC: $t_R$ 2.73 min (Method A); M+H=459 MS-ES; $^1$H-NMR ($d_6$-DMSO, 400 MHz) 8.96 (s, 1H), 8.11-8.07 (m, 2H), 7.97-7.93 (m, 1H), 7.92-7.90 (m, 1H), 7.53-7.51 (m, 1H), 7.23-7.21 (m, 1H), 4.70 (hp, 2H), 3.89 (s, 3H), 3.89 (s, 3H), 3.58 (s, 3H), 1.98 (s, 3H), 1.36-1.30 (m, 6H))

Stage 93.1.1. 3-Isopropoxy-2-methoxy-5-(4,4,5,5-tetramethyl-[1,3,2]dioxaborolan-2-yl)-pyridine

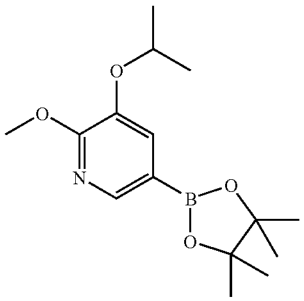

The title compound was synthesized in a similar manner as described for Stage 5.1.1 using 5- or 6-bromo-3-isopropoxy-2-methoxy-pyridine mixture (Stage 93.1.2) to give the title compound as an orange oil after silica gel flash chromatography purification ($CH_2Cl_2$/iPrOH 0% to 3.5%). (HPLC: $t_R$ 2.24 min (Method A); M+H=294 MS-ES)

Stage 93.1.2. 5- or 6-Bromo-3-isopropoxy-2-methoxy-pyridine

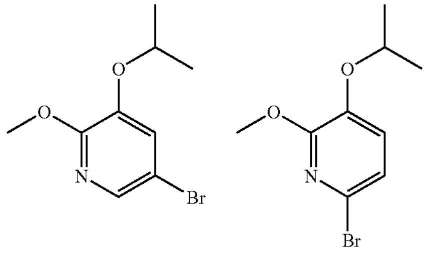

To a solution at 10° C. of 3-Isopropoxy-2-methoxy-pyridine (Stage 93.1.3, 865 mg, 5.17 mmol) and potassium acetate (635 mg, 6.47 mmol) in acetic acid (4 ml) was added over 1.5 h a solution of bromine (1.1 g, 6.88 mmol) in acetic acid (2 ml). The reaction was stirred for 1 h at rt an then basified with 20% aqueous NaOH and extracted with EtOAc (2×). The organic layers were washed with saturated aqueous $NaHCO_3$, dried over $Na_2SO_4$, filtered and evaporated. The crude product is purified by flash chromatography (hexane/EtOAc 40:1 to 15:1) to give the title compounds as an oil (1:2). (HPLC: $t_R$ 3.55 min (Method A); M+H=246, 248 MS-ES)

Stage 93.1.3. 3-Isopropoxy-2-methoxy-pyridine

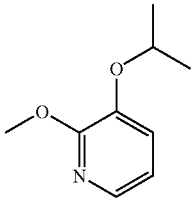

To a solution of methanolate obtained by dissolving sodium (534 mg, 23.25 mmol) in MeOH (8 ml) was added a solution of 2-chloro-3-isopropoxy-pyridine (Stage 93.1.4, 1.14 g, 6.64 mmol) in MeOH (2 ml). The reaction mixture was heated at 150° C. by microwave irradiation for 25 min then concentrated and quenched with EtOAc and brine. The organic layer was dried over $Na_2SO_4$, filtered and evaporated to give the title compound as an oil (HPLC: $t_R$ 2.66 min (Method A); M+H=264 MS-ES)

Stage 93.1.4. 2-Chloro-3-isopropoxy-pyridine

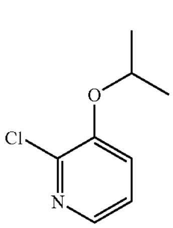

The title compound was synthesized in a similar manner as described for Stage 29.1.1 using 2-chloro-3-hydroxypyridine (Aldrich, Buchs, Switzerland). The crude product obtained was bulb-to-bulb distilled (160° C., ~0.1 mmbar) and then purified by MPLC (heptane/EtOAc 0% to 35%) to give the title compound as an oil. (HPLC: $t_R$ 2.97 min (Method A); M+H=172 MS-ES)

Example 94

1-(1,3-Dimethyl-1H-pyrazol-4-yl)-8-(5-ethoxy-6-methoxy-pyridin-3-yl)-3-methyl-1,3-dihydro-imidazo[4,5-c]quinolin-2-one

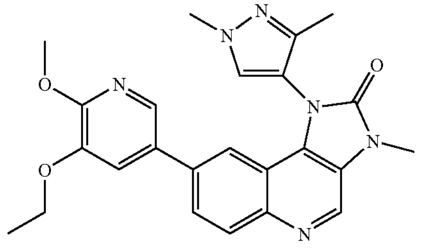 [SMILES: CCOc1cc(-c2ccc3ncc4c(c3c2)n(-c2cn(C)nc2C)c(=O)n4C)cnc1OC]

The title compound was synthesized in a similar manner as described for Example 1.1 using 8-bromo-1-(1,3-dimethyl-1H-pyrazol-4-yl)-3-methyl-1,3-dihydro-imidazo[4,5-c] quinolin-2-one (Intermediate A) and 3-ethoxy-2-methoxy-5-(4,4,5,5-tetramethyl-[1,3,2]dioxaborolan-2-yl)-pyridine (Stage 92.1.1) to give the title compound as a white solid. (HPLC: $t_R$ 2.63 min (Method A); M+H=445 MS-ES; $^1$H-NMR ($d_6$-DMSO, 400 MHz) 8.96 (s, 1H), 8.11-8.07 (m, 2H), 7.98-7.94 (m, 1H), 7.92-7.90 (m, 1H), 7.54-7.53 (m, 1H), 7.22-7.21 (m, 1H), 4.16-4.09 (m, 2H), 3.90 (s, 3H), 3.89 (s, 3H), 3.58 (s, 3H), 1.97 (s, 3H), 1.41 (t, 3H))

Stage 94.1.1. 3-Ethoxy-2-methoxy-5-(4,4,5,5-tetramethyl-[1,3,2]dioxaborolan-2-yl)-pyridine

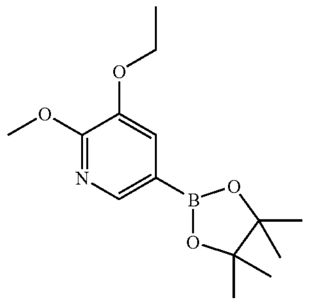

The title compound was synthesized in a similar manner as described for Stage 93.1.1-4 using isopropanol as replacement for ethanol to give the title compound as a brown oil. (HPLC: $t_R$ 2.09 min (Method A))

Example 95

8-(5-Diethylamino-pyridin-3-yl)-1-(1,3-dimethyl-1H-pyrazol-4-yl)-3-methyl-1,3-dihydro-imidazo[4,5-c]quinolin-2-one

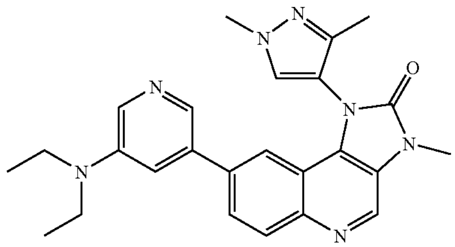 [SMILES: CCN(CC)c1cncc(-c2ccc3ncc4c(c3c2)n(-c2cn(C)nc2C)c(=O)n4C)c1]

The title compound was synthesized in a similar manner as described for Example 1.1 using 8-bromo-1-(1,3-dimethyl-1H-pyrazol-4-yl)-3-methyl-1,3-dihydro-imidazo[4,5-c] quinolin-2-one (Intermediate A) and diethyl-[5-(4,4,5,5-tetramethyl-[1,3,2]dioxaborolan-2-yl)-pyridin-3-yl]-amine (Stage 95.1.1) to give the title compound as a white solid. (HPLC: $t_R$ 2.31 min (Method A); M+H=442 MS-ES; $^1$H-NMR ($d_6$-DMSO, 400 MHz) 8.98 (s, 1H), 8.13-8.09 (m, 2H), 8.07-8.05 (m, 1H), 7.96-7.91 (m, 2H), 7.60-7.58 (m, 1H), 6.95-6.92 (m, 1H), 3.87 (s, 3H), 3.58 (s, 3H), 3.46-3.39 (m, 4H), 1.97 (s, 3H), 1.13 (t, 6H))

Stage 95.1.1. Diethyl-[5-(4,4,5,5-tetramethyl-[1,3,2] dioxaborolan-2-yl)-pyridin-3-yl]-amine

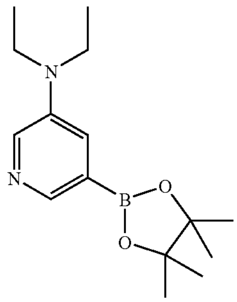 [SMILES: CCN(CC)c1cncc(B2OC(C)(C)C(C)(C)O2)c1]

The title compound was synthesized in a similar manner as described for Stage 5.1.1 using (5-bromo-pyridin-3-yl)-diethyl-amine (Stage 95.1.2) to give the title compound as a brown oil. (HPLC: $t_R$ 2.14 min (Method A); M+H=277 MS-ES)

Stage 91.1.2. (5-Bromo-pyridin-3-yl)-diethyl-amine

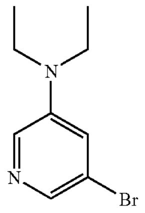

A solution of 3-amino-5-bromopyridine (Aldrich, Buchs, Switzerland, 400 mg, 2.31 mmol), acetic acid (0.4 ml, 6.99 mmol) and acetaldehyde (Fluka, Buchs, Switzerland, 153 mg, 3.47 mmol) in dichloromethane was stirred for 1.5 h at rt then was added sodium triacetoxyborohydride (980 mg, 4.62 mmol). The reaction mixture was stirred 17.5 h at rt then were added at 1.5 h interval acetaldehyde (153 mg, 3.47 mmol) and sodium tracetoxyborohydride (490 mg, 2.31 mmol). The RM was stirred 7 h at rt then were added at 1.5 h interval acetaldehyde (77 mg, 1.75 mmol) and sodium tracetoxyborohydride (490 mg, 2.31 mmol). After 15 h stirring at rt, the reaction mixture was diluted with dichloromethane and quenched with saturated aqueous $NaHCO_3$. The aqueous layer was extracted with dichloromethane and the combined organic layers were dried over $Na_2SO_4$, filtered and evaporated. The crude product was purified by flash chromatography (DCM/iPrOH 1% to 3.5%) to give the title compound as a yellowish oil. (HPLC: $t_R$ 2.31 min (Method A); M+H=229, 231 MS-ES)

Example 96

1-(1,3-Dimethyl-1H-pyrazol-4-yl)-3-methyl-8-[6-(4-methyl-piperazin-1-yl)-pyridin-3-yl]-1,3-dihydro-imidazo[4,5-c]quinolin-2-one

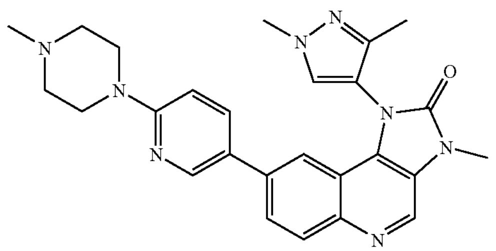

The title compound was synthesized in a similar manner as described for Example 1.1 using 8-bromo-1-(1,3-dimethyl-1H-pyrazol-4-yl)-3-methyl-1,3-dihydro-imidazo[4,5-c]quinolin-2-one (Intermediate A, 40 mg, 0.107 mmol) and 2-(4-methylpiperazine-1-yl)pyridine-5-boronic acid pinacol ester (Combi-Blocks, San Diego, USA, 40 mg, 0.132 mmol) to give the title compound as a white solid. (HPLC: $t_R$ 2.04 min (Method A); M+H=469 MS-ES; $^1$H-NMR ($d_6$-DMSO, 400 MHz) 8.91 (s, 1H), 8.30-8.24 (m, 1H), 8.14-8.10 (m, 1H), 8.07-8.01 (m, 1H), 7.90-7.83 (m, 1H), 7.62-7.56 (m, 1H), 7.45-7.41 (m, 1H), 6.97-6.90 (m, 1H), 3.92 (s, 3H), 3.55 (s, 7H), 2.41-2.35 (m, 4H), 2.21 (s, 3H), 1.95 (s, 3H))

Example 97

1-(1,3-Dimethyl-1H-pyrazol-4-yl)-3-methyl-8-(6-pyrrolidin-1-yl-pyridin-3-yl)-1,3-dihydro-imidazo[4,5-c]quinolin-2-one

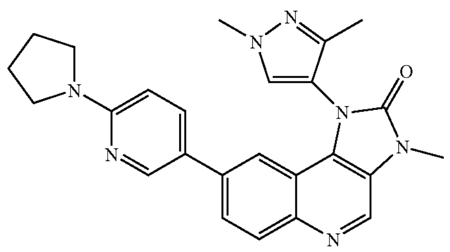 [SMILES: Cc1nn(C)cc1-n1c(=O)n(C)c2cnc3ccc(-c4ccc(N5CCCC5)nc4)cc3c21]

The title compound was synthesized in a similar manner as described for Example 1.1 using 8-bromo-1-(1,3-dimethyl-1H-pyrazol-4-yl)-3-methyl-1,3-dihydro-imidazo[4,5-c]quinolin-2-one (Intermediate A) and 2-pyrrolidin-1-ylpyridine-5-boronic acid pinacol ester (Boron Molecular, Research Triangle Park, USA) to give the title compound as a white solid. (HPLC: $t_R$ 2.23 min (Method A); M+H=440 MS-ES; $^1$H-NMR ($d_6$-DMSO, 400 MHz) 8.90 (s, 1H), 8.25-8.23 (m, 1H), 8.13-8.11 (m, 1H), 8.05-8.01 (m, 1H), 7.87-7.83 (m, 1H), 7.58-7.53 (m, 1H), 7.42-7-40 (m, 1H), 6.56-6.52 (m, 1H), 3.92 (s, 3H), 3.56 (s, 3H), 3.44-3.38 (m, 4H), 1.97-1.92 (m, 7H))

Example 98.1

1-(1,3-Dimethyl-1H-pyrazol-4-yl)-8-[6-(ethyl-methyl-amino)-pyridin-3-yl]-3-methyl-1,3-dihydro-imidazo[4,5-c]quinolin-2-one

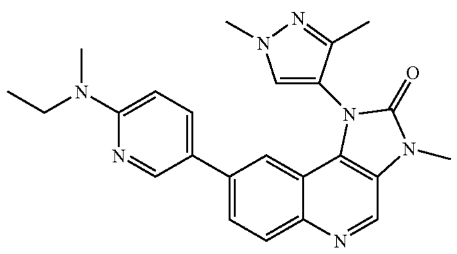 [SMILES: CCN(C)c1ccc(-c2ccc3ncc4c(c3c2)n(-c2cn(C)nc2C)c(=O)n4C)cn1]

The title compound was synthesized in a similar manner as described for Example 1.1 using 8-bromo-1-(1,3-dimethyl-1H-pyrazol-4-yl)-3-methyl-1,3-dihydro-imidazo[4,5-c]quinolin-2-one (Intermediate A) and ethyl-methyl-[5-(4,4,5,5-tetramethyl-[1,3,2]dioxaborolan-2-yl)-pyridin-2-yl]-amine (stage 98.1.1) to give the title compound as a white solid. (HPLC: $t_R$ 2.18 min (Method A); M+H=428 MS-ES; $^1$H-NMR ($d_6$-DMSO, 400 MHz) 8.90 (s, 1H), 8.26-8.24 (m, 1H), 8.14-8.12 (m, 1H), 8.04-8.01 (m, 1H), 7.88-7.84 (m, 1H), 7.57-7.52 (m, 1H), 7.43-7-40 (m, 1H), 6.73-6.69 (m, 1H), 3.93 (s, 3H), 3.62-3.53 (m, 51-1), 3.01 (s, 3H), 1.96 (s, 3H), 1.07 (t, 3H))

Stage 98.1.1. Ethyl-methyl-[5-(4,4,5,5-tetramethyl-[1,3,2]dioxaborolan-2-yl)-pyridin-2-yl]-amine

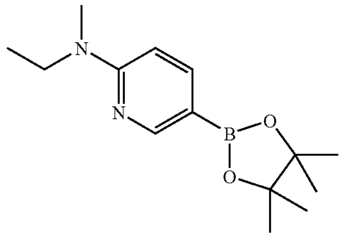 [SMILES: CCN(C)c1ccc(B2OC(C)(C)C(C)(C)O2)cn1]

The title compound was synthesized in a similar manner as described for Stage 5.1.1-2 using methylethylamine (Aldrich, Buchs, Switzerland) to give the title compound as a brown solid. (HPLC: $t_R$ 1.77 min (Method A); M+H=263 MS-ES)

The following examples were synthesized in a similar manner as described for Example 1.1 using ethyl-methyl-[5-(4,4,5,5-tetramethyl-[1,3,2]dioxaborolan-2-yl)-pyridin-2-yl]-amine (Stage 98.1.1) and the specified intermediate.

| Example | Intermed. | structure | Name of the example | MS-ES (M + H) | HPLC $t_R$ (min) |
|---|---|---|---|---|---|
| 98.2 | G | 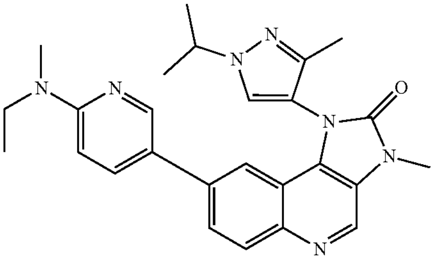 [SMILES: CCN(C)c1ccc(-c2ccc3ncc4c(c3c2)n(-c2cn(C(C)C)nc2C)c(=O)n4C)cn1] | 8-[6-(Ethyl-methyl-amino)-pyridin-3-yl]-1-(1-isopropyl-3-methyl-1H-pyrazol-4-yl]-3-methyl-1,3-dihydro-imidazo[4,5-c] quinolin-2-one | 456 | 2.31 |
| 98.3 | F | 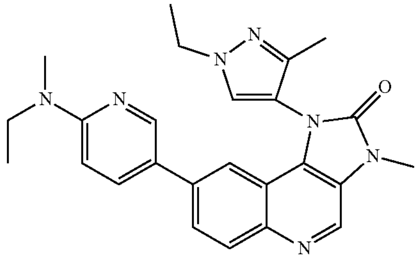 [SMILES: CCN(C)c1ccc(-c2ccc3ncc4c(c3c2)n(-c2cn(CC)nc2C)c(=O)n4C)cn1] | 8-[6-(Ethyl-methyl-amino)-pyridin-3-yl]-1-(1-ethyl-3-methyl-1H-pyrazol-4-yl]-3-methyl-1,3-dihydro-imidazo[4,5-c] quinolin-2-one | 442 | 2.25 |

Example 99

1-(1,3-Dimethyl-1H-pyrazol-4-yl)-3-methyl-8-(1H-pyrrolo[3,2-b]pyridin-6-yl)-1,3-dihydro-imidazo[4,5-c]quinolin-2-one

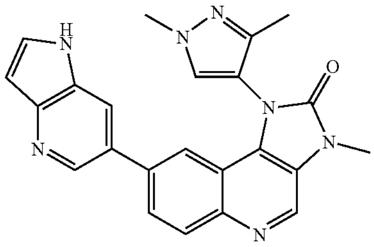 [SMILES: Cc1nn(C)cc1-n1c(=O)n(C)c2cnc3ccc(-c4cnc5cc[nH]c5c4)cc3c21]

The title compound was synthesized in a similar manner as described for Example 1.1 using 8-bromo-1-(1,3-dimethyl-1H-pyrazol-4-yl)-3-methyl-1,3-dihydro-imidazo[4,5-c] quinolin-2-one (Intermediate A) and 6-(4,4,5,5-tetramethyl-[1,3,2]dioxaborolan-2-yl)-1H-pyrrolo[3,2-b]pyridine (PepTech, Burlington, USA) to give the title compound as a white solid. (HPLC: $t_R$ 2.03 min (Method A); M+H=410 MS-ES; $^1$H-NMR ($d_6$-DMSO, 400 MHz) 11.52 (s, 1H), 8.96 (s, 1H), 8.43-8.41 (m, 1H), 8.18-8.16 (m, 1H), 8.13-8.10 (m, 1H), 8.00-7.95 (m, 1H), 7.83-7.81 (m, 1H), 7.72-7.69 (m, 1H), 7.60-7.58 (m, 1H), 6.60-6.58 (m, 1H), 3.94 (s, 3H), 3.58 (s, 3H), 1.97 (s, 3H))

Example 100

5-[1-(1,3-Dimethyl-1H-pyrazol-4-yl)-3-methyl-2-oxo-2,3-dihydro-1H-imidazo[4,5-c]quinolin-8-yl]-pyridine-2-carboxylic acid methyl ester

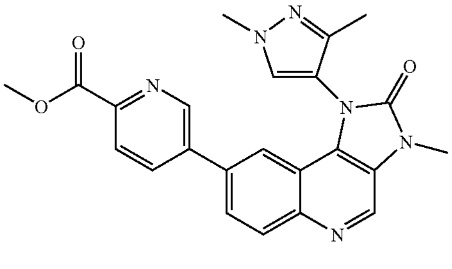

A mixture of 8-bromo-1-(1,3-dimethyl-1H-pyrazol-4-yl)-3-methyl-1,3-dihydro-imidazo[4,5-c]quinolin-2-one (Intermediate A, 39 mg, 0.105 mmol), 2-methylcarboxypyridine-5-boronic acid pinacol ester (Aalen Chemical, Nanjing, China, 49 mg, 0.186 mmol), potassium fluoride (22 mg, 0.379 mmol), $Pd_2(dba)_3$ (7.7 mg, 0.0085 mmol) and tri-t-butylphosphonium tetrafluoroborate (4.9 mg, 0.017 mmol) in dioxane (0.6 ml) was stirred under argon in a sealed microwave tube at rt for 20 h. The reaction was not completed. Therefore, again $Pd_2(dba)_3$ (7.7 mg, 0.0085 mmol) and tri-t-butylphosphonium tetrafluoroborate (4.9 mg, 0.017 mmol) and 2-methylcarboxypyridine-5-boronic acid pinacol ester (Combi-Blocks, San Diego, USA, 15 mg, 0.186 mmol) were added, the mixture was flushed with argon and stirred at it for further 23 h. The RM was diluted with EtOAc. The organic layer was washed with brine, dried over $Na_2SO_4$, filtered and evaporated. The residue was dissolved in MeOH and purified directly by Prep.HPLC ($H_2O$ (0.1% TFA)/$CH_3CN$ 95:5 to 60:30). The fractions containing products were collected together and basified with $NaHCO_3$ (0.3 g), before being concentrated. The resulting suspension was filtered and the cake was washed with water, before being dried under high vacuum to give the title compound as a white solid. (HPLC: $t_R$ 2.45 min (Method A); M+H=429 MS-ES; $^1$H-NMR ($d_6$-DMSO, 400 MHz) 8.99 (s, 1H), 8.83-8.78 (m, 1H), 8.20-8.12 (m, 3H), 8.11-8.06 (m, 1H), 8.05-7.98 (m, 1H), 7.69-7.62 (m, 1H), 3.92 (s, 3H), 3.90 (s, 3H), 3.58 (s, 3H), 1.96 (s, 3H))

Example 101

{4-[8-(6-Methoxy-pyridin-3-yl)-3-methyl-2-oxo-2,3-dihydro-imidazo[4,5-c]quinolin-1-yl]-3-methyl-pyrazol-1-yl}-acetic acid

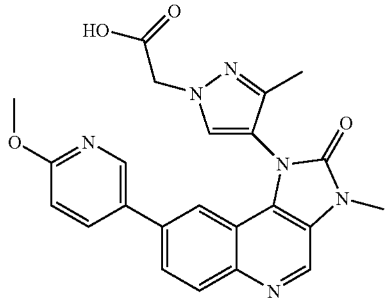 [SMILES: COc1ccc(-c2ccc3ncc4c(c3c2)n(-c2cn(CC(=O)O)nc2C)c(=O)n4C)cn1]

A mixture of [4-(8-bromo-3-methyl-2-oxo-2,3-dihydro-imidazo[4,5-c]quinolin-1-yl)-3-methyl-pyrazol-1-yl]-acetic acid (Stage 101.1.1b, 161 mg, 0.387 mmol), 2-methoxypyridine-5-boronic acid (Aldrich, Buchs, Switzerland, 77 mg, 0.503 mmol), and $PdCl_2(PPh_3)_2$ (17 mg, 0.024 mmol) in DMF (4.0 ml) and 1 M aqueous $K_2CO_3$ (1.16 ml) was stirred under argon at 105° C. for 1.25 h. The RM was cooled to rt. The mixture was diluted with MeOH+3 drops TFA and purified directly by Prep.HPLC ($H_2O$ (0.1% TFA)/$CH_3CN$ 95:5 to 65:35). The fractions containing products were collected together concentrated, before being lyophilized to give the title compound as a TFA-salt and white powder. (HPLC: $t_R$ 2.38 min (Method A); M+H=446 MS-ES; $^1$H-NMR ($d_6$-DMSO, 400 MHz) 9.22 (s, 1H), 8.46 (s, 1H), 8.23-8.14 (m, 3H), 7.87-7.79 (m, 1H), 7.74-7.68 (m, 1H), 6.94-6.88 (m, 1H), 5.15-4.98 (m, 2H), 3.89 (s, 3H), 3.60 (s, 3H), 1.97 (s, 3H))

Stage 101.1.1b [4-(8-Bromo-3-methyl-2-oxo-2,3-dihydro-imidazo[4,5-c]quinolin-1-yl)-3-methyl-pyrazol-1-yl]-acetic acid

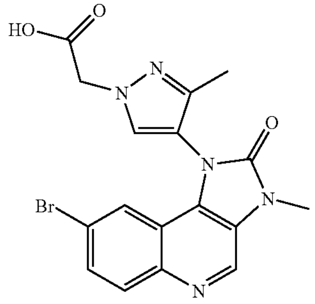 [SMILES: Cc1nn(CC(=O)O)cc1-n1c(=O)n(C)c2cnc3ccc(Br)cc3c21]

To a mixture of [4-(8-bromo-2-oxo-2,3-dihydro-imidazo[4,5-c]quinolin-1-yl)-3-methyl-pyrazol-1-yl]-acetic acid (Stage 101.1.2, 422 mg, 1.050 mmol) in DMF (6 ml) cooled to 0° C. was added NaH 55% (92 mg, 2 mmol). The cooling bath was removed and the RM was stirred for 45 min at rt. Then iodomethane (0.132 ml, 2 mmol) was added and the RM was stirred for 1 h. The reaction was not completed. Therefore again NaH 55% (50 mg, 1.2 mmol) was added and stirred for 15 min and after that iodomethane (0.070 ml, 1.2 mmol) was added and stirred at rt for one further hour. Then the RM was quenched with saturated aqueous $NaHCO_3$ and extracted with EtOAc (2×) in the organic layer was found the ester side product: [4-(8-Bromo-3-methyl-2-oxo-2,3-dhydro-imidazo[4,5-c]quinolin-1-yl)-3-methyl-pyrazol-1-yl]-acetic acid methyl ester (Stage 101.1.1a).

The aqueous layer was adjusted with 4 M aqueous HCl to pH 5. The mixture was then extracted with n-butanol (2×). The combined organic layer was evaporated. The residue was diluted with DCM/MeOH. The mixture was filtered over celite, and the filtrate was evaporated to give the title compound as a orange sticky solid. (HPLC: $t_R$ 2.21 min (Method A); M+H=416, 418 Br-Pattern MS-ES)

Stage 101.1.2 [4-(8-Bromo-2-oxo-2,3-dihydro-imidazo[4,5-c]quinolin-1-yl)-3-methyl-pyrazol-1-yl]-acetic acid

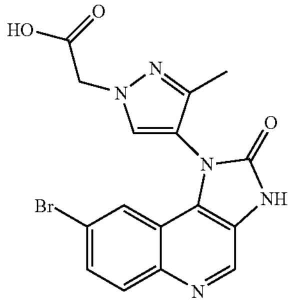 [SMILES: Cc1nn(CC(=O)O)cc1-n1c(=O)[nH]c2cnc3ccc(Br)cc3c21]

To a mixture of [4-(8-bromo-2-oxo-2,3-dihydro-imidazo[4,5-c]quinolin-1-yl)-3-methyl-pyrazol-1-yl]-acetic acid methyl ester (Stage 101.1.3, 3.22 g, 7.73 mmol) and tetrabutylammonium (250 mg, 0.773 mmol) in $CH_2Cl_2$ (150 ml) was added 1 M aqueous NaOH (80 ml). The reaction mixture was energetically stirred for 4 h 30 at rt. The organic layer was separted and the aqueous layer washed with $CH_2Cl_2$ (2×), adjusted to pH 4 with concentrated aqueous HCl and extracted with n-butanol (5×). The combined organic layers were washed with brine adjusted to pH 4 with HCl and evaporated to dryness. The residue was dry loaded on Isolute, washed with water/1-propanol 3% and eluted with acetonitrile/1-propanol 3% on reverse phase silica gel plug. To acetonitrile filtrate was added water and solution was concentrated. The formed precipitate was filtered, washed with water and dried to give the title compound as a yellow solid. (HPLC: $t_R$ 2.08 min (Method A); M+H=402, 404 Br-Pattern MS-ES)

Stage 101.1.3 [4-(8-Bromo-2-oxo-2,3-dihydro-imidazo[4,5-c]quinolin-1-yl)-3-methyl-pyrazol-1-yl]-acetic acid methyl ester

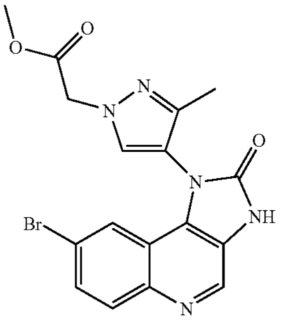 [SMILES: COC(=O)Cn1cc(-n2c(=O)[nH]c3cnc4ccc(Br)cc4c32)c(C)n1]

The title compound was synthesized in a similar manner as described in Stage A.1-3 using (4-amino-3-methyl-pyrazol-1-yl)-acetic acid methyl ester (Stage 101.1.4) to give the title compound as green solid. (HPLC: $t_R$ 2.35 min (Method A))

Stage 101.1.4 (4-Amino-3-methyl-pyrazol-1-yl)-acetic acid methyl ester

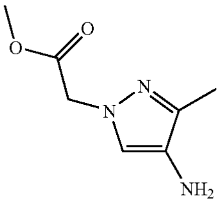

The title compound was synthesized in a similar manner as described in Stage A.2 starting from 3-Methyl-4-nitro-pyrazol-1-yl-acetic acid methylester (ChemCollect, Remscheid, Germany) to give the title compound as a pinkish oil. (HPLC: $t_R$ 0.96 min (Method A); M+H=170 MS-ES)

Example 102

2-{4-[8-(6-Methoxy-pyridin-3-yl)-3-methyl-2-oxo-2,3-dihydro-imidazo[4,5-c]quinolin-1-yl]-3-methyl-pyrazol-1-yl}-N,N-dimethyl-acetamide

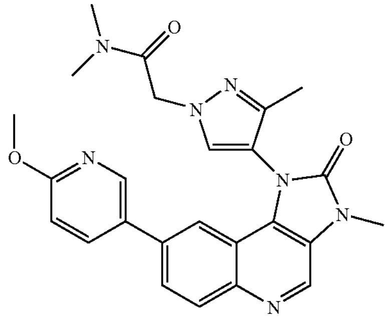 [SMILES: COc1ccc(-c2ccc3ncc4c(c3c2)n(-c2cn(CC(=O)N(C)C)nc2C)c(=O)n4C)cn1]

A mixture of {4-[8-(6-Methoxy-pyridin-3-yl)-3-methyl-2-oxo-2,3-dihydro-imidazo[4,5-c]quinolin-1-yl]-3-methyl-pyrazol-1-yl}-acetic acid TFA salt (Example 101, 60 mg, 0.107 mmol), TPTU (128 mg, 0.430 mmol) and DIPEA (0.094 ml, 0.537 mmol) in DMA (1.5 ml) was stirred under argon at rt for 20 min. Then dimethtylamine in THF 2 M (Aldrich, Buchs, Switzerland, 0.242 ml, 0.483 mmol) was added and the RM was stirred at rt for 3 h. The RM was directly purified by Prep.HPLC ($H_2O$ (0.1% TFA)/$CH_3CN$ 95:5 to 50:50). The fractions containing products were collected together and basified with $NaHCO_3$ (0.3 g), before being concentrated. The resulting layer was extracted with EtOAc, washed with bine, dried over $Na_2SO_4$, filtered and evaporated to dryness to give the title compound as a white solid. (HPLC: $t_R$ 2.57 min (Method A); M+H=472 MS-ES; $^1$H-NMR ($d_6$-DMSO, 400 MHz) 8.95 (s, 1H), 8.50-8.43 (m, 1H), 8.14-8.04 (m, 2H), 8.01-7.96 (m, 1H), 7.95-7.90 (m, 1H), 7-77-7.71 (m, 1H), 6.87-6.81 (m, 1H), 5.25-5.09 (m, 2H), 3.86 (s, 3H), 3.56 (s, 3H), 3.05 (s, 3H), 2.88 (s, 3H), 1.93 (s, 3H))

Example 103.1

1-[1-(2-Hydroxy-ethyl)-3-methyl-1H-pyrazol-4-yl]-8-(6-methoxy-pyridin-3-yl)-3-methyl-1,3-dihydro-imidazo[4,5-c]quinolin-2-one

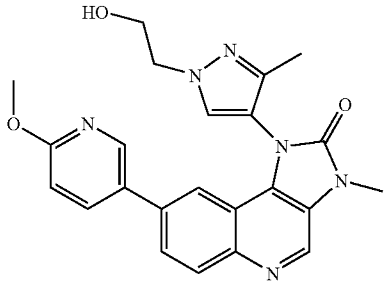 [SMILES: COc1ccc(-c2ccc3ncc4c(c3c2)n(-c2cn(CCO)nc2C)c(=O)n4C)cn1]

The title compound was synthesized in a similar manner as described for Example 1.1 using 8-bromo-1-[1-(2-hydroxy-ethyl)-3-methyl-1H-pyrazol-4-yl]-3-methyl-1,3-dihydro-imidazo[4,5-c]quinolin-2-one (Stage 103.1.1, 37.4 mg, 0.093 mmol) and 2-methoxypyridine-5-boronic acid (Aldrich, Buchs, Switzerland, 20 mg, 0.131 mmol) to give the title compound as a white solid. (HPLC: $t_R$ 2.42 min (Method A); M+H=431 MS-ES; $^1$H-NMR ($d_6$-DMSO, 400 MHz) 8.95 (s, 1H), 8.35 (s, 1H), 8.13 (s, 1H), 8.10-8.05 (m, 1H), 7.95-7.88 (m, 1H), 7.81-7.75 (m, 1H), 7.51-7.46 (m, 1H), 6.93-6.86 (m, 1H), 5.00-4.94 (m, 1H), 4.24-4.17 (m, 2H), 3.88 (s, 3H), 3.86-3.74 (m, 2H), 3.57 (s, 3H), 1.94 (s, 3H))

Stage 103.1.1 8-Bromo-1-[1-(2-hydroxy-ethyl)-3-methyl-1H-pyrazol-4-yl]-3-methyl-1,3-dihydro-imidazo[4,5-c]quinolin-2-one

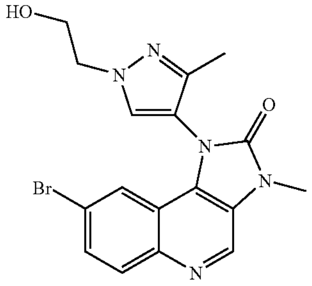 [SMILES: Cc1nn(CCO)cc1-n1c(=O)n(C)c2cnc3ccc(Br)cc3c21]

A mixture of [4-(8-bromo-3-methyl-2-oxo-2,3-dihydro-imidazo[4,5-c]quinolin-1-yl)-3-methyl-pyrazol-1-yl]-acetic acid methyl ester (Stage 101.1.1a, 60 mg, 0.139 mmol) and MeOH (0.021 ml, 0.519 mmol) in THF (1.5 ml) was cooled to 0° C. Then $NaBH_4$ (14 mg, 0.370 mmol) was added and the RM was heated to 50° C. for 30 min. After that, the RM was quenched with saturated aqueous $NaHCO_3$ (20 ml) and extracted with EtOAc (2×). The combined organic layers were washed with brine, dried over $Na_2SO_4$, filtered and evaporated to dryness to give the title compound as a lightly yellow solid. (HPLC: $t_R$ 2.23 min (Method A); M+H=402, 404 Br-Pattern MS-ES)

Alternatively, the title compound was synthesized in a similar manner as described for intermediate A starting from 2-(4-amino-3-methyl-pyrazol-1-yl)-ethanol (Stage 103.1.2).

The following example was synthesized in a similar manner as described for Example 1.1 using 6-ethoxypyridine-3-boronic acid (ABCR, Karlsruhe, Germany) and 8-bromo-1-[1-(2-hydroxy-ethyl)-3-methyl-1H-pyrazol-4-yl]-3-methyl-1,3-dihydro-imidazo[4,5-c]quinolin-2-one (Stage 103.1.1).

Stage 103.1.2 2-(4-Amino-3-methyl-pyrazol-1-yl)-ethanol

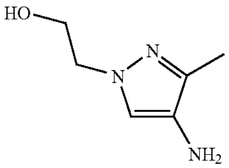

To solution of 3-methyl-4-nitropyrazol-1-yl-acetic acid methylester (ChemCollect, Remscheid, Germany, 297 mg, 1.491 mmol) in THF (12 ml) cooled with an ice-bath was added a 1 M solution of lithium aluminium hydride in THF (1.5 ml, 1.5 mmol). The reaction mixture was stirred 1 h at rt then was added more of the reducing reagent (0.75 ml, 0.75 mmol), stirring 2 h at rt, (1.5 ml, 1.5 mmol), stirring 45 min, (2 ml, 2 mmol) and the reaction mixture was stirred 17 h at rt before being quenched with water and taken in EtOAc. The suspension was filtered and the solid washed with EtOAc. The filtrate was dried over $Na_2SO_4$, filtered and evaporated to give crude brown solid. (HPLC: $t_R$ 0.85 min (Method A); M+H=142 MS-ES)

Example 104

1-(1-Ethyl-3-methyl-1H-pyrazol-4-yl)-8-(6-methoxymethyl-pyridin-3-yl)-3-methyl-1,3-dihydro-imidazo[4,5-c]quinolin-2-one

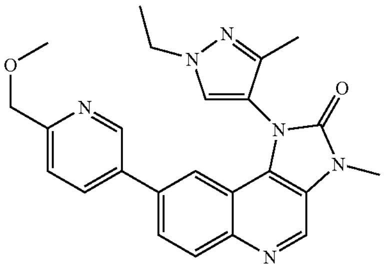

| Example | structure | Name of the example | MS-ES (M + H) | HPLC $t_R$ (min) |
|---|---|---|---|---|
| 103.2 | 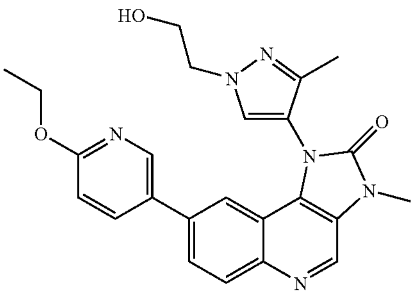 [SMILES: CCOc1ccc(-c2ccc3ncc4c(c3c2)n(-c2cn(CCO)nc2C)c(=O)n4C)cn1] | 8-(6-Ethoxy-pyridin-3-yl)-1-[1-(2-hydroxy-ethyl)-3-methyl-1H-pyrazol-4-yl]-3-methyl-1,3-dihydro-imidazo[4,5-c]quinolin-2-one | 445 | 2.47 |

To a mixture of 1-(1-ethyl-3-methyl-1H-pyrazol-4-yl)-8-(6-hydroxymethyl-pyridin-3-yl)-3-methyl-1,3-dihydro-imidazo[4,5-c]quinolin-2-one (Example 16.1, 28 mg, 0.068 mmol) in DMF (1 ml) was added NaH 55% (4 mg, 0.092 mmol) and the mixture was stirred for 20 min. Then iodomethane (0.006 ml, 0.096 mmol) was added and the RM was stirred again at rt for 30 min. After that, the RM was quenched with saturated aqueous $NaHCO_3$ (20 ml) and extracted with EtOAc (2×). The combined organic layers were washed with brine, dried over $Na_2SO_4$, filtered and evaporated. The residue was dissolved in DMA and purified directly by Prep.HPLC ($H_2O$ (0.1% TFA)/$CH_3CN$ 95:5 to 65:35). The fractions containing products were collected together and basified with $NaHCO_3$ (0.3 g), before being concentrated. The resulting suspension was filtered and the cake was washed with water, before being dried under high vacuum to give the title compound as a white solid. (HPLC: $t_R$ 2.30 min (Method A); M+H=429 MS-ES; $^1$H-NMR ($d_6$-DMSO, 400 MHz) 8.98 (s, 1H), 8.63 (s, 1H), 8.20 (s, 1H), 8.15-8.10 (m, 1H), 7.98-7.93 (m, 1H), 7.92-7.87 (m, 1H), 7.58-7.53 (m, 1H), 7.49-7.44 (m, 1H), 4.54-4.50 (m, 2H), 4.23-4.15 (m, 2H), 3.58 (s, 3H), 3.37 (s, 3H), 1.95 (s, 3H), 1.32 (t, 3H))

Example 105

1-(1-Isopropyl-3-methyl-1H-pyrazol-4-yl)-8-(6-methoxymethyl-pyridin-3-yl)-3-methyl-1,3-dihydro-imidazo[4,5-c]quinolin-2-one

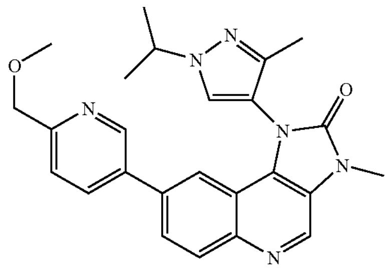 [SMILES: COCc1ccc(-c2ccc3ncc4c(c3c2)n(-c2cn(C(C)C)nc2C)c(=O)n4C)cn1]

The title compound was synthesized in a similar manner as described for Example 104 using 8-(6-hydroxymethyl-pyridin-3-yl)-1-(1-isopropyl-3-methyl-1H-pyrazol-4-yl)-3-methyl-1,3-dihydro-imidazo[4,5-c]quinolin-2-one (Example 16.3, 26 mg, 0.061 mmol) to give the title compound as an off-white solid. (HPLC: $t_R$ 2.39 min (Method A); M+H=443 MS-ES; $^1$H-NMR ($d_6$-DMSO, 400 MHz) 8.98 (s, 1H), 8.68-8.59 (m, 1H), 8.27-8.20 (m, 1H), 8.17-8.09 (m, 1H), 7.99-7.85 (m, 2H), 7.59-7.51 (m, 1H), 7.49-7.41 (m, 1H), 4.60-4.49 (m, 3H), 3.59 (s, 3H), 3.38 (s, 3H), 1.98 (s, 3H), 1.47 (s, 6H))

Example 106

1-(1,3-Dimethyl-1H-pyrazol-4-yl)-8-[1-(2-hydroxy-ethyl)-1H-pyrazol-4-yl]-3-methyl-1,3-dihydro-imidazo[4,5-c]quinolin-2-one

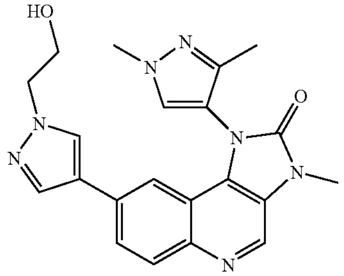 [SMILES: Cc1nn(C)cc1-n1c(=O)n(C)c2cnc3ccc(-c4cnn(CCO)c4)cc3c21]

To a mixture of 1-(1,3-dimethyl-1H-pyrazol-4-yl)-3-methyl-8-{1-[2-(tetrahydro-pyran-2-yloxy)-ethyl]-1H-pyrazol-4-yl}-1,3-dihydro-imidazo[4,5-c]quinolin-2-one (Stage 106.1.1, 95 mg, 0.195 mmol) in MeOH (2 ml) was added dioxane 4 M (0.248 ml, 0.993 mmol) and the RM was stirred at rt for 45 min. Then the RM was evaporated, before being quenched with saturated aqueous $NaHCO_3$ (20 ml) and extracted with DCM (2×). The combined organic layers were washed with brine, dried over $Na_2SO_4$, filtered and evaporated. The residue was diluted with MeOH+2 drops TFA and purified directly by Prep.HPLC ($H_2O$ (0.1% TFA)/$CH_3CN$ 95:5 to 65:35). The fractions containing product were collected together and basified with $NaHCO_3$ (0.3 g), before being concentrated. The resulting layer was extracted with DCM, washed with brine, dried over $Na_2SO_4$, filtered and evaporated to dryness to give the title compound as a white solid. (HPLC: $t_R$ 2.24 min (Method A); M+H=404 MS-ES; $^1$H-NMR ($d_6$-DMSO, 400 MHz) 8.87 (s, 1H), 8.14-8.08 (m, 1H), 8.01-7.92 (m, 2H), 7.82-7.75 (m, 1H), 7.52-7.47 (m, 1H), 7.39-7.35 (m, 1H), 4.96-4.89 (m, 1H), 4.17-4.11 (m, 2H), 3.96 (s, 3H), 3.77-3.69 (m, 2H), 3.55 (s, 3H), 1.94 (s, 3H))

Stage 106.1.1 1-(1,3-Dimethyl-1H-pyrazol-4-yl)-3-methyl-8-{1-[2-(tetrahydro-pyran-2-yloxy)-ethyl]-1H-pyrazol-4-yl}-1,3-dihydro-imidazo[4,5-c]quinolin-2-one

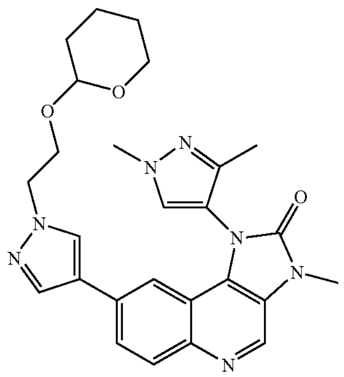 [SMILES: Cc1nn(C)cc1-n1c(=O)n(C)c2cnc3ccc(-c4cnn(CCOC5CCCCO5)c4)cc3c21]

The title compound was synthesized in a similar manner as described for Example 1.1 using 8-bromo-1-(1,3-dimethyl- 1H-pyrazol-4-yl)-3-methyl-1,3-dihydro-imidazo[4,5-c]quinolin-2-one (Intermediate A, 80 mg, 0.215 mmol) and 1-[2-(tetrahydro-pyran-2-yloxy)-ethyl]-4-(4,4,5,5-tetramethyl-[1,3,2]dioxaborolan-2-yl)-1H-pyrazole (Stage 106.1.2, 91 mg, 0.279 mmol) to give the title compound as red sticky oil. Used for next step without further purification. (HPLC: $t_R$ 2.66 min (Method A); M+H=488 MS-ES)

Stage 106.1.2 1-[2-(Tetrahydro-pyran-2-yloxy)-ethyl]-4-(4,4,5,5-tetramethyl-[1,3,2]dioxaborolan-2-yl)-1H-pyrazole

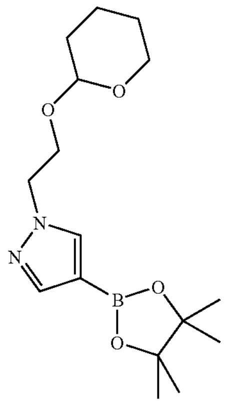 [SMILES: CC1(C)OB(c2cnn(CCOC3CCCCO3)c2)OC1(C)C]

To a solution of 4-iodo-1-[2-(tetrahydro-pyran-2-yloxy)-ethyl]-1H-pyrazole (Stage 106.1.3, 8.50 g, 26.4 mmol) in THF at 0° C. under argon was added dropwise iPrMgCl 2 M in THF (26.4 ml, 52.8 mmol). The RM was stirred at 0° C. for 1 h. Then 2-methoxy-4,4,5,5-tetramethyl-1,3,2-dioxaborolane (Aldrich, Buchs, Switzerland, 6.25 g, 52.8 mmol) was added at 0° C. and the solution was stirred again and allowed to warm to rt for 1 h. After that, the RM was quenched with saturated aqueous $NH_4Cl$ (140 ml) and extracted with EtOAc (3×). The combined organic layers were washed with saturated aqueous $NH_4Cl$, dried over $Na_2SO_4$, filtered and evaporated. The residue was purified by flash chromatography (hexane/EtOAc 5% to 45%). The fractions containing product were combined and evaporated to dryness to give the title compound as a colorless oil. (HPLC: $t_R$ 3.23 min (Method A); M+H=323 MS-ES)

Stage 106.1.3 4-Iodo-1[2-(tetrahydro-pyran-2-yloxy)-ethyl]-1H-pyrazole

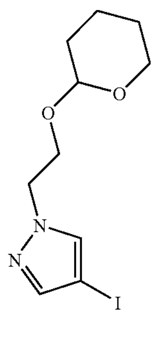 [SMILES: Ic1cnn(CCOC2CCCCO2)c1]

To a mixture of 4-iodopyrazole (Aldrich, Buchs, Switzerland, 10 g, 51.6 mmol) and $Cs_2CO_3$ (20.16 g 61.9 mmol) was added 2-(2-bromoethoxy)tetrahydro-2H-pyran (Aldrich, Buchs, Switzerland, 9.74 ml, 61.9 mmol). The RM was stirred at 70° C. for 17 h. Then the RM was quenched with water (100 ml) and extracted with EtOAc (3×). The combined organic layers were washed with brine, dried over $Na_2SO_4$, filtered and evaporated. The residue was absorbed on silica gel and purified by flash chromatography (hexane/EtOAc 0% to 30%). The fractions containing product were combined and evaporated to dryness to give the title compound as a colorless oil. (HPLC: $t_R$ 3.12 min (Method A); M+H=323 MS-ES)

Example 107

1-(1,3-Dimethyl-1H-pyrazol-4-yl)-8-[6-(2-hydroxy-ethoxy)-pyridin-3-yl]-3-methyl-1,3-dihydro-imidazo[4,5-c]quinolin-2-one

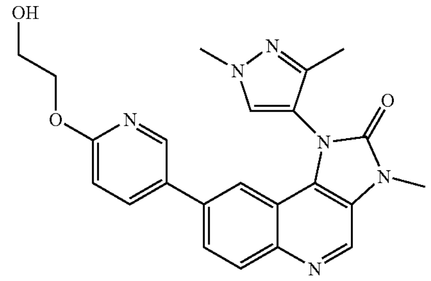 [SMILES: Cc1nn(C)cc1-n1c(=O)n(C)c2cnc3ccc(-c4ccc(OCCO)nc4)cc3c21]

To a mixture of 1-(1,3-Dimethyl-1H-pyrazol-4-yl)-8-[6-(2-hydroxy-ethylamino)-pyridin-3-yl]-3-methyl-1,3-dihydro-imidazo[4,5-c]quinolin-2-one (Example 19, 40 mg, 0.077 mmol) in MeOH/THF=1:1 (4 ml) was added under nitrogen Pd/C 10% (20 mg, 0.026 mmol). The RM was shacked under $H_2$ at rt for 22 h. The reaction was not completed, again Pd/C catalyst (20 mg) was added and the mixture was stirred under $H_2$ at rt for 22 h. This procedure was repeated for a third time. Then the suspension was filtered over celite and washed with MeOH. The filtrate was evaporated. The residue was dissolved in MeOH and purified directly by Prep.HPLC ($H_2O$ (0.1% TFA)/$CH_3CN$ 95:5 to 65:35). The fractions containing product were collected together and basified with $NaHCO_3$ (0.3 g), before being concentrated. The resulting suspension was filtered and the cake was washed with water, before being dried under high vacuum to give the title compound as a white solid. (HPLC: $t_R$ 2.32 min (Method A); M+H=431 MS-ES; $^1$H-NMR ($d_6$-DMSO, 400 MHz) 8.97 (s, 1H), 8.30-8.26 (m, 1H), 8.17-8.06 (m, 2H), 7.93-7.86 (m, 1H), 7.81-7.75 (m, 1H), 7.50-7.46 (m, 1H), 6.97-6.91 (m, 1H), 4.80-4.86 (m, 1H), 4.34-4.28 (m, 2H), 3.92 (s, 31-1), 3.75-3.69 (m, 2H), 3.58 (s, 3H), 1.95 (s, 3H))

Example 108

1-(1,3-Dimethyl-1H-pyrazol-4-yl)-8-[6-(3-hydroxy-propoxy)-pyridin-3-yl]-3-methyl-1,3-dihydro-imidazo[4,5-c]quinolin-2-one

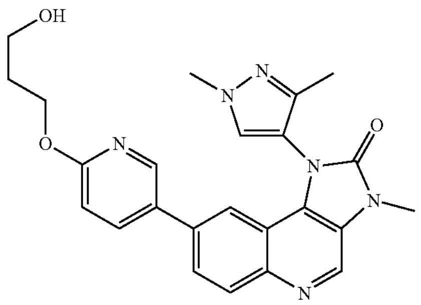 [SMILES: Cc1nn(C)cc1-n1c(=O)n(C)c2cnc3ccc(-c4ccc(OCCCO)nc4)cc3c21]

The title compound was synthesized in a similar manner as described for Example 107 using 1-(1,3-dimethyl-1H-pyrazol-4-yl)-8-[6-(2-hydroxy-ethylamino)-pyridin-3-yl]-3-methyl-1,3-dihydro-imidazo[4,5-c]quinolin-2-one (Example 20, 42 mg, 0.078 mmol) to give the title compound as a white solid. (HPLC: $t_R$ 2.42 min (Method A); M+H=445 MS-ES; $^1$H-NMR ($d_6$-DMSO, 400 MHz) 8.95 (s, 1H), 8.33-8.25 (m, 1H), 8.18-8.05 (m, 2H), 7.93-7.86 (m, 1H), 7.80-7.73 (m, 1H), 7.51-7.45 (m, 1H), 6.97-6.89 (m, 1H), 4.57-4.50 (m, 1H), 4.41-4.31 (m, 2H), 3.93 (s, 3H), 3.61-3.52 (m, 5H), 1.97 (s, 31-1), 1.91-1.82 (m, 2H))

Example 109

1-(1,3-Dimethyl-1H-pyrazol-4-yl)-8-(6-methoxy-pyridin-3-yl)-1,3-dihydro-imidazo[4,5-c]quinolin-2-one

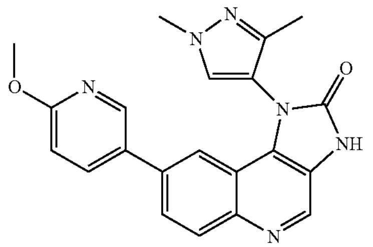 [SMILES: COc1ccc(-c2ccc3ncc4[nH]c(=O)n(-c5cn(C)nc5C)c4c3c2)cn1]

A mixture of 8-bromo-1-(1,3-dimethyl-1H-pyrazol-4-yl)-3-methyl-1,3-dihydro-imidazo[4,5-c]quinolin-2-one (Stage A.1, 49 mg, 0.137 mmol), 2-methoxypyridine-5-boronic acid (Sigma-Aldrich, Buchs, Switzerland, 26 mg, 0.170 mmol), and $PdCl_2(PPh_3)_2$ (6 mg, 0.0085 mmol) in DMF (1.2 ml) and 1 M aqueous $K_2CO_3$ (0.343 ml) was stirred under argon at 105° C. for 1.5 h. The RM was cooled toll. The mixture was diluted with MeOH+3 drops TFA and purified directly by Prep.HPLC ($H_2O$ (0.1% TFA)/$CH_3CN$ 95:5 to 60:40). The fractions containing products were collected together and basified with $NaHCO_3$ (0.3 g), before being concentrated. The resulting suspension was filtered and the cake was washed with water, before being dried under high vacuum to give the title compound as a white solid. (HPLC: $t_R$ 2.46 min (Method A); M+H=387 MS-ES; $^1$H-NMR ($d_6$-DMSO, 400 MHz) 11.66 (s, br, 1H), 8.72 (s, 1H), 8.33-8.26 (m, 1H), 8.16-8.10 (m, 1H), 8.09-8.01 (m, 1H), 7.91-7.84 (m, 1H), 7.81-7.74 (m, 1H), 7.51-7.43 (m, 1H), 6.98-6.91 (m, 1H), 3.90 (s, 3H), 3.87 (s, 3H), 1.95 (s, 3H))

Example 110

1-(1,3-Dimethyl-1H-pyrazol-4-yl)-8-(6-ethoxy-pyridin-3-yl)-1,3-dihydro-imidazo[4,5-c]quinolin-2-one

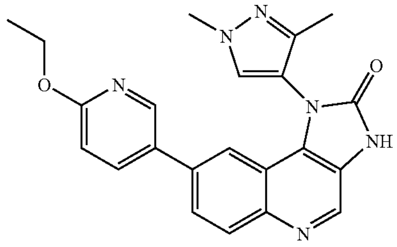 [SMILES: CCOc1ccc(-c2ccc3ncc4[nH]c(=O)n(-c5cn(C)nc5C)c4c3c2)cn1]

The title compound was synthesized in a similar manner as described for Example 109 using 2-ethoxypyridine-5-boronic acid (ABCR, Karlsruhe, Germany, 29 mg, 0.170 mmol) to give the title compound as a white solid. (HPLC: $t_R$ 2.59 min (Method A); M+H=401 MS-ES; $^1$H-NMR ($d_6$-DMSO, 400 MHz) 11.67 (s, br, 1H), 8.71 (s, 1H), 8.30-8.25 (m, 1H), 8.15-8.11 (m, 1H), 8.07-8.02 (m, 1H), 7.90-7.84 (m, 1H), 7.79-7.73 (m, 1H), 7.49-7.44 (m, 1H), 6.95-6.88 (m, 1H), 4.33 (q, 2H), 3.89 (s, 3H), 1.95 (s, 3H), 1.33 (t, 3H))

Example 111

8-(3,4-Dimethoxy-phenyl)-1-(1,3-dimethyl-1H-pyrazol-4-yl)-1,3-dihydro-imidazo[4,5-c]quinolin-2-one

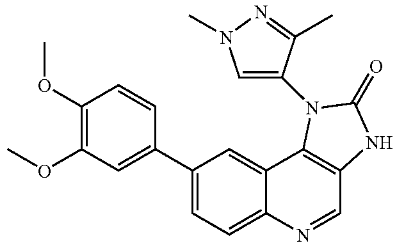 [SMILES: COc1ccc(-c2ccc3ncc4[nH]c(=O)n(-c5cn(C)nc5C)c4c3c2)cc1OC]

The title compound was synthesized in a similar manner as described for Example 109 using (3,4-dimethoxyphenyl)boronic acid (Aldrich, Buchs, Switzerland, 31 mg, 0.167 mmol) to give the title compound as a white solid. (HPLC: $t_R$ 2.57 min (Method A); M+H=416 MS-ES; $^1$H-NMR ($d_6$-DMSO, 400 MHz) 11.67 (s, br, 1H), 8.68 (s, 1H), 8.14-8.09 (m, 1H), 8.05-7.98 (m, 1H), 7.94-7.87 (m, 1H), 7.56-7.51 (m, 1H), 7.12-7.07 (m, 1H), 7.07-7.00 (m, 1H), 6.97-6.92 (m, 1H), 3.88 (s, 3H), 3.83 (s, 3H), 3.78 (s, 3H), 1.97 (s, 3H))

Example 112

5-[1-(1-Isopropyl-3-methyl-1H-pyrazol-4-yl)-3-methyl-2-oxo-2,3-dihydro-1H-imidazo[4,5-c]quinolin-8-yl]-pyridine-2-carboxylic acid amide

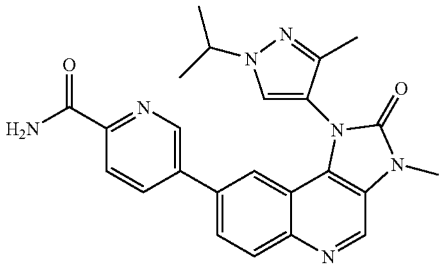 [SMILES: Cc1nn(C(C)C)cc1-n1c(=O)n(C)c2cnc3ccc(-c4ccc(C(N)=O)nc4)cc3c21]

A mixture of 1-(1-isopropyl-3-methyl-1H-pyrazol-4-yl)-3-methyl-8-(4,4,5,5-tetramethyl-[1,3,2]dioxaborolan-2-yl)-1,3-dihydro-imidazo[4,5-c]quinolin-2-one (Stage 112.1.1, 34 mg, 0.075 mmol), 5-bromo-pyridine-2-carboxylic acid amide (Combi-Blocks, San Diego, USA, 20 mg, 0.099 mmol), and $PdCl_2(PPh_3)_2$ (3.5 mg, 0.005 mmol) in DMF (0.9 ml) and 1 M aqueous $K_2CO_3$ (0.187 ml) was stirred under argon at 105° C. for 2.5 h. The RM was cooled to rt. The mixture was diluted with MeOH+3 drops TFA and purified directly by Prep.HPLC ($H_2O$ (0.1% TFA)/$CH_3CN$ 97:3 to 55:45). The fractions containing product were collected together and basified with $NaHCO_3$ (0.3 g), before being concentrated. The resulting layer was extracted with DCM, washed with brine, dried over $Na_2SO_4$, filtered and evaporated to dryness to give the title compound as a white solid. (HPLC: $t_R$ 2.44 min (Method A); M+H=442 MS-ES; $^1$H-NMR ($d_6$-DMSO, 400 MHz) 9.00 (s, 1H), 8.75-8.69 (m, 1H), 8.24-8.19 (m, 1H), 8.18-8.07 (m, 2H), 8.07-7.98 (m, 3H), 7.75-7.67 (m, 1H), 7.61-7.56 (m, 1H), 4.61-4.48 (m, 1H), 3.58 (s, 3H), 1.97 (s, 3H), 1.45 (s, 3H), 1.43 (s, 3H))

Stage 112.1.1 1-(1-Isopropyl-3-methyl-1H-pyrazol-4-yl)-3-methyl-8-(4,4,5,5-tetramethyl-[1,3,2]dioxaborolan-2-yl)-1,3-dihydro-imidazo[4,5-c]quinolin-2-one

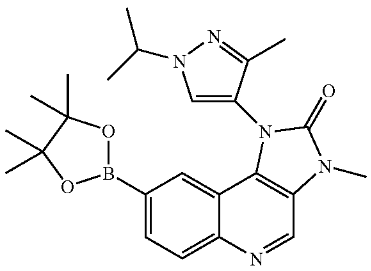

A mixture of 8-bromo-1-(1-isopropyl-3-methyl-1H-pyrazol-4-yl)-3-methyl-1,3-dihydro-imidazo[4,5-c]quinolin-2-one (Intermediate G, 100 mg, 0.250 mmol), bis(pinacolato)-diborane (Aldrich, Buchs, Switzerland, 78 mg, 0.3 mmol), potassium acetate (74 mg, 0.754 mmol) and $PdCl_2$(dppf) (8 mg, 0.011 mmol) in dioxane (1.1 ml) and DMSO (0.02 ml) was stirred in a closed microwave vial flushed with argon at 90° C. for 7.5 h. Then the RM was diluted with EtOAc and washed with brine (2×). The organic layer was dried over $Na_2SO_4$, filtered and evaporated to dryness. The residue was dissolved in DCM and purified by flash chromatography (DCM/MeOH 0% to 4%). The fractions containing product were evaporated together to give the title compound as an off-white solid. (HPLC: $t_R$ 2.16 min (Method A); M+H=448 MS-ES)

Example 113

1-(1-Isopropyl-3-methyl-1H-pyrazol-4-yl)-3-methyl-8-pyridin-2-yl-1,3-dihydro-imidazo[4,5-c]quinolin-2-one

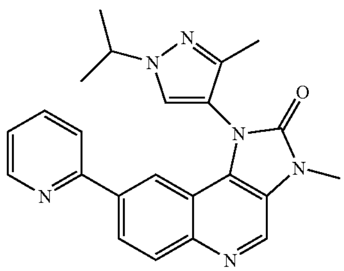 [SMILES: Cc1nn(C(C)C)cc1-n1c(=O)n(C)c2cnc3ccc(-c4ccccn4)cc3c21]

The title compound was synthesized in a similar manner as described in Example 112 using 2-bromopyridine (Aldrich, Buchs, Switzerland, 0.009 ml, 0.093 mmol) to give the title compound as a white solid. (HPLC: $t_R$ 2.49 min (Method A); M+H=399 MS-ES; $^1$H-NMR ($d_6$-DMSO, 400 MHz) 8.98 (s, 1H), 8.61-8.56 (m, 1H), 8.28-8.23 (m, 1H), 8.23-8.19 (m, 1H), 8.13-8.06 (m, 2H), 7.88-7.81 (m, 1H), 7.69-7.63 (m, 1H), 7.38-7.31 (m, 1H), 4.63-4.52 (m, 1H), 3.58 (s, 3H), 1.95 (s, 3H), 1.51 (d, 6H))

Example 114

1-(1,3-Dimethyl-1H-pyrazol-4-yl)-3-methyl-8-pyridin-2-yl-1,3-dihydro-imidazo[4,5-c]quinolin-2-one

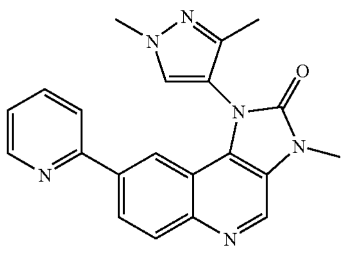 [SMILES: Cc1nn(C)cc1-n1c(=O)n(C)c2cnc3ccc(-c4ccccn4)cc3c21]

The title compound was synthesized in a similar manner as described in Example 112 using 1-(1,3-dimethyl-1H-pyrazol-4-yl)-3-methyl-8-(4,4,5,5-tetramethyl-[1,3,2]dioxaborolan-2-yl)-1,3-dihydro-imidazo[4,5-c]quinolin-2-one (Stage 114.1.1, 34.5 mg, 0.082 mmol) and 2-bromopyridine (Aldrich, Buchs, Switzerland, 0.011 ml, 0.114 mmol) to give the title compound as a white solid. (HPLC: $t_R$ 2.25 min (Method A); M+H=371 MS-ES; $^1$H-NMR ($d_6$-DMSO, 400 MHz) 8.98 (s, 1H), 8.67-8.61 (m, 1H), 8.30-8.24 (m, 1H), 8.17-8.06 (m, 3H), 7.94-7.86 (m, 1H), 7.67-7.61 (m, 1H), 7.39-7.32 (m, 1H), 3.95 (s, 3H), 3.57 (s, 3H), 1.95 (s, 3H))

Stage 114.1.1 1-(1,3-Dimethyl-1H-pyrazol-4-yl)-3-methyl-8-(4,4,5,5-tetramethyl-[1,3,2]dioxaborolan-2-yl)-1,3-dihydro-imidazo[4,5-c]quinolin-2-one

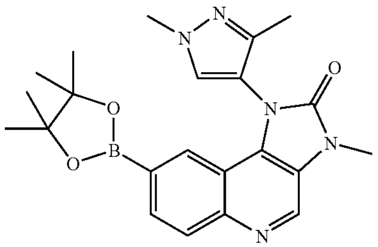

The title compound was synthesized in a similar manner as described in stage 112.1.1 using 8-bromo-1-(1,3-dimethyl-1H-pyrazol-4-yl)-3-methyl-1,3-dihydro-imidazo[4,5-c]quinolin-2-one (Intermediate A, 200 mg, 0.532 mmol) to give the title compound as an off-white solid. (HPLC: $t_R$ 2.00 min (Method A); M+H=420 MS-ES)

Example 115

1-(1,3-Dimethyl-1H-pyrazol-4-yl)-3-methyl-8-pyrazin-2-yl-1,3-dihydro-imidazo[4,5-c]quinolin-2-one

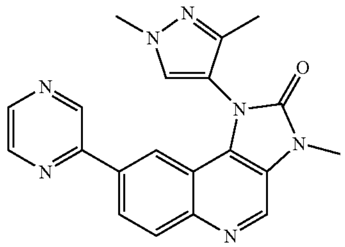 [SMILES: Cc1nn(C)cc1-n1c(=O)n(C)c2cnc3ccc(-c4cnccn4)cc3c21]

The title compound was synthesized in a similar manner as described in Example 112 using 1-(1,3-dimethyl-1H-pyrazol-4-yl)-3-methyl-8-(4,4,5,5-tetramethyl-[1,3,2]dioxaborolan-2-yl)-1,3-dihydro-imidazo[4,5-c]quinolin-2-one (Stage 114.1.1, 33.5 mg, 0.080 mmol) and 2-bromopyrazine (Synchem, Huddersfield, UK, 17.2 mg, 0.108 mmol) to give the title compound as a white solid. (HPLC: $t_R$ 2.34 min (Method A); M+H=372 MS-ES; $^1$H-NMR ($d_6$-DMSO, 400 MHz) 9.01 (s, 1H), 8.98 (s, 1H), 8.72-8.70 (m, 1H), 8.62-8.60 (m, 1H), 8.32-8.28 (m, 1H), 8.16-8.13 (m, 3H), 3.94 (s, 3H), 3.59 (s, 3H), 1.95 (s, 3H))

Example 116

1-(1,3-Dimethyl-1H-pyrazol-4-yl)-3-methyl-8-(1-methyl-1H-pyrrolo[2,3-b]pyridin-5-yl)-1,3-dihydro-imidazo[4,5-c]quinolin-2-one

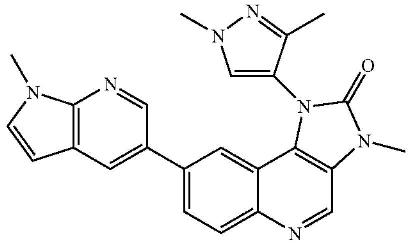 [SMILES: Cc1nn(C)cc1-n1c(=O)n(C)c2cnc3ccc(-c4cnc5c(ccn5C)c4)cc3c21]

A mixture of a new batch of 1-(1,3-dimethyl-1H-pyrazol-4-yl)-3-methyl-8-(1H-pyrrolo[2,3-b]pyridin-5-yl)-1,3-dihydro-imidazo[4,5-c]quinolin-2-one (Example 36, 45.4 mg, 0.111 mmol) in 1.5 ml anhydrous DMF was treated with 55% NaH in oil (6.0 mg, 0.138 mmol). The reaction mixture was stirred for 20 min at rt, then was added iodomethane (0.009 ml, 138 mmol). The reaction mixture was stirred for 1.5 h at rt. The RM was diluted with MeOH+3 drops TFA and purified directly by Prep.HPLC ($H_2O$ (0.1% TFA)/$CH_3CN$ 95:5 to 60:40). The fractions containing products were collected together and basified with $NaHCO_3$ (0.3 g), before being concentrated. The resulting suspension was filtered and the cake was washed with water, before being dried under high vacuum to give the title compound as a white solid. (HPLC: $t_R$ 2.62 min (Method A); M+H=424 MS-ES; $^1$H-NMR ($d_6$-DMSO, 400 MHz) 8.96 (s, 1H), 8.38-8.36 (m, 1H), 8.18-8.16 (m, 1H), 8.13-8.09 (m, 1H), 8.06-8.04 (m, 1H), 7.99-7.95 (m, 1H), 7.60-7.58 (m, 1H), 7.57-7.55 (m, 1H), 6.54-6.51 (m, 1H), 3.93 (s, 3H), 3.85 (s, 3H), 3.58 (s, 3H), 1.97 (s, 3H))

Example 117

N-{3-[1-(1,3-Dimethyl-1H-pyrazol-4-yl)-3-methyl-2-oxo-2,3-dihydro-1H-imidazo[4,5-c]quinolin-8-yl]-phenyl}-N-methyl-methanesulfonamide

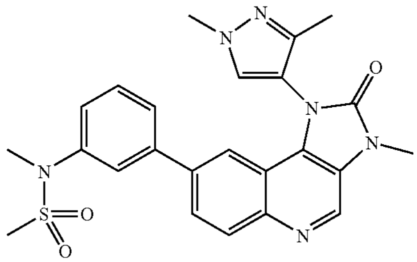

The title compound was synthesized in a similar manner as described for Stage 62.1.2 using N-{3-[1-(1,3-dimethyl-1H-pyrazol-4-yl)-3-methyl-2-oxo-2,3-dihydro-1H-imidazo[4,5-c]quinolin-8-yl]-phenyl}-methanesulfonamide (Example 47) to give the title compound as a white solid. (HPLC: $t_R$ 2.59 min (Method A); M+H=477 MS-ES; $^1$H-NMR ($d_6$-DMSO, 400 MHz) 8.97 (s, 1H), 8.16-8.07 (m, 2H), 7.95-7.90 (m, 1H), 7.60-7.56 (m, 1H), 7.54-7.48 (m, 1H), 7.47-7.40 (m, 3H), 3.90 (s, 3H), 3.57 (s, 31-1), 3.29 (s, 3H), 2.99 (s, 3H), 1.95 (s, 3H))

Example 118.1

1-(1-Isopropyl-3-methyl-1H-pyrazol-4-yl)-3-methyl-8-(6-methylamino-pyridin-3-yl)-1,3-dihydro-imidazo[4,5-c]quinolin-2-one

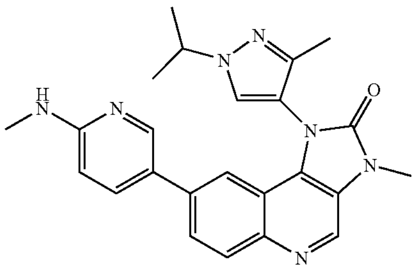

The title compound was synthesized in a similar manner as described for Example 1.1 using 8-bromo-1-(1-isopropyl-3-methyl-1H-pyrazol-4-yl)-3-methyl-1,3-dihydro-imidazo[4,5-c]quinolin-2-one (Intermediate G, 58.8 mg, 0.147 mmol) and 6-(N-boc-methylamino)pyridine-3-boronic acid pinacol ester (Alfa Aesar, Heysham, UK, 58.8 mg, 0.176 mmol) to give crude boc-protected title compound that is treated for 25 min at rt with trifluoroacetic acid (1.5 ml) and then purified by prep. HPLC to give the title compound as a light yellow solid. (HPLC: $t_R$ 2.21 min (Method A); M+H=428 MS-ES; $^1$H-NMR ($d_6$-DMSO, 400 MHz) 8.90 (s, 1H), 8.23-8.14 (m, 2H), 8.05-7.98 (m, 1H), 7.87-7.79 (m, 1H), 7.48-7.37 (m, 2H), 6.78-6.70 (m, 1H), 6.49-6.42 (m, 1H), 4.61-4.50 (m, 1H), 3.56 (s, 3H), 2.77 (d, 3H), 1.95 (d, 3H), 1.51-1.45 (m, 6H))

The following examples were synthesized in a similar manner as described for Example 118 using the specified intermediate.

| Example | Intermed. | structure | Name of the example | MS-ES (M + H) | HPLC $t_R$ (min) |
|---|---|---|---|---|---|
| 118.2 | A | 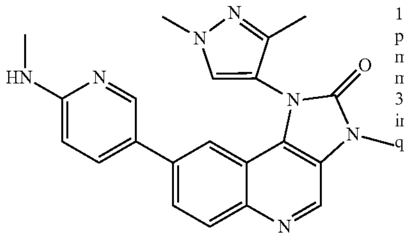 | 1-(1,3-Dimethyl-1H-pyrazol-4-yl)-3-methyl-8-(6-methylamino-pyridin-3-yl)-1,3-dihydro-imidazo[4,5-c]quinolin-2-one | 400 | 2.09 |
| 118.3 | L | 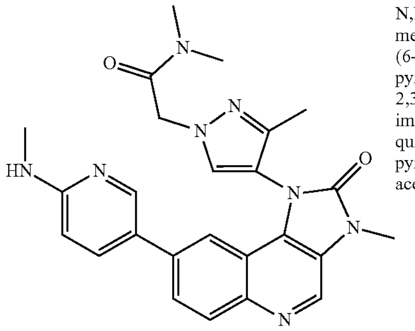 | N,N-Dimethyl-2-{3-methyl-4-[3-methyl-8-(6-methylamino-pyridin-3-yl)-2-oxo-2,3-dihydro-imidazo[4,5-c]quinolin-1-yl]-pyrazol-1-yl}-acetamide | 471 | 2.09 |
| 118.4 | F | 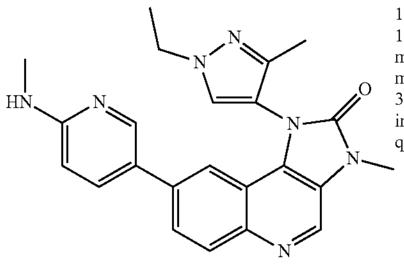 | 1-(1-Ethyl-3-methyl-1H-pyrazol-4-yl)-3-methyl-8-(6-methylamino-pyridin-3-yl)-1,3-dihydro-imidazo[4,5-c]quinolin-2-one | 414 | 2.07 |

-continued

| Example | Intermed. | structure | Name of the example | MS-ES (M + H) | HPLC $t_R$ (min) |
|---|---|---|---|---|---|
| 118.5 | K | 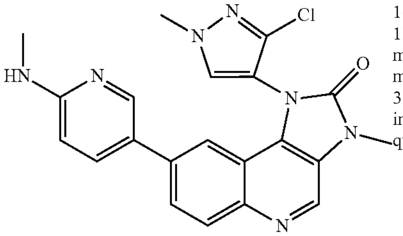 | 1-(3-Chloro-1-methyl-1H-pyrazol-4-yl)-3-methyl-8-(6-methylamino-pyridin-3-yl)-1,3-dihydro-imidazo[4,5-c]quinolin-2-one | 420 | 2.18 |

Example 119

1-(3-Chloro-1-methyl-1H-pyrazol-4-yl)-3-methyl-8-(5-methyl-6-methylamino-pyridin-3-yl)-1,3-dihydro-imidazo[4,5-c]quinolin-2-one

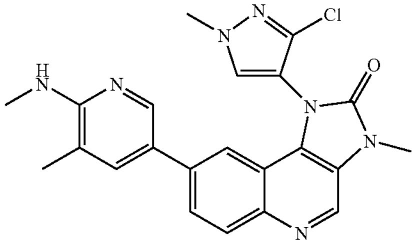

The title compound was synthesized in a similar manner as described for Example 1.1 using 8-bromo-1-(3-chloro-1-methyl-1H-pyrazol-4-yl)-3-methyl-1,3-dihydro-imidazo[4,5-c]quinolin-2-one (Intermediate K) and 6-(N-boc-methylamino)-5-methylpyridine-3-boronic acid pinacol ester (Combi-Blocks, San Diego, USA, 58.8 mg, 0.176 mmol) to give crude boc-protected title compound that was treated for 30 min at rt with trifluoroacetic acid (0.5 ml) and then purified by prep. HPLC to give the title compound as an off-white foam. (HPLC: $t_R$ 2.24 min (Method A); M+H=434 MS-ES; $^1$H-NMR ($d_6$-DMSO, 400 MHz) 8.92 (s, 1H), 8.40 (s, 1H), 8.14-8.12 (m, 1H), 8.05-8.03 (m, 1H), 7.90-7.85 (m, 1H), 7.38-7.37 (m, 2H), 6.28-6.20 (br, 1H), 4.01 (s, 3H), 3.58 (s, 3H), 2.88 (m, 3H), 2.11 (s, 3H))

Example 120

N-{5-[1-(1,3-Dimethyl-1H-pyrazol-4-yl)-3-methyl-2-oxo-2,3-dihydro-1H-imidazo[4,5-c]quinolin-8-yl]-pyridin-3-yl}-methanesulfonamide

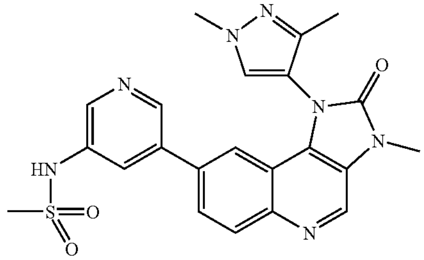

The title compound was synthesized in a similar manner as described for Stage 75.1.3 using 8-(5-amino-pyridin-3-yl)-1-(1,3-dimethyl-1H-pyrazol-4-yl)-3-methyl-1,3-dihydro-imidazo[4,5-c]quinolin-2-one (Example 45, 72 mg, 0.187 mmol) to give the title compound as a white solid. (HPLC: $t_R$ 2.19 min (Method A); M+H=464 MS-ES; $^1$H-NMR ($d_6$-DMSO, 400 MHz) 10.20-10.15 (m, 1H), 9.00 (s, 1H), 8.43-8.37 (m, 2H), 8.19-8.09 (m, 2H), 7.92-7.84 (m, 1H), 7.72-7.66 (m, 1H), 7.61-7.56 (m, 1H), 3.88 (s, 3H), 3.58 (s, 3H), 3.11 (s, 3H), 1.96 (s, 3H))

Example 121

N-{5-[1-(1,3-Dimethyl-1H-pyrazol-4-yl)-3-methyl-2-oxo-2,3-dihydro-1H-imidazo[4,5-c]quinolin-8-yl]-pyridin-3-yl}-N-methyl-methanesulfonamide

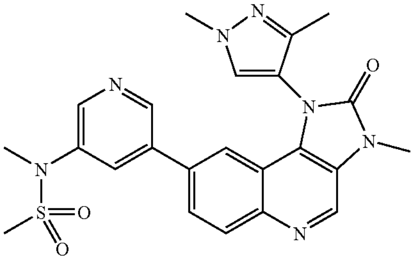

The title compound was synthesized in a similar manner as described for stage 62.1.2 using N-{5-[1-(1,3-dimethyl-1H-pyrazol-4-yl)-3-methyl-2-oxo-2,3-dihydro-1H-imidazo[4,5-c]quinolin-8-yl]-pyridin-3-yl}-methanesulfonamide (Example 120) to give the title compound as an off-white solid. (HPLC: $t_R$ 2.28 min (Method A); M+H=478 MS-ES; $^1$H-NMR ($d_6$-DMSO, 400 MHz) 9.00 (s, 1H), 8.64-8.58 (m, 2H), 8.17-8.12 (m, 2H), 8.03-7.97 (m, 1H), 7.92-7.88 (m, 1H), 7.63-7.59 (m, 1H), 3.88 (s, 3H), 3.58 (s, 3H), 3.35 (s, 3H), 3.07 (s, 3H), 1.96 (s, 3H))

Example 122

1-(1,3-Dimethyl-1H-pyrazol-4-yl)-8-(5-ethylamino-pyridin-3-yl)-3-methyl-1,3-dihydro-imidazo[4,5-c]quinolin-2-one

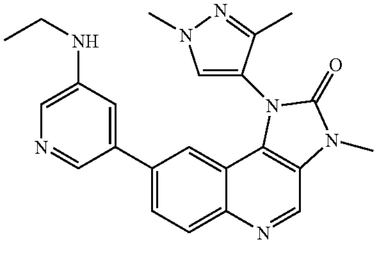 [SMILES: CCNc1cncc(-c2ccc3ncc4c(c3c2)n(-c2cn(C)nc2C)c(=O)n4C)c1]

A solution of 8-(5-amino-pyridin-3-yl)-1-(1,3-dimethyl-1H-pyrazol-4-yl)-3-methyl-1,3-dihydro-imidazo[4,5-c]quinolin-2-one (Example 45, 38 mg, 0.099 mmol), acetaldehyde (Fluka, Buchs, Switzerland, 4.8 mg, 0.108 mmol) in DCM (2 ml) was stirred for 1.5 h at rt in presence of acetic acid (0.02 ml, 3.54 mmol). Was added sodium triacetoxyborohydride (52.2 mg, 0.246 mmol) and the RM was stirred 1.5 h at rt, before being quenched with aqueous saturated $NaHCO_3$ and extracted with DCM (2×). The combined organic layers were dried over $Na_2SO_4$, filtered and evaporated to dryness. The residue was purified by Prep.HPLC ($H_2O$ (0.1% TFA)/$CH_3CN$ 95:5 to 60:40). The fractions containing products were collected together and basified with $NaHCO_3$ (0.3 g), before being concentrated, saturated with NaCl and extracted with EtOAc (3×). The combined organic layers were dried over $Na_2SO_4$, filtered and evaporated to give the title compound as an off-white solid. (HPLC: $t_R$ 2.13 min (Method A); M+H=414 MS-ES; $^1$H-NMR ($d_6$-DMSO, 400 MHz) 8.97 (s, 1H), 8.13-8.08 (m, 2H), 7.97-7.95 (m, 1H), 7.92-7.88 (m, 2H), 7.60-7.58 (m, 1H), 6.88-6.85 (m, 1H), 6.01 (t, 1H), 3.89 (s, 3H), 3.58 (s, 3H), 3.15-3.06 (m, 2H), 1.95 (s, 3H), 1.21 (t, 3H))

Example 123

1-(1,3-Dimethyl-1H-pyrazol-4-yl)-3-methyl-8-[6-(2H-tetrazol-5-yl)-pyridin-3-yl]-1,3-dihydro-imidazo[4,5-c]quinolin-2-one

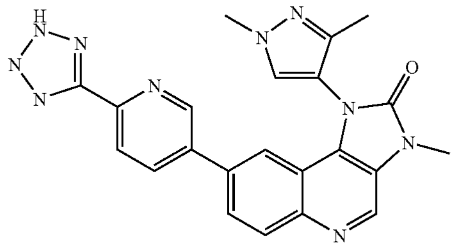 [SMILES: Cc1nn(C)cc1-n1c(=O)n(C)c2cnc3ccc(-c4ccc(C5=NNNN5)nc4)cc3c21]

A mixture of 5-[1-(1,3-dimethyl-1H-pyrazol-4-yl)-3-methyl-2-oxo-2,3-dihydro-1H-imidazo[4,5-c]quinolin-8-yl]-pyridine-2-carbonitrile (stage 123.1.1, 41.1 mg, 0.104 mmol), sodium azide (10 mg, 0.154 mmol) and ammonium chloride (18 mg, 0.337 mmol) in DMF (0.3 ml) was sealed and heated at 120° C. for 80 min. The reaction mixture was quenched with aqueous $NaHCO_3$ and washed with EtOAc (2×). The aqueous layer was adjusted to pH 5 with 1 M aqueous HCl and extracted with dichloromethane (3×). The combined organic layers were dried over $Na_2SO_4$, filtered and evaporated. The crude product was purified by Prep.HPLC ($H_2O$ (0.1% TFA)/$CH_3CN$ 95:5 to 65:35). The fractions containing products were collected together and lyophilized to give the title compound as a white lyophilizate TFA salt. (HPLC: $t_R$ 2.34 min (Method A); M+H=439 MS-ES; $^1$H-NMR ($d_6$-DMSO, 400 MHz) 9.18 (s, 1H), 8.90-8.85 (m, 1H), 8.37-8.32 (m, 1H), 8.26-8.15 (m, 4H), 7.75-7.70 (m, 1H), 3.94 (s, 3H), 3.61 (s, 3H), 2.00 (s, 3H))

Stage 123.1.1 5-[1-(1,3-Dimethyl-1H-pyrazol-4-yl)-3-methyl-2-oxo-2,3-dihydro-1H-imidazo[4,5-c]quinolin-8-yl]-pyridine-2-carbonitrile

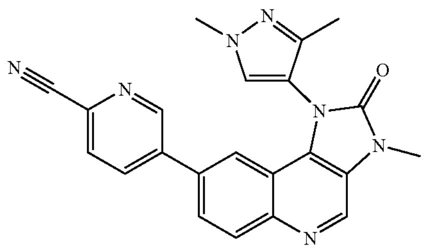 [SMILES: Cc1nn(C)cc1-n1c(=O)n(C)c2cnc3ccc(-c4ccc(C#N)nc4)cc3c21]

The title compound was synthesized in a similar manner as described for Example 1.1 using 8-bromo-1-(1,3-dimethyl-1H-pyrazol-4-yl)-3-methyl-1,3-dihydro-imidazo[4,5-c]quinolin-2-one (Intermediate A) and 2-cyanopyridine-5-boronic acid pinacol ester (Frontier Scientific, Logan, USA) to give the title compound as a brown solid. (HPLC: $t_R$ 2.42 min (Method A); M+H=396 MS-ES)

Example 124

5-[1-(1,3-Dimethyl-1H-pyrazol-4-yl)-3-methyl-2-oxo-2,3-dihydro-1H-imidazo[4,5-c]quinolin-8-yl]-2-methoxy-nicotinic acid

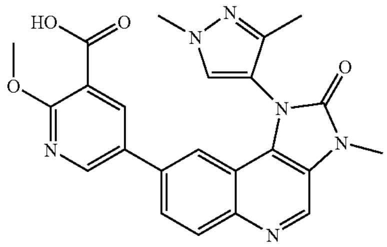 [SMILES: COc1ncc(-c2ccc3ncc4c(c3c2)n(-c2cn(C)nc2C)c(=O)n4C)cc1C(=O)O]

The title compound was synthesized in a similar manner as described for Example 1.1 using 8-bromo-1-(1,3-dimethyl-1H-pyrazol-4-yl)-3-methyl-1,3-dihydro-imidazo[4,5-c]quinolin-2-one (Intermediate A) and 2-methoxy-3-(carbomethoxy)pyridine-5-boronic acid pinacol ester (Combi-Blocks, San Diego, USA) to give the title compound as a white lyophilizate TFA salt. (HPLC: $t_R$ 2.31 min (Method A); M+H=445 MS-ES; $^1$H-NMR ($d_6$-DMSO, 400 MHz) 9.21 (s, br, 1H), 8.62-8.56 (m, 1H), 8.23-8.16 (m, 3H), 8.11-8.07 (m, 1H), 7.62-7.57 (m, 1H), 3.96 (s, 3H), 3.93 (s, 3H), 3.59 (s, 3H), 1.94 (s, 3H))

Example 125.1

5-[1-(1,3-Dimethyl-1H-pyrazol-4-yl)-3-methyl-2-oxo-2,3-dihydro-1H-imidazo[4,5-c]quinolin-8-yl]-2-methoxy-N-methyl-nicotinamide

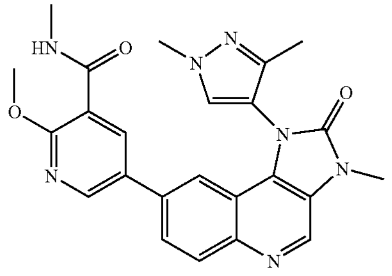 [SMILES: CNC(=O)c1cc(-c2ccc3ncc4c(c3c2)n(-c2cn(C)nc2C)c(=O)n4C)cnc1OC]

To a cooled with an ice-bath suspension of 5-[1-(1,3-dimethyl-1H-pyrazol-4-yl)-3-methyl-2-oxo-2,3-dihydro-1H-imidazo[4,5-c]quinolin-8-yl]-2-methoxy-nicotinic acid TFA salt (Example 124, 60 mg, 0.089 mmol) in dichloromethane (1.5 ml) containing DMF (0.005 ml) was added oxallyl chloride (0.038 ml, 0.449 mmol). The reaction mixture was stirred for 1 h at rt then cooled with an ice-bath and quenched with 8 M methylamine in ethanol (2.5 ml, 20 mmol). After 5 min stirring, the reaction mixture was evaporated to dryness and the residue purified by Prep.HPLC ($H_2O$ (0.1% TFA)/$CH_3CN$ 95:5 to 65:35). The fractions containing products were collected together, basified with $NaHCO_3$, concentrated and the formed precipitate was filtered, washed with water and dried to give the title compound as white solid. (HPLC: $t_R$ 2.45 min (Method A); M+H=458 MS-ES; $^1$H-NMR ($d_6$-DMSO, 400 MHz) 8.97 (s, 1H), 8.52-8.46 (m, 1H), 8.35-8.27 (m, 1H), 8.19-8.07 (m, 3H), 7.99-7.93 (m, 1H), 7.56-7.51 (m, 1H), 4.00 (s, 3H), 3.95 (s, 3H), 3.57 (s, 3H), 2.83 (d, 3H), 1.94 (s, 3H))

The following example was synthesized in a similar manner as described for Example 125.1 using ammonia.

| Example | structure | Name of the example | MS-ES (M + H) | HPLC $t_R$ (min) |
|---|---|---|---|---|
| 125.2 | 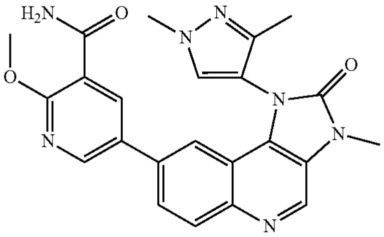 [SMILES: COc1ncc(-c2ccc3ncc4c(c3c2)n(-c2cn(C)nc2C)c(=O)n4C)cc1C(N)=O] | 5-[1-(1,3-Dimethyl-1H-pyrazol-4-yl)-3-methyl-2-oxo-2,3-dihydro-1H-imidazo[4,5-c] quinolin-8-yl]-2-methoxy-nicotinamide | 444 | 2.35 |

Example 126

1-(1,3-Dimethyl-1H-pyrazol-4-yl)-3-methyl-8-(6-piperazin-1-yl-pyridin-3-yl)-1,3-dihydro-imidazo[4,5-c]quinolin-2-one

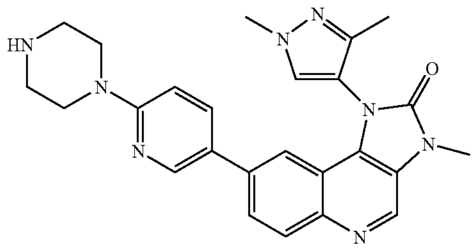 [SMILES: Cc1nn(C)cc1-n1c(=O)n(C)c2cnc3ccc(-c4ccc(N5CCNCC5)nc4)cc3c21]

The title compound was synthesized in a similar manner as described for Example 118.1 using 8-bromo-1-(1,3-dimethyl-1H-pyrazol-4-yl)-3-methyl-1,3-dihydro-imidazo[4,5-c]quinolin-2-one (Intermediate A) and 2-(4-boc-piperazine)pyridine-5-boronic acid pinacol ester (Combi-Blocks, San Diego, USA) to give the title compound as a white solid. (HPLC: $t_R$ 1.97 min (Method A); M+H=455 MS-ES; $^1$H-NMR ($d_6$-DMSO, 400 MHz) 8.91 (s, 1H), 8.30-8.25 (m, 1H), 8.14-8.11 (m, 1H), 8.07-8.01 (m, 1H), 7.90-7.84 (m, 1H), 7.62-7.56 (m, 1H), 7.46-7.41 (m, 1H), 6.95-6.89 (m, 1H), 3.92 (s, 3H), 3.57 (s, 3H), 3.53-3.46 (m, 4H), 2.86-2.76 (m, 4H), 1.95 (s, 3H))

Example 127

8-(5-Amino-6-methoxy-pyridin-3-yl)-1-(1,3-dimethyl-1H-pyrazol-4-yl)-3-methyl-1,3-dihydro-imidazo[4,5-c]quinolin-2-one

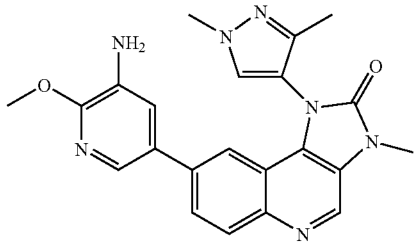

A solution of 1-(1,3-dimethyl-1H-pyrazol-4-yl)-8-(6-methoxy-5-nitro-pyridin-3-yl)-3-methyl-1,3-dihydro-imidazo[4,5-c]quinolin-2-one (Example 66, 50 mg, 0.112 mmol) in 5 ml THF and 5 ml MeOH was stirred in presence of palladium 10% on charcoal under 1.1 bar of hydrogen for 5 h at rt. The reaction mixture was filtered over Celite and the catalyst was washed with MeOH/THF. The filtrate was evaporated and the crude product was purified by Prep.HPLC ($H_2O$ (0.1% TFA)/$CH_3CN$ 95:5 to 50:50). The fractions containing products were collected together, basified with $NaHCO_3$, concentrated and extracted with EtOAc (3×). The combined organic layers were dried over $Na_2SO_4$, filtered and evaporated to give the title compound as a light yellow solid. (HPLC: $t_R$ 2.29 min (Method A); M+H=416 MS-ES; $^1$H-NMR ($d_6$-DMSO, 400 MHz) 8.94 (s, 1H), 8.12-8.10 (m, 1H), 8.08-8.05 (m, 1H), 7.76-7.72 (m, 1H), 7.47-7.45 (m, 1H), 7.43-7.41 (m, 1H), 7.00-6.97 (m, 11-1), 5.11 (s, br, 2H), 3.92 (s, 3H), 3.89 (s, 3H), 3.57 (s, 3H), 1.94 (s, 3H))

Example 128.1

1-(1,3-Dimethyl-1H-pyrazol-4-yl)-3-methyl-8-pyridin-3-yl-1,3-dihydro-imidazo[4,5-c]quinoline-2-thione

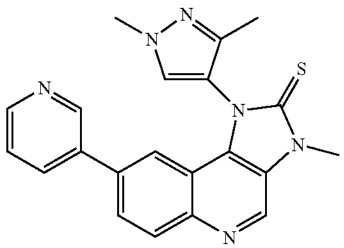 [SMILES: Cc1nn(C)cc1-n1c(=S)n(C)c2cnc3ccc(-c4cccnc4)cc3c21]

A mixture of a new batch of 1-(1,3-dimethyl-1H-pyrazol-4-yl)-3-methyl-8-pyridin-3-yl-1,3-dihydro-imidazo[4,5-c]quinolin-2-one (Example 10.2, 8 mg, 0.219 mmol) and Lawesson's reagent (98 mg, 0.242 mmol) in dioxane (1 ml) was stirred in a seal vial for 28 h at 100° C. The reaction mixture was quenched with saturated aqueous $NaHCO_3$ and extracted with DCM (2×). The combined organic layers were washed with brine, dried over $Na_2SO_4$, filtered and evaporated to dryness. The residue was taken in NMP and purified by Prep.HPLC ($H_2O$ (0.1% TFA)/$CH_3CN$ 95:5 to 65:35). The fractions containing products were collected together and basified with $NaHCO_3$ (0.3 g), before being concentrated. The resulting suspension was filtered and the cake was washed with water, before being dried under high vacuum to give the title compound as a white solid. (HPLC: $t_R$ 2.32 min (Method A); M+H=387 MS-ES; $^1$H-NMR ($d_6$-DMSO, 400 MHz) 9.21 (s, 1H), 8.72-8.68 (m, 1H), 8.62-8.58 (m, 1H), 8.23-8.16 (m, 2H), 8.08-8.04 (m, 1H), 7.93-7.88 (m, 1H), 7.56-7.48 (m, 2H), 3.97-3.93 (m, 6H), 1.92 (s, 3H))

The following example was synthesized in a similar manner as described for Example 128.1 using Example 1.8 as starting material.

| Example | structure | Name of the example | MS-ES (M + H) | HPLC $t_R$ (min) |
|---|---|---|---|---|
| 128.2 | 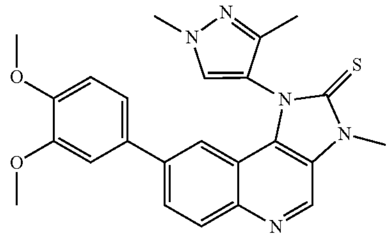 [SMILES: COc1ccc(-c2ccc3ncc4c(c3c2)n(-c2cn(C)nc2C)c(=S)n4C)cc1OC] | 8-(3,4-Dimethoxy-phenyl)-1-(1,3-dimethyl-1H-pyrazol-4-yl)-3-methyl-1,3-dihydro-imidazo[4,5-c]quinoline-2-thione | 446 | 2.85 |

Example 129

1-(1,3-Dimethyl-1H-pyrazol-4-yl)-3-methyl-8-(1-methyl-1H-pyrrolo[3,2-b]pyridin-6-yl)-1,3-dihydro-imidazo[4,5-c]quinolin-2-one

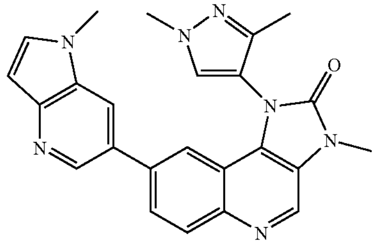 [SMILES: Cc1nn(C)cc1-n1c(=O)n(C)c2cnc3ccc(-c4cnc5ccn(C)c5c4)cc3c21]

The title compound was synthesized in a similar manner as described for Example 116 using 1-(1,3-dimethyl-1H-pyrazol-4-yl)-3-methyl-8-(1H-pyrrolo[3,2-b]pyridin-6-yl)-1,3-dihydro-imidazo[4,5-c]quinolin-2-one (Example 99) to give the title compound as an off-white solid. (HPLC: $t_R$ 2.11 min (Method A); M+H=424 MS-ES; $^1$H-NMR ($d_6$-DMSO, 400 MHz) 8.97 (s, 1H), 8.47-8.45 (m, 1H), 8.18-8.16 (m, 1H), 8.15-8.11 (m, 1H), 8.08-8.04 (m, 1H), 8.00-7.98 (m, 1H), 7.71-7.69 (m, 1H), 7.65-7.63 (m, 1H), 6.59-6.57 (m, 1H), 3.92 (s, 3H), 3.89 (s, 3H), 3.59 (s, 3H), 1.97 (s, 3H))

Example 130

1-(1,3-Dimethyl-1H-pyrazol-4-yl)-8-[2-(isopropyl-methyl-amino)-pyridin-4-yl]-3-methyl-1,3-dihydro-imidazo[4,5-c]quinolin-2-one

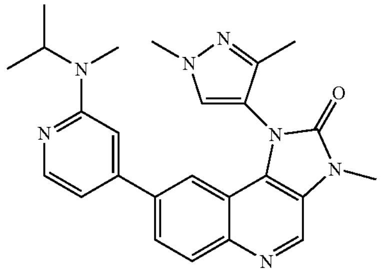 [SMILES: Cc1nn(C)cc1-n1c(=O)n(C)c2cnc3ccc(-c4ccnc(N(C)C(C)C)c4)cc3c21]

The title compound was synthesized in a similar manner as described for Example 1.1 using 8-bromo-1-(1,3-dimethyl-1H-pyrazol-4-yl)-3-methyl-1,3-dihydro-imidazo[4,5-c] quinolin-2-one (Intermediate A) and isopropyl-methyl-[4-(4,4,5,5-tetramethyl-[1,3,2]dioxaborolan-2-yl)-pyridin-2-yl]-amine (Stage 130.1.1) to give the title compound as a white solid. (HPLC: $t_R$ 2.24 min (Method A); M+H=442 MS-ES; $^1$H-NMR ($d_6$-DMSO, 400 MHz) 8.98 (s, 1H), 8.14-8.08 (m, 3H), 7.97-7.93 (m, 1H), 7.69-7.66 (m, 1H), 6.69-6.66 (m, 1H), 6.56-6.53 (m, 1H), 4.90 (hp, 1H), 3.89 (s, 3H), 3.58 (s, 3H), 2.85 (s, 3H), 1.96 (s, 3H), 1.17-1.11 (m, 6H))

Stage 130.1.1 Isopropyl-methyl-[4-(4,4,5,5-tetramethyl-[1,3,2]dioxaborolan-2-yl)-pyridin-2-yl]-amine

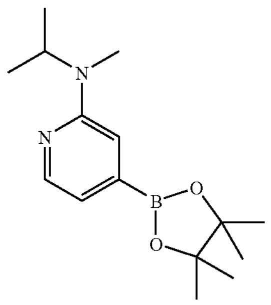 [SMILES: CC(C)N(C)c1cc(B2OC(C)(C)C(C)(C)O2)ccn1]

The title compound was synthesized in a similar manner as described for stage 5.1.1-2 using 4-bromo-2-chloropyridine (Aldrich, Buchs, Switzerland) and N-methylisopropylamine (Aldrich, Buchs, Switzerland) to give the title compound as a brown oil. (HPLC: $t_R$ 2.06 min (Method A); M+H=277 MS-ES).

Example 131

8-(6-Ethoxy-pyridin-3-yl)-1-[1-(2-methoxy-ethyl)-3-methyl-1H-pyrazol-4-yl]-3-methyl-1,3-dihydro-imidazo[4,5-c]quinolin-2-one

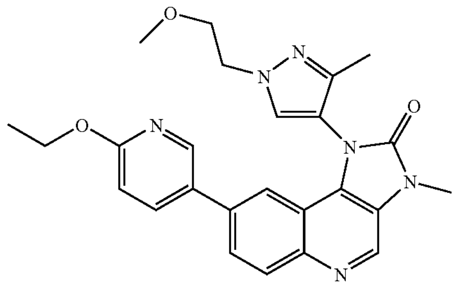 [SMILES: CCOc1ccc(-c2ccc3ncc4c(c3c2)n(-c2cn(CCOC)nc2C)c(=O)n4C)cn1]

The title compound was synthesized in a similar manner as described for Example 104 using 8-(6-ethoxy-pyridin-3-yl)-1-[1-(2-hydroxy-ethyl)-3-methyl-1H-pyrazol-4-yl]-3-methyl-1,3-dihydro-imidazo[4,5-c]quinolin-2-one (Example 103.2) to give the title compound as an off-white solid. (HPLC: $t_R$ 2.70 min (Method A); M+H=459 MS-ES; $^1$H-NMR ($d_6$-DMSO, 400 MHz) 8.96 (s, 1H), 8.28-8.26 (m, 1H), 8.12-8.06 (m, 2H), 7.91-7.87 (m, 1H), 7.81-7.78 (m, 1H), 7.49-7.47 (m, 1H), 6.90-6.87 (m, 1H), 4.37-4.29 (m, 4H), 3.71 (q, 2H), 3.58 (s, 3H), 3.12 (s, 3H), 1.97 (s, 3H), 1.33 (t, 3H))

Example 132

5-[1-(1,3-Dimethyl-1H-pyrazol-4-yl)-3-methyl-2-oxo-2,3-dihydro-1H-imidazo[4,5-c]quinolin-8-yl]-2-methoxy-nicotinonitrile

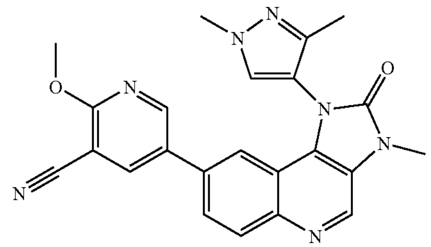 [SMILES: COc1ncc(-c2ccc3ncc4c(c3c2)n(-c2cn(C)nc2C)c(=O)n4C)cc1C#N]

The title compound was synthesized in a similar manner as described for Example 1.1 using 8-bromo-1-(1,3-dimethyl-1H-pyrazol-4-yl)-3-methyl-1,3-dihydro-imidazo[4,5-c] quinolin-2-one (Intermediate A) and 2-Methoxy-5-(4,4,5,5-tetramethyl-[1,3,2]dioxaborolan-2-yl)-nicotinonitrile (Combi-Blocks, San Diego, USA) to give the title compound as a white solid. (HPLC: $t_R$ 2.60 min (Method A); M+H=426 MS-ES)

Example 133

8-(6-Ethoxy-pyridin-3-yl)-1-{3-methyl-1-[2-(4-methyl-piperazin-1-yl)-2-oxo-ethyl]-1H-pyrazol-4-yl}-1,3-dihydro-imidazo[4,5-c]quinolin-2-one

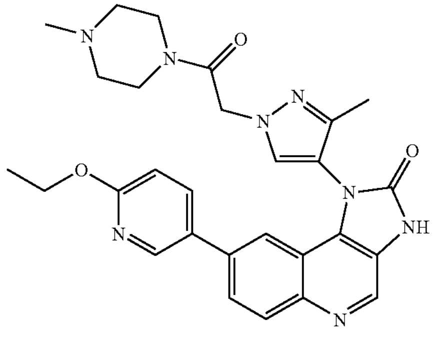 [SMILES: CCOc1ccc(-c2ccc3ncc4[nH]c(=O)n(-c5cn(CC(=O)N6CCN(C)CC6)nc5C)c4c3c2)cn1]

The title compound was synthesized in a similar manner as described for Example 1.1 using 8-bromo-1-{3-methyl-1-[2-(4-methyl-piperazin-1-yl)-2-oxo-ethyl]-1H-pyrazol-4-yl}-1,3-dihydro-imidazo[4,5-c]quinolin-2-one (Stage 133.1.1) and 6-ethoxypyridine-3-boronic acid (ABCR, Karlsruhe, Germany) to give the title compound as a white solid. (HPLC: $t_R$ 2.27 min (Method A); M+H=527 MS-ES; $^1$H-NMR ($d_6$-DMSO, 400 MHz) 11.69 (s, br, 1H), 8.71 (s, 1H), 8.45-8.42 (m, 1H), 8.08-8.03 (m, 2H), 7.96-7.88 (m, 2H), 7.74-7.71 (m, 1H), 6.81-6.67 (m, 1H), 5.27-5.11 (m, 2H), 4.32 (q, 2H), 3.58-3.38 (m, 4H), 2.38-2.26 (m, 4H), 2.19 (s, 3H), 1.92 (s, 3H), 1.31 (t, 2H))

Stage 133.1. 8-Bromo-1-{3-methyl-1-[2-(4-methyl-piperazin-1-yl)-2-oxo-ethyl]-1H-pyrazol-4-yl}-1,3-dihydro-imidazo[4,5-c]quinolin-2-one

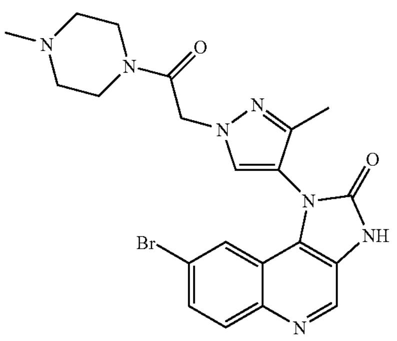 [SMILES: Cc1nn(CC(=O)N2CCN(C)CC2)cc1-n1c(=O)[nH]c2cnc3ccc(Br)cc3c21]

A solution of [4-(8-bromo-2-oxo-2,3-dihydro-imidazo[4,5-c]quinolin-1-yl)-3-methyl-pyrazol-1-yl]-acetic acid (Stage 101.1.2, 178 mg, 0.443 mmol), DIPE (0.232 ml, 1.33 mmol), TPTU (223 mg, 0.752 mmol) in DMA (5 ml) was stirred at rt for 5 min, then was added N-methylpiperazine (0.1 ml, 0.90 mmol). The reaction mixture was stirred 19 h at rt and then was added N-methylpiperazine (0.1 ml, 0.90 mmol) and the reaction mixture was stirred 25 h at rt. The reaction mixture was purified by prep. HPLC to give the title compound as an off-white solid. (HPLC: $t_R$ 1.98 min (Method A); M+H=484, 486 MS-ES)

Example 134

3-Methyl-1-{3-methyl-1-[2-(4-methyl-piperazin-1-yl)-2-oxo-ethyl]-1H-pyrazol-4-yl}-8-phenyl-1,3-dihydro-imidazo[4,5-c]quinolin-2-one

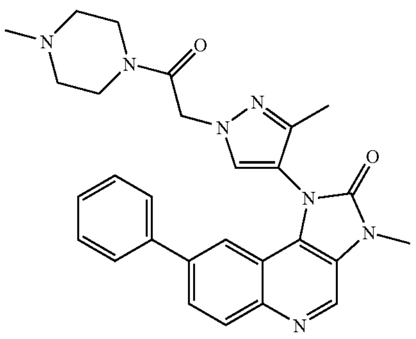

The title compound was synthesized in a similar manner as described for Example 1.1 using 8-bromo-3-methyl-1-{3-methyl-1-[2-(4-methyl-piperazin-1-yl)-2-oxo-ethyl]-1H-pyrazol-4-yl}-1,3-dihydro-imidazo[4,5-c]quinolin-2-one (Stage 134.1.1) and phenylboronic acid (Aldrich, Buchs, Switzerland) to give the title compound as a white solid. (HPLC: $t_R$ 2.32 min (Method A); M+H=496 MS-ES; $^1$H-NMR ($d_6$-DMSO, 400 MHz) 8.96 (s, 1H), 8.11-8.07 (m, 2H), 7.96-7.92 (m, 1H), 7.81-7.79 (m, 1H), 7.69-7.65 (m, 2H), 7.45-7.39 (m, 2H), 7.37-7.32 (m, 1H), 5.28-5.16 (m, 21-1), 3.59-3.43 (m, 7H), 2.40-2.29 (m, 4H), 2.20 (s, 3H), 1.92 (s, 3H))

Stage 134.1 8-Bromo-3-methyl-1-{3-methyl-1-[2-(4-methyl-piperazin-1-yl)-2-oxo-ethyl]-1H-pyrazol-4-yl}-1,3-dihydro-imidazo[4,5-c]quinolin-2-one

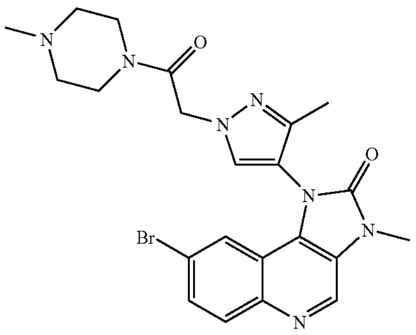

The title compound was synthesized in a similar manner as described for Intermediate A using 8-bromo-1-{3-methyl-1-[2-(4-methyl-piperazin-1-yl)-2-oxo-ethyl]-1H-pyrazol-4-yl}-1,3-dihydro-imidazo[4,5-c]quinolin-2-one (Stage 133.1.1) to give the title compound as an off-white solid. (HPLC: $t_R$ 2.06 min (Method A); M+H=498, 500 MS-ES)

Example 135

N-Ethyl-N-methyl-2-[3-methyl-4-(3-methyl-2-oxo-8-phenyl-2,3-dihydro-imidazo[4,5-c]quinolin-1-yl)-pyrazol-1-yl]-acetamide

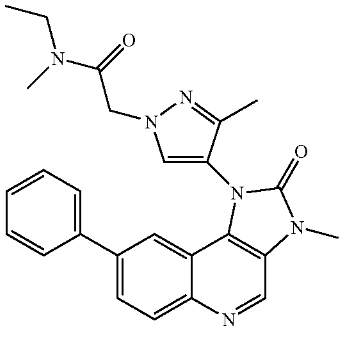 [SMILES: CCN(C)C(=O)Cn1cc(-n2c(=O)n(C)c3cnc4ccc(-c5ccccc5)cc4c32)c(C)n1]

The title compound was synthesized in a similar manner as described for Example 134 using N-ethyl-N-methylamine (Aldrich, Buchs, Switzerland) to give the title compound as a white solid. (HPLC: $t_R$ 2.76 min (Method A); M+H=455 MS-ES; $^1$H-NMR ($d_6$-DMSO, 500 MHz) 8.98 (s, 1H), 8.14-8.09 (m, 2H), 7.98-7.94 (m, 1H), 7.83-7.81 (m, 1H), 7.72-7.68 (m, 2H), 7.47-7.42 (m, 2H), 7.38-7.34 (m, 11-1), 5.25-5.15 (m, 2H), 3.60 (s, 3H), 3.48-3.36 (m, 2H), 3.05 and 2.90 (2×s, 3H), 1.93 and 1.93 (2×s, 3H), 1.20 and 1.08 (2×t, 3H))

Example 136

2-{4-[8-(6-Ethoxy-pyridin-3-yl)-3-methyl-2-oxo-2,3-dihydro-imidazo[4,5-c]quinolin-1-yl]-3-methyl-pyrazol-1-yl}-N-ethyl-N-methyl-acetamide

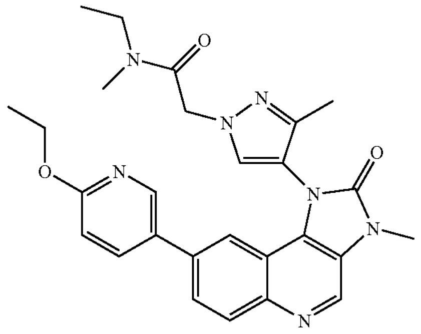 [SMILES: CCOc1ccc(-c2ccc3ncc4c(c3c2)n(-c2cn(CC(=O)N(C)CC)nc2C)c(=O)n4C)cn1]

The title compound was synthesized in a similar manner as described for Example 135 using 6-ethoxypyridine-3-boronic acid (ABCR, Karlsruhe, Germany) to give the title compound as a white solid. (HPLC: $t_R$ 2.70 min (Method A); M+H=500 MS-ES; $^1$H-NMR ($d_6$-DMSO, 400 MHz) 8.95 (s, 1H), 8.46-8.43 (m, 1H), 8.11-8.05 (m, 2H), 8.00-7.91 (m, 2H), 7.74-7.71 (m, 1H), 6.77-6.82 (m, 1H), 5.24-5.10 (m, 2H), 4.36-4.28 (m, 2H), 3.57 (s, 3H), 3.46-3.30 (m, 2H), 3.02 and 2.86 (2×s, 3H), 1.92 and 1.91 (2×s, 3H), 1.31 (t, 3H), 1.18 and 1.03 (2×t, 3H))

Example 137

N-(2-Methoxy-ethyl)-N-methyl-2-[3-methyl-4-(3-methyl-2-oxo-8-phenyl-2,3-dihydro-imidazo[4,5-c]quinolin-1-yl)-pyrazol-1-yl]-acetamide

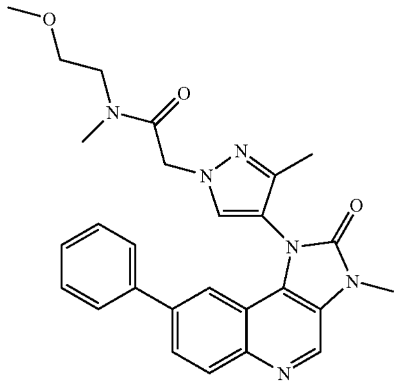

The title compound was synthesized in a similar manner as described for Example 134 using N-(2-methoxyethyl)-N-methylamine (ABCR, Karlsruhe, Germany) to give the title compound as a white foam. (HPLC: $t_R$ 2.73 min (Method A); M+H=485 MS-ES; $^1$H-NMR ($d_6$-DMSO, 500 MHz) 8.96 (s, 1H), 8.12-8.07 (m, 2H), 7.97-7.93 (m, 1H), 7.82-7.79 (m, 1H), 7.70-7.65 (m, 2H), 7.45-7.40 (m, 2H), 7.38-7.32 (m, 1H), 5.28-5.15 (m, 2H), 3.62-3.44 (m, 7H), 3.33 and 3.26 (2×s, 3H), 3.09 and 2.93 (2×s, 3H), 1.92 and 1.91 (2×s, 3H))

Example 138

1-[1-(2-Azetidin-1-yl-2-oxo-ethyl)-3-methyl-1H-pyrazol-4-yl]-8-(6-ethoxy-pyridin-3-yl)-3-methyl-1,3-dihydro-imidazo[4,5-c]quinolin-2-one

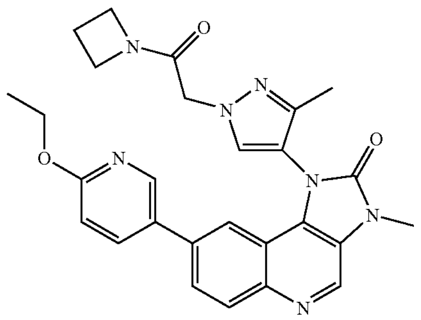 [SMILES: CCOc1ccc(-c2ccc3ncc4c(c3c2)n(-c2cn(CC(=O)N3CCC3)nc2C)c(=O)n4C)cn1]

The title compound was synthesized in a similar manner as described for Example 134 using azetidine (Fluka, Buchs, Switzerland) and 6-ethoxypyridine-3-boronic acid (ABCR, Karlsruhe, Germany) to give the title compound as a white solid. (HPLC: $t_R$ 2.62 min (Method A); M+H=498 MS-ES; $^1$H-NMR ($d_6$-DMSO, 500 MHz) 8.95 (s, 1H), 8.41-8.39 (m, 1H), 8.13-8.07 (m, 2H), 7.95-7.88 (m, 2H), 7.61-7.63 (m, 1H), 6.86-6.82 (m, 1H), 4.94-4.84 (m, 2H), 4.34 (q, 2H), 4.27-4.15 (m, 2H), 3.99-3.88 (m, 2H), 3.58 (s, 3H), 2.28-2.14 (m, 2H), 1.94 (s, 3H), 1.33 (t, 3H))

Example 139

N,N-Diethyl-2-{3-methyl-4-[3-methyl-8-(6-methyl-pyridin-3-yl)-2-oxo-2,3-dihydro-imidazo[4,5-c]quinolin-1-yl]-pyrazol-1-yl}-acetamide

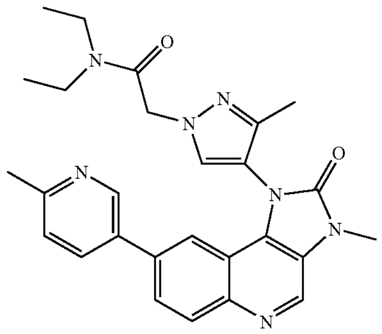

The title compound was synthesized in a similar manner as described for Example 134 using dimethylamine (Fluka, Buchs, Switzerland) and 2-methylpyridine-5-boronic acid (Frontier Scientific, Logan, USA) to give the title compound as a white foam. (HPLC: $t_R$ 2.21 min (Method A); M+H=484 MS-ES; $^1$H-NMR ($d_6$-DMSO, 500 MHz) 8.97 (s, 1H), 8.71-8.69 (m, 1H), 8.13-8.08 (m, 2H), 7.97-7.92 (m, 2H), 7.80-

7.78 (m, 1H), 7.28-7.25 (m, 1H), 5.21-5.09 (m, 2H), 3.59 (s, 3H), 3.44-3.28 (m, 7H), 1.93 (s, 3H), 1.20 (t, 3H), 1.05 (t, 3H))

Example 140.1

N-Ethyl-N-methyl-2-{3-methyl-4-[3-methyl-2-oxo-8-(2-pyrrolidin-1-yl-pyrimidin-5-yl)-2,3-dihydro-imidazo[4,5-c]quinolin-1-yl]-pyrazol-1-yl}-acetamide

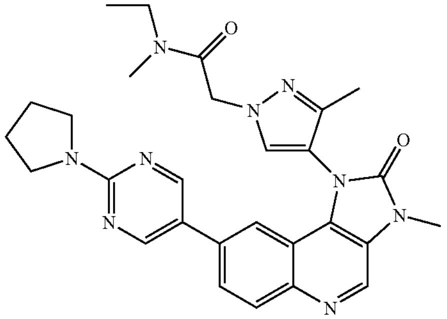 [SMILES: CCN(C)C(=O)Cn1cc(-n2c(=O)n(C)c3cnc4ccc(-c5cnc(N6CCCC6)nc5)cc4c32)c(C)n1]

The title compound was synthesized in a similar manner as described for Example 1.1 using 2-[4-(8-bromo-3-methyl-2-oxo-2,3-dihydro-imidazo[4,5-c]quinolin-1-yl)-3-methyl-pyrazol-1-yl]-N-ethyl-N-methyl-acetamide (Intermediate P) and 2-(pyrrolidin-1-yl)pyrimidine-5-boronic acid pinacol ester (Frontier Scientific, Logan, USA, 37 mg, 0.132 mmol) to give the title compound as an off-white solid. (HPLC: $t_R$ 2.53 min (Method A); M+H=526 MS-ES; $^1$H-NMR ($d_6$-DMSO, 400 MHz) cis&trans amide 8.92 (s, 1H), 8.59-8.55 (m, 2H), 8.08-8.01 (m, 2H), 7.88-7.84 (m, 1H), 7.68-7.63 (m, 1H), 5.23-5.15 (m, 1H), 5.11-5.04 (m, 1H), 3.57 (s, 3H), 3.53-3.21 (m, 6H), 3.01, 2.83 (2×s, 3H), 1.97-1.89 (m, 4H), 1.94, 1.93 (2×s, 3H), 1.17, 0.99 (2×t, 3H))

The following example was synthesized in a similar manner as described for Example 1.1 using 2-(pyrrolidin-1-yl) pyrimidine-5-boronic acid pinacol ester and the specified intermediate.

| Example | Intermed. | structure | Name of the example | MS-ES (M + H) | HPLC $t_R$ (min) |
|---|---|---|---|---|---|
| 140.2 | A | 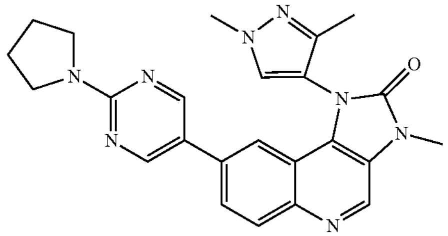 [SMILES: Cc1nn(C)cc1-n1c(=O)n(C)c2cnc3ccc(-c4cnc(N5CCCC5)nc4)cc3c21] | 1-(1,3-Dimethyl-1H-pyrazol-4-yl)-3-methyl-8-(2-pyrrolidin-1-yl-pyrimidin-5-yl)-1,3-dihydro-imidazo[4,5-c]quinolin-2-one | 441 | 2.44 |

Example 141.1

8-(5-Fluoro-6-methylamino-pyridin-3-yl)-3-methyl-1-(1,3,5-trimethyl-1H-pyrazol-4-yl)-1,3-dihydro-imidazo[4,5-c]quinolin-2-one

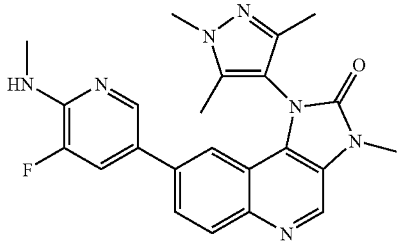 [SMILES: CNc1ncc(-c2ccc3ncc4c(c3c2)n(-c2c(C)nn(C)c2C)c(=O)n4C)cc1F]

The title compound was synthesized in a similar manner as described for Example 1.1 using 8-bromo-3-methyl-1-(1,3,5-trimethyl-1H-pyrazol-4-yl)-1,3-dihydro-imidazo[4,5-c]quinolin-2-one (Intermediate H) and [3-fluoro-5-(4,4,5,5-tetramethyl-[1,3,2]dioxaborolan-2-yl)-pyridin-2-yl]-methyl-amine (stage 141.1.1) to give the title compound as a yellow foam. (HPLC: $t_R$ 2.15 min (Method A); M+H=432 MS-ES; $^1$H-NMR ($d_6$-DMSO, 400 MHz) 8.92 (s, 1H), 8.05-7.99 (m, 2H), 7.89-7.84 (m, 1H), 7.41-7.36 (m, 1H), 7.35-7.33 (m, 1H), 6.92-6.86 (m, 1H), 3.83 (s, 3H), 3.58 (s, 3H), 2.88 (d, 3H), 2.07 (s, 3H), 1.91 (s, 3H))

Stage 141.1.1 [3-Fluoro-5-(4,4,5,5-tetramethyl-[1,3,2]dioxaborolan-2-yl)-pyridin-2-yl]-methyl-amine

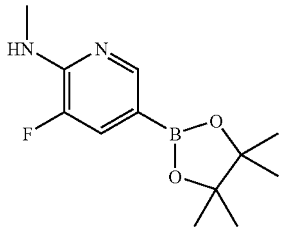 [SMILES: CNc1ncc(B2OC(C)(C)C(C)(C)O2)cc1F]

A mixture of (5-bromo-3-fluoro-pyridin-2-yl)-methyl-amine (Stage 141.1.2, 1.255 mmol), bis(pinacolato)-diborane (1.381 mmol), potassium acetate (3.77 mmol) and $PdCl_2$(dppf) (0.063 mmol) in dioxane (7 ml) was stirred in a closed vial flushed with argon at 90° C. for 15 h. Then the RM was diluted with toluene (7 ml), sonicated and filtered. The solid residue is washed with hot toluene and the filtrated is evaporated to dryness to give the crude title product as a brown oil. (HPLC: $t_R$ 3.68 min (Method A); M+H=253 MS-ES)

Stage 141.1.2

(5-Bromo-3-fluoro-pyridin-2-yl)-methyl-amine

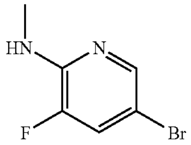

A mixture of 5-bromo-2,3-difluoropyridine (Matrix, Columbia, USA, 2.53 mmol) and 8 M methylamine in EtOH (Aldrich, Buchs, Switzerland, 2 ml, 16 mmol) was sealed in a vial and heated with microwave irradiation at 100° C. for 30 min. The cooled RM was diluted with EtOAc, washed with brine, dried over $Na_2SO_4$, filtered and evaporated to dryness to give the title product as an off-white solid. (HPLC: $t_R$ 1.94 min (Method A); M+H=205, 207, M−H=203, 205 MS-ES)

The following examples were synthesized in a similar manner as described for Example 1.1 using [3-fluoro-5-(4,4,5,5-tetramethyl-[1,3,2]dioxaborolan-2-yl)-pyridin-2-yl]-methyl-amine (stage 141.1.1) and the specified intermediate.

| Example | Intermed. | structure | Name of the example | MS-ES (M + H) | HPLC $t_R$ (min) |
|---|---|---|---|---|---|
| 141.2 | A | 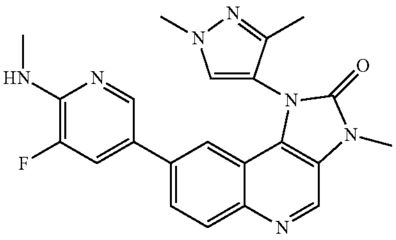 [SMILES: CNc1ncc(-c2ccc3ncc4c(c3c2)n(-c2cn(C)nc2C)c(=O)n4C)cc1F] | 1-(1,3-Dimethyl-1H-pyrazol-4-yl)-8-(5-fluoro-6-methylamino-pyridin-3-yl)-3-methyl-1,3-dihydro-imidazo[4,5-c] quinolin-2-one | 418 | 2.09 |
| 141.3 | G | 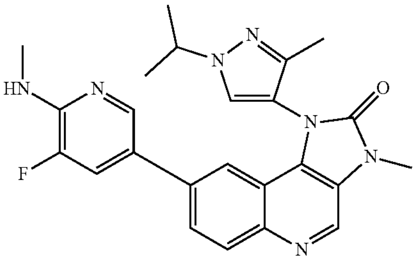 [SMILES: CNc1ncc(-c2ccc3ncc4c(c3c2)n(-c2cn(C(C)C)nc2C)c(=O)n4C)cc1F] | 8-(5-Fluoro-6-methylamino-pyridin-3-yl)-1-(1-isopropyl-3-methyl-1H-pyrazol-4-yl)-3-methyl-1,3-dihydro-imidazo[4,5-c] quinolin-2-one | 446 | 2.25 |

Example 142.1

8-(6-Amino-5-fluoro-pyridin-3-yl)-3-methyl-1-(1,3,5-trimethyl-1H-pyrazol-4-yl)-1,3-dihydro-imidazo[4,5-c]quinolin-2-one

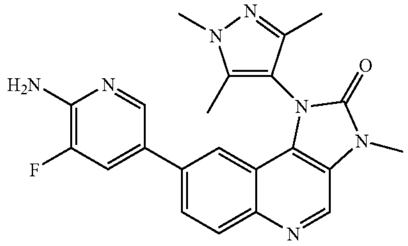 [SMILES: Cc1nn(C)c(C)c1-n1c(=O)n(C)c2cnc3ccc(-c4cnc(N)c(F)c4)cc3c21]

The title compound was synthesized in a similar manner as described for Example 1.1 using 8-bromo-3-methyl-1-(1,3,5-trimethyl-1H-pyrazol-4-yl)-1,3-dihydro-imidazo[4,5-c] quinolin-2-one (Intermediate H) and 3-fluoro-5-(4,4,5,5-tetramethyl-[1,3,2]dioxaborolan-2-yl)-pyridin-2-ylamine (stage 142.1.1) to give the title compound as a yellow foam. (HPLC: $t_R$ 2.07 min (Method A); M+H=418 MS-ES; $^1$H-NMR ($d_6$-DMSO, 400 MHz) 8.92 (s, 1H), 8.05-8.01 (m, 1H), 7.91-7.84 (m, 2H), 7.47-7.42 (m, 1H), 7.35-7.32 (m, 1H), 6.49 (s, 2H), 3.83 (s, 3H), 3.58 (s, 3H), 2.07 (s, 3H), 1.90 (s, 3H))

Stage 142.1.1 3-Fluoro-5-(4,4,5,5-tetramethyl-[1,3,2]dioxaborolan-2-yl)-pyridin-2-ylamine

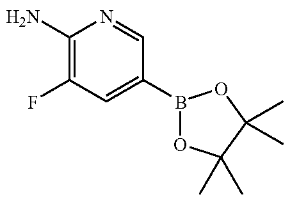 [SMILES: CC1(C)OB(c2cnc(N)c(F)c2)OC1(C)C]

The title compound was synthesized in a similar manner as described for stage 141.1.1-2 using 2 M ammonia in isopropanol (Aldrich, Buchs, Switzerland) and heating up to 195° C. (unstable in the HPLC condition (Method A); M+H=239 MS-ES)

The following examples were synthesized in a similar manner as described for Example 1.1 using 3-fluoro-5-(4,4,5,5-tetramethyl-[1,3,2]dioxaborolan-2-yl)-pyridin-2-ylamine (stage 142.1.1) and the specified intermediate.

Example 143

3-Methyl-8-(6-trideuteromethylamino-5-trifluoromethyl-pyridin-3-yl)-1-(1,3,5-trimethyl-1H-pyrazol-4-yl)-1,3-dihydro-imidazo[4,5-c]quinolin-2-one

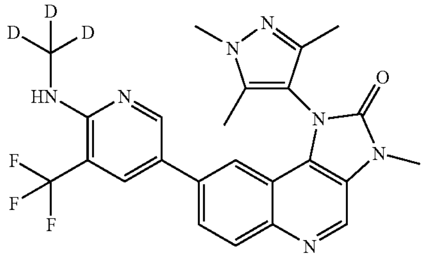

The title compound was synthesized in a similar manner as described for Example 1.1 using 8-bromo-3-methyl-1-(1,3,5-trimethyl-1H-pyrazol-4-yl)-1,3-dihydro-imidazo[4,5-c]quinolin-2-one (Intermediate H, 0.104 mmol) and trideuter-

| Example | Intermed. | structure | Name of the example | MS-ES (M + H) | HPLC $t_R$ (min) |
|---|---|---|---|---|---|
| 142.2 | A | 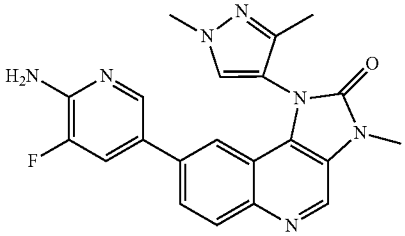 [SMILES: Cc1nn(C)cc1-n1c(=O)n(C)c2cnc3ccc(-c4cnc(N)c(F)c4)cc3c21] | 8-(6-Amino-5-fluoro-pyridin-3-yl)-1-(1,3-dimethyl-1H-pyrazol-4-yl)-3-methyl-1,3-dihydro-imidazo[4,5-c]quinolin-2-one | 404 | 2.02 |
| 142.3 | G | 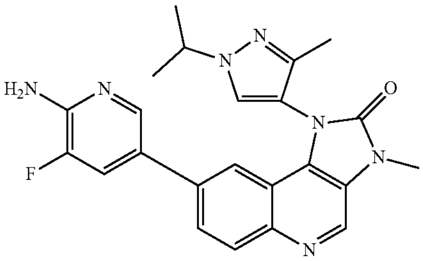 [SMILES: Cc1nn(C(C)C)cc1-n1c(=O)n(C)c2cnc3ccc(-c4cnc(N)c(F)c4)cc3c21] | 8-(6-Amino-5-fluoro-pyridin-3-yl)-1-(1-isopropyl-3-methyl-1H-pyrazol-4-yl)-3-methyl-1,3-dihydro-imidazo[4,5-c]quinolin-2-one | 432 | 2.17 |

omethyl-[5-(4,4,5,5-tetramethyl-[1,3,2]dioxaborolan-2-yl)-3-trifluoromethyl-pyridin-2-yl]-amine (stage 143.1.1) to give the title compound as a yellow foam. (HPLC: $t_R$ 2.53 min (Method A); M+H=485 MS-ES; $^1$H-NMR ($d_6$-DMSO, 400 MHz) 8.94 (s, 1H), 8.51-8.49 (m, 1H), 8.08-8.04 (m, 1H), 7.96-7.92 (m, 1H), 7.72-7.69 (m, 1H), 7.39-7.36 (m, 1H), 6.74 (s, br, 1H), 3.80 (s, 3H), 3.58 (s, 3H), 2.08 (s, 3H), 1.89 (s, 3H))

Stage 143.1.1 Trideuteromethyl-[5-(4,4,5,5-tetramethyl-[1,3,2]dioxaborolan-2-yl)-3-trifluoromethyl-pyridin-2-yl]-amine

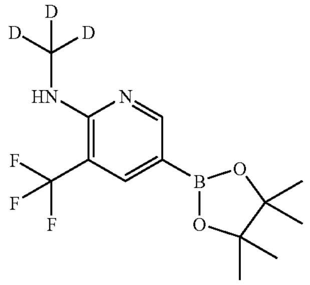 [SMILES: [2H]C([2H])([2H])Nc1ncc(B2OC(C)(C)C(C)(C)O2)cc1C(F)(F)F]

The title compound was synthesized in a similar manner as described for stage 5.1.1 using (5-bromo-3-trifluoromethyl-pyridin-2-yl)-trideuteromethyl-amine (Stage 143.1.2, 0.833 mmol) to give the title compound as a crude brown oil. (degrading under the HPLC condition (Method A); M+H=306 MS-ES)

Stage 143.1.2 (5-Bromo-3-trifluoromethyl-pyridin-2-yl)-trideuteromethyl-amine

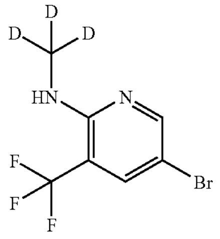 [SMILES: [2H]C([2H])([2H])Nc1ncc(Br)cc1C(F)(F)F]

To a solution of 5-bromo-3-trifluoromethyl-pyridin-2-ylamine (Stage 25.1.2, 1.66 mmol) in DMF cooled with an ice-bath was added 55% sodium hydride in oil (1.66 mmol). The RM was stirred for 30 min at 0° C. then was added $d_3$-iodomethane (Aldrich, Buchs, Switzerland, 1.66 mmol) and the RM was stirred for 30 min at it and the formed slurry was sonicated for 30 min at rt. The RM was quenched with saturated aqueous $NaHCO_3$ and extracted with EtOAc (2×). The combined organic layers were washed with saturated aqueous $NaHCO_3$ (3×), with brine, dried over $Na_2SO_4$, filtered and evaporated. The residue was purified by flash chromatography (hexane/$CH_2Cl_2$ 1:1 to 1:8) to give the title compound as an oil (HPLC: $t_R$ 3.30 min (Method A); M+H=258, 260 MS-ES)

Example 144.1

3-Methyl-8-(6-methylamino-5-trifluoromethyl-pyridin-3-yl)-1-(1,3,5-trimethyl-1H-pyrazol-4-yl)-1,3-dihydro-imidazo[4,5-c]quinolin-2-one

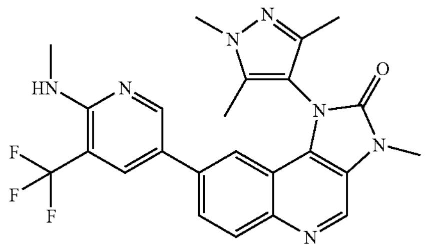 [SMILES: CNc1ncc(-c2ccc3ncc4c(c3c2)n(-c2c(C)nn(C)c2C)c(=O)n4C)cc1C(F)(F)F]

The title compound was synthesized in a similar manner as described for Example 143 using iodomethane as replacement for $d_3$-iodomethane to give the title compound as a yellow film. (HPLC: $t_R$ 2.53 min (Method A); M+H=482 MS-ES; $^1$H-NMR ($d_6$-DMSO, 400 MHz) 8.94 (s, 1H), 8.51-8.49 (m, 1H), 8.08-8.04 (m, 1H), 7.96-7.92 (m, 1H), 7.72-7.69 (m, 1H), 7.38-7.36 (m, 1H), 6.77 (q, 1H), 3.79 (s, 3H), 3.58 (s, 3H), 2.92 (d, 3H), 2.07 (s, 3H), 1.89 (s, 3H))

The following examples were synthesized in a similar manner as described for Example 144.1 using the specified intermediate.

| Example | Intermed. | structure | Name of the example | MS-ES (M + H) | HPLC $t_R$ (min) |
|---|---|---|---|---|---|
| 144.2 | G | 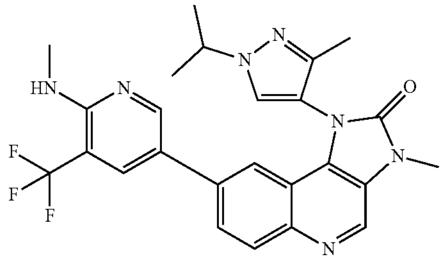 [SMILES: CNc1ncc(-c2ccc3ncc4c(c3c2)n(-c2cn(C(C)C)nc2C)c(=O)n4C)cc1C(F)(F)F] | 1-(1-Isopropyl-3-methyl-1H-pyrazol-4-yl)-3-methyl-8-(6-methylamino-5-trifluoromethyl-pyridin-3-yl)-1,3-dihydro-imidazo[4,5-c] quinolin-2-one | 496 | 2.73 |

-continued

| Example | Intermed. | structure | Name of the example | MS-ES (M + H) | HPLC $t_R$ (min) |
|---|---|---|---|---|---|
| 144.3 | A | 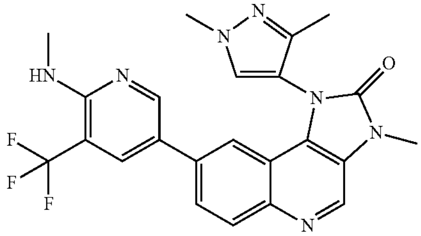 [SMILES: CNc1ncc(-c2ccc3ncc4c(c3c2)n(-c2cn(C)nc2C)c(=O)n4C)cc1C(F)(F)F] | 1-(1,3-Dimethyl-1H-pyrazol-4-yl)-3-methyl-8-(6-methylamino-5-trifluoromethyl-pyridin-3-yl)-1,3-dihydro-imidazo[4,5-c]quinolin-2-one | 468 | 2.47 |

Example 145.1

8-(6-Ethylamino-5-trifluoromethyl-pyridin-3-yl)-3-methyl-1-(1,3,5-trimethyl-1H-pyrazol-4-yl)-1,3-dihydro-imidazo[4,5-c]quinolin-2-one

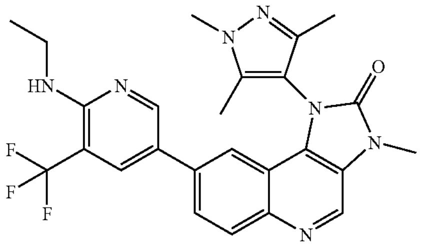 [SMILES: CCNc1ncc(-c2ccc3ncc4c(c3c2)n(-c2c(C)nn(C)c2C)c(=O)n4C)cc1C(F)(F)F]

The title compound was synthesized in a similar manner as described for Example 143 using iodoethane as replacement for $d_3$-iodomethane to give the title compound as a yellow foam. (HPLC: $t_R$ 2.74 min (Method A); M+H=496 MS-ES; $^1$H-NMR ($d_6$-DMSO, 400 MHz) 8.94 (s, 1H), 8.50-8.47 (m, 1H), 8.08-8.03 (m, 1H), 7.96-7.91 (m, 1H), 7.71-7.67 (m, 1H), 7.37-7.34 (m, 1H), 6.74 (t, 1H), 3.79 (s, 3H), 3.58 (s, 3H), 3.49 (qt, 2H), 2.08 (s, 3H), 1.89 (s, 3H), 1.14 (t, 3H))

The following example was synthesized in a similar manner as described for Example 145.1 using the specified intermediate.

| Example | Intermed. | structure | Name of the example | MS-ES (M + H) | HPLC $t_R$ (min) |
|---|---|---|---|---|---|
| 145.2 | A | 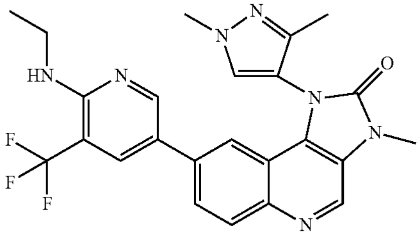 [SMILES: CCNc1ncc(-c2ccc3ncc4c(c3c2)n(-c2cn(C)nc2C)c(=O)n4C)cc1C(F)(F)F] | 1-(1,3-Dimethyl-1H-pyrazol-4-yl)-8-(6-ethylamino-5-trifluoromethyl-pyridin-3-yl)-3-methyl-1,3-dihydro-imidazo[4,5-c]quinolin-2-one | 482 | 2.70 |

Example 146.1

8-(5-Chloro-6-methylamino-pyridin-3-yl)-1-(1,3-dimethyl-1H-pyrazol-4-yl)-3-methyl-1,3-dihydro-imidazo[4,5-c]quinolin-2-one

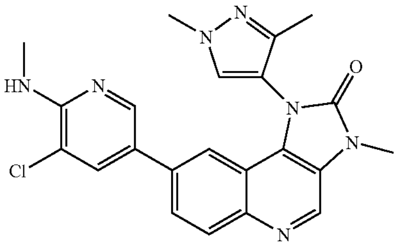 [SMILES: CNc1ncc(-c2ccc3ncc4c(c3c2)n(-c2cn(C)nc2C)c(=O)n4C)cc1Cl]

The title compound was synthesized in a similar manner as described for Example 1.1 using 8-bromo-1-(1,3-dimethyl-1H-pyrazol-4-yl)-3-methyl-1,3-dihydro-imidazo[4,5-c]quinolin-2-one (Intermediate A, 0.107 mmol) and [3-chloro-5-(4,4,5,5-tetramethyl-[1,3,2]dioxaborolan-2-yl)-pyridin-2-yl]-methyl-amine (stage 146.1.1) to give the title compound as a yellow foam. (HPLC: $t_R$ 2.53 min (Method A); M+H=485 MS-ES; $^1$H-NMR ($d_6$-DMSO, 400 MHz) 8.91 (s, 1H), 8.24-8.21 (m, 1H), 8.15 (s, 1H), 8.06-8.01 (m, 1H), 7.92-7.87 (m, 1H), 7.62-7.57 (m, 1H), 7.40-7.37 (m, 1H), 6.81-6.76 (m, 1H), 3.95 (s, 3H), 3.57 (s, 3H), 2.89 (d, 3H), 1.95 (s, 3H))

Stage 146.1.1 [3-Chloro-5-(4,4,5,5-tetramethyl-[1,3,2]dioxaborolan-2-yl)-pyridin-2-yl]-methyl-amine

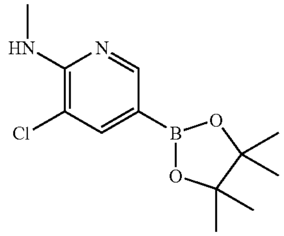 [SMILES: CNc1ncc(B2OC(C)(C)C(C)(C)O2)cc1Cl]

The title compound was synthesized in a similar manner as described for Stage 141.1-2 using 5-bromo-2,3-dichloropyridine (Asymchem Laboratories, Morrisville, N.C., USA) and heating to 150° C. as replacement for 5-bromo-2,3-difluoropyridine to give the title compound as a crude brown oil. (HPLC: $t_R$ 1.62 min (Method A); M+H=269 MS-ES)

The following examples were synthesized in a similar manner as described for Example 1.1 using [3-chloro-5-(4,4,5,5-tetramethyl-[1,3,2]dioxaborolan-2-yl)-pyridin-2-yl]-methyl-amine and the specified intermediate.

| Example | Intermed. | structure | Name of the example | MS-ES (M + H) | HPLC $t_R$ (min) |
|---|---|---|---|---|---|
| 146.2 | F | 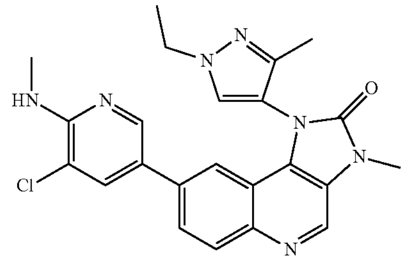 [SMILES: CCn1cc(-n2c(=O)n(C)c3cnc4ccc(-c5cnc(NC)c(Cl)c5)cc4c32)c(C)n1] | 8-(5-Chloro-6-methylamino-pyridin-3-yl)-1-(1-ethyl-3-methyl-1H-pyrazol-4-yl)-3-methyl-1,3-dihydro-imidazo[4,5-c] quinolin-2-one | 448 | 2.30 |
| 146.3 | G | 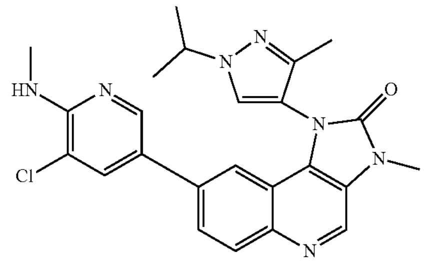 | 8-(5-Chloro-6-methylamino-pyridin-3-yl)-1-(1-isopropyl-3-methyl-1H-pyrazol-4-yl)-3-methyl-1,3-dihydro-imidazo[4,5-c] quinolin-2-one | 462 | 2.40 |
| 146.4 | H | 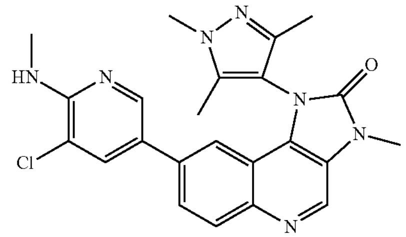 [SMILES: CNc1ncc(-c2ccc3ncc4c(c3c2)n(-c2c(C)nn(C)c2C)c(=O)n4C)cc1Cl] | 8-(5-Chloro-6-methylamino-pyridin-3-yl)-3-methyl-1-(1,3,5-trimethyl-1H-pyrazol-4-yl)-1,3-dihydro-imidazo[4,5-c] quinolin-2-one | 448 | 2.27 |
| 146.5 | C | 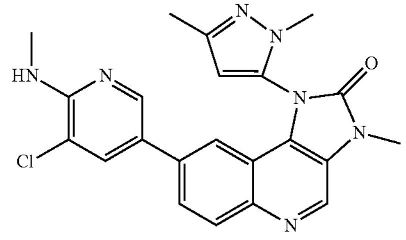 [SMILES: CNc1ncc(-c2ccc3ncc4c(c3c2)n(-c2cc(C)nn2C)c(=O)n4C)cc1Cl] | 8-(5-Chloro-6-methylamino-pyridin-3-yl)-1-(2,5-dimethyl-2H-pyrazol-3-yl)-3-methyl-1,3-dihydro-imidazo[4,5-c] quinolin-2-one | 434 | 2.39 |

-continued

| Example | Intermed. | structure | Name of the example | MS-ES (M + H) | HPLC $t_R$ (min) |
|---|---|---|---|---|---|
| 146.6 | Q | 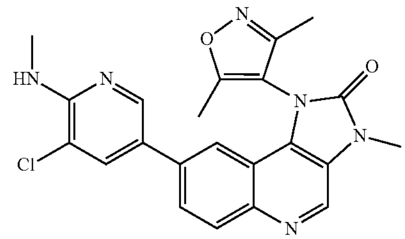 [SMILES: CNc1ncc(-c2ccc3ncc4c(c3c2)n(-c2c(C)noc2C)c(=O)n4C)cc1Cl] | 8-(5-Chloro-6-methylamino-pyridin-3-yl)-1-(3,5-dimethyl-isoxazol-4-yl)-3-methyl-1,3-dihydro-imidazo[4,5-c] quinolin-2-one | 435 | 2.35 |

Example 147

8-(5-Chloro-6-ethylamino-pyridin-3-yl)-1-(1,3-dimethyl-1H-pyrazol-4-yl)-3-methyl-1,3-dihydro-imidazo[4,5-c]quinolin-2-one

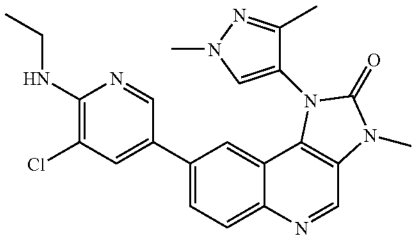 [SMILES: CCNc1ncc(-c2ccc3ncc4c(c3c2)n(-c2cn(C)nc2C)c(=O)n4C)cc1Cl]

The title compound was synthesized in a similar manner as described for Example 146.1 using 2 M ethylamine in MeOH (Aldrich, Buchs, Switzerland) as replacement for the methylamine to give the title compound as a beige foam. (HPLC: $t_R$ 2.35 min (Method A); M+H=448 MS-ES; $^1$H-NMR ($d_6$-DMSO, 400 MHz) 8.92 (s, 1H), 8.22-8.20 (m, 1H), 8.16 (s, 1H), 8.05-8.01 (m, 1H), 7.91-7.87 (m, 1H), 7.61-7.58 (m, 1H), 7.39-7.36 (m, 1H), 6.74 (t, 1H), 3.94 (s, 3H), 3.57 (s, 3H), 3.43 (qt, 2H), 1.94 (s, 3H), 1.15 (t, 3H))

Example 148

8-(6-Amino-5-chloro-pyridin-3-yl)-3-methyl-1-(1,3,5-trimethyl-1H-pyrazol-4-yl)-1,3-dihydro-imidazo[4,5-c]quinolin-2-one

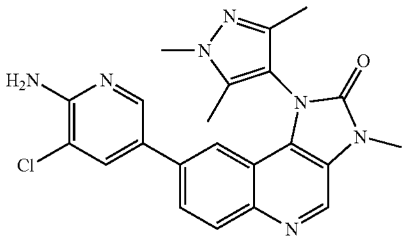 [SMILES: Cc1nn(C)c(C)c1-n1c(=O)n(C)c2cnc3ccc(-c4cnc(N)c(Cl)c4)cc3c21]

The title compound was synthesized in a similar manner as described for Example 1.1 using 8-bromo-3-methyl-1-(1,3,5-trimethyl-1H-pyrazol-4-yl)-1,3-dihydro-imidazo[4,5-c]quinolin-2-one (Intermediate H, 0.075 mmol) and 3-chloro-5-(4,4,5,5-tetramethyl-[1,3,2]dioxaborolan-2-yl)-pyridin-2-ylamine (stage 148.1.1) to give the title compound as a yellow foam. (HPLC: $t_R$ 2.53 min (Method A); M+H=485 MS-ES; $^1$H-NMR ($d_6$-DMSO, 400 MHz) 8.94 (s, 1H), 8.51-8.49 (m, 1H), 8.08-8.04 (m, 1H), 7.96-7.92 (m, 1H), 7.72-7.69 (m, 1H), 7.39-7.36 (m, 1H), 6.74 (s, br, 2H), 3.80 (s, 3H), 3.58 (s, 3H), 2.08 (s, 3H), 1.89 (s, 3H))

Stage 148.1.1 3-Chloro-5-(4,4,5,5-tetramethyl-[1,3,2]dioxaborolan-2-yl)-pyridin-2-ylamine

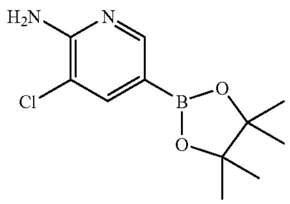 [SMILES: CC1(C)OB(c2cnc(N)c(Cl)c2)OC1(C)C]

The title compound was synthesized in a similar manner as described for Stage 5.1.1 using 2-amino-5-bromo-3-chloro-pyridine (Beta Pharma, New Haven, Conn., USA) to give the title compound as a crude sticky black solid. (degrading under the HPLC condition: $t_R$ 1.44 min (Method A); M+H=255 MS-ES).

The following examples were synthesized in a similar manner as described for Example 1.1 using 3-chloro-5-(4,4,5,5-tetramethyl-[1,3,2]dioxaborolan-2-yl)-pyridin-2-ylamine and the specified intermediate.

| Example | Intermed. | structure | Name of the example | MS-ES (M + H) | HPLC $t_R$ (min) |
|---|---|---|---|---|---|
| 148.2 | A | 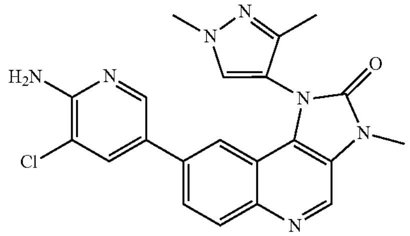 | 8-(6-Amino-5-chloro-pyridin-3-yl)-1-(1,3-dimethyl-1H-pyrazol-4-yl)-3-methyl-1,3-dihydro-imidazo[4,5-c] quinolin-2-one | 420 | 2.14 |
| 148.3 | F | 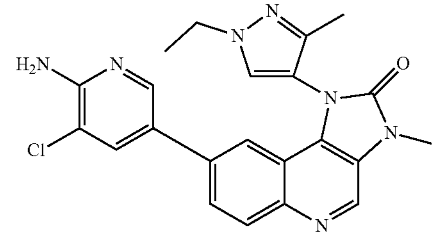 [SMILES: CCn1cc(-n2c(=O)n(C)c3cnc4ccc(-c5cnc(N)c(Cl)c5)cc4c32)c(C)n1] | 8-(6-Amino-5-chloro-pyridin-3-yl)-1-(1-ethyl-3-methyl-1H-pyrazol-4-yl)-3-methyl-1,3-dihydro-imidazo[4,5-c] quinolin-2-one | 434 | 2.21 |
| 148.4 | Q | 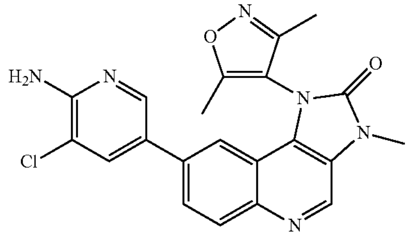 [SMILES: Cc1noc(C)c1-n1c(=O)n(C)c2cnc3ccc(-c4cnc(N)c(Cl)c4)cc3c21] | 8-(6-Amino-5-chloro-pyridin-3-yl)-1-(3,5-dimethyl-isoxazol-4-yl)-3-methyl-1,3-dihydro-imidazo[4,5-c] quinolin-2-one | 421 | 2.24 |

Example 149

8-(5-Amino-6-fluoro-pyridin-3-yl)-1-(1-isopropyl-3-methyl-1H-pyrazol-4-yl)-3-methyl-1,3-dihydro-imidazo[4,5-c]quinolin-2-one

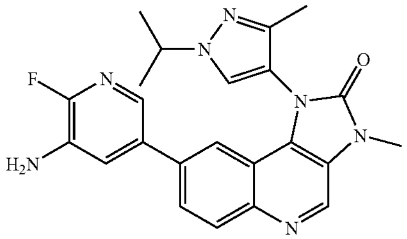 [SMILES: Cc1nn(C(C)C)cc1-n1c(=O)n(C)c2cnc3ccc(-c4cnc(F)c(N)c4)cc3c21]

The title compound was synthesized in a similar manner as described for Example 1.1 using 8-bromo-1-(1-isopropyl-3-methyl-1H-pyrazol-4-yl)-3-methyl-1,3-dihydro-imidazo[4,5-c]quinolin-2-one (Intermediate G, 0.098 mmol) and 2-fluoro-5-(4,4,5,5-tetramethyl-[1,3,2]dioxaborolan-2-yl)-pyridin-3-ylamine (stage 149.1.1) to give the title compound as a yellow foam. (HPLC: $t_R$ 2.53 min (Method A); M+H=485 MS-ES; $^1$H-NMR ($d_6$-DMSO, 400 MHz) 8.97 (s, 1H), 8.20 (s, 1H), 8.12-8.08 (m, 1H), 7.76-7.72 (m, 1H), 7.47-7.44 (m, 1H), 7.29-7.23 (m, 2H), 5.57 (s, br, 2H), 4.54 (hp, 1H), 3.58 (s, 3H), 1.95 (s, 3H), 1.44 (d, 6H))

Stage 149.1.1 2-Fluoro-5-(4,4,5,5-tetramethyl-[1,3,2]dioxaborolan-2-yl)-pyridin-3-ylamine

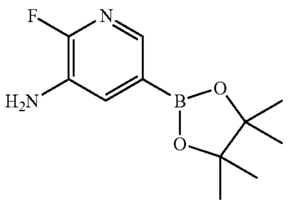 [SMILES: CC1(C)OB(c2cnc(F)c(N)c2)OC1(C)C]

The title compound was synthesized in a similar manner as described for Stage 5.1.1 using 3-amino-5-bromo-2-fluoro-pyridine (Matrix Scientific, Columbia, S.C., USA) to give the title compound as a crude sticky black solid. (degrading under the HPLC condition (Method A); M+H=239 MS-ES).

The following examples were synthesized in a similar manner as described for Example 1.1 using 2-fluoro-5-(4,4,5,5-tetramethyl-[1,3,2]dioxaborolan-2-yl)-pyridin-3-ylamine and the specified intermediate.

| Example | Intermed. | structure | Name of the example | MS-ES (M + H) | HPLC $t_R$ (min) |
|---|---|---|---|---|---|
| 149.2 | A | 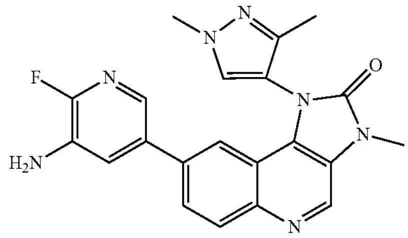 [SMILES: Cc1nn(C)cc1-n1c(=O)n(C)c2cnc3ccc(-c4cnc(F)c(N)c4)cc3c21] | 8-(5-Amino-6-fluoro-pyridin-3-yl)-1-(1,3-dimethyl-1H-pyrazol-4-yl)-3-methyl-1,3-dihydro-imidazo[4,5-c] quinolin-2-one | 404 | 2.27 |
| 149.3 | C | 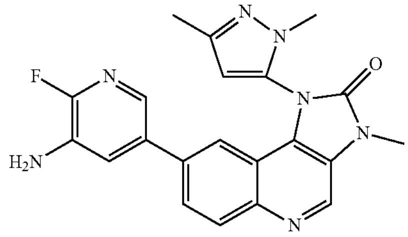 [SMILES: Cc1cc(-n2c(=O)n(C)c3cnc4ccc(-c5cnc(F)c(N)c5)cc4c32)n(C)n1] | 8-(5-Amino-6-fluoro-pyridin-3-yl)-1-(2,5-dimethyl-2H-pyrazol-3-yl)-3-methyl-1,3-dihydro-imidazo[4,5-c] quinolin-2-one | 404 | 2.21 |

Example 150.1

1-(1-Ethyl-3-methyl-1H-pyrazol-4-yl)-8-(6-fluoro-5-methylamino-pyridin-3-yl)-3-methyl-1,3-dihydro-imidazo[4,5-c]quinolin-2-one

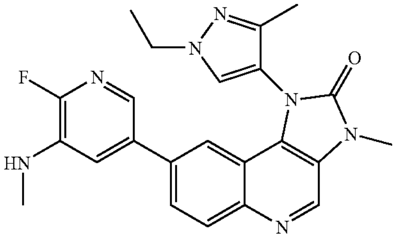 [SMILES: CCn1cc(-n2c(=O)n(C)c3cnc4ccc(-c5cnc(F)c(NC)c5)cc4c32)c(C)n1]

The title compound was synthesized in a similar manner as described for Example 1.1 using 8-bromo-1-(1-ethyl-3-methyl-1H-pyrazol-4-yl)-3-methyl-1,3-dihydro-imidazo[4,5-c] quinolin-2-one (Intermediate F, 0.078 mmol) and [2-fluoro-5-(4,4,5,5-tetramethyl-[1,3,2]dioxaborolan-2-yl)-pyridin-3-yl]-methyl-amine (stage 150.1.1) to give the title compound as a yellow foam. (HPLC: $t_R$ 2.53 min (Method A); M+H=485 MS-ES; $^1$H-NMR ($d_6$-DMSO, 400 MHz) 8.97 (s, 1H), 8.16 (s, 1H), 8.11-8.07 (m, 1H), 7.95-7.90 (m, 1H), 7.53-7.51 (m, 1H), 7.42-7.39 (m, 1H), 7.01-6.97 (m, 1H), 6.08 (q, br, 1H), 4.15 (q, 2H), 3.58 (s, 3H), 2.80 (d, 3H), 1.97 (s, 3H), 1.37 (t, 3H))

Stage 150.1.1 [2-Fluoro-5-(4,4,5,5-tetramethyl-[1,3,2]dioxaborolan-2-yl)-pyridin-3-yl]-methyl-amine

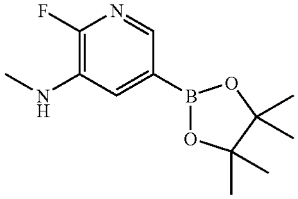

The title compound was synthesized in a similar manner as described for Stage 5.1.1 using 5-bromo-2-fluoro-3-methylaminopyridine (Stage 150.1.2) to give the title compound as a crude black oil. (degrading under the HPLC condition: $t_R$ 1.70 min (Method A); M+H=239 MS-ES).

Stage 150.1.2
(5-Bromo-2-fluoro-pyridin-3-yl)-methyl-amine

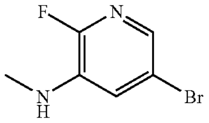

A mixture of 3-amino-5-bromo-2-fluoropyridine (Matrix Scientific, Columbia, S.C., USA, 1.571 mmol) in DMF (3 ml) and 55% NaH in oil (1.571 mmol) was stirred for 15 min at rt. Was added iodomethane (Aldrich, Buchs, Switzerland, 1.571 mmol) and the RM was stirred for 13 h at rt. The RM was diluted with EtOAc, washed with brine (4×), dried over $Na_2SO_4$, filtered and evaporated. The residue was absorbed on silica gel and purified by flash chromatography (heptane/EtOAc 0% to 40%). The fraction containing the first eluting product were evaporated to give (5-bromo-2-fluoro-pyridin-3-yl)-dimethyl-amine as an orange oil (HPLC: $t_R$ 3.15 min (Method A); M+H=219, 221 MS-ES) and the fraction containing the second eluting product were evaporated to give the title compound as a red solid (HPLC: $t_R$ 2.90 min (Method A); M+H=205, 207 MS-ES).

The following example was synthesized in a similar manner as described for Example 1.1 using [2-fluoro-5-(4,4,5,5-tetramethyl-[1,3,2]dioxaborolan-2-yl)-pyridin-3-yl]-methyl-amine and the specified intermediate.

| Example | Intermed. | structure | Name of the example | MS-ES (M + H) | HPLC $t_R$ (min) |
|---|---|---|---|---|---|
| 150.2 | A | 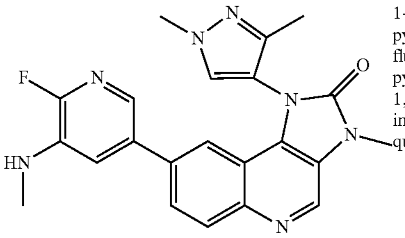 | 1-(1,3-Dimethyl-1H-pyrazol-4-yl)-8-(6-fluoro-5-methylamino-pyridin-3-yl)-3-methyl-1,3-dihydro-imidazo[4,5-c]quinolin-2-one | 418 | 2.45 |

Example 151

8-(5-Dimethylamino-6-fluoro-pyridin-3-yl)-1-(1,3-dimethyl-1H-pyrazol-4-yl)-3-methyl-1,3-dihydro-imidazo[4,5-c]quinolin-2-one

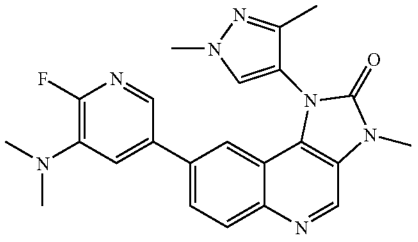

The title compound was synthesized in a similar manner as described for Example 1.1 using 8-bromo-1-(1-isopropyl-3-methyl-1H-pyrazol-4-yl)-3-methyl-1,3-dihydro-imidazo[4,5-c]quinolin-2-one (Intermediate G, 0.098 mmol) and [2-fluoro-5-(4,4,5,5-tetramethyl-[1,3,2]dioxaborolan-2-yl)-pyridin-3-yl]-dimethyl-amine (stage 151.1.1) to give the title compound as a yellow foam. (HPLC: $t_R$ 2.59 min (Method A); M+H=432 MS-ES; $^1$H-NMR ($d_6$-DMSO, 400 MHz) 8.98 (s, 1H), 8.13-8.08 (m, 2H), 7.99-7.94 (m, 1H), 7.80-7.77 (m, 1H), 7.57-7.54 (m, 1H), 7.28-7.23 (m, 1H), 3.88 (s, 3H), 3.58 (s, 3H), 2.89 (s, 6H), 1.96 (s, 3H))

Stage 151.1.1 [2-Fluoro-5-(4,4,5,5-tetramethyl-[1,3,2]dioxaborolan-2-yl)-pyridin-3-yl]-dimethyl-amine

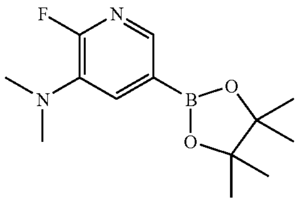

The title compound was synthesized in a similar manner as described for Stage 5.1.1 using 5-bromo-2-fluoro-3-dimethylaminopyridine (Stage 150.1.2, side product) to give the title compound as a crude black oil. (degrading under the HPLC condition: $t_R$ 1.77 min (Method A); M+H=267 MS-ES).

Example 152.1

8-(5-Amino-6-chloro-pyridin-3-yl)-1-(1-isopropyl-3-methyl-1H-pyrazol-4-yl)-3-methyl-1,3-dihydro-imidazo[4,5-c]quinolin-2-one

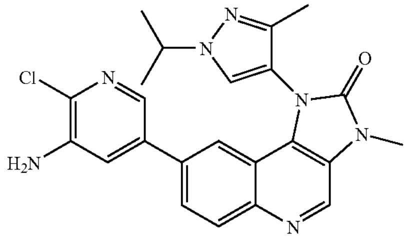 [SMILES: Cc1nn(C(C)C)cc1-n1c(=O)n(C)c2cnc3ccc(-c4cnc(Cl)c(N)c4)cc3c21]

The title compound was synthesized in a similar manner as described for Example 1.1 using 8-bromo-1-(1-isopropyl-3-methyl-1H-pyrazol-4-yl)-3-methyl-1,3-dihydro-imidazo[4,5-c]quinolin-2-one (Intermediate G, 0.098 mmol) and 2-chloro-5-(4,4,5,5-tetramethyl-[1,3,2]dioxaborolan-2-yl)-pyridin-3-ylamine (stage 152.1.1) to give the title compound as a yellow foam. (HPLC: $t_R$ 2.55 min (Method A); M+H=448 MS-ES; $^1$H-NMR ($d_6$-DMSO, 400 MHz) 8.99 (s, 1H), 8.19 (s, 1H), 8.14-8.09 (m, 1H), 7.78-7.73 (m, 1H), 7.57-7.53 (m, 1H), 7.50-7.47 (m, 1H), 7.28-7.24 (m, 1H), 5.68 (s, br, 2H), 4.55 (hp, 1H), 3.58 (s, 3H), 1.95 (s, 3H), 1.44 (d, 6H))

Stage 152.1.1 2-Chloro-5-(4,4,5,5-tetramethyl-[1,3,2]dioxaborolan-2-yl)-pyridin-3-ylamine

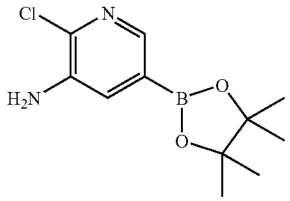 [SMILES: CC1(C)OB(c2cnc(Cl)c(N)c2)OC1(C)C]

The title compound was synthesized in a similar manner as described for Stage 5.1.1 using 5-bromo-2-chloro-pyridin-3-ylamine (stage 152.1.2, 2.6 mmol) to give the title compound as a crude black solid. (degrading under the HPLC condition: $t_R$ 1.57 min (Method A); M+H=255 MS-ES).

Stage 152.1.2 5-Bromo-2-chloro-pyridin-3-ylamine

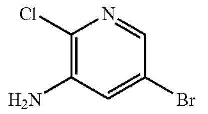

A suspension of 5-bromo-2-chloro-3-nitropyridine (Combi-Blocks, San Diego, USA, 41.3 mmol) in concentrated HCl (45 ml) was cooled with an ice-bath. Was added portionwise over 1.5 h $SnCl_2$ dihydrate (124 mmol). The RM was stirred for 24 h at rt then poured on ice and basified with 6 M aqueous NaOH (125 ml). The resulting slurry was filtered and the solid was taken in aqueous $NaHCO_3$, sonicated and filtered. The solid was dissolved in EtOAc and water and the aqueous layer was separated and extracted with EtOAc. The combined organic layers were washed with water, brine, dried over $Na_2SO_4$, filtered and evaporated to give the title compound as an off-white solid. (HPLC: $t_R$ 2.52 min (Method A); M+H=207 (BrCl pattern) MS-ES)

The following examples were synthesized in a similar manner as described for Example 1.1 using 2-chloro-5-(4,4,5,5-tetramethyl-[1,3,2]dioxaborolan-2-yl)-pyridin-3-ylamine and the specified intermediate.

Example 153.1

8-(6-Chloro-5-ethylamino-pyridin-3-yl)-3-methyl-1-(1,3,5-trimethyl-1H-pyrazol-4-yl)-1,3-dihydro-imidazo[4,5-c]quinolin-2-one

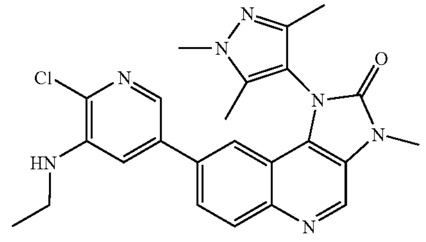 [SMILES: CCNc1cc(-c2ccc3ncc4c(c3c2)n(-c2c(C)nn(C)c2C)c(=O)n4C)cnc1Cl]

The title compound was synthesized in a similar manner as described for Example 1.1 using 8-bromo-3-methyl-1-(1,3,5-trimethyl-1H-pyrazol-4-yl)-1,3-dihydro-imidazo[4,5-c]quinolin-2-one (Intermediate H, 0.101 mmol) and [2-chloro-5-(4,4,5,5-tetramethyl-[1,3,2]dioxaborolan-2-yl)-pyridin-3-yl]-ethyl-amine (stage 153.1.1) to give the title compound as a yellow solid. (HPLC: $t_R$ 2.74 min (Method A); M+H=462 MS-ES; $^1$H-NMR ($d_6$-DMSO, 400 MHz) 8.99 (s, 1H), 8.13-8.08 (m, 1H), 7.98-7.93 (m, 1H), 7.76-7.73 (m, 1H), 7.58-

| Example | Intermed. | structure | Name of the example | MS-ES (M + H) | HPLC $t_R$ (min) |
|---|---|---|---|---|---|
| 152.2 | A | 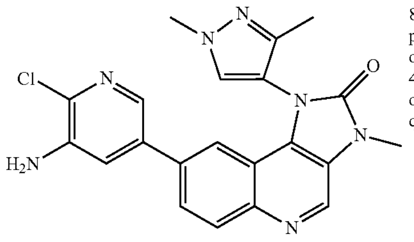 | 8-(5-Amino-6-chloro-pyridin-3-yl)-1-(1,3-dimethyl-1H-pyrazol-4-yl)-3-methyl-1,3-dihydro-imidazo[4,5-c] quinolin-2-one | 420 | 2.36 |
| 152.3 | H | 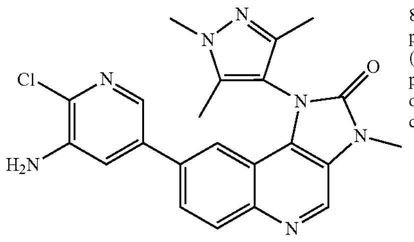 | 8-(5-Amino-6-chloro-pyridin-3-yl)-3-methyl-1-(1,3,5-trimethyl-1H-pyrazol-4-yl)-1,3-dihydro-imidazo[4,5-c] quinolin-2-one | 434 | 2.43 |

7.54 (m, 1H), 6.97-6.93 (m, 1H), 5.72 (t, 1H), 3.79 (s, 3H), 3.59 (s, 3H), 3.26 (qt, 2H), 2.07 (s, 3H), 1.91 (s, 3H), 1.22 (t, 3H))

Stage 153.1.1 [2-Chloro-5-(4,4,5,5-tetramethyl-[1,3,2]dioxaborolan-2-yl)-pyridin-3-yl]-ethyl-amine

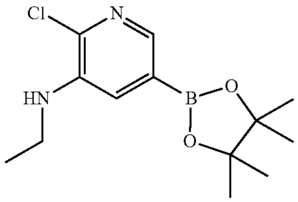 [SMILES: CCNc1cc(B2OC(C)(C)C(C)(C)O2)cnc1Cl]

The title compound was synthesized in a similar manner as described for Stage 5.1.1 using (5-bromo-2-chloro-pyridin-3-yl)-ethyl-amine (stage 153.1.2, 3.71 mmol) to give the title compound as a crude black oil. (degrading under the HPLC condition: $t_R$ 2.17 min (Method A); M+H=283 MS-ES).

Stage 153.1.2 (5-Bromo-2-chloro-pyridin-3-yl)-ethyl-amine

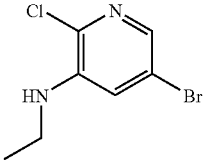

The title compound was synthesized in a similar manner as described for (Stage 87.1.2.) using 3-amino-5-bromo-2-chloropyridine (stage 152.1.2, 4.34 mmol) to give the title compound as an oil (HPLC: $t_R$ 3.38 min (Method A); M+H=235 (BrCl pattern) MS-ES).

The following examples were synthesized in a similar manner as described for Example 1.1 using 2-chloro-5-(4,4,5,5-tetramethyl-[1,3,2]dioxaborolan-2-yl)-pyridin-3-yl]-ethyl-amine and the specified intermediate.

| Example | Intermed. | structure | Name of the example | MS-ES (M + H) | HPLC $t_R$ (min) |
|---|---|---|---|---|---|
| 153.2 | A | 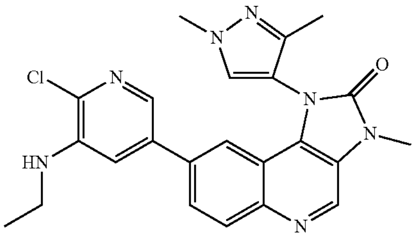 [SMILES: CCNc1cc(-c2ccc3ncc4c(c3c2)n(-c2cn(C)nc2C)c(=O)n4C)cnc1Cl] | 8-(6-Chloro-5-ethylamino-pyridin-3-yl)-1-(1,3-dimethyl-1H-pyrazol-4-yl)-3-methyl-1,3-dihydro-imidazo[4,5-c] quinolin-2-one | 448 | 2.69 |
| 153.3 | Q | 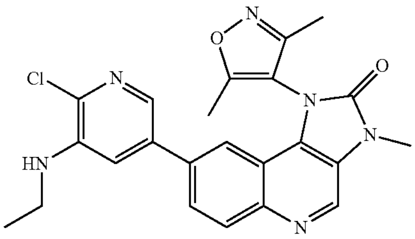 | 8-(6-Chloro-5-ethylamino-pyridin-3-yl)-1-(3,5-dimethyl-isoxazol-4-yl)-3-methyl-1,3-dihydro-imidazo[4,5-c] quinolin-2-one | 448 | 2.88 |

Example 154.1

8-(5-Ethylamino-6-fluoro-pyridin-3-yl)-3-methyl-1-(1,3,5-trimethyl-1H-pyrazol-4-yl)-1,3-dihydro-imidazo[4,5-c]quinolin-2-one

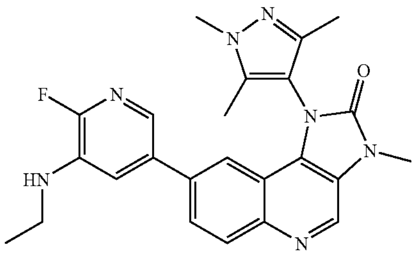 [SMILES: CCNc1cc(-c2ccc3ncc4c(c3c2)n(-c2c(C)nn(C)c2C)c(=O)n4C)cnc1F]

The title compound was synthesized in a similar manner as described for Example 1.1 using 8-bromo-3-methyl-1-(1,3,5-trimethyl-1H-pyrazol-4-yl)-1,3-dihydro-imidazo[4,5-c]quinolin-2-one (Intermediate H, 0.104 mmol) and ethyl-[2-fluoro-5-(4,4,5,5-tetramethyl-[1,3,2]dioxaborolan-2-yl)-pyridin-3-yl]-amine (stage 154.1.1) to give the title compound as a white solid. (HPLC: $t_R$ 2.63 min (Method A); M+H=446 MS-ES; $^1$H-NMR ($d_6$-DMSO, 400 MHz) 8.97 (s, 1H), 8.11-8.07 (m, 1H), 7.96-7.91 (m, 1H), 7.55-7.52 (m, 1H), 7.48-7.45 (m, 1H), 7.00-6.95 (m, 1H), 5.96 (t, 1H), 3.78 (s, 3H), 3.59 (s, 3H), 3.20 (qt, 2H), 2.07 (s, 3H), 1.91 (s, 3H), 1.23 (t, 3H))

Stage 154.1.1 Ethyl-[2-fluoro-5-(4,4,5,5-tetramethyl-[1,3,2]dioxaborolan-2-yl)-pyridin-3-yl]-amine

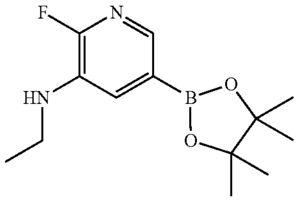 [SMILES: CCNc1cc(B2OC(C)(C)C(C)(C)O2)cnc1F]

The title compound was synthesized in a similar manner as described for Stage 5.1.1 using (5-bromo-2-fluoro-pyridin-3-yl)-ethyl-amine (stage 154.1.2, 2.283 mmol) to give the title compound as a crude black oil. (degrading under the HPLC condition: $t_R$ 1.92 min (Method A); M+H=267 MS-ES).

Stage 154.1.2
(5-Bromo-2-fluoro-pyridin-3-yl)-ethyl-amine

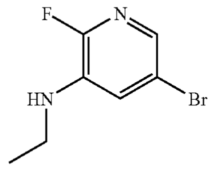

The title compound was synthesized in a similar manner as described for (Stage 87.1.2.) using 3-amino-5-bromo-2-fluoropyridine (Matrix Scientific, Columbia, S.C., USA, 3.14 mmol) to give the title compound as greenish solid (HPLC: $t_R$ 3.20 min (Method A); M+H=219, 221 MS-ES).

The following example was synthesized in a similar manner as described for Example 1.1 using ethyl-[2-fluoro-5-(4,4,5,5-tetramethyl-[1,3,2]dioxaborolan-2-yl)-pyridin-3-yl]-amine and the specified intermediate.

| Example | Intermed. | structure | Name of the example | MS-ES (M + H) | HPLC $t_R$ (min) |
|---|---|---|---|---|---|
| 154.2 | Q | 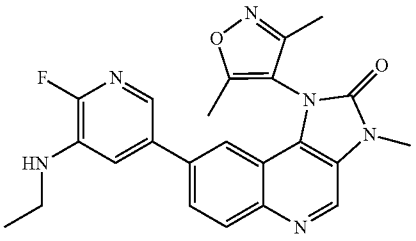 [SMILES: CCNc1cc(-c2ccc3ncc4c(c3c2)n(-c2c(C)noc2C)c(=O)n4C)cnc1F] | 1-(3,5-Dimethyl-isoxazol-4-yl)-8-(5-ethylamino-6-fluoro-pyridin-3-yl)-3-methyl-1,3-dihydro-imidazo[4,5-c]quinolin-2-one | 433 | 2.76 |

Example 155.1

1-(1,3-Dimethyl-1H-pyrazol-4-yl)-8-(5-ethylamino-6-hydroxymethyl-pyridin-3-yl)-3-methyl-1,3-dihydro-imidazo[4,5-c]quinolin-2-one

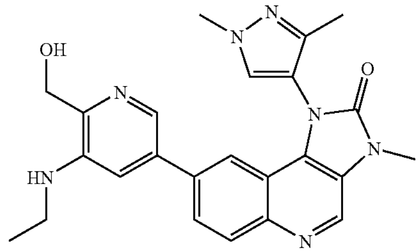 [SMILES: CCNc1cc(-c2ccc3ncc4c(c3c2)n(-c2cn(C)nc2C)c(=O)n4C)cnc1CO]

A solution of acetic acid 3-(tert-butoxycarbonyl-ethyl-amino)-5-[1-(1,3-dimethyl-1H-pyrazol-4-yl)-3-methyl-2-oxo-2,3-dihydro-1H-imidazo[4,5-c]quinolin-8-yl]-pyridin-2-ylmethyl ester 155.1.1, 0.041 mmol) in dioxane (0.33 ml) was treated with 1 M aqueous LiOH (0.082 ml) for 1.5 h at rt then was added 1 M aqueous LiOH (0.082 ml) and the RM was stirred for 2 h at rt. The RM was diluted with EtOAc and washed with sat. aqueous $NaHCO_3$, dried over $Na_2SO_4$, filtered and evaporated. The residue was taken in DMA and purified by preparative HPLC. The pure fraction was basified with $NaHCO_3$, concentrated and extracted with EtOAc (3×). The combined organic layers were dried over $Na_2SO_4$, filtered, evaporated and dried under vacuum to give the title compound as a film. (HPLC: $t_R$ 2.10 min (Method A); M+H=444 MS-ES; $^1$H-NMR ($d_6$-DMSO, 400 MHz) 8.97 (s, 1H), 8.12-8.08 (m, 2H), 7.97-7.90 (m, 2H), 7.63-7.60 (m, 1H), 6.87 (s, 1H), 5.49 (t, 1H), 5.31 (t, 1H), 4.57 (d, 2H), 3.88 (s, 3H), 3.58 (s, 3H), 3.19 (qt, 2H), 1.96 (s, 3H), 1.25 (t, 3H))

Stage 155.1.1 Acetic acid 3-(tert-butoxycarbonyl-ethyl-amino)-5-[1-(1,3-dimethyl-1H-pyrazol-4-yl)-3-methyl-2-oxo-2,3-dihydro-1H-imidazo[4,5-c]quinolin-8-yl]-pyridin-2-ylmethyl ester

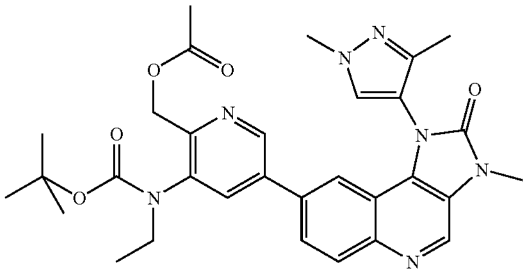 [SMILES: CCN(C(=O)OC(C)(C)C)c1cc(-c2ccc3ncc4c(c3c2)n(-c2cn(C)nc2C)c(=O)n4C)cnc1COC(C)=O]

The title compound was synthesized in a similar manner as described for Example 1.1 using 8-bromo-1(1,3-dimethyl-1H-pyrazol-4-yl)-3-methyl-1,3-dihydro-imidazo[4,5-c]quinolin-2-one (Intermediate A, 0.109 mmol) and acetic acid 3-(tert-butoxycarbonyl-ethyl-amino)-5-(4,4,5,5-tetramethyl-[1,3,2]dioxaborolan-2-yl)-pyridin-2-ylmethyl ester (stage 155.1.2) to give the title compound as an off-white solid. (HPLC: $t_R$ 2.88 min (Method A); M+H=586 MS-ES)

Stage 155.1.2 Acetic acid 3-(tert-butoxycarbonyl-ethyl-amino)-5-(4,4,5,5-tetramethyl-[1,3,2]dioxaborolan-2-yl)-pyridin-2-ylmethyl ester

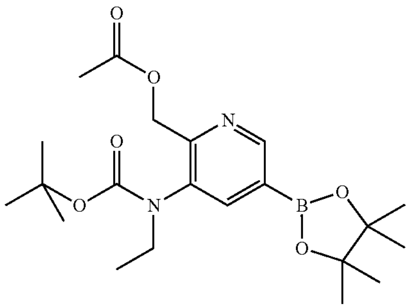 [SMILES: CCN(C(=O)OC(C)(C)C)c1cc(B2OC(C)(C)C(C)(C)O2)cnc1COC(C)=O]

The title compound was synthesized in a similar manner as described for Stage 5.1.1 using acetic acid 5-bromo-3-(tert-butoxycarbonyl-ethyl-amino)-pyridin-2-ylmethyl ester (stage 155.1.3, 0.968 mmol) to give the title compound as a crude black oil. (degrading under the HPLC condition: $t_R$ 3.09 min (Method A); M+H=421 MS-ES).

Stage 155.1.3 Acetic acid 5-bromo-3-(tert-butoxycarbonyl-ethyl-amino)-pyridin-2-ylmethyl ester

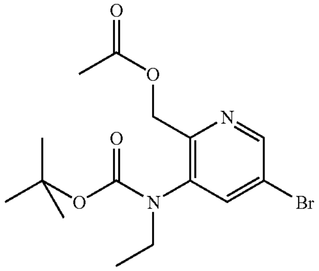 [SMILES: CCN(C(=O)OC(C)(C)C)c1cc(Br)cnc1COC(C)=O]

(5-Bromo-2-methyl-1-oxy-pyridin-3-yl)-ethyl-carbamic acid tert-butyl ester (Stage 155.1.4, 1.467 mmol) in acetic anhydride (1.5 ml) was stirred under Ar for 35 min at 120° C. The RM was quenched with EtOH and stirred then diluted with water, neutralized with saturated aqueous $NaHCO_3$ and extracted with EtOAc. The organic layer was washed with brine, dried over $Na_2SO_4$, filtered and evaporated. The residue was purified by flash chromatography (heptane/EtOAc 0% to 30%) to give after evaporation of the fractions containing the title compound an oil (HPLC: $t_R$ 3.51 min (Method A); M+H=373, 375 MS-ES).

Stage 155.1.4 (5-Bromo-2-methyl-1-oxy-pyridin-3-yl)-ethyl-carbamic acid tert-butyl ester

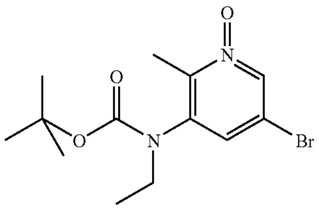 [SMILES: CCN(C(=O)OC(C)(C)C)c1cc(Br)c[n+]([O-])c1C]

A mixture of (5-bromo-2-methyl-pyridin-3-yl)-ethyl-carbamic acid tert-butyl ester (stage 155.1.5, 1.508 mmol) in dichloromethane (13 ml) and 65% m-chloroperbenzoic acid (3.02 mmol) was stirred for 4 h at rt. The RM was diluted with dichloromethane, washed with saturated aqueous $Na_2CO_3$, saturated aqueous $NaHCO_3$ (4×) and brine, dried over $Na_2SO_4$, filtered, evaporated and dried under vacuum to give the title compound as an oil (HPLC: $t_R$ 3.02 min (Method A); M+H=331, 333 MS-ES).

Stage 155.1.5 (5-Bromo-2-methyl-pyridin-3-yl)-ethyl-carbamic acid tert-butyl ester

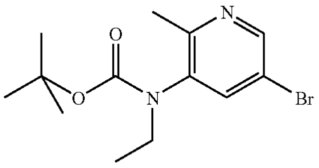 [SMILES: CCN(C(=O)OC(C)(C)C)c1cc(Br)cnc1C]

A mixture of (5-bromo-2-methyl-pyridin-3-yl)-ethyl-amine (Stage 87.1.2, 1.634 mmol) and di-tertbutyl dicarbonate (Fluka, Buchs, Switzerland, 1.961 mmol) in THF (1.6 ml) was stirred for 1 h at rt and 3 h at 65° C. Was added di-tertbutyl dicarbonate (Fluka, Buchs, Switzerland, 1.961 mmol) and an extra stirring for 22 h at 65° C. to bring reaction to completion. The RM was diluted with EtOAc, washed with saturated aqueous $NaHCO_3$, with brine, dried over $Na_2SO_4$, filtered and evaporated. The residue was absorbed on silica gel and purified by flash chromatography (heptane/EtOAc 0% to 30%) to give after evaporation of the fractions containing the title compound an oil (HPLC: $t_R$ 3.41 min (Method A); M+H=315, 317 MS-ES).

The following examples were synthesized in a similar manner as described for Example 155.1 using the specified intermediate.

| Example | Intermed. | structure | Name of the example | MS-ES (M + H) | HPLC $t_R$ (min) |
|---|---|---|---|---|---|
| 155.2 | F | 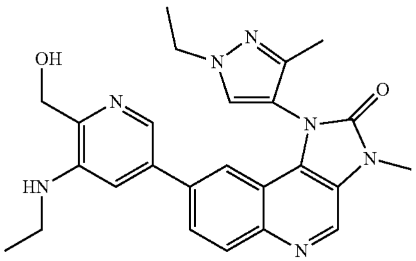 [SMILES: CCNc1cc(-c2ccc3ncc4c(c3c2)n(-c2cn(CC)nc2C)c(=O)n4C)cnc1CO] | 8-(5-Ethylamino-6-hydroxymethyl-pyridin-3-yl)-1-(1-ethyl-3-methyl-1H-pyrazol-4-yl)-3-methyl-1,3-dihydro-imidazo[4,5-c] quinolin-2-one | 458 | 2.15 |
| 155.3 | G | 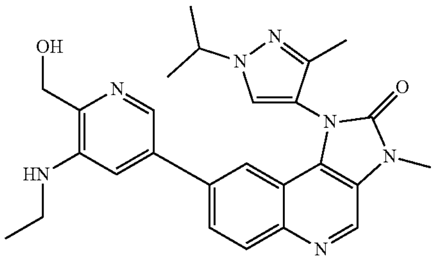 [SMILES: CCNc1cc(-c2ccc3ncc4c(c3c2)n(-c2cn(C(C)C)nc2C)c(=O)n4C)cnc1CO] | 8-(5-Ethylamino-6-hydroxymethyl-pyridin-3-yl)-1-(1-isopropyl-3-methyl-1H-pyrazol-4-yl)-3-methyl-1,3-dihydro-imidazo[4,5-c] quinolin-2-one | 472 | 2.21 |
| 155.4 | H | 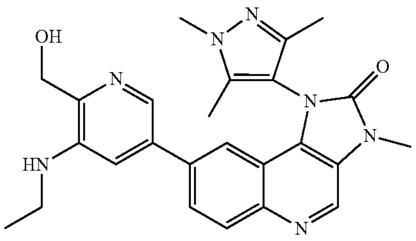 [SMILES: CCNc1cc(-c2ccc3ncc4c(c3c2)n(-c2c(C)nn(C)c2C)c(=O)n4C)cnc1CO] | 8-(5-Ethylamino-6-hydroxymethyl-pyridin-3-yl)-3-methyl-1-(1,3,5-trimethyl-1H-pyrazol-4-yl)-1,3-dihydro-imidazo[4,5-c] quinolin-2-one | 458 | 2.16 |

Example 156

1-(1,3-Dimethyl-1H-pyrazol-4-yl)-8-(5-ethylamino-6-methoxymethyl-pyridin-3-yl)-3-methyl-1,3-dihydro-imidazo[4,5-c]quinolin-2-one

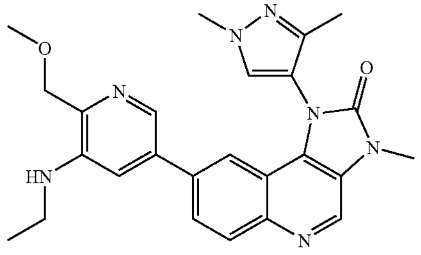 [SMILES: CCNc1cc(-c2ccc3ncc4c(c3c2)n(-c2cn(C)nc2C)c(=O)n4C)cnc1COC]

A solution of 1-(1,3-dimethyl-1H-pyrazol-4-yl)-8-(5-ethylamino-6-hydroxymethyl-pyridin-3-yl)-3-methyl-1,3-dihydro-imidazo[4,5-c]quinolin-2-one (Example 155.1, 0.086 mmol) in DMF (0.5 ml) was treated with 55% NaH in oil (0.086 mmol) and the RM was stirred for 10 min at rt, then was added iodomethane (0.086 mmol) and the RM was stirred for 2 h at rt. The RM was quenched with water, diluted with DMF, filtered and purified by preparative HPLC. The pure fractions were basified with $NaHCO_3$, concentrated and extracted with $CH_2Cl_2$ (3×) and with EtOAc. The combined organic layers were dried over $Na_2SO_4$, filtered, evaporated and dried under vacuum to give the title compound as a film. (HPLC: $t_R$ 2.24 min (Method A); M+H=458 MS-ES; $^1$H-NMR ($d_6$-DMSO, 400 MHz) 8.97 (s, 1H), 8.13-8.08 (m, 2H), 7.98-7.91 (m, 2H), 7.64-7.61 (m, 1H), 6.90 (s, 1H), 5.32 (t, 1H), 4.53 (s, 2H), 3.88 (s, 3H), 3.58 (s, 3H), 3.28 (s, 3H), 3.20 (qt, 2H), 1.97 (s, 3H), 1.23 (t, 3H))

Example 157

8-(5-Ethylamino-6-methoxymethyl-pyridin-3-yl)-1-(1-ethyl-3-methyl-1H-pyrazol-4-yl)-3-methyl-1,3-dihydro-imidazo[4,5-c]quinolin-2-one

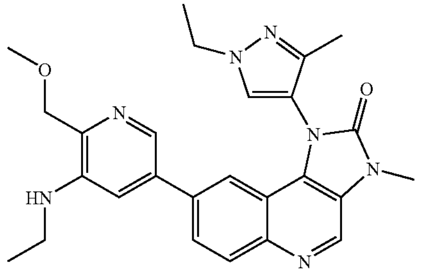 [SMILES: CCNc1cc(-c2ccc3ncc4c(c3c2)n(-c2cn(CC)nc2C)c(=O)n4C)cnc1COC]

The title compound was synthesized in a similar manner as described for Example 156.1 using 8-(5-ethylamino-6-hydroxymethyl-pyridin-3-yl)-1-(1-ethyl-3-methyl-1H-pyrazol-4-yl)-3-methyl-1,3-dihydro-imidazo[4,5-c]quinolin-2-one (Example 155.2) to give the title compound as an off-white solid. (HPLC: $t_R$ 2.29 min (Method A); M+H=472 MS-ES; $^1$H-NMR ($d_6$-DMSO, 400 MHz) 8.97 (s, 1H), 8.16 (s, 1H), 8.12-8.08 (m, 1H), 7.96-7.92 (m, 1H), 7.87-7.85 (m, 1H), 7.58-7.56 (m, 1H), 6.95-6.92 (m, 1H), 5.31 (t, 1H), 4.52 (s, 2H), 4.15 (q, 2H), 3.58 (s, 3H), 3.26 (s, 3H), 3.25-3.17 (m, 2H), 1.97 (s, 3H), 1.37 (t, 3H), 1.22 (t, 3H))

Example 158.1

1-(1,3-Dimethyl-1H-pyrazol-4-yl)-8-(6-hydroxymethyl-5-methylamino-pyridin-3-yl)-3-methyl-1,3-dihydro-imidazo[4,5-c]quinolin-2-one

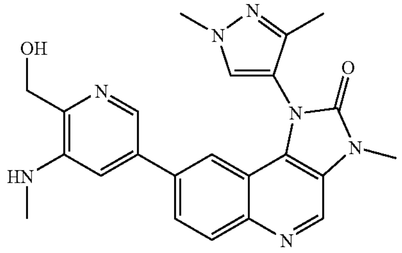 [SMILES: CNc1cc(-c2ccc3ncc4c(c3c2)n(-c2cn(C)nc2C)c(=O)n4C)cnc1CO]

The title compound was synthesized in a similar manner as described for Example 155.1 using (5-bromo-2-methyl-pyridin-3-yl)-methyl-carbamic acid tert-butyl ester (stage 158.1.1) to give the title compound as an off-white solid. (HPLC: $t_R$ 2.02 min (Method A); M+H=430 MS-ES; $^1$H-NMR ($d_6$-DMSO, 400 MHz) 8.97 (s, 1H), 8.13-8.07 (m, 2H), 7.99-7.90 (m, 2H), 7.65-7.61 (m, 1H), 6.85-6.80 (m, 1H), 5.67 (q, br, 1H), 5.22 (br, 1H), 4.55 (d, 2H), 3.88 (s, 3H), 3.58 (s, 3H), 2.83 (d, 3H), 1.97 (s, 3H))

Stage 158.1.1 (5-Bromo-2-methyl-pyridin-3-yl)-methyl-carbamic acid tert-butyl ester

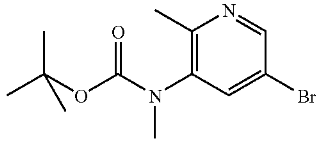 [SMILES: Cc1ncc(Br)cc1N(C)C(=O)OC(C)(C)C]

A solution of (5-bromo-2-methyl-pyridin-3-yl)-carbamic acid tert-butyl ester (Stage 158.1.2, 4.53 mmol) in DMF (20 ml) was cooled with an ice-bath and 55% NaH in oil (5.89 mmol) was added. The RM was stirred for 25 min at 0° C. then was added iodomethane (5.22 mmol). The RM was stirred for 2 h at it then was quenched with aqueous $NaHCO_3$ and extracted with EtOAc. The organic layer was washed with water (3×), with brine (3×), dried over $Na_2SO_4$, filtered, evaporated and dried under vacuum to give the title compound as a brown solid (HPLC: $t_R$ 3.20 min (Method A); M+H=301, 303 MS-ES).

Stage 158.1.2

(5-Bromo-2-methyl-pyridin-3-yl)-carbamic acid tert-butyl ester

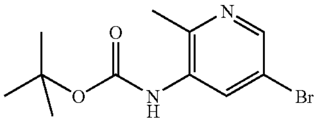 [SMILES: Cc1ncc(Br)cc1NC(=O)OC(C)(C)C]

The title compound was synthesized in a similar manner as described for stage 155.1.5 using 5-bromo-2-methyl-pyridin-3-ylamine (Stage 75.1.4, 7.86 mmol) to give the title compound as an oil (HPLC: $t_R$ 2.88 min (Method A); M+H=287, 289 MS-ES).

The following examples were synthesized in a similar manner as described for Example 158.1 using the specified intermediate.

| Example | Intermed. | structure | Name of the example | MS-ES (M + H) | HPLC $t_R$ (min) |
|---|---|---|---|---|---|
| 158.2 | G | 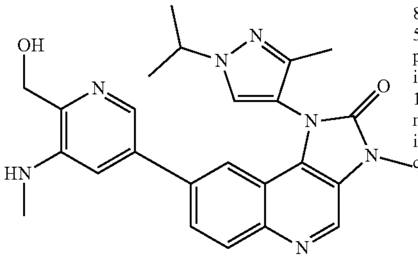 | 8-(6-Hydroxymethyl-5-methylamino-pyridin-3-yl)-1-(1-isopropyl-3-methyl-1H-pyrazol-4-yl)-3-methyl-1,3-dihydro-imidazo[4,5-c] quinolin-2-one | 458 | 2.12 |
| 158.3 | K | 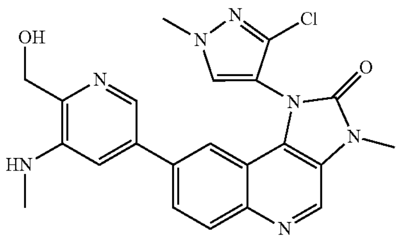 [SMILES: CNc1cc(-c2ccc3ncc4c(c3c2)n(-c2cn(C)nc2Cl)c(=O)n4C)cnc1CO] | 1-(3-Chloro-1-methyl-1H-pyrazol-4-yl)-8-(6-hydroxymethyl-5-methylamino-pyridin-3-yl)-3-methyl-1,3-dihydro-imidazo[4,5-c] quinolin-2-one | 450 | 2.20 |
| 158.4 | H | 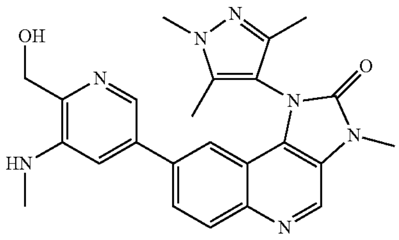 [SMILES: CNc1cc(-c2ccc3ncc4c(c3c2)n(-c2c(C)nn(C)c2C)c(=O)n4C)cnc1CO] | 8-(6-Hydroxymethyl-5-methylamino-pyridin-3-yl)-3-methyl-1-(1,3,5-trimethyl-1H-pyrazol-4-yl)-1,3-dihydro-imidazo[4,5-c] quinolin-2-one | 444 | 2.07 |
| 158.5 | F | 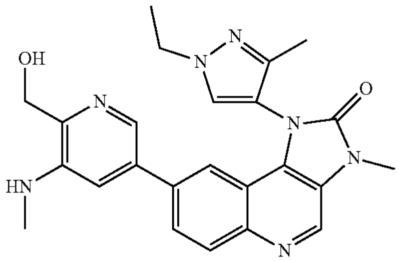 [SMILES: CCn1cc(-n2c(=O)n(C)c3cnc4ccc(-c5cnc(CO)c(NC)c5)cc4c32)c(C)n1] | 1-(1-Ethyl-3-methyl-1H-pyrazol-4-yl)-8-(6-hydroxymethyl-5-methylamino-pyridin-3-yl)-3-methyl-1,3-dihydro-imidazo[4,5-c] quinolin-2-one | 444 | 2.07 |

Example 159

1-(1,3-Dimethyl-1H-pyrazol-4-yl)-8-(6-methoxymethyl-5-methylamino-pyridin-3-yl)-3-methyl-1,3-dihydro-imidazo[4,5-c]quinolin-2-one

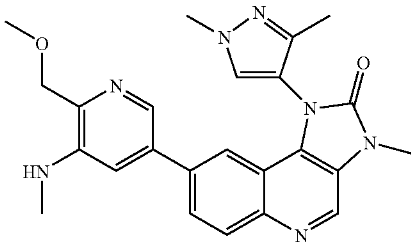

The title compound was synthesized in a similar manner as described for Example 156.1 using 1-(1,3-dimethyl-1H-pyrazol-4-yl)-8-(6-hydroxymethyl-5-methylamino-pyridin-3-yl)-3-methyl-1,3-dihydro-imidazo[4,5-c]quinolin-2-one (Example 158.1) to give the title compound as an off-white foam. (HPLC: $t_R$ 2.15 min (Method A); M+H=444 MS-ES; $^1$H-NMR ($d_6$-DMSO, 400 MHz) 8.97 (s, 1H), 8.12-8.08 (m, 2H), 7.99-7.91 (m, 2H), 7.65-7.62 (m, 1H), 6.85-6.82 (m, 1H), 5.57 (q, 1H), 4.49 (s, 2H), 3.88 (s, 3H), 3.58 (s, 3H), 3.27 (s, 3H), 2.82 (d, 3H), 1.97 (s, 3H))

Example 160.1

1-(3-Chloro-1-methyl-1H-pyrazol-4-yl)-8-(6-methoxymethyl-5-methylamino-pyridin-3-yl)-3-methyl-1,3-dihydro-imidazo[4,5-c]quinolin-2-one

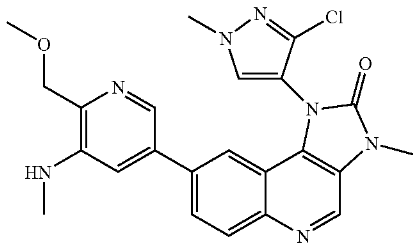

The title compound was synthesized in a similar manner as described for Example 156.1 using 1-(3-chloro-1-methyl-1H-pyrazol-4-yl)-8-(6-hydroxymethyl-5-methylamino-pyridin-3-yl)-3-methyl-1,3-dihydro-imidazo[4,5-c]quinolin-2-one (Example 158.3) to give the title compound as an off-white solid. (HPLC: $t_R$ 2.32 min (Method A); M+H=464 MS-ES; $^1$H-NMR ($d_6$-DMSO, 400 MHz) 9.00 (s, 1H), 8.37 (s, 1H), 8.14-8.09 (m, 1H), 8.02-7.94 (m, 2H), 7.63-7.60 (m, 1H), 6.90-6.86 (m, 1H), 5.60 (q, br, 1H), 4.50 (s, 2H), 3.95 (s, 3H), 3.59 (s, 3H), 3.28 (s, 3H), 2.83 (d, 3H))

The following example was synthesized in a similar manner as described for Example 156.1 using the specified example as intermediate.

| Example | Intermed. | structure | Name of the example | MS-ES (M + H) | HPLC $t_R$ (min) |
|---|---|---|---|---|---|
| 160.2 | 158.5 | 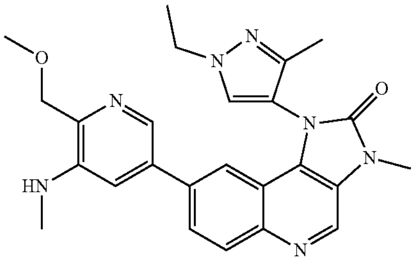 | 1-(1-Ethyl-3-methyl-1H-pyrazol-4-yl)-8-(6-methoxymethyl-5-methylamino-pyridin-3-yl)-3-methyl-1,3-dihydro-imidazo[4,5-c]quinolin-2-one | 458 | 2.19 |

Example 161

1-(1,3-Dimethyl-1H-pyrazol-4-yl)-8-(6-ethyl-5-ethylamino-pyridin-3-yl)-3-methyl-1,3-dihydro-imidazo[4,5-c]quinolin-2-one

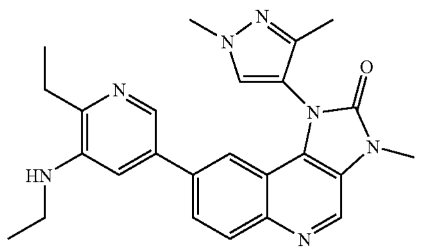 [SMILES: CCNc1cc(-c2ccc3ncc4c(c3c2)n(-c2cn(C)nc2C)c(=O)n4C)cnc1CC]

The title compound was synthesized in a similar manner as described for Example 87.1 using diethyl methylmalonate (Fluka, Buchs, Switzerland) to give the title compound as a white solid. (HPLC: $t_R$ 2.26 min (Method A); M+H=442 MS-ES; $^1$H-NMR ($d_6$-DMSO, 400 MHz) 8.96 (s, 1H), 8.12-8.07 (m, 2H), 7.96-7.91 (m, 2H), 7.63-7.59 (m, 1H), 6.78-6.75 (m, 1H), 5.29 (t, 1H), 3.88 (s, 3H), 3.58 (s, 3H), 3.18 (qt, 2H), 2.67 (q, 2H), 1.97 (s, 3H), 1.25 (t, 3H), 1.20 (t, 3H))

Example 162

1-(1,3-Dimethyl-1H-pyrazol-4-yl)-8-(6-ethyl-5-isopropylamino-pyridin-3-yl)-3-methyl-1,3-dihydro-imidazo[4,5-c]quinolin-2-one

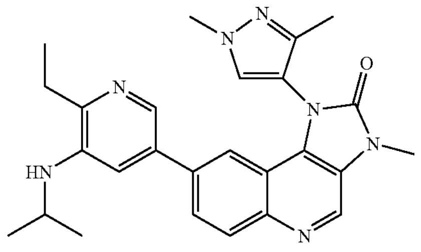 [SMILES: CCc1ncc(-c2ccc3ncc4c(c3c2)n(-c2cn(C)nc2C)c(=O)n4C)cc1NC(C)C]

The title compound was synthesized in a similar manner as described for Example 161 using (5-bromo-2-ethyl-pyridin-3-yl)-isopropyl-amine (Stage 162.1.1) to give the title compound as an off-white foam. (HPLC: $t_R$ 2.34 min (Method A); M+H=456 MS-ES; $^1$H-NMR ($d_6$-DMSO, 400 MHz) 8.96 (s, 1H), 8.12-8.07 (m, 2H), 7.95-7.90 (m, 2H), 7.61-7.58 (m, 1H), 6.81-6.78 (m, 1H), 4.88 (d, 1H), 3.88 (s, 3H), 3.76-3.62 (m, 1H), 3.58 (s, 3H), 2.67 (q, 2H), 1.97 (s, 3H), 1.25 (d, 3H), 1.21 (d, 3H), 1.19 (t, 3H))

Stage 162.1.1

(5-Bromo-2-ethyl-pyridin-3-yl)-isopropyl-amine

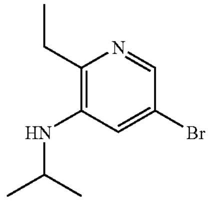

To solution of (5-bromo-2-ethyl-pyridin-3-yl)-isopropylidene-amine (Stage 162.1.2, 1.17 mmol) in dichloromethane (25 ml) was added AcOH (0.25 ml) and sodium triacetoxyborohydride (3.51 mmol). The reaction mixture was stirred for 4 h at rt. The RM was quenched with aqueous $NaHCO_3$ and extracted with dichloromethane (2×). The combined organic layers were washed with saturated aqueous $NaHCO_3$, with brine, dried over $Na_2SO_4$, filtered and evaporated. The residue was absorbed on silica gel and eluted ($CH_2Cl_2$/MeOH 0% to 3%). The fractions containing the product were purified by preparative HPLC. The fractions containing pure product were basified with $NaHCO_3$, concentrated and extracted with EtOAc (3×). The combined organic layers were dried over $Na_2SO_4$, filtered and evaporated to the title compound as an oil (HPLC: $t_R$ 2.40 min (Method A); M+H=243, 245 MS-ES).

Stage 162.1.2 (5-Bromo-2-ethyl-pyridin-3-yl)-isopropylidene-amine

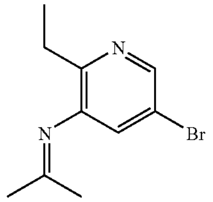

To a solution of 5-bromo-2-ethyl-pyridin-3-ylamine (1.492 mmol), synthesized in a similar manner as described for 5-bromo-2-methyl-pyridin-3-ylamine (Stage 75.1.4) using diethyl methylmalonate (HPLC: $t_R$ 1.71min (Method A); M+H=201, 203 MS-ES), in chloroform (0.75 ml) and 2-methoxypropene (Aldrich, Buchs, Switzerland, 7.46 mmol) were added triethylamine (1.492 mmol) and pyridinium para-toluensulfonate (0.149 mmol). The RM was stirred for 17 h at 100° C., then was quenched with aqueous $Na_2CO_3$ and extracted with EtOAc (2×). The combined organic layers were washed with brine, dried over $Na_2SO_4$, filtered, evaporated and dried under vacuum to give the title compound as a brown oil (M+H=241, 243 MS-ES).

Example 163

1-(1,3-Dimethyl-1H-pyrazol-4-yl)-3-methyl-8-(6-methyl-5-methylamino-pyridin-3-yl)-1,3-dihydro-imidazo[4,5-c]quinolin-2-one

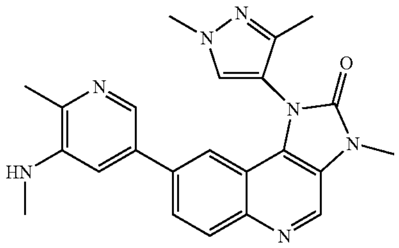

The title compound was synthesized in a similar manner as described for Example 1.1 using 8-bromo-1-(1,3-dimethyl-1H-pyrazol-4-yl)-3-methyl-1,3-dihydro-imidazo[4,5-c]quinolin-2-one (Intermediate A) and methyl-[2-methyl-5-(4,4,5,5-tetramethyl-[1,3,2]dioxaborolan-2-yl)-pyridin-3-yl]-amine (Stage 163.1.1) to give the title compound as a white solid. (HPLC: $t_R$ 2.10 min (Method A); M+H=414 MS-ES; $^1$H-NMR ($d_6$-DMSO, 400 MHz) 8.95 (s, 1H), 8.12-8.06 (m, 2H), 7.96-7.92 (m, 1H), 7.89-7.87 (m, 1H), 7.62-7.60 (m, 1H), 6.73-6.70 (m, 1H), 5.51 (q, br, 1H), 3.88 (s, 3H), 3.57 (s, 3H), 2.80 (d, 3H), 2.31 (s, 3H), 1.97 (s, 3H))

Stage 163.1.1 Methyl[2-methyl-5-(4,4,5,5-tetramethyl-[1,3,2]dioxaborolan-2-yl)-pyridin-3-yl]-amine

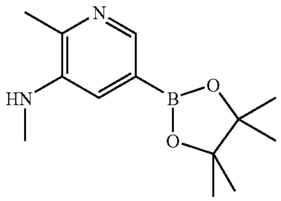

The title compound was synthesized in a similar manner as described for Stage 5.1.1 using (5-bromo-2-methyl-pyridin-3-yl)-methyl-amine (stage 163.1.2, 1.194 mmol) to give the title compound as a crude black oil. (degrading under the HPLC condition: $t_R$ 1.64 min (Method A); M+H=249 MS-ES).

Stage 163.1.2 (5-Bromo-2-methyl-pyridin-3-yl)-methyl-amine

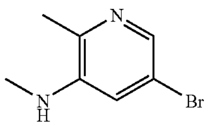

To a solution of 5-bromo-2-methyl-pyridin-3-ylamine (Stage 75.1.4, 3.81 mmol) in THF (25 ml) cooled with an ice-bath was added 1 M bis(trimethylsilyl)amide in THF (4.38 mmol). The RM was stirred for 1 h at rt then was added iodomethane (4.38 mmol). The RM was stirred for 1 h at rt. The RM was cooled with an ice-bath and was added 1 M bis(trimethylsilyl)amide in THF (1.9 mmol). The RM was stirred for 30 min at it then was added iodomethane (1.9 mmol). The RM was stirred for 1 h at it then was diluted with EtOAc and washed with aqueous $Na_2CO_3$, with brine, dried over $Na_2SO_4$, filtered and evaporated. The residue was taken in MeOH and separated by preparative HPLC. The first eluting pure fractions containing product were basified with $NaHCO_3$, concentrated and extracted with dichloromethane (2×). The combined fractions were washed with brine, dried over $Na_2SO_4$, filtered and evaporated to give the title compound as a brown oil (HPLC: $t_R$ 1.88 min (Method A); M+H=201, 203 MS-ES). The second eluting pure fractions, that contained (5-bromo-2-methyl-pyridin-3-yl)-dimethyl-amine side product, were basified with $NaHCO_3$, concentrated and extracted with dichloromethane (2×). The combined fractions were washed with brine, dried over $Na_2SO_4$, filtered and evaporated to give the title compound as a brown oil (HPLC: $t_R$ 2.01 min (Method A); M+H=215, 217 MS-ES).

Example 164

8-(5-Dimethylamino-6-methyl-pyridin-3-yl)-1-(1,3-dimethyl-1H-pyrazol-4-yl)-3-methyl-1,3-dihydro-imidazo[4,5-c]quinolin-2-one

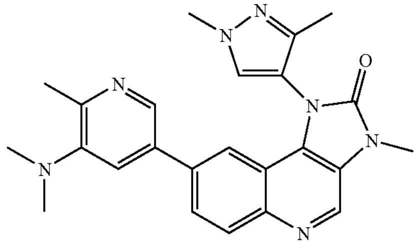

The title compound was synthesized in a similar manner as described for Example 1.1 using 8-bromo-1-(1,3-dimethyl-1H-pyrazol-4-yl)-3-methyl-1,3-dihydro-imidazo[4,5-c]quinolin-2-one (Intermediate A) and dimethyl-[2-methyl-5-(4,4,5,5-tetramethyl-[1,3,2]dioxaborolan-2-yl)-pyridin-3-yl]-amine (Stage 164.1.1) to give the title compound as an off-white foam. (HPLC: $t_R$ 2.15 min (Method A); M+H=428 MS-ES; $^1$H-NMR ($d_6$-DMSO, 400 MHz) 8.97 (s, 1H), 8.30-8.27 (m, 1H), 8.13-8.08 (m, 2H), 7.99-7.94 (m, 1H), 7.59-7.56 (m, 1H), 7.33-7.30 (m, 1H), 3.88 (s, 3H), 3.58 (s, 3H), 2.72 (s, 6H), 2.50 (s, 3H), 1.97 (s, 3H))

Stage 164.1.1 Dimethyl-[2-methyl-5-(4,4,5,5-tetramethyl-[1,3,2]dioxaborolan-2-yl)-pyridin-3-yl]-amine

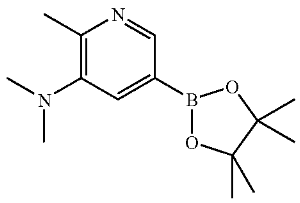

The title compound was synthesized in a similar manner as described for Stage 5.1.1 using (5-bromo-2-methyl-pyridin-3-yl)-dimethyl-amine (stage 163.1.2, 1.255 mmol) to give the title compound as a crude black oil. (degrading under the HPLC condition: $t_R$ 1.93 min (Method A); M+H=263 MS-ES).

Example 165

1-(1,3-Dimethyl-1H-pyrazol-4-yl)-8-[5-(ethyl-methyl-amino)-6-methyl-pyridin-3-yl]-3-methyl-1,3-dihydro-imidazo[4,5-c]quinolin-2-one

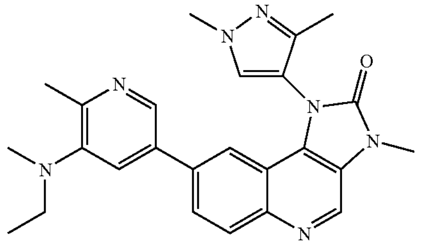

The title compound was synthesized in a similar manner as described for Example 1.1 using 8-bromo-1-(1,3-dimethyl-1H-pyrazol-4-yl)-3-methyl-1,3-dihydro-imidazo[4,5-c]quinolin-2-one (Intermediate A) and ethyl-methyl-[2-methyl-5-(4,4,5,5-tetramethyl-[1,3,2]dioxaborolan-2-yl)-pyridin-3-yl]-amine (Stage 165.1.1) to give the title compound as a white foam. (HPLC: $t_R$ 2.26 min (Method A); M+H=442 MS-ES; $^1$H-NMR ($d_6$-DMSO, 400 MHz) 8.95 (s, 1H), 8.32-8.29 (m, 1H), 8.13-8.09 (m, 2H), 7.99-7.94 (m, 1H), 7.61-7.58 (m, 1H), 7.35-7.32 (m, 1H), 3.89 (s, 3H), 3.58 (s, 3H), 2.97 (q, 2H), 2.71 (s, 31-1), 2.45 (s, 3H), 1.97 (s, 3H), 1.09 (t, 3H))

Stage 165.1.1 Ethyl-methyl-[2-methyl-5-(4,4,5,5-tetramethyl-[1,3,2]dioxaborolan-2-yl)-pyridin-3-yl]-amine

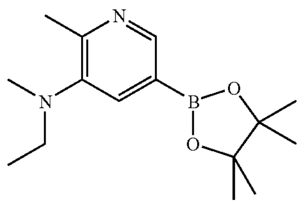

The title compound was synthesized in a similar manner as described for Stage 5.1.1 using (5-bromo-2-methyl-pyridin-3-yl)-ethyl-methyl-amine (stage 165.1.2, 0.646 mmol) to give the title compound as a crude black oil. (degrading under the HPLC condition: $t_R$ 2.12 min (Method A); M+H=277 MS-ES).

Stage 165.1.2 (5-Bromo-2-methyl-pyridin-3-yl)-ethyl-methyl-amine

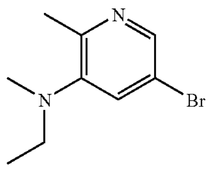

The title compound was synthesized in a similar manner as described for Stage 163.1.2 using (5-bromo-2-methyl-pyridin-3-yl)-ethyl-amine (Stage 87.1.2, 0.677 mmol) to give the title compound as a brown oil (HPLC: $t_R$ 2.22 min (Method A); M+H=229, 231 MS-ES).

Example 166.1

8-(6-Amino-5-ethoxymethyl-pyridin-3-yl)-1-(1,3-dimethyl-1H-pyrazol-4-yl)-3-methyl-1,3-dihydro-imidazo[4,5-c]quinolin-2-one

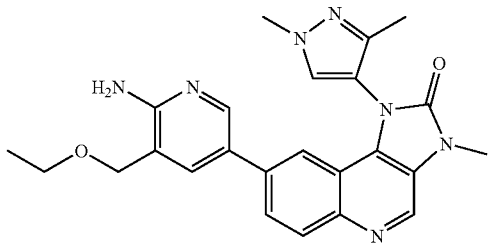 [SMILES: CCOCc1cc(-c2ccc3ncc4c(c3c2)n(-c2cn(C)nc2C)c(=O)n4C)cnc1N]

The title compound was synthesized in a similar manner as described for Example 1.1 using 8-bromo-1-(1,3-dimethyl-1H-pyrazol-4-yl)-3-methyl-1,3-dihydro-imidazo[4,5-c]quinolin-2-one (Intermediate A) and 3-ethoxymethyl-5-(4,4,5,5-tetramethyl-[1,3,2]dioxaborolan-2-yl)-pyridin-2-ylamine (Stage 166.1.1) to give the title compound as a white solid. (HPLC: $t_R$ 2.17 min (Method A); M+H=444 MS-ES; $^1$H-NMR ($d_6$-DMSO, 400 MHz) 8.90 (s, 1H), 8.13 (s, 1H), 8.08-8.06 (m, 1H), 8.05-8.01 (m, 1H), 7.86-7.82 (m, 1H), 7.49-7.47 (m, 1H), 7.44-7.42 (m, 1H), 6.02 (s, br, 2H), 4.37 (s, 2H), 3.92 (s, 3H), 3.57 (s, 3H), 3.51 (q, 2H), 1.95 (s, 3H), 1.18 (t, 3H))

Stage 166.1.1 3-Ethoxymethyl-5-(4,4,5,5-tetramethyl-[1,3,2]dioxaborolan-2-yl)-pyridin-2-ylamine

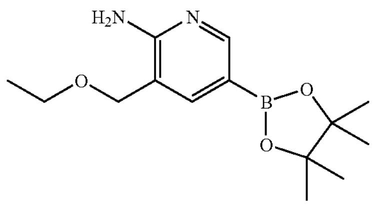 [SMILES: CCOCc1cc(B2OC(C)(C)C(C)(C)O2)cnc1N]

The title compound was synthesized in a similar manner as described for Stage 5.1.1 using 5-bromo-3-ethoxymethyl-pyridin-2-ylamine (stage 166.1.2, 1.082 mmol) to give the title compound as a crude black oil. (degrading under the HPLC condition: $t_R$ 1.72 min (Method A); M+H=279 MS-ES).

Stage 166.1.2

5-Bromo-3-ethoxymethyl-pyridin-2-ylamine

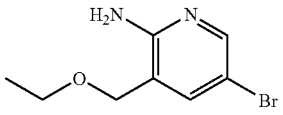

A solution of (2-amino-5-bromo-pyridin-3-yl)-methanol hydrobromide (Apollo, Cheshire, UK, 3.52 mmol) in DMF (15 ml) cooled with an ice-bath was treated with 55% NaH in oil (7.4 mmol) and the RM was stirred for 5 min at 0° C. and 30 min at rt, then was added iodoethane (3.87 mmol) and the RM was stirred for 1 h 15 min at rt. The RM was quenched with water and extracted with EtOAc. The organic layer was washed with saturated aqueous $NaHCO_3$, with brine (2×), dried over $Na_2SO_4$, filtered and evaporated. The residue was taken in DMF and purified by preparative HPLC. The fractions containing product were basified with $NaHCO_3$, concentrated and extracted with $CH_2Cl_2$ (2×). The combined organic layers were washed with brine, dried over $Na_2SO_4$, filtered, evaporated and dried under vacuum to give the title compound as a light yellow oil. (HPLC: $t_R$ 2.07 min (Method A); M+H=231, 233 MS-ES)

The following examples were synthesized in a similar manner as described for Example 1.1 using 3-ethoxymethyl-5-(4,4,5,5-tetramethyl-[1,3,2]dioxaborolan-2-yl)-pyridin-2-ylamine (Stage 166.1.1) and the specified intermediate.

| Example | Intermed. | structure | Name of the example | MS-ES (M + H) | HPLC $t_R$ (min) |
|---|---|---|---|---|---|
| 166.2 | F | 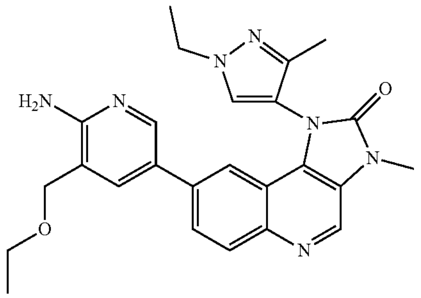 [SMILES: CCOCc1cc(-c2ccc3ncc4c(c3c2)n(-c2cn(CC)nc2C)c(=O)n4C)cnc1N] | 8-(6-Amino-5-ethoxymethyl-pyridin-3-yl)-1-(1-ethyl-3-methyl-1H-pyrazol-4-yl)-3-methyl-1,3-dihydro-imidazo[4,5-c]quinolin-2-one | 458 | 2.22 |
| 166.3 | G | 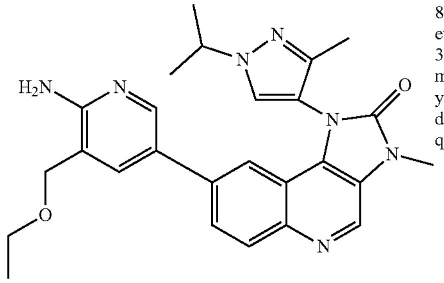 | 8-(6-Amino-5-ethoxymethyl-pyridin-3-yl)-1-(1-isopropyl-3-methyl-1H-pyrazol-4-yl)-3-methyl-1,3-dihydro-imidazo[4,5-c]quinolin-2-one | 472 | 2.29 |
| 166.4 | K | 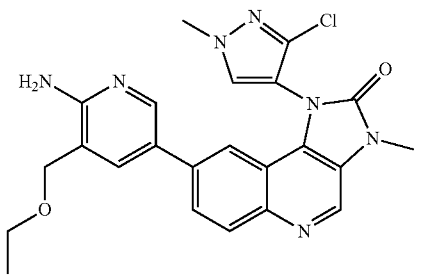 [SMILES: CCOCc1cc(-c2ccc3ncc4c(c3c2)n(-c2cn(C)nc2Cl)c(=O)n4C)cnc1N] | 8-(6-Amino-5-ethoxymethyl-pyridin-3-yl)-1-(3-chloro-1-methyl-1H-pyrazol-4-yl)-3-methyl-1,3-dihydro-imidazo[4,5-c]quinolin-2-one | 464 | 2.33 |

-continued

| Example | Intermed. | structure | Name of the example | MS-ES (M + H) | HPLC $t_R$ (min) |
|---|---|---|---|---|---|
| 166.5 | H | 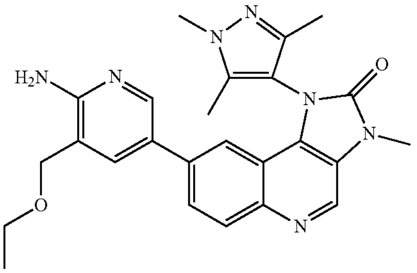 [SMILES: CCOCc1cc(-c2ccc3ncc4c(c3c2)n(-c2c(C)nn(C)c2C)c(=O)n4C)cnc1N] | 8-(6-Amino-5-ethoxymethyl-pyridin-3-yl)-3-methyl-1-(1,3,5-trimethyl-1H-pyrazol-4-yl)-1,3-dihydro-imidazo[4,5-c]quinolin-2-one | 458 | 2.21 |

Example 167

1-(1,3-Dimethyl-1H-pyrazol-4-yl)-8-(5-ethoxymethyl-6-ethylamino-pyridin-3-yl)-3-methyl-1,3-dihydro-imidazo[4,5-c]quinolin-2-one

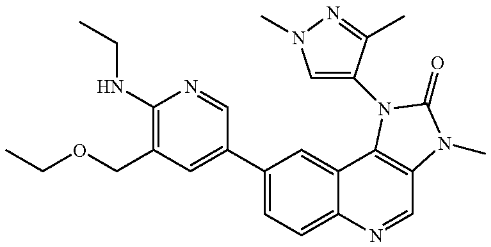 [SMILES: CCNc1ncc(-c2ccc3ncc4c(c3c2)n(-c2cn(C)nc2C)c(=O)n4C)cc1COCC]

The title compound was synthesized in a similar manner as described for Example 1.1 using 8-bromo-1-(1,3-dimethyl-1H-pyrazol-4-yl)-3-methyl-1,3-dihydro-imidazo[4,5-c]quinolin-2-one (Intermediate A) and [3-ethoxymethyl-5-(4,4,5,5-tetramethyl-[1,3,2]dioxaborolan-2-yl)-pyridin-2-yl]-ethyl-amine (Stage 167.1.1) to give the title compound as a white solid. (HPLC: $t_R$ 2.30 min (Method A); M+H=472 MS-ES; $^1$H-NMR ($d_6$-DMSO, 400 MHz) 8.90 (s, 1H), 8.19-8.16 (m, 1H), 8.12 (s, 1H), 8.05-8.01 (m, 1H), 7.87-7.83 (m, 1H), 7.44-7.41 (m, 2H), 6.07 (t, 1H), 4.39 (s, 2H), 3.92 (s, 3H), 3.56 (s, 3H), 3.51 (q, 2H), 3.46-3.37 (m, 2H), 1.95 (s, 3H), 1.19 (t, 3H), 1.15 (t, 3H))

Stage 167.1.1 [3-Ethoxymethyl-5-(4,4,5,5-tetramethyl-[1,3,2]dioxaborolan-2-yl)-pyridin-2-yl]-ethyl-amine

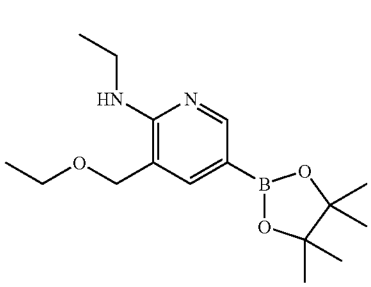 [SMILES: CCNc1ncc(B2OC(C)(C)C(C)(C)O2)cc1COCC]

The title compound was synthesized in a similar manner as described for Stage 5.1.1 using (5-bromo-3-ethoxymethyl-pyridin-2-yl)-ethyl-amine (stage 167.1.2, 0.99 mmol) to give the title compound as a crude black oil. (degrading under the HPLC condition: $t_R$ 1.98 min (Method A); M+H=307 MS-ES).

Stage 167.1.2 (5-Bromo-3-ethoxymethyl-pyridin-2-yl)-ethyl-amine

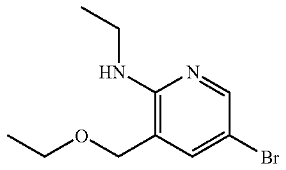

The title compound was synthesized in a similar manner as described for Stage 87.1.2 using 5-bromo-3-ethoxymethyl-pyridin-2-ylamine (stage 166.1.2, 1.082 mmol) to give the title compound as a yellow oil. (HPLC: $t_R$ 2.30 min (Method A); M+H=259, 261 MS-ES)

Example 168.1

8-(6-Amino-5-methoxymethyl-pyridin-3-yl)-1-(1-isopropyl-3-methyl-1H-pyrazol-4-yl)-3-methyl-1,3-dihydro-imidazo[4,5-c]quinolin-2-one

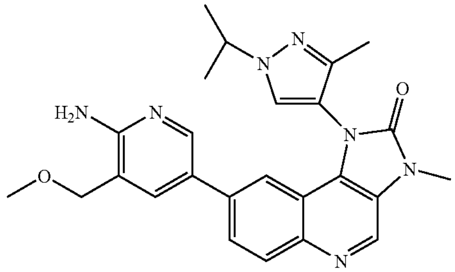

The title compound was synthesized in a similar manner as described for Example 1.1 using 8-bromo-1-(1-isopropyl-3-methyl-1H-pyrazol-4-yl)-3-methyl-1,3-dihydro-imidazo[4,5-c]quinolin-2-one (Intermediate G) and 3-methoxymethyl- 5-(4,4,5,5-tetramethyl-[1,3,2]dioxaborolan-2-yl)-pyridin-2-ylamine (Stage 168.1.1) to give the title compound as a white solid. (HPLC: $t_R$ 2.19 min (Method A); M+H=458 MS-ES; $^1$H-NMR ($d_6$-DMSO, 400 MHz) 8.91 (s, 1H), 8.20 (s, 1H), 8.06-8.01 (m, 2H), 7.85-7.80 (m, 1H), 7.53-7.50 (m, 1H), 7.44-7.41 (m, 1H), 5.99 (s, br, 2H), 4.54 (hp, 1H), 4.30 (s, 2H), 3.57 (s, 3H), 3.31 (s, 3H), 1.95 (s, 3H), 1.47 (d, 6H))

Stage 168.1.1 3-Methoxymethyl-5-(4,4,5,5-tetramethyl-[1,3,2]dioxaborolan-2-yl)-pyridin-2-ylamine

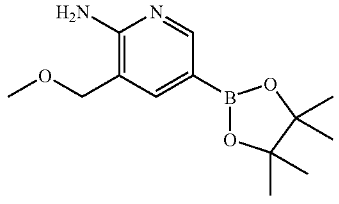

The title compound was synthesized in a similar manner as described for Stage 166.1.1-2 using iodomethane as replacement for iodoethane to give the title compound as a crude black soft solid. (degrading under the HPLC condition: $t_R$ 1.47 min (Method A); M+H=265 MS-ES).

The following examples were synthesized in a similar manner as described for Example 1.1 using 3-methoxymethyl-5-(4,4,5,5-tetramethyl-[1,3,2]dioxaborolan-2-yl)-pyridin-2-ylamine (Stage 168.1.1) and the specified intermediate.

Example 169.1

8-(6-Amino-5-hydroxymethyl-pyridin-3-yl)-1-(1-isopropyl-3-methyl-1H-pyrazol-4-yl)-3-methyl-1,3-dihydro-imidazo[4,5-c]quinolin-2-one

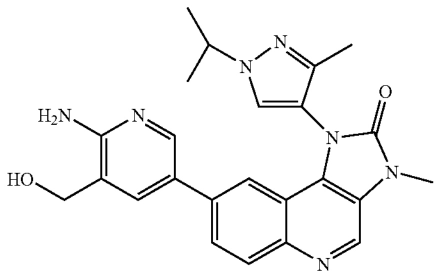

A mixture of 8-bromo-1-(1-isopropyl-3-methyl-1H-pyrazol-4-yl)-3-methyl-1,3-dihydro-imidazo[4,5-c]quinolin-2-one (Intermediate G, 0.098 mmol), crude acetic acid 2-di-acetylamino-5-(4,4,5,5-tetramethyl-[1,3,2]dioxaborolan-2-yl)-pyridin-3-ylmethyl ester (stage 169.1.1, 0.92 mg) and $PdCl_2(PPh_3)_2$ (0.0057 mmol) in DMF (1.2 ml) and 1 M aqueous $K_2CO_3$ (0.245 ml) was stirred under argon at 105° C. for 1 h. Then the RM was cooled to it and 2 M aqueous LiOH (0.245 ml) was added. The RM was stirred for 1 h 15 min at rt then quenched with 2 M aqueous HCl (0.245 ml), diluted with MeOH and purified directly by Prep.HPLC. The frac-

| Example | Intermed. | structure | Name of the example | MS-ES (M + H) | HPLC $t_R$ (min) |
|---|---|---|---|---|---|
| 168.2 | F | 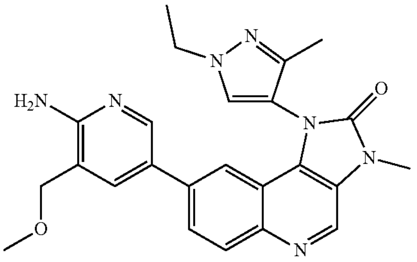 | 8-(6-Amino-5-methoxymethyl-pyridin-3-yl)-1-(1-ethyl-3-methyl-1H-pyrazol-4-yl)-3-methyl-1,3-dihydro-imidazo[4,5-c] quinolin-2-one | 444 | 2.12 |
| 168.3 | K | 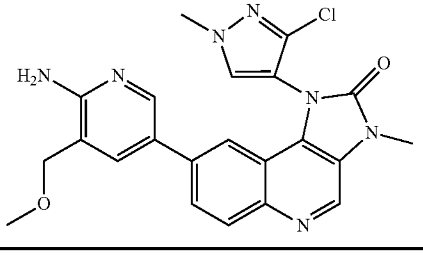 | 8-(6-Amino-5-methoxymethyl-pyridin-3-yl)-1-(3-chloro-1-methyl-1H-pyrazol-4-yl)-3-methyl-1,3-dihydro-imidazo[4,5-c] quinolin-2-one | 472 | 2.29 |

tions containing product were collected together, basified with $NaHCO_3$, concentrated and extracted with dichloromethane (2×). The combined organic layers were washed with brine, dried over $Na_2SO_4$, filtered, evaporated and dried under vacuum to give the title compound as a white solid. (HPLC: $t_R$ 2.04 min (Method A); M+H=444 MS-ES; $^1$H-NMR ($d_6$-DMSO, 400 MHz) 8.91 (s, 1H), 8.20 (s, 1H), 8.06-8.02 (m, 1H), 7.97-7.94 (m, 1H), 7.83-7.78 (m, 1H), 7.57-7.54 (m, 1H), 7.45-7.42 (m, 1H), 5.95 (s, br, 2H), 5.20 (t, 1H), 4.55 (hp, 1H), 4.37 (d, 2H), 3.57 (s, 3H), 1.95 (s, 3H), 1.47 (d, 6H))

Stage 169.1.1 Acetic acid 2-diacetylamino-5-(4,4,5,5-tetramethyl-[1,3,2]dioxaborolan-2-yl)-pyridin-3-ylmethyl ester

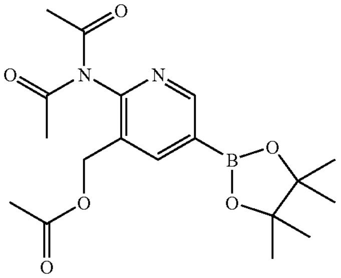 [SMILES: CC(=O)OCc1cc(B2OC(C)(C)C(C)(C)O2)cnc1N(C(C)=O)C(C)=O]

The title compound was synthesized in a similar manner as described for Stage 5.1.1 using acetic acid 2-diacetylamino-5-(4,4,5,5-tetramethyl-[1,3,2]dioxaborolan-2-yl)-pyridin-3-ylmethyl ester (stage 169.1.2, 1.762 mmol) to give the title compound as a crude black oil. (degrading under the HPLC condition: $t_R$ 2.05 min (Method A); M+H=377 MS-ES).

Stage 169.1.2 Acetic acid 2-diacetylamino-5-(4,4,5,5-tetramethyl-[1,3,2]dioxaborolan-2-yl)-pyridin-3-ylmethyl ester

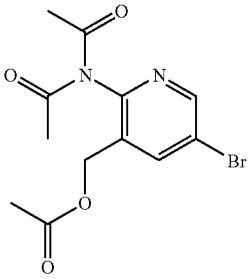 [SMILES: CC(=O)OCc1cc(Br)cnc1N(C(C)=O)C(C)=O]

To a suspension of 2-amino-5-bromo-3-hydroxymethylpyridine hydrobromide (Apollo, Cheshire, UK, 1.761 mmol) in dichloromethane (9 ml) were added triethylamine (7.92 mmol) and then acetyl chloride (5.81 mmol). The RM was stirred for 1.5 h at it then was diluted with dichloromethane, washed with brine (2×), dried over $Na_2SO_4$, filtered, evaporated and dried under vacuum to give the title compound as an oil. (HPLC: $t_R$ 1.69 min (Method A); M+H=329, 331 MS-ES).

The following examples were synthesized in a similar manner as described for Example 169.1 using the specified intermediate.

| Example | Intermed. | structure | Name of the example | MS-ES (M + H) | HPLC $t_R$ (min) |
|---|---|---|---|---|---|
| 169.2 | H | 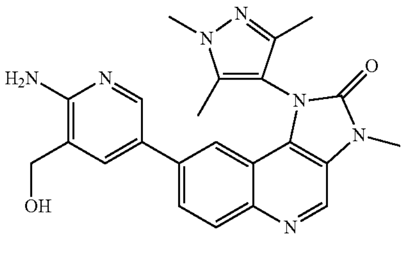 [SMILES: Cc1nn(C)c(C)c1-n1c(=O)n(C)c2cnc3ccc(-c4cnc(N)c(CO)c4)cc3c21] | 8-(6-Amino-5-hydroxymethyl-pyridin-3-yl)-3-methyl-1-(1,3,5-trimethyl-1H-pyrazol-4-yl)-1,3-dihydro-imidazo[4,5-c]quinolin-2-one | 430 | 1.98 |
| 169.3 | K | 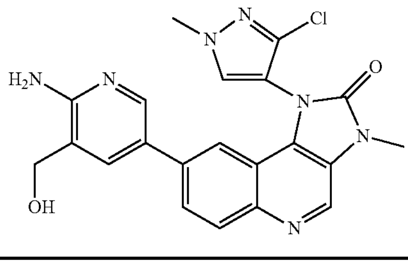 | 8-(6-Amino-5-hydroxymethyl-pyridin-3-yl)-1-(3-chloro-1-methyl-1H-pyrazol-4-yl)-3-methyl-1,3-dihydro-imidazo[4,5-c]quinolin-2-one | 436 | 2.06 |

Example 170

1-(1-Isopropyl-3-methyl-1H-pyrazol-4-yl)-3-methyl-8-(1-methyl-2-oxo-1,4-dihydro-2H-pyrido[2,3-d][1,3]oxazin-6-yl)-1,3-dihydro-imidazo[4,5-c]quinolin-2-one

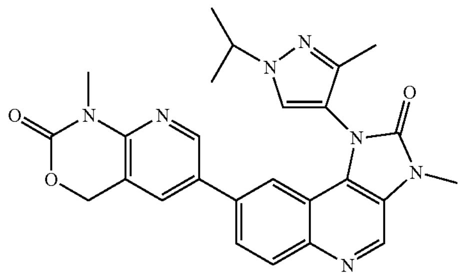 [SMILES: Cc1nn(C(C)C)cc1-n1c(=O)n(C)c2cnc3ccc(-c4cnc5c(c4)COC(=O)N5C)cc3c21]

The title compound was synthesized in a similar manner as described for Example 1.1 using 8-bromo-1-(1-isopropyl-3-methyl-1H-pyrazol-4-yl)-3-methyl-1,3-dihydro-imidazo[4,5-c]quinolin-2-one (Intermediate G, 0.125 mmol) and 1-methyl-6-(4,4,5,5-tetramethyl-[1,3,2]dioxaborolan-2-yl)-1,4-dihydro-pyrido[2,3-d][1,3]oxazin-2-one (Stage 170.1.1) to give the title compound as a beige solid. (HPLC: $t_R$ 2.59 min (Method A); M+H=484 MS-ES; $^1$H-NMR ($d_6$-DMSO, 400 MHz) 8.98 (s, 1H), 8.35-8.33 (m, 1H), 8.21 (s, 1H), 8.15-8.11 (m, 1H), 7.91-7.83 (m, 2H), 7.52-7.49 (m, 1H), 5.36-5.29 (m, 2H), 4.56 (qt, 1H), 3.58 (s, 3H), 3.35 (s, 3H), 1.95 (s, 3H), 1.46 (d, 6H))

Stage 170.1.1 1-Methyl-6-(4,4,5,5-tetramethyl-[1,3,2]dioxaborolan-2-yl)-1,4-dihydro-pyrido[2,3-d][1,3]oxazin-2-one

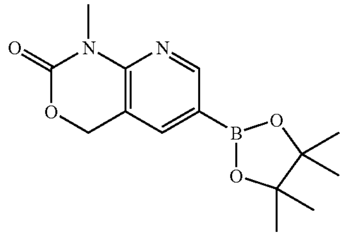 [SMILES: CN1C(=O)OCc2cc(B3OC(C)(C)C(C)(C)O3)cnc21]

The title compound was synthesized in a similar manner as described for Stage 5.1.1 using 6-bromo-1-methyl-1,4-dihydro-pyrido[2,3-d][1,3]oxazin-2-one (stage 170.1.2, 0.30 mmol) to give the title compound as a crude brown soft solid. (degrading partially under the HPLC condition: $t_R$ 1.87 and 3.68 min (Method A); M+H=291 MS-ES).

Stage 170.1.2 6-Bromo-1-methyl-1,4-dihydro-pyrido[2,3-d][1,3]oxazin-2-one

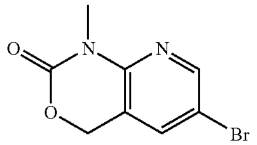

To a solution of 6-bromo-1,4-dihydro-pyrido[2,3-d][1,3]oxazin-2-one (Stage 170.1.3, 0.707 mmol) in DMF (1.4 ml) was added 55% sodium hydride in oil (0.778 mmol). The RM was stirred for 5 min at rt then was added iodomethane (0.778 mmol) and the RM was stirred for 30 min at rt. The RM was diluted with EtOAc, washed with saturated $NaHCO_3$, with brine (3×), dried over $Na_2SO_4$, filtered and evaporated. The residue was absorbed on silica gel and separated by flash chromatography (heptane/EtOAc 0% to 70%). The fractions containing product were evaporated together to give the title compound as a yellow solid. (HPLC: $t_R$ 2.64 min (Method A).

Stage 170.1.3

6-Bromo-1,4-dihydro-pyrido[2,3-d][1,3]oxazin-2-one

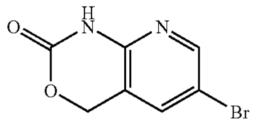 [SMILES: O=C1Nc2ncc(Br)cc2CO1]

A mixture of 2-amino-5-bromo-3-hydroxymethylpyridine hydrobromide (Apollo, Cheshire, UK, 0.528 mmol) in dichloromethane (1.25 ml) and triethylamine (1.162 mmol) was cooled with an ice-bath. Was added to the RM trichloromethyl chloroformate (0.317 mmol) in dichloromethane and the RM was stirred for 30 min at 0° C. and 1 h at rt. The RM was diluted with dichloromethane, washed with saturated aqueous $NaHCO_3$, dried over $Na_2SO_4$, filtered and evaporated. The residue was absorbed on silica gel and separated by flash chromatography (heptane/EtOAc 0% to 80%). The fractions containing product were evaporated together to give the title compound as a yellow solid. (HPLC: $t_R$ 2.16 min (Method A); M+H=229, 231 MS-ES)

Example 171

8-(5-Hydroxymethyl-6-methylamino-pyridin-3-yl)-1-(1-isopropyl-3-methyl-1H-pyrazol-4-yl)-3-methyl-1,3-dihydro-imidazo[4,5-c]quinolin-2-one

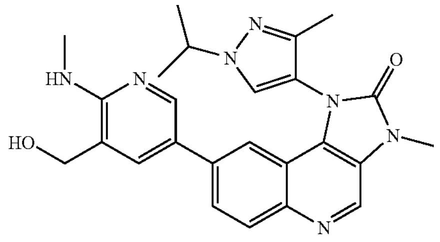 [SMILES: CNc1ncc(-c2ccc3ncc4c(c3c2)n(-c2cn(C(C)C)nc2C)c(=O)n4C)cc1CO]

A solution of 1-(1-isopropyl-3-methyl-1H-pyrazol-4-yl)-3-methyl-8-(1-methyl-2-oxo-1,4-dihydro-2H-pyrido[2,3-d][1,3]oxazin-6-yl)-1,3-dihydro-imidazo[4,5-c]quinolin-2-one (Example 170, 0.04 mmol) in dioxane (0.32 ml) and 1 M aqueous LiOH (0.08 ml) was stirred for 1.5 h at rt. The reaction mixture was diluted with EtOAc and quenched with 2 M aqueous HCl (0.12 ml) and water. Then was added saturated aqueous $NaHCO_3$ and the aqueous layer was extracted with EtOAc (2×). The combined organic layers were dried over $Na_2SO_4$, filtered, evaporated and dried under vacuum to give the title compound as an off-white solid. (HPLC: $t_R$ 2.09 min (Method A); M+H=458 MS-ES; $^1$H-NMR ($d_6$-DMSO, 400 MHz) 8.90 (s, 1H), 8.20 (s, 1H), 8.09-8.01 (m, 2H), 7.83-7.79 (m, 1H), 7.52-7.49 (m, 1H), 7.45-7.42 (m, 1H), 6.10 (q, br, 1H), 5.21 (t, 1H), 4.56 (qt, 1H), 4.38 (d, 2H), 3.57 (s, 3H), 2.86 (d, 3H), 1.95 (s, 3H), 1.49-1.45 (m, 6H))

Example 172

8-(5-Cyclobutylamino-pyridin-3-yl)-1-(1,3-dimethyl-1H-pyrazol-4-yl)-3-methyl-1,3-dihydro-imidazo[4,5-c]quinolin-2-one

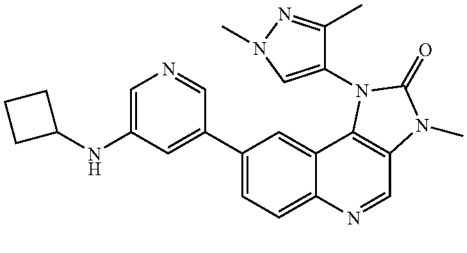 [SMILES: Cc1nn(C)cc1-n1c(=O)n(C)c2cnc3ccc(-c4cncc(NC5CCC5)c4)cc3c21]

The title compound was synthesized in a similar manner as described for Example 1.1 using 8-bromo-1-(1,3-dimethyl-1H-pyrazol-4-yl)-3-methyl-1,3-dihydro-imidazo[4,5-c]quinolin-2-one (Intermediate A) and cyclobutyl-[5-(4,4,5,5-tetramethyl-[1,3,2]dioxaborolan-2-yl)-pyridin-3-yl]-amine (Stage 172.1.1) to give the title compound as a white solid. (HPLC: $t_R$ 2.29 min (Method A); M+H=440 MS-ES; $^1$H-NMR ($d_6$-DMSO, 400 MHz) 8.97 (s, 1H), 8.13-8.07 (m, 2H), 7.93-7.84 (m, 3H), 7.58-7.55 (m, 1H), 6.80-6.76 (m, 1H), 6.34 (d, 1H), 3.94-3.85 (m, 1H), 3.90 (s, 3H), 3.58 (s, 3H), 2.44-2.34 (m, 2H), 1.96 (s, 3H), 1.93-1.73 (m, 4H))

Stage 172.1.1 Cyclobutyl-[5-(4,4,5,5-tetramethyl-[1,3,2]dioxaborolan-2-yl)-pyridin-3-yl]-amine

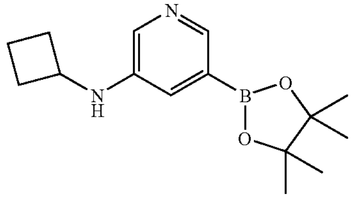 [SMILES: CC1(C)OB(c2cncc(NC3CCC3)c2)OC1(C)C]

The title compound was synthesized in a similar manner as described for Stage 5.1.1 using (5-bromo-pyridin-3-yl)-cyclobutyl-amine (stage 172.1.2, 2.349 mmol) to give the title compound as a crude brown foam. (degrading under the HPLC condition: $t_R$ 2.06 min (Method A); M+H=275 MS-ES).

Stage 172.1.2

(5-Bromo-pyridin-3-yl)-cyclobutyl-amine

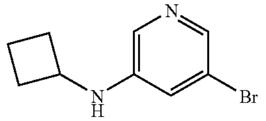 [SMILES: Brc1cncc(NC2CCC2)c1]

A mixture of 3-bromo-5-fluoropyridine (Frontier Scientific, Logan, USA, 5.63 mmol) and cyclobutylamine (Fluka, Buchs, Switzerland, 12.38 mmol) in NMP (8 ml) was heated under microwave irradiation for 1 h at 190° C. and for 5.5 h at 200° C. The reaction mixture was diluted with EtOAc and washed with saturated aqueous $NaHCO_3$, with brine (3×), dried over $Na_2SO_4$, filtered, evaporated and dried under vacuum to give the title compound as an off-white solid. (HPLC: $t_R$ 2.31 min (Method A); M+H=227, 229 MS-ES)

Example 173

1-(1,3-Dimethyl-1H-pyrazol-4-yl)-8-[5-(isopropyl-methyl-amino)-pyridin-3-yl]-3-methyl-1,3-dihydro-imidazo[4,5-c]quinolin-2-one

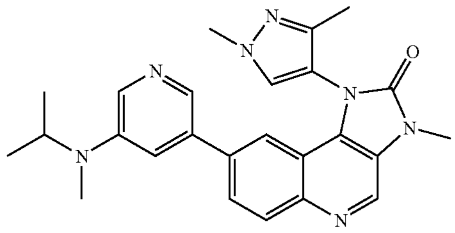 [SMILES: Cc1nn(C)cc1-n1c(=O)n(C)c2cnc3ccc(-c4cncc(N(C)C(C)C)c4)cc3c21]

The title compound was synthesized in a similar manner as described for Example 172 using N-isopropylmethylamine (Fluka, Buchs, Switzerland, 7.61 mmol) as replacement of the cyclobutylamine to give the title compound as a white solid. (HPLC: $t_R$ 2.29 min (Method A); M+H=442 MS-ES; $^1$H-NMR ($d_6$-DMSO, 400 MHz) 8.98-8.97 (m, 1H), 8.18-8.15 (m, 1H), 8.13-8.08 (m, 2H), 8.03-8.00 (m, 1H), 7.98-7.93 (m, 1H), 7.61-7.58 (m, 1H), 7.05-7.03 (m, 1H), 4.20 (qt, 1H), 3.87 (s, 3H), 3.58 (s, 3H), 2.77 (s, 3H), 1.97 (s, 3H), 1.17 (d, 3H), 1.16 (d, 3H))

Example 174

8-[5-(Cyclobutyl-methyl-amino)-pyridin-3-yl]-1-(1,3-dimethyl-1H-pyrazol-4-yl)-3-methyl-1,3-dihydro-imidazo[4,5-c]quinolin-2-one

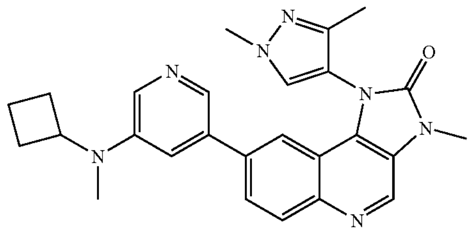 [SMILES: Cc1nn(C)cc1-n1c(=O)n(C)c2cnc3ccc(-c4cncc(N(C)C5CCC5)c4)cc3c21]

The title compound was synthesized in a similar manner as described for Example 1.1 using 8-bromo-1-(1,3-dimethyl-1H-pyrazol-4-yl)-3-methyl-1,3-dihydro-imidazo[4,5-c]quinolin-2-one (Intermediate A) and Cyclobutyl-methyl-[5-(4,4,5,5-tetramethyl-[1,3,2]dioxaborolan-2-yl)-pyridin-3-yl]-amine (Stage 174.1.1) to give the title compound as a white solid. (HPLC: $t_R$ 2.39 min (Method A); M+H=454 MS-ES; $^1$H-NMR ($d_6$-DMSO, 400 MHz) 8.97 (s, 1H), 8.15-8.04 (m, 4H), 7.96-7.92 (m, 1H), 7.60-7.57 (m, 11-1), 7.06-7.03 (m, 1H), 4.17 (qt, 1H), 3.88 (s, 3H), 3.58 (s, 3H), 2.89 (s, 3H), 2.28-2.02 (m, 4H), 1.97 (s, 3H), 1.81-1.63 (m, 2H))

Stage 174.1.1 Cyclobutyl-methyl-[5-(4,4,5,5-tetramethyl-[1,3,2]dioxaborolan-2-yl)-pyridin-3-yl]-amine

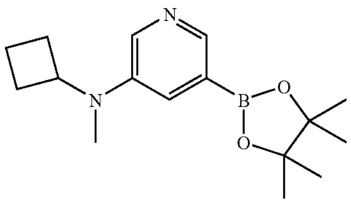 [SMILES: CN(c1cncc(B2OC(C)(C)C(C)(C)O2)c1)C1CCC1]

The title compound was synthesized in a similar manner as described for Stage 5.1.1 using (5-bromo-pyridin-3-yl)-cyclobutyl-methyl-amine (stage 174.1.2, 2.349 mmol) to give the title compound as a crude black sticky oil. (degrading under the HPLC condition: $t_R$ 2.27 min (Method A); M+H=289 MS-ES).

Stage 174.1.2 (5-Bromo-pyridin-3-yl)-cyclobutyl-methyl-amine

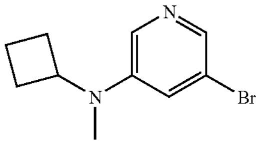

The title compound was synthesized in a similar manner as described for Stage 163.1.2 using (5-bromo-pyridin-3-yl)-cyclobutyl-amine (stage 172.1.2, 0.427 mmol) to give the title compound as a crude brown oil. (HPLC: $t_R$ 2.49 min (Method A); M+H=241, 243 MS-ES).

Example 175.1

1-(1,3-Dimethyl-1H-pyrazol-4-yl)-3-methyl-8-(5-morpholin-4-yl-pyridin-3-yl)-1,3-dihydro-imidazo[4,5-c]quinolin-2-one

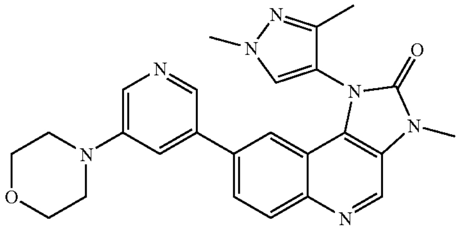 [SMILES: Cc1nn(C)cc1-n1c(=O)n(C)c2cnc3ccc(-c4cncc(N5CCOCC5)c4)cc3c21]

The title compound was synthesized in a similar manner as described for Example 172 using morpholine (Fluka, Buchs, Switzerland, 6.02 mmol) as replacement of the cyclobutylamine to give the title compound as an off-white solid. (HPLC: $t_R$ 2.10 min (Method A); M+H=456 MS-ES; $^1$H-NMR ($d_6$-DMSO, 400 MHz) 8.98 (s, 1H), 8.34-8.31 (m, 1H), 8.20-8.17 (m, 1H), 8.14-8.09 (m, 2H), 8.01-7.96 (m, 1H), 7.60-7.58 (m, 1H), 7.29-7.26 (m, 1H), 3.88 (s, 3H), 3.82-3.77 (m, 4H), 3.58 (s, 3H), 3.27-3.21 (m, 4H), 1.95 (s, 3H))

The following examples were synthesized in a similar manner as described for Example 175.1 using the specified intermediate.

| Example | Intermed. | structure | Name of the example | MS-ES (M + H) | HPLC $t_R$ (min) |
|---|---|---|---|---|---|
| 175.2 | C | 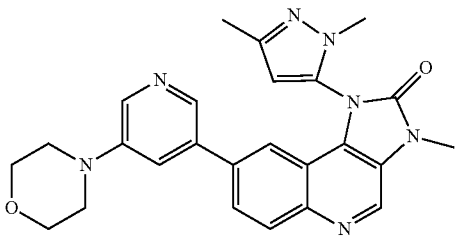 [SMILES: Cc1cc(-n2c(=O)n(C)c3cnc4ccc(-c5cncc(N6CCOCC6)c5)cc4c32)n(C)n1] | 1-(2,5-Dimethyl-2H-pyrazol-3-yl)-3-methyl-8-(5-morpholin-4-yl-pyridin-3-yl)-1,3-dihydro-imidazo[4,5-c] quinolin-2-one | 456 | 2.26 |
| 175.3 | Stage 103.1.1 | 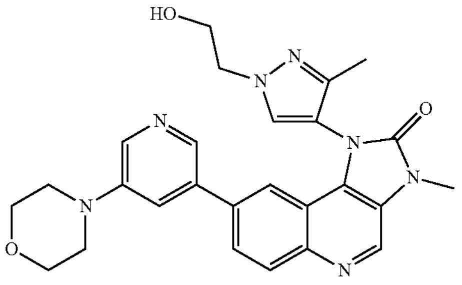 [SMILES: Cc1nn(CCO)cc1-n1c(=O)n(C)c2cnc3ccc(-c4cncc(N5CCOCC5)c4)cc3c21] | 1-[1-(2-Hydroxy-ethyl)-3-methyl-1H-pyrazol-4-yl]-3-methyl-8-(5-morpholin-4-yl-pyridin-3-yl)-1,3-dihydro-imidazo[4,5-c] quinolin-2-one | 486 | 2.05 |

Example 176

1-(1,3-Dimethyl-1H-pyrazol-4-yl)-8-[5-(ethyl-methyl-amino)-pyridin-3-yl]-3-methyl-1,3-dihydro-imidazo[4,5-c]quinolin-2-one

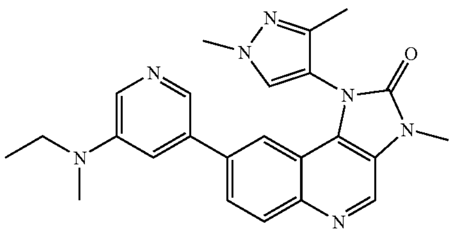 [SMILES: CCN(C)c1cncc(-c2ccc3ncc4c(c3c2)n(-c2cn(C)nc2C)c(=O)n4C)c1]

The title compound was synthesized in a similar manner as described for Example 172 using N-ethylmethylamine (Aldrich, Buchs, Switzerland, 5.75 mmol) as replacement for the cyclobutylamine to give the title compound as a yellowish solid. (HPLC: $t_R$ 2.21 min (Method A); M+H=428 MS-ES; $^1$H-NMR ($d_6$-DMSO, 400 MHz) 8.97 (s, 1H), 8.13-8.07 (m, 3H), 8.02-7.99 (m, 1H), 7.98-7.93 (m, 1H), 7.62-7.58 (m, 1H), 6.99-6.96 (m, 1H), 3.87 (s, 3H), 3.58 (s, 3H), 3.53-3.43 (m, 2H), 2.95 (s, 3H), 1.96 (s, 3H), 1.07 (t, 3H))

Example 177.1

1-(1,3-Dimethyl-1H-pyrazol-4-yl)-8-(5-isopropylamino-pyridin-3-yl)-3-methyl-1,3-dihydro-imidazo [4,5-c]quinolin-2-one

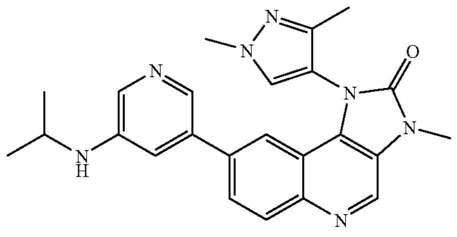 [SMILES: Cc1nn(C)cc1-n1c(=O)n(C)c2cnc3ccc(-c4cncc(NC(C)C)c4)cc3c21]

The title compound was synthesized in a similar manner as described for Example 172 using isopropylamine (Aldrich, Buchs, Switzerland, 6.27 mmol) as replacement of the cyclobutylamine to give the title compound as an off-white solid. (HPLC: $t_R$ 2.21 min (Method A); M+H=428 MS-ES; $^1$H-NMR ($d_6$-DMSO, 400 MHz) 8.97 (s, 1H), 8.13-8.07 (m, 2H), 7.96-7.92 (m, 1H), 7.90-7.84 (m, 2H), 7.59-7.56 (m, 1H), 6.87-6.84 (m, 1H), 5.87 (d, 1H), 3.88 (s, 3H), 3.63 (oc, 1H), 3.58 (s, 3H), 1.95 (s, 3H), 1.22-1.13 (m, 6H))

The following example was synthesized in a similar manner as described for Example 177.1 using the specified intermediate.

| Example | Intermed. | structure | Name of the example | MS-ES (M + H) | HPLC $t_R$ (min) |
|---|---|---|---|---|---|
| 177.2 | N | 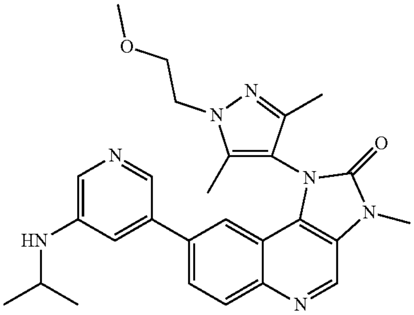 [SMILES: COCCn1nc(C)c(-n2c(=O)n(C)c3cnc4ccc(-c5cncc(NC(C)C)c5)cc4c32)c1C] | 8-(5-Isopropylamino-pyridin-3-yl)-1-[1-(2-methoxy-ethyl)-3,5-dimethyl-1H-pyrazol-4-yl]-3-methyl-1,3-dihydro-imidazo[4,5-c]quinolin-2-one | 486 | 2.33 |

Example 178

8-(5-Dimethylamino-pyridin-3-yl)-1-(1,3-dimethyl-1H-pyrazol-4-yl)-3-methyl-1,3-dihydro-imidazo[4,5-c]quinolin-2-one

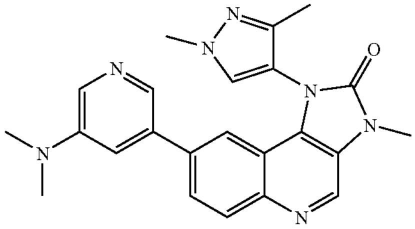

The title compound was synthesized in a similar manner as described for Example 172 using 2 M dimethylamine in THF (Aldrich, Buchs, Switzerland, 6.11 mmol) as replacement of the cyclobutylamine to give the title compound as a yellowish solid. (HPLC: $t_R$ 2.12 min (Method A); M+H=414 MS-ES; $^1$H-NMR ($d_6$-DMSO, 400 MHz) 8.97 (s, 1H), 8.13-8.04 (m, 4H), 7.99-7.94 (m, 1H), 7.62-7.59 (m, 1H), 7.02-6.99 (m, 1H), 3.88 (s, 3H), 3.58 (s, 3H), 3.00 (s, 6H), 1.96 (s, 3H))

Example 179

8-(5-Azetidin-1-yl-pyridin-3-yl)-1-(1,3-dimethyl-1H-pyrazol-4-yl)-3-methyl-1,3-dihydro-imidazo[4,5-c]quinolin-2-one

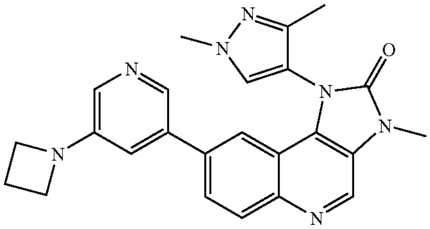 [SMILES: Cc1nn(C)cc1-n1c(=O)n(C)c2cnc3ccc(-c4cncc(N5CCC5)c4)cc3c21]

The title compound was synthesized in a similar manner as described for Example 172 using azetidine (Fluka, Buchs, Switzerland, 8.79 mmol) as replacement of the cyclobutylamine to give the title compound as a yellowish solid. (HPLC: $t_R$ 2.18 min (Method A); M+H=426 MS-ES; $^1$H-NMR ($d_6$-DMSO, 400 MHz) 8.97 (s, 1H), 8.13-8.05 (m, 3H), 7.97-7.92 (m, 1H), 7.81-7.77 (m, 1H), 7.60-7.57 (m, 1H), 6.78-6.74 (m, 1H), 3.98-3.86 (m, 7H), 3.58 (s, 3H), 2.39 (qt, 2H), 1.96 (s, 3H))

Example 180.1

1-(1-Ethyl-3-methyl-1H-pyrazol-4-yl)-3-methyl-8-(5-methylamino-pyridin-3-yl)-1,3-dihydro-imidazo[4,5-c]quinolin-2-one

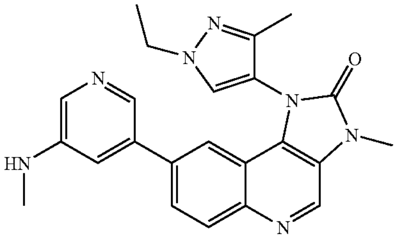 [SMILES: CCn1cc(-n2c(=O)n(C)c3cnc4ccc(-c5cncc(NC)c5)cc4c32)c(C)n1]

The title compound was synthesized in a similar manner as described for Example 172 using 8-bromo-1-(1-ethyl-3-methyl-1H-pyrazol-4-yl)-3-methyl-1,3-dihydro-imidazo[4,5-c]quinolin-2-one (Intermediate F, 0.071 mmol) and 8 M methylamine in ethanol (Fluka, Buchs, Switzerland, 6.48 mmol) as replacement of the cyclobutylamine to give the title compound as an off-white solid. (HPLC: $t_R$ 2.08 min (Method A); M+H=414 MS-ES; $^1$H-NMR ($d_6$-DMSO, 400 MHz) 8.97 (s, 1H), 8.17 (s, 1H), 8.12-8.08 (m, 1H), 7.94-7.92 (m, 1H), 7.91-7.87 (m, 1H), 7.86-7.84 (m, 1H), 7.57-7.55 (s, 1H), 6.89-6.86 (s, 1H), 6.05 (q, br, 1H), 4.16 (q, 2H), 3.58 (s, 3H), 2.75 (d, 3H), 1.97 (s, 3H), 1.39 (t, 3H))

The following example was synthesized in a similar manner as described for Example 180.1 using the specified intermediate.

| Example | Intermed. | structure | Name of the example | MS-ES (M + H) | HPLC $t_R$ (min) |
|---|---|---|---|---|---|
| 180.2 | G | 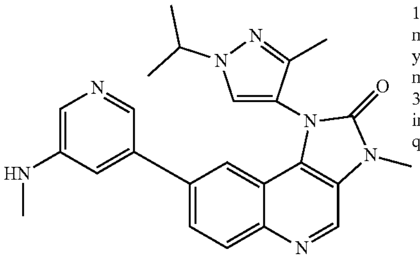 | 1-(1-Isopropyl-3-methyl-1H-pyrazol-4-yl)-3-methyl-8-(5-methylamino-pyridin-3-yl)-1,3-dihydro-imidazo[4,5-c] quinolin-2-one | 428 | 2.15 |

Example 181

1-(1,3-Dimethyl-1H-pyrazol-4-yl)-8-[5-(2-fluoro-ethoxy)-pyridin-3-yl]-3-methyl-1,3-dihydro-imidazo [4,5-c]quinolin-2-one

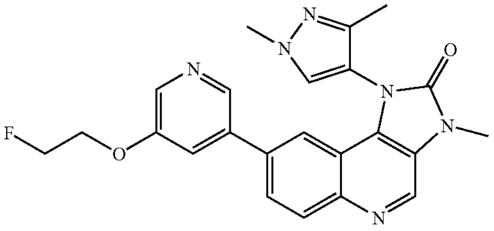 [SMILES: Cc1nn(C)cc1-n1c(=O)n(C)c2cnc3ccc(-c4cncc(OCCF)c4)cc3c21]

The title compound was synthesized in a similar manner as described for Example 1.1 using 8-bromo-1-(1,3-dimethyl-1H-pyrazol-4-yl)-3-methyl-1,3-dihydro-imidazo[4,5-c] quinolin-2-one (Intermediate A) and 3-(2-fluoro-ethoxy)-5-(4,4,5,5-tetramethyl-[1,3,2]dioxaborolan-2-yl)-pyridine (Stage 181.1.1) to give the title compound as a white solid. (HPLC: $t_R$ 2.20 min (Method A); M+H=433 MS-ES; $^1$H-NMR ($d_6$-DMSO, 400 MHz) 8.99 (s, 1H), 8.36-8.32 (m, 2H), 8.17-8.10 (m, 2H), 8.03-7.98 (m, 1H), 7.61-7.57 (m, 1H), 7.47-7.44 (m, 1H), 4.89-4.73 (m, 2H), 4.48-4.36 (m, 2H), 3.90 (s, 3H), 3.58 (s, 3H), 1.96 (s, 3H))

Stage 181.1.1 3-(2-Fluoro-ethoxy)-5-(4,4,5,5-tetramethyl-[1,3,2]dioxaborolan-2-yl)-pyridine

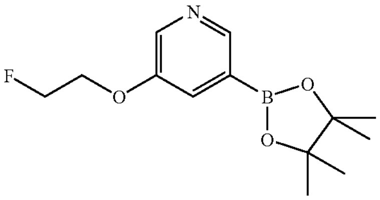 [SMILES: CC1(C)OB(c2cncc(OCCF)c2)OC1(C)C]

The title compound was synthesized in a similar manner as described for Stage 58.1.1 using 2-fluoroethanol (Aldrich, Buchs, Switzerland, 1.672 mmol) as replacement for isopropanol to give the title compound as a crude brown sticky oil. (degrading under HPLC condition: $t_R$ 2.10 min (Method A); M+H=268 MS-ES).

Example 182

1-(1,3-Dimethyl-1H-pyrazol-4-yl)-8-[5-(2-fluoro-1-fluoromethyl-ethoxy)-pyridin-3-yl]-3-methyl-1,3-dihydro-imidazo[4,5-c]quinolin-2-one

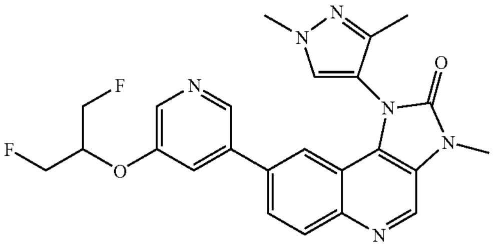 [SMILES: Cc1nn(C)cc1-n1c(=O)n(C)c2cnc3ccc(-c4cncc(OC(CF)CF)c4)cc3c21]

The title compound was synthesized in a similar manner as described for Example 1.1 using 8-bromo-1-(1,3-dimethyl-1H-pyrazol-4-yl)-3-methyl-1,3-dihydro-imidazo[4,5-c] quinolin-2-one (Intermediate A) and 3-(2-fluoro-1-fluoromethyl-ethoxy)-5-(4,4,5,5-tetramethyl-[1,3,2]dioxaborolan-2-yl)-pyridine (Stage 182.1.1) to give the title compound as a white solid. (HPLC: $t_R$ 2.31 min (Method A); M+H=465 MS-ES; $^1$H-NMR ($d_6$-DMSO, 400 MHz) 8.99 (s, 1H), 8.40-8.37 (m, 1H), 8.36-8.33 (m, 1H), 8.16-8.10 (m, 2H), 8.02-7.97 (m, 1H), 7.59-7.54 (m, 2H), 5.24-5.08 (m, 1H), 4.91-4.65 (m, 4H), 3.90 (s, 3H), 3.58 (s, 3H), 1.96 (s, 3H))

Stage 182.1.1 3-(2-Fluoro-1-fluoromethyl-ethoxy)-5-(4,4,5,5-tetramethyl-[1,3,2]dioxaborolan-2-yl)-pyridine

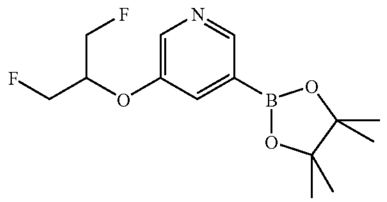 [SMILES: CC1(C)OB(c2cncc(OC(CF)CF)c2)OC1(C)C]

The title compound was synthesized in a similar manner as described for Stage 58.1.1 using 1,3-difluoro-2-propanol (Aldrich, Buchs, Switzerland, 1.672 mmol) as replacement for isopropanol to give the title compound as a crude black oil. (degrading under HPLC condition: $t_R$ 2.00 min (Method A); M+H=300 MS-ES).

Example 183

8-(5-Difluoromethoxy-pyridin-3-yl)-1-(1,3-dimethyl-1H-pyrazol-4-yl)-3-methyl-1,3-dihydro-imidazo[4,5-c]quinolin-2-one

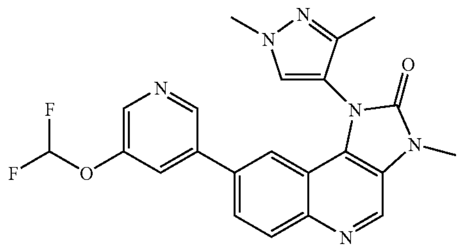 [SMILES: Cc1nn(C)cc1-n1c(=O)n(C)c2cnc3ccc(-c4cncc(OC(F)F)c4)cc3c21]

The title compound was synthesized in a similar manner as described for Example 1.1 using 8-bromo-1-(1,3-dimethyl-1H-pyrazol-4-yl)-3-methyl-1,3-dihydro-imidazo[4,5-c]quinolin-2-one (Intermediate A) and 3-difluoromethoxy-5-(4,4,5,5-tetramethyl-[1,3,2]dioxaborolan-2-yl)-pyridine (Stage 183.1.1) to give the title compound as a white foam. (HPLC: $t_R$ 2.48 min (Method A); M+H=437 MS-ES; $^1$H-NMR ($d_6$-DMSO, 400 MHz) 9.01 (s, 1H), 8.61-8.59 (m, 1H), 8.52-8.50 (m, 1H), 8.17-8.13 (m, 2H), 8.02-7.98 (m, 1H), 7.74-7.71 (m, 1H), 7.61-7.59 (m, 1H), 7.39 (t, 1H), 3.90 (s, 3H), 3.59 (s, 3H), 1.95 (s, 3H))

Stage 183.1.1 3-Difluoromethoxy-5-(4,4,5,5-tetramethyl-[1,3,2]dioxaborolan-2-yl)-pyridine

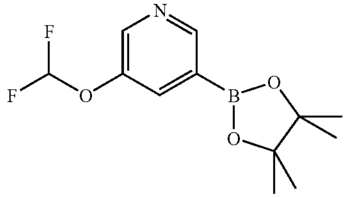 [SMILES: CC1(C)OB(c2cncc(OC(F)F)c2)OC1(C)C]

The title compound was synthesized in a similar manner as described for Stage 5.1.1 using 3-bromo-5-difluoromethoxy-pyridine (stage 183.1.2, 0.192 mmol) to give the title compound as a crude brown oil. (degrading under the HPLC condition: $t_R$ 2.27 min (Method A); M+H=227 MS-ES).

Stage 183.1.2 3-Bromo-5-difluoromethoxy-pyridine

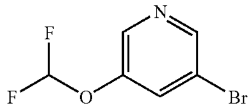

A mixture of 3-bromo-5-hydroxypyridine (Aldrich, Buchs, Switzerland, 1.394 mmol), sodium chlorodifluoroacetate (Aldrich, Buchs, Switzerland, 1.672 mmol) and potassium carbonate (2.79 mmol) in acetonitrile (10 ml) was refluxed for 4 h 45 min. The reaction was cooled and diluted with dichloromethane, washed with saturated aqueous $NaHCO_3$, with brine, dried over $Na_2SO_4$, filtered and evaporated. The residue was taken in DMA and purified by preparative HPLC. The fractions containing product were basified with $NaHCO_3$, concentrated and extracted with dichloromethane (2×). The combined organic layers were washed with brine, dried over $Na_2SO_4$, filtered, evaporated to give the title compound as a brown oil. (HPLC: $t_R$ 2.91 min (Method A); M+H=224, 226 MS-ES).

Example 184

1-(1,3-Dimethyl-1H-pyrazol-4-yl)-8-(5-methoxy-6-methyl-pyridin-3-yl)-3-methyl-1,3-dihydro-imidazo[4,5-c]quinolin-2-one

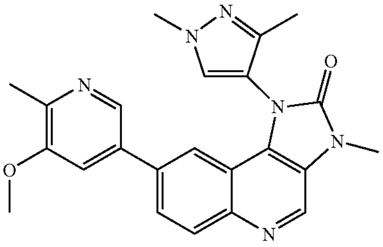

The title compound was synthesized in a similar manner as described for Example 84 using methanol (Fluka, Buchs, Switzerland) as replacement for the isopropanol to give the title compound as a white solid. (HPLC: $t_R$ 2.10 min (Method A); M+H=415 MS-ES; $^1$H-NMR ($d_6$-DMSO, 400 MHz) 8.98 (s, 1H), 8.20-8.17 (m, 1H), 8.14-8.10 (m, 2H), 8.03-7.98 (m, 1H), 7.62-7.59 (m, 1H), 7.32-7.29 (m, 1H), 3.92 (s, 3H), 3.89 (s, 3H), 3.59 (s, 3H), 2.39 (s, 3H), 1.98 (s, 3H))

Example 185.1

1-(1,3-Dimethyl-1H-pyrazol-4-yl)-8-(5-hydroxy-6-methyl-pyridin-3-yl)-3-methyl-1,3-dihydro-imidazo[4,5-c]quinolin-2-one

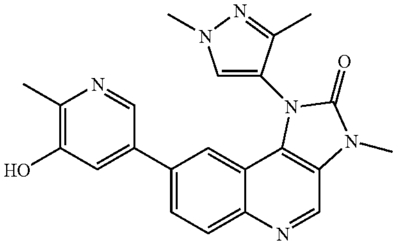

The title compound was synthesized in a similar manner as described for Example 84 using dioxane/water 1:1 as replacement for the isopropanol to give the title compound as a white solid. (HPLC: $t_R$ 1.98 min (Method A); M+H=401 MS-ES; MS-ES; $^1$H-NMR ($d_6$-DMSO, 400 MHz) 9.97 (s, 1H), 8.97 (s, 1H), 8.14-8.09 (m, 2H), 7.99-7.96 (m, 1H), 7.82-7.77 (m, 1H), 7.55-7.52 (m, 1H), 7.21-7.18 (m, 1H), 3.92 (s, 3H), 3.58 (s, 3H), 2.36 (s, 3H), 1.96 (s, 3H))

The following example was synthesized in a similar manner as described for Example 185.1 using the specified intermediate.

| Example | Intermed. | structure | Name of the example | MS-ES (M + H) | HPLC $t_R$ (min) |
|---|---|---|---|---|---|
| 185.2 | C | 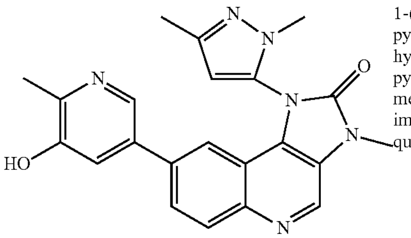 | 1-(2,5-Dimethyl-2H-pyrazol-3-yl)-8-(5-hydroxy-6-methyl-pyridin-3-yl)-3-methyl-1,3-dihydro-imidazo[4,5-c]quinolin-2-one | 401 | 2.14 |

Example 186

1-(1,3-Dimethyl-1H-pyrazol-4-yl)-8-(6-ethyl-5-iso-propoxy-pyridin-3-yl)-3-methyl-1,3-dihydro-imidazo[4,5-c]quinolin-2-one

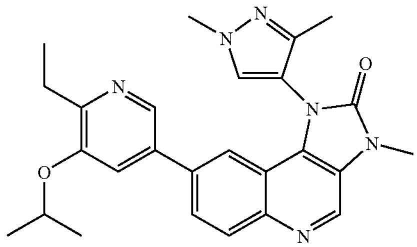

The title compound was synthesized in a similar manner as described for Example 84 using diethyl methylmalonate (Fluka, Buchs, Switzerland) as replacement for the diethyl malonate to give the title compound as a white solid. (HPLC: $t_R$ 2.44 min (Method A); M+H=467 MS-ES; $^1$H-NMR ($d_6$-DMSO, 400 MHz) 8.98 (s, 1H), 8.23-8.20 (m, 1H), 8.13-8.09 (m, 2H), 8.01-7.96 (m, 1H), 7.61-7.58 (m, 1H), 7.31-7.28 (m, 1H), 4.75 (hp, 1H), 3.89 (s, 3H), 3.58 (s, 3H), 2.75 (q, 2H), 1.98 (s, 3H), 1.37-1.33 (m, 6H), 1.19 (t, 3H))

Example 187

1-(1,3-Dimethyl-1H-pyrazol-4-yl)-8-(5-ethoxy-6-ethyl-pyridin-3-yl)-3-methyl-1,3-dihydro-imidazo[4,5-c]quinolin-2-one

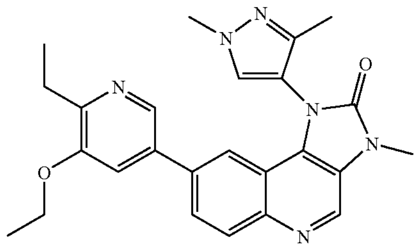 [SMILES: CCOc1cc(-c2ccc3ncc4c(c3c2)n(-c2cn(C)nc2C)c(=O)n4C)cnc1CC]

The title compound was synthesized in a similar manner as described for Example 186 using ethanol as replacement for isopropanol to give the title compound as a white solid. (HPLC: $t_R$ 2.32 min (Method A); M+H=443 MS-ES; $^1$H-NMR ($d_6$-DMSO, 400 MHz) 8.98 (s, 1H), 8.25-8.22 (m, 1H), 8.14-8.09 (m, 2H), 8.02-7.98 (m, 1H), 7.62-7.59 (m, 1H), 7.30-7.27 (m, 1H), 4.24-4.10 (m, 2H), 3.89 (s, 3H), 3.58 (s, 3H), 2.77 (q, 2H), 1.97 (s, 3H), 1.43 (t, 3H), 1.20 (t, 3H))

Example 188

1-(1,3-Dimethyl-1H-pyrazol-4-yl)-8-(6-ethyl-5-hydroxy-pyridin-3-yl)-3-methyl-1,3-dihydro-imidazo[4,5-c]quinolin-2-one

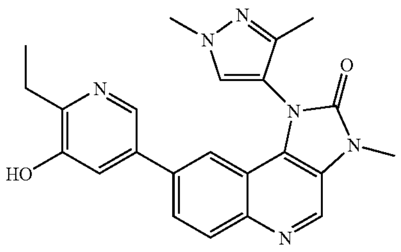 [SMILES: CCc1ncc(-c2ccc3ncc4c(c3c2)n(-c2cn(C)nc2C)c(=O)n4C)cc1O]

The title compound was synthesized in a similar manner as described for Example 186 using dioxane/water 1:1 as replacement for isopropanol to give the title compound as an off-white solid. (HPLC: $t_R$ 2.07 min (Method A); M+H=415 MS-ES; $^1$H-NMR ($d_6$-DMSO, 400 MHz) 9.98 (s, br, 1H), 8.97 (s, 1H), 8.14-8.08 (m, 2H), 8.03-7.99 (m, 1H), 7.82-7.76 (m, 1H), 7.55-7.52 (m, 1H), 7.20-7.17 (m, 1H), 3.91 (s, 3H), 3.58 (s, 3H), 2.73 (q, 2H), 1.96 (s, 3H), 1.18 (t, 3H))

Example 189

1-(1,3-Dimethyl-1H-pyrazol-4-yl)-8-[5-(2-fluoro-1-fluoromethyl-ethoxy)-6-methyl-pyridin-3-yl]-3-methyl-1,3-dihydro-imidazo[4,5-c]quinolin-2-one

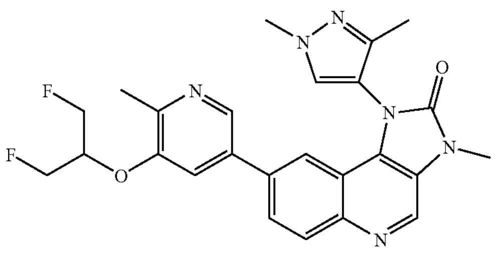 [SMILES: Cc1ncc(-c2ccc3ncc4c(c3c2)n(-c2cn(C)nc2C)c(=O)n4C)cc1OC(CF)CF]

The title compound was synthesized in a similar manner as described for Example 1.1 using 8-bromo-1-(1,3-dimethyl-1H-pyrazol-4-yl)-3-methyl-1,3-dihydro-imidazo[4,5-c]quinolin-2-one (Intermediate A) and 3-(2-fluoro-1-fluoromethyl-ethoxy)-2-methyl-5-(4,4,5,5-tetramethyl-[1,3,2]dioxaborolan-2-yl)-pyridine (Stage 189.1.1) to give the title compound as a white foam. (HPLC: $t_R$ 2.26 min (Method A); M+H=479 MS-ES; $^1$H-NMR ($d_6$-DMSO, 400 MHz) 8.98 (s, 1H), 8.19-8.17 (m, 1H), 8.14-8.10 (m, 2H), 8.00-7.95 (m, 1H), 7.58-7.52 (m, 2H), 5.16-5.01 (m, 1H), 4.92-4.66 (m, 4H), 3.89 (s, 3H), 3.58 (s, 3H), 2.41 (s, 3H), 1.97 (s, 3H))

Stage 189.1.1 3-(2-Fluoro-1-fluoromethyl-ethoxy)-2-methyl-5-(4,4,5,5-tetramethyl-[1,3,2]dioxaborolan-2-yl)-pyridine

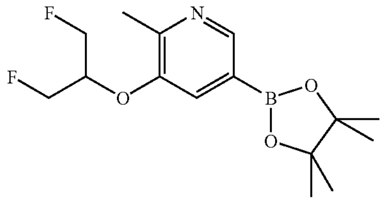 [SMILES: Cc1ncc(B2OC(C)(C)C(C)(C)O2)cc1OC(CF)CF]

The title compound was synthesized in a similar manner as described for Stage 182.1.1 using 5-bromo-2-methyl-pyridin-3-ol (stage 189.1.2) as replacement for 3-bromo-5-hydroxypyridine to give the title compound as a crude black oil. (degrading under the HPLC condition: $t_R$ 2.06 min (Method A); M+H=314 MS-ES).

Stage 189.1.2 5-Bromo-2-methyl-pyridin-3-ol

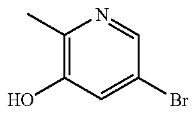

The title compound was synthesized in a similar manner as described for Stage 84.1.2 using dioxane/water 1:1 as replacement for isopropanol to give the title compound as an orange solid. (HPLC: $t_R$ 1.41 min (Method A); M+H=188, 190 MS-ES).

Example 190

1-(1,3-Dimethyl-1H-pyrazol-4-yl)-8-(6-hydroxymethyl-5-isopropoxy-pyridin-3-yl)-3-methyl-1,3-dihydro-imidazo[4,5-c]quinolin-2-one

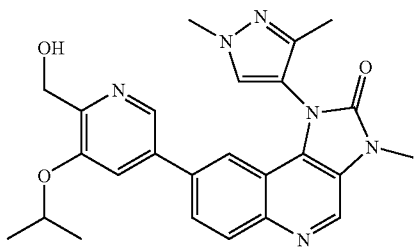 [SMILES: Cc1nn(C)cc1-n1c(=O)n(C)c2cnc3ccc(-c4cnc(CO)c(OC(C)C)c4)cc3c21]

The title compound was synthesized in a similar manner as described for Example 1.1 using 8-bromo-1-(1,3-dimethyl-1H-pyrazol-4-yl)-3-methyl-1,3-dihydro-imidazo[4,5-c]quinolin-2-one (Intermediate A) and [3-isopropoxy-5-(4,4,5,5-tetramethyl-[1,3,2]dioxaborolan-2-yl)-pyridin-2-yl]-methanol (Stage 190.1.1) to give the title compound as a white solid. (HPLC: $t_R$ 2.19 min (Method A); M+H=459 MS-ES; $^1$H-NMR ($d_6$-DMSO, 400 MHz) 8.99 (s, 1H), 8.27-

8.23 (m, 1H), 8.15-8.10 (m, 2H), 8.03-7.98 (m, 1H), 7.62-7.59 (m, 1H), 7.40-7.37 (m, 1H), 4.84 (br, 1H), 4.76 (hp, 1H), 4.55 (s, 2H), 3.88 (s, 3H), 3.58 (s, 3H), 1.97 (s, 3H), 1.36-1.31 (m, 6H))

Stage 190.1.1 [3-Isopropoxy-5-(4,4,5,5-tetramethyl-[1,3,2]dioxaborolan-2-yl)-pyridin-2-yl]-methanol

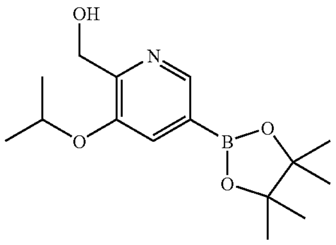 [SMILES: CC(C)Oc1cc(B2OC(C)(C)C(C)(C)O2)cnc1CO]

The title compound was synthesized in a similar manner as described for Stage 5.1.1 using (5-bromo-3-isopropoxy-pyridin-2-yl)-methanol (stage 190.1.2, 0.546 mmol) to give the title compound as a crude black oil. (degrading under the HPLC condition: $t_R$ 2.06 min (Method A)).

Stage 190.1.2 (5-Bromo-3-isopropoxy-pyridin-2-yl)-methanol

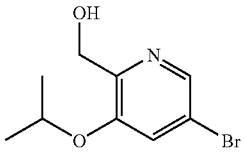

To a solution of 5-bromo-3-isopropoxy-2-methyl-pyridine 1-oxide (Stage 190.1.3, 2.054 mmol) in THF (13 ml) was added trifluoroacetic anhydride (10.27 mmol). The RM was stirred for 4 h at rt. The RM was evaporated to dryness. The residue was treated with saturated aqueous $NaHCO_3$ (20 ml), stirred for 15 h at it and then extracted with EtOAc (2×). The combined organic layers were washed with brine, dried over $Na_2SO_4$, filtered and evaporated. The residue was taken in DMA and purified by preparative HPLC. The fractions containing the product are basified with $NaHCO_3$, concentrated and extracted with dichloromethane (2×). The combined organic layers were washed with brine, dried over $Na_2SO_4$, filtered and evaporated to give a yellowish slowly crystallizing solid. (HPLC: $t_R$ 2.21 min (Method A); M+H=246, 248 MS-ES).

Stage 190.1.3 5-Bromo-3-isopropoxy-2-methyl-pyridine 1-oxide

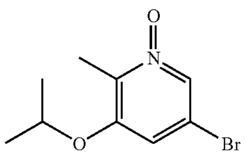

The title compound was synthesized in a similar manner as described for Stage 155.1.4 using 5-bromo-3-isopropoxy-2-methyl-pyridine (Stage 84.1.2, 2.108 mmol) as replacement for (5-bromo-2-methyl-pyridin-3-yl)-ethyl-carbamic acid tert-butyl ester to give the title compound as a slowly crystallizing orange solid. (HPLC: $t_R$ 2.75 min (Method A); M+H=246, 248 MS-ES).

Example 191.1

1-(1,3-Dimethyl-1H-pyrazol-4-yl)-8-(5-isopropoxy-6-methoxymethyl-pyridin-3-yl)-3-methyl-1,3-dihydro-imidazo[4,5-c]quinolin-2-one

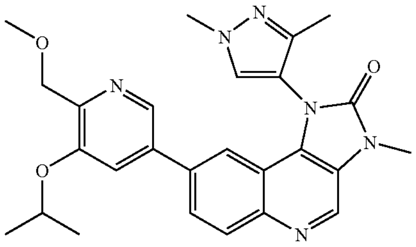

The title compound was synthesized in a similar manner as described for Example 1.1 using 8-bromo-1-(1,3-dimethyl-1H-pyrazol-4-yl)-3-methyl-1,3-dihydro-imidazo[4,5-c]quinolin-2-one (Intermediate A) and 3-isopropoxy-2-methoxymethyl-5-(4,4,5,5-tetramethyl-[1,3,2]dioxaborolan-2-yl)-pyridine (Stage 191.1.1) to give the title compound as a white foam. (HPLC: $t_R$ 2.41 min (Method A); M+H=473 MS-ES; $^1$H-NMR ($d_6$-DMSO, 400 MHz) 8.99 (s, 1H), 8.27-8.25 (m, 1H), 8.15-8.10 (m, 2H), 8.03-7.98 (m, 1H), 7.62-7.60 (m, 1H), 7.42-7.40 (m, 1H), 4.77 (hp, 1H), 4.47 (s, 2H), 3.88 (s, 3H), 3.58 (s, 3H), 3.31 (s, 3H), 1.97 (s, 3H), 1.37-1.32 (m, 6H))

Stage 191.1.1 3-Isopropoxy-2-methoxymethyl-5-(4,4,5,5-tetramethyl-[1,3,2]dioxaborolan-2-yl)-pyridine

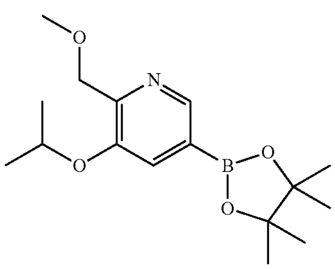 [SMILES: COCc1ncc(B2OC(C)(C)C(C)(C)O2)cc1OC(C)C]

The title compound was synthesized in a similar manner as described for Stage 5.1.1 using 5-bromo-3-isopropoxy-2-methoxymethyl-pyridine (stage 191.1.2, 0.142 mmol) to give the title compound as a crude brown oil. (degrading under the HPLC condition: $t_R$ 2.40 min (Method A); M+H=308 MS-ES).

Stage 191.1.2

5-Bromo-3-isopropoxy-2-methoxymethyl-pyridine

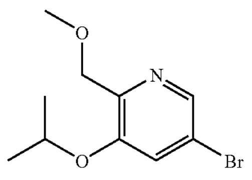

To a solution of (5-bromo-3-isopropoxy-pyridin-2-yl)-methanol (stage 190.1.2, 0.61 mmol) in DMF (3 ml) was added 55% NaH in oil (0.688 mmol) was added. The RM was stirred for 30 min at rt then was added iodomethane (0.684 mmol). The RM was stirred for 2.5 h at rt then was quenched with MeOH and purified by preparative HPLC. The fractions containing product were combined, basified with $NaHCO_3$, concentrated and extracted with dichloromethane (2×). The combined organic layers were washed with brine, dried over $Na_2SO_4$, filtered and evaporated to dryness to give the title compound as a yellow oil. (HPLC: $t_R$ 2.83 min (Method A); M+H=260, 262 MS-ES).

The following example was synthesized in a similar manner as described for Example 191.1 using the specified intermediate.

| Example | Intermed. | structure | Name of the example | MS-ES (M + H) | HPLC $t_R$ (min) |
|---|---|---|---|---|---|
| 191.2 | F | 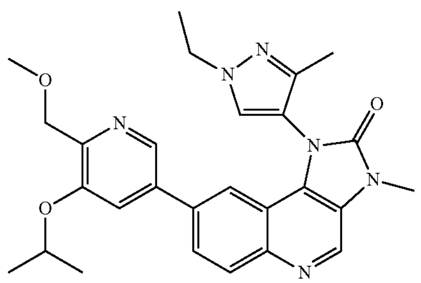 | 1-(1-Ethyl-3-methyl-1H-pyrazol-4-yl)-8-(5-isopropoxy-6-methoxymethyl-pyridin-3-yl)-3-methyl-1,3-dihydro-imidazo[4,5-c]quinolin-2-one | 487 | 2.49 |

Example 192

1-(1,3-Dimethyl-1H-pyrazol-4-yl)-8-[5-(2-fluoro-1-fluoromethyl-ethoxy)-6-hydroxymethyl-pyridin-3-yl]-3-methyl-1,3-dihydro-imidazo[4,5-c]quinolin-2-one

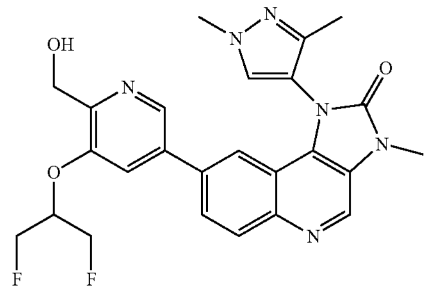 [SMILES: Cc1nn(C)cc1-n1c(=O)n(C)c2cnc3ccc(-c4cnc(CO)c(OC(CF)CF)c4)cc3c21]

The title compound was synthesized in a similar manner as described for Example 190 using 5-bromo-3-(2-fluoro-1-fluoromethyl-ethoxy)-2-methyl-pyridine (Stage 192.1.1) to give the title compound as a white solid. (HPLC: $t_R$ 2.15 min (Method A); M+H=495 MS-ES; $^1$H-NMR NMR ($d_6$-DMSO, 400 MHz) 8.99 (s, 1H), 8.29-8.26 (m, 1H), 8.15-8.10 (m, 2H), 8.02-7.98 (m, 1H), 7.63-7.58 (m, 2H), 5.19-5.04 (m, 1H), 4.93 (t, 1H), 4.91-4.66 (m, 4H), 4.60 (d, 2H), 3.89 (s, 3H), 3.58 (s, 3H), 1.97 (s, 3H))

Stage 192.1.1 5-Bromo-3-(2-fluoro-1-fluoromethyl-ethoxy)-2-methyl-pyridine

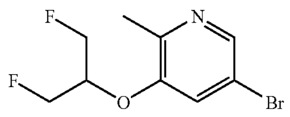

The title compound was synthesized in a similar manner as described for stage 58.1.2 using 5-bromo-2-methyl-pyridin-3-ol (stage 189.1.2, 2.234 mmol) and 1,3-difluoro-2-propanol (Aldrich, Buchs, Switzerland, 2.68 mmol) to give the title compound as a yellow oil. (HPLC: $t_R$ 2.41 min (Method A); M+H=266, 268 MS-ES).

Example 193

1-(1,3-Dimethyl-1H-pyrazol-4-yl)-8-(6-hydroxymethyl-5-methoxy-pyridin-3-yl)-3-methyl-1,3-dihydro-imidazo[4,5-c]quinolin-2-one

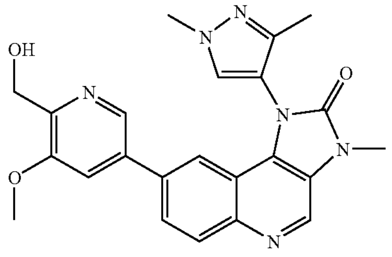 [SMILES: COc1cc(-c2ccc3ncc4c(c3c2)n(-c2cn(C)nc2C)c(=O)n4C)cnc1CO]

The title compound was synthesized in a similar manner as described for Example 190 using methanol as replacement for isopropanol to give the title compound as a white foam. (HPLC: $t_R$ 1.99 min (Method A); M+H=431 MS-ES; $^1$H-NMR ($d_6$-DMSO, 400 MHz) 8.99 (s, 1H), 8.28-8.25 (m, 1H), 8.15-8.11 (m, 2H), 8.05-8.01 (m, 1H), 7.64-7.62 (m, 1H), 7.40-7.37 (m, 1H), 4.90 (t, 1H), 4.56 (d, 2H), 3.92 (s, 3H), 3.89 (s, 3H), 3.58 (s, 3H), 1.98 (s, 3H))

Example 194.1

8-(6-Hydroxymethyl-5-methoxy-pyridin-3-yl)-1-(1-isopropyl-3-methyl-1H-pyrazol-4-yl)-3-methyl-1,3-dihydro-imidazo[4,5-c]quinolin-2-one

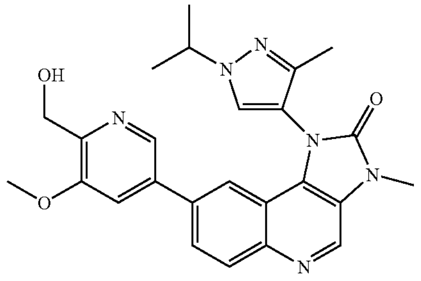

The title compound was synthesized in a similar manner as described for Example 169.1 using acetic acid 3-methoxy-5-(4,4,5,5-tetramethyl-[1,3,2]dioxaborolan-2-yl)-pyridin-2-ylmethyl ester (stage 194.1) to give the title compound as an off-white solid. (HPLC: $t_R$ 2.13 min (Method A); M+H=459 MS-ES; $^1$H-NMR ($d_6$-DMSO, 400 MHz) 8.99 (s, 1H), 8.22-8.11 (m, 3H), 8.03-7.98 (m, 1H), 7.58-7.54 (m, 1H), 7.48-7.45 (m, 1H), 4.96 (t, 1H), 4.54 (d, 2H), 4.52 (hp, 1H), 3.92 (s, 3H), 3.59 (s, 3H), 1.99 (s, 3H), 1.46-1.40 (m, 6H))

Stage 194.1.1 Acetic acid 3-methoxy-5-(4,4,5,5-tetramethyl-[1,3,2]dioxaborolan-2-yl)-pyridin-2-ylmethyl ester

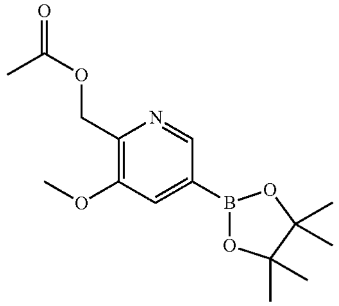 [SMILES: COc1cc(B2OC(C)(C)C(C)(C)O2)cnc1COC(C)=O]

The title compound was synthesized in a similar manner as described for Stage 5.1.1 using acetic acid 5-bromo-3-methoxy-pyridin-2-ylmethyl ester (stage 194.1.2, 0.142 mmol) to give the title compound as a crude brown oil. (degrading under the HPLC condition: $t_R$ 2.54, 3.69 min (Method A); M+H=308 MS-ES).

Stage 194.1.2 Acetic acid 5-bromo-3-methoxy-pyridin-2-ylmethyl ester

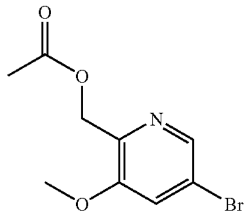

To a mixture of (5-bromo-3-methoxy-pyridin-2-yl)-methanol (Stage 194.1.3, 2.79 mmol) and triethylamine (4.18 mmol) in dichloromethane was added slowly acetyl chloride (3.35 mmol) and the RM was stirred for 1 h at rt. The RM was diluted with dichloromethane, washed with saturated aqueous $NaHCO_3$, with brine, dried over $Na_2SO_4$, filtered and evaporated. The residue was absorbed on silica gel and purified by flash chromatography (heptane/EtOAc 0% to 60%). The fractions containing product were evaporated together to give the title compound as a white solid. (HPLC: $t_R$ 2.72 min (Method A); M+H=260, 262 MS-ES)

Stage 194.1.3 (5-Bromo-3-methoxy-pyridin-2-yl)-methanol

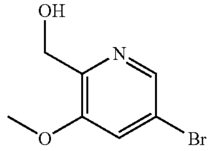

The title compound was synthesized in a similar manner as described for Stage 190.1.2 using methanol as replacement for isopropanol to give the title compound as an off-white solid. (HPLC: $t_R$ 1.76 min (Method A); M+H=218, 220 MS-ES).

The following example was synthesized in a similar manner as described for Example 194.1 using the specified intermediate.

Example 195.1

1-(1,3-Dimethyl-1H-pyrazol-4-yl)-8-(5-methoxy-6-methoxymethyl-pyridin-3-yl)-3-methyl-1,3-dihydro-imidazo[4,5-c]quinolin-2-one

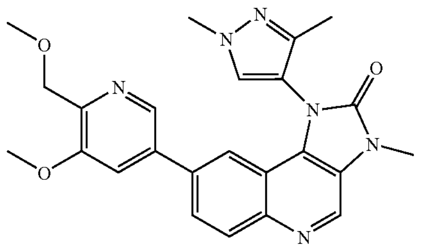

The title compound was synthesized in a similar manner as described for Example 191 using (5-bromo-3-methoxy-pyridin-2-yl)-methanol (Stage 194.1.3) to give the title compound as a white foam. (HPLC: $t_R$ 2.21 min (Method A); M+H=445 MS-ES; $^1$H-NMR ($CDCl_3$, 400 MHz) 8.81 (s, 1H), 8.40-8.38 (m, 1H), 8.31-8.24 (m, 1H), 7.91-7.86 (m, 1H), 7.73-7.70 (m, 1H), 7.66-7.64 (m, 1H), 7.19-7.17 (m, 1H), 4.68 (s, 2H), 3.97 (s, 3H), 3.96 (s, 3H), 3.70 (s, 3H), 3.53 (s, 3H), 2.14 (s, 3H))

The following examples were synthesized in a similar manner as described for Example 195.1 using the specified intermediate.

| Example | Intermed. | structure | Name of the example | MS-ES (M + H) | HPLC $t_R$ (min) |
|---|---|---|---|---|---|
| 194.2 | K | 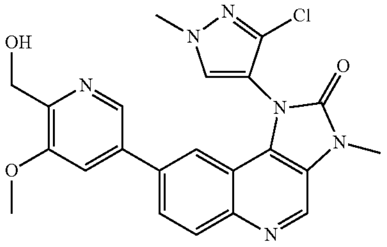 [SMILES: COc1cc(-c2ccc3ncc4c(c3c2)n(-c2cn(C)nc2Cl)c(=O)n4C)cnc1CO] | 1-(3-Chloro-1-methyl-1H-pyrazol-4-yl)-8-(6-hydroxymethyl-5-methoxy-pyridin-3-yl)-3-methyl-1,3-dihydro-imidazo[4,5-c]quinolin-2-one | 451 | 2.18 |

| Example | Intermed. | structure | Name of the example | MS-ES (M + H) | HPLC $t_R$ (min) |
|---|---|---|---|---|---|
| 195.2 | G | 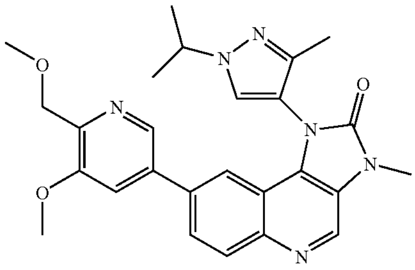 | 1-(1-Isopropyl-3-methyl-1H-pyrazol-4-yl)-8-(5-methoxy-6-methoxymethyl-pyridin-3-yl)-3-methyl-1,3-dihydro-imidazo[4,5-c]quinolin-2-one | 473 | 2.37 |
| 195.3 | F | 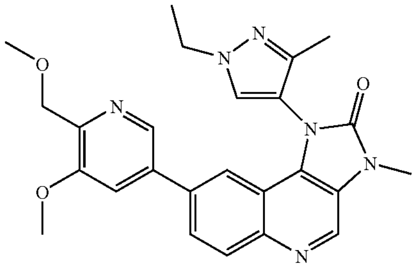 | 1-(1-Ethyl-3-methyl-1H-pyrazol-4-yl)-8-(5-methoxy-6-methoxymethyl-pyridin-3-yl)-3-methyl-1,3-dihydro-imidazo[4,5-c]quinolin-2-one | 459 | 2.28 |
| 195.4 | K | 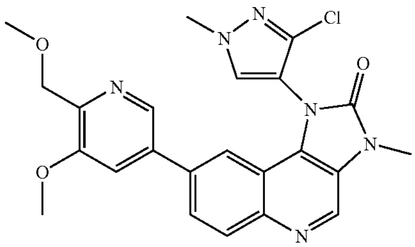 | 1-(3-Chloro-1-methyl-1H-pyrazol-4-yl)-8-(5-methoxy-6-methoxymethyl-pyridin-3-yl)-3-methyl-1,3-dihydro-imidazo[4,5-c]quinolin-2-one | 459 | 2.28 |

Example 196.1

1-(3-Chloro-1-methyl-1H-pyrazol-4-yl)-8-(6-ethoxymethyl-5-methoxy-pyridin-3-yl)-3-methyl-1,3-dihydro-imidazo[4,5-c]quinolin-2-one

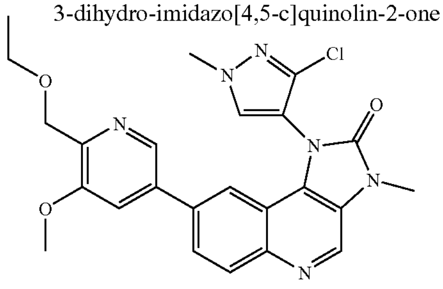

The title compound was synthesized in a similar manner as described for Example 195.1 using iodoethane as replacement for iodomethane to give the title compound as a white foam. (HPLC: $t_R$ 2.51 min (Method A); M+H=479 MS-ES; $^1$H-NMR ($d_6$-DMSO, 400 MHz) 9.02 (s, 1H), 8.38-8.37 (m, 1H), 8.31-8.29 (m, 1H), 8.17-8.14 (m, 1H), 8.07-8.03 (m, 1H), 7.63-7.61 (m, 1H), 7.47-7.45 (m, 1H), 4.53 (s, 2H), 3.96 (s, 3H), 3.93 (s, 3H), 3.60 (s, 3H), 3.52 (q, 2H), 1.11 (t, 3H))

The following example was synthesized in a similar manner as described for Example 196.1 using the specified intermediate.

| Example | Intermed. | structure | Name of the example | MS-ES (M + H) | HPLC $t_R$ (min) |
|---|---|---|---|---|---|
| 196.2 | A | 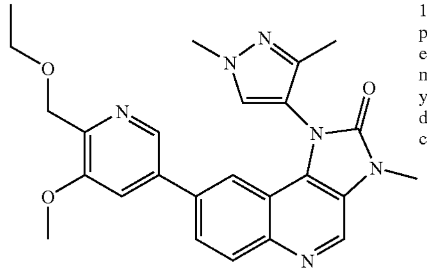 | 1-(1,3-Dimethyl-1H-pyrazol-4-yl)-8-(6-ethoxymethyl-5-methoxy-pyridin-3-yl)-3-methyl-1,3-dihydro-imidazo[4,5-c]quinolin-2-one | 459 | 2.31 |

Example 197.1

1-(1,3-Dimethyl-1H-pyrazol-4-yl)-8-(5-ethoxy-6-methoxymethyl-pyridin-3-yl)-3-methyl-1,3-dihydro-imidazo[4,5-c]quinolin-2-one

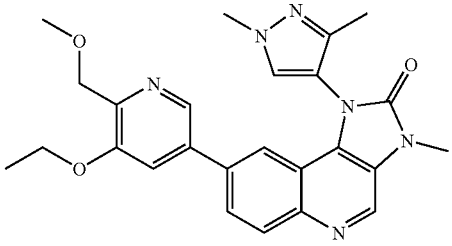 [SMILES: CCOc1cc(-c2ccc3ncc4c(c3c2)n(-c2cn(C)nc2C)c(=O)n4C)cnc1COC]

The title compound was synthesized in a similar manner as described for Example 191 using (5-bromo-3-ethoxy-pyridin-2-yl)-methanol (Stage 197.1.2) to give the title compound as a white foam. (HPLC: $t_R$ 2.33 min (Method A); M+H=459 MS-ES; $^1$H-NMR ($d_6$-DMSO, 400 MHz) 8.99 (s, 1H), 8.28-8.26 (m, 1H), 8.15-8.10 (m, 2H), 8.04-8.00 (m, 1H), 7.64-7.61 (m, 1H), 7.41-7.38 (m, 1H), 4.49 (s, 2H), 4.22-4.14 (m, 2H), 3.89 (s, 3H), 3.58 (s, 3H), 3.31 (s, 3H), 1.97 (s, 31-1), 1.41 (t, 3H))

Stage 197.1.2
(5-Bromo-3-ethoxy-pyridin-2-yl)-methanol

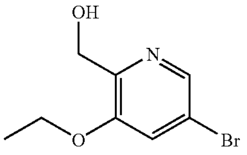

The title compound was synthesized in a similar manner as described for Stage 190.1.2 using ethanol as replacement for isopropanol to give the title compound as an orange solid. (HPLC: $t_R$ 2.03 min (Method A); M+H=232, 234 MS-ES).

The following example was synthesized in a similar manner as described for Example 197.1 using the specified intermediate.

| Example | Intermed. | structure | Name of the example | MS-ES (M + H) | HPLC $t_R$ (min) |
|---|---|---|---|---|---|
| 197.2 | G | 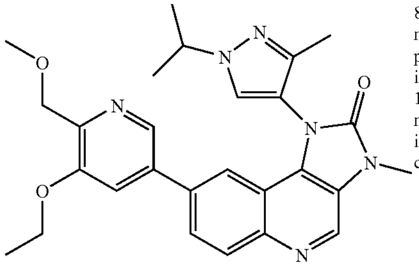 | 8-(5-Ethoxy-6-methoxymethyl-pyridin-3-yl)-1-(1-isopropyl-3-methyl-1H-pyrazol-4-yl)-3-methyl-1,3-dihydro-imidazo[4,5-c]quinolin-2-one | 487 | 2.49 |

Example 198

1-(1,3-Dimethyl-1H-pyrazol-4-yl)-8-(5-ethoxy-6-trideuteromethoxymethyl-pyridin-3-yl)-3-methyl-1,3-dihydro-imidazo[4,5-c]quinolin-2-one

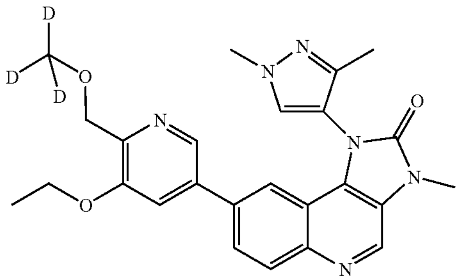 [SMILES: [2H]C([2H])([2H])OCc1ncc(-c2ccc3ncc4c(c3c2)n(-c2cn(C)nc2C)c(=O)n4C)cc1OCC]

The title compound was synthesized in a similar manner as described for Example 197.1 using $d_3$-iodomethane (Aldrich, Buchs, Switzerland) as replacement for iodomethane to give the title compound as an off-white foam. (HPLC: $t_R$ 2.33 min (Method A); M+H=462 MS-ES; $^1$H-NMR ($d_6$-DMSO, 400 MHz) 8.99 (s, 1H), 8.29-8.26 (m, 1H), 8.15-8.11 (m, 2H), 8.04-8.00 (m, 1H), 7.64-7.61 (m, 1H), 7.41-7.38 (m, 1H), 4.49 (s, 2H), 4.22-4.14 (m, 2H), 3.89 (s, 3H), 3.58 (s, 3H), 1.97 (s, 3H), 1.41 (t, 3H))

Example 199

1-(3-Chloro-1-methyl-1H-pyrazol-4-yl)-8-(5-methoxy-6-trideuteromethoxymethyl-pyridin-3-yl)-3-methyl-1,3-dihydro-imidazo[4,5-c]quinolin-2-one

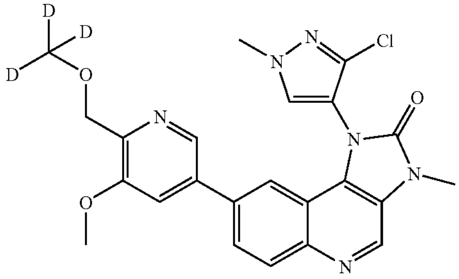 [SMILES: [2H]C([2H])([2H])OCc1ncc(-c2ccc3ncc4c(c3c2)n(-c2cn(C)nc2Cl)c(=O)n4C)cc1OC]

A solution of 1-(3-chloro-1-methyl-1H-pyrazol-4-yl)-8-(6-hydroxymethyl-5-methoxy-pyridin-3-yl)-3-methyl-1,3-dihydro-imidazo[4,5-c]quinolin-2-one (Example 194.2, 0.033 mmol) in DMF (0.4 ml) was treated with 55% NaH in oil (0.037 mmol) and the RM was stirred for 5 min at rt, then was added $d_3$-iodomethane (Aldrich, Buchs, Switzerland, 0.037 mmol) and the RM was stirred for 30 min at rt. The RM was quenched with water, diluted with DMF, filtered and purified by preparative HPLC. The pure fractions were basified with $NaHCO_3$, concentrated and extracted with EtOAc (3×). The combined organic layers were dried over $Na_2SO_4$, filtered, evaporated and dried under vacuum to give the title compound as a foam. (HPLC: $t_R$ 2.40 min (Method A); M+H=468 MS-ES; $^1$H-NMR ($d_6$-DMSO, 400 MHz) 9.02 (s, 1H), 8.37 (s, 1H), 8.32-8.30 (m, 1H), 8.17-8.13 (m, 1H), 8.07-8.03 (m, 1H), 7.63-7.61 (s, 1H), 7.48-7.45 (m, 1H), 4.49 (s, 2H), 3.96 (s, 3H), 3.93 (s, 3H), 3.60 (s, 3H))

Example 200

1-(3-Chloro-1-methyl-1H-pyrazol-4-yl)-8-(5-hydroxymethyl-6-methoxy-pyridin-3-yl)-3-methyl-1,3-dihydro-imidazo[4,5-c]quinolin-2-one

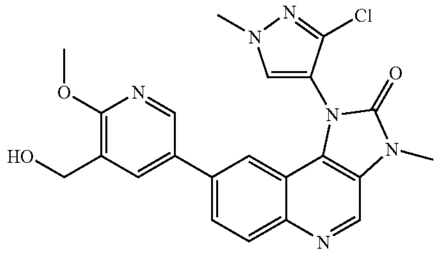 [SMILES: COc1ncc(-c2ccc3ncc4c(c3c2)n(-c2cn(C)nc2Cl)c(=O)n4C)cc1CO]

To a solution of 5-[1-(3-chloro-1-methyl-1H-pyrazol-4-yl)-3-methyl-2-oxo-2,3-dihydro-1H-imidazo[4,5-c]quinolin-8-yl]-2-methoxy-nicotinic acid methyl ester (stage 200.1, 0.176 mmol) in THF (2 ml) cooled with an ice-bath was added dropwise a 1 M solution of $LiAlH_4$ in THF (0.150 mmol). The reaction mixture was stirred for 1 h 15 min at rt, then quenched with water, diluted with EtOAc and filtered over Celite. The filtrate was washed with saturated aqueous $NaHCO_3$, with water, with brine, dried over $Na_2SO_4$, filtered and evaporated. The residue was dissolved in MeOH/TFA and purified by preparative HPLC. The fractions containing pure product were basified with $NaHCO_3$ and concentrated. The precipitate was filtered, washed with water (2×) and dried under vacuum to give the title compound as a white solid. (HPLC: $t_R$ 2.53 min (Method A); M+H=451 MS-ES; $^1$H-NMR ($d_6$-DMSO, 400 MHz) 8.99 (s, 1H), 8.41 (s, 1H), 8.30-8.27 (m, 1H), 8.14-8.10 (m, 1H), 7.98-7.93 (m, 1H), 7.84-7.81 (m, 1H), 7.53-7.50 (m, 1H), 5.32 (t, 1H), 4.51 (d, 2H), 4.01 (s, 3H), 3.92 (s, 3H), 3.59 (s, 3H))

Stage 200.1.1 5-[1-(3-Chloro-1-methyl-1H-pyrazol-4-yl)-3-methyl-2-oxo-2,3-dihydro-1H-imidazo[4,5-c]quinolin-8-yl]-2-methoxy-nicotinic acid methyl ester

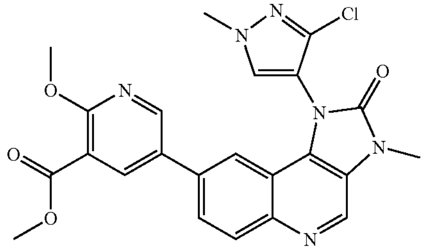 [SMILES: COC(=O)c1cc(-c2ccc3ncc4c(c3c2)n(-c2cn(C)nc2Cl)c(=O)n4C)cnc1OC]

The title compound was synthesized in a similar manner as described for Example 1 using 8-bromo-1-(3-chloro-1-methyl-1H-pyrazol-4-yl)-3-methyl-1,3-dihydro-imidazo[4,5-c]quinolin-2-one (Intermediate K) and 2-methoxy-3-(carbomethoxy)pyridine-5-boronic acid pinacol ester (Combi- Blocks, San Diego, USA) to give the title compound as a white solid. (HPLC: $t_R$ 2.75 min (Method A); M+H=479 MS-ES).

Example 201

1-(3-Chloro-1-methyl-1H-pyrazol-4-yl)-8-(6-methoxy-5-methoxymethyl-pyridin-3-yl)-3-methyl-1,3-dihydro-imidazo[4,5-c]quinolin-2-one

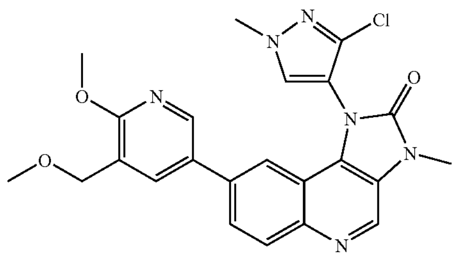

The title compound was synthesized in a similar manner as described for Example 156 using 1-(3-chloro-1-methyl-1H-pyrazol-4-yl)-8-(5-hydroxymethyl-6-methoxy-pyridin-3-yl)-3-methyl-1,3-dihydro-imidazo[4,5-c]quinolin-2-one (Example 200, 0.081 mmol) to give the title compound as a white foam. (HPLC: $t_R$ 2.82 min (Method A); M+H=465 MS-ES; $^1$H-NMR ($d_6$-DMSO, 400 MHz) 8.99 (s, 1H), 8.40 (s, 1H), 8.35-8.32 (m, 1H), 8.14-8.10 (m, 1H), 7.98-7.93 (m, 1H), 7.75-7.72 (m, 1H), 7.50-7.47 (m, 1H), 4.43 (s, 2H), 3.99 (s, 3H), 3.93 (s, 3H), 3.59 (s, 3H), 3.40 (s, 3H))

Example 202

1-(1,3-Dimethyl-1H-pyrazol-4-yl)-8-(6-methoxy-5-methoxymethyl-pyridin-3-yl)-3-methyl-1,3-dihydro-imidazo[4,5-c]quinolin-2-one

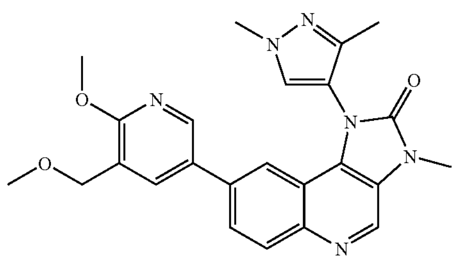

The title compound was synthesized in a similar manner as described for Example 201 using 8-bromo-1-(1,3-dimethyl-1H-pyrazol-4-yl)-3-methyl-1,3-dihydro-imidazo[4,5-c]quinolin-2-one (Intermediate A) to give the title compound as a yellow solid. (HPLC: $t_R$ 2.36 min (Method A); M+H=431 MS-ES; $^1$H-NMR ($d_6$-DMSO, 400 MHz) 8.96 (s, 1H), 8.31-8.28 (m, 1H), 8.13 (s, 1H), 8.11-8.07 (m, 1H), 7.94-7.90 (m, 1H), 7.72-7.69 (m, 1H), 7.54-7.51 (m, 1H), 4.42 (s, 2H), 3.92 (s, 3H), 3.92 (s, 3H), 3.58 (s, 3H), 3.39 (s, 3H), 1.95 (s, 3H))

Example 203

1-(3-Chloro-1-methyl-1H-pyrazol-4-yl)-8-(6-methoxymethyl-pyridin-3-yl)-3-methyl-1,3-dihydro-imidazo[4,5-c]quinolin-2-one

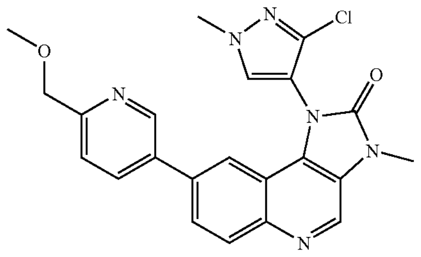

The title compound was synthesized in a similar manner as described for Example 104 using 1-(3-chloro-1-methyl-1H-pyrazol-4-yl)-8-(6-hydroxymethyl-pyridin-3-yl)-3-methyl-1,3-dihydro-imidazo[4,5-c]quinolin-2-one (Example 16.5, 0.085 mmol) to give the title compound as a white solid. (HPLC: $t_R$ 2.31 min (Method A); M+H=435 MS-ES; $^1$H-NMR ($d_6$-DMSO, 400 MHz) 9.02 (s, 1H), 8.67-8.65 (m, 1H), 8.40 (s, 1H), 8.17-8.13 (m, 1H), 8.01-7.91 (m, 2H), 7.56-7.51 (m, 2H), 4.54 (s, 2H), 3.99 (s, 3H), 3.60 (s, 3H), 3.39 (s, 3H))

Example 204

8-(5,6-Dimethoxy-pyridin-3-yl)-1-(1,3-dimethyl-1H-pyrazol-4-yl)-3-methyl-1,3-dihydro-imidazo[4,5-c]quinolin-2-one

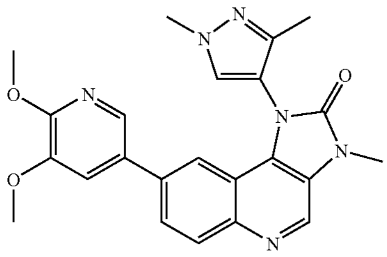 [SMILES: COc1cc(-c2ccc3ncc4c(c3c2)n(-c2cn(C)nc2C)c(=O)n4C)cnc1OC]

The title compound was synthesized in a similar manner as described for Example 93.1 using 2-chloro-3-methoxy-pyridine (Apollo, Cheshire, UK, 7.1 mmol) to give the title compound as a white solid. (HPLC: $t_R$ 2.52 min (Method A); M+H=431 MS-ES; $^1$H-NMR ($d_6$-DMSO, 400 MHz) 8.96 (s, 1H), 8.12-8.07 (m, 2H), 7.99-7.95 (m, 1H), 7.92-7.90 (m, 1H), 7.55-7.53 (m, 1H), 7.25-7.23 (m, 1H), 3.90 (s, 3H), 3.89 (s, 6H), 3.58 (s, 3H), 1.98 (s, 3H))

Example 205

1-[1-(2-Azetidin-1-yl-2-oxo-ethyl)-3-methyl-1H-pyrazol-4-yl]-8-(5-isopropoxy-pyridin-3-yl)-3-methyl-1,3-dihydro-imidazo[4,5-c]quinolin-2-one

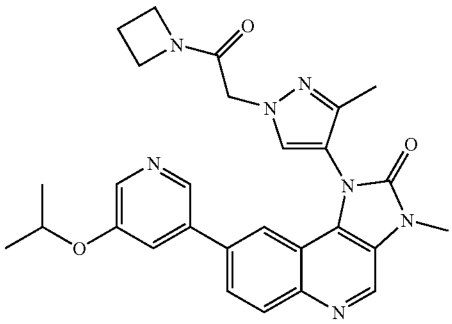 [SMILES: Cc1nn(CC(=O)N2CCC2)cc1-n1c(=O)n(C)c2cnc3ccc(-c4cncc(OC(C)C)c4)cc3c21]

The title compound was synthesized in a similar manner as described for Example 1.1 using 8-bromo-1-(1,3-dimethyl-1H-pyrazol-4-yl)-3-methyl-1,3-dihydro-imidazo[4,5-c]quinolin-2-one (stage 205.1.1, 0.067 mmol) and 3-isopropoxy-5-(4,4,5,5-tetramethyl-[1,3,2]dioxaborolan-2-yl)-pyridine (Stage 58.1.1, 0.102 mmol) to give the title compound as a white foam. (HPLC: $t_R$ 2.35 min (Method A); M+H=512 MS-ES; $^1$H-NMR ($d_6$-DMSO, 400 MHz) 8.99 (s, 1H), 8.34-8.32 (m, 1H), 8.24-8.21 (m, 1H), 8.13-8.09 (m, 2H), 8.01-7.96 (m, 1H), 7.67-7.64 (m, 1H), 7.38-7.35 (m, 1H), 4.91-4.73 (m, 3H), 4.18-4.07 (m, 2H), 3.91-3.78 (m, 2H), 3.58 (s, 3H), 2.22-2.05 (m, 2H), 1.98 (s, 3H), 1.33 (d, 3H), 1.31 (d, 3H))

Stage 205.1.1 1-[1-(2-Azetidin-1-yl-2-oxo-ethyl)-3-methyl-1H-pyrazol-4-yl]-8-bromo-3-methyl-1,3-dihydro-imidazo[4,5-c]quinolin-2-one

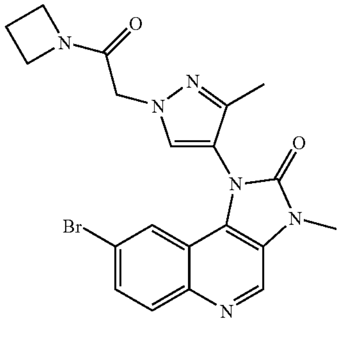 [SMILES: Cc1nn(CC(=O)N2CCC2)cc1-n1c(=O)n(C)c2cnc3ccc(Br)cc3c21]

The title compound was synthesized in a similar manner as described for Stage 134.1 using azetidine (Fluka, Buchs, Switzerland) as replacement for N-methylpiperazine to give the title compound as a white solid. (HPLC: $t_R$ 2.28 min (Method A); M+H=441, 443 MS-ES).

Example 206.1

1-(1,3-Dimethyl-1H-pyrazol-4-yl)-8-(6-ethylamino-5-methoxymethyl-pyridin-3-yl)-3-methyl-1,3-dihydro-imidazo[4,5-c]quinolin-2-one

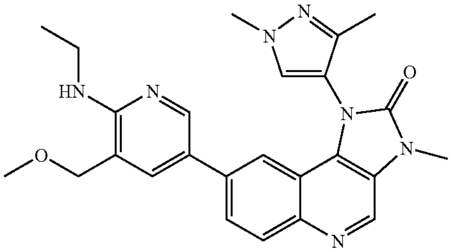

The title compound was synthesized in a similar manner as described for Example 1.1 using 8-bromo-1-(1,3-dimethyl-1H-pyrazol-4-yl)-3-methyl-1,3-dihydro-imidazo[4,5-c]quinolin-2-one (stage 205.1.1, 0.067 mmol) and ethyl-[3-methoxymethyl-5-(4,4,5,5-tetramethyl-[1,3,2]dioxaborolan-2-yl)-pyridin-2-yl]-amine (Stage 206.1.1) to give the title compound as a yellow solid. (HPLC: $t_R$ 2.20 min (Method A); M+H=458 MS-ES; $^1$H-NMR ($d_6$-DMSO, 400 MHz) 8.90 (s, 1H), 8.22-8.18 (m, 1H), 8.13 (s, 1H), 8.05-8.00 (m, 1H), 7.88-7.84 (m, 1H), 7.45-7.40 (m, 2H), 6.09 (t, 1H), 4.38-4.30 (m, 2H), 3.92 (s, 3H), 3.56 (s, 3H), 3.45-3.37 (m, 2H), 3.33 (s, 3H), 1.95 (s, 3H), 1.14 (t, 3H))

Stage 206.1.1 Ethyl-[3-methoxymethyl-5-(4,4,5,5-tetramethyl-[1,3,2]dioxaborolan-2-yl)-pyridin-2-yl]-amine

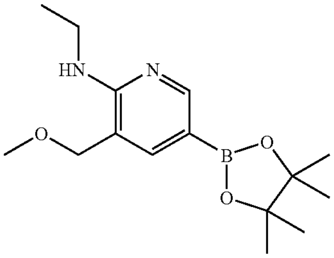

The title compound was synthesized in a similar manner as described for Stage 167.1.1 using iodomethane as replacement for iodoethane to give the title compound as a crude black oil. (degrading under the HPLC condition: $t_R$ 1.81 min (Method A); M+H=293 MS-ES).

The following example was synthesized in a similar manner as described for Example 206.1 using the specified intermediate.

| Example | Intermed. | structure | Name of the example | MS-ES (M + H) | HPLC $t_R$ (min) |
|---|---|---|---|---|---|
| 206.2 | H | 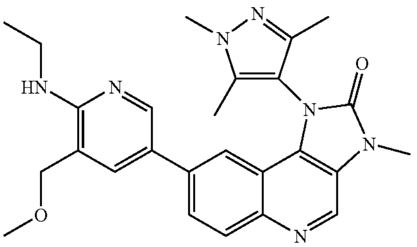 [SMILES: CCNc1ncc(-c2ccc3ncc4c(c3c2)n(-c2c(C)nn(C)c2C)c(=O)n4C)cc1COC] | 8-(6-Ethylamino-5-methoxymethyl-pyridin-3-yl)-3-methyl-1-(1,3,5-trimethyl-1H-pyrazol-4-yl)-1,3-dihydro-imidazo[4,5-c]quinolin-2-one | 472 | 2.24 |

Example 207

8-(2-Dimethylamino-pyrimidin-5-yl)-1-(1,3-dimethyl-1H-pyrazol-4-yl)-1,3-dihydro-imidazo[4,5-c]quinolin-2-one

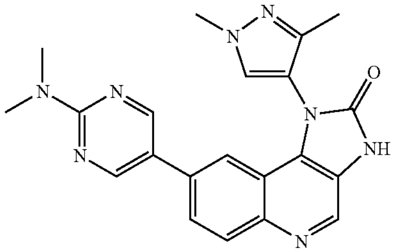 [SMILES: Cc1nn(C)cc1-n1c(=O)[nH]c2cnc3ccc(-c4cnc(N(C)C)nc4)cc3c21]

The title compound was synthesized in a similar manner as described for Example 109 using 2-dimethylamino-pyrimidine-5-boronic acid pinacol ester (Frontier Scientific, Logan, USA) to give the title compound as a white solid. (HPLC: $t_R$ 2.31 min (Method A); M+H=401 MS-ES; $^1$H-NMR ($d_6$-DMSO, 400 MHz) 11.66 (s, br, 1H), 8.69 (s, 1H), 8.46 (s, 2H), 8.10 (s, 1H), 8.05-8.00 (m, 1H), 7.87-7.82 (m, 1H), 7.43-7.40 (m, 1H), 3.90 (s, 3H), 3.16 (s, 6H), 1.96 (s, 3H))

Example 208

8-(5-Amino-6-ethyl-pyridin-3-yl)-1-(1,3-dimethyl-1H-pyrazol-4-yl)-3-methyl-1,3-dihydro-imidazo[4,5-c]quinolin-2-one

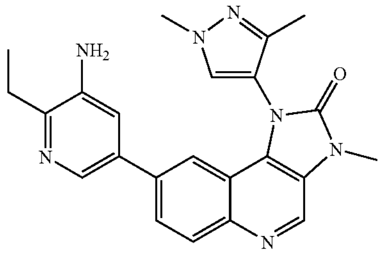 [SMILES: CCc1ncc(-c2ccc3ncc4c(c3c2)n(-c2cn(C)nc2C)c(=O)n4C)cc1N]

The title compound was synthesized in a similar manner as described for Stage A2 using 1-(1,3-dimethyl-1H-pyrazol-4-yl)-8-(6-ethyl-5-nitro-pyridin-3-yl)-3-methyl-1,3-dihydro-imidazo[4,5-c]quinolin-2-one (Stage 208.1.1, 0.06 mmol) to give the title compound after purification as a white foam (HPLC: $t_R$ 2.06 min (Method A); M+H=414 MS-ES; $^1$H-NMR ($d_6$-DMSO, 400 MHz) 8.96 (s, 1H), 8.13-8.07 (m, 2H), 7.79-7.74 (m, 2H), 7.54-7.51 (m, 1H), 7.06-7.03 (m, 1H), 5.18 (s, br, 2H), 3.92 (s, 3H), 3.58 (s, 3H), 2.64 (q, 2H), 1.96 (s, 3H), 1.19 (t, 3H))

Stage 208.1.1 1-(1,3-Dimethyl-1H-pyrazol-4-yl)-8-(6-ethyl-5-nitro-pyridin-3-yl)-3-methyl-1,3-dihydro-imidazo[4,5-c]quinolin-2-one

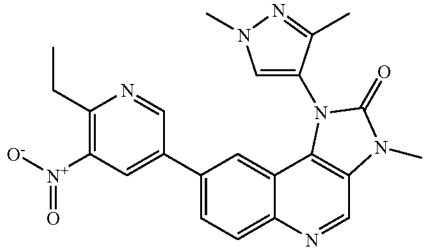 [SMILES: CCc1ncc(-c2ccc3ncc4c(c3c2)n(-c2cn(C)nc2C)c(=O)n4C)cc1[N+](=O)[O-]]

The title compound was synthesized in a similar manner as described for for Example 1.1 using 8-bromo-1-(1,3-dimethyl-1H-pyrazol-4-yl)-3-methyl-1,3-dihydro-imidazo[4,5-c]quinolin-2-one (Intermediate A) and 2-ethyl-3-nitro-5-(4,4,5,5-tetramethyl-[1,3,2]dioxaborolan-2-yl)-pyridine (stage 208.1.2) to give the title compound as a yellow foam. (HPLC: $t_R$ 2.72 min (Method A); M+H=444 MS-ES).

Stage 208.1.2 2-Ethyl-3-nitro-5-(4,4,5,5-tetramethyl-[1,3,2]dioxaborolan-2-yl)-pyridine

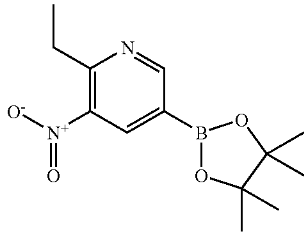 [SMILES: CCc1ncc(B2OC(C)(C)C(C)(C)O2)cc1[N+](=O)[O-]]

The title compound was synthesized in a similar manner as described for Stage 5.1.1 using 5-bromo-2-ethyl-3-nitro-pyridine (stage 208.1.3, 0.493 mmol) to give the title compound as a crude brown oil. (degrading under the HPLC condition: $t_R$ 2.65 min (Method A); M+H=279 MS-ES).

Stage 208.1.3 5-Bromo-2-ethyl-3-nitro-pyridine

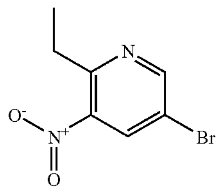

The title compound was synthesized in a similar manner as described for Stage 75.1.5 using diethyl methylmalonate (Fluka, Buchs, Switzerland) as replacement for diethyl malonate to give the title compound as a brown oil. (HPLC: $t_R$ 3.34 min (Method A); M+H=231, 233 MS-ES).

Example 209

1-(1,3-Dimethyl-1H-pyrazol-4-yl)-3-methyl-8-(4-methyl-3,4-dihydro-2H-pyrido[3,2-b][1,4]oxazin-7-yl)-1,3-dihydro-imidazo[4,5-c]quinolin-2-one

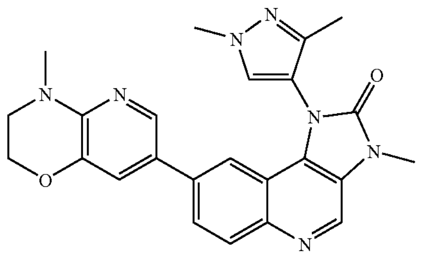 [SMILES: Cc1nn(C)cc1-n1c(=O)n(C)c2cnc3ccc(-c4cnc5c(c4)OCCN5C)cc3c21]

The title compound was synthesized in a similar manner as described for Example 1.1 using 8-bromo-1-(1,3-dimethyl-1H-pyrazol-4-yl)-3-methyl-1,3-dihydro-imidazo[4,5-c]quinolin-2-one (Intermediate A) and 4-methyl-7-(4,4,5,5-tetramethyl-1,3,2-dioxaborolan-2-yl)-3,4-dihydro-2H-pyrido[3,2-b][1,4]oxazine (ABCR, Karlsruhe, Germany) to give the title compound as a yellow foam. (HPLC: $t_R$ 2.15 min (Method A); M+H=442 MS-ES; $^1$H-NMR ($d_6$-DMSO, 400 MHz) 8.90 (s, 1H), 8.13 (s, 1H), 8.03-7.99 (m, 1H), 7.89-7.82 (m, 2H), 7.40-7.37 (m, 1H), 6.97-6.94 (m, 1H), 4.25 (t, 2H), 3.92 (s, 3H), 3.56 (s, 3H), 3.47 (t, 2H), 3.06 (s, 3H), 1.95 (s, 3H))

Example 210

8-(5-Ethylamino-6-methyl-pyridin-3-yl)-1-[1-(2-hydroxy-ethyl)-3,5-dimethyl-1H-pyrazol-4-yl]-3-methyl-1,3-dihydro-imidazo[4,5-c]quinolin-2-one

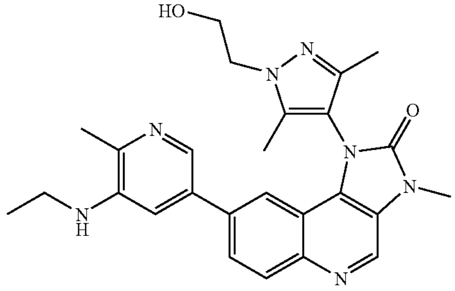 [SMILES: CCNc1cc(-c2ccc3ncc4c(c3c2)n(-c2c(C)nn(CCO)c2C)c(=O)n4C)cnc1C]

The title compound was synthesized in a similar manner as described for Example 1.1 using 8-Bromo-1-{1-[2-(tert-butyl-dimethyl-silanyloxy)-ethyl]-3,5-dimethyl-1H-pyrazol-4-yl}-3-methyl-1,3-dihydro-imidazo[4,5-c]quinolin-2-one (stage 210.1.1) and ethyl-[2-methyl-5-(4,4,5,5-tetramethyl-[1,3,2]dioxaborolan-2-yl)-pyridin-3-yl]-amine (Stage 87.1.1) to give the title compound as an off-white solid; deprotection of the silyl group occurred during the purification step. (HPLC: $t_R$ 2.16 min (Method A); M+H=472 MS-ES; $^1$H-NMR ($d_6$-DMSO, 400 MHz) 8.96 (s, 1H), 8.10-8.06 (m, 1H), 7.94-7.90 (m, 1H), 7.85-7.82 (m, 1H), 7.55-7.52 (m, 1H), 6.83-6.80 (m, 1H), 5.21 (t, 1H), 4.92 (t, 1H), 4.21-4.03 (m, 2H), 3.81-3.67 (m, 2H), 3.59 (s, 3H), 3.24-3.14 (m, 2H), 2.32 (s, 3H), 2.09 (s, 3H), 1.94 (s, 3H), 1.24 (t, 3H))

Stage 210.1.2 8-Bromo-1-{1-[2-(tert-butyl-dimethyl-silanyloxy)-ethyl]-3,5-dimethyl-1H-pyrazol-4-yl}-3-methyl-1,3-dihydro-imidazo[4,5-c]quinolin-2-one

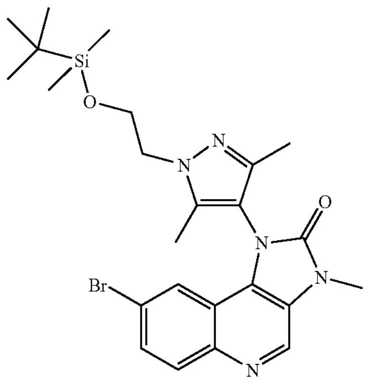 [SMILES: Cc1nn(CCO[Si](C)(C)C(C)(C)C)c(C)c1-n1c(=O)n(C)c2cnc3ccc(Br)cc3c21]

The title compound was synthesized in a similar manner as described for intermediate N using (2-bromoethoxy)-tertbutyldimethylsilane (Frontier Scientific, Logan, USA) as replacement for the 2-bromoethyl methyl ether to give the title compound as a brown foam. (HPLC: $t_R$ 3.61 min (Method A); M+H=530, 532 MS-ES).

Example 211.1

1-[1-(2-Hydroxy-ethyl)-3-methyl-1H-pyrazol-4-yl]-8-(5-methoxy-6-methyl-pyridin-3-yl)-3-methyl-1,3-dihydro-imidazo[4,5-c]quinolin-2-one

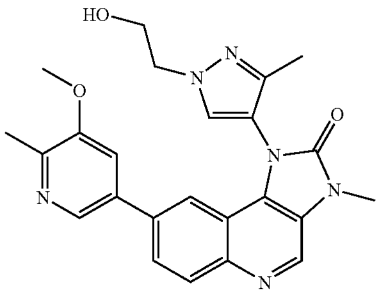

The title compound was synthesized in a similar manner as described for Example 103.1 using 3-methoxy-2-methyl-5-(4,4,5,5-tetramethyl-[1,3,2]dioxaborolan-2-yl)-pyridine (stage 211.1.1) to give the title compound as a white solid. (HPLC: $t_R$ 2.02 min (Method A); M+H=445 MS-ES; $^1$H-NMR ($d_6$-DMSO, 400 MHz) 9.00-8.96 (m, 1H), 8.19-8.09 (m, 3H), 8.03-7.97 (m, 1H), 7.58 (s, 1H), 7.33 (s, 1H), 4.94 (t, 1H), 4.25-4.11 (m, 2H), 3.92 (s, 3H), 3.84-3.69 (m, 2H), 3.59 (s, 3H), 2.38 (s, 3H), 1.98 (s, 3H))

Stage 211.1.1 3-Methoxy-2-methyl-5-(4,4,5,5-tetramethyl-[1,3,2]dioxaborolan-2-yl)-pyridine

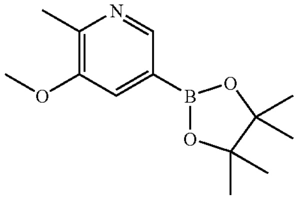

The title compound was synthesized in a similar manner as described for Stage 84.1.1 using methanol as replacement for isopropanol to give the title compound as a crude black oil. (degrading under the HPLC condition: $t_R$ 1.86 min (Method A); M+H=250 MS-ES).

The following example was synthesized in a similar manner as described for Example 211.1 using 3-ethoxy-2-methyl-5-(4,4,5,5-tetramethyl-[1,3,2]dioxaborolan-2-yl)-pyridine (Stage 85.1.1).

| Example | structure | Name of the example | MS-ES (M + H) | HPLC $t_R$ (min) |
|---|---|---|---|---|
| 211.2 | 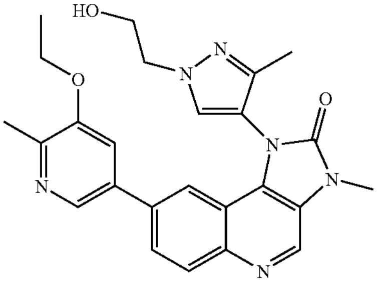 | 8-(5-Ethoxy-6-methyl-pyridin-3-yl)-1-[1-(2-hydroxy-ethyl)-3-methyl-1H-pyrazol-4-yl]-3-methyl-1,3-dihydro-imidazo[4,5-c]quinolin-2-one | 459 | 2.14 |

Example 212.1

1-(1,3-Dimethyl-1H-pyrazol-4-yl)-8-[6-((R)-3-hydroxy-pyrrolidin-1-yl)-pyridin-3-yl]-3-methyl-1,3-dihydro-imidazo[4,5-c]quinolin-2-one

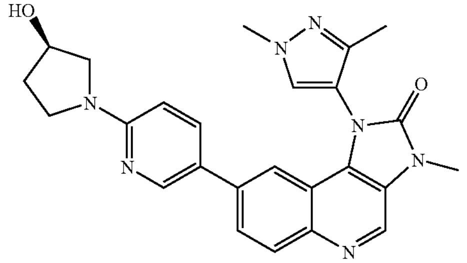 [SMILES: Cc1nn(C)cc1-n1c(=O)n(C)c2cnc3ccc(-c4ccc(N5CC[C@@H](O)C5)nc4)cc3c21]

The title compound was synthesized in a similar manner as described for Example 1.1 using 8-bromo-1-(1,3-dimethyl-1H-pyrazol-4-yl)-3-methyl-1,3-dihydro-imidazo[4,5-c]quinolin-2-one (Intermediate A) and (R)-1-[5-(4,4,5,5-tetramethyl-[1,3,2]dioxaborolan-2-yl)-pyridin-2-yl]-pyrrolidin-3-ol (stage 212.1.1) to give the title compound as a white solid. (HPLC: $t_R$ 2.03 min (Method A); M+H=456 MS-ES; $^1$H-NMR ($d_6$-DMSO, 400 MHz) 8.90 (s, 1H), 8.25-8.22 (m, 1H), 8.12 (s, 1H), 8.05-8.01 (m, 1H), 7.87-7.83 (m, 1H), 7.57-7.53 (m, 1H), 7.43-7.41 (m, 1H), 6.55-6.51 (m, 1H), 4.95 (d, 1H), 4.42-4.36 (m, 1H), 3.92 (s, 3H), 3.56 (s, 3H), 3.54-3.43 (m, 3H), 3.37-3.31 (m, 1H), 2.08-1.86 (m, 2H), 1.96 (s, 3H))

Stage 212.1.1 (R)-1-[5-(4,4,5,5-Tetramethyl-[1,3,2]dioxaborolan-2-yl)-pyridin-2-yl]-pyrrolidin-3-ol

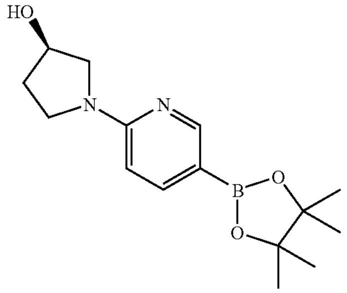 [SMILES: CC1(C)OB(c2ccc(N3CC[C@@H](O)C3)nc2)OC1(C)C]

The title compound was synthesized in a similar manner as described for Stage 5.1.1-2 using (R)-3-hydroxypyrrolidine (Fluka, Buchs, Switzerland) to give the title compound as a crude black oil. (degrading under the HPLC condition: $t_R$ 1.54 min (Method A); M+H=291 MS-ES).

The following example was synthesized in a similar manner as described for Example 212.1 using (S)-3-hydroxypyrrolidine (Fluka, Buchs, Switzerland).

| Example | structure | Name of the example | MS-ES (M + H) | HPLC $t_R$ (min) |
|---|---|---|---|---|
| 212.2 | 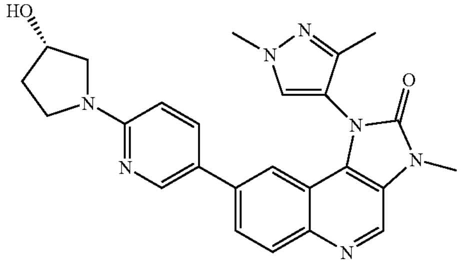 [SMILES: Cc1nn(C)cc1-n1c(=O)n(C)c2cnc3ccc(-c4ccc(N5CC[C@H](O)C5)nc4)cc3c21] | 1-(1,3-Dimethyl-1H-pyrazol-4-yl)-8-[6-((S)-3-hydroxy-pyrrolidin-1-yl)-pyridin-3-yl]-3-methyl-1,3-dihydro-imidazo[4,5-c]quinolin-2-one | 456 | 2.04 |

Example 213.1

1-(1,3-Dimethyl-1H-pyrazol-4-yl)-8-[6-((R)-3-methoxy-pyrrolidin-1-yl)-pyridin-3-yl]-3-methyl-1,3-dihydro-imidazo[4,5-c]quinolin-2-one

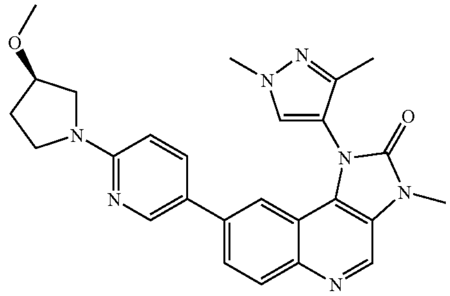 [SMILES: CO[C@@H]1CCN(c2ccc(-c3ccc4ncc5c(c4c3)n(-c3cn(C)nc3C)c(=O)n5C)cn2)C1]

The title compound was synthesized in a similar manner as described for Example 104 using 1-(1,3-Dimethyl-1H-pyrazol-4-yl)-8-[6-((R)-3-hydroxy-pyrrolidin-1-yl)-pyridin-3-yl]-3-methyl-1,3-dihydro-imidazo[4,5-c]quinolin-2-one (Example 212.1, 0.116 mmol) to give the title compound as a white solid. (HPLC: $t_R$ 2.20 min (Method A); M+H=470 MS-ES; $^1$H-NMR ($d_6$-DMSO, 400 MHz) 8.90 (s, 1H), 8.26-8.23 (m, 1H), 8.12 (s, 1H), 8.05-8.02 (m, 1H), 7.88-7.84 (m, 1H), 7.59-7.55 (m, 1H), 7.44-7.41 (m, 1H), 6.59-6.54 (m, 1H), 4.08 (qt, 1H), 3.93 (s, 3H), 3.57 (s, 3H), 3.56-3.49 (m, 4H), 3.45-3.34 (m, 1H), 3.27 (s, 3H), 2.11-2.02 (m, 2H), 1.97 (s, 3H))

The following example was synthesized in a similar manner as described for Example 213.1 using (S)-3-hydroxypyrrolidine (Fluka, Buchs, Switzerland).

| Example | structure | Name of the example | MS-ES (M + H) | HPLC $t_R$ (min) |
|---|---|---|---|---|
| 213.2 | 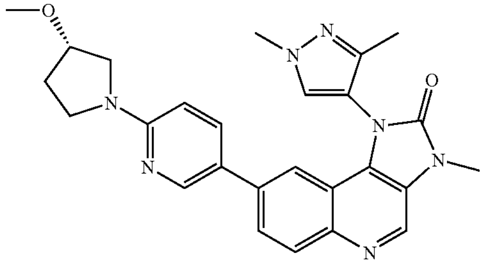 | 1-(1,3-Dimethyl-1H-pyrazol-4-yl)-8-[6-((S)-3-methoxy-pyrrolidin-1-yl)-pyridin-3-yl]-3-methyl-1,3-dihydro-imidazo[4,5-c]quinolin-2-one | 470 | 2.19 |

Example 214

1-(1,3-Dimethyl-1H-pyrazol-4-yl)-3-methyl-8-[6-(tetrahydro-pyran-4-ylamino)-pyridin-3-yl]-1,3-dihydro-imidazo[4,5-c]quinolin-2-one

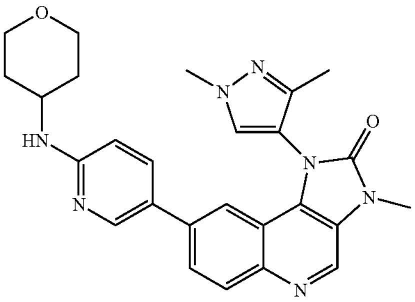 [SMILES: Cc1nn(C)cc1-n1c(=O)n(C)c2cnc3ccc(-c4ccc(NC5CCOCC5)nc4)cc3c21]

The title compound was synthesized in a similar manner as described for Example 1.1 using 8-bromo-1-(1,3-dimethyl-1H-pyrazol-4-yl)-3-methyl-1,3-dihydro-imidazo[4,5-c]quinolin-2-one (Intermediate A) and (tetrahydro-pyran-4-yl)-[5-(4,4,5,5-tetramethyl-[1,3,2]dioxaborolan-2-yl)-pyridin-2-yl]-amine (stage 214.1.1) to give the title compound as a white solid. (HPLC: $t_R$ 2.13 min (Method A); M+H=470 MS-ES; $^1$H-NMR ($d_6$-DMSO, 400 MHz) 8.89 (s, 1H), 8.15-8.10 (m, 2H), 8.04-8.00 (m, 1H), 7.84-7.79 (m, 1H), 7.47-7.42 (m, 1H), 7.41-7.38 (m, 1H), 6.78-6.73 (m, 1H), 6.57-6.53 (m, 1H), 4.00-3.82 (m, 3H), 3.91 (s, 3H), 3.56 (s, 3H), 3.45-3.37 (m, 2H), 1.96 (s, 3H), 1.91-1.83 (m, 2H), 1.49-1.37 (m, 2H))

Stage 214.1.1 (Tetrahydro-pyran-4-yl)-[5-(4,4,5,5-tetramethyl-[1,3,2]dioxaborolan-2-yl)-pyridin-2-yl]-amine

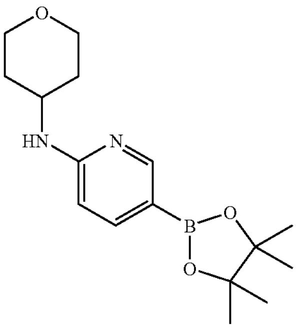 [SMILES: CC1(C)OB(c2ccc(NC3CCOCC3)nc2)OC1(C)C]

The title compound was synthesized in a similar manner as described for Stage 5.1.1-2 using 4-aminotetrahydropyran (Maybridge, Basel, Switzerland) to give the title compound as a crude brown sticky solid. (degrading under the HPLC condition: $t_R$ 1.74 min (Method A); M+H=305 MS-ES).

Example 215.1

8-[5-(1-Hydroxy-1-methyl-ethyl)-pyridin-3-yl]-1-(1-isopropyl-3-methyl-1H-pyrazol-4-yl)-3-methyl-1,3-dihydro-imidazo[4,5-c]quinolin-2-one

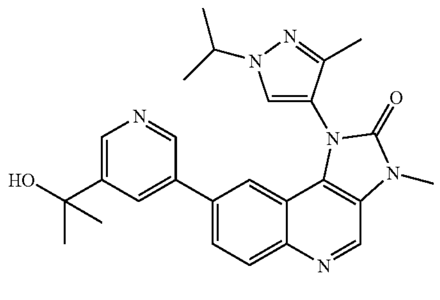 [SMILES: Cc1nn(C(C)C)cc1-n1c(=O)n(C)c2cnc3ccc(-c4cncc(C(C)(C)O)c4)cc3c21]

The title compound was synthesized in a similar manner as described for Example 1.1 using 8-bromo-1-(1-isopropyl-3-methyl-1H-pyrazol-4-yl)-3-methyl-1,3-dihydro-imidazo[4,5-c]quinolin-2-one (Intermediate G) and 2-[5-(4,4,5,5-tetramethyl-[1,3,2]dioxaborolan-2-yl)-pyridin-3-yl]-propan-2-ol (Stage 215.1.1) to give the title compound as a white foam. (HPLC: $t_R$ 2.13 min (Method A); M+H=457 MS-ES; $^1$H-NMR ($d_6$-DMSO, 400 MHz) 8.99 (s, 1H), 8.69-8.66 (m, 1H), 8.46-8.44 (m, 1H), 8.21 (s, 1H), 8.16-8.12 (m, 1H), 7.98-7.91 (m, 2H), 7.58-7.56 (m, 1H), 5.26 (s, 1H), 4.53 (hp, 1H), 3.59 (s, 3H), 1.97 (s, 3H), 1.49 (s, 6H), 1.44 (d, 6H))

Stage 215.1.1 2-[5-(4,4,5,5-Tetramethyl-[1,3,2]dioxaborolan-2-yl)-pyridin-3-yl]-propan-2-ol

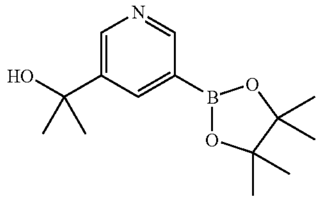 [SMILES: CC(C)(O)c1cncc(B2OC(C)(C)C(C)(C)O2)c1]

The title compound was synthesized in a similar manner as described for Stage 5.1.1 using 2-(5-bromo-pyridin-3-yl)-propan-2-ol (stage 215.1.2, 1.518 mmol) to give the title compound as a crude black sticky oil. (degrading under the HPLC condition: $t_R$ 1.87, 3.68 min (Method A); M+H=264 MS-ES).

Stage 215.1.2 2-(5-Bromo-pyridin-3-yl)-propan-2-ol

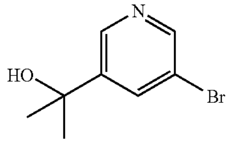

To a solution of 3,5-dibromopyridine (Aldrich, Buchs, Switzerland, 4.6 mmol) in dry THF under Ar was added slowly a ~2 M solution of isopropylmagnesium chloride in THF (2.76 ml). The RM was stirred for 2 h at it then was added acetone (6.9 mmol) and the RM was stirred for 2 h at rt. The RM was quenched with brine and extracted with EtOAc (2×). The combined organic layers were washed with brine, dried over $Na_2SO_4$, filtered and evaporated. The residue was absorbed on silica gel and purified by flash chromatography (heptane/EtOAc 0% to 70%). The fractions containing product were evaporated together to give the title compound as an oil. (HPLC: $t_R$ 1.82 min (Method A); M+H=216, 218 MS-ES)

The following examples were synthesized in a similar manner as described for Example 215.1 using the specified intermediate.

| Example | Intermed. | structure | Name of the example | MS-ES (M + H) | HPLC $t_R$ (min) |
|---|---|---|---|---|---|
| 215.2 | A | 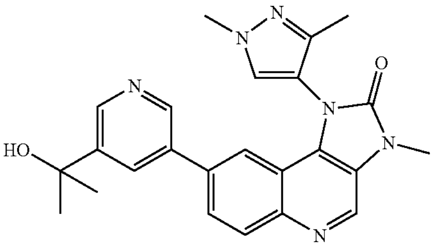 [SMILES: Cc1nn(C)cc1-n1c(=O)n(C)c2cnc3ccc(-c4cncc(C(C)(C)O)c4)cc3c21] | 1-(1,3-Dimethyl-1H-pyrazol-4-yl)-8-[5-(1-hydroxy-1-methyl-ethyl)-pyridin-3-yl]-3-methyl-1,3-dihydro-imidazo[4,5-c]quinolin-2-one | 429 | 1.98 |
| 215.3 | K | 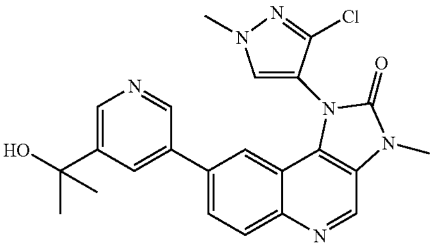 [SMILES: Cn1cc(-n2c(=O)n(C)c3cnc4ccc(-c5cncc(C(C)(C)O)c5)cc4c32)c(Cl)n1] | 1-(3-Chloro-1-methyl-1H-pyrazol-4-yl)-8-[5-(1-hydroxy-1-methyl-ethyl)-pyridin-3-yl]-3-methyl-1,3-dihydro-imidazo[4,5-c]quinolin-2-one | 459 | 2.16 |
| 215.4 | F | 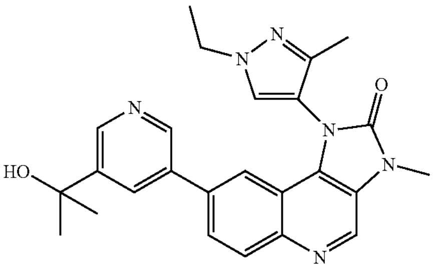 [SMILES: CCn1cc(-n2c(=O)n(C)c3cnc4ccc(-c5cncc(C(C)(C)O)c5)cc4c32)c(C)n1] | 1-(1-Ethyl-3-methyl-1H-pyrazol-4-yl)-8-[5-(1-hydroxy-1-methyl-ethyl)-pyridin-3-yl]-3-methyl-1,3-dihydro-imidazo[4,5-c]quinolin-2-one | 443 | 2.05 |

Example 216

1-(1,3-Dimethyl-1H-pyrazol-4-yl)-8-[5-(1-ethyl-1-hydroxy-propyl)-pyridin-3-yl]-3-methyl-1,3-dihydro-imidazo[4,5-c]quinolin-2-one

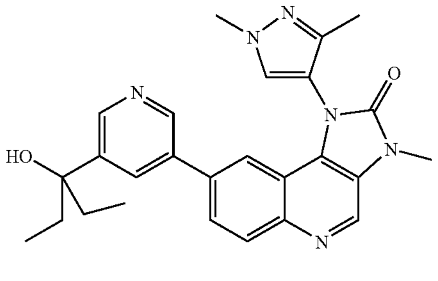 [SMILES: CCC(O)(CC)c1cncc(-c2ccc3ncc4c(c3c2)n(-c2cn(C)nc2C)c(=O)n4C)c1]

The title compound was synthesized in a similar manner as described for Example 215.1 using 8-bromo-1-(1,3-dimethyl-1H-pyrazol-4-yl)-3-methyl-1,3-dihydro-imidazo[4,5-c]quinolin-2-one (Intermediate A) and 3-pentanone (Fluka, Buchs, Switzerland) to give the title compound as a white solid. (HPLC: $t_R$ 2.13 min (Method A); M+H=457 MS-ES; $^1$H-NMR ($d_6$-DMSO, 400 MHz) 8.99 (s, 1H), 8.63-8.57 (m, 2H), 8.16-8.11 (m, 2H), 8.01-7.96 (m, 1H), 7.76-7.73 (m, 1H), 7.65-7.62 (m, 1H), 4.82 (s, 1H), 3.90 (s, 3H), 3.58 (s, 3H), 1.96 (s, 3H), 1.87-1.72 (m, 4H), 0.72-0.65 (m, 6H))

Example 217

(rac)-1-(1,3-Dimethyl-1H-pyrazol-4-yl)-8-[5-(1-hydroxy-ethyl)-pyridin-3-yl]-3-methyl-1,3-dihydro-imidazo[4,5-c]quinolin-2-one

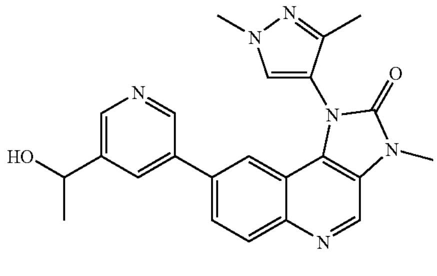 [SMILES: Cc1nn(C)cc1-n1c(=O)n(C)c2cnc3ccc(-c4cncc(C(C)O)c4)cc3c21]

The title compound was synthesized in a similar manner as described for Example 1.1 using 8-bromo-1-(1,3-dimethyl-1H-pyrazol-4-yl)-3-methyl-1,3-dihydro-imidazo[4,5-c]quinolin-2-one (Intermediate A) and acetaldehyde (Fluka, Buchs, Switzerland) to give the title compound as a white solid. (HPLC: $t_R$ 1.95 min (Method A); M+H=415 MS-ES; $^1$H-NMR ($d_6$-DMSO, 400 MHz) 8.99 (s, 1H), 8.63-8.60 (m, 1H), 8.56-8.53 (m, 1H), 8.16-8.11 (m, 2H), 8.00-7.95 (m, 1H), 7.81-7.76 (m, 1H), 7.61-7.58 (m, 1H), 5.42-5.38 (m, 1H), 4.88-4.80 (m, 1H), 3.94-3.90 (m, 3H), 3.58 (s, 3H), 1.97-1.92 (m, 3H), 1.43-1.39 (m, 3H))

Example 218

1-(1,3-Dimethyl-1H-pyrazol-4-yl)-8-[5-(1-hydroxy-cyclopentyl)-pyridin-3-yl]-3-methyl-1,3-dihydro-imidazo[4,5-c]quinolin-2-one

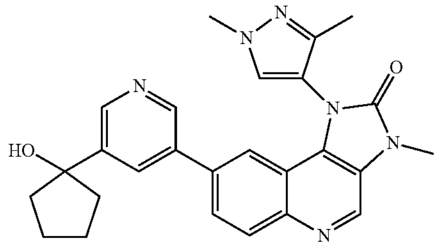 [SMILES: Cc1nn(C)cc1-n1c(=O)n(C)c2cnc3ccc(-c4cncc(C5(O)CCCC5)c4)cc3c21]

The title compound was synthesized in a similar manner as described for Example 1.1 using 8-bromo-1-(1,3-dimethyl-1H-pyrazol-4-yl)-3-methyl-1,3-dihydro-imidazo[4,5-c]quinolin-2-one (Intermediate A) and cyclopentanone (Fluka, Buchs, Switzerland) to give the title compound as a white solid. (HPLC: $t_R$ 2.14 min (Method A); M+H=455 MS-ES; $^1$H-NMR ($d_6$-DMSO, 400 MHz) 8.99 (s, 1H), 8.71-8.68 (m, 1H), 8.61-8.58 (m, 1H), 8.16-8.11 (m, 2H), 8.01-7.96 (m, 1H), 7.85-7.81 (m, 1H), 7.63-7.59 (m, 1H), 5.05 (s, 1H), 3.90 (s, 3H), 3.58 (s, 3H), 1.98-1.77 (m, 8H), 1.95 (s, 3H))

Example 219

8-[5-(2-Fluoro-1-fluoromethyl-1-hydroxy-ethyl)-pyridin-3-yl]-1-(1-isopropyl-3-methyl-1H-pyrazol-4-yl)-3-methyl-1,3-dihydro-imidazo[4,5-c]quinolin-2-one

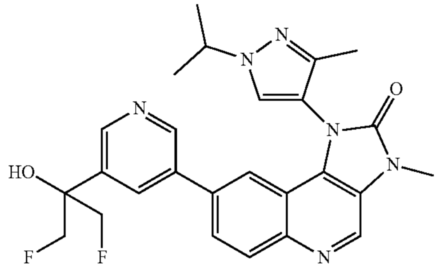 [SMILES: Cc1nn(C(C)C)cc1-n1c(=O)n(C)c2cnc3ccc(-c4cncc(C(O)(CF)CF)c4)cc3c21]

The title compound was synthesized in a similar manner as described for Example 215.1 using 1,3-difluoropropanone (Apollo Scientific, Cheshire, United Kingdom) to give the title compound as a yellow solid. (HPLC: $t_R$ 2.24 min (Method A); M+H=493 MS-ES; $^1$H-NMR ($d_6$-DMSO, 400 MHz) 9.00 (s, 1H), 8.72-8.70 (m, 1H), 8.55-8.52 (m, 1H), 8.22 (s, 1H), 8.18-8.14 (m, 1H), 8.09-8.07 (m, 1H), 7.96-7.92 (m, 1H), 7.59-7.57 (m, 1H), 6.31 (s, 1H), 4.78-4.70 (m, 2H), 4.66-4.58 (m, 2H), 4.54 (hp, 1H), 3.59 (s, 3H), 1.97 (s, 3H), 1.47-1.42 (m, 6H))

Example 220.1

2-{5-[1-(1,3-Dimethyl-1H-pyrazol-4-yl)-3-methyl-2-oxo-2,3-dihydro-1H-imidazo[4,5-c]quinolin-8-yl]-pyridin-3-yl}-2-methyl-propionitrile

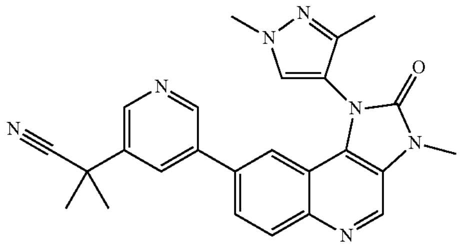 [SMILES: Cc1nn(C)cc1-n1c(=O)n(C)c2cnc3ccc(-c4cncc(C(C)(C)C#N)c4)cc3c21]

The title compound was synthesized in a similar manner as described for Example 1.1 using 8-bromo-1-(1,3-dimethyl-1H-pyrazol-4-yl)-3-methyl-1,3-dihydro-imidazo[4,5-c]quinolin-2-one (Intermediate A) and 2-methyl-2-[5-(4,4,5,5-tetramethyl-[1,3,2]dioxaborolan-2-yl)-pyridin-3-yl]-propionitrile (Stage 220.1.1) to give the title compound as a white solid. (HPLC: $t_R$ 2.36 min (Method A); M+H=438 MS-ES; $^1$H-NMR ($d_6$-DMSO, 400 MHz) 9.01 (s, 1H), 8.78-8.76 (m, 1H), 8.73-8.71 (m, 1H), 8.18-8.14 (m, 1H), 8.12 (s, 1H), 8.05-8.01 (m, 1H), 7.93-7.90 (m, 1H), 7.62-7.60 (m, 1H), 3.88 (s, 3H), 3.59 (s, 3H), 1.97 (s, 3H), 1.80 (s, 3H), 1.79 (s, 3H))

Stage 220.1.1 2-Methyl-2-[5-(4,4,5,5-tetramethyl-[1,3,2]dioxaborolan-2-yl)-pyridin-3-yl]-propionitrile

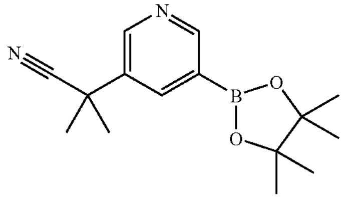 [SMILES: CC(C)(C#N)c1cncc(B2OC(C)(C)C(C)(C)O2)c1]

The title compound was synthesized in a similar manner as described for Stage 5.1.1 using 2-(5-bromo-pyridin-3-yl)-2-methyl-propionitrile (stage 220.1.2, 1.111 mmol) to give the title compound as a crude brown soft solid. (degrading under the HPLC condition (Method A); M+H=273 MS-ES).

Stage 220.1.2 2-(5-Bromo-pyridin-3-yl)-2-methyl-propionitrile

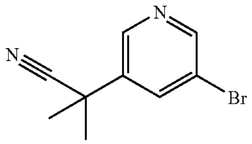

To a solution of (5-bromo-pyridin-3-yl)-acetonitrile (Stage 220.1.3, 4.61 mmol) in dry DMF (15 ml) cooled with an ice-bath was added portionwise 55% sodium hydride in oil (9.97 mmol). Was then added iodomethane (13.56 mmol) and DMF (5 ml). The RM was stirred for 3 h at 0° C. then was quenched with saturated aqueous $NH_4Cl$, diluted with water and extracted with EtOAc(3×). The combined organic layers were washed with brine, dried over $Na_2SO_4$, filtered and evaporated. The residue was purified by flash chromatography (heptane/EtOAc 25%). The fractions containing product were evaporated together to give the title compound as an oil. (HPLC: $t_R$ 2.72 min (Method A); M+H=225, 227 MS-ES)

Stage 220.1.3 (5-Bromo-pyridin-3-yl)-acetonitrile

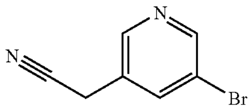

To $SOCl_2$ (26.7 ml) cooled with an ice-bath was added portionwise (5-bromo-pyridin-3-yl)-methanol (ABCR, Karlsruhe, Germany, 26.6 mmol). The RM was refluxed for 1 h then was cooled at 0° C. and quenched with diethyl ether. The resulting precipitate was filtered, washed with cooled diethyl ether and dried under vacuum at 50° C. The solid was mixed with potassium cyanide (64.5 mmol), MeOH (35 ml) and water (14 ml) and the RM was refluxed for 2 h. The RM was cooled, quenched with aqueous $K_2CO_3$ and extracted with diethyl ether (3×). The combined organic layers dried over $Na_2SO_4$, filtered and evaporated to give the title compound as a purple solid. (HPLC: $t_R$ 2.16 min (Method A); M+H=197, 199 MS-ES)

The following examples were synthesized in a similar manner as described for Example 220.1 using the specified intermediate.

| Example | Intermed. | structure | Name of the example | MS-ES (M + H) | HPLC $t_R$ (min) |
|---|---|---|---|---|---|
| 220.2 | F | 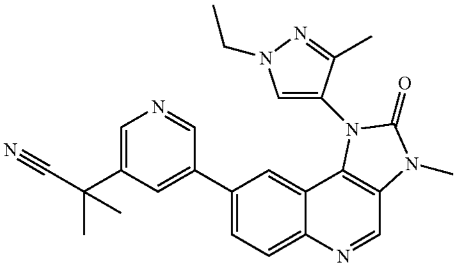 [SMILES: CCn1cc(-n2c(=O)n(C)c3cnc4ccc(-c5cncc(C(C)(C)C#N)c5)cc4c32)c(C)n1] | 2-{5-[1-(1-Ethyl-3-methyl-1H-pyrazol-4-yl)-3-methyl-2-oxo-2,3-dihydro-1H-imidazo[4,5-c]quinolin-8-yl]-pyridin-3-yl}-2-methyl-propionitrile | 452 | 2.45 |
| 220.3 | K | 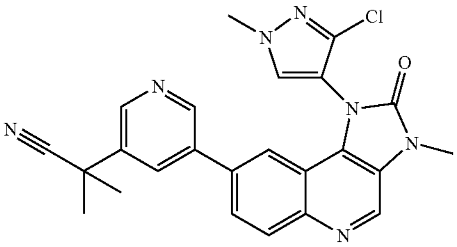 [SMILES: Cn1cc(-n2c(=O)n(C)c3cnc4ccc(-c5cncc(C(C)(C)C#N)c5)cc4c32)c(Cl)n1] | 2-{5-[1-(3-Chloro-1-methyl-1H-pyrazol-4-yl)-3-methyl-2-oxo-2,3-dihydro-1H-imidazo[4,5-c]quinolin-8-yl]-pyridin-3-yl}-2-methyl-propionitrile | 458 | 2.55 |

Example 221.1

1-{5-[1-(1,3-Dimethyl-1H-pyrazol-4-yl)-3-methyl-2-oxo-2,3-dihydro-1H-imidazo[4,5-c]quinolin-8-yl]-pyridin-3-yl}-cyclobutanecarbonitrile

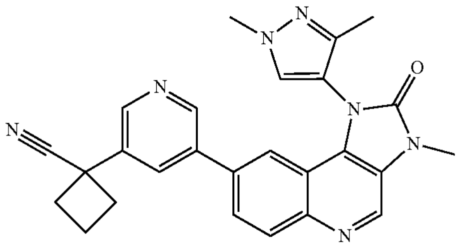 [SMILES: Cc1nn(C)cc1-n1c(=O)n(C)c2cnc3ccc(-c4cncc(C5(C#N)CCC5)c4)cc3c21]

The title compound was synthesized in a similar manner as described for Example 1.1 using 8-bromo-1-(1,3-dimethyl-1H-pyrazol-4-yl)-3-methyl-1,3-dihydro-imidazo[4,5-c]quinolin-2-one (Intermediate A) and 1-[5-(4,4,5,5-tetramethyl-[1,3,2]dioxaborolan-2-yl)-pyridin-3-yl]-cyclobutanecarbonitrile (Stage 221.1.1) to give the title compound as an off-white foam. (HPLC: $t_R$ 2.43 min (Method A); M+H=450 MS-ES; $^1$H-NMR ($d_6$-DMSO, 400 MHz) 9.01 (s, 1H), 8.74-8.73 (m, 1H), 8.70-8.68 (m, 1H), 8.17-8.12 (m, 2H), 8.06-8.03 (m, 1H), 7.90-7.88 (m, 1H), 7.63-7.61 (m, 1H), 3.89 (s, 3H), 3.59 (s, 3H), 2.86-2.71 (m, 4H), 2.13-2.01 (m, 2H), 1.97 (s, 3H))

Stage 221.1.1 1-[5-(4,4,5,5-Tetramethyl-[1,3,2]dioxaborolan-2-yl)-pyridin-3-yl]-cyclobutanecarbonitrile

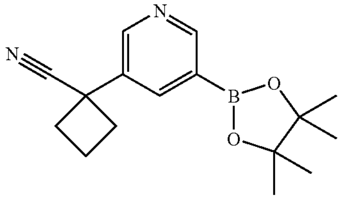 [SMILES: CC1(C)OB(c2cncc(C3(C#N)CCC3)c2)OC1(C)C]

The title compound was synthesized in a similar manner as described for Stage 5.1.1 using 1-(5-bromo-pyridin-3-yl)-cyclobutanecarbonitrile (stage 221.1.2, 0.476 mmol) to give the title compound as a crude back oil. (degrading under the HPLC condition: $t_R$ 2.69 min (Method A); M+H=285 MS-ES).

Stage 221.1.2
1-(5-Bromo-pyridin-3-yl)-cyclobutanecarbonitrile

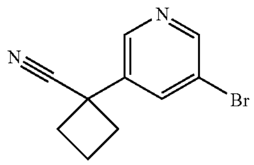 [SMILES: N#CC1(c2cncc(Br)c2)CCC1]

To a solution of (5-bromo-pyridin-3-yl)-acetonitrile (Stage 220.1.3, 1.37 mmol) in dry DMF (10 ml) was added 55% sodium hydride in oil (1.507 mmol). After 30 min stirring at rt was added 1-bromo-3-chloropropane (1.507 mmol). The RM was stirred for 1 h at rt then was added 55% sodium hydride in oil (1.507 mmol). The RM was stirred for 1 h at it then quenched with saturated aqueous $NaHCO_3$ and extracted with EtOAc. The organic layer was washed with brine (2×), dried over $Na_2SO_4$, filtered and evaporated. The residue was taken in DMA and purified by preparative HPLC. The fractions containing product were basified with $NaHCO_3$, concentrated and extracted with EtOAc (2×). The combined organic layers were washed with brine, dried over $Na_2SO_4$, filtered, evaporated and dried under vacuum to give the title compound as a red oil. (HPLC: $t_R$ 2.86 min (Method A); M+H=237, 239 MS-ES)

The following example was synthesized in a similar manner as described for Example 221.1 using the specified intermediate.

| Example | Intermed. | structure | Name of the example | MS-ES (M + H) | HPLC $t_R$ (min) |
|---|---|---|---|---|---|
| 221.2 | F | 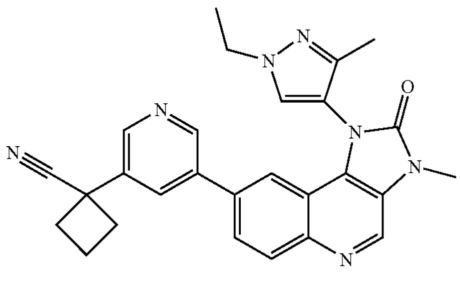 [SMILES: CCn1cc(-n2c(=O)n(C)c3cnc4ccc(-c5cncc(C6(C#N)CCC6)c5)cc4c32)c(C)n1] | 1-{5-[1-(1-Ethyl-3-methyl-1H-pyrazol-4-yl)-3-methyl-2-oxo-2,3-dihydro-1H-imidazo[4,5-c]quinolin-8-yl]-pyridin-3-yl}-cyclobutanecarbonitrile | 464 | 2.52 |

Example 222

N-{2-Chloro-5-[1-(1,3-dimethyl-1H-pyrazol-4-yl)-3-methyl-2-oxo-2,3-dihydro-1H-imidazo[4,5-c]quinolin-8-yl]-pyridin-3-yl}-acetamide

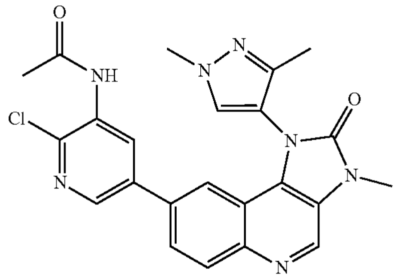 [SMILES: CC(=O)Nc1cc(-c2ccc3ncc4c(c3c2)n(-c2cn(C)nc2C)c(=O)n4C)cnc1Cl]

The title compound was synthesized in a similar manner as described for Example 1.1 using 8-bromo-1-(1,3-dimethyl-1H-pyrazol-4-yl)-3-methyl-1,3-dihydro-imidazo[4,5-c]quinolin-2-one (Intermediate A) and N-[2-chloro-5-(4,4,5,5-tetramethyl-[1,3,2]dioxaborolan-2-yl)-pyridin-3-yl]-acetamide (Stage 222.1.1) to give the title compound as an off-white solid. (HPLC: $t_R$ 2.33 min (Method A); M+H=462 MS-ES; $^1$H-NMR ($d_6$-DMSO, 400 MHz) 9.80 (s, 1H), 9.01 (s, 1H), 8.34-8.28 (m, 2H), 8.17-8.11 (m, 2H), 7.95-7.90 (m, 1H), 7.61-7.58 (m, 1H), 3.92 (s, 3H), 3.59 (s, 3H), 2.18 (s, 3H), 1.93 (s, 3H))

Stage 222.1.1 N-[2-Chloro-5-(4,4,5,5-tetramethyl-[1,3,2]dioxaborolan-2-yl)-pyridin-3-yl]-acetamide

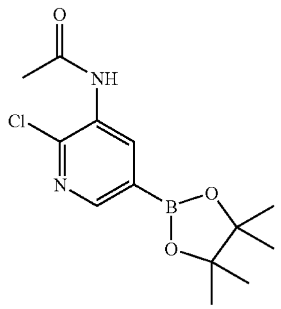 [SMILES: CC(=O)Nc1cc(B2OC(C)(C)C(C)(C)O2)cnc1Cl]

The title compound was synthesized in a similar manner as described for Stage 5.1.1 using N-(5-bromo-2-chloro-pyridin-3-yl)-acetamide (stage 222.1.2, 2.434 mmol) to give the title compound as a crude back oil. (degrading under the HPLC condition: $t_R$ 1.71 min (Method A); M+H=297 MS-ES).

Stage 222.1.2
N-(5-Bromo-2-chloro-pyridin-3-yl)-acetamide

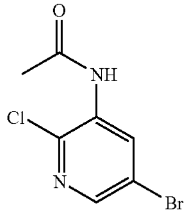

To a solution of 3-amino-5-bromo-2-chloropyridine (stage 152.1.2, 3.59 mmol) and triethylamine (1 ml) in dichloromethane (20 ml) was added acetyl chloride (Aldrich, Buchs, Switzerland, 0.312 ml). The RM was stirred for 17 h at rt then was added acetyl chloride (0.3 ml), the RM was stirred for 3 h at rt. Acetyl chloride (0.1 ml) was added and the RM was stirred for 1 h at rt. The RM was quenched with aqueous $NaHCO_3$ and extracted with EtOAc. The organic layer was washed with brine, dried over $Na_2SO_4$, filtered and evaporated. The residue was absorbed on silica gel and purified by flash chromatography (heptane/EtOAc 0% to 40%). The fractions containing product were evaporated together to give the title compound as a white solid. (HPLC: $t_R$ 2.46 min (Method A); M+H=249, 251 MS-ES)

Example 223

N-{2-Chloro-5-[1-(1,3-dimethyl-1H-pyrazol-4-yl)-3-methyl-2-oxo-2,3-dihydro-1H-imidazo[4,5-c]quinolin-8-yl]-pyridin-3-yl}-methanesulfonamide

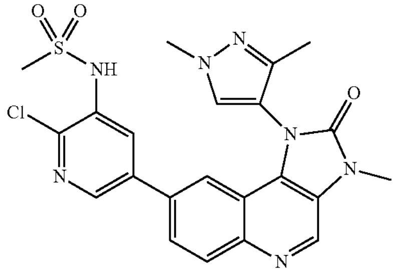 [SMILES: Cc1nn(C)cc1-n1c(=O)n(C)c2cnc3ccc(-c4cnc(Cl)c(NS(C)(=O)=O)c4)cc3c21]

The title compound was synthesized in a similar manner as described for Example 1.1 using 8-bromo-1-(1,3-dimethyl-1H-pyrazol-4-yl)-3-methyl-1,3-dihydro-imidazo[4,5-c]quinolin-2-one (Intermediate A) and N-[2-chloro-5-(4,4,5,5-tetramethyl-[1,3,2]dioxaborolan-2-yl)-pyridin-3-yl]-methanesulfonamide (Stage 223.1.1) to give the title compound as a white solid. (HPLC: $t_R$ 2.31 min (Method A); M+H=498 MS-ES; $^1$H-NMR ($d_6$-DMSO, 400 MHz) 9.87 (s, 1H), 9.01 (s, 1H), 8.41-8.38 (m, 1H), 8.18-8.11 (m, 2H), 7.98-7.93 (m, 1H), 7.91-7.88 (m, 1H), 7.62-7.59 (m, 1H), 3.92 (s, 3H), 3.59 (s, 3H), 3.18 (s, 3H), 1.95 (s, 3H))

Stage 223.1.1 N-[2-Chloro-5-(4,4,5,5-tetramethyl-[1,3,2]dioxaborolan-2-yl)-pyridin-3-yl]-methane-sulfonamide

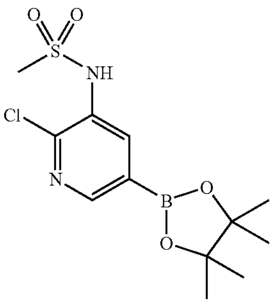

The title compound was synthesized in a similar manner as described for Stage 5.1.1 using N-(5-bromo-2-chloro-pyridin-3-yl)-methanesulfonamide (stage 223.1.2, 3.56 mmol) to give the title compound as a crude back oil. (degrading under the HPLC condition: $t_R$ 2.05 min (Method A); M+H=333 MS-ES).

Stage 223.1.2 N-(5-Bromo-2-chloro-pyridin-3-yl)-methanesulfonamide

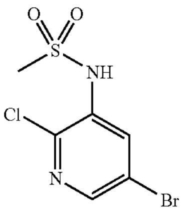

To a solution of 3-amino-5-bromo-2-chloropyridine (stage 152.1.2, 3.59 mmol) in pyridine (7 ml) was added methanesulfonyl chloride (Fluka, Buchs, Switzerland, 0.365 ml). The RM was stirred for 22 h at rt then was added methanesulfonyl chloride (0.2 ml), the RM was stirred for 5 h at rt. Methanesulfonyl chloride (0.2 ml) was added and the RM was stirred for 17 h at rt. The RM was evaporated to dryness and then taken in EtOAc, washed with aqueous $NaHCO_3$, with brine, dried over $Na_2SO_4$, filtered and evaporated. The residue was absorbed on silica gel and purified by flash chromatography (heptane/EtOAc 0% to 40%). The fractions containing product were evaporated together to give the title compound as a pink solid. (HPLC: $t_R$ 2.91 min (Method A); M+H=285, 287 MS-ES)

Example 224.1

2-Amino-5-[1-(1,3-dimethyl-1H-pyrazol-4-yl)-3-methyl-2-oxo-2,3-dihydro-1H-imidazo[4,5-c]quinolin-8-yl]-N-methyl-nicotinamide

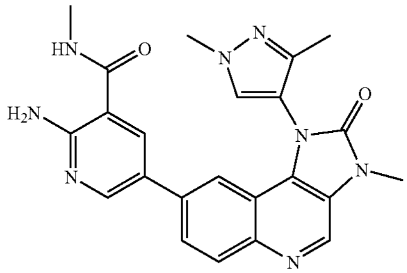 [SMILES: CNC(=O)c1cc(-c2ccc3ncc4c(c3c2)n(-c2cn(C)nc2C)c(=O)n4C)cnc1N]

The title compound was synthesized in a similar manner as described for Example 1.1 using 8-bromo-1-(1,3-dimethyl-1H-pyrazol-4-yl)-3-methyl-1,3-dihydro-imidazo[4,5-c]quinolin-2-one (Intermediate A) and 2-amino-N-methyl-5-(4,4,5,5-tetramethyl-[1,3,2]dioxaborolan-2-yl)-nicotinamide (Stage 224.1.1) to give the title compound as an off-white solid. (HPLC: $t_R$ 2.01 min (Method A); M+H=443 MS-ES; $^1$H-NMR ($d_6$-DMSO, 400 MHz) 8.92 (s, 1H), 8.54 (q, 1H), 8.14-8.11 (m, 2H), 8.10-8.06 (m, 2H), 7.96-7.92 (m, 1H), 7.47-7.44 (m, 1H), 7.27 (s, br, 2H), 3.89 (s, 3H), 3.57 (s, 3H), 2.78 (d, 3H), 1.95 (s, 3H))

Stage 224.1.1 2-Amino-N-methyl-5-(4,4,5,5-tetramethyl-[1,3,2]dioxaborolan-2-yl)-nicotinamide

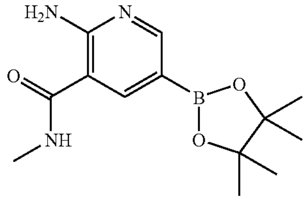 [SMILES: CNC(=O)c1cc(B2OC(C)(C)C(C)(C)O2)cnc1N]

The title compound was synthesized in a similar manner as described for Stage 5.1.1 using 2-amino-5-bromo-N-methyl-nicotinamide (stage 224.1.2, 0.352 mmol) to give the title compound as a crude brown oil. (degrading under the HPLC condition: $t_R$ 1.46 min (Method A); M+H=278 MS-ES).

Stage 224.1.2

2-Amino-5-bromo-N-methyl-nicotinamide

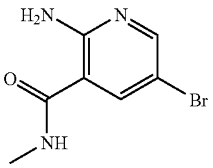

To a solution of 2-amino-5-bromonicotinic acid (Combi-Blocks, San Diego, USA, 1.355 mmol) and triethylamine (0.378 ml) in dichloromethane (10 ml) cooled with an ice-bath was added a solution of trichloromethyl chloroformate (Acros, Basel, Switzerland, 0.677 mmol) in dichloromethane (10 ml). After 40 min stirring at 0° C., was added a solution 8 M of methylamine in EtOH (1.7 ml). The RM was stirred for 30 min at rt then was diluted with dichloromethane, washed with saturated aqueous $NaHCO_3$, with brine, dried over $Na_2SO_4$, filtered and evaporated. The residue was taken in DMF and purified by preparative HPLC. The fractions containing product were basified with $NaHCO_3$, concentrated and extracted with dichloromethane (2×). The combined organic layers were washed with brine, dried over $Na_2SO_4$, filtered, evaporated and dried under vacuum to give the title compound as a white solid. (HPLC: $t_R$ 1.69 min (Method A); M+H=230, 232 MS-ES)

The following example was synthesized in a similar manner as described for Example 224.1 using the specified intermediate.

| Example | Intermed. | structure | Name of the example | MS-ES (M + H) | HPLC $t_R$ (min) |
| --- | --- | --- | --- | --- | --- |
| 224.2 | G | 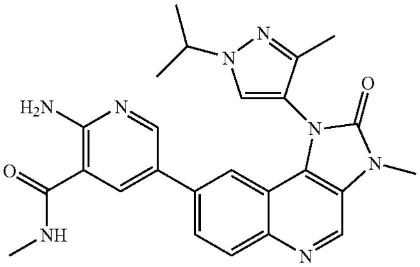 [SMILES: CNC(=O)c1cc(-c2ccc3ncc4c(c3c2)n(-c2cn(C(C)C)nc2C)c(=O)n4C)cnc1N] | 2-Amino-5-[1-(1-isopropyl-3-methyl-1H-pyrazol-4-yl)-3-methyl-2-oxo-2,3-dihydro-1H-imidazo[4,5-c]quinolin-8-yl]-N-methyl-nicotinamide | 471 | 2.12 |

Example 225

2-Amino-5-[1-(1,3-dimethyl-1H-pyrazol-4-yl)-3-methyl-2-oxo-2,3-dihydro-1H-imidazo[4,5-c]quinolin-8-yl]-N-isopropyl-nicotinamide

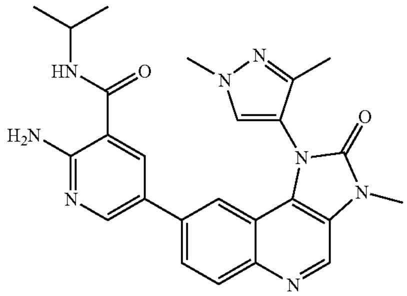 [SMILES: Cc1nn(C)cc1-n1c(=O)n(C)c2cnc3ccc(-c4cnc(N)c(C(=O)NC(C)C)c4)cc3c21]

The title compound was synthesized in a similar manner as described for Example 224 using isopropylamine (Aldrich, Buchs, Switzerland) as replacement for methylamine to give the title compound as an off-white solid. (HPLC: $t_R$ 2.20 min (Method A); M+H=471 MS-ES; $^1$H-NMR ($d_6$-DMSO, 400 MHz) 8.93 (s, 1H), 8.30 (d, 1H), 8.13-8.04 (s, 4H), 7.97-7.92 (m, 1H), 7.45-7.42 (m, 1H), 7.21 (s, br, 2H), 4.08 (oc, 1H), 3.88 (s, 3H), 3.57 (s, 3H), 1.97 (s, 3H), 1.22-1.15 (m, 6H))

Example 226

2-Amino-5-[1-(1,3-dimethyl-1H-pyrazol-4-yl)-3-methyl-2-oxo-2,3-dihydro-1H-imidazo[4,5-c]quinolin-8-yl]-N-(2-methoxy-ethyl)-nicotinamide

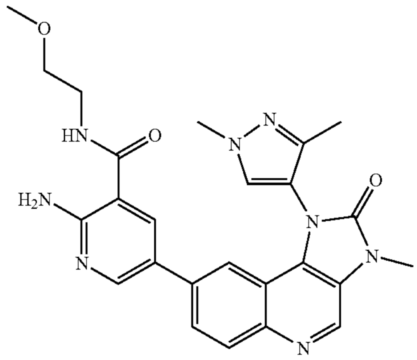

The title compound was synthesized in a similar manner as described for Example 224 using 2-methoxyethylamine (Fluka, Buchs, Switzerland) as replacement for methylamine to give the title compound as a white solid. (HPLC: $t_R$ 2.10 min (Method A); M+H=487 MS-ES; $^1$H-NMR ($d_6$-DMSO, 400 MHz) 8.93 (s, 1H), 8.65 (t, 1H), 8.15-8.06 (m, 4H), 7.97-7.93 (m, 1H), 7.47-7.44 (m, 1H), 7.27 (s, br, 2H), 3.89 (s, 3H), 3.57 (s, 3H), 3.50-3.34 (m, 4H), 3.26 (s, 3H), 1.96 (s, 3H))

Example 227

2-Amino-N-ethyl-5-[1-(1-isopropyl-3-methyl-1H-pyrazol-4-yl)-3-methyl-2-oxo-2,3-dihydro-1H-imidazo[4,5-c]quinolin-8-yl]-nicotinamide

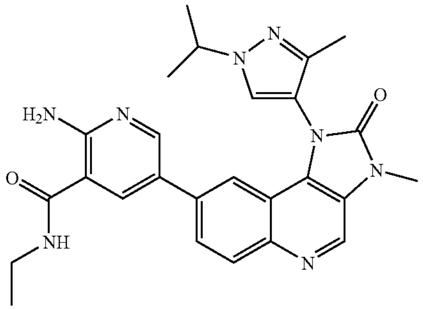 [SMILES: CCNC(=O)c1cc(-c2ccc3ncc4c(c3c2)n(-c2cn(C(C)C)nc2C)c(=O)n4C)cnc1N]

The title compound was synthesized in a similar manner as described for Example 1.1 using 8-bromo-1-(1-isopropyl-3-methyl-1H-pyrazol-4-yl)-3-methyl-1,3-dihydro-imidazo[4,5-c]quinolin-2-one (Intermediate G, 0.098 mmol) and 2-amino-N-methyl-5-(4,4,5,5-tetramethyl-[1,3,2]dioxaborolan-2-yl)-nicotinamide (stage 227.1.1) to give the title compound as a white solid. (HPLC: $t_R$ 2.22 min (Method A); M+H=485 MS-ES; $^1$H-NMR ($d_6$-DMSO, 400 MHz) 8.93 (s, 1H), 8.53 (t, 1H), 8.19 (s, 1H), 8.11-8.06 (m, 3H), 7.95-7.91 (m, 1H), 7.44-7.41 (m, 1H), 7.22 (s, br, 2H), 4.52 (hp, 1H), 3.57 (s, 3H), 3.35-3.18 (m, 2H), 1.96 (s, 3H), 1.47-1.42 (m, 6H), 1.14 (t, 3H))

Stage 227.1.1 2-Amino-N-methyl-5-(4,4,5,5-tetramethyl-[1,3,2]dioxaborolan-2-yl)-nicotinamide

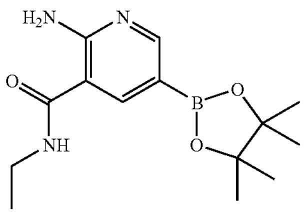 [SMILES: CCNC(=O)c1cc(B2OC(C)(C)C(C)(C)O2)cnc1N]

The title compound was synthesized in a similar manner as described for Stage 224.1.1 using 2 M ethylamine in MeOH (Aldrich, Buchs, Switzerland) as replacement for the methylamine to give the title compound as a crude brown sticky oil. (degrading under the HPLC condition: $t_R$ 1.69 min (Method A); M+H=292 MS-ES).

Example 228

2-{5-[1-(1,3-Dimethyl-1H-pyrazol-4-yl)-3-methyl-2-oxo-2,3-dihydro-1H-imidazo[4,5-c]quinolin-8-yl]-pyridin-3-yl}-N-methyl-acetamide

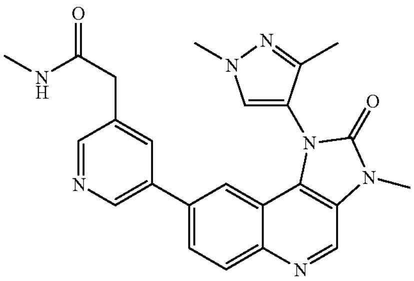

The title compound was synthesized in a similar manner as described for Example 1.1 using 8-bromo-1-(1,3-dimethyl-1H-pyrazol-4-yl)-3-methyl-1,3-dihydro-imidazo[4,5-c]quinolin-2-one (Intermediate A) and N-methyl-2-[5-(4,4,5,5-tetramethyl-[1,3,2]dioxaborolan-2-yl)-pyridin-3-yl]-acetamide (Stage 228.1.1) to give the title compound as an off-white foam. (HPLC: $t_R$ 1.97 min (Method A); M+H=442 MS-ES; $^1$H-NMR ($d_6$-DMSO, 400 MHz) 8.99 (s, 1H), 8.55-8.53 (m, 1H), 8.45-8.43 (m, 1H), 8.16-8.12 (m, 2H), 8.07-8.01 (m, 1H), 7.95-7.90 (m, 1H), 7.77-7.74 (m, 1H), 7.59-7.57 (m, 1H), 3.92 (s, 3H), 3.58 (s, 3H), 3.51 (s, 2H), 2.60 (d, 3H), 1.95 (s, 3H))

Stage 228.1.1 N-Methyl-2-[5-(4,4,5,5-tetramethyl-[1,3,2]dioxaborolan-2-yl)-pyridin-3-yl]-acetamide

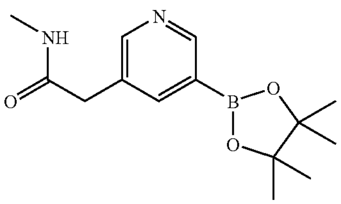 [SMILES: CNC(=O)Cc1cncc(B2OC(C)(C)C(C)(C)O2)c1]

The title compound was synthesized in a similar manner as described for Stage 5.1.1 using 2-(5-bromo-pyridin-3-yl)-N-methyl-acetamide (stage 228.1.2, 0.851 mmol) to give the title compound as a crude black oil. (degrading under the HPLC condition (Method A); M+H=277 MS-ES).

Stage 228.1.2 2-(5-Bromo-pyridin-3-yl)-N-methyl-acetamide

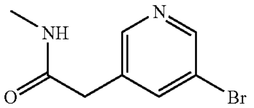

The title compound was synthesized in a similar manner as described for Example 103 using (5-bromo-pyridin-3-yl)-acetic acid (ABCR, Karlsruhe, Germany, 1.815 mmol) and 8 M methylamine in EtOH (Aldrich, Buchs, Switzerland, 7.26 mmol) to give the title compound as an off-white solid. (HPLC: $t_R$ 1.74 min (Method A); M+H=229, 231 MS-ES)

Example 229

1-(1,3-Dimethyl-1H-pyrazol-4-yl)-8-[5-(2-hydroxy-1,1-dimethyl-ethyl)-pyridin-3-yl]-3-methyl-1,3-dihydro-imidazo[4,5-c]quinolin-2-one

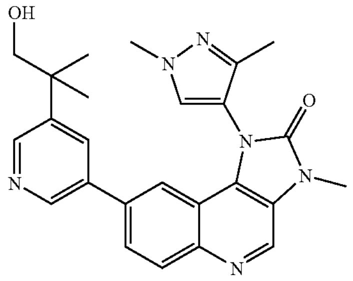 [SMILES: Cc1nn(C)cc1-n1c(=O)n(C)c2cnc3ccc(-c4cncc(C(C)(C)CO)c4)cc3c21]

To a solution of 2-{5-[1-(1,3-dimethyl-1H-pyrazol-4-yl)-3-methyl-2-oxo-2,3-dihydro-1H-imidazo[4,5-c]quinolin-8-yl]-pyridin-3-yl}-2-methyl-propionic acid methyl ester (Stage 229.1.1, 0.134 mmol) in THF (1.2 ml) were added MeOH (0.009 ml) and $NaBH_4$ (0.185 mmol) four times during the course of the heating at 40° C. for 39 h. After that, the RM was quenched with saturated aqueous $NaHCO_3$ and extracted with EtOAc (2×). The combined organic layers were washed with brine, dried over $Na_2SO_4$, filtered and evaporated. The residue was taken in DMF and purified by preparative HPLC. The fractions containing product were basified with $NaHCO_3$, concentrated and extracted with dichloromethane (2×). The combined organic layers were washed with brine, dried over $Na_2SO_4$, filtered, evaporated and dried under vacuum to give the title compound as a white foam. (HPLC: $t_R$ 2.06 min (Method A); M+H=442 MS-ES; $^1$H-NMR ($d_6$-DMSO, 400 MHz) 8.99 (s, 1H), 8.62-8.58 (m, 2H), 8.15-8.11 (m, 2H), 8.01-7.96 (m, 1H), 7.74-7.71 (m, 1H), 7.62-7.59 (m, 1H), 4.79 (t, 1H), 3.88 (s, 3H), 3.58 (s, 3H), 3.50 (d, 2H), 1.96 (s, 3H), 1.30 (s, 6H))

Stage 229.1.1 2-{5-[1-(1,3-Dimethyl-1H-pyrazol-4-yl)-3-methyl-2-oxo-2,3-dihydro-1H-imidazo[4,5-c]quinolin-8-yl]-pyridin-3-yl}-2-methyl-propionic acid methyl ester

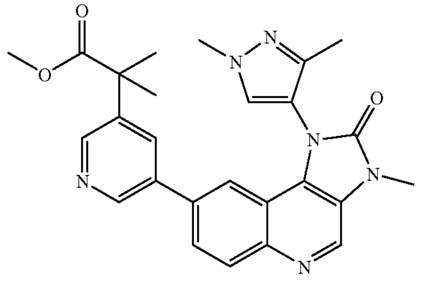

The title compound was synthesized in a similar manner as described for Example 1.1 using 8-bromo-1-(1,3-dimethyl-1H-pyrazol-4-yl)-3-methyl-1,3-dihydro-imidazo[4,5-c]quinolin-2-one (Intermediate A, 0.215 mmol) and 2-methyl-2-[5-(4,4,5,5-tetramethyl-[1,3,2]dioxaborolan-2-yl)-pyridin-3-yl]-propionic acid methyl ester (Stage 229.1.1, 0.279 mmol) to give the title compound as a brown solid. (HPLC: $t_R$ 2.28 min (Method A); M+H=471 MS-ES)

Stage 229.1.2 2-Methyl-2-[5-(4,4,5,5-tetramethyl-[1,3,2]dioxaborolan-2-yl)-pyridin-3-yl]-propionic acid methyl ester

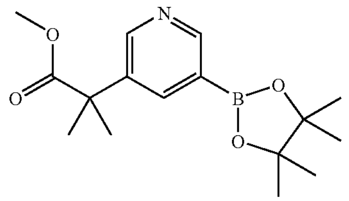 [SMILES: COC(=O)C(C)(C)c1cncc(B2OC(C)(C)C(C)(C)O2)c1]

The title compound was synthesized in a similar manner as described for Stage 5.1.1 using 2-(5-bromo-pyridin-3-yl)-2-methyl-propionic acid methyl ester (stage 229.1.2, 0.872 mmol) to give the title compound as a crude black sticky solid. (degrading under the HPLC condition: $t_R$ 2.20 min (Method A); M+H=306 MS-ES).

Stage 229.1.3

2-(5-Bromo-pyridin-3-yl)-2-methyl-propionic acid methyl ester

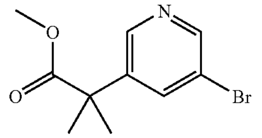

The title compound was synthesized in a similar manner as described for stage 220.1.2 using (5-bromo-pyridin-3-yl)-acetic acid methyl ester (stage 229.1.4, 1.815 mmol) to give the title compound as yellowish oil. (HPLC: $t_R$ 2.74 min (Method A); M+H=258, 260 MS-ES)

Stage 229.1.4 (5-Bromo-pyridin-3-yl)-acetic acid methyl ester

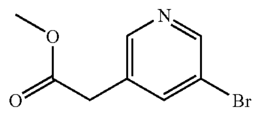

A mixture of (5-bromo-pyridin-3-yl)-acetic acid (ABCR, Karlsruhe, Germany, 4.54 mmol) and concentrated sulfuric acid (0.02 ml) in MeOH was refluxed for 13.5 h. The RM was concentrated, taken in EtOAc and sonicated. The organic layer was washed with saturated aqueous $NaHCO_3$, with brine, dried over $Na_2SO_4$, filtered and evaporated to dryness to give the title compound as a brown oil. (HPLC: $t_R$ 2.21 min (Method A); M+H=230, 232 MS-ES)

Example 230

8-(5-Aminomethyl-pyridin-3-yl)-1-(1,3-dimethyl-1H-pyrazol-4-yl)-3-methyl-1,3-dihydro-imidazo[4,5-c]quinolin-2-one

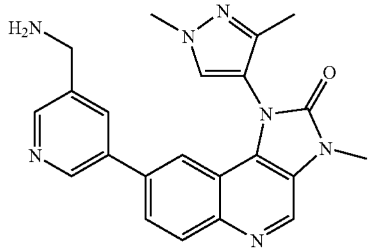 [SMILES: Cc1nn(C)cc1-n1c(=O)n(C)c2cnc3ccc(-c4cncc(CN)c4)cc3c21]

The title compound was synthesized in a similar manner as described for Example 1.1 using 8-bromo-1-(1,3-dimethyl-1H-pyrazol-4-yl)-3-methyl-1,3-dihydro-imidazo[4,5-c] quinolin-2-one (Intermediate A) and 3-(N-boc-aminomethyl) pyridine-5-boronic acid pinacol ester (Frontier Scientific, Logan, USA) to give the title compound as an off-white solid. (HPLC: $t_R$ 1.87 min (Method A); M+H=400 MS-ES; $^1$H-NMR ($d_6$-DMSO, 400 MHz) 8.99 (s, 1H), 8.56-8.51 (m, 2H), 8.17-8.11 (m, 2H), 7.99-7.95 (m, 1H), 7.86-7.83 (m, 1H), 7.61-7.58 (m, 1H), 3.92 (s, 3H), 3.79 (s, 2H), 3.58 (s, 3H), 2.06-1.97 (br, 2H), 1.95 (s, 3H))

Example 231

N-{5-[1-(1,3-Dimethyl-1H-pyrazol-4-yl)-3-methyl-2-oxo-2,3-dihydro-1H-imidazo[4,5-c]quinolin-8-yl]-pyridin-3-ylmethyl}-acetamide

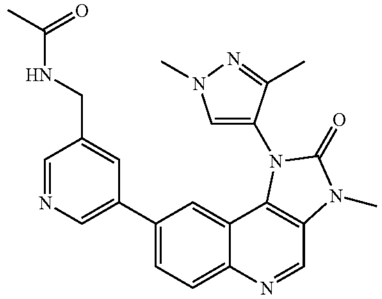 [SMILES: CC(=O)NCc1cncc(-c2ccc3ncc4c(c3c2)n(-c2cn(C)nc2C)c(=O)n4C)c1]

To a mixture of 8-(5-aminomethyl-pyridin-3-yl)-1-(1,3-dimethyl-1H-pyrazol-4-yl)-3-methyl-1,3-dihydro-imidazo [4,5-c]quinolin-2-one (Example 230, 0.053 mmol) and Hünig's base (0.014 ml) in dichloromethane (1 ml) was added acetyl chloride (Aldrich, Buchs, Switzerland, 0.058 mmol). The RM was stirred for 45 min at it then evaporated to dryness. The residue was taken in MeOH and purified by preparative HPLC. The fractions containing product were basified with $NaHCO_3$, concentrated and extracted with dichloromethane (2×). The combined organic layers were washed with brine, dried over $Na_2SO_4$, filtered, evaporated and dried under vacuum to give the title compound as a white solid. (HPLC: $t_R$ 1.95 min (Method A); M+H=442 MS-ES; $^1$H-NMR ($d_6$-DMSO, 400 MHz) 8.99 (s, 1H), 8.56-8.53 (m, 1H), 8.48-8.46 (m, 1H), 8.40 (t, 1H), 8.16-8.12 (m, 2H), 7.94-7.90 (m, 1H), 7.78-7.75 (m, 1H), 7.58-7.56 (m, 1H), 4.38-4.27 (m, 2H), 3.92 (s, 3H), 3.58 (s, 3H), 1.95 (s, 3H), 1.89 (s, 3H))

Example 232

8-(5-Aminomethyl-pyridin-3-yl)-1-(1,3-dimethyl-1H-pyrazol-4-yl)-3-methyl-1,3-dihydro-imidazo[4,5-c]quinolin-2-one

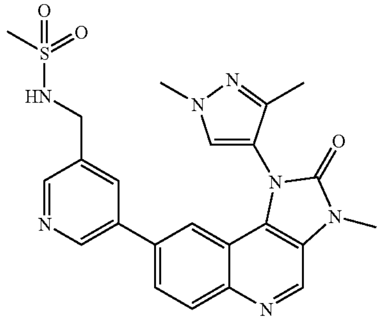

The title compound was synthesized in a similar manner as described for Example 231 using methanesulfonyl chloride (Aldrich, Buchs, Switzerland) to give the title compound as a white solid. (HPLC: $t_R$ 1.98 min (Method A); M+H=478 MS-ES; $^1$H-NMR ($d_6$-DMSO, 400 MHz) 9.01-8.99 (m, 1H), 8.58-8.55 (m, 2H), 8.17-8.13 (m, 2H), 7.95-7.91 (m, 2H), 7.65-7.58 (m, 2H), 4.26 (s, 2H), 3.92 (s, 3H), 3.58 (s, 3H), 2.96 (s, 3H), 1.95 (s, 3H))

Example 233

1-(1,3-Dimethyl-1H-pyrazol-4-yl)-3-methyl-8-(1,3,3-trimethyl-2-oxo-2,3-dihydro-1H-pyrrolo[2,3-b]pyridin-5-yl)-1,3-dihydro-imidazo[4,5-c]quinolin-2-one

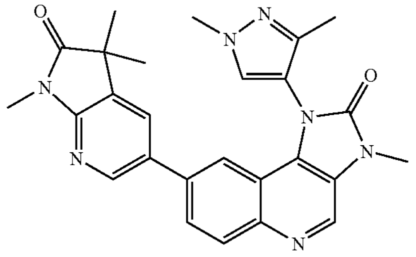

The title compound was synthesized in a similar manner as described for Example 1.1 using 8-bromo-1-(1,3-dimethyl-1H-pyrazol-4-yl)-3-methyl-1,3-dihydro-imidazo[4,5-c]quinolin-2-one (Intermediate A) and 1,3,3-trimethyl-5-(4,4,5,5-tetramethyl-[1,3,2]dioxaborolan-2-yl)-1,3-dihydro-pyrrolo[2,3-b]pyridin-2-one (Stage 233.1.1) to give the title compound as a white solid. (HPLC: $t_R$ 2.53 min (Method A); M+H=468 MS-ES; $^1$H-NMR ($d_6$-DMSO, 400 MHz) 8.96 (s, 1H), 8.32-8.29 (m, 1H), 8.14-8.09 (m, 2H), 7.96-7.91 (m, 1H), 7.79-7.76 (m, 1H), 7.54-7.51 (m, 1H), 3.90 (s, 3H), 3.58 (s, 3H), 3.18 (s, 3H), 1.96 (s, 3H), 1.37 (s, 3H), 1.36 (s, 3H))

Stage 233.1.1 1,3,3-Trimethyl-5-(4,4,5,5-tetramethyl-[1,3,2]dioxaborolan-2-yl)-1,3-dihydro-pyrrolo[2,3-b]pyridin-2-one

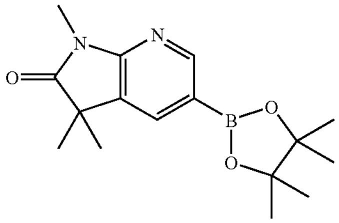 [SMILES: CN1C(=O)C(C)(C)c2cc(B3OC(C)(C)C(C)(C)O3)cnc21]

The title compound was synthesized in a similar manner as described for Stage 5.1.1 using 5-bromo-1,3,3-trimethyl-1,3-dihydro-pyrrolo[2,3-b]pyridin-2-one (stage 233.1.2, 0.779 mmol) to give the title compound as a crude black solid. (degrading under the HPLC condition: $t_R$ 2.05 min (Method A); M+H=303 MS-ES).

Stage 233.1.2 5-Bromo-1,3,3-trimethyl-1,3-dihydro-pyrrolo[2,3-b]pyridin-2-one

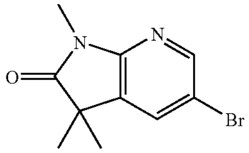

To a mixture of 5-bromo-1,3-dihydro-pyrrolo[2,3-b]pyridin-2-one (Aldrich, Buchs, Switzerland, 1.394 min) in DMF (7 ml) cooled with an ice-bath was added 55% NaH in oil (1.6 mmol) and the RM was stirred for 30 min at rt, then was added iodomethane (0.1 ml) and the RM was stirred for 30 min at rt. The RM was cooled with an ice-bath and was added 55% NaH in oil (1.6 mmol) and the RM was stirred for 15 min at rt, then was added iodomethane (0.1 ml) and the RM was stirred for 30 min at rt. The RM was cooled with an ice-bath and was added 55% NaH in oil (1.6 mmol) and the RM was stirred for 15 min at rt, then was added iodomethane (0.1 ml) and the RM was stirred for 1.5 h at rt. The RM was quenched with saturated aqueous $NaHCO_3$ and extracted with EtOAc. The organic layer was washed with brine (3×), dried over $Na_2SO_4$, filtered and evaporated. The residue was absorbed on silica gel and purified by flash chromatography (heptane/EtOAc 0% to 40%). The fractions containing product were evaporated together to give the title compound as an off-white solid. (HPLC: $t_R$ 2.99 min (Method A); M+H=255, 257 MS-ES)

Example 234.1

8-(2,4-Dimethoxy-pyrimidin-5-yl)-1-(1-ethyl-3-methyl-1H-pyrazol-4-yl)-3-methyl-1,3-dihydro-imidazo[4,5-c]quinolin-2-one

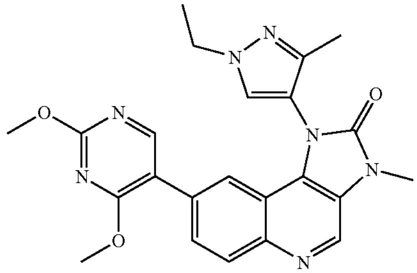

The title compound was synthesized in a similar manner as described for Example 1.1 using 8-bromo-1-(1-ethyl-3-methyl-1H-pyrazol-4-yl)-3-methyl-1,3-dihydro-imidazo[4,5-c]quinolin-2-one (Intermediate F, 0.101 mmol) and 2,4-dimethoxypyrimidine-5-boronic acid pinacol ester (Frontier Scientific, Logan, USA, 0.119 mmol) to give the title compound as a white foam. (HPLC: $t_R$ 2.51 min (Method A); M+H=446 MS-ES; $^1$H-NMR ($d_6$-DMSO, 400 MHz) 8.97 (s, 1H), 8.32 (s, 1H), 8.11 (s, 1H), 8.07-8.04 (m, 1H), 7.78-7.74 (m, 1H), 7.56-7.54 (m, 1H), 4.14 (q, 2H), 3.92 (s, 1H), 3.92 (s, 3H), 3.57 (s, 3H), 1.95 (s, 3H), 1.33 (t, 3H))

The following examples were synthesized in a similar manner as described for Example 234.1 using the specified intermediate.

| Example | Intermed. | structure | Name of the example | MS-ES (M + H) | HPLC $t_R$ (min) |
|---|---|---|---|---|---|
| 234.2 | A | 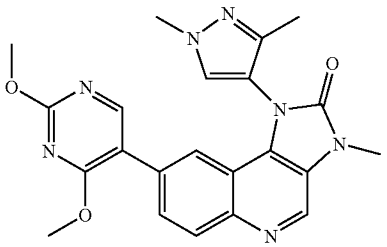 [SMILES: COc1ncc(-c2ccc3ncc4c(c3c2)n(-c2cn(C)nc2C)c(=O)n4C)c(OC)n1] | 8-(2,4-Dimethoxy-pyrimidin-5-yl)-1-(1,3-dimethyl-1H-pyrazol-4-yl)-3-methyl-1,3-dihydro-imidazo[4,5-c]quinolin-2-one | 432 | 2.43 |
| 234.3 | G | 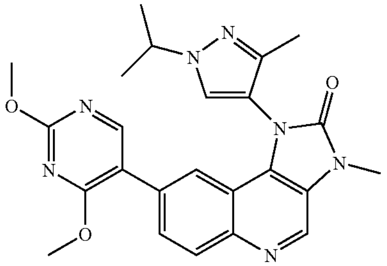 [SMILES: COc1ncc(-c2ccc3ncc4c(c3c2)n(-c2cn(C(C)C)nc2C)c(=O)n4C)c(OC)n1] | 8-(2,4-Dimethoxy-pyrimidin-5-yl)-1-(1-isopropyl-3-methyl-1H-pyrazol-4-yl)-3-methyl-1,3-dihydro-imidazo[4,5-c]quinolin-2-one | 460 | 2.62 |
| 234.4 | C | 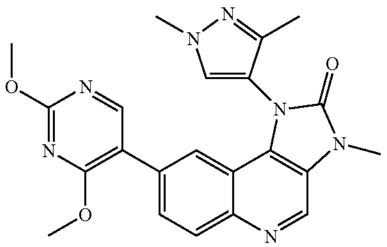 [SMILES: COc1ncc(-c2ccc3ncc4c(c3c2)n(-c2cn(C)nc2C)c(=O)n4C)c(OC)n1] | 8-(2,4-Dimethoxy-pyrimidin-5-yl)-1-(2,5-dimethyl-2H-pyrazol-3-yl)-3-methyl-1,3-dihydro-imidazo[4,5-c]quinolin-2-one | 432 | 2.56 |

Example 235

1-(1,3-Dimethyl-1H-pyrazol-4-yl)-8-(2-ethylamino-4-methoxy-pyrimidin-5-yl)-3-methyl-1,3-dihydro-imidazo[4,5-c]quinolin-2-one

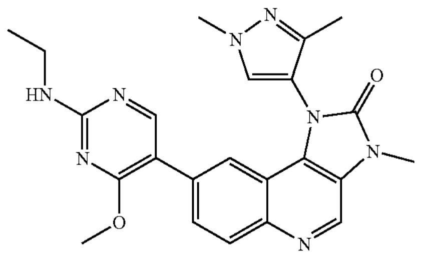 [SMILES: CCNc1ncc(-c2ccc3ncc4c(c3c2)n(-c2cn(C)nc2C)c(=O)n4C)c(OC)n1]

The title compound was synthesized in a similar manner as described for Example 1.1 using 8-bromo-1-(1,3-dimethyl-1H-pyrazol-4-yl)-3-methyl-1,3-dihydro-imidazo[4,5-c]quinolin-2-one (Intermediate A) and ethyl-[4-methoxy-5-(4,4,5,5-tetramethyl-[1,3,2]dioxaborolan-2-yl)-pyrimidin-2-yl]-amine (Stage 235.1.1) to give the title compound as a white solid. (HPLC: $t_R$ 2.24 min (Method A); M+H=445 MS-ES; $^1$H-NMR ($d_6$-DMSO, 400 MHz) 8.91 (s, 1H), 8.16-8.06 (m, 3H), 8.01-7.97 (m, 1H), 7.74-7.69 (m, 1H), 7.61-7.58 (m, 1H), 3.88 (s, 3H), 3.84 (s, br, 3H), 3.56 (s, 3H), 3.36-3.28 (m, 2H), 1.93 (s, 3H), 1.13 (t, 3H))

Stage 235.1.1 Ethyl-[4-methoxy-5-(4,4,5,5-tetramethyl-[1,3,2]dioxaborolan-2-yl)-pyrimidin-2-yl]-amine

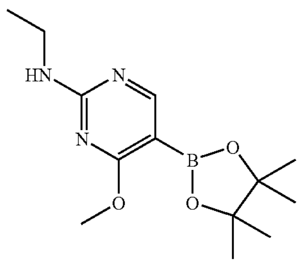 [SMILES: CCNc1ncc(B2OC(C)(C)C(C)(C)O2)c(OC)n1]

The title compound was synthesized in a similar manner as described for Stage 5.1.1 using (5-bromo-4-methoxy-pyrimidin-2-yl)-ethyl-amine (stage 235.1.2, 0.366 mmol) to give the title compound as a crude back oil. (degrading under the HPLC condition: $t_R$ 1.91 min (Method A); M+H=280 MS-ES).

Stage 235.1.2 (5-Bromo-4-methoxy-pyrimidin-2-yl)-ethyl-amine

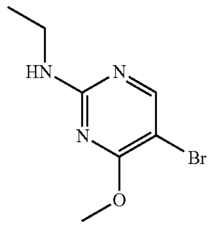

To a solution of 5-bromo-2-chloro-4-methoxypyrimidine (Frontier Scientific, Logan, USA, 0.895 mmol) in THF (2.5 ml) cooled with an ice-bath was added a 2 M solution of ethylamine in MeOH (Aldrich, Buchs, Switzerland, 0.492 ml). The RM was stirred at 0° C. for 1 h and at rt for 66 h then the reaction mixture was diluted with EtOAc, washed with saturated aqueous $NaHCO_3$, with brine, dried over $Na_2SO_4$, filtered and evaporated. The residue was absorbed on silica gel and purified by flash chromatography ($CH_2Cl_2$/iPrOH 0% to 6%) to give after evaporation of the fractions containing the title compound an off-white solid. (HPLC: $t_R$ 2.16min (Method A); M+H=232, 234 MS-ES)

Example 236

1-(1-Ethyl-3-methyl-1H-pyrazol-4-yl)-8-(4-methoxy-2-methylamino-pyrimidin-5-yl)-3-methyl-1,3-dihydro-imidazo[4,5-c]quinolin-2-one

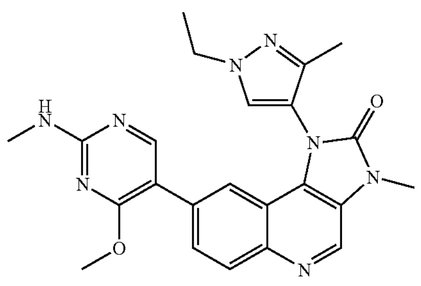

The title compound was synthesized in a similar manner as described for Example 1.1 using 8-bromo-1-(1-ethyl-3-methyl-1H-pyrazol-4-yl)-3-methyl-1,3-dihydro-imidazo[4,5-c]quinolin-2-one (Intermediate F) and [4-methoxy-5-(4,4,5,5-tetramethyl-[1,3,2]dioxaborolan-2-yl)-pyrimidin-2-yl]-methyl-amine (stage 236.1.1) to give the title compound as a white solid. (HPLC: $t_R$ 2.19 min (Method A); M+H=445 MS-ES; $^1$H-NMR ($d_6$-DMSO, 400 MHz) 8.91 (s, 1H), 8.11 (s, 1H), 8.08-8.02 (m, 1H), 8.01-7.97 (m, 1H), 7.74-7.69 (m, 1H), 7.50-7.48 (m, 1H), 7.27-7.16 (m, 1H), 4.15 (q, 2H), 3.85 (s, br, 3H), 3.56 (s, 3H), 2.82 (d, 3H), 1.95 (s, 3H) 1.36 (t, 3H))

Stage 236.1.1 [4-Methoxy-5-(4,4,5,5-tetramethyl-[1,3,2]dioxaborolan-2-yl)-pyrimidin-2-yl]-methyl-amine

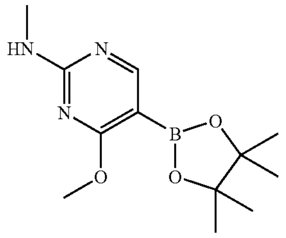 [SMILES: CNc1ncc(B2OC(C)(C)C(C)(C)O2)c(OC)n1]

The title compound was synthesized in a similar manner as described for Stage 235.1.1 using 8 M methylamine in EtOH (Fluka, Buchs, Switzerland, 0.366 mmol) to give the title compound as a crude back oil. (degrading under the HPLC condition: $t_R$ 1.69 min (Method A); M+H=266 MS-ES).

Example 237

1-(1,3-Dimethyl-1H-pyrazol-4-yl)-8-(1-ethyl-2-oxo-1,4-dihydro-2H-pyrido[3,2-d][1,3]oxazin-7-yl)-3-methyl-1,3-dihydro-imidazo[4,5-c]quinolin-2-one

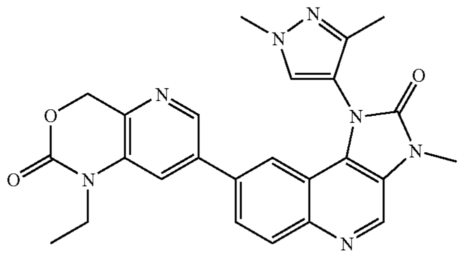 [SMILES: CCN1C(=O)OCc2ncc(-c3ccc4ncc5c(c4c3)n(-c3cn(C)nc3C)c(=O)n5C)cc21]

A mixture of acetic acid 3-(tert-butoxycarbonyl-ethyl-amino)-5-[1-(1,3-dimethyl-1H-pyrazol-4-yl)-3-methyl-2-oxo-2,3-dihydro-1H-imidazo[4,5-c]quinolin-8-yl]-pyridin-2-ylmethyl ester (stage 155.1.1, 0.107 mmol) and KCN (0.16 mmol) in EtOH (0.6 ml) was stirred for 17 h at 80° C. The RM was diluted with EtOAc and washed with water, with brine, dried over $Na_2SO_4$, filtered and evaporated. The residue The residue was absorbed on silica gel and purified by flash chromatography ($CH_2Cl_2$/MeOH 0% to 8%). The fractions containing product were evaporated together to give the title compound as an off-white solid. (HPLC: $t_R$ 2.42 min (Method A); M+H=470 MS-ES; $^1$H-NMR ($d_6$-DMSO, 400 MHz) 9.00 (s, 1H), 8.35-8.32 (m, 1H), 8.17-8.13 (m, 1H), 8.11 (s, 1H), 8.04-8.00 (m, 1H), 7.62-7.59 (m, 1H), 7.49-7.47 (m, 1H), 5.40-5.31 (m, 2H), 4.04-3.85 (m, 2H), 3.87 (s, 3H), 3.59 (s, 3H), 1.97 (s, 3H), 1.24 (t, 3H))

Example 238

8-(5-Chloro-6-hydroxymethyl-pyridin-3-yl)-1-(1,3-dimethyl-1H-pyrazol-4-yl)-3-methyl-1,3-dihydro-imidazo[4,5-c]quinolin-2-one

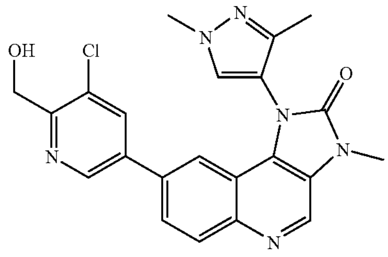 [SMILES: Cc1nn(C)cc1-n1c(=O)n(C)c2cnc3ccc(-c4cnc(CO)c(Cl)c4)cc3c21]

The title compound was synthesized in a similar manner as described for Example 169.1 using 8-bromo-1-(1,3-dimethyl-1H-pyrazol-4-yl)-3-methyl-1,3-dihydro-imidazo[4,5-c]quinolin-2-one (Intermediate A) and acetic acid 3-chloro-5-(4,4,5,5-tetramethyl-[1,3,2]dioxaborolan-2-yl)-pyridin-2-ylmethyl ester (Stage 238.1.1) to give the title compound as an off-white solid. (HPLC: $t_R$ 2.27 min (Method A); M+H=435 MS-ES; $^1$H-NMR ($d_6$-DMSO, 400 MHz) 9.00 (s, 1H), 8.65-8.62 (m, 1H), 8.18-8.11 (m, 2H), 8.05-8.00 (m, 1H), 7.97-7.94 (m, 1H), 7.58-7.55 (m, 1H), 5.30 (t, 1H), 4.67 (d, 2H), 3.94 (s, 3H), 3.58 (s, 3H), 1.95 (s, 3H))

Stage 238.1.1 Acetic acid 3-chloro-5-(4,4,5,5-tetramethyl-[1,3,2]dioxaborolan-2-yl)-pyridin-2-ylmethyl ester

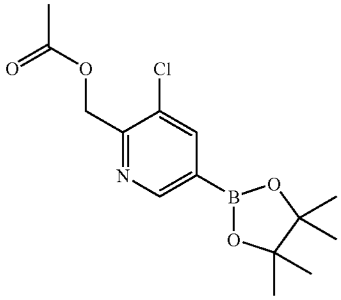 [SMILES: CC(=O)OCc1ncc(B2OC(C)(C)C(C)(C)O2)cc1Cl]

The title compound was synthesized in a similar manner as described for Stage 5.1.1 using acetic acid 5-bromo-3-chloro-pyridin-2-ylmethyl ester (stage 238.1.2, 0.306 mmol) to give the title compound as a crude back oil. (degrading under the HPLC condition: $t_R$ 2.65 min (Method A); M+H=312 MS-ES).

Stage 238.1.2 Acetic acid 5-bromo-3-chloro-pyridin-2-ylmethyl ester

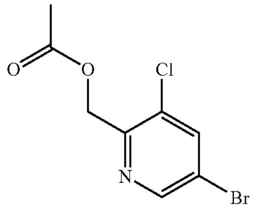

The title compound was synthesized in a similar manner as described for Stage 194.1.2 using (5-bromo-3-chloro-pyridin-2-yl)-methanol (stage 238.1.3, 0.351 mmol) to give the title compound as an oil. (HPLC: $t_R$ 3.04 min (Method A); M+H=264 (BrCl pattern) MS-ES)

Stage 238.1.3 (5-Bromo-3-chloro-pyridin-2-yl)-methanol

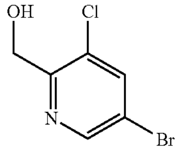

The title compound was synthesized in a similar manner as described for Stage 190.1.2-3 using 5-bromo-3-chloro-2-methyl-pyridine (stage 238.1.4, 0.801 mmol) to give the title compound as a white solid. (HPLC: $t_R$ 2.40 min (Method A); M+H=222, 244 MS-ES)

Stage 238.1.4 5-Bromo-3-chloro-2-methyl-pyridine

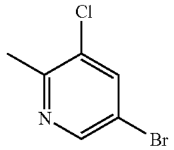

The title compound was synthesized in a similar manner as described for Stage 75.1.5 using 5-bromo-2,3-dichloropyridine (Asymchem Laboratories, Morrisville, N.C., USA, 2.182 mmol) to give the title compound as a crude black solid. (HPLC: $t_R$ 3.29 min (Method A); M+H=206, 208 MS-ES)

Example 239

1-(1,3-Dimethyl-1H-pyrazol-4-yl)-8-[5-(1-methoxy-1-methyl-ethyl)-pyridin-3-yl]-3-methyl-1,3-dihydro-imidazo[4,5-c]quinolin-2-one

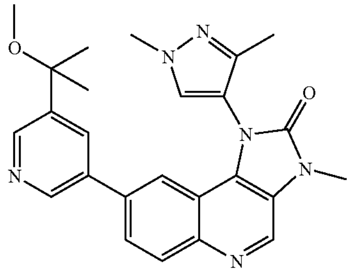 [SMILES: COC(C)(C)c1cncc(-c2ccc3ncc4c(c3c2)n(-c2cn(C)nc2C)c(=O)n4C)c1]

The title compound was synthesized in a similar manner as described for Example 104 using 1-(1,3-dimethyl-1H-pyrazol-4-yl)-8-[5-(1-hydroxy-1-methyl-ethyl)-pyridin-3-yl]-3-methyl-1,3-dihydro-imidazo[4,5-c]quinolin-2-one (Example 215.2, 0.121 mmol) to give the title compound as a film. (HPLC: $t_R$ 2.19 min (Method A); M+H=443 MS-ES; $^1$H-NMR ($d_6$-DMSO, 400 MHz) 8.99 (s, 1H), 8.71-8.68 (m, 1H), 8.62-8.59 (m, 1H), 8.16-8.11 (m, 2H), 8.04-7.99 (m, 1H), 7.76-7.73 (m, 1H), 7.63-7.60 (m, 1H), 3.89 (s, 3H), 3.58 (s, 3H), 3.05 (s, 3H), 1.97 (s, 3H), 1.54 (s, 6H))

Example 240

1-(1,3-Dimethyl-1H-pyrazol-4-yl)-8-[5-(1-ethoxy-1-methyl-ethyl)-pyridin-3-yl]-3-methyl-1,3-dihydro-imidazo[4,5-c]quinolin-2-one

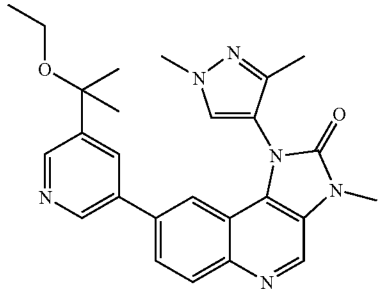 [SMILES: CCOC(C)(C)c1cncc(-c2ccc3ncc4c(c3c2)n(-c2cn(C)nc2C)c(=O)n4C)c1]

The title compound was synthesized in a similar manner as described for Example 104 using 1-(1,3-dimethyl-1H-pyrazol-4-yl)-8-[5-(1-hydroxy-1-methyl-ethyl)-pyridin-3-yl]-3-methyl-1,3-dihydro-imidazo[4,5-c]quinolin-2-one (Example 215.2, 0.063 mmol) and iodethane as replacement for the iodomethane to give the title compound as a film. (HPLC: $t_R$ 2.30 min (Method A); M+H=457 MS-ES; $^1$H-NMR ($d_6$-DMSO, 400 MHz) 8.99 (s, 1H), 8.69-8.67 (m, 1H), 8.63-8.61 (m, 1H), 8.16-8.12 (m, 2H), 8.03-7.98 (m, 1H), 7.77-7.74 (m, 1H), 7.63-7.61 (m, 1H), 3.89 (s, 3H), 3.58 (s, 3H), 3.21 (q, 2H), 1.97 (s, 3H), 1.55 (s, 3H), 1.54 (s, 3H), 1.09 (t, 3H))

Example 241

1-(1-isopropyl-3-methyl-1H-pyrazol-4-yl)-3-methyl-8-(6-(methylamino)pyridin-3-yl)-1H-imidazo[4,5-c]quinoline-2(3H)-thione

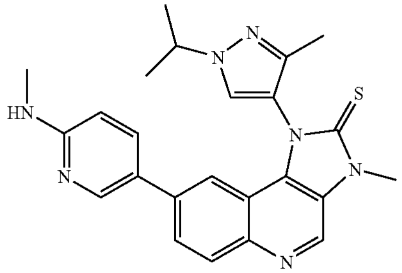 [SMILES: CNc1ccc(-c2ccc3ncc4c(c3c2)n(-c2cn(C(C)C)nc2C)c(=S)n4C)cn1]

The title compound was synthesized in a similar manner as described for Example 128.1 using 1-(1-isopropyl-3-methyl-1H-pyrazol-4-yl)-3-methyl-8-(6-methylamino-pyridin-3-yl)-1,3-dihydro-imidazo[4,5-c]quinolin-2-one (Example 118.1, 0.051 mmol) to give the title compound as a white solid. (HPLC: $t_R$ 2.44 min (Method A); M+H=444 MS-ES; $^1$H-NMR ($d_6$-DMSO, 400 MHz) 9.11 (s, 1H), 8.21-8.17 (m, 2H), 8.12-8.08 (m, 1H), 7.95-7.90 (m, 1H), 7.49-7.44 (m, 1H), 7.39-7.36 (m, 1H), 6.75 (q, 1H), 6.50-6.45 (m, 1H), 4.58 (hp, 1H), 3.94 (s, 3H), 2.79 (d, 3H), 1.93 (s, 3H), 1.52-1.46 (m, 6H))

Example 242.1

5-[1-(1,3-Dimethyl-1H-pyrazol-4-yl)-3-methyl-2-oxo-2,3-dihydro-1H-imidazo[4,5-c]quinolin-8-yl]-N-ethyl-2-methylamino-nicotinamide

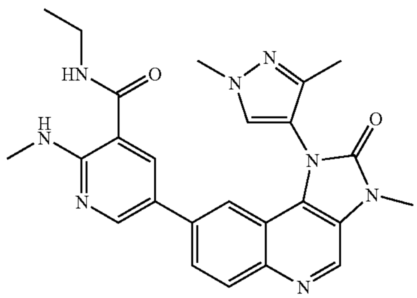

The title compound was synthesized in a similar manner as described for Example 1.1 using 8-bromo-1-(1,3-dimethyl-1H-pyrazol-4-yl)-3-methyl-1,3-dihydro-imidazo[4,5-c]quinolin-2-one (Intermediate A) and N-ethyl-2-methylamino-5-(4,4,5,5-tetramethyl-[1,3,2]dioxaborolan-2-yl)-nicotinamide (Stage 242.1.1) to give the title compound as a yellowish foam. (HPLC: $t_R$ 2.17 min (Method A); M+H=471 MS-ES; $^1$H-NMR ($d_6$-DMSO, 400 MHz) 8.92 (s, 1H), 8.58 (t, 1H), 8.25-8.20 (m, 2H), 8.11-8.06 (m, 2H), 8.05-8.02 (m, 1H), 7.96-7.92 (m, 1H), 7.47-7.44 (m, 1H), 3.89 (s, 3H), 3.57 (s, 3H), 3.40-3.19 (m, 2H), 2.93 (d, 3H), 1.97 (s, 3H), 1.15 (t, 3H))

Stage 242.1.1 N-Ethyl-2-methylamino-5-(4,4,5,5-tetramethyl-[1,3,2]dioxaborolan-2-yl)-nicotinamide

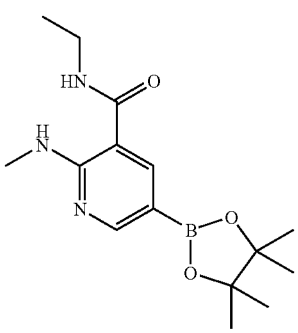

The title compound was synthesized in a similar manner as described for Stage 227.1.1 using 5-bromo-2-methylamino-nicotinic acid (Princeton BioMolecular Research, Monmouth Junction, N.J., USA) to give the title compound as a crude brown oil. (degrading under the HPLC condition: $t_R$ 1.81 min (Method A); M+H=306 MS-ES).

The following example was synthesized in a similar manner as described for Example 242.1 using the specified intermediate.

Example 243

1-(1,3-Dimethyl-1H-pyrazol-4-yl)-8-(5-ethoxy-6-hydroxymethyl-pyridin-3-yl)-3-methyl-1,3-dihydro-imidazo[4,5-c]quinolin--one

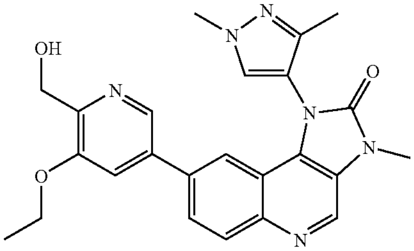 [SMILES: CCOc1cc(-c2ccc3ncc4c(c3c2)n(-c2cn(C)nc2C)c(=O)n4C)cnc1CO]

The title compound was synthesized in a similar manner as described for Example 190 using ethanol as replacement for isopropanol to give the title compound as a white solid. (HPLC: $t_R$ 2.11 min (Method A); M+H=445 MS-ES; $^1$H-NMR ($d_6$-DMSO, 400 MHz) 8.99 (s, 1H), 8.28-8.25 (m, 1H), 8.14-8.10 (m, 2H), 8.04-8.00 (m, 1H), 7.63-7.61 (m, 1H), 7.38-7.35 (m, 1H), 4.88 (t, 1H), 4.57 (d, 2H), 4.22-4.14 (m, 2H), 3.89 (s, 3H), 3.58 (s, 3H), 1.97 (s, 3H), 1.41 (t, 3H))

Example 244

1-(1,3-Dimethyl-1H-pyrazol-4-yl)-8-[6-hydroxymethyl-5-(2-methoxy-ethoxy)-pyridin-3-yl]-3-methyl-1,3-dihydro-imidazo[4,5-c]quinolin-2-one

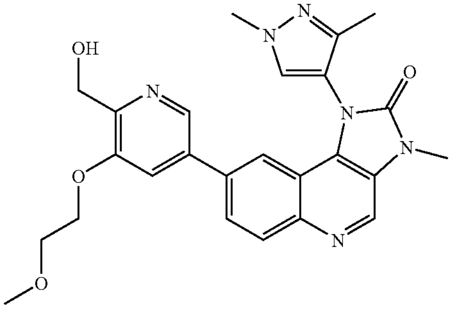

| Example | Intermed. | structure | Name of the example | MS-ES (M + H) | HPLC $t_R$ (min) |
|---|---|---|---|---|---|
| 242.2 | H | 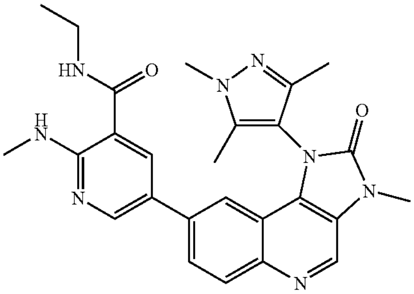 | N-Ethyl-2-methylamino-5-[3-methyl-2-oxo-1-(1,3,5-trimethyl-1H-pyrazol-4-yl)-2,3-dihydro-1H-imidazo[4,5-c]quinolin-8-yl]-nicotinamide | 432 | 2.43 |

The title compound was synthesized in a similar manner as described for Example 190 using 2-methoxyethanol as replacement for isopropanol to give the title compound as a white solid. (HPLC: $t_R$ 2.09 min (Method A); M+H=475 MS-ES; $^1$H-NMR ($d_6$-DMSO, 400 MHz) 8.99 (s, 1H), 8.27-8.25 (m, 1H), 8.15-8.11 (m, 2H), 8.04-8.00 (m, 1H), 7.63-7.60 (m, 1H), 7.44-7.41 (m, 1H), 4.87 (t, 1H), 4.57 (d, 2H), 4.31-4.22 (m, 2H), 3.89 (s, 3H), 3.75 (t, 2H), 3.58 (s, 3H), 3.35 (s, 3H), 1.97 (s, 3H))

Example 245

8-(5-Amino-pyridin-3-yl)-1-(1,3-dimethyl-1H-pyrazol-4-yl)-3-ethyl-1,3-dihydro-imidazo[4,5-c]quinolin-2-one

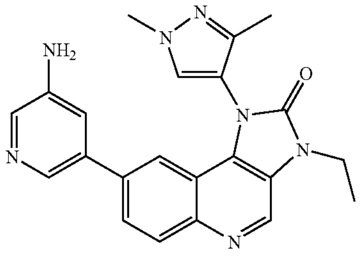 [SMILES: CCn1c(=O)n(-c2cn(C)nc2C)c2c3cc(-c4cncc(N)c4)ccc3ncc21]

The title compound was synthesized in a similar manner as described for Example 1.1 using 8-bromo-1-(1,3-dimethyl-1H-pyrazol-4-yl)-3-ethyl-1,3-dihydro-imidazo[4,5-c]quinolin-2-one (stage 245.1.1) and 3-aminopyridine-5-boronic acid pinacol ester (Apollo Scientific, Cheshire, United Kingdom) to give the title compound as a white solid. (HPLC: $t_R$ 2.02 min (Method A); M+H=400 MS-ES; $^1$H-NMR ($d_6$-DMSO, 400 MHz) 9.02 (s, 1H), 8.15 (s, 1H), 8.12-8.07 (m, 1H), 7.94-7.91 (m, 1H), 7.81-7.76 (m, 2H), 7.54-7.51 (m, 1H), 7.03-7.00 (m, 1H), 5.44 (s, 2H), 4.11 (q, 2H), 3.91 (s, 3H), 1.94 (s, 3H), 1.35 (t, 3H))

Stage 245.1.1 8-Bromo-1-(1,3-dimethyl-1H-pyrazol-4-yl)-3-ethyl-1,3-dihydro-imidazo[4,5-c]quinolin-2-one

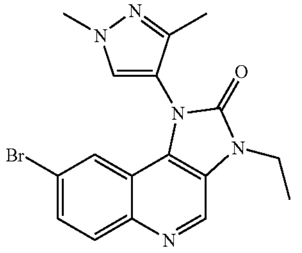 [SMILES: CCn1c(=O)n(-c2cn(C)nc2C)c2c3cc(Br)ccc3ncc21]

To a solution of 8-bromo-1-(1,3-dimethyl-1H-pyrazol-4-yl)-3-methyl-1,3-dihydro-imidazo[4,5-c]quinolin-2-one (Stage A.1, 0.698 mmol) in DMF (5 ml) cooled with an ice-bath was added 55% NaH in oil (1.398 mmol). The RM was stirred for 30 min at rt then was added iodoethane (0.085 ml) and the RM was stirred for 30 min at rt. The RM was diluted with EtOAc and washed with saturated aqueous $NaHCO_3$, with brine (2×), dried over $Na_2SO_4$, filtered and evaporated. The residue was absorbed on silica gel and purified by flash chromatography ($CH_2Cl_2$/MeOH 0% to 3.5%). The fractions containing product were evaporated together to give the title compound as a brown solid. (HPLC: $t_R$ 2.41 min (Method A); M+H=386, 388 MS-ES)

Example 246

3-Allyl-8-(5-amino-pyridin-3-yl)-1-(1,3-dimethyl-1H-pyrazol-4-yl)-1,3-dihydro-imidazo[4,5-c]quinolin-2-one

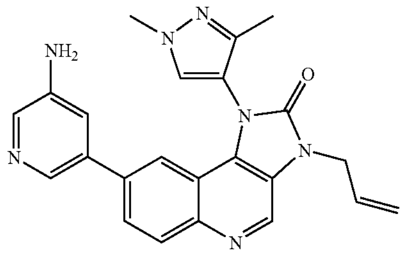 [SMILES: C=CCn1c(=O)n(-c2cn(C)nc2C)c2c3cc(-c4cncc(N)c4)ccc3ncc21]

The title compound was synthesized in a similar manner as described for Example 245 using allyl bromide (Fluka, Buchs, Switzerland) as replacement for iodoethane to give the title compound as a white solid. (HPLC: $t_R$ 2.08 min (Method A); M+H=412 MS-ES; $^1$H-NMR ($d_6$-DMSO, 400 MHz) 8.89 (s, 1H), 8.17 (s, 1H), 8.11-8.08 (m, 1H), 7.94-7.92 (m, 1H), 7.81-7.77 (m, 2H), 7.55-7.53 (m, 1H), 7.03-7.01 (m, 1H), 6.09-5.98 (m, 1H), 5.44 (s, 2H), 5.26-5.17 (m, 2H), 4.72 (d, 2H), 3.92 (s, 3H), 1.95 (s, 3H))

Example 247.1

N,N-Diethyl-2-{3-methyl-4-[3-methyl-2-oxo-8-(2-pyrrolidin-1-yl-pyrimidin-5-yl)-2,3-dihydro-imidazo[4,5-c]quinolin-1-yl]-pyrazol-1-yl}-acetamide

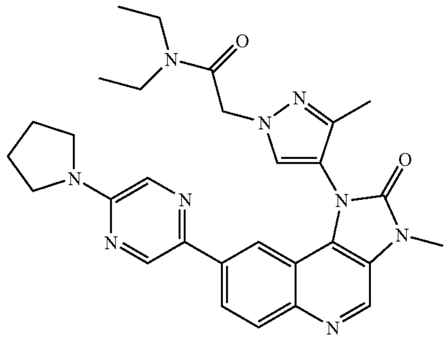 [SMILES: CCN(CC)C(=O)Cn1cc(-n2c(=O)n(C)c3cnc4ccc(-c5cnc(N6CCCC6)cn5)cc4c32)c(C)n1]

To a solution of {3-methyl-4-[3-methyl-2-oxo-8-(2-pyrrolidin-1-yl-pyrimidin-5-yl)-2,3-dihydro-imidazo[4,5-c]quinolin-1-yl]-pyrazol-1-yl}-acetic acid (Stage 247.1.1, 0.12 mmol) and DMF (0.007 ml) in dichloromethane (2 ml) was added oxallyl chloride (0.36 mmol) and the RM was stirred for 45 min at rt. The RM was quenched with diethylamine (Riedel-deHaën, Buchs, Switzerland, 2.4 mmol) and stirred for 5 min at it then diluted with saturated aqueous $NaHCO_3$ and extracted with EtOAc (2×). The combined organic layers were washed with brine (2×), dried over $Na_2SO_4$, filtered and evaporated. The residue was taken in MeOH/DMF and purified by preparative HPLC. The fractions containing pure product were basified with $NaHCO_3$, concentrated, cooled at 4° C. and the precipitate was filtered, washed with water and dried under vacuum to give the title compound as white solid. (HPLC: $t_R$ 2.63 min (Method A); M+H=540 MS-ES; $^1$H-NMR ($d_6$-DMSO, 400 MHz) 8.92 (s, 1H), 8.57 (s, 2H), 8.07-8.04 (m, 2H), 7.87-7.84 (m, 1H), 7.67-7.65 (m, 1H), 5.21-5.04 (m, 2H), 3.57 (s, 3H), 3.52-3.46 (m, 4H), 3.42-3.34 (m, 2H), 3.32-3.34 (m, 2H), 1.96-1.90 (m, 4H), 1.94 (s, 3H), 1.18 (t, 3H), 0.99 (t, 3H))

Stage 247.1.1 {3-Methyl-4-[3-methyl-2-oxo-8-(2-pyrrolidin-1-yl-pyrimidin-5-yl)-2,3-dihydro-imidazo[4,5-c]quinolin-1-yl]-pyrazol-1-yl}-acetic acid

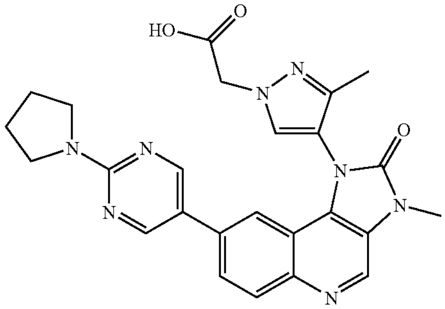 [SMILES: Cc1nn(CC(=O)O)cc1-n1c(=O)n(C)c2cnc3ccc(-c4cnc(N5CCCC5)nc4)cc3c21]

The title compound was synthesized in a similar manner as described for Example 1.1 using [4-(8-bromo-3-methyl-2-oxo-2,3-dihydro-imidazo[4,5-c]quinolin-1-yl)-3-methyl-pyrazol-1-yl]-acetic acid methyl ester (stage 247.1.2) and 2-(pyrrolidin-1-yl)pyrimidine-5-boronic acid pinacol ester (Frontier Scientific, Logan, USA) to give the title compound as a yellow hydrochloride salt after evaporation of the fractions containing pure product and exchange of the trifluoroacetate to the chlorure. (HPLC: $t_R$ 2.29 min (Method A); M+H=485, M−H=483 MS-ES)

Stage 247.1.2 [4-(8-Bromo-3-methyl-2-oxo-2,3-dihydro-imidazo[4,5-c]quinolin-1-yl)-3-methyl-pyrazol-1-yl]-acetic acid methyl ester

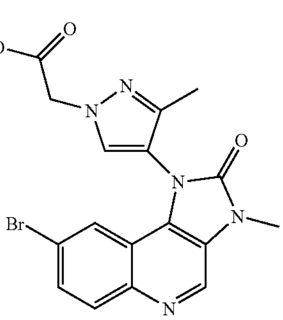

The title compound was synthesized in a similar manner as described for Stage 245.1.1 using [4-(8-bromo-2-oxo-2,3-dihydro-imidazo[4,5-c]quinolin-1-yl)-3-methyl-pyrazol-1-yl]-acetic acid methyl ester (Stage 101.1.3, 3.43 mmol) and iodomethane to give the title compound as brown solid. (HPLC: $t_R$ 2.42 min (Method A); M+H=430, 432 MS-ES)

The following examples were synthesized in a similar manner as described for Example 247.1 using the specified amines (Fluka, Buchs, Switzerland).

| Example | amine | structure | Name of the example | MS-ES (M + H) | HPLC $t_R$ (min) |
|---|---|---|---|---|---|
| 247.2 | azetidine | 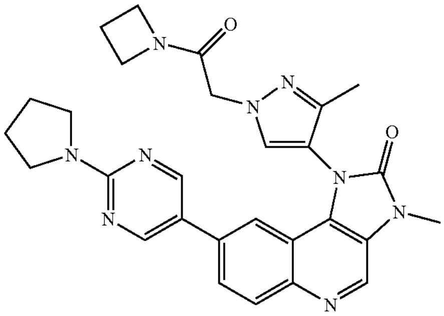 [SMILES: Cc1nn(CC(=O)N2CCC2)cc1-n1c(=O)n(C)c2cnc3ccc(-c4cnc(N5CCCC5)nc4)cc3c21] | 1-[1-(2-Azetidin-1-yl-2-oxo-ethyl)-3-methyl-1H-pyrazol-4-yl]-3-methyl-8-(2-pyrrolidin-1-yl-dihydro-imidazo[4,5-c]quinolin-2-one | 524 | 2.48 |
| 247.3 | Morpholine | 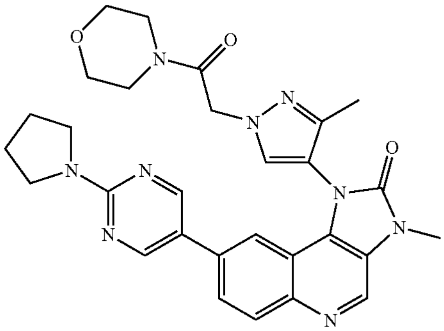 [SMILES: Cc1nn(CC(=O)N2CCOCC2)cc1-n1c(=O)n(C)c2cnc3ccc(-c4cnc(N5CCCC5)nc4)cc3c21] | 3-Methyl-1-[3-methyl-1-(2-morpholin-4-yl-2-oxo-ethyl)-1H-pyrazol-4-yl]-8-(2-pyrrolidin-1-yl-pyrimidin-5-yl)-1,3-dihydro-imidazo[4,5-c]quinolin-2-one | 554 | 2.44 |

-continued

| Example | amine | structure | Name of the example | MS-ES (M + H) | HPLC $t_R$ (min) |
|---|---|---|---|---|---|
| 247.4 | Pyrrolidine | 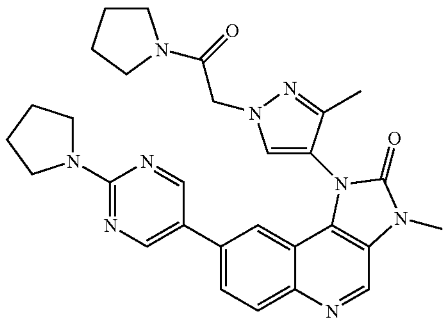 [SMILES: Cc1nn(CC(=O)N2CCCC2)cc1-n1c(=O)n(C)c2cnc3ccc(-c4cnc(N5CCCC5)nc4)cc3c21] | 3-Methyl-1-[3-methyl-1-(2-oxo-2-pyrrolidin-1-yl-ethyl)-1H-pyrazol-4-yl]-8-(2-pyrrolidin-1-yl-dihydro-imidazo[4,5-c]quinolin-2-one | 538 | 2.57 |
| 247.5 | Morpholine | 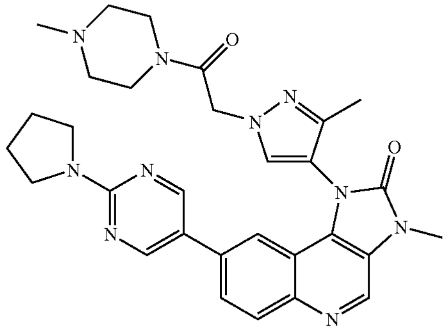 [SMILES: Cc1nn(CC(=O)N2CCN(C)CC2)cc1-n1c(=O)n(C)c2cnc3ccc(-c4cnc(N5CCCC5)nc4)cc3c21] | 3-Methyl-1-{3-methyl-1-[2-(4-methyl-piperazin-1-yl)-2-oxo-ethyl]-1H-pyrazol-4-yl}-8-(2-pyrrolidin-l-yl-pyrimidin-5-yl)-1,3-dihydro-imidazo[4,5-c]quinolin-2-one | 567 | 2.26 |

Example 248.1

1-(1-Isopropyl-3-methyl-1H-pyrazol-4-yl)-8-(5-methoxymethyl-6-methylamino-pyridin-3-yl)-3-methyl-1,3-dihydro-imidazo[4,5-c]quinolin-2-one

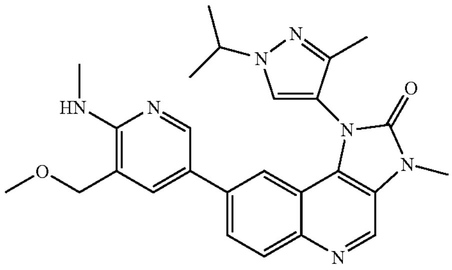

The title compound was synthesized in a similar manner as described for Example 1.1 using 8-bromo-1-(1-isopropyl-3-methyl-1H-pyrazol-4-yl)-3-methyl-1,3-dihydro-imidazo[4,5-c]quinolin-2-one (Intermediate G) and [3-methoxymethyl-5-(4,4,5,5-tetramethyl-[1,3,2]dioxaborolan-2-yl)-pyridin-2-yl]-methyl-amine (Stage 248.1.1) to give the title compound as a yellowish foam. (HPLC: $t_R$ 2.24 min (Method A); M+H=472 MS-ES; $^1$H-NMR ($d_6$-DMSO, 400 MHz) 8.90 (s, 1H), 8.20 (s, 1H), 8.15-8.13 (m, 1H), 8.05-8.02 (m, 1H), 7.85-7.81 (m, 1H), 7.48-7.45 (m, 1H), 7.43-7.41 (m, 1H), 6.13 (q, 1H), 4.55 (hp, 1H), 4.30 (s, 2H), 3.57 (s, 3H), 3.31 (s, 3H), 2.86 (d, 3H), 1.96 (s, 3H), 1.49-1.45 (m, 6H))

Stage 248.1.1 [3-Methoxymethyl-5-(4,4,5,5-tetramethyl-[1,3,2]dioxaborolan-2-yl)-pyridin-2-yl]-methyl-amine

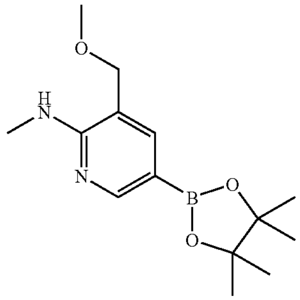

The title compound was synthesized in a similar manner as described for Stage 168.1.1 using (5-bromo-2-methylamino-pyridin-3-yl)-methanol (stage 248.1.2) to give the title compound as a crude back oil. (degrading under the HPLC condition (Method A); M+H=279 MS-ES).

Stage 248.1.2 (5-Bromo-2-methylamino-pyridin-3-yl)-methanol

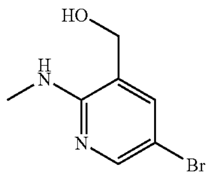

The title compound was synthesized in a similar manner as described for Example 171 using 6-bromo-1,4-dihydro-pyrido[2,3-d][1,3]oxazin-2-one (Stage 170.1.3) to give the title compound as a solid. (HPLC: $t_R$ 1.92 min (Method A); M+H=217, 219 MS-ES).

The following examples were synthesized in a similar manner as described for Example 1.1 using [3-methoxymethyl-5-(4,4,5,5-tetramethyl-[1,3,2]dioxaborolan-2-yl)-pyridin-2-yl]-methyl-amine (Stage 248.1.1) and the specified intermediate.

| Example | Intermed. | structure | Name of the example | MS-ES (M + H) | HPLC $t_R$ (min) |
|---|---|---|---|---|---|
| 248.2 | F | 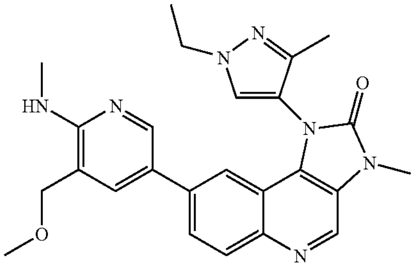 | 1-(1-Ethyl-3-methyl-1H-pyrazol-4-yl)-8-(5-methoxymethyl-6-methylamino-pyridin-3-yl)-3-methyl-1,3-dihydro-imidazo[4,5-c]quinolin-2-one | 458 | 2.18 |
| 248.3 | A | 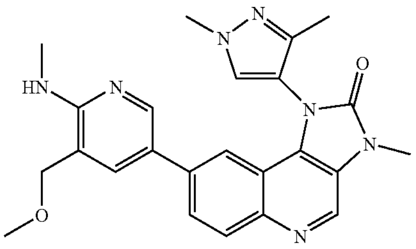 | 1-(1,3-Dimethyl-1H-pyrazol-4-yl)-8-(5-methoxymethyl-6-methylamino-pyridin-3-yl)-3-methyl-1,3-dihydro-imidazo[4,5-c]quinolin-2-one | 444 | 2.12 |
| 248.4 | K | 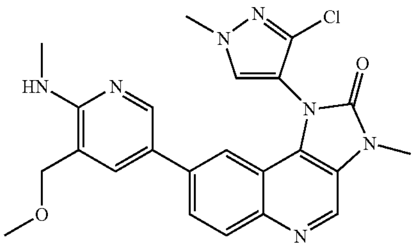 | 1-(3-Chloro-1-methyl-1H- pyrazol-4-yl)-8-(5-methoxymethyl-6-methylamino-pyridin-3-yl)-3-methyl-1,3-dihydro-imidazo[4,5-c]quinolin-2-one | 464 | 2.27 |
| 248.5 | H | 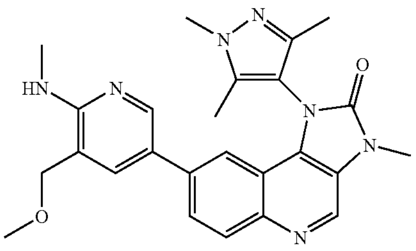 | 8-(5-Methoxymethyl-6-methylamino-pyridin-3-yl)-3-methyl-1-(1,3,5-trimethyl-1H-pyrazol-4-yl)-1,3-dihydro-imidazo[4,5-c]quinolin-2-one | 458 | 2.17 |

Example 249

8-(3,4-dimethoxy-phenyl)-1-(1,3-dimethyl-1H-pyrazol-4-yl)-1,3-dihydro-1,3,5,9-tetraaza-cyclopenta[a]naphthalen-2-one

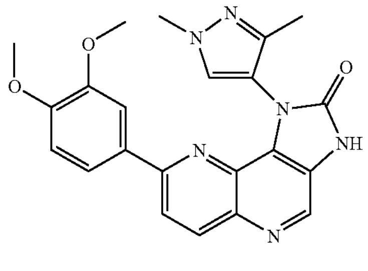 [SMILES: COc1ccc(-c2ccc3ncc4[nH]c(=O)n(-c5cn(C)nc5C)c4c3n2)cc1OC]

A mixture of 6-(3,4-dimethoxy-phenyl)-4-(1,3-dimethyl-1H-pyrazol-4-ylamino)-[1,5]naphthyridine-3-carboxylic acid ethyl ester (Stage 249.1.1, 160 mg, 0.358 mmol) and LiOH 1 M (0.715 ml, 0.715 mmol) in dioxane (2.6 ml) was stirred at 50° C. for 2.5 h. The RM was then quenched with 2 M aqueous HCl (0.36 ml, 0.072 mmol) and evaporated to dryness. The residue was diluted with toluene (2.6 ml) and NMP (1.3 ml) and treated under argon with TEA (0.164 ml) and diphenylphosphorylazide (0.231 ml). The RM was stirred again at 95° C. for 2.5 h. After that, the RM was quenched with saturated aqueous $NaHCO_3$, the suspension was then filtered. The cake was dissolved with EtOAc (200 ml) and THF (30 ml). The solution was extracted with brine (2×). The combined organic layers were dried over $Na_2SO_4$, filtered and evaporated to dryness to give the title compound as an off-white solid. (HPLC: $t_R$ 2.56 min (Method A); M+H=417 MS-ES; $^1$H-NMR ($d_6$-DMSO, 400 MHz) 11.80 (s, 1H), 8.75 (s, 1H), 8.38 (d, 1H), 8.22 (d, 1H), 7.96 (s, 1H), 7.60-7.55 (m, 1H), 7.42-7.38 (m, 1H), 7.02-6.98 (m, 1H), 3.83 (s, 6H), 3.81 (s, 3H), 1.97 (s, 3H))

Stage 249.1.1 6-(3,4-Dimethoxy-phenyl)-4-(1,3-dimethyl-1H-pyrazol-4-ylamino)-[1,5]naphthyridine-3-carboxylic acid ethyl ester

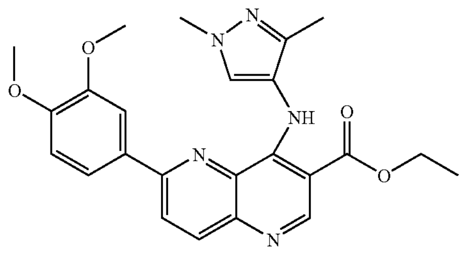 [SMILES: CCOC(=O)c1cnc2ccc(-c3ccc(OC)c(OC)c3)nc2c1Nc1cn(C)nc1C]

A mixture of 4-chloro-6-(3,4-dimethoxy-phenyl)-[1,5]naphthyridine-3-carboxylic acid ethyl ester (Stage 249.1.2, 170 mg, 0.456 mmol), 1,3-dimethyl-4-aminopyrazole. HCl (ChemCollect, Remscheid, Germany, 85 mg, 0.576 mmol) and 1,2,2,6,6-pentamethylpiperidine (0.292 ml, 1.596 mmol) in DMA (2 ml) was stirred at 50° C. for 5.5 h. Then the RM was cooled to rt and quenched with water, before being extracted with EtOAc (2×). The combined organic layers were dried over $Na_2SO_4$, filtered and evaporated to dryness to give the title compound as an orange solid. (HPLC: $t_R$ 2.93 min (Method A); M+H=448 MS-ES)

Stage 249.1.2 4-Chloro-6-(3,4-dimethoxy-phenyl)-[1,5]naphthyridine-3-carboxylic acid ethyl ester

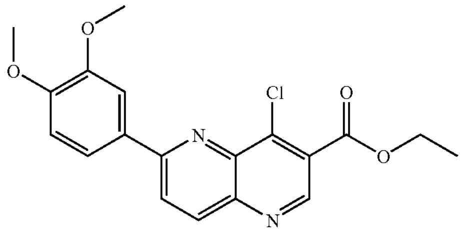 [SMILES: CCOC(=O)c1cnc2ccc(-c3ccc(OC)c(OC)c3)nc2c1Cl]

A mixture of 6-(3,4-dimethoxy-phenyl)-4-hydroxy-[1,5]naphthyridine-3-carboxylic acid ethyl ester (Stage 249.1.3, 493 mg, 1.391 mmol) in $POCl_3$ was stirred at 125° C. for 1.5 h. Then the RM was evaporated to dryness. The residue was quenched with saturated aqueous $NaHCO_3$. The suspension was filtered, the cake was washed with water and dried in the vacuum oven to give the title compound as a brown solid. Used for next step without further purification. (HPLC: $t_R$ 3.80 min (Method A); M+H=373 MS-ES)

Stage 249.1.3 6-(3,4-Dimethoxy-phenyl)-4-hydroxy-[1,5]naphthyridine-3-carboxylic acid ethyl ester

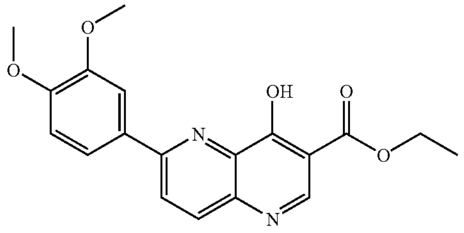 [SMILES: CCOC(=O)c1cnc2ccc(-c3ccc(OC)c(OC)c3)nc2c1O]

A mixture of 6-(3,4-dimethoxy-phenyl)-pyridin-3-ylamine (Stage 249.1.4, 2.0 g, 8.69 mmol) and diethyl ethoxymethylenemalonate (Aldrich, Buchs, Switzerland, 2.087 ml, 10.42 mmol) in o-xylene (22 ml) was heated by microwaves at 150° C. for 45 min and at 250° C. for 9 h. The RM was cooled to rt and crystallized with diethylether. The suspension was filtered and the cake was triturated again in hot EtOAc and cooled after in the freezer. The suspension was filtered again. The cake was washed with EtOAc and dried in the vacuum oven to give the title compound as a brown solid. Used for next step without further purification. (HPLC: $t_R$ 2.58 min (Method A); M+H=355 MS-ES)

Stage 249.1.4

6-(3,4-dimethoxy-phenyl)-pyridin-3-ylamine

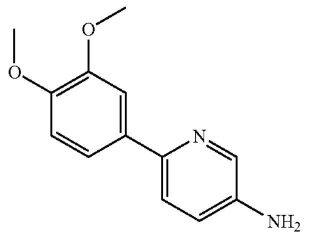 [SMILES: COc1ccc(-c2ccc(N)cn2)cc1OC]

To a mixture of 2-(3,4-dimethoxyphenyl)-5-nitropyridine (Interchim, Montlucon, France, 2.85 g, 10.95 mmol) in MeOH (27 ml) and THF (27 ml), Ra/Ni catalyst (1.10 g, 10.95 mmol) was added and shaked under hydrogen at rt for 15 h. After that, the RM was filtered over celite, the catalyst was washed with MeOH and the filtrate was evaporated to dryness to give the title compound as an off-white solid. (HPLC: $t_R$ 2.22 min (Method A); M+H=231 MS-ES)

Example 250

8-(3,4-Dimethoxy-phenyl)-1-(1,3-dimethyl-1H-pyrazol-4-yl)-3-methyl-1,3-dihydro-1,3,5,9-tetraaza-cyclopenta[a]naphthalen-2-one

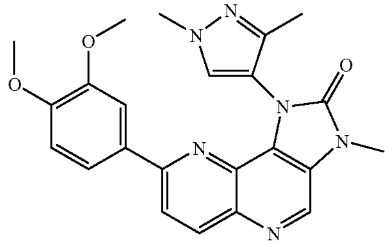 [SMILES: COc1ccc(-c2ccc3ncc4c(c3n2)n(-c2cn(C)nc2C)c(=O)n4C)cc1OC]

A mixture of 8-(3,4-dimethoxy-phenyl)-1-(1,3-dimethyl-1H-pyrazol-4-yl)-1,3-dihydro-1,3,5,9-tetraaza-cyclopenta[a]naphthalen-2-one (Example 249, 50 mg, 0.120 mmol) and NaH 55% (8 mg, 0.183 mmol) in DMF (1.2 ml) was stirred at rt for 20 min. Then iodomethane (0.011 ml, 0.180 mmol) was added and the RM was stirred at rt for 2.25 h. After that, the RM was quenched with saturated aqueous $NaHCO_3$, the suspension was then filtered, the cake was washed with water and dried in the vacuum oven to give the title compound as an off-white solid. (HPLC: $t_R$ 2.67 min (Method A); M+H=431 MS-ES; $^1$H-NMR ($d_6$-DMSO, 400 MHz) 8.98 (s, 1H), 8.38 (d, 1H), 8.24 (d, 1H), 7.96 (s, 1H), 7.62-7.54 (m, 1H), 7.42-7.38 (m, 1H), 7.02 (d, 1H), 3.85 (s, 6H), 3.81 (s, 3H), 3.59 (s, 3H), 1.97 (s, 3H))

Example 251

8-(3,4-Dimethoxy-phenyl)-1-(1,3-dimethyl-1H-pyrazol-4-yl)-3-ethyl-1,3-dihydro-1,3,5,9-tetraaza-cyclopenta[a]naphthalen-2-one

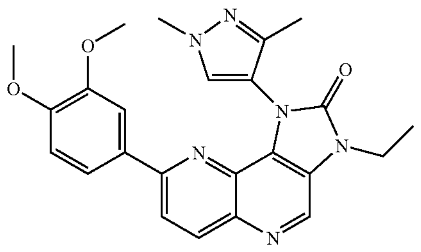 [SMILES: CCn1c(=O)n(-c2cn(C)nc2C)c2c3nc(-c4ccc(OC)c(OC)c4)ccc3ncc21]

A mixture of 8-(3,4-dimethoxy-phenyl)-1-(1,3-dimethyl-1H-pyrazol-4-yl)-1,3-dihydro-1,3,5,9-tetraaza-cyclopenta[a]naphthalen-2-one (Example 249, 50 mg, 0.120 mmol) and NaH 55% (8 mg, 0.183 mmol) in DMF was stirred at rt for 25 min. Then iodoethane (0.015 ml, 0.186 mmol) was added and the RM was stirred at rt for 5.5 h. After that, the RM was quenched with saturated aqueous $NaHCO_3$, the suspension was then filtered, the cake was washed with water and dried in the vacuum oven to give the title compound as a white solid. (HPLC: $t_R$ 2.74 min (Method A); M+H=445 MS-ES; $^1$H-NMR ($d_6$-DMSO, 400 MHz) 9.03 (s, 1H), 8.40-8.32 (m, 1H), 8.25-8.19 (m, 1H), 7.95 (s, 1H), 7.60-7.52 (m, 1H), 7.41-7.36 (m, 1H), 7.04-6.97 (m, 1H), 4.11 (q, 2H), 3.85 (s, 3H), 3.83 (s, 3H), 3.81 (s, 3H), 1.94 (s, 3H), 1.37 (t, 3H))

Example 252

8-(3,4-Dimethoxy-phenyl)-1-(2,5-dimethyl-2H-pyrazol-3-yl)-1,3-dihydro-1,3,5,9-tetraaza-cyclopenta[a]naphthalen-2-one

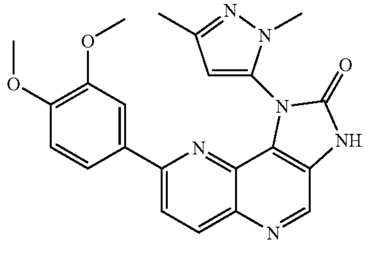 [SMILES: COc1ccc(-c2ccc3ncc4[nH]c(=O)n(-c5cc(C)nn5C)c4c3n2)cc1OC]

The title compound was synthesized in a similar manner as described for Example 249 using 2,5-dimethyl-2H-pyrazol-3-ylamine (Aldrich, Buchs, Switzerland, 130 mg, 1.170 mmol) to give the title compound as an off-white solid. (HPLC: $t_R$ 2.73 min (Method A); M+H=417 MS-ES; $^1$H-NMR ($d_6$-DMSO, 400 MHz) 11.96 (s, 1H), 8.79 (s, 1H), 8.38 (d, 1H), 8.25 (d, 1H), 7.62-7.56 (m, 1H), 7.42-7.38 (m, 1H), 7.02-6.97 (m, 1H), 6.26 (s, 1H), 3.85 (s, 3H), 3.81 (s, 3H), 3.58 (s, 3H), 2.23 (s, 3H))

Example 253

8-(3,4-Dimethoxy-phenyl)-1-(2,5-dimethyl-2H-pyrazol-3-yl)-3-methyl-1,3-dihydro-1,3,5,9-tetraaza-cyclopenta[a]naphthalen-2-one

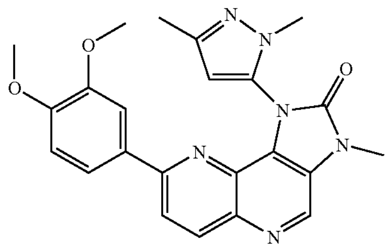 [SMILES: COc1ccc(-c2ccc3ncc4c(c3n2)n(-c2cc(C)nn2C)c(=O)n4C)cc1OC]

The title compound was synthesized in a similar manner as described for Example 250 using 8-(3,4-dimethoxy-phenyl)-1-(2,5-dimethyl-2H-pyrazol-3-yl)-1,3-dihydro-1,3,5,9-tetraaza-cyclopenta[a]naphthalen-2-one (Example 252, 37 mg, 0.088 mmol) to give the title compound as an off-white solid. (HPLC: $t_R$ 2.90 min (Method A); M+H=431 MS-ES; $^1$H-NMR ($d_6$-DMSO, 400 MHz) 9.03 (s, 1H), 8.43-8.35 (m, 1H), 8.29-8.22 (m, 1H), 7.62-7.54 (m, 1H), 7.38 (s, 1H), 7.03-6.95 (m, 1H), 6.31-6.23 (m, 1H), 3.86 (s, 3H), 3.81 (s, 3H), 3.60 (s, 3H), 3.52 (s, 3H), 2.23 (s, 3H))

Example 254

8-(3,4-Dimethoxy-phenyl)-1-(1-ethyl-3-methyl-1H-pyrazol-4-yl)-3-methyl-1,3-dihydro-1,3,5,9-tetraaza-cyclopenta[a]naphthalen-2-one

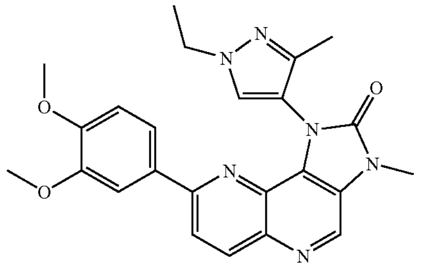

The title compound was synthesized in a similar manner as described for Example 250 using 1-ethyl-3-methyl-1H-pyrazol-4-ylamine. HCl (ChemCollect, Remscheid, Germany, 95 mg, 0.587 mmol) to give the title compound as a light yellow foam. (HPLC: $t_R$ 2.74 min (Method A); M+H=445 MS-ES; $^1$H-NMR ($d_6$-DMSO, 400 MHz) 8.98 (s, 1H), 8.41-8.32 (m, 1H), 8.25-8.18 (m, 1H), 7.95 (s, 1H), 7.56-7.49 (m, 1H), 7.46-7.39 (m, 1H), 7.02-6.94 (m, 1H), 4.18-4.07 (m, 2H), 3.87 (s, 3H), 3.81 (s, 3H), 3.60 (s, 3H), 1.97 (s, 3H), 1.46-1.35 (m, 3H))

Physicochemical Properties

The physicochemical properties of relevance for the absorption of the compound, such as the solubility and the membrane permeability, especially at a pH close to neutral pH can be measured using the procedure as described by L. ZHOU et al. in JOURNAL OF PHARMACEUTICAL SCIENCES, VOL. 96, NO. 11, p. 3052-3071 (2007) for the solubility at pH 6.8 and the procedure as described by F. Wohnsland and B. Faller in Journal of Medicinal Chemistry Vol 44, p. 923-930 (2001) for the Parallel Artificial Membrane Permeability Assay (PAMPA) at pH 6.8.

The following solubility in mg/l was measured at pH 6.8 for compounds of formula (I) as exemplified below:

| | | | | | | | | | | |
|---|---|---|---|---|---|---|---|---|---|---|
| solubility | 4 | 15 | 3 | 466 | 10 | 2 | 8 | 49 | 22 | 3 |
| Example | 150.2 | 189 | 37.1 | 58.5 | 1.8 | 79 | 199 | 107 | 234.2 | 146.5 |
| solubility | 3 | 84 | 2 | 43 | 10 | 7 | 11 | 92 | 10 | 4 |
| Example | 211.2 | 183 | 1.3 | 212.2 | 169.3 | 29.2 | 52 | 244 | 103.2 | 51.2 |
| solubility | >486 | 10 | >458 | 5 | 217 | 14 | 5 | 3 | 129 | >429 |
| Example | 56.2 | 180.2 | 158.2 | 1.5 | 213.1 | 237 | 142.3 | 29.1 | 245 | 169.2 |
| solubility | 4 | 5 | 2 | 3 | 4 | 414 | 136 | >403 | 410 | 2 |
| Example | 2.2 | 122 | 154.1 | 118.1 | 240 | 217 | 88.2 | 106 | 87.1 | 28.3 |
| solubility | 41 | 242 | 2 | 13 | 2 | >429 | 11 | 35 | 42 | 4 |
| Example | 73 | 26 | 3.6 | 234.3 | 40 | 158.1 | 180.1 | 75 | 10.2 | 104 |
| solubility | >473 | 128 | 70 | 4 | 9 | 17 | 17 | 21 | 5 | 36 |
| Example | 195.2 | 115 | 118.4 | 167 | 30.2 | 132 | 185.1 | 215.3 | 250 | 140.1 |
| solubility | 16 | 14 | 3 | 14 | 3 | 400 | 150 | >417 | 9 | 36 |
| Example | 202 | 218 | 28.2 | 56.4 | 35 | 164 | 193 | 142.1 | 28.1 | 6.4 |
| solubility | 8 | 30 | 33 | >431 | 41 | 2 | 37 | 439 | >459 | 240 |
| Example | 74 | 118.2 | 49 | 141.1 | 37.3 | 27.1 | 72 | 195.1 | 195.3 | 18 |
| solubility | 14 | >513 | 3 | 65 | 75 | 4 | 47 | 24 | >502 | 164 |
| Example | 41 | 87.5 | 53.1 | 123 | 146.4 | 3.5 | 121 | 168.2 | 90.2 | 54.1 |
| solubility | 3 | 2 | 18 | 7 | >485 | 3 | >428 | 8 | 16 | 5 |
| Example | 64 | 140.2 | 8.1 | 2.3 | 242.2 | 148.4 | 215.2 | 46 | 249 | 190 |
| solubility | 6 | 76 | 164 | 102 | 5 | >435 | 6 | 5 | 8 | 16 |
| Example | 1.7 | 60.2 | 135 | 16.2 | 15.3 | 54.2 | 153.1 | 242.1 | 61 | 224.2 |
| solubility | 43 | 3 | 6 | 37 | 2 | 3 | 16 | 2 | 2 | 133 |
| Example | 243 | 88.1 | 146.2 | 37.4 | 220.1 | 69 | 56.5 | 32.1 | 11 | 81.2 |
| solubility | 125 | 7 | 15 | 361 | 433 | 9 | 7 | 355 | >472 | 59 |
| Example | 239 | 253 | 3.1 | 197.1 | 161 | 9 | 5.2 | 37.2 | 155.3 | 176 |
| solubility | 33 | 7 | 427 | 445 | 40 | >444 | 47 | 13 | >486 | 13 |
| Example | 166.1 | 4.2 | 137 | 210 | 53.2 | 59.1 | 70 | 149.1 | 175.3 | 91 |

-continued

| | | | | | | | | | | |
|---|---|---|---|---|---|---|---|---|---|---|
| solubility | 5 | 10 | 2 | >428 | 2 | 12 | 413 | 38 | 58 | >456 |
| Example | 150.1 | 15.1 | 209 | 16.3 | 141.2 | 251 | 231 | 103.1 | 234.1 | 162 |
| solubility | 4 | 26 | 4 | 25 | 2 | 9 | 27 | 8 | 16 | 39 |
| Example | 17.3 | 138 | 8.2 | 56.1 | 29.3 | 7.2 | 58.4 | 186 | 23.1 | 12 |
| solubility | >487 | 32 | 219 | >457 | 62 | 19 | 3 | >500 | 8 | >484 |
| Example | 85.2 | 17.2 | 84.1 | 215.1 | 155.4 | 43.1 | 4.7 | 3.12 | 184 | 139 |
| solubility | 72 | 44 | 18 | >472 | >444 | 55 | 81 | >473 | 45 | >385 |
| Example | 133 | 144.3 | 207 | 157 | 159 | 212.1 | 17.1 | 3.11 | 23.2 | 45.1 |
| solubility | >544 | >434 | 21 | >399 | 71 | 14 | >443 | 11 | 141 | 14 |
| Example | 93.2 | 146.1 | 149.2 | 230 | 4.3 | 168.3 | 215.4 | 233 | 136 | 51.5 |
| solubility | 41 | 300 | 26 | 194 | 5 | 6 | >512 | 4 | 5 | 50 |
| Example | 6.2 | 56.3 | 3.10 | 32.2 | 224.1 | 85.1 | 205 | 30.1 | 252 | 2.4 |
| solubility | 44 | >443 | >486 | 5 | >384 | 8 | 76 | 6 | >472 | 8 |
| Example | 188 | 105 | 63 | 141.3 | 10.1 | 206.1 | 85.3 | 125.1 | 206.2 | 2.1 |
| solubility | 3 | 32 | 75 | 104 | 30 | 2 | 3 | 225 | >428 | 10 |
| Example | 3.7 | 108 | 98.2 | 3.3 | 113 | 110 | 158.3 | 197.2 | 58.1 | 98.3 |
| solubility | 10 | 3 | 56 | 16 | 27 | 12 | 74 | 2 | 8 | 24 |
| Example | 45.2 | 89 | 247.2 | 220.3 | 192 | 203 | 130 | 99 | 173 | 163 |
| solubility | 31 | 28 | >442 | 53 | 12 | 133 | 4 | 8 | 237 | 7 |
| Example | 65 | 179 | 165 | 14 | 100 | 208 | 93.1 | 98.1 | 160.2 | 4.5 |
| solubility | 2 | >455 | 65 | >442 | >458 | 65 | 3 | 4 | 13 | 21 |
| Example | 66 | 126 | 1.6 | 87.3 | 155.2 | 3.9 | 5.1 | 27.2 | 2.5 | 129 |
| solubility | 13 | 73 | >415 | 289 | 11 | 222 | 6 | 3 | 4 | 25 |
| Example | 38 | 155.1 | 21.1 | 169.1 | 172 | 87.2 | 4.6 | 116 | 1.4 | 24 |
| solubility | >414 | 15 | 21 | >459 | 386 | 35 | 336 | 6 | 25 | 246 |
| Example | 16.4 | 16.5 | 221.1 | 196.2 | 127 | 175.1 | 4.1 | 58.3 | 178 | 84.2 |
| solubility | 4 | 8 | 2 | 3 | 5 | 7 | 6 | 3 | 13 | 3 |
| Example | 45.3 | 44 | 48 | 187 | 51.1 | 92 | 59.2 | 2.7 | 76 | 109 |
| solubility | 2 | 2 | >481 | 71 | 243 | 83 | 92 | 4 | 56 | >441 |
| Example | 3.4 | 67 | 144.1 | 15.2 | 191.2 | 232 | 148.1 | 148.2 | 182 | 228 |
| solubility | 2 | 4 | >473 | 69 | 3 | 7 | 2 | 61 | 75 | 94 |
| Example | 125.2 | 152.2 | 191.1 | 247.1 | 117 | 102 | 236 | 114 | 16.1 | 194.2 |
| solubility | 21 | 5 | 11 | 2 | 3 | >486 | 169 | 44 | 129 | 32 |
| Example | 118.3 | 171 | 51.4 | 2.8 | 211.1 | 87.4 | 177.1 | 196.1 | 194.1 | 160.1 |
| solubility | 3 | 75 | 315 | >469 | 4 | 479 | 8 | >458 | | |
| Example | 55 | 246 | 1.9 | 96 | 131 | 177.2 | 238 | 156 | | |

The following permeability log Pe was measured for compound of formula (I) as exemplified below:

| | | | | | | | | | | |
|---|---|---|---|---|---|---|---|---|---|---|
| Log Pe | −3.6 | −3.8 | −3.8 | −3.9 | −3.6 | −3.4 | −3.9 | −4.9 | −4.4 | −4 |
| Example | 146.5 | 27.1 | 51.1 | 28.1 | 37.1 | 92 | 3.8 | 196.1 | 160.1 | 248.1 |
| Log Pe | −4.4 | −4.3 | −3.9 | −4.7 | −4.6 | −3.6 | −3.9 | −3.7 | −3.8 | −3.7 |
| Example | 248.5 | 189 | 206.2 | 150.2 | 7.2 | 2.3 | 28.2 | 4.6 | 27.2 | 84.1 |
| Log Pe | −4 | −3.9 | −3.9 | −4.8 | −4.5 | −4.7 | −3.9 | −5 | −4.4 | −3.5 |
| Example | 51.3 | 9 | 141.3 | 148.1 | 141.2 | 182 | 250 | 200 | 53.1 | 42 |
| Log Pe | −4.6 | −4.7 | −4.7 | −4.7 | −4.5 | −3.9 | −3.8 | −4.8 | −4.9 | −3.9 |
| Example | 248.3 | 24 | 87.4 | 135 | 30.1 | 2.5 | 8.1 | 190 | 179 | 173 |
| Log Pe | −3.7 | −3.9 | −3.7 | −4 | −4.9 | −4 | −4.7 | −4.7 | −4.9 | −4.5 |
| Example | 201 | 60.1 | 186 | 4.4 | 32.2 | 5.2 | 191.1 | 89 | 10.1 | 203 |
| Log Pe | −3.8 | −3.8 | −3.6 | −4.4 | −5 | −3.8 | −3.9 | −4.5 | −3.9 | −3.8 |
| Example | 113 | 1.3 | 90.2 | 164 | 103.2 | 130 | 146.2 | 156 | 4.9 | 25.4 |
| Log Pe | −3.7 | −3.6 | −3.9 | −4.1 | −4.7 | −3.8 | −4.5 | −3.9 | −3.7 | −4.7 |
| Example | 2.6 | 3.11 | 153.2 | 209 | 220.1 | 234.4 | 31 | 85.1 | 3.5 | 87.3 |
| Log Pe | −3.9 | −3.9 | −3.5 | −3.9 | −4 | −3.9 | −4.2 | −4.1 | −4.2 | −4.1 |
| Example | 98.3 | 98.1 | 3.4 | 144.1 | 19 | 144.2 | 53.2 | 252 | 161 | 44 |
| Log Pe | −4.4 | −4.7 | −4 | −4.4 | −4.5 | −4.8 | −3.8 | −5 | −4.2 | −3.8 |
| Example | 220.3 | 142.3 | 61 | 86 | 148.3 | 87.1 | 128.2 | 148.2 | 248.2 | 98.2 |
| Log Pe | −3.7 | −4.9 | −3.8 | −3.8 | −4.6 | −4.1 | −4.2 | −3.3 | −4 | −3.6 |
| Example | 13 | 127 | 4.1 | 90.1 | 25.3 | 66 | 132 | 1.4 | 4.5 | 93.1 |
| Log Pe | −3.7 | −3.7 | −4 | −3.9 | −4.2 | −4.5 | −4.6 | −4.8 | −3.8 | −3.9 |
| Example | 1.2 | 3.3 | 146.4 | 165 | 221.2 | 220.2 | 86.2 | 136 | 55 | 29.1 |
| Log Pe | −5.6 | −4 | −5 | −3.7 | −3.8 | −3.9 | −4 | −3.9 | −4.7 | −4.6 |
| Example | 93.2 | 140.2 | 115 | 1.7 | 2.7 | 3.1 | 6.3 | 167 | 17.3 | 195.2 |
| Log Pe | −4 | −3.8 | −4.4 | −4.1 | −3.7 | −3.7 | −3.7 | −3.8 | −4.8 | −4.1 |
| Example | 206.1 | 145.2 | 248.4 | 197.2 | 8.2 | 146.3 | 58.4 | 1.5 | 54.2 | 38 |
| Log Pe | −3.6 | −4.6 | −3.8 | −3.8 | −4 | −3.8 | −5 | −4.3 | −4.3 | −4.2 |
| Example | 79 | 233 | 58.1 | 82 | 28.3 | 56.3 | 137 | 240 | 6.2 | 150.1 |
| Log Pe | −3.8 | −4.6 | −4.7 | −3.9 | −4.9 | −4.1 | −3.8 | −4.4 | −3.8 | −4.9 |
| Example | 58.2 | 104 | 178 | 148.4 | 180.2 | 1.8 | 25.5 | 56.1 | 35 | 194.1 |
| Log Pe | −4.6 | −4.6 | −3.8 | −4.4 | −3.8 | −3.8 | −3.8 | −4.8 | −4.2 | −3.9 |
| Example | 5.1 | 236 | 2.8 | 116 | 2.4 | 234.3 | 6.4 | 52 | 184 | 4.3 |
| Log Pe | −4.9 | −3.7 | −3.7 | −4.3 | −3.7 | −3.7 | −4.8 | −4.4 | −4.2 | −4.6 |
| Example | 177.2 | 187 | 153.1 | 119 | 144.3 | 131 | 172 | 30.2 | 234.1 | 239 |

-continued

| | | | | | | | | | | |
|---|---|---|---|---|---|---|---|---|---|---|
| Log Pe | −4.3 | −4.6 | −4.3 | −4.2 | −4.8 | −4 | −3.4 | −4.5 | −4.1 | −5.5 |
| Example | 183 | 242.1 | 249 | 157 | 12 | 29.2 | 154.2 | 34 | 162 | 211.2 |
| Log Pe | −3.9 | −4 | −4.3 | −4.2 | −3.7 | −5 | −3.8 | −3.5 | −3.6 | −3.6 |
| Example | 128.1 | 1.6 | 213.1 | 20 | 37.2 | 65 | 50 | 202 | 4.8 | 51.5 |
| Log Pe | −5 | −3.7 | −4.5 | −4.4 | −3.7 | −4.1 | −4 | −4.1 | −5.2 | −4.8 |
| Example | 197.1 | 58.3 | 114 | 118.1 | 4.2 | 191.2 | 105 | 154.1 | 177.1 | 37.4 |
| Log Pe | −4 | −3.9 | −4.5 | −4 | −4.4 | −3.9 | −3.4 | −3.4 | −4 | −3.9 |
| Example | 94 | 85.2 | 18 | 11 | 176 | 251 | 3.6 | 83 | 1.9 | 4.7 |
| Log Pe | −4.1 | −3.8 | −4.6 | −4.6 | −4 | −3.8 | −4.8 | −4.7 | −3.7 | −3.8 |
| Example | 3.2 | 3.7 | 160.2 | 25.1 | 29.3 | 56.5 | 118.5 | 87.2 | 91 | 97 |
| Log Pe | −4.1 | −4.5 | −3.8 | −4.8 | −4.5 | −3.6 | −4.6 | −4.3 | −4 | −3.3 |
| Example | 146.1 | 221.1 | 2.1 | 59.2 | 141.1 | 174 | 234.2 | 242.2 | 56.4 | 6.1 |
| Log Pe | −3.8 | −3.8 | | | | | | | | |
| Example | 84.2 | 84.2 | | | | | | | | |

The permeability in $10^{-6}$ cm/s of compounds of formula (I) have been confirmed for selected example using a cellular CaCo2 permeability assay from apical to basal (A-B):

| | | | | | | | | | | |
|---|---|---|---|---|---|---|---|---|---|---|
| Pe A-B | 6.0 | 20.5 | 29.4 | 35.1 | 39.7 | 29.9 | 33.5 | 29.7 | 7.7 | 15.8 |
| Example | 96 | 104 | 252 | 4.1 | 56.1 | 87.2 | 54.2 | 6.4 | 102 | 197.1 |
| Pe A-B | 17.0 | 26.7 | 5.6 | 35.5 | 21.0 | 26.4 | 24.0 | 15.9 | 28.6 | 22.1 |
| Example | 136 | 84.1 | 16.2 | 234.1 | 3.3 | 84.2 | 12 | 118.4 | 3.1 | 249 |
| Pe A-B | 30.5 | 21.5 | 31.6 | 7.8 | 29.1 | 26.1 | 18.4 | 31.2 | 17.0 | 10.9 |
| Example | 58.1 | 2.7 | 1.6 | 175.1 | 146.1 | 189 | 28.1 | 3.5 | 87.1 | 155.2 |
| Pe A-B | 27.8 | 5.9 | 16.1 | 28.6 | 38.4 | 26.6 | 13.9 | 14.8 | 16.0 | |
| Example | 3.7 | 215.1 | 4.5 | 1.8 | 2.5 | 6.2 | 159 | 3.9 | 179 | |

Skin Penetration

The skin penetration/permeation properties of two representative compounds of the present invention were tested as follows:

In Vitro Test to Determine Skin Penetration and Permeation Properties

The compounds were applied as 0.5% solutions in propylene glycol to pig skin mounted in static Franz-type diffusion cells. At the end of a 48 hours exposure time, drug concentrations were measured in the skin (after removal of stratum corneum) and in the receiver.

Skin penetration and permeation in vitro

| Example | Skin | Formulation | Concentration [%] | Skin concentration [μg/g] | Permeation rate [ng/cm²/hr] |
|---|---|---|---|---|---|
| 84.1 | Pig+ | PG | 0.5 | 6.4 ± 3.5 | <0.4 |
| 58.1 | Pig+ | PG | 0.5 | 9.3 ± 6.2 | 0.5 ± 0.3 |

Mean ± standard deviation of triplicate determinations are given; +: skin from 4 months old farm pigs (Landrace X Deutsches Edelschwein).
PG: propylene glycol In conclusion, both examples penetrate well into pig skin (pig skin is similar to human skin regarding barrier function and architecture) in vitro, while permeation rate through pig skin is low, indicating a low systemic exposure.

In Vivo Test to Determine Penetration into Dermis of Topically Treated Pigs

Small skin areas (4 $cm^2$) on the dorsolateral back of young domestic pigs were treated topically with 0.5% solutions at different time intervals (1-8 hrs) prior to drug level determination. Skin flaps with the treated sites in the centre were dissected and removed. The skin flaps were spread, and heated metal blocks placed on the test sites for 1 minute to induce separation of epidermis from the dermis. After removal of the loosened epidermal sheets, 1 mm thick dermal sheets were prepared from the treated, de-epidermized skin with a dermatome. From these sheets 6 mm punch samples (6 mm Ø) were collected and analysed for test compound concentration by LC/MS. The procedure described was done with careful avoidance of contamination of the dermal samples with compound attached superficially to the epidermis.

The following table provides AUC values of the agents of the invention in pig dermis when applied epicutaneously in the identified compositions (n=8).

Skin PK in vivo

| Example | Dermis | Formulation | Concentration [%] | AUC (0-8 h) [μg * h/g] |
|---|---|---|---|---|
| 84.1 | Pig | PG/EtOH 7:3 | 0.5 | 2.8 ± 1.0 |
| 58.1 | Pig | PG/EtOH 7:3 | 0.5 | 3.7 ± 1.3 |

Mean ± standard error mean of eight determinations are given.
PG: propylene glycol
EtOH: ethanol AUC means area under the curve, and is a well known term in clinical pharmacology. The AUC value describes the total uptake of the agent in a time interval.

In conclusion, both examples penetrate well into pig skin in vivo after a single application, confirming in vitro data described above.

Biological Activity

The efficacy of the compounds of formula I and salts thereof as PI3 kinase inhibitors can be demonstrated as follows:

The kinase reaction is performed in a final volume of 50 μL per well of a half area COSTAR, 96 well plate. The final concentrations of ATP and phosphatidyl inositol in the assay are 5 μM and 6 μg/mL respectively. The reaction is started by the addition of PI3 kinase, e.g. PI3 kinase.

p110β. The components of the assay are added per well as follows:

10 μL test compound in 5% DMSO per well in columns 2-1.

Total activity is determined by addition 10 μL of 5% vol/vol DMSO in the first 4 wells of column 1 and the last 4 wells of column 12.

The background is determined by addition of 10 μM control compound to the last 4 wells of column 1 and the first 4 wells of column 12.

2 mL 'Assay mix' are prepared per plate:

1.912 mL of HEPES assay buffer 8.33 μL of 3 mM stock of ATP giving a final concentration of 5 μM per well 1 μL of [$^{33}$P]ATP on the activity date giving 0.05 μCi per well 30 μL of 1 mg/mL PI stock giving a final concentration of 6 μg/mL per well 5 μL of 1 M stock $MgCl_2$ giving a final concentration of 1 mM per well 20 μL of the assay mix are added per well.

2 mL 'Enzyme mix' are prepared per plate (x'* μL PI3 kinase p110 in 2 mL of kinase buffer). The 'Enzyme mix' is kept on ice during addition to the assay plates.

*The volume of enzyme is dependent on the enzymatic activity of the batch in use.

20 μl 'Enzyme mix' are added/well to start the reaction.

The plate is then incubated at room temperature for 90 minutes.

The reaction is terminated by the addition of 50 L WGA-SPA bead (wheat germ agglutinin-coated Scintillation Proximity Assay beads) suspension per well.

The assay plate is sealed using TopSeal-S) heat seal for polystyrene microplates, PerkinElmer LAS (Deutschland) GmbH, Rodgau, Germany) and incubated at room temperature for at least 60 minutes.

The assay plate is then centrifuged at 1500 rpm for 2 minutes using the Jouan bench top centrifuge (Jouan Inc., Nantes, France).

The assay plate is counted using a Packard TopCount, each well being counted for 20 seconds.

In a more preferred assay, the kinase reaction is performed in a final volume of 10 μL per well of a low volume non binding CORNING, 384 well black plate (Cat. No. #3676). The final concentrations of ATP and phosphatidyl inositol (PI) in the assay are 1 μM and 10 μg/mL respectively. The reaction is started by the addition of ATP.

The components of the assay are added per well as follows:

50 nL test compounds in 90% DMSO per well, in columns 1-20, 8 concentrations (1/3 and 1/3.33 serial dilution step) in single.

Low control: 50 nL of 90% DMSO in half the wells of columns 23-24 (0.45% in final).

High control: 50 nL of reference compound (e.g. compound of Example 7 in WO 2006/122806) in the other half of columns 23-24 (2.5 μM in final).

Standard: 50 nL of reference compound as just mentioned diluted as the test compounds in columns 21-22

20 mL 'buffer' are prepared per assay:

200 μL of 1M TRIS HCl pH7.5 (10 mM in final)

60 μL of 1M $MgCl_2$ (3 mM in final)

500 μL of 2M NaCl (50 mM in final)

100 μL of 10% CHAPS (0.05% in final)

200 μL of 100 mM DTT (1 mM in final)

18.94 mL of nanopure water 10 mL 'PI' are prepared per assay:

200 μL of 1 mg/ml L-alpha-Phosphatidylinositol (Liver Bovine, Avanti Polar Lipids Cat. No. 840042C MW=909.12) prepared in 3% OctylGlucoside (10 μg/ml in final)

9.8 mL of 'buffer'

10 mL 'ATP' are prepared per assay:

6.7 μL of 3 mM stock of ATP giving a final concentration of 1 μM per well 10 mL of 'buffer'

2.5 mL of each PI3K construct are prepared per assay in 'PI' with the following final concentration:

10 nM PI3K alfa EMV B1075

25 nM beta EMV BV949

10 nM delta EMV BV1060

150 nM gamma EMV BV950

5 μL of 'PI/PI3K' are added per well.

5 μl 'ATP' are added per well to start the reaction.

The plates are then incubated at room temperature for 60 minutes (alfa, beta, delta) or 120 minutes (gamma).

The reaction is terminated by the addition of 10 μL Kinase-Glo (Promega Cat. No. #6714).

The assay plates are read after 10 minutes in Synergy 2 reader (BioTek, Vermont USA) with an integration time of 100 milliseconds and sensitivity set to 191.

Output: The High control is around 60,000 counts and the Low control is 30,000 or lower This luminescence assay gives a useful Z' ratio between 0.4 and 0.7

The Z' value is a universal measurement of the robustness of an assay. A Z' between 0.5 and 1.0 is considered an excellent assay.

For this assay, the PI3K constructs mentioned are prepared as follows:

Molecular Biology:

Two different constructs, BV 1052 and BV 1075, are used to generate the PI3 Kinase α proteins for compound screening.

PI3Kα BV-1052 p85(iSH2)-Gly Linker-p110a(D20aa)-C-Term His Tag

PCR products for the inter SH2 domain (iSH2) of the p85 subunit and for the p110-a subunit (with a deletion of the first 20 amino acids) are generated and fused by overlapping PCR.

The iSH2 PCR product is generated from first strand cDNA using initially primers

```
gwG130-p01
                                        (SEQ ID NO: 1)
(5'-CGAGAATATGATAGATTATATGAAGAAT-3')
and

gwG130-p02
                                        (SEQ ID NO: 2)
(5'-TGGTTT-AATGCTGTTCATACGTTTGTCAAT-3').
```

Subsequently in a secondary PCR reaction, Gateway (Invitrogen AG, Basel, Switzerland) recombination AttB1 sites and linker sequences are added at the 5'end and 3'end of the p85 iSH2 fragment respectively, using primers

```
gwG130-p03
                                        (SEQ ID NO: 3)
(5'-GGGACAAGTTTGTACAAAAAAGCAGGCTACGAAGGAGATATAC
ATAT-GCGAGAATATGATAGATTATATGAAGAAT-3')
and

gwG152-p04
                                        (SEQ ID NO: 4)
(5'-TACCATAATTCCACCACCACCACCGGAAATTCCCCCTGGTTT-
AATGCTGTTCATACGTTTGTCAAT-3').
```

The p110-a fragment is also generated from first strand cDNA, initially using primers

```
gwG152-p01
                                        (SEQ ID NO: 5)
(5'-CTAGTGGAATGTTTACTACCAAATGG-3')
and
gwG152-p02
                                        (SEQ ID NO: 6)
(5'-GTTCAATG-CATGCTGTTTAATTGTGT-3').
```

In a subsequent PCR reaction, linker sequence and a Histidine tag are added at the 5'end and 3'end of the p110-a fragment respectively, using primers

```
gw152-p03
                                        (SEQ ID NO: 7)
(5'-GGGGGAATTTCCGGTGGTGGTGGTGGAATTATGGTAC-

TAGTGGAATGTTTACTACC-AAATGGA-3')
and

gwG152-p06
                                        (SEQ ID NO: 8)
(5'-AGCTCCGTGATGGTGATGGTGATGTGCTCCGTTCAATG-

CATGCTGTTTAATTGTGT-3').
```

The p85-iSH2/p110-a fusion protein is assembled in a third PCR reaction by the overlapping linkers at the 3'end of the iSH2 fragment and the 5'end of the p110-a fragment, using the above mentioned gwG130-p03 primer and a primer containing an overlapping Histidine tag and the AttB2 recombination sequences

```
                                        (SEQ ID NO: 9)
(5'-GGGACCACTTTGTACAAGAAAGCTGGGTTTAAGCTCCGTGATG

GTGATGGTGAT-GTGCTCC-3').
```

This final product is recombined in a (Invitrogen) OR reaction into the donor vector pDONR201 to generate the ORF318 entry clone. This clone is verified by sequencing and used in a Gateway LR reaction to transfer the insert into the Gateway adapted pBlueBac4.5 (Invitrogen) vector for generation of the baculovirus expression vector LR410.

PI3Kα BV-1075 p85(iSH2)-12 XGly Linker-p110a(D20aa)-C-Term His Tag

The construct for Baculovirus BV-1075 is generated by a three-part ligation comprised of a p85 fragment and a p110-a fragment cloned into vector pBlueBac4.5. The p85 fragment is derived from plasmid p1661-2 digested with Nhe/Spe. The p110-a fragment derived from LR410 (see above) as a SpeI/HindIII fragment. The cloning vector pBlueBac4.5 (Invitrogen) is digested with Nhe/HindIII. This results in the construct PED 153.8

The p85 component (iSH2) is generated by PCR using ORF 318 (described above) as a template and one forward primer

```
KAC1028
                                        (SEQ ID NO: 10)
(5'-GCTAGCATGCGAGAATATGATAGATTATATGAAGAATATACC)
```

and two reverse primers,

```
KAC1029
                                        (SEQ ID NO: 11)
(5'-GCCTCCACCACCTCCGCCTGGTTTAATGCTGTTCATACGTTTG
TC)
and
```

-continued

```
KAC1039
                                        (SEQ ID NO: 12)
(5'-TACTAGTCCGCCTCCACCACCTCCGCCTCCACCACCTCCGCC).
```

The two reverse primers overlap and incorporate the 12x Gly linker and the N-terminal sequence of the p110a gene to the SpeI site. The 12x Gly linker replaces the linker in the BV1052 construct. The PCR fragment is cloned into pCR2.1 TOPO (Invitrogen). Of the resulting clones, p1661-2 is determined to be correct. This plasmid is digested with Nhe and SpeI and the resulting fragment is gel-isolated and purified for sub-cloning.

The p110-a cloning fragment is generated by enzymatic digest of clone LR410 (see above) with Spe I and HindIII. The SpeI site is in the coding region of the p110a gene. The resulting fragment is gel-isolated and purified for sub-cloning.

The cloning vector, pBlueBac4.5 (Invitrogen) is prepared by enzymatic digestion with Nhe and HindIII. The cut vector is purified with Qiagen (Quiagen N.V, Venlo, Netherlands) column and then dephosphorylated with Calf Intestine alkaline phosphatase (CIP) (New England BioLabs, Ipswich, Mass.). After completion of the CIP reaction the cut vector is again column purified to generate the final vector. A 3 part ligation is performed using Roche Rapid ligase and the vendor specifications.

PI3Kβ BV-949 p85(iSH2)-Gly Linker-p110b(Full-Length)-C-Term His Tag

PCR products for the inter SH2 domain (iSH2) of the p85 subunit and for the full-length p110-b subunit are generated and fused by overlapping PCR.

The iSH2 PCR product is generated from first strand cDNA initially using primers

```
gwG130-p01
                                        (SEQ ID NO: 1)
(5'-CGAGAATATGATAGATTATATGAAGAAT-3')
and

gwG130-p02
                                        (SEQ ID NO: 2)
(5'-TGGTTT-AATGCTGTTCATACGTTTGTCAAT-3').
```

Subsequently, in a secondary PCR reaction Gateway (Invitrogen) recombination AttB1 sites and linker sequences are added at the 5'end and 3'end of the p85 iSH2 fragment respectively, using primers

```
gwG130-p03
                                        (SEQ ID NO: 3)
(5'-GGGACAAGTTTGTACAAAAAAGCAGGCTACGAAGGAGATA-
TACATATGCGAGAATATGATAGATTATATGAAGAAT-3')
and

gwG130-p05
                                        (SEQ ID NO: 13)
(5'-ACTGAAGCATCCTCCTCCTCCTCCTCCTGGTTTAAT-
GCTGTTCATACGTTTGTC-3').
```

The p110-b fragment is also generated from first strand cDNA initially using primers gwG130-p04 (5'-ATTAAACCAGGAGGAGGAGGAGGAGGATGCTTCAGTTTCATAATGCC-TCCTGCT-3') (SEQ ID NO: 4)

which contains linker sequences and the 5'end of p110-b and gwG130-p06 (SEQ ID NO: 14)
(5'-AGCTCCGTGATGGTGATGGTGATGTGCTCCAGATCTGTAGTCT TT-CCGAACTGTGTG-3')

which contains sequences of the 3'end of p110-b fused to a Histidine tag.

The p85-iSH2/p110-b fusion protein is assembled by an overlapping PCR a reaction of the linkers at the 3'end of the iSH2 fragment and the 5'end of the p110-b fragment, using the above mentioned gwG130-p03 primer and a primer containing an overlapping Histidine tag and the AttB2 recombination sequences (5'-GGGACCACTTTGTACAA-GAAAGCTGGGTTT-AAGCTCCGTGATGGTGATGGTGATGTGCTCC-3) (SEQ ID NO: 9).

This final product is recombined in a Gateway (Invitrogen) OR reaction into the donor vector pDONR201 to generate the ORF253 entry clone. This clone is verified by sequencing and used in a Gateway LR reaction to transfer the insert into the Gateway adapted pBlueBac4.5 (Invitrogen) vector for generation of the baculovirus expression vector LR280.

PI3Kδ BV-1060 p85(iSH2)-Gly Linker-p110d(Full-Length)-C-Term His Tag.

PCR products for the inter SH2 domain (iSH2) of the p85 subunit and for the full-length p110-d subunit are generated and fused by overlapping PCR.

The iSH2 PCR product is generated from first strand cDNA using initially primers gwG130-p01 (SEQ ID NO: 1)
(5'-CGAGAATATGATAGATTATATGAAGAAT-3')
and gwG130-p02 (SEQ ID NO: 2)
(5'-TGGTTT-AATGCTGTTCATACGTTTGTCAAT-3').

Subsequently, in a secondary PCR reaction Gateway (Invitrogen) recombination AttB1 sites and linker sequences are added at the 5'end and 3'end of the p85 iSH2 fragment respectively, using primers gwG130-p03 (SEQ ID NO: 3)
(5'-GGGACAAGTTTGTACAAAAAAGCAGGCTACGAAGGAGATATAC AT-ATGCGAGAATATGATAGATTATATGAAGAAT-3')
and gwG154-p04 (SEQ ID NO: 15)
(5'-TCCTCCTCCTCCTCCTCCTGGTTTAATGCTGTTCATACGTTTG TC-3').

The p110-a fragment is also generated from first strand cDNA using initially primers gwG154-p01 (SEQ ID NO: 16)
(5'-ATGCCCCCTGGGGTGGACTGCCCCAT-3')
and gwG154-p02 (SEQ ID NO: 17)
(5'-CTACTG-CCTGTTGTCTTTGGACACGT-3').

In a subsequent PCR reaction linker sequences and a Histidine tag is added at the 5'end and 3'end of the p110-d fragment respectively, using primers gw154-p03 (SEQ ID NO: 18)
(5'-ATTAAACCAGGAGGAGGAGGAGGAGGACCCCCTGGGGTGGAC-TGCCCCATGGA-3')
and gwG154-p06 (SEQ ID NO: 19)
(5'-AGCTCCGTGATGGTGAT-GGTGATGTGCT-CCCTGCCTGTTGT CTTTGGACACGTTGT-3').

The p85-iSH2/p110-d fusion protein is assembled in a third PCR reaction by the overlapping linkers at the 3'end of the iSH2 fragment and the 5'end of the p110-d fragment, using the above mentioned gwG130-p03 primer and a primer containing an overlapping Histidine tag and the Gateway (Invitrogen) AttB2 recombination sequences (5'-GGGAC-CACTTTGTA-CAAGAAAGCTGGGTTT-AAGCTCCGT-GATGGTGATGGTGATGTGCTCC-3) (SEQ ID NO: 09).

This final product is recombined in a Gateway (Invitrogen) OR reaction into the donor vector pDONR201 to generate the ORF319 entry clone. This clone is verified by sequencing and used in a Gateway LR reaction to transfer the insert into the Gateway adapted pBlueBac4.5 (Invitrogen) vector for generation of the baculovirus expression vector LR415.

PI3Kγ BV-950 p110g(D144aa)-C-Term His Tag

This construct is obtained from Roger Williams lab, MRC Laboratory of Molecular Biology, Cambridge, UK (November, 2003). Description of the construct in: Pacold M. E. et al. (2000) Cell 103, 931-943.

Expression:

Methods to Generate Recombinant Baculovirus and Protein for PI3K Isoforms:

The pBlue-Bac4.5 (for a, b, and d isoforms) or pVL1393 (for g) plasmids containing the different PI3 kinase genes are co-transfected with BaculoGold WT genomic DNA (BD Biosciences, Franklin Lakes, N.J., USA) using methods recommended by the vendor. Subsequently, the recombinant baculovirus obtained from the transfection is plaque-purified on Sf9 insect cells to yield several isolates expressing recombinant protein. Positive clones are selected by anti-HIS or anti-isoform antibody western. For PI3K alpha and delta isoforms, a secondary plaque-purification is performed on the first clonal virus stocks of PI3K. Amplification of all baculovirus isolates is performed at low multiplicity of infection (moi) to generate high-titer, low passage stock for protein production. The baculoviruses are designated BV1052 (α) and BV1075 (α), BV949 (β), BV1060 (δ) and BV950 (γ).

Protein production involves infection (passage 3 or lower) of suspended Tn5 (Trichoplusia ni) or TiniPro (Expression Systems, LLC, Woodland, Calif., USA) cells in protein-free media at moi of 2-10 for 39-48 hours in 2 L glass Erlenmyer flasks (110 rpm) or wave-bioreactors (22-25 rpm). Initially, 10 L working volume wave-bioreactors are seeded at a density of 3e5 cells/ml at half capacity (5 L). The reactor is rocked at 15 rpm during the cell growth phase for 72 hours, supplemented with 5% oxygen mixed with air (0.2 L per minute). Immediately prior to infection, the wave-reactor cultures are analyzed for density, viability and diluted to approximately 1.5e6 cell/ml. 100-500 ml of high titer, low passage virus is added following 2-4 hours of additional culture. Oxygen is increased to 35% for the 39-48 hour infection period and rocking platform rpm increased to 25. During infection, cells are monitored by Vicell viability analyzer (Beckman Coulter, Inc, Fullerton, Calif., USA) bioprocess for viability, diameter and density. Nova Bioanalyzer (NOVA Biomedical Corp., Waltham, Mass., USA) readings of various parameters and metabolites (pH, $O_2$ saturation, glucose, etc.) are taken every 12-18 hours until harvest. The wave-bioreactor cells are collected within 40 hours post infection. Cells are collected by centrifugation (4 degrees C. at 1500 rpm), and subsequently maintained on ice during pooling of pellets for lysis and purification. Pellet pools are made with small amounts of cold, un-supplemented Grace's media (w/o protease inhibitors).

PI3K Alpha Purification Protocol For HTS (BV1052)

PI3K alpha is purified in three chromatographic steps: immobilized metal affinity chromatography on a Ni Sepharose resin (GE Healthcare, belonging to General Electric Company, Fairfield, Conn., USA), gel filtration utilizing a Superdex 200 26160 column (GE Healthcare), and finally a cation exchange step on a SP-XL column (GE Healthcare). All buffers are chilled to 4° C. and lysis is performed chilled on ice. Column fractionation is performed rapidly at room temperature.

Typically frozen insect cells are lysed in a hypertonic lysis buffer and applied to a prepared IMAC column. The resin is washed with 3-5 column volumes of lysis buffer, followed by 3-5 column volumes wash buffer containing 45 mM imidazole, and the target protein is then eluted with a buffer containing 250 mM imidazole. Fractions are analyzed by Coomassie stained SDS-PAGE gels, and fractions containing target protein are pooled and applied to a prepared GFC column. Fractions from the GFC column are analyzed by Coomassie stained SDS-PAGE gels, and fractions containing target protein are pooled. The pool from the GFC column is diluted into a low salt buffer and applied to a prepared SP-XL column. The column is washed with low salt buffer until a stable A280 baseline absorbance is achieved, and eluted using a 20 column volume gradient from 0 mM NaCl to 500 mM NaCl. Again, fractions from the SP-XL column are analyzed by Coomassie stained SDS-PAGE gels, and fractions containing the target protein are pooled. The final pool is dialyzed into a storage buffer containing 50% glycerol and stored at −20° C. The final pool is assayed for activity in a phosphoinositol kinase assay.

PI3K Beta Purification Protocol For HTS (BV949)

PI3K beta is purified in two chromatographic steps: immobilized metal affinity chromatography (IMAC) on a Ni Sepharose resin (GE Healthcare) and gel filtration (GFC) utilizing a Superdex 200 26/60 column (GE Healthcare). All buffers are chilled to 4° C. and lysis is performed chilled on ice. Column fractionation is performed rapidly at room temperature.

Typically frozen insect cells are lysed in a hypertonic lysis buffer and applied to a prepared IMAC column. The resin is washed with 3-5 column volumes of lysis buffer, followed by 3-5 column volumes wash buffer containing 45 mM imidazole, and the target protein is then eluted with a buffer containing 250 mM imidazole. Fractions are analyzed by Coomassie stained SDS-PAGE gels, and fractions containing target protein are pooled and applied to a prepared GFC column. Fractions from the GFC column are analyzed by Coomassie stained SDS-PAGE gels, and fractions containing target protein are pooled. The final pool is dialyzed into a storage buffer containing 50% glycerol and stored at −20° C. The final pool is assayed for activity in the phosphoinostitol kinase assay.

PI3K Gamma Purification Protocol For HTS (BV950)

PI3K gamma is purified in two chromatographic steps: immobilized metal affinity chromatography (IMAC) on a Ni Sepharose resin (GE Healthcare) and gel filtration (GFC) utilizing a Superdex 200 26/60 column (GE Healthcare). All buffers are chilled to 4° C. and lysis is performed chilled on ice. Column fractionation is performed rapidly at room temperature. Typically frozen insect cells are lysed in a hypertonic lysis buffer and applied to a prepared IMAC column. The resin is washed with 3-5 column volumes of lysis buffer, followed by 3-5 column volumes wash buffer containing 45 mM imidazole, and the target protein is then eluted with a buffer containing 250 mM imidazole. Fractions are analyzed by Coomassie stained SDS-PAGE gels, and fractions containing target protein are pooled and applied to a prepared GFC column. Fractions from the GFC column are analyzed by Coomassie stained SDS-PAGE gels, and fractions containing target protein are pooled. The final pool is dialyzed into a storage buffer containing 50% glycerol and stored at −20° C. The final pool is assayed for activity in the phosphoinostitol kinase assay.

PI3K Delta Purification Protocol For HTS (BV1060)

PI3K delta is purified in three chromatographic steps: immobilized metal affinity chromatography on a Ni Sepharose resin (GE Healthcare), gel filtration utilizing a Superdex 200 26/60 column (GE Healthcare), and finally a anion exchange step on a Q-HP column (GE Healthcare). All buffers are chilled to 4° C. and lysis is performed chilled on ice. Column fractionation is performed rapidly at room temperature. Typically frozen insect cells are lysed in a hypertonic lysis buffer and applied to a prepared IMAC column. The resin is washed with 3-5 column volumes of lysis buffer, followed by 3-5 column volumes wash buffer containing 45 mM imidazole, and the target protein is then eluted with a buffer containing 250 mM imidazole. Fractions are analyzed by Coomassie stained SDS-PAGE gels, and fractions containing the target protein are pooled and applied to a prepared GFC column. Fractions from the GFC column are analyzed by Coomassie stained SDS-PAGE gels, and fractions containing the target protein are pooled. The pool from the GFC column is diluted into a low salt buffer and applied to a prepared Q-HP column. The column is washed with low salt buffer until a stable A280 baseline absorbance is achieved, and eluted using a 20 column volume gradient from 0 mM NaCl to 500 mM NaCl. Again, fractions from the Q-HP column are analyzed by Coomassie stained SDS-PAGE gels, and fractions containing the target protein are pooled. The final pool is dialyzed into a storage buffer containing 50% glycerol and stored at −20° C. The final pool is assayed for activity in the phosphoinostitol kinase assay.

IC50 is determined by a four parameter curve fitting routine that comes along with "excel fit". A 4 Parameter logistic equation is used to calculate $IC_{50}$ values (IDBS XLfit) of the percentage inhibition of each compound at 8 concentrations (usually 10, 3.0, 1.0, 0.3, 0.1, 0.030, 0.010 and 0.003 μM). Alternatively, IC50 values are calculated using idbsXLfit model 204, which is a 4 parameter logistic model.

Yet alternatively, for an ATP depletion assay, compounds of the formula (I) to be tested are dissolved in DMSO and directly distributed into a white 384-well plate at 0.5 μL per well. To start the reaction, 10 μL of 10 nM PI3 kinase and 5 μg/mL 1-alpha-phosphatidylinositol (PI) are added into each well followed by 10 μL of 2 μM ATP. The reaction is performed until approx 50% of the ATP is depleted, and then stopped by the addition of 20 μL of Kinase-Glo solution (Promega Corp., Madison, Wis., USA). The stopped reaction is incubated for 5 minutes and the remaining ATP is then detected via luminescence. $IC_{50}$ values are then determined.

Some of the compounds of formula (I) show a certain level of selectivity against the different paralogs PI3K alpha, beta, gamma and delta.

The range of activity, expressed as $IC_{50}$, in these assays is preferably between 1 nM and 5000 nM, more preferably between 1 nM and about 1000 nM

| | | | | | | | | | | |
|---|---|---|---|---|---|---|---|---|---|---|
| PI3K alpha $IC_{50}$ [nM] | 9 | 60 | 155 | 5 | 37 | 62 | 14 | 18 | 16 | 17 |
| Example | 182 | 4.1 | 56.5 | 56.4 | 124 | 2.2 | 177.1 | 148.2 | 119 | 107 |
| PI3K alpha $IC_{50}$ [nM] | 138 | 39 | 44 | 11 | 21 | 42 | 5 | 39 | 12 | 938 |
| Example | 132 | 82 | 175.3 | 128.2 | 3.9 | 103.2 | 110 | 179 | 116 | 133 |
| PI3K alpha $IC_{50}$ [nM] | 35 | 11 | 9 | 61 | 25 | 24 | 4 | 30 | 70 | 86 |
| Example | 146.4 | 243 | 36 | 3.7 | 56.2 | 2.7 | 189 | 17.1 | 42 | 18 |
| PI3K alpha $IC_{50}$ [nM] | 59 | 92 | <3 | 14 | 7 | 10 | 12 | 18 | 83 | 30 |
| Example | 1.7 | 146.6 | 234.2 | 207 | 34 | 239 | 215.1 | 195.1 | 91 | 30.2 |
| PI3K alpha $IC_{50}$ [nM] | 20 | 63 | 19 | 70 | 9 | 33 | 32 | 13 | 125 | 4 |
| Example | 234.1 | 149.3 | 193 | 177.2 | 168.3 | 167 | 171 | 218 | 155.4 | 56.1 |
| PI3K alpha $IC_{50}$ [nM] | 8 | 65 | 4 | 23 | 56 | 7 | 10 | 6 | 50 | 13 |
| Example | 248.2 | 2.4 | 194.2 | 4.5 | 55 | 32.1 | 166.3 | 211.2 | 125.2 | 191.2 |
| PI3K alpha $IC_{50}$ [nM] | 30 | 9 | <3 | 8 | 6 | 23 | 12 | 42 | 91 | 44 |
| Example | 155.3 | 87.3 | 60.1 | 1.6 | 58.2 | 168.2 | 13 | 87.4 | 3.10 | 152.3 |
| PI3K alpha $IC_{50}$ [nM] | 8 | 9 | 27 | 28 | 16 | 215 | 22 | 14 | 9 | 11 |
| Example | 144.2 | 33 | 152.1 | 246 | 99 | 212.2 | 51.4 | 155.2 | 17.3 | 202 |
| PI3K alpha $IC_{50}$ [nM] | 14 | 14 | 32 | 39 | 4 | 26 | 87 | 210 | 18 | 8 |
| Example | 45.1 | 25.1 | 21.2 | 172 | 184 | 16.2 | 64 | 8.1 | 241 | 237 |
| PI3K alpha $IC_{50}$ [nM] | 11 | 94 | 76 | 5 | 17 | 85 | 28 | 14 | 11 | 30 |
| Example | 254 | 2.1 | 135 | 249 | 198 | 97 | 125.1 | 141.2 | 128.1 | 93.2 |
| PI3K alpha $IC_{50}$ [nM] | 20 | 18 | 11 | 6 | 56 | 14 | 24 | 79 | 51 | 48 |
| Example | 127 | 14 | 120 | 76 | 52 | 75 | 210 | 104 | 126 | 4.6 |
| PI3K alpha $IC_{50}$ [nM] | <3 | 123 | 59 | 817 | 20 | 27 | 27 | 28 | 9 | 6 |
| Example | 39 | 15.3 | 16.3 | 141.1 | 248.1 | 51.3 | 145.2 | 1.9 | 166.4 | 240 |
| PI3K alpha $IC_{50}$ [nM] | 99 | 10 | 17 | 184 | 10 | 61 | 146 | 37 | 70 | 3 |
| Example | 4.3 | 24 | 176 | 16.4 | 1.5 | 51.6 | 3.3 | 3.5 | 44 | 252 |
| PI3K alpha $IC_{50}$ [nM] | 119 | 7 | 17 | 7 | 27 | 22 | 161 | 29 | 10 | 20 |
| Example | 146.2 | 150.1 | 54.1 | 148.3 | 111 | 180.2 | 137 | 31 | 248.3 | 74 |
| PI3K alpha $IC_{50}$ [nM] | 17 | 118 | 9 | 14 | 29 | 9 | 16 | 64 | 47 | 22 |
| Example | 88.2 | 98.2 | 4.9 | 7.2 | 72 | 188 | 15.1 | 234.4 | 96 | 6.2 |
| PI3K alpha $IC_{50}$ [nM] | 43 | 41 | 157 | 100 | 38 | 50 | 56 | 36 | 73 | 94 |
| Example | 87.5 | 186 | 154.1 | 230 | 29.2 | 3.6 | 17.2 | 95 | 47 | 53.2 |
| PI3K alpha $IC_{50}$ [nM] | 17 | 18 | 12 | 7 | 5 | 163 | 8 | 11 | 8 | 41 |
| Example | 152.2 | 89 | 86 | 157 | 203 | 247.3 | 23.1 | 185.2 | 6.3 | 25.6 |
| PI3K alpha $IC_{50}$ [nM] | 15 | 20 | 461 | 24 | 14 | 482 | 11 | 13 | 7 | 110 |
| Example | 187 | 103.1 | 4.7 | 169.1 | 160.1 | 19 | 29.3 | 155.1 | 165 | 51.5 |
| PI3K alpha $IC_{50}$ [nM] | 14 | 5 | 13 | 29 | 17 | 15 | 3 | 11 | 220 | 34 |
| Example | 215.2 | 77 | 138 | 238 | 174 | 208 | 183 | 118.2 | 213.2 | 5.2 |
| PI3K alpha $IC_{50}$ [nM] | 60 | 7 | 5 | 11 | 14 | 375 | 55 | 8 | 6 | 246 |
| Example | 6.4 | 58.5 | 101 | 88.1 | 146.1 | 70 | 170 | 229 | 211.1 | 9 |
| PI3K alpha $IC_{50}$ [nM] | 161 | 7 | 59 | 9 | 9 | 71 | 8 | 6 | 462 | 38 |
| Example | 131 | 149.2 | 25.3 | 158.1 | 220.1 | 37.3 | 12 | 209 | 213.1 | 57 |
| PI3K alpha $IC_{50}$ [nM] | 8 | 13 | 34 | 22 | 30 | 6 | 26 | 100 | 14 | 15 |
| Example | 215.3 | 221.2 | 85.3 | 30.1 | 244 | 22 | 206.1 | 148.4 | 87.1 | 234.3 |
| PI3K alpha $IC_{50}$ [nM] | 15 | 34 | 74 | 15 | 58 | 14 | 10 | 82 | 30 | 250 |
| Example | 195.4 | 98.1 | 83 | 166.2 | 117 | 158.5 | 144.3 | 56.3 | 87.2 | 37.2 |
| PI3K alpha $IC_{50}$ [nM] | 39 | 23 | 48 | 199 | 36 | 5 | 44 | 9 | 78 | 26 |
| Example | 69 | 173 | 27.2 | 175.2 | 144.1 | 205 | 90.2 | 1.10 | 3.2 | 148.1 |
| PI3K alpha IC50 [nM] | 6 | 29 | 5 | 12 | 110 | 15 | 32 | 51 | 34 | 9 |

-continued

| | | | | | | | | | | |
|---|---|---|---|---|---|---|---|---|---|---|
| Example | 1.8 | 2.8 | 35 | 181 | 105 | 236 | 248.5 | 81.2 | 37.1 | 86.2 |
| PI3K alpha $IC_{50}$ [nM] | 15 | 8 | 39 | 43 | 16 | 14 | 46 | 57 | 188 | 25 |
| Example | 4.2 | 51.2 | 160.2 | 222 | 156 | 122 | 85.2 | 3.12 | 50 | 136 |
| PI3K alpha $IC_{50}$ [nM] | 13 | 132 | 186 | 9 | 971 | 16 | 5 | 4 | 47 | 4 |
| Example | 190 | 108 | 206.2 | 118.5 | 247.5 | 10.2 | 185.1 | 84.2 | 49 | 93.1 |
| PI3K alpha $IC_{50}$ [nM] | 5 | 22 | 5 | 21 | 9 | 28 | 9 | 28 | 217 | 42 |
| Example | 169.3 | 233 | 220.3 | 141.3 | 150.2 | 166.5 | 166.1 | 142.1 | 3.4 | 145.1 |
| PI3K alpha $IC_{50}$ [nM] | 175 | 5 | 14 | 154 | 6 | 103 | 10 | 14 | 785 | 44 |
| Example | 196.2 | 250 | 221.1 | 106 | 151 | 26 | 43.1 | 168.1 | 130 | 232 |
| PI3K alpha $IC_{50}$ [nM] | 4 | 10 | 43 | 146 | 6 | 9 | 45 | 29 | 74 | 95 |
| Example | 201 | 153.1 | 90.1 | 2.6 | 85.1 | 200 | 4.4 | 196.1 | 45.2 | 8.2 |
| PI3K alpha $IC_{50}$ [nM] | 46 | 93 | 29 | 42 | 8 | 30 | 82 | 24 | 33 | 30 |
| Example | 7.1 | 224.2 | 6.1 | 80.2 | 43.2 | 32.2 | 178 | 29.1 | 226 | 5.1 |
| PI3K alpha $IC_{50}$ [nM] | 85 | 28 | 5 | 14 | 61 | 148 | 12 | 22 | 168 | 34 |
| Example | 228 | 251 | 164 | 58.4 | 62 | 115 | 25.4 | 245 | 140.1 | 159 |
| PI3K alpha $IC_{50}$ [nM] | 41 | 19 | 17 | 25 | 8 | 7 | 18 | 16 | 249 | 66 |
| Example | 197.2 | 143 | 139 | 147 | 27.1 | 158.3 | 142.2 | 3.8 | 15.2 | 175.1 |
| PI3K alpha $IC_{50}$ [nM] | 446 | 7 | 34 | 34 | 39 | 8 | 9 | 3 | 460 | 41 |
| Example | 123 | 248.4 | 194.1 | 197.1 | 1.4 | 38 | 161 | 223 | 65 | 180.1 |
| PI3K alpha $IC_{50}$ [nM] | 12 | 8 | 12 | 543 | 21 | 18 | 20 | 207 | 173 | 12 |
| Example | 61 | 217 | 109 | 134 | 3.1 | 59.1 | 225 | 3.11 | 73 | 219 |
| PI3K alpha $IC_{50}$ [nM] | 13 | 8 | <3 | 5 | 272 | 36 | 17 | 21 | 81 | 72 |
| Example | 25.2 | 162 | 192 | 59.2 | 21.1 | 66 | 2.5 | 68 | 242.2 | 158.4 |
| PI3K alpha $IC_{50}$ [nM] | 30 | 12 | 136 | 38 | 44 | 75 | 79 | 16 | 37 | 43 |
| Example | 25.5 | 129 | 10.1 | 247.2 | 158.2 | 81.1 | 112 | 53.1 | 195.2 | 2.9 |
| PI3K alpha $IC_{50}$ [nM] | 4 | 48 | 48 | 15 | 92 | <9 | 15 | 6 | 6 | 16 |
| Example | 253 | 195.3 | 79 | 199 | 63 | 41 | 224.1 | 163 | 58.1 | 118.3 |
| PI3K alpha $IC_{50}$ [nM] | 104 | 6 | 53 | 173 | 26 | 33 | 93 | 50 | 10 | 35 |
| Example | 92 | 84.1 | 212.1 | 154.2 | 118.1 | 16.1 | 247.1 | 146.3 | 220.2 | 23.2 |
| PI3K alpha $IC_{50}$ [nM] | 405 | 50 | 266 | 14 | 139 | 55 | 30 | 62 | 315 | 20 |
| Example | 231 | 46 | 37.4 | 1.3 | 153.3 | 98.3 | 2.3 | 28.2 | 60.2 | 118.4 |
| PI3K alpha $IC_{50}$ [nM] | 20 | 19 | 13 | 13 | 236 | 71 | <3 | 76 | 30 | 14 |
| Example | 40 | 121 | 28.3 | 102 | 58.3 | 227 | 28.1 | 45.3 | 54.2 | 191.1 |
| PI3K alpha $IC_{50}$ [nM] | 3 | 50 | 15 | 48 | 34 | 23 | 18 | 23 | 25 | 6 |
| Example | 16.5 | 1.2 | 153.2 | 149.1 | 169.2 | 242.1 | 100 | 51.1 | 142.3 | 215.4 |
| PI3K alpha $IC_{50}$ [nM] | 9 | | | | | | | | | |
| Example | 146.5 | | | | | | | | | |
| PI3K beta $IC_{50}$ [nM] | 252 | 10 | 206 | 17 | 7 | 11 | 28 | 13 | 370 | 7 |
| Example | 18 | 158.1 | 116 | 211.2 | 220.3 | 182 | 54.1 | 39 | 74 | 168.3 |
| PI3K beta $IC_{50}$ [nM] | 241 | 13 | 24 | 161 | 150 | 37 | 506 | 184 | 122 | 48 |
| Example | 2.1 | 239 | 77 | 195.3 | 234.3 | 166.1 | 49 | 158.2 | 27.1 | 25.3 |
| PI3K beta $IC_{50}$ [nM] | 274 | 31 | 123 | 19 | 166 | 39 | 504 | 14 | 59 | 537 |
| Example | 178 | 28.3 | 3.8 | 25.1 | 2.9 | 1.9 | 251 | 153.1 | 4.9 | 3.7 |
| PI3K beta $IC_{50}$ [nM] | 40 | 6 | 134 | 6 | 68 | 10 | 407 | 83 | 302 | 163 |
| Example | 38 | 192 | 222 | 194.2 | 149.1 | 163 | 98.1 | 62 | 118.1 | 195.2 |
| PI3K beta $IC_{50}$ [nM] | 21 | 185 | 112 | 103 | 44 | 33 | 130 | 19 | 391 | 51 |
| Example | 158.5 | 6.2 | 72 | 197.2 | 225 | 99 | 179 | 59.2 | 112 | 148.1 |
| PI3K beta $IC_{50}$ [nM] | 83 | 79 | 21 | 167 | 559 | 120 | 16 | 67 | 382 | 213 |
| Example | 124 | 152.1 | 12 | 146.5 | 175.3 | 2.4 | 144.3 | 242.1 | 4.3 | 4.5 |
| PI3K beta $IC_{50}$ [nM] | 56 | 101 | 129 | 32 | 340 | 114 | 43 | 140 | 404 | 61 |
| Example | 185.2 | 153.3 | 1.3 | 198 | 3.5 | 147 | 32.1 | 100 | 7.1 | 68 |
| PI3K beta $IC_{50}$ [nM] | 332 | 51 | 6 | 344 | 12 | 20 | 68 | 799 | 9 | 843 |
| Example | 103.2 | 6.3 | 56.4 | 230 | 87.3 | 162 | 88.2 | 10.1 | 185.1 | 53.2 |
| PI3K beta $IC_{50}$ [nM] | 120 | 17 | 7 | 17 | 246 | 526 | 197 | 21 | 38 | 46 |

-continued

| | | | | | | | | | | |
|---|---|---|---|---|---|---|---|---|---|---|
| Example | 17.1 | 150.1 | 237 | 160.1 | 92 | 15.3 | 23.2 | 86.2 | 109 | 155.3 |
| PI3K beta $IC_{50}$ [nM] | 359 | 110 | 17 | 112 | 62 | 152 | 28 | 19 | 239 | 192 |
| Example | 234.4 | 63 | 128.2 | 41 | 254 | 1.7 | 187 | 218 | 30.2 | 3.1 |
| PI3K beta $IC_{50}$ [nM] | 25 | 35 | 56 | 40 | 44 | 82 | 281 | 34 | 18 | 495 |
| Example | 13 | 128.1 | 43.2 | 215.1 | 127 | 118.2 | 81.2 | 129 | 161 | 6.4 |
| PI3K beta $IC_{50}$ [nM] | 103 | 733 | 33 | 28 | 16 | 12 | 33 | 109 | 28 | 322 |
| Example | 238 | 4.4 | 152.2 | 88.1 | 25.4 | 85.1 | 249 | 2.8 | 157 | 64 |
| PI3K beta $IC_{50}$ [nM] | 336 | 291 | 35 | 335 | 23 | 13 | 385 | 126 | 787 | 23 |
| Example | 4.6 | 102 | 148.2 | 87.5 | 89 | 200 | 142.3 | 93.2 | 5.1 | 248.3 |
| PI3K beta $IC_{50}$ [nM] | 432 | 104 | 71 | 25 | 111 | 132 | 41 | 41 | 115 | 9 |
| Example | 206.2 | 203 | 248.1 | 234.2 | 143 | 28.2 | 118.5 | 220.2 | 90.2 | 153.2 |
| PI3K beta $IC_{50}$ [nM] | 228 | 22 | 157 | 22 | 86 | 68 | 91 | 163 | 165 | 23 |
| Example | 56.3 | 87.2 | 30.1 | 122 | 10.2 | 168.2 | 2.7 | 105 | 32.2 | 221.1 |
| PI3K beta $IC_{50}$ [nM] | 76 | 8 | 324 | 188 | 7 | 69 | 15 | 15 | 72 | 29 |
| Example | 154.2 | 229 | 194.1 | 244 | 169.3 | 58.5 | 28.1 | 34 | 195.1 | 45.2 |
| PI3K beta $IC_{50}$ [nM] | 21 | 23 | 46 | 473 | 377 | 167 | 13 | 193 | 578 | 612 |
| Example | 151 | 220.1 | 33 | 3.11 | 138 | 207 | 86 | 56.5 | 25.2 | 2.6 |
| PI3K beta $IC_{50}$ [nM] | 39 | 42 | 51 | 278 | 287 | 5 | 409 | 27 | 76 | 56 |
| Example | 233 | 180.1 | 54.2 | 2.2 | 142.2 | 215.3 | 91 | 199 | 208 | 66 |
| PI3K beta $IC_{50}$ [nM] | 49 | 145 | 207 | 287 | 407 | 81 | 5 | 162 | 119 | 13 |
| Example | 210 | 171 | 146.3 | 227 | 141.3 | 166.2 | 58.2 | 145.1 | 234.1 | 217 |
| PI3K beta $IC_{50}$ [nM] | 19 | 80 | 112 | 91 | 25 | 515 | 17 | 95 | 20 | 25 |
| Example | 155.1 | 144.1 | 158.4 | 81.1 | 165 | 16.4 | 205 | 148.4 | 119 | 61 |
| PI3K beta $IC_{50}$ [nM] | 79 | 36 | 477 | 61 | 517 | 144 | 28 | 93 | 281 | 180 |
| Example | 152.3 | 174 | 3.6 | 125.1 | 26 | 248.5 | 16.5 | 87.4 | 146.6 | 2.3 |
| PI3K beta $IC_{50}$ [nM] | 57 | 43 | 6 | 34 | 100 | 17 | 50 | 10 | 101 | 169 |
| Example | 29.1 | 1.6 | 1.10 | 168.1 | 159 | 155.2 | 193 | 215.2 | 232 | 45.3 |
| PI3K beta $IC_{50}$ [nM] | 24 | 18 | 23 | 178 | 12 | 8 | 144 | 101 | 66 | 98 |
| Example | 252 | 177.1 | 101 | 191.2 | 149.2 | 158.3 | 29.3 | 1.5 | 146.2 | 154.1 |
| PI3K beta $IC_{50}$ [nM] | 162 | 173 | 171 | 62 | 45 | 29 | 184 | 41 | 6 | 39 |
| Example | 245 | 27.2 | 16.2 | 224.1 | 146.1 | 221.2 | 241 | 23.1 | 201 | 90.1 |
| PI3K beta $IC_{50}$ [nM] | 84 | 142 | 280 | 167 | 95 | 133 | 22 | 37 | 130 | 10 |
| Example | 167 | 141.2 | 224.2 | 29.2 | 107 | 25.6 | 248.2 | 35 | 118.4 | 166.4 |
| PI3K beta $IC_{50}$ [nM] | 66 | 802 | 3 | 603 | 387 | 29 | 18 | 222 | 93 | 49 |
| Example | 7.2 | 126 | 148.3 | 242.2 | 8.2 | 156 | 211.1 | 166.5 | 125.2 | 219 |
| PI3K beta $IC_{50}$ [nM] | 47 | 811 | 206 | 762 | 12 | 273 | 4 | 970 | 343 | 41 |
| Example | 45.1 | 47 | 17.2 | 4.1 | 215.4 | 209 | 93.1 | 37.1 | 52 | 111 |
| PI3K beta $IC_{50}$ [nM] | 468 | 7 | 129 | 87 | 47 | 13 | 6 | 695 | 73 | 77 |
| Example | 197.1 | 58.1 | 69 | 169.1 | 243 | 181 | 56.1 | 118.3 | 186 | 196.1 |
| PI3K beta $IC_{50}$ [nM] | 81 | 176 | 378 | 130 | 988 | 33 | 13 | 327 | 37 | 288 |
| Example | 166.3 | 146.4 | 1.4 | 160.2 | 15.2 | 176 | 202 | 177.2 | 75 | 80.2 |
| PI3K beta $IC_{50}$ [nM] | 67 | 201 | 90 | 544 | 38 | 11 | 227 | 89 | 8 | 3 |
| Example | 31 | 142.1 | 236 | 96 | 206.1 | 22 | 6.1 | 59.1 | 84.1 | 60.1 |
| PI3K beta $IC_{50}$ [nM] | 34 | 93 | 24 | 395 | 946 | 26 | 101 | 86 | 10 | 225 |
| Example | 40 | 121 | 195.4 | 170 | 21.1 | 24 | 103.1 | 2.5 | 76 | 4.2 |
| PI3K beta $IC_{50}$ [nM] | 29 | 51 | 24 | 7 | 190 | 165 | 30 | 218 | 137 | 37 |
| Example | 58.4 | 53.1 | 191.1 | 223 | 43.1 | 169.2 | 25.5 | 44 | 110 | 17.3 |
| PI3K beta $IC_{50}$ [nM] | 205 | 907 | 30 | 139 | 404 | 317 | 10 | 477 | 5 | 280 |
| Example | 21.2 | 117 | 188 | 85.2 | 16.3 | 56.2 | 184 | 85.3 | 189 | 1.2 |
| PI3K beta $IC_{50}$ [nM] | 20 | 146 | 32 | 255 | 68 | 130 | 18 | 71 | 228 | 154 |
| Example | 1.8 | 172 | 36 | 15.1 | 250 | 14 | 120 | 226 | 16.1 | 82 |
| PI3K beta $IC_{50}$ [nM] | 951 | 41 | 82 | 161 | 202 | 8 | 148 | 50 | 563 | 12 |

-continued

| | | | | | | | | | | |
|---|---|---|---|---|---|---|---|---|---|---|
| Example | 55 | 95 | 246 | 132 | 149.3 | 248.4 | 173 | 145.2 | 46 | 150.2 |
| PI3K beta $IC_{50}$ [nM] | 21 | 40 | 11 | 8 | 42 | 180 | 215 | 4 | 469 | 30 |
| Example | 87.1 | 144.2 | 164 | 253 | 180.2 | 175.1 | 57 | 183 | 141.1 | 84.2 |
| PI3K beta $IC_{50}$ [nM] | 91 | 36 | 401 | 203 | 55 | | | | | |
| Example | 240 | 190 | 3.3 | 58.3 | 155.4 | | | | | |
| PI3K delta $IC_{50}$ [nM] | 44 | 24 | 8 | 234 | 40 | 4 | 14 | 91 | 166 | 28 |
| Example | 6.4 | 36 | 203 | 83 | 125.2 | 158.3 | 171 | 4.6 | 228 | 6.1 |
| PI3K delta $IC_{50}$ [nM] | 9 | 800 | 101 | 118 | 24 | <3 | 9 | 16 | 10 | 16 |
| Example | 119 | 115 | 98.2 | 51.1 | 95 | 201 | 157 | 116 | 246 | 62 |
| PI3K delta $IC_{50}$ [nM] | 37 | <3 | 29 | 441 | 271 | 8 | 5 | 15 | 9 | 11 |
| Example | 52 | 248.3 | 68 | 42 | 131 | 150.1 | 253 | 233 | 89 | 168.2 |
| PI3K delta $IC_{50}$ [nM] | 10 | 922 | 71 | 7 | 11 | 13 | 10 | 56 | 4 | 15 |
| Example | 120 | 137 | 103.2 | 1.5 | 1.6 | 118.2 | 200 | 29.2 | 183 | 158.1 |
| PI3K delta $IC_{50}$ [nM] | 141 | 58 | 129 | 5 | 8 | 5 | 25 | 148 | 50 | 16 |
| Example | 104 | 132 | 56.3 | 86 | 249 | 192 | 159 | 3.3 | 27.2 | 146.1 |
| PI3K delta $IC_{50}$ [nM] | 53 | 147 | 87 | 20 | 19 | 75 | 28 | 13 | 283 | 50 |
| Example | 5.2 | 241 | 179 | 17.1 | 103.1 | 51.3 | 107 | 219 | 3.4 | 111 |
| PI3K delta $IC_{50}$ [nM] | 85 | 4 | 45 | 7 | 292 | 30 | 18 | 57 | 32 | 598 |
| Example | 2.6 | 88.1 | 148.4 | 220.2 | 10.1 | 146.2 | 1.9 | 85.2 | 25.6 | 51.4 |
| PI3K delta $IC_{50}$ [nM] | 4 | 24 | 69 | 9 | 7 | 12 | 10 | 38 | 41 | 329 |
| Example | 25.4 | 181 | 139 | 145.2 | 158.5 | 4.9 | 146.6 | 32.2 | 24 | 15.3 |
| PI3K delta $IC_{50}$ [nM] | 9 | 8 | 40 | <3 | 36 | 465 | 20 | 3 | 17 | 44 |
| Example | 234.1 | 182 | 3.5 | 166.4 | 30.1 | 37.2 | 54.2 | 85.1 | 4.5 | 141.1 |
| PI3K delta $IC_{50}$ [nM] | 10 | 4 | 372 | 9 | 14 | 43 | 19 | 235 | 9 | 89 |
| Example | 45.3 | 142.1 | 73 | 22 | 155.1 | 3.7 | 234.4 | 175.2 | 144.3 | 4.4 |
| PI3K delta $IC_{50}$ [nM] | 12 | 8 | 30 | 5 | 5 | 126 | 68 | 5 | 24 | 794 |
| Example | 53.1 | 58.1 | 81.2 | 151 | 229 | 175.3 | 7.1 | 163 | 197.2 | 247.2 |
| PI3K delta $IC_{50}$ [nM] | 5 | 7 | 56 | 15 | 26 | 160 | 17 | 57 | 386 | 3 |
| Example | 168.1 | 252 | 2.2 | 194.1 | 225 | 196.2 | 193 | 206.2 | 130 | 146.5 |
| PI3K delta $IC_{50}$ [nM] | 120 | 932 | 4 | 33 | 336 | 6 | 121 | 9 | 7 | 3 |
| Example | 8.2 | 133 | 164 | 142.2 | 26 | 191.1 | 56.2 | 59.2 | 198 | 220.3 |
| PI3K delta $IC_{50}$ [nM] | 777 | 15 | 11 | 17 | 6 | 15 | 18 | 118 | 144 | 18 |
| Example | 247.1 | 101 | 190 | 61 | 221.2 | 13 | 118.1 | 58.3 | 5.1 | 21.2 |
| PI3K delta $IC_{50}$ [nM] | 6 | 6 | 3 | 6 | 647 | 112 | 19 | <3 | 13 | 19 |
| Example | 218 | 208 | 153.2 | 202 | 212.2 | 10.2 | 45.1 | 194.2 | 7.2 | 217 |
| PI3K delta $IC_{50}$ [nM] | <3 | 127 | 33 | 737 | 7 | 196 | 6 | 11 | 5 | 28 |
| Example | 60.1 | 92 | 2.4 | 9 | 206.1 | 56.5 | 99 | 158.4 | 196.1 | 44 |
| PI3K delta $IC_{50}$ [nM] | 37 | 175 | 16 | 3 | 106 | 13 | 10 | 4 | 3 | 437 |
| Example | 173 | 65 | 160.2 | 153.1 | 49 | 25.1 | 215.4 | 144.2 | 239 | 230 |
| PI3K delta $IC_{50}$ [nM] | 12 | 102 | 23 | 394 | 33 | 47 | 25 | 11 | 77 | 29 |
| Example | 177.1 | 126 | 40 | 3.2 | 172 | 32.1 | 80.2 | 191.2 | 82 | 207 |
| PI3K delta $IC_{50}$ [nM] | 236 | 170 | 19 | 19 | 5 | 51 | 31 | 52 | 26 | 48 |
| Example | 97 | 251 | 66 | 87.2 | 195.4 | 64 | 90.1 | 105 | 125.1 | 98.1 |
| PI3K delta $IC_{50}$ [nM] | 9 | 37 | 98 | 8 | 721 | 98 | 111 | 10 | 147 | 84 |
| Example | 127 | 3.1 | 141.2 | 152.1 | 3.12 | 4.3 | 212.1 | 143 | 117 | 118.3 |
| PI3K delta $IC_{50}$ [nM] | 34 | 9 | 163 | 4 | 42 | 12 | 40 | 11 | 5 | 262 |
| Example | 195.3 | 211.2 | 70 | 184 | 138 | 1.3 | 29.3 | 128.2 | 199 | 71 |
| PI3K delta $IC_{50}$ [nM] | 25 | 39 | 19 | 18 | 468 | 6 | 10 | 83 | 70 | 46 |
| Example | 167 | 4.1 | 146.4 | 145.1 | 19 | 223 | 2.5 | 1.4 | 175.1 | 25.3 |
| PI3K delta $IC_{50}$ [nM] | 72 | 14 | 29 | 6 | 5 | 31 | 7 | 432 | 199 | 16 |
| Example | 98.3 | 122 | 224.1 | 221.1 | 118.5 | 12 | 150.2 | 2.1 | 96 | 33 |
| PI3K delta $IC_{50}$ [nM] | 6 | 27 | 10 | 30 | 22 | 8 | 82 | 14 | 43 | 0 |

-continued

| | | | | | | | | | | |
|---|---|---|---|---|---|---|---|---|---|---|
| Example | 189 | 29.1 | 162 | 31 | 155.2 | 187 | 41 | 248.5 | 23.2 | 204 |
| PI3K delta $IC_{50}$ [nM] | 318 | 19 | 22 | 18 | 3 | 11 | 211 | 39 | 17 | 42 |
| Example | 79 | 2.7 | 169.1 | 186 | 16.5 | 215.2 | 213.2 | 242.2 | 250 | 28.3 |
| PI3K delta $IC_{50}$ [nM] | 8 | 33 | 13 | 26 | 23 | 22 | 7 | 6 | 6 | 292 |
| Example | 147 | 166.5 | 144.1 | 102 | 170 | 128.1 | 38 | 4.2 | 28.1 | 46 |
| PI3K delta $IC_{50}$ [nM] | 6 | 29 | 94 | 61 | 27 | 17 | 8 | 30 | <3 | <3 |
| Example | 166.3 | 35 | 100 | 1.2 | 169.2 | 244 | 149.2 | 245 | 240 | 234.3 |
| PI3K delta $IC_{50}$ [nM] | 14 | 169 | 810 | 115 | 228 | 3 | 17 | 6 | 371 | 11 |
| Example | 215.1 | 1.7 | 11 | 18 | 3.11 | 248.2 | 87.4 | 56.4 | 50 | 155.4 |
| PI3K delta $IC_{50}$ [nM] | 39 | 18 | 70 | 82 | 4 | 17 | 29 | <3 | 147 | 32 |
| Example | 148.2 | 16.2 | 177.2 | 222 | 248.1 | 149.1 | 72 | 234.2 | 106 | 6.2 |
| PI3K delta $IC_{50}$ [nM] | 10 | 19 | 6 | 453 | 9 | 26 | 37 | 39 | 7 | 3 |
| Example | 25.5 | 109 | 56.1 | 51.2 | 129 | 254 | 154.1 | 81.1 | 75 | 166.1 |
| PI3K delta $IC_{50}$ [nM] | 4 | 42 | 10 | 93 | 10 | 3 | 20 | 28 | 178 | 13 |
| Example | 84.1 | 30.2 | 87.1 | 53.2 | 242.1 | 39 | 124 | 152.2 | 47 | 148.3 |
| PI3K delta $IC_{50}$ [nM] | 4 | 449 | 4 | 8 | 17 | 5 | 431 | 7 | 14 | 8 |
| Example | 188 | 37.1 | 165 | 88.2 | 156 | 1.8 | 3.10 | 166.2 | 146.3 | 161 |
| PI3K delta $IC_{50}$ [nM] | 60 | 27 | 30 | 161 | 38 | 5 | 17 | 21 | 10 | 12 |
| Example | 232 | 16.3 | 2.3 | 16.4 | 149.3 | 17.3 | 27.1 | 226 | 1.10 | 58.4 |
| PI3K delta $IC_{50}$ [nM] | 18 | 46 | 5 | 5 | 362 | 54 | 34 | 7 | 167 | 7 |
| Example | 142.3 | 85.3 | 215.3 | 84.2 | 51.5 | 2.9 | 14 | 236 | 8.1 | 34 |
| PI3K delta $IC_{50}$ [nM] | <3 | 8 | 35 | 257 | 9 | 6 | 20 | 18 | <3 | 7 |
| Example | 169.3 | 220.1 | 197.1 | 15.1 | 141.3 | 180.2 | 180.1 | 121 | 248.4 | 152.3 |
| PI3K delta $IC_{50}$ [nM] | 34 | 26 | 14 | 35 | 203 | 6 | 32 | 3 | 116 | 41 |
| Example | 3.8 | 227 | 195.1 | 195.2 | 91 | 87.3 | 25.2 | 168.3 | 21.1 | 224.2 |
| PI3K delta $IC_{50}$ [nM] | 43 | 19 | 4 | 9 | 26 | 21 | 19 | 39 | <3 | 7 |
| Example | 74 | 54.1 | 58.2 | 237 | 90.2 | 148.1 | 118.4 | 58.5 | 93.1 | 243 |
| PI3K delta $IC_{50}$ [nM] | <3 | 6 | 35 | 14 | 36 | 4 | 821 | 80 | 85 | 7 |
| Example | 160.1 | 86.2 | 87.5 | 211.1 | 69 | 45.2 | 15.2 | 154.2 | 178 | 6.3 |
| PI3K delta $IC_{50}$ [nM] | 8 | 15 | 91 | 53 | 13 | 41 | 23 | 34 | 15 | 215 |
| Example | 158.2 | 23.1 | 59.1 | 28.2 | 210 | 93.2 | 174 | 43.2 | 2.8 | 57 |
| PI3K delta $IC_{50}$ [nM] | 158 | 15 | 473 | 12 | 132 | 214 | 209 | 9 | 6 | 42 |
| Example | 3.6 | 176 | 238 | 205 | 55 | 136 | 112 | 209 | 185.2 | 110 |
| PI3K delta $IC_{50}$ [nM] | 9 | 20 | 38 | 694 | 8 | 10 | 3 | 556 | 691 | 25 |
| Example | 185.1 | 63 | 17.2 | 60.2 | 77 | 155.3 | 76 | 108 | 213.1 | 16.1 |
| PI3K delta $IC_{50}$ [nM] | 218 | 112 | 22 | | | | | | | |
| Example | 43.1 | 3.9 | 153.3 | | | | | | | |
| PI3K gamma $IC_{50}$ [nM] | 82 | 386 | 246 | 415 | 283 | 390 | 213 | 307 | 303 | 777 |
| Example | 34 | 17.1 | 3.1 | 16.1 | 45 | 2.5 | 51.1 | 74 | 25 | 68 |
| PI3K gamma $IC_{50}$ [nM] | 140 | 150 | 212 | 287 | 191 | 147 | 69 | 453 | 253 | 319 |
| Example | 32.1 | 30.2 | 251 | 100 | 7.2 | 107 | 29.1 | 68 | 58.4 | 6.2 |
| PI3K gamma $IC_{50}$ [nM] | 118 | 160 | 100 | 212 | 184 | 157 | 217 | 190 | 242 | 178 |
| Example | 31 | 32.2 | 1.9 | 14 | 121 | 54.1 | 2.7 | 53.1 | 4.2 | 30.1 |
| PI3K gamma $IC_{50}$ [nM] | 341 | 391 | 205 | 179 | 83 | 529 | 199 | 337 | 528 | 292 |
| Example | 72 | 21.2 | 2.8 | 59.1 | 40 | 3.8 | 56.2 | 110 | 15.1 | 4.5 |
| PI3K gamma $IC_{50}$ [nM] | 309 | 185 | 182 | 144 | 121 | 129 | 489 | 125 | 157 | 114 |
| Example | 5.1 | 250 | 6.1 | 1.8 | 127 | 10.2 | 16.2 | 249 | 1.6 | 43.2 |
| PI3K gamma $IC_{50}$ [nM] | 121 | 113 | 95 | 96 | 123 | 128 | 138 | 118 | 238 | 150 |
| Example | 56.4 | 35 | 58.1 | 76 | 38 | 33 | 51.2 | 36 | 1.10 | 4.9 |
| PI3K gamma $IC_{50}$ [nM] | 138 | 160 | 92 | 73 | 165 | 132 | 111 | 150 | 145 | 169 |
| Example | 101 | 23 | 12 | 22 | 41 | 1.5 | 24 | 43.1 | 254 | 29.3 |
| PI3K gamma $IC_{50}$ [nM] | 286 | 144 | 236 | 227 | 194 | 540 | 246 | 356 | 357 | 197 |

-continued

| | | | | | | | | | | |
|---|---|---|---|---|---|---|---|---|---|---|
| Example | 109 | 37.1 | 116 | 5.2 | 28.3 | 1.3 | 102 | 66 | 3.5 | 57 |
| PI3K gamma $IC_{50}$ [nM] | 646 | 341 | 481 | 388 | 182 | 597 | 225 | 120 | 408 | 407 |
| Example | 69 | 4.4 | 4.6 | 46 | 3.6 | 52 | 117 | 1.7 | 16.3 | 4.1 |
| PI3K gamma $IC_{50}$ [nM] | 206 | 278 | 137 | 216 | 873 | 343 | 701 | 590 | 237 | 199 |
| Example | 2.9 | 49 | 27.2 | 1.2 | 17.2 | 55 | 47 | 42 | 44 | 2.4 |
| PI3K gamma $IC_{50}$ [nM] | 559 | 471 | 582 | 257 | 250 | 397 | 867 | 760 | 971 | 173 |
| Example | 3.2 | 112 | 104 | 56.3 | 91 | 18 | 3.10 | 48 | 19 | 123 |
| PI3K gamma $IC_{50}$ [nM] | 334 | 359 | 851 | 309 | 788 | 273 | 535 | 325 | 310 | 777 |
| Example | 50 | 16.3 | 115 | 3.3 | 2.6 | 10.1 | 108 | 15.3 | 105 | 26 |
| PI3K gamma $IC_{50}$ [nM] | 816 | 183 | 142 | 75 | 191 | 75 | 117 | 45 | 138 | 123 |
| Example | 63 | 53.2 | 128.1 | 28.1 | 103.1 | 39 | 128.2 | 252 | 118.3 | 56.1 |
| PI3K gamma $IC_{50}$ [nM] | 142 | 140 | 335 | 548 | 164 | 174 | 363 | 303 | 118 | 145 |
| Example | 4.3 | 2.1 | 37.2 | 15.2 | 118.1 | 28.2 | 125.1 | 3.7 | 124 | 29.2 |
| PI3K gamma $IC_{50}$ [nM] | 215 | 88 | 116 | 87 | 279 | 75 | | | | |
| Example | 27.1 | 253 | 120 | 13 | 118.2 | 77 | | | | |

The efficacy of the compounds of formula I and salts thereof as mTor kinase inhibitors can be demonstrated as follows Biochemical Assay for m-TOR by TR-FRET.

Assay components are purchased from Invitrogen Corporation (Carlsbad/Calif., USA): GFP-4EBP1 (Cat. No. PV4759), Tb3+-α-p4EBP1 [pThr46] Antibody (Cat. No. PV4757), proprietary TR-FRET dilution buffer (Cat. No. PV3574), mTOR protein (Cat. No. PV4753).

50 nL of compound dilutions (final concentration of 10, 3.0, 1.0, 0.3, 0.1, 0.03, 0.01 and 0.003 μM) are dispensed onto black 384-well low volume non-binding polystyrene (Cat. No. NBS#3676, Corning, Lowell/Mass., USA). Then 5 μL of ATP (8 μM final concentration) and GFP-4EBP1 (400 nM final concentration) with 5 μL mTOR proteins (0.5 nM final concentration) are incubated at rt. The standard reaction buffer for the TR-FRET mTOR assay contained 50 mM HEPES pH 7.5, 10 mM MnCl2, 50 mM NaCl, 1 mM EGTA, 1 mM DTT. Reactions were stopped with 10 μL of a mixture of EDTA containing the Tb3+-α-p4EBP1[pT46] detection Ab (0.5 nM) in TR-FRET dilution buffer (proprietary to IVG). Plates are read 15 mins later in a Synergy2 reader using an integration time of 0.2 seconds and a delay of 0.1 seconds. Control for the 100% inhibition of the kinase reaction is performed by replacing the mTOR kinase by the standard reaction buffer. The control for the 0% inhibition is given by the solvent vehicle of the compounds (90% DMSO in H2O). A standard compound is used as a reference compound and included in all assay plates in the form of 16 dilution points in duplicate.

The range of activity, expressed as $IC_{50}$, in this assay is preferably between 1 nM and 5000 nM, more preferably between 1 nM and about 1000 nM.

| | | | | | | | | | | |
|---|---|---|---|---|---|---|---|---|---|---|
| mTOR $IC_{50}$ [nM] | <3 | 672 | 5 | 21 | 174 | 210 | 22 | 15 | 22 | <3 |
| Example | 164 | 106 | 120 | 209 | 238 | 149.3 | 98.3 | 248.3 | 4.5 | 79 |
| mTOR $IC_{50}$ [nM] | 82 | 7 | 15 | 92 | 12 | 91 | 135 | 96 | <3 | 13 |
| Example | 25.6 | 45.3 | 178 | 212.2 | 148.3 | 121 | 250 | 59.1 | 165 | 15.1 |
| mTOR $IC_{50}$ [nM] | 11 | 94 | 97 | 778 | 3 | 28 | 1821 | 3 | 101 | 677 |
| Example | 51.1 | 54.2 | 126 | 29.2 | 89 | 247.3 | 170 | 144.3 | 194.1 | 8.2 |
| mTOR $IC_{50}$ [nM] | 19 | 6 | 4 | 8 | 30 | 17 | 30 | 34 | 4 | 15 |
| Example | 175.3 | 182 | 43.2 | 88.1 | 249 | 189 | 74 | 16.1 | 158.2 | 4.2 |
| mTOR $IC_{50}$ [nM] | 95 | 12 | 9 | 161 | 13 | <3 | 43 | 70 | 14 | 152 |
| Example | 148.1 | 155.2 | 25.1 | 227 | 5.2 | 87.2 | 6.2 | 237 | 110 | 25.2 |
| mTOR $IC_{50}$ [nM] | 15 | <3 | 123 | 5 | 11 | 14 | 76 | 20 | 191 | 347 |
| Example | 203 | 99 | 18 | 127 | 109 | 234.1 | 195.3 | 112 | 3.6 | 2.2 |
| mTOR $IC_{50}$ [nM] | 56 | 6 | 10 | 179 | 112 | 512 | 17 | 5 | <3 | 27 |
| Example | 232 | 25.4 | 1.6 | 72 | 26 | 91 | 234.3 | 155.3 | 161 | 141.3 |
| mTOR $IC_{50}$ [nM] | 9 | 12 | 639 | 34 | 58 | 9 | 147 | 71 | 481 | 231 |
| Example | 146.3 | 158.3 | 69 | 247.4 | 167 | 2.5 | 246 | 40 | 142.1 | 46 |
| mTOR $IC_{50}$ [nM] | 542 | 3 | 133 | 10 | 5 | 132 | 30 | 703 | 642 | 52 |
| Example | 231 | 58.2 | 34 | 157 | 90.1 | 1.3 | 64 | 60.2 | 62 | 56.2 |
| mTOR $IC_{50}$ [nM] | 160 | 3 | 5 | <3 | 548 | 7 | 5 | 49 | 68 | 58 |

-continued

| | | | | | | | | | | |
|---|---|---|---|---|---|---|---|---|---|---|
| Example | 73 | 87.1 | 156 | 180.2 | 3.12 | 208 | 129 | 27.1 | 17.2 | 242.1 |
| mTOR $IC_{50}$ [nM] | 18 | 7 | 3 | 24 | 140 | 31 | 5 | 25 | 139 | 3 |
| Example | 5.1 | 23.2 | 158.5 | 224.2 | 135 | 243 | 41 | 191.1 | 219 | 162 |
| mTOR $IC_{50}$ [nM] | 120 | 16 | 20 | 6 | 11 | 45 | 21 | 51 | 48 | 11 |
| Example | 80.2 | 56.4 | 98.1 | 248.4 | 4.9 | 196.1 | 139 | 125.1 | 10.2 | 147 |
| mTOR $IC_{50}$ [nM] | <3 | 479 | 373 | 113 | <3 | 27 | 3 | 6 | 172 | <3 |
| Example | 185.1 | 146.6 | 213.1 | 143 | 144.2 | 82 | 200 | 142.2 | 145.1 | 168.3 |
| mTOR $IC_{50}$ [nM] | 72 | 10 | 110 | 470 | 505 | 7 | 69 | 678 | 13 | 207 |
| Example | 212.1 | 252 | 33 | 117 | 4.7 | 97 | 128.1 | 148.4 | 133 | 66 |
| mTOR $IC_{50}$ [nM] | 60 | 363 | 16 | 32 | <3 | 14 | 14 | 4 | 28 | 4 |
| Example | 108 | 27.2 | 166.4 | 220.2 | 236 | 1.10__ | 58.1 | 158.1 | 32.1 | 173 |
| mTOR $IC_{50}$ [nM] | 329 | 34 | <3 | 6 | 56 | 118 | 26 | 79 | 6 | 162 |
| Example | 85.3 | 7.2 | 160.1 | 184 | 221.2 | 93.2 | 59.2 | 54.1 | 16.5 | 2.6 |
| mTOR $IC_{50}$ [nM] | 34 | 19 | 113 | 155 | 11 | 5 | 12 | 15 | 322 | 55 |
| Example | 206.1 | 185.2 | 248.1 | 1.2 | 211.2 | 60.1 | 17.3 | 56.1 | 57 | 166.3 |
| mTOR $IC_{50}$ [nM] | 20 | 105 | 666 | 33 | 9 | | <3 | 33 | 41 | 157 |
| Example | 146.2 | 251 | 16.4 | 6.4 | 118.3 | 214 | 87.3 | 166.1 | 168.2 | 50 |
| mTOR $IC_{50}$ [nM] | 12 | 213 | 25 | 48 | 11 | 274 | 5 | <3 | <3 | 447 |
| Example | 128.2 | 37.1 | 160.2 | 195.1 | 102 | 144.1 | 6.3 | 172 | 43.1 | 141.1 |
| mTOR $IC_{50}$ [nM] | 8 | 99 | 16 | 7 | <3 | 143 | <3 | 105 | 17 | 934 |
| Example | 187 | 51.4 | 28.1 | 141.2 | 119 | 131 | 171 | 7.1 | 85.1 | 132 |
| mTOR $IC_{50}$ [nM] | 462 | 5 | 129 | 26 | 42 | 95 | 19 | 193 | 9 | 33 |
| Example | 68 | 152.2 | 90.2 | 225 | 4.6 | 105 | 37.3 | 196.2 | 148.2 | 2.8 |
| mTOR $IC_{50}$ [nM] | 20 | 6 | 5 | 25 | 29 | 149 | 151 | 13 | 45 | 201 |
| Example | 95 | 100 | 220.3 | 55 | 87.5 | 169.2 | 2.9 | 28.3 | 16.3 | 21.1 |
| mTOR $IC_{50}$ [nM] | 309 | 564 | 563 | 16 | 48 | 79 | 60 | 161 | 52 | 4 |
| Example | 146.4 | 71 | 44 | 145.2 | 146.5 | 240 | 107 | 3.4 | 30.1 | 118.2 |
| mTOR $IC_{50}$ [nM] | 58 | 9 | <3 | 10 | 34 | 7 | 9 | 23 | 383 | 27 |
| Example | 65 | 215.2 | 223 | 125.2 | 224.1 | 45.1 | 136 | 58.5 | 9 | 51.6 |
| mTOR $IC_{50}$ [nM] | 35 | 54 | 22 | 4 | 3 | 734 | 6 | 99 | 30 | <3 |
| Example | 215.1 | 30.2 | 103.2 | 118.4 | 155.1 | 8.1 | 194.2 | 247.5 | 6.1 | 77 |
| mTOR $IC_{50}$ [nM] | 565 | 30 | 61 | 155 | 335 | 11 | 65 | 26 | 324 | 10 |
| Example | 248.5 | 98.2 | 83 | 175.2 | 15.2 | 207 | 61 | 29.1 | 137 | 138 |
| mTOR $IC_{50}$ [nM] | 46 | 15 | 10 | 15 | 49 | 100 | 30 | 448 | 432 | 13 |
| Example | 49 | 116 | 181 | 151 | 239 | 134 | 4.1 | 2.4 | 25.5 | 179 |
| mTOR $IC_{50}$ [nM] | 51 | 8 | 27 | 13 | 6 | 6 | 87 | 59 | 96 | 566 |
| Example | 35 | 150.2 | 201 | 88.2 | 1.8 | 38 | 96 | 17.1 | 2.3 | 58.3 |
| mTOR $IC_{50}$ [nM] | 324 | 79 | 53 | 17 | 22 | 6 | 121 | 12 | 12 | <3 |
| Example | 81.2 | 149.1 | 104 | 3.5 | 205 | 175.1 | 22 | 247.2 | 199 | 101 |
| mTOR $IC_{50}$ [nM] | <3 | 22 | 87 | 619 | 107 | 31 | 65 | 465 | 69 | 4 |
| Example | 51.2 | 222 | 195.2 | 154.1 | 53.1 | 58.4 | 254 | 230 | 39 | 81.1 |
| mTOR $IC_{50}$ [nM] | 98 | 21 | 4 | 76 | 6 | 177 | <3 | 39 | <3 | 189 |
| Example | 153.1 | 193 | 84.1 | 245 | 51.3 | 31 | 153.2 | 197.1 | 183 | 152.3 |
| mTOR $IC_{50}$ [nM] | 61 | 232 | 549 | 7 | 107 | 56 | 11 | 7 | 9 | 13 |
| Example | 1.5 | 123 | 28.2 | 174 | 197.2 | 186 | 3.1 | 215.3 | 3.8 | 80.1 |
| mTOR $IC_{50}$ [nM] | 23 | 308 | 260 | <3 | 41 | 77 | 3 | 100 | 15 | 39 |
| Example | 16.2 | 1.9 | 75 | 188 | 218 | 87.4 | 253 | 4.4 | 176 | 149.2 |
| mTOR $IC_{50}$ [nM] | 4 | <3 | 543 | 74 | 79 | 36 | 251 | 5 | 27 | 79 |
| Example | 23.1 | 36 | 4.3 | 52 | 241 | 140.1 | 4.8 | 180.1 | 220.1 | 244 |
| mTOR $IC_{50}$ [nM] | 31 | 7 | 13 | 12 | 17 | 87 | 22 | 40 | 17 | 169 |
| Example | 86.2 | 29.3 | 247.1 | 168.1 | 150.1 | 1.4 | 155.4 | 210 | 12 | 226 |
| mTOR $IC_{50}$ [nM] | 17 | 70 | 6 | 494 | 3 | 763 | 24 | 12 | <3 | <3 |

-continued

| | | | | | | | | | | |
|---|---|---|---|---|---|---|---|---|---|---|
| Example | 142.3 | 158.4 | 14 | 130 | 177.1 | 56.5 | 45.2 | 15.3 | 146.1 | 93.1 |
| mTOR $IC_{50}$ [nM] | <3 | 64 | 6 | 81 | 63 | 10 | 34 | <3 | 4 | 5 |
| Example | 118.5 | 233 | 192 | 70 | 13 | 234.2 | 191.2 | 169.1 | 216 | 122 |
| mTOR $IC_{50}$ [nM] | 651 | 23 | 12 | <3 | 13 | 5 | 187 | 123 | 376 | 55 |
| Example | 3.3 | 3.7 | 217 | 163 | 211.1 | 118.1 | 234.4 | 213.2 | 92 | 166.2 |
| mTOR $IC_{50}$ [nM] | 12 | 116 | 6 | 21 | 65 | 8 | 37 | 13 | 13 | <3 |
| Example | 159 | 25.3 | 86 | 103.1 | 42 | 195.4 | 190 | 215.4 | 152.1 | 169.3 |
| mTOR $IC_{50}$ [nM] | 19 | 13 | 29 | 37 | 15 | 306 | 665 | 281 | 11 | 18 |
| Example | 84.2 | 2.7 | 202 | 24 | 248.2 | 63 | 153.3 | 47 | 3.9 | 3.10 |
| mTOR $IC_{50}$ [nM] | 53 | 5 | 32 | 73 | | | | | | |
| Example | 124 | 76 | 221.1 | 198 | | | | | | |

The efficacy of the compounds of the invention in blocking the activation of the PI3K/PKB pathway was demonstrated in cellular settings using a reverse protein array assay for sensitive quantification of compound of formula I mediated inhibition of PKB Ser473 phosphorylation in Rat1 cells stably transfected with activated versions of PI3-kinase isoforms alpha, beta or delta:

Cells and Cell Culture Conditions:

Rat1 cell lines stably expressing a myr-HA-tagged, constitutively active subunit of the catalytic PI3K class I p110 isoform α, β or δ (addition of a myristylation signal at the N-terminus of p110 isoforms has been shown to lead to constitutive activation of PI3K and corresponding downstream signals, such as phosphorylation of PKB at Ser473) were cultivated in Dulbecco's modified Eagle's medium (DMEM high Glucose, GIBCO, cat. No. 41956-039) supplemented with 10% heat inactivated fetal bovine calf serum (Amimed, cat. No. 2-01F16-I), 1% L-Glutamine (Invitrogen, cat. No. 25030-02), 1% penicillin-streptomycin (GIBCO, cat. No. 15140-114) and 10 μg/ml Puromycine (Sigma, cat. No. P9620).

Compound Treatment of Cells and Preparation of Samples:

The Rat1-myr-HA-p110 alpha, beta and delta cells were trypsinized and counted with a CASY TT cell counter (Schärfe System GmbH, Reutlingen Germany). The cells were diluted in fresh DMEM complete medium and $3\times10^4$cells/150 μl/well seeded in 96-well TPP-tissue culture plates (TPP, cat. No. 92096). The plates were incubated at 37° C. and 5% $CO_2$ under humidified condition for at least 20 h. Compound of formula I working solutions were prepared freshly as serial 8 step dilutions (vol/vol) in DMSO on the day of the experiment. The working solutions were further diluted 1/500 in cell culture medium to get final compound concentrations of 10, 3.333, 1.111, 0.370, 0.123, 0.041, 0.014, 0.005 μM. The final DMSO concentration was kept constant at 0.2%. cell culture medium containing 0.2% DMSO was used as vehicle treatment control. Post incubation, the cells were treated with the serial compound dilution. 50 μl of the compound medium mixture was added to the wells containing cells and 150 μl DMEM medium and incubated for 30 minutes (37° C., 5% $CO_2$). After 30 minutes of incubation, the medium mixture was quickly removed by aspiration. For cell lysis, a mixture of 10% CLB1 CeLyA lysis buffer (Zeptosens, cat. No. 9000), 90% CSBL1 CeLyA spotting buffer (Zeptosens, cat. No. 9020) was freshly prepared and supplemented with 1% Octyl β-D-glucopyranoside (SIGMA, cat. No. 08001-5G) and 1 mM Na-Orthovanadate (Sigma, cat No. S-6508). 50 μl of the described lysis buffer mix was added to each well, followed by 10 minutes of incubation on ice. After an additional freeze-thaw cycle, another 50 μl of the lysis buffer mix without Octyl β-D-glucopyranoside was added to the wells, and 90 μl of the cell lysate was transferred to a 96-well V-bottom plate (Fisher Scientific, cat. No. 6067Y), followed by a centrifugation step (5 min, 1500 rpm at 19° C. in an Eppendorf 5810R centrifuge) to remove the unlysed cell debris.

Spotting of the ZeptoMARK® Chips:

The samples were spotted onto ZeptoMARK® PWG protein microarray chips (Zeptosens, Witterswil, Switzerland) with the piezoelectric microdispense-based, non-contact Nano-Plotter 2.1 (GeSiM, Grosserknnannsdorf, Germany). Each sample was spotted at 4 different sample concentrations (d1=100%, d2=75%, d3=50%, d4=25%) by diluting the cell lysate with the corresponding volume of lysis buffer mix. After spotting the ZeptoMARK® protein microarrays, the chips are incubated for 1 hour at 37° C. To receive a uniform blocking result, the CeLyA blocking buffer BB1 (Zeptosens, cat. No. 9040) is administered via an ultrasonic nebulizer. After 20 minutes of blocking the chips are extensively rinsed with deionized water (Milli-Q quality, 18 MΩ×cm) and dried in a nitrogen air flow.

ZeptoREADER Signal Detection and Data Analysis:

After the sample spotting and blocking procedure, the ZeptoMARK® chips were transferred to the ZeptoCARRIER (Zeptosens, cat. No. 1100), whose six flow cells individually address the six arrays on a chip, and washed twice with 200 μl CAB1 CeLyA assay buffer (Zeptosens, cat. No. 9032). The assay buffer was then aspirated and each compartment incubated with 100 μl of the primary target antibody (pAkt Ser473; CST#9271) at RT over night. Post incubation, the primary antibody was removed, the arrays washed twice with CAB1 buffer and further incubated with 100 μl of Alexa fluor 647-labeled anti rabbit IgG Fab fragments (Invitrogen; #Z25305) for one hour at RT in the dark. After incubation, the arrays were washed twice with 200 μl CAB1 buffer. The fluorescence of the target-bound Fab fragments is read out on the ZeptoReader (Zeptosens, Witterswil, Switzerland) using a laser (excitation wavelength 635 nm) and a CCD camera. The fluorescence signal was assessed with exposure times of 1, 3, 5 and 10 seconds, depending on the intensity of the signal. The resulting four images taken per array are stored as 16-bit TIF files.

The fluorescence images for each array were analyzed with the ZeptoVIEW Pro 2.0 software (Zeptosens, Witterswil, Switzerland) and the relative fluorescence intensity for each signal was calculated. The range of activity, expressed as $IC_{50}$, in this assay is preferably between about 1 nM and about 10 μM, more preferably between about 1 nM and about 1 μM.

| Rat1-myr-p110 alpha | | | | | | | | | | | |
|---|---|---|---|---|---|---|---|---|---|---|---|
| p-PKB $IC_{50}$ [nM] | 51 | 17 | 9 | 41 | 264 | 383 | 50 | 21 | 129 | 134 | 38 |
| Example | 132 | 27.1 | 174 | 250 | 78 | 58.3 | 10.2 | 151 | 196.2 | 108 | 166.2 |
| p-PKB $IC_{50}$ [nM] | 7 | 25 | 139 | 30 | <5 | 150 | <5 | 253 | 136 | 14 | 8 |
| Example | 249 | 25.3 | 18 | 30.1 | 161 | 141.1 | 146.1 | 154.2 | 227 | 5.2 | 193 |
| p-PKB $IC_{50}$ [nM] | 14 | 5 | 23 | 7 | 552 | 72 | 197 | <5 | 371 | 151 | 46 |
| Example | 43.1 | 29.1 | 202 | 97 | 2.1 | 240 | 83 | 87.3 | 242.2 | 148.4 | 1.3 |
| p-PKB $IC_{50}$ [nM] | 344 | <5 | 45 | <5 | 9 | 33 | 33 | 30 | 88 | 7 | 8 |
| Example | 175.3 | 144.3 | 196.1 | 94 | 58.2 | 87.4 | 102 | 254 | 155.4 | 28.1 | 51.3 |
| p-PKB $IC_{50}$ [nM] | 35 | 20 | <5 | 12 | 55 | 70 | 21 | 82 | 20 | 28 | 352 |
| Example | 3.5 | 168.1 | 84.1 | 98.3 | 109 | 146.4 | 58.1 | 1.7 | 178 | 15.3 | 15.2 |
| p-PKB $IC_{50}$ [nM] | 13 | 9 | 65 | 7 | 168 | 36 | 47 | 35 | 6 | 12 | 166 |
| Example | 99 | 1.8 | 207 | 103.2 | 22 | 138 | 65 | 39 | 220.3 | 64 | 67 |
| p-PKB $IC_{50}$ [nM] | 5 | 32 | 143 | 9 | 244 | <5 | 206 | 7 | <5 | 128 | 26 |
| Example | 36 | 6.2 | 93.2 | 28.3 | 92 | 153.2 | 75 | 159 | 163 | 3.12 | 45.2 |
| p-PKB $IC_{50}$ [nM] | 44 | <5 | 29 | 5 | 22 | 124 | 234 | 7 | 17 | 18 | <5 |
| Example | 247.4 | 122 | 31 | 166.4 | 1.1 | 177.2 | 91 | 5.1 | 234.4 | 2.5 | 160.1 |
| p-PKB $IC_{50}$ [nM] | <5 | 175 | 324 | <5 | 16 | <5 | 60 | 846 | 14 | 11 | 6 |
| Example | 146.2 | 247.3 | 137 | 180.1 | 215.1 | 118.5 | 45.1 | 56.5 | 51.4 | 206.1 | 142.2 |
| p-PKB $IC_{50}$ [nM] | 13 | 96 | 25 | 10 | 12 | 8 | <5 | 63 | 18 | <5 | 50 |
| Example | 155.1 | 66 | 58.4 | 142.3 | 100 | 25.6 | 186 | 195.1 | 221.2 | 116 | 29.2 |
| p-PKB $IC_{50}$ [nM] | <5 | 26 | 10 | <5 | 138 | 43 | 115 | <5 | 53 | 73 | 45 |
| Example | 93.1 | 144.1 | 168.3 | 241 | 34 | 215.2 | 212.2 | 118.4 | 4.4 | 17.1 | 3.6 |
| p-PKB $IC_{50}$ [nM] | 47 | 9 | 50 | 30 | 192 | <5 | 6 | 5 | <5 | 26 | 38 |
| Example | 103.1 | 6.3 | 3.3 | 4.6 | 8.2 | 148.2 | 187 | 155.2 | 248.1 | 233 | 185.2 |
| p-PKB $IC_{50}$ [nM] | 8 | 95 | 14 | 7 | 23 | 162 | 17 | 51 | 49 | 214 | 28 |
| Example | 188 | 54.1 | 27.2 | 152.1 | 199 | 33 | 90.2 | 57 | 149.3 | 46 | 2.7 |
| p-PKB $IC_{50}$ [nM] | 191 | 107 | 9 | <5 | 20 | 265 | 10 | 14 | 24 | 208 | 10 |
| Example | 21.1 | 118.3 | 177.1 | 148.3 | 74 | 63 | 1.6 | 191.1 | 3.1 | 115 | 111 |
| p-PKB $IC_{50}$ [nM] | 44 | 180 | 13 | 10 | 5 | 134 | 8 | 16 | 46 | 44 | 77 |
| Example | 2.9 | 76 | 23.1 | 203 | 4.9 | 4.7 | 204 | 4.1 | 2.8 | 194.1 | 197.2 |
| p-PKB $IC_{50}$ [nM] | 5 | 6 | 37 | 282 | 104 | <5 | 125 | 123 | <5 | 6 | 102 |
| Example | 25.1 | 165 | 71 | 117 | 224.2 | 95 | 213.1 | 152.3 | 164 | 52 | 154.1 |
| p-PKB $IC_{50}$ [nM] | 1 | 55 | 33 | 63 | 26 | 13 | 141 | 166 | 285 | 227 | <5 |
| Example | 79 | 222 | 86.2 | 148.1 | 1.9 | 215.3 | 126 | 72 | 214 | 246 | 89 |
| p-PKB $IC_{50}$ [nM] | 59 | 14 | 9 | 10 | 74 | 187 | 12 | 159 | <5 | 28 | <5 |
| Example | 175.2 | 4.2 | 172 | 156 | 16.1 | 85.2 | 51.6 | 2.2 | 128.2 | 247.1 | 144.2 |
| p-PKB $IC_{50}$ [nM] | 52 | 25 | 45 | 82 | 829 | 16 | 33 | <5 | 126 | 40 | 7 |
| Example | 139 | 15.1 | 242.1 | 125.2 | 60.2 | 173 | 1.2 | 157 | 206.2 | 166.3 | 77 |
| p-PKB $IC_{50}$ [nM] | 21 | 8 | 8 | 23 | 76 | 32 | 375 | 13 | 85 | 77 | 13 |
| Example | 129 | 118.1 | 86 | 183 | 205 | 238 | 53.2 | 234.2 | 107 | 105 | 81.1 |
| p-PKB $IC_{50}$ [nM] | 108 | 29 | 19 | 13 | 9 | 75 | 51 | 65 | 23 | 120 | 8 |
| Example | 217 | 140.2 | 153.1 | 61 | 171 | 125.1 | 49 | 2.4 | 197.1 | 3.2 | 35 |
| p-PKB $IC_{50}$ [nM] | 12 | 18 | 214 | 10 | 26 | <5 | 5 | 68 | 21 | 279 | 26 |
| Example | 2.3 | 179 | 3.4 | 216 | 135 | 1.10 | 127 | 4.3 | 17.3 | 229 | 14 |
| p-PKB $IC_{50}$ [nM] | 42 | 6 | 44 | 7 | 20 | 157 | 41 | 375 | 14 | 61 | 98 |
| Example | 54.2 | 43.2 | 30.2 | 158.2 | 215.4 | 142.1 | 131 | 21.2 | 7.2 | 6.1 | 37.1 |
| p-PKB $IC_{50}$ [nM] | 9 | 22 | <5 | 44 | 14 | 10 | 304 | 20 | 11 | 24 | 730 |
| Example | 145.2 | 1.4 | 155.3 | 82 | 45.3 | 3.9 | 56.3 | 208 | 211.1 | 112 | 245 |
| p-PKB $IC_{50}$ [nM] | 97 | 80 | 18 | 5 | 126 | 69 | <5 | 28 | 71 | 41 | 36 |
| Example | 25.5 | 149.2 | 253 | 184 | 59.1 | 145.1 | 141.2 | 198 | 104 | 44 | 243 |
| p-PKB $IC_{50}$ [nM] | <5 | 10 | 51 | 19 | 17 | 9 | 77 | 28 | <5 | 237 | 22 |

-continued

| Rat1-myr-p110 alpha | | | | | | | | | | | |
|---|---|---|---|---|---|---|---|---|---|---|---|
| Example | 189 | 220.1 | 181 | 169.3 | 51.5 | 194.2 | 40 | 239 | 236 | 87.5 | 166.1 |
| p-PKB $IC_{50}$ [nM] | 172 | <5 | 221 | 237 | 19 | 36 | <5 | 114 | 52 | 337 | 268 |
| Example | 146.6 | 118.2 | 32.2 | 3.11 | 190 | 42 | 248.4 | 158.4 | 219 | 73 | 170 |
| p-PKB $IC_{50}$ [nM] | 40 | 57 | 594 | 15 | 35 | 10 | <5 | 10 | 9 | 27 | 20 |
| Example | 143 | 210 | 10.1 | 182 | 167 | 141.3 | 60.1 | 234.1 | 150.1 | 169.1 | 146.3 |
| p-PKB $IC_{50}$ [nM] | 20 | <5 | <5 | 108 | 755 | 13 | 5 | 589 | 84 | 32 | 18 |
| Example | 195.4 | 88.1 | 200 | 80.2 | 69 | 185.1 | 128.1 | 8.1 | 140.1 | 251 | 209 |
| p-PKB $IC_{50}$ [nM] | <5 | <5 | <5 | 18 | 254 | 158 | 11 | 78 | 6 | 85 | 6 |
| Example | 84.2 | 85.1 | 90.1 | 237 | 121 | 4.8 | 23.2 | 24 | 119 | 32.1 | 158.1 |
| p-PKB $IC_{50}$ [nM] | <5 | 9 | 27 | 14 | <5 | 8 | 296 | 42 | 828 | 7 | 15 |
| Example | 51.1 | 56.4 | 191.2 | 221.1 | 162 | 211.2 | 85.3 | 6.4 | 247.5 | 150.2 | 51.2 |
| p-PKB $IC_{50}$ [nM] | <5 | 22 | 59 | 48 | 92 | 135 | 12 | 90 | 48 | 73 | 16 |
| Example | 98.1 | 218 | 3.10 | 195.2 | 195.3 | 212.1 | 96 | 25.2 | 41 | 47 | 56.1 |
| p-PKB $IC_{50}$ [nM] | 8 | 10 | 818 | 15 | 12 | <5 | 301 | 72 | 8 | 303 | 115 |
| Example | 16.5 | 98.2 | 113 | 3.8 | 59.2 | 87.2 | 166.5 | 50 | 29.3 | 114 | 244 |
| p-PKB $IC_{50}$ [nM] | 159 | 9 | 19 | 15 | 7 | 34 | <5 | 20 | 220 | 37 | 67 |
| Example | 26 | 248.3 | 224.1 | 234.3 | 38 | 153.3 | 158.3 | 55 | 81.2 | 12 | 16.3 |
| p-PKB $IC_{50}$ [nM] | 58 | 67 | 12 | <5 | 12 | 13 | 53 | 80 | 11 | 151 | 469 |
| Example | 213.2 | 110 | 192 | 25.4 | 146.5 | 80.1 | 58.5 | 225 | 223 | 16.2 | 62 |
| p-PKB $IC_{50}$ [nM] | 19 | 15 | 24 | 17 | 11 | 31 | 12 | 303 | 40 | 19 | 22 |
| Example | 17.2 | 53.1 | 88.2 | 175.1 | 136 | 149.1 | 201 | 56.2 | 37.3 | 220.2 | 4.5 |
| p-PKB $IC_{50}$ [nM] | 43 | <5 | 76 | 45 | <5 | 16 | 12 | 460 | 234 | <5 | 17 |
| Example | 3.7 | 180.2 | 28.2 | 247.2 | 176 | 1.5 | 252 | 169.2 | 16.4 | 87.1 | 147 |
| p-PKB $IC_{50}$ [nM] | <5 | 141 | 12 | 330 | | | | | | | |
| Example | 152.2 | 2.6 | 168.2 | 130 | | | | | | | |

| Rat1-myr-p110 beta | | | | | | | | | | | |
|---|---|---|---|---|---|---|---|---|---|---|---|
| p-PKB $IC_{50}$ [nM] | 63 | 7 | 386 | <5 | 21 | 141 | 86 | 21 | 49 | 5 | 84 |
| Example | 207 | 155.2 | 244 | 153.2 | 55 | 2.9 | 66 | 27.1 | 144.1 | 156 | 149.3 |
| p-PKB $IC_{50}$ [nM] | <5 | 38 | 17 | 36 | 9 | 173 | 25 | 89 | 6 | 24 | 88 |
| Example | 43.2 | 211.2 | 95 | 45.3 | 52 | 21.1 | 168.1 | 109 | 236 | 64 | 158.4 |
| p-PKB $IC_{50}$ [nM] | 21 | 111 | 22 | 114 | 6 | 24 | 14 | 207 | 118 | 38 | 37 |
| Example | 179 | 225 | 86 | 195.1 | 148.2 | 169.3 | 58.2 | 148.4 | 135 | 2.7 | 175.1 |
| p-PKB $IC_{50}$ [nM] | 153 | 196 | <5 | 70 | 22 | 37 | 77 | 18 | 64 | 41 | 87 |
| Example | 34 | 80.2 | 200 | 16.2 | 209 | 169.1 | 197.2 | 81.1 | 251 | 2.8 | 247.2 |
| p-PKB $IC_{50}$ [nM] | 168 | 13 | 16 | 22 | 308 | 7 | 10 | 72 | 38 | 135 | 15 |
| Example | 145.1 | 141.3 | 177.1 | 5.2 | 115 | 23.1 | 35 | 167 | 138 | 37.1 | 234.3 |
| p-PKB $IC_{50}$ [nM] | 52 | 30 | <5 | 725 | 9 | 148 | 185 | 223 | 13 | 93 | 11 |
| Example | 6.4 | 103.1 | 118.5 | 32.2 | 127 | 22 | 212.2 | 206.1 | 203 | 29.1 | 142.2 |
| p-PKB $IC_{50}$ [nM] | 386 | 23 | <5 | 22 | <5 | 275 | 386 | 16 | 34 | 11 | 220 |
| Example | 2.4 | 1.5 | 162 | 210 | 118.4 | 229 | 245 | 215.3 | 186 | 43.1 | 227 |
| p-PKB $IC_{50}$ [nM] | 196 | 16 | <5 | 389 | 41 | 72 | 428 | 52 | 937 | 29 | <5 |
| Example | 47 | 99 | 171 | 27.2 | 105 | 4.6 | 137 | 247.1 | 10.1 | 131 | 118.2 |
| p-PKB $IC_{50}$ [nM] | 659 | 497 | 119 | 45 | 245 | 37 | 171 | 6 | 55 | 189 | 13 |
| Example | 117 | 219 | 3.6 | 243 | 154.2 | 96 | 67 | 85.1 | 233 | 195.2 | 80.1 |
| p-PKB $IC_{50}$ [nM] | 634 | 52 | 92 | 22 | 22 | 66 | 51 | 18 | 110 | 86 | 8 |
| Example | 53.2 | 183 | 54.1 | 155.1 | 151 | 149.1 | 3.7 | 182 | 32.1 | 166.2 | 1.8 |
| p-PKB $IC_{50}$ [nM] | 795 | 20 | 6 | 124 | 15 | <5 | 8 | 9 | 8 | 295 | 13 |

-continued

| Rat1-myr-p110 beta | | | | | | | | | | | |
|---|---|---|---|---|---|---|---|---|---|---|---|
| Example | 2.1 | 252 | 152.1 | 24 | 29.3 | 141.2 | 248.4 | 146.1 | 84.1 | 81.2 | 172 |
| p-PKB $IC_{50}$ [nM] | 98 | 29 | 139 | 265 | <5 | 139 | 8 | 115 | 240 | 8 | 8 |
| Example | 125.1 | 173 | 58.4 | 59.1 | 87.1 | 148.1 | 88.1 | 25.5 | 247.3 | 159 | 5.1 |
| p-PKB $IC_{50}$ [nM] | 29 | 160 | 11 | 57 | 7 | 64 | 383 | 16 | 10 | 31 | 457 |
| Example | 56.1 | 193 | 56.4 | 17.1 | 176 | 39 | 75 | 136 | 90.2 | 84.2 | 226 |
| p-PKB $IC_{50}$ [nM] | 40 | 25 | 6 | 586 | 20 | 18 | 11 | 16 | 15 | 18 | 14 |
| Example | 17.2 | 248.3 | 168.3 | 169.2 | 221.1 | 14 | 150.1 | 184 | 6.3 | 2.5 | 118.1 |
| p-PKB $IC_{50}$ [nM] | 266 | 766 | 29 | 59 | 110 | 12 | 48 | 43 | 38 | 548 | 81 |
| Example | 205 | 85.3 | 202 | 224.1 | 4.4 | 144.2 | 215.1 | 118.3 | 192 | 3.3 | 248.1 |
| p-PKB $IC_{50}$ [nM] | 42 | 6 | <5 | 97 | 356 | 6 | <5 | 110 | 13 | 22 | 113 |
| Example | 44 | 25.1 | 90.1 | 250 | 76 | 4.9 | 160.1 | 71 | 111 | 1.6 | 110 |
| p-PKB $IC_{50}$ [nM] | 28 | 10 | 96 | 68 | 516 | <5 | 6 | 46 | 37 | 36 | 16 |
| Example | 61 | 16.5 | 1.3 | 149.2 | 62 | 87.2 | 158.2 | 185.1 | 41 | 140.2 | 129 |
| p-PKB $IC_{50}$ [nM] | 47 | 407 | 386 | 85 | 37 | 18 | 231 | 9 | 417 | 127 | 161 |
| Example | 155.4 | 87.5 | 78 | 87.4 | 187 | 168.2 | 18 | 51.3 | 73 | 146.4 | 175.2 |
| p-PKB $IC_{50}$ [nM] | 22 | 14 | 715 | 959 | 136 | 29 | 428 | 154 | <5 | 30 | 299 |
| Example | 17.3 | 103.2 | 92 | 206.2 | 2.6 | 28.1 | 146.6 | 4.8 | 163 | 58.1 | 72 |
| p-PKB $IC_{50}$ [nM] | 6 | 94 | 88 | 12 | 26 | <5 | 157 | 128 | 29 | 23 | 38 |
| Example | 23.2 | 239 | 185.2 | 204 | 254 | 161 | 1.4 | 240 | 146.5 | 3.8 | 30.1 |
| p-PKB $IC_{50}$ [nM] | 20 | 57 | 26 | 19 | 510 | 273 | 6 | 43 | 130 | 119 | 23 |
| Example | 3.1 | 143 | 234.2 | 4.1 | 3.11 | 21.2 | 220.3 | 65 | 224.2 | 213.2 | 60.1 |
| p-PKB $IC_{50}$ [nM] | 108 | 70 | 199 | 37 | 166 | 116 | 113 | 103 | 22 | 15 | 444 |
| Example | 196.2 | 3.10 | 212.1 | 104 | 3.12 | 2.3 | 1.9 | 221.2 | 122 | 25.6 | 121 |
| p-PKB $IC_{50}$ [nM] | 17 | 21 | 59 | 28 | 29 | 342 | 995 | 119 | 92 | 49 | 13 |
| Example | 234.1 | 15.1 | 234.4 | 88.2 | 3.5 | 213.1 | 242.2 | 146.3 | 68 | 31 | 98.1 |
| p-PKB $IC_{50}$ [nM] | 18 | 61 | 125 | 9 | 55 | 725 | 8 | 16 | 176 | 17 | 10 |
| Example | 116 | 59.2 | 28.2 | 38 | 153.3 | 114 | 77 | 253 | 70 | 153.1 | 152.2 |
| p-PKB $IC_{50}$ [nM] | 81 | 66 | <5 | 26 | 6 | 16 | 73 | 409 | 99 | 103 | 19 |
| Example | 194.1 | 1.1 | 189 | 199 | 128.2 | 98.3 | 25.3 | 56.2 | 132 | 196.1 | 3.9 |
| p-PKB $IC_{50}$ [nM] | 52 | 58 | 30 | <5 | 265 | 65 | 300 | 35 | 58 | 121 | 17 |
| Example | 222 | 10.2 | 147 | 180.1 | 126 | 40 | 142.1 | 7.2 | 191.2 | 4.7 | 97 |
| p-PKB $IC_{50}$ [nM] | 19 | 391 | 541 | 530 | 6 | 39 | 106 | 235 | 284 | 22 | 41 |
| Example | 142.3 | 91 | 46 | 15.2 | 51.2 | 16.3 | 57 | 37.3 | 82 | 249 | 247.4 |
| p-PKB $IC_{50}$ [nM] | 17 | 17 | 55 | 53 | 744 | 152 | 40 | 38 | 11 | 49 | 128 |
| Example | 158.1 | 4.5 | 237 | 86.2 | 63 | 49 | 197.1 | 12 | 146.2 | 178 | 108 |
| p-PKB $IC_{50}$ [nM] | 32 | 9 | 104 | <5 | 353 | 692 | 101 | 47 | 248 | 17 | 43 |
| Example | 180.2 | 93.1 | 154.1 | 241 | 83 | 175.3 | 107 | 6.2 | 3.4 | 208 | 53.1 |
| p-PKB $IC_{50}$ [nM] | 187 | 39 | 80 | 615 | <5 | 10 | 37 | <5 | <5 | 113 | 27 |
| Example | 125.2 | 139 | 45.1 | 4.3 | 1.10 | 174 | 198 | 164 | 51.1 | 215.2 | 218 |
| p-PKB $IC_{50}$ [nM] | 10 | 21 | 184 | 162 | 19 | <5 | 516 | 143 | 294 | 10 | 553 |
| Example | 194.2 | 1.2 | 195.3 | 141.1 | 201 | 144.3 | 85.2 | 29.2 | 246 | 150.2 | 2.2 |
| p-PKB $IC_{50}$ [nM] | 10 | 100 | 66 | 214 | 15 | 226 | 136 | 18 | 608 | 94 | 11 |
| Example | 148.3 | 140.1 | 42 | 33 | 28.3 | 26 | 215.4 | 220.1 | 214 | 242.1 | 165 |
| p-PKB $IC_{50}$ [nM] | 54 | 494 | 73 | 43 | 119 | <5 | 281 | 7 | 24 | 138 | 13 |
| Example | 181 | 177.2 | 112 | 30.2 | 50 | 155.3 | 58.3 | 79 | 223 | 3.2 | 145.2 |
| p-PKB $IC_{50}$ [nM] | 8 | 116 | 56 | 43 | 22 | 6 | 34 | 61 | 161 | 10 | 12 |
| Example | 157 | 238 | 74 | 54.2 | 188 | 36 | 16.1 | 211.1 | 217 | 119 | 51.6 |
| p-PKB $IC_{50}$ [nM] | 14 | 11 | 119 | 19 | 113 | 11 | 57 | 27 | 102 | <5 | 326 |
| Example | 100 | 94 | 166.3 | 4.2 | 152.3 | 166.4 | 216 | 128.1 | 58.5 | 158.3 | 8.2 |
| p-PKB $IC_{50}$ [nM] | 36 | 54 | 21 | <5 | 147 | 23 | 43 | 370 | 32 | 18 | 34 |

-continued

| Rat1-myr-p110 beta | | | | | | | | | | | |
|---|---|---|---|---|---|---|---|---|---|---|---|
| Example | 45.2 | 191.1 | 15.3 | 87.3 | 1.7 | 195.4 | 6.1 | 170 | 220.2 | 98.2 | 102 |
| p-PKB $IC_{50}$ [nM] | 16 | 7 | <5 | 54 | | | | | | | |
| Example | 190 | 25.4 | 89 | 166.1 | | | | | | | |

| Rat1-myr-p110 delta | | | | | | | | | | | |
|---|---|---|---|---|---|---|---|---|---|---|---|
| p-PKB $IC_{50}$ [nM] | 140 | 5 | 7 | 24 | 399 | 56 | 15 | 516 | 37 | 298 | 28 |
| Example | 1.3 | 153.2 | 164 | 146.1 | 33 | 216 | 51.3 | 51.5 | 3.8 | 67 | 16.5 |
| p-PKB $IC_{50}$ [nM] | 564 | 19 | 8 | 88 | 141 | 323 | 131 | 266 | 54 | 13 | 72 |
| Example | 146.6 | 38 | 248.4 | 191.2 | 154.1 | 80.2 | 240 | 126 | 190 | 236 | 192 |
| p-PKB $IC_{50}$ [nM] | 810 | 69 | 59 | 9 | 5 | 53 | 10 | 356 | 26 | 10 | 59 |
| Example | 69 | 225 | 4.1 | 155.3 | 189 | 210 | 118.2 | 63 | 23.1 | 160.1 | 29.1 |
| p-PKB $IC_{50}$ [nM] | 154 | 15 | 92 | 84 | 38 | 58 | 15 | 86 | 19 | 18 | 508 |
| Example | 45.1 | 150.2 | 41 | 144.1 | 4.5 | 138 | 88.1 | 58.4 | 142.2 | 146.2 | 27.2 |
| p-PKB $IC_{50}$ [nM] | 234 | 238 | 71 | 401 | 906 | 10 | 177 | 140 | 90 | 45 | 297 |
| Example | 29.2 | 207 | 68 | 108 | 21.1 | 201 | 75 | 1.9 | 6.1 | 28.1 | 219 |
| p-PKB $IC_{50}$ [nM] | 636 | 30 | 127 | 202 | 433 | 9 | 471 | 158 | 869 | 11 | 21 |
| Example | 247.3 | 234.3 | 131 | 34 | 226 | 241 | 93.2 | 185.2 | 169.2 | 144.3 | 141.2 |
| p-PKB $IC_{50}$ [nM] | 634 | 530 | 9 | 11 | 882 | 25 | 22 | 219 | 42 | 115 | 69 |
| Example | 87.5 | 73 | 25.1 | 56.4 | 2.4 | 95 | 51.2 | 37.1 | 145.2 | 215.4 | 59.2 |
| p-PKB $IC_{50}$ [nM] | 839 | 91 | 541 | 9 | 83 | 895 | 12 | 370 | 559 | 8 | 138 |
| Example | 47 | 15.1 | 2.2 | 25.4 | 208 | 242.2 | 157 | 148.4 | 177.2 | 36 | 40 |
| p-PKB $IC_{50}$ [nM] | 672 | 38 | 833 | 314 | 249 | 130 | 341 | 64 | 772 | 577 | 362 |
| Example | 53.2 | 29.3 | 166.5 | 18 | 1.7 | 16.1 | 121 | 31 | 205 | 58.3 | 37.3 |
| p-PKB $IC_{50}$ [nM] | 631 | 46 | 158 | 66 | 91 | 132 | 154 | 14 | 50 | 22 | 73 |
| Example | 91 | 129 | 42 | 103.1 | 243 | 197.1 | 224.1 | 1.8 | 168.1 | 77 | 248.1 |
| p-PKB $IC_{50}$ [nM] | 84 | 26 | 768 | 56 | 84 | 50 | 41 | 224 | 79 | 170 | 1630 |
| Example | 3.10 | 203 | 212.1 | 221.2 | 39 | 56.1 | 169.3 | 85.2 | 12 | 24 | 10.1 |
| p-PKB $IC_{50}$ [nM] | 275 | 280 | 10 | 22 | 21 | 15 | 157 | 44 | 442 | 12 | 68 |
| Example | 70 | 74 | 128.2 | 86 | 195.4 | 172 | 25.5 | 4.2 | 49 | 144.2 | 222 |
| p-PKB $IC_{50}$ [nM] | 473 | 247 | 43 | 101 | 24 | 44 | 118 | 43 | 7 | 131 | 5 |
| Example | 3.2 | 25.2 | 100 | 193 | 187 | 253 | 149.1 | 98.3 | 168.3 | 1.4 | 1.10 |
| p-PKB $IC_{50}$ [nM] | 62 | 946 | 33 | 32 | 41 | 91 | 8 | 363 | 56 | 450 | 19 |
| Example | 6.4 | 2.1 | 152.2 | 25.6 | 221.1 | 87.4 | 93.1 | 135 | 149.2 | 26 | 155.1 |
| p-PKB $IC_{50}$ [nM] | 137 | 29 | 57 | 140 | 547 | 42 | 74 | 58 | 25 | 106 | 12 |
| Example | 3.5 | 199 | 86.2 | 251 | 4.7 | 98.1 | 14 | 196.1 | 179 | 103.2 | 148.2 |
| p-PKB $IC_{50}$ [nM] | 377 | 133 | 232 | <5 | 288 | 14 | 1508 | 90 | 8 | 314 | 41 |
| Example | 71 | 146.4 | 3.6 | 90.1 | 57 | 148.3 | 16.4 | 175.1 | 4.9 | 82 | 188 |
| p-PKB $IC_{50}$ [nM] | 66 | 178 | 134 | 276 | 120 | 119 | 479 | 41 | 403 | 66 | 343 |
| Example | 136 | 215.2 | 44 | 62 | 109 | 234.4 | 206.2 | 171 | 141.1 | 1.2 | 195.2 |
| p-PKB $IC_{50}$ [nM] | 24 | 103 | 255 | 196 | 78 | 62 | 212 | 66 | 59 | 50 | 390 |
| Example | 146.3 | 17.1 | 195.3 | 110 | 152.3 | 140.2 | 28.2 | 209 | 98.2 | 173 | 76 |
| p-PKB $IC_{50}$ [nM] | 749 | 59 | 58 | 11 | 30 | 186 | 56 | 19 | 235 | 7 | 631 |
| Example | 85.3 | 25.3 | 17.2 | 166.4 | 1.6 | 3.7 | 122 | 153.1 | 229 | 119 | 213.1 |
| p-PKB $IC_{50}$ [nM] | 157 | 16 | 86 | 211 | 366 | 51 | 9 | 595 | 89 | 91 | 35 |
| Example | 64 | 79 | 147 | 3.12 | 32.2 | 183 | 94 | 137 | 198 | 167 | 141.3 |
| p-PKB $IC_{50}$ [nM] | 249 | 193 | 396 | 307 | 48 | 13 | 26 | 204 | 719 | 112 | 69 |
| Example | 217 | 32.1 | 118.3 | 140.1 | 176 | 155.2 | 234.1 | 59.1 | 245 | 153.3 | 112 |
| p-PKB $IC_{50}$ [nM] | 5 | 168 | 165 | 96 | 240 | 22 | 425 | 145 | 34 | 95 | 240 |

-continued

| Rat1-myr-p110 delta | | | | | | | | | | | |
|---|---|---|---|---|---|---|---|---|---|---|---|
| Example | 80.1 | 149.3 | 2.9 | 52 | 227 | 35 | 117 | 132 | 116 | 158.4 | 2.3 |
| p-PKB $IC_{50}$ [nM] | 145 | 59 | 56 | 336 | 27 | 12 | 86 | 91 | 12 | 211 | 347 |
| Example | 194.1 | 88.2 | 27.1 | 197.2 | 194.2 | 174 | 143 | 30.1 | 156 | 211.1 | 244 |
| p-PKB $IC_{50}$ [nM] | 21 | <5 | 23 | 85 | 28 | 132 | 357 | 837 | 100 | 30 | 127 |
| Example | 118.4 | 87.1 | 220.1 | 242.1 | 7.2 | 224.2 | 58.5 | 246 | 15.3 | 97 | 128.1 |
| p-PKB $IC_{50}$ [nM] | 46 | 118 | 40 | 70 | 213 | 223 | 7 | 959 | 90 | 27 | 44 |
| Example | 43.1 | 250 | 151 | 139 | 45.3 | 51.4 | 89 | 78 | 148.1 | 186 | 54.2 |
| p-PKB $IC_{50}$ [nM] | 28 | 33 | 41 | 151 | 602 | 412 | 18 | 7 | 306 | 382 | 128 |
| Example | 17.3 | 85.1 | 180.1 | 16.2 | 21.2 | 8.2 | 84.1 | 87.3 | 142.1 | 81.2 | 53.1 |
| p-PKB $IC_{50}$ [nM] | 154 | 418 | 280 | 297 | 927 | 50 | 205 | 219 | 360 | 45 | 43 |
| Example | 195.1 | 3.4 | 145.1 | 22 | 3.3 | 1.5 | 4.6 | 2.6 | 175.2 | 206.1 | 58.1 |
| p-PKB $IC_{50}$ [nM] | 22 | 278 | 81 | 91 | 13 | 24 | 116 | 39 | 21 | 53 | 468 |
| Example | 215.3 | 4.8 | 1.1 | 125.1 | 220.3 | 28.3 | 254 | 252 | 150.1 | 218 | 56.2 |
| p-PKB $IC_{50}$ [nM] | 29 | 326 | 49 | 42 | 56 | 197 | 106 | 45 | <5 | 7 | 12 |
| Example | 51.1 | 185.1 | 237 | 3.1 | 182 | 10.2 | 247.4 | 158.1 | 161 | 200 | 43.2 |
| p-PKB $IC_{50}$ [nM] | 70 | 50 | 103 | 225 | 78 | 105 | 29 | 162 | 56 | 246 | 26 |
| Example | 169.1 | 3.9 | 223 | 72 | 102 | 2.8 | 249 | 105 | 191.1 | 61 | 233 |
| p-PKB $IC_{50}$ [nM] | 24 | 18 | 458 | 489 | 9 | 105 | 110 | 16 | 508 | 288 | 330 |
| Example | 6.3 | 23.2 | 154.2 | 46 | 204 | 211.2 | 104 | 152.1 | 83 | 247.2 | 215.1 |
| p-PKB $IC_{50}$ [nM] | 570 | 33 | 24 | 327 | 6 | 102 | 54 | 19 | 772 | 15 | 8 |
| Example | 50 | 60.1 | 180.2 | 238 | 118.5 | 65 | 55 | 168.2 | 3.11 | 158.2 | 165 |
| p-PKB $IC_{50}$ [nM] | 62 | 41 | 61 | 12 | 24 | 335 | 59 | <5 | 45 | 36 | 23 |
| Example | 181 | 239 | 125.2 | 58.2 | 159 | 196.2 | 146.5 | 87.2 | 220.2 | 2.5 | 142.3 |
| p-PKB $IC_{50}$ [nM] | 16 | 39 | 112 | 27 | 23 | 28 | 46 | 59 | 25 | 11 | 60 |
| Example | 184 | 177.1 | 54.1 | 5.2 | 234.2 | 202 | 90.2 | 155.4 | 248.3 | 81.1 | 96 |
| p-PKB $IC_{50}$ [nM] | 19 | 85 | 57 | 12 | 607 | 157 | 203 | 18 | 50 | 62 | 16 |
| Example | 99 | 178 | 166.1 | 163 | 170 | 247.1 | 45.2 | 111 | 166.2 | 2.7 | 84.2 |
| p-PKB $IC_{50}$ [nM] | 111 | 15 | 76 | 155 | <5 | 125 | 155 | 176 | 18 | 18 | 193 |
| Example | 166.3 | 51.6 | 6.2 | 4.4 | 158.3 | 16.3 | 30.2 | 66 | 127 | 5.1 | 107 |
| p-PKB $IC_{50}$ [nM] | 787 | 12 | | | | | | | | | |
| Example | 4.3 | 118.1 | | | | | | | | | |

The efficacy of the compounds of the invention in displaying an inhibitory effect downstream of mTORC1 complex (mTOR/raptor) was demonstrated in cellular setting using a reverse protein array assay for sensitive quantification of drug-mediated inhibition of S6 Ribosomal Protein phosphorylation Ser235/236 in TSC1 null mouse embryo fibroblast (MEF) cells.

Cells and Cell Culture Conditions:

TSC1−/− MEFs cells (provided by D. Kwiatkowski), were cultivated in Dulbecco's modified Eagle's medium (DMEM high Glucose, GIBCO, cat. No. 41956-039) supplemented with 10% heat inactivated fetal bovine calf serum (Amimed, cat. No. 2-01F16-I), 1% L-Glutamine (Invitrogen, cat. No. 25030-02), 1% penicillin-streptomycin (GIBCO, cat. No. 15140-114) at 37° C. in a 5% CO2 and 95% relative humidity atmosphere incubator.

Treatment of Cells and Preparation of Samples:

The TSC1−/− cells were trypsinized and counted with a CASY TT cell counter (Schärfe System GmbH, Reutlingen Germany). The cells were diluted in fresh DMEM complete medium and $0.75\times10^4$ cells/150 μl/well seeded in 96-well TPP-tissue culture plates (TPP, cat. No. 92096). The plates were incubated at 37° C. and 5% $CO_2$ under humidified condition for at least 20 h. Working solutions were prepared freshly as serial 8 step dilutions (vol/vol) in DMSO on the day of the experiment. The working solutions were further diluted 1/5000 in cell culture medium to get final compound concentrations of 1, 0.3333, 0.1111, 0.037, 0.0123, 0.041, 0.0014, 0.005 μM. The final DMSO concentration was kept constant at 0.02%. cell culture medium containing 0.02% DMSO was used as vehicle treatment control. Post incubation, the cells were treated with the serial compound dilution. 50 μl of the compound medium mixture was added to the wells containing cells and 150 μl DMEM medium and incubated for 60 minutes (37° C., 5% $CO_2$). After 60 minutes of incubation, the medium mixture was quickly removed by aspiration. For cell lysis, a mixture of 10% CLB1 CeLyA lysis buffer (Zeptosens, cat. No. 9000), 90% CSBL1 CeLyA spotting buffer (Zeptosens, cat. No. 9020) was freshly prepared and supplemented with 1% Octyl β-D-glucopyranoside (SIGMA, cat. No. 08001-5G) and 1 mM Na-Orthovanadate (Sigma, cat No.

S-6508). 50 μl of the described lysis buffer mix was added to each well, followed by 10 minutes of incubation on ice. After an additional freeze-thaw cycle, another 50 μl of the lysis buffer mix without Octyl β-D-glucopyranoside was added to the wells, and 90 μl of the cell lysate was transferred to a 96-well V-bottom plate (Fisher Scientific, cat. No. 6067Y), followed by a centrifugation step (5 min, 1500 rpm at 19° C. in an Eppendorf 5810R centrifuge) to remove the unlysed cell debris.

Spotting of the ZeptoMARK° Chips:

The spotting of the chips follows the previous described method.

ZeptoREADER Signal Detection and Data Analysis:

The signal detection and the data analysis follows the previous described method using the pS6 ribosomal protein Ser235/236 (CST, cat. No. #2211) as a primary antibody.

The range of activity, expressed as $IC_{50}$, in this assay is preferably between about 0.1 nM and about 1 μM, more preferably between about 0.1 nM and about 0.5 μM.

| | | | | | | | | | | |
|---|---|---|---|---|---|---|---|---|---|---|
| p-S6 $IC_{50}$ [nM] | 3 | 60 | 1 | 6 | 61 | 31 | 36 | 4 | 14 | 46 |
| Example | 132 | 112 | 202 | 2.7 | 16.3 | 195.2 | 153.3 | 100 | 30.1 | 107 |
| p-S6 $IC_{50}$ [nM] | 30 | 11 | 1 | 8 | 39 | 24.99 | 2 | 15 | <0.5 | 1 |
| Example | 37.1 | 15.1 | 25.6 | 25.5 | 215.1 | 51.5 | 88.1 | 3.6 | 144.3 | 87.2 |
| p-S6 $IC_{50}$ [nM] | 5 | 9 | 7 | 5.63 | 3 | 7 | 3 | 21 | <0.5 | 4 |
| Example | 195.1 | 29.1 | 96 | 169.1 | 215.2 | 12 | 206.1 | 211.1 | 118.5 | 247.4 |
| p-S6 $IC_{50}$ [nM] | 1 | 174 | 3 | 5 | 1 | 10 | 7 | <0.5 | 2 | 6.94 |
| Example | 118.2 | 58.3 | 247.1 | 77 | 51.2 | 2.5 | 167 | 43.2 | 28.3 | 149.3 |
| p-S6 $IC_{50}$ [nM] | 6 | 3.56 | 10 | 2.66 | 2 | 4 | 35 | 23 | 5 | <5 |
| Example | 59.1 | 34 | 56.2 | 146.5 | 51.3 | 56.1 | 90.2 | 74 | 84.2 | 1.8 |
| p-S6 $IC_{50}$ [nM] | 19 | 8 | <0.5 | 75 | 1 | <5 | 41 | 78 | 4 | 46 |
| Example | 81.2 | 158.1 | 168.2 | 92 | 156 | 102 | 246 | 110 | 153.1 | 45.3 |
| p-S6 $IC_{50}$ [nM] | 666 | 1 | 17 | 5 | 13 | 1 | 11 | 1 | 5 | 2 |
| Example | 21.2 | 172 | 108 | 54.1 | 4.5 | 183 | 109 | 201 | 140.1 | 234.3 |
| p-S6 $IC_{50}$ [nM] | 1 | 3 | 41 | <0.5 | 6 | 38 | 91 | <5 | 2 | 5 |
| Example | 215.3 | 174 | 87.4 | 146.1 | 135 | 83 | 50 | 1.5 | 190 | 208 |
| p-S6 $IC_{50}$ [nM] | 4 | 3 | 4 | 1.02 | 43 | 355 | 37 | 234 | 111 | 4 |
| Example | 99 | 86 | 191.1 | 186 | 53.1 | 120 | 205 | 27.2 | 85.3 | 222 |
| p-S6 $IC_{50}$ [nM] | 2 | 44 | 3 | <5 | 5 | 66 | <5 | <0.5 | 11 | 5 |
| Example | 199 | 1.9 | 233 | 253 | 86.2 | 65 | 28.1 | 25.4 | 51.4 | 118.1 |
| p-S6 $IC_{50}$ [nM] | 98 | <0.5 | 20 | 1 | <0.5 | 1.69 | 5 | 4 | 4 | 7 |
| Example | 62 | 241 | 152.3 | 148.3 | 142.2 | 81.1 | 79 | 1.1 | 243 | 88.2 |
| p-S6 $IC_{50}$ [nM] | 13 | 2 | 2 | 1.32 | 11 | 43.5 | 3 | 5 | 3 | 91.69 |
| Example | 27.1 | 152.1 | 23.2 | 169.3 | 3.8 | 45.1 | 43.1 | 131 | 136 | 166.5 |
| p-S6 $IC_{50}$ [nM] | 15 | 8.15 | 1 | 199 | 1 | 3 | 4 | 11 | 3 | 13 |
| Example | 4.1 | 188 | 152.2 | 3.4 | 158.2 | 224.1 | 151 | 229 | 181 | 250 |
| p-S6 $IC_{50}$ [nM] | 5 | 13 | 1 | <5 | 3 | 35 | 50 | 17 | 1 | 1 |
| Example | 64 | 103.1 | 144.2 | 1.6 | 220.2 | 247.3 | 145.1 | 15.3 | 60.1 | 150.1 |
| p-S6 $IC_{50}$ [nM] | 1 | 13.5 | 17 | 80 | 32 | 2 | 33 | 2 | 1 | 2 |
| Example | 221.2 | 7.2 | 82 | 44 | 175.2 | 177.1 | 17.2 | 125.1 | 119 | 118.4 |
| p-S6 $IC_{50}$ [nM] | 558 | 77 | 2 | 31 | 33 | <0.5 | 1 | 3 | 58 | 48 |
| Example | 32.2 | 206.2 | 194.2 | 195.3 | 251 | 51.6 | 175.1 | 146.3 | 72 | 52 |
| p-S6 $IC_{50}$ [nM] | 22 | 1 | 1 | 20 | 3 | 1 | 7 | 49.41 | 127 | 1 |
| Example | 203 | 85.1 | 54.2 | 194.1 | 171 | 141.2 | 197.2 | 213.1 | 47 | 129 |
| p-S6 $IC_{50}$ [nM] | 27 | 79 | 32 | <0.5 | 4 | 10 | 46 | 5.53 | 2 | 3 |
| Example | 22 | 170 | 210 | 122 | 58.2 | 5.1 | 214 | 193 | 178 | 58.5 |
| p-S6 $IC_{50}$ [nM] | 3 | 10 | 2 | 9 | 1 | 35 | 87 | 1 | 6 | 5.53 |
| Example | 127 | 13 | 195.4 | 149.1 | 157 | 223 | 17.1 | 221.1 | 219 | 147 |
| p-S6 $IC_{50}$ [nM] | 1 | 4 | 278 | 6 | 5 | 36 | 130 | 1 | <0.5 | 2 |
| Example | 166.4 | 139 | 146.6 | 116 | 182 | 40 | 56.5 | 148.2 | 220.3 | 173 |
| p-S6 $IC_{50}$ [nM] | 21 | 22 | 2 | 7 | <0.5 | 508 | <0.5 | 15 | 181 | 1 |
| Example | 2.8 | 148.1 | 176 | 4.2 | 90.1 | 133 | 204 | 118.3 | 16.2 | 95 |
| p-S6 $IC_{50}$ [nM] | 3 | 9 | 32 | 6 | 6 | 5 | 7 | 1 | 11 | 3 |

-continued

| | | | | | | | | | | |
|---|---|---|---|---|---|---|---|---|---|---|
| Example | 38 | 128.1 | 185.2 | 237 | 87.3 | 184 | 212.1 | 128.2 | 32.1 | 80.1 |
| p-S6 $IC_{50}$ [nM] | 41 | 1 | 25 | 1.89 | 11 | 1 | <0.5 | 3 | 3 | 2 |
| Example | 30.2 | 59.2 | 244 | 187 | 60.2 | 164 | 168.3 | 154.1 | 98.1 | 209 |
| p-S6 $IC_{50}$ [nM] | 20 | 39 | 201 | 4 | 1 | 5 | 12 | 123 | 1 | 9 |
| Example | 224.2 | 104 | 247.5 | 29.3 | 234.2 | 192 | 146.4 | 14 | 155.2 | 247.2 |
| p-S6 $IC_{50}$ [nM] | 28 | 2 | 30 | 23 | 2 | 1 | 72 | 5 | 17 | 10.11 |
| Example | 80.2 | 141.3 | 3.7 | 41 | 4.9 | 150.2 | 45.2 | 51.1 | 180.2 | 234.4 |
| p-S6 $IC_{50}$ [nM] | 2 | 2 | 2 | 9 | 18 | <0.5 | 7 | 33 | 33 | 18 |
| Example | 242.1 | 155.1 | 58.4 | 234.1 | 55 | 218 | 197.1 | 16.1 | 6.1 | 155.4 |
| p-S6 $IC_{50}$ [nM] | 36 | 0.94 | 3 | 2 | 24 | 1 | 1 | 6 | 255 | <0.5 |
| Example | 142.1 | 145.2 | 166.1 | 84.1 | 10.2 | 155.3 | 168.1 | 25.2 | 3.3 | 89 |
| p-S6 $IC_{50}$ [nM] | 1 | <0.5 | 40 | 88 | 16 | <0.5 | 39 | 10 | 27 | 11 |
| Example | 1.10 | 36 | 3.1 | 242.2 | 70 | 215.4 | 154.2 | 179 | 2.9 | 240 |
| p-S6 $IC_{50}$ [nM] | 36 | 37 | 1 | 1 | 2 | 1 | 6 | 13 | 13 | 180 |
| Example | 91 | 39 | 142.3 | 239 | 161 | 93.1 | 140.2 | 16.5 | 71 | 87.5 |
| p-S6 $IC_{50}$ [nM] | 43 | 22 | 10 | 22 | 2 | 13.38 | 3 | 2 | 175 | 3 |
| Example | 245 | 207 | 6.4 | 93.2 | 146.2 | 63 | 42 | 249 | 3.12 | 149.2 |
| p-S6 $IC_{50}$ [nM] | 1 | 10 | 200 | 1 | <0.5 | 151 | 3 | 5 | 9 | 1 |
| Example | 165 | 217 | 76 | 61 | 158.3 | 175.3 | 198 | 57 | 137 | 220.1 |
| p-S6 $IC_{50}$ [nM] | 3 | 98 | 154 | 217 | 58 | 17.7 | 5 | 7 | 8 | 5.33 |
| Example | 111 | 46 | 117 | 49 | 3.5 | 148.4 | 26 | 226 | 159 | 126 |
| p-S6 $IC_{50}$ [nM] | 1 | 9 | 2 | <0.5 | 125 | 10 | 5 | 2 | 12 | 11 |
| Example | 189 | 24 | 144.1 | 200 | 196.2 | 196.1 | 252 | 163 | 227 | 211.2 |
| p-S6 $IC_{50}$ [nM] | 3 | 3 | 2 | 2.26 | 15 | 58 | 1 | 8 | 4 | 5 |
| Example | 103.2 | 17.3 | 35 | 166.2 | 37.3 | 254 | 56.4 | 6.2 | 225 | 3.9 |
| p-S6 $IC_{50}$ [nM] | <0.5 | 844 | 3 | 5 | 5 | 10 | <0.5 | 5 | 2 | 34 |
| Example | 216 | 37.4 | 138 | 191.2 | 166.3 | 3.10 | 160.1 | 5.2 | 25.3 | 141.1 |
| p-S6 $IC_{50}$ [nM] | 5 | 9 | 8 | 3 | 4 | 1 | 6 | 10 | 35 | 150 |
| Example | 125.2 | 143 | 6.3 | 97 | 23.1 | 25.1 | 238 | 4.4 | 185.1 | 158.4 |
| p-S6 $IC_{50}$ [nM] | 3 | | | | | | | | | |
| Example | 58.1 | | | | | | | | | |

There are also experiments to demonstrate the antitumor activity of compounds of the formula (I) in vivo.

For example, female Harlan (Indianapolis, Ind., USA) athymic nu/nu mice with s.c. transplanted human glioblastoms U87MG tumors can be used to determine the anti-tumor activity of PI3 kinase inhibitors. On day 0, with the animals under peroral Forene® (1-chloro-2,2,2-trifluoroethyldifluormethylether, Abbot, Wiesbaden, Germany) narcosis, a tumor fragment of approximately 25 mg is placed under the skin on the animals' left flank and the small incised wound is closed by means of suture clips. When tumors reach a volume of 100 $mm^3$, the mice are divided at random into groups of 6-8 animals and treatment commences. The treatment is carried out for a 2-3 weeks period with peroral, intravenous or intraperitoneal administration once daily (or less frequently) of a compound of formula (I) in a suitable vehicle at defined doses. The tumors are measured twice a week with a slide gauge and the volume of the tumors is calculated.

As an alternative to cell line U87MG, other cell lines may also be used in the same manner, for example, the MDA-MB 468 breast adenocarcinoma cell line (ATCC No. HTB 132; see also In Vitro 14, 911-15 [1978]);

the MDA-MB 231 breast carcinoma cell line (ATCC No. HTB-26; see also In Vitro 12, 331 [1976]);

the MDA-MB 453 breast carcinoma cell line (ATCC No. HTB-131);

the Colo 205 colon carcinoma cell line (ATCC No. CCL 222; see also Cancer Res. 38, 1345-55 [1978]);

the DU145 prostate carcinoma cell line DU 145 (ATCC No. HTB 81; see also Cancer Res. 37, 4049-58 [1978]), the PC-3 prostate carcinoma cell line PC-3 (especially preferred; ATCC No. CRL 1435; see also Cancer Res. 40, 524-34 [1980]) and the PC-3M prostate carcinoma cell line;

the A549 human lung adenocarcinoma (ATCC No. CCL 185; see also Int. J. Cancer 17, 62-70 [1976]), the NCI-H596 cell line (ATCC No. HTB 178; see also Science 246, 491-4 [1989]);

the pancreatic cancer cell line SUIT-2 (see Tomioka et al., Cancer Res. 61, 7518-24 [2001]).

What is claimed is:

1. A pharmaceutical composition comprising a compound selected from 8-(2,4-dimethoxypyrimidin-5-yl)-1-(1-ethyl-3-methyl-1H-pyrazol-4-yl)-3-methyl-1H-imidazo[4,5-c]quinolin-2(3H)-one and 1-(1-ethyl-3-methyl-1H-pyrazol-4-yl)-8-(6-(methoxymethyl)-5-(methylamino)pyridin-3-yl)-3-methyl-1H-imidazo[4,5-c]quinolin-2(3H)-one, or a pharmaceutically acceptable salt thereof, and optionally a further therapeutic agent, together with a pharmaceutically acceptable carrier.

2. A compound of formula:

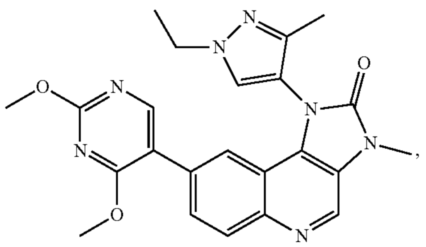

or a pharmaceutically acceptable salt thereof.

3. A compound of formula:

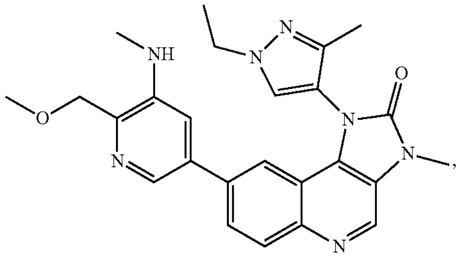

or a pharmaceutically acceptable salt thereof.

* * * * *

SEQUENCE LISTING

<160> NUMBER OF SEQ ID NOS: 19

<210> SEQ ID NO 1
<211> LENGTH: 28
<212> TYPE: DNA
<213> ORGANISM: Artificial
<220> FEATURE:
<223> OTHER INFORMATION: PCR primer

<400> SEQUENCE: 1
cgagaatatg atagattata tgaagaat 28

<210> SEQ ID NO 2
<211> LENGTH: 30
<212> TYPE: DNA
<213> ORGANISM: Artificial
<220> FEATURE:
<223> OTHER INFORMATION: PCR primer

<400> SEQUENCE: 2
tggtttaatg ctgttcatac gtttgtcaat 30

<210> SEQ ID NO 3
<211> LENGTH: 76
<212> TYPE: DNA
<213> ORGANISM: Artificial
<220> FEATURE:
<223> OTHER INFORMATION: PCR primer

<400> SEQUENCE: 3
gggacaagtt tgtacaaaaa agcaggctac gaaggagata tacatatgcg agaatatgat 60
agattatatg aagaat 76

<210> SEQ ID NO 4
<211> LENGTH: 54
<212> TYPE: DNA
<213> ORGANISM: Artificial
<220> FEATURE:
<223> OTHER INFORMATION: PCR primer

<400> SEQUENCE: 4
attaaaccag gaggaggagg aggaggatgc ttcagtttca taatgcctcc tgct 54

<210> SEQ ID NO 5
<211> LENGTH: 26
<212> TYPE: DNA
<213> ORGANISM: Artificial
<220> FEATURE:
<223> OTHER INFORMATION: PCR primer

<400> SEQUENCE: 5
ctagtggaat gtttactacc aaatgg 26

<210> SEQ ID NO 6
<211> LENGTH: 26
<212> TYPE: DNA
<213> ORGANISM: Artificial
<220> FEATURE:
<223> OTHER INFORMATION: PCR primer

<400> SEQUENCE: 6
gttcaatgca tgctgtttaa ttgtgt 26

<210> SEQ ID NO 7
<211> LENGTH: 63
<212> TYPE: DNA
<213> ORGANISM: Artificial
<220> FEATURE:
<223> OTHER INFORMATION: PCR primer

<400> SEQUENCE: 7
gggggaattt ccggtggtgg tggtggaatt atggtactag tggaatgttt actaccaaat 60
gga 63

<210> SEQ ID NO 8
<211> LENGTH: 56
<212> TYPE: DNA
<213> ORGANISM: Artificial
<220> FEATURE:
<223> OTHER INFORMATION: PCR primer

<400> SEQUENCE: 8
agctccgtga tggtgatggt gatgtgctcc gttcaatgca tgctgtttaa ttgtgt 56

<210> SEQ ID NO 9
<211> LENGTH: 61
<212> TYPE: DNA
<213> ORGANISM: Artificial
<220> FEATURE:
<223> OTHER INFORMATION: PCR primer

<400> SEQUENCE: 9
gggaccactt tgtacaagaa agctgggttt aagctccgtg atggtgatgg tgatgtgctc 60
c 61

<210> SEQ ID NO 10
<211> LENGTH: 42
<212> TYPE: DNA
<213> ORGANISM: Artificial
<220> FEATURE:
<223> OTHER INFORMATION: PCR Primer

<400> SEQUENCE: 10
gctagcatgc gagaatatga tagattatat gaagaatata cc 42

<210> SEQ ID NO 11
<211> LENGTH: 45
<212> TYPE: DNA
<213> ORGANISM: Artificial
<220> FEATURE:
<223> OTHER INFORMATION: PCR primer

<400> SEQUENCE: 11
gcctccacca cctccgcctg gtttaatgct gttcatacgt ttgtc 45

<210> SEQ ID NO 12
<211> LENGTH: 42
<212> TYPE: DNA
<213> ORGANISM: Artificial
<220> FEATURE:
<223> OTHER INFORMATION: PCR primer

<400> SEQUENCE: 12
tactagtccg cctccaccac ctccgcctcc accacctccg cc 42

<210> SEQ ID NO 13
<211> LENGTH: 54

<212> TYPE: DNA
<213> ORGANISM: Artificial
<220> FEATURE:
<223> OTHER INFORMATION: PCR primer

<400> SEQUENCE: 13
actgaagcat cctcctcctc ctcctcctgg tttaatgctg ttcatacgtt tgtc 54

<210> SEQ ID NO 14
<211> LENGTH: 57
<212> TYPE: DNA
<213> ORGANISM: Artificial
<220> FEATURE:
<223> OTHER INFORMATION: PCR primer

<400> SEQUENCE: 14
agctccgtga tggtgatggt gatgtgctcc agatctgtag tctttccgaa ctgtgtg 57

<210> SEQ ID NO 15
<211> LENGTH: 45
<212> TYPE: DNA
<213> ORGANISM: Artificial
<220> FEATURE:
<223> OTHER INFORMATION: PCR primer

<400> SEQUENCE: 15
tcctcctcct cctcctcctg gtttaatgct gttcatacgt ttgtc 45

<210> SEQ ID NO 16
<211> LENGTH: 26
<212> TYPE: DNA
<213> ORGANISM: Artificial
<220> FEATURE:
<223> OTHER INFORMATION: PCR primer

<400> SEQUENCE: 16
atgccccctg ggtggactg ccccat 26

<210> SEQ ID NO 17
<211> LENGTH: 26
<212> TYPE: DNA
<213> ORGANISM: Artificial
<220> FEATURE:
<223> OTHER INFORMATION: PCR primer

<400> SEQUENCE: 17
ctactgcctg ttgtctttgg acacgt 26

<210> SEQ ID NO 18
<211> LENGTH: 53
<212> TYPE: DNA
<213> ORGANISM: Artificial
<220> FEATURE:
<223> OTHER INFORMATION: PCR primer

<400> SEQUENCE: 18
attaaaccag gaggaggagg aggaggaccc cctggggtgg actgccccat gga 53

<210> SEQ ID NO 19
<211> LENGTH: 56
<212> TYPE: DNA
<213> ORGANISM: Artificial
<220> FEATURE:
<223> OTHER INFORMATION: PCR primer -continued

<400> SEQUENCE: 19
agctccgtga tggtgatggt gatgtgctcc ctgcctgttg tctttggaca cgttgt 56